US 7,612,178 B2
Nov. 3, 2009

(12) United States Patent
Hariharan et al.

(54) ANTI-IGF-1R ANTIBODIES AND USES THEREOF

(75) Inventors: Kandasamy Hariharan, San Diego, CA (US); Scott Glaser, San Diego, CA (US); Ellen Garber, Cambridge, MA (US); Christilyn Graff, Cambridge, MA (US); Christopher L. Reyes, San Diego, CA (US); Stephen Demarest, San Diego, CA (US)

(73) Assignee: Biogen Idec MA Inc, Cambridge, MA (US)

( * ) Notice: Subject to any disclaimer, the term of this patent is extended or adjusted under 35 U.S.C. 154(b) by 88 days.

(21) Appl. No.: 11/727,887

(22) Filed: Mar. 28, 2007

(65) Prior Publication Data

US 2007/0243194 A1      Oct. 18, 2007

Related U.S. Application Data

(60) Provisional application No. 60/876,554, filed on Dec. 22, 2006, provisional application No. 60/786,347, filed on Mar. 28, 2006.

(51) Int. Cl.
   *C07K 16/00* (2006.01)
   *C12P 21/08* (2006.01)
(52) U.S. Cl. ................................. 530/387.1; 435/70.21
(58) Field of Classification Search ........................ None
   See application file for complete search history.

(56) References Cited

U.S. PATENT DOCUMENTS

| | | | |
|---|---|---|---|
| 5,587,458 | A | 12/1996 | King et al. |
| 6,159,730 | A | 12/2000 | Reff |
| 6,632,927 | B2 * | 10/2003 | Adair et al. ............ 530/387.3 |
| 7,217,796 | B2 | 5/2007 | Wang |
| 2002/0123057 | A1 | 9/2002 | Zauderer et al. |
| 2005/0249730 | A1 | 11/2005 | Goetsch et al. |
| 2005/0281812 | A1 | 12/2005 | Cohen et al. |
| 2005/0288217 | A1 | 12/2005 | Clemmons et al. |
| 2007/0059305 | A1 | 3/2007 | Wang et al. |
| 2009/0092614 | A1 | 4/2009 | Demarest et al. |
| 2009/0130105 | A1 * | 5/2009 | Glaser et al. ............ 424/136.1 |

FOREIGN PATENT DOCUMENTS

| | | |
|---|---|---|
| WO | WO 2005/089285 A2 | 9/2005 |
| WO | WO 2007/126876 A2 | 11/2007 |
| WO | WO 2009/032145 | 3/2009 |

OTHER PUBLICATIONS

Rudikoff et al. 1982, Proc. Natl. Acad. Sci. USA, 79: 1979-1983.*
Panka et al., 1988, Proc. Natl. Acad. Sci. USA, 85: 3080-3084.*
Altundag, K., et al., "Insulinlike growth factor-1 receptor: predictive factor in breast cancer patients treated with trastuzumab?," *Hum. Pathol.* 36:448-449, W.B. Saunders (Apr. 2005).

Baserga, R., "Oncogenes and the Strategy of Growth Factors," *Cell* 79:927-930, Cell Press (1994).
Baserga, R., "The IGF-I Receptor in Cancer Research," *Exp. Cell Res.* 253:1-6, Academic Press (1999).
Baserga, R., et al., "The IGF-I Receptor in Cancer Biology," *Int. J. Cancer.* 107:873-877, Wiley-Liss (2003).
Baserga, R., et al., "The IGF-I receptor in cell growth, transformation and apoptosis," *Biochim. Biophys. Acta* 1332:F105-F126, Elsevier Science B.V. (1997).
Beste, G., et al., "Small antibody-like proteins with prescribed ligand specificities derived from the lipocalin fold," *Proc. Natl. Acad. Sci. U.S.A.* 96: 1898-1903, National Academy of Sciences (1999).
Binz, H.K., et al., "High-affinity binders selected from designed ankyrin repeat protein libraries," *Nat. Biotechnol.* 22:575-582, Nature America Publishing (2004).
Blakesley, V.A., et al., "Signaling via the Insulin-like Growth Factor-I Receptor: Does it Differ from Insulin Receptor Signaling," *Cytokine Growth Factor Rev.* 7:153-159, Elsevier Science (1996).
Brezinsky, S.C., et al., "A simple method for enriching populations of transfected CHO cells for cells of higher specific productivity," *J. Immunol. Methods* 277:141-155, Elsevier Science (2003).
Burtrum, D., et al., "A fully human monoclonal antibody to the insulin-like growth factor I receptor blocks ligand-dependent signaling and inhibits human tumor growth in vivo," *Cancer Res.* 63:8912-21(2003).
Chakravarti, A., et al., "Insulin-like Growth Factor Receptor I Mediates Resistance to Anti-Epidermal Growth Factor Receptor Therapy in Primary Human Glioblastoma Cells through Continued Activation of Phosphoinositide 3-Kinase Signaling," *Cancer Res.* 62:200-207, American Association for Cancer Research (2002).
Chan, J.M., et al., "Plasma Insulin-Like Growth Factor-I and Prostate Cancer Risk: A Prospective Study," *Science* 279:563-566, American Association for the Advancement of Science (1998).
Cohen, B.D., et al., "Combination therapy enhances the inhibition of tumor growth with the fully human anti-type 1 insulin-like growth factor receptor monoclonal antibody CP-751,871," *Clin. Cancer Res.* 11:2063-2073 (2005).

(Continued)

*Primary Examiner*—Ilia Ouspenski
(74) *Attorney, Agent, or Firm*—Sterne, Kessler, Goldstein & Fox P.L.L.C.

(57) ABSTRACT

The invention relates to antibodies which bind to insulin like growth factor receptor-1 (IGF-1R) and uses thereof, in particular in the diagnosis and treatment of cancer. Specific human and murine monoclonal antibodies which inhibit IGF-1R-mediated pro-survival and tumor proliferation pathways, and variants, fragments, and derivatives thereof are provided. Also provided are specific human and murine monoclonal antibodies which block the ability of the ligands, insulin like growth factor 1 (IGF-1) and insulin like growth factor 2 (IGF-2) to bind to IGF-1R, as well as fragments, variants and derivatives of such antibodies. The invention also includes polynucleotides encoding the above antibodies or fragments, variants or derivatives thereof, as well as vectors and host cells comprising such polynucleotides. The invention further includes methods of diagnosing and treating cancer using antibodies of the invention.

16 Claims, 43 Drawing Sheets

OTHER PUBLICATIONS

Davies, D. R., and Cohen, G.H., "Interactions of protein antigens with antibodies," *Proc. Natl. Acad. Sci. U.S.A.* 93:7-12, National Academy of Sciences (1996).

De Meyts, P. and Whittaker, J., "Structural Biology of Insulin and IGF1 Receptors: Implications for Drug Design," *Nat. Rev. Drug Discov.* 1:769-783, Nature Publishing Group (2002).

De Souza, A. T., et al., "Imprinted genes in liver carcinogenesis," *FASEB J.* 11:60-67, The Federation of American Societies for Experimental Biology (1997).

Del Valle, L., et al., "Insulin-like Growth Factor I Receptor Activity in Human Medulloblastomas," *Clin. Cancer Res.* 8:1822-1830, The Association (2002).

Demarest, S.J, et al., "An intermediate pH Unfolding Transition Abrogates the Ability of IgE to Interact with Its High Affinity Receptor FcεRIα," *J. Biol. Chem.* 281:30755-30767, American Society for Biochemistry and Molecular Biology (Oct. 2006).

Demarest, S.J., et al., "Engineering stability into Escerichia coli secreted Fabs leads to increased functional expression," *Protein Eng. Des. Sel.* 19:325-336, Oxford University Press (May 2006).

Feinberg, A.P. and Tycko, B., "The history of cancer epigenetics," *Nat. Rev. Cancer* 4:143-153, Nature Publishing Group (2004).

Feng, Y., et al., "Novel human monoclonal antibodies to insulin-like growth factor (IGF)-II that potently inhibit the IGF receptor type I signal transduction function," *Mol. Cancer Ther.* 5:114-120, American Association for Cancer Research, Inc. (Jan. 2006).

Furukawa, M., et al., "Increased Expression of Insulin-Like Growth Factor I and/or Its Receptor in Gastrinomas Is Associated with Low Curability, Increased Growth, and Development of Metastases," *Clin. Cancer Res.* 11:3233-3242, The Association for Cancer Research (May 2005).

García-Echeverría, C., et al.,"In vivo anti-tumor activity of NVP-AEW541—A novel, potent, and selective inhibitor of the IGF-IR kinase," *Cancer Cell* 5:231-239, Cell Press (2004).

Giovannucci, E., "Nutrition, Insulin, Insulin-like Growth Factors and Cancer," *Horm. Metab. Res.* 35:694-704, Georg Thieme Verlag (2003).

Goetsch, L, et al., "A Recombinant Humanized Anti-Insulin-Like Growth Factor Receptor Type I Antibody (h7C10) Enhances the Antitumor Activity of Vinorelbine and Anti-Epidermal Growth Factor Receptor Therapy Against Human Cancer Xenografts," *Int. J Cancer* 113:316-328, Wiley-Liss (2005).

Hakam, A., et al., "Coexpression of IGF-1R and c-Src Proteins in Human Pancreatic Ductal Adenocarcinoma," *Dig. Dis. Sci.* 48:1972-1978, Plenum Pub. Corp. (2003).

Hakam, A., et al., "Expression of Insulin-like Growth Factor-1 Receptor in Human Colorectal Cancer," *Hum. Pathol.* 30:1128-1133, W.B. Saunders (1999).

Hanahan, D., and Weinberg, R.A., "The Hallmarks of Cancer," *Cell* 100:57-70, Cell Press (2000).

Hankinson, S.E., et al., "Circulating concentrations of insulin-like growth factor-I and risk of breast cancer," *Lancet* 351:1393-1396, Lancet Publishing Group (1998).

Hellawell, G.O., et al., "Expression of the Type 1 Insulin-like Growth Factor Receptor Is Up-Regulated in Primary Prostate Cancer and Commonly Persists in Metastatic Disease," *Cancer Res.* 62:2942-2950, American Association for Cancer Research (2002).

Hey, T., et al., "Artificial, Non-antibody binding proteins for pharmaceutical and industrial applications," *TRENDS Biotechnol.* 23:514-522, Elsevier Science (Oct. 2005).

Hoet, R.M., et al. ,"Generation of high-affinity human antibodies by combining donor-derived and synthetic complementarity-determining-region diversity," *Nat Biotechnol.* 23:344-348, Nature America Publishing (Mar. 2005).

Jackson, J.G., et al., "Regulation of breast cancer cell motility by insulin receptor substrate-2 (IRS-2) in metastatic variants of human breast cancer cell lines," *Oncogene* 20:7318-7325, Nature Publishing Group (2001).

Jerome, L., et al.., "The potential utility of recombinant human IGF binding protein-3 (rh1GFBP-3) for the treatment of HER-2-positive breast cancer," AACR Meeting Abstracts Online, Abstract No. 5334, American Association for Cancer Research (2004).

Jiang, Y., et al., "A high expression level of insulin-like growth factor I receptor is associated with increased expression of transcription factor Sp1 and regional lymph node metastasis of human gastric cancer," *Clin. Exp. Metastasis* 21:755-764, Kluwer Academic Publishers (2004).

Jones, J., and Clemmons, D.R., "Insulin-Like Growth Factors and Their Binding Proteins: Biological Actions," *Endocr. Rev.* 16:3-34, Endocrine Society (1995).

Kaiser, U., et al., "Expression of insulin-like growth factor receptors I and II in normal human lung and in lung cancer," *J. Cancer Res. Clin. Oncol.* 119:665-668, Springer Verlag (1993).

Kalebic, T., et al., "Expression of a Kinase-Deficient IGF-I-R Suppresses Tumorigenicity of Rhabdomyosarcoma Cells Constitutively Expressing a Wild Type IGF-I-R," *Int. J. Cancer* 76:223-227, Wiley-Liss (1998).

Kalebic, T., et al., "In vivo Treatment with Antibody against IGF-1 Receptor Suppresses Growth of Human Rhabdomyosarcoma and Down-Regulates p34(cdc2)," *Cancer Res.* 54:5531-5534, American Association for Cancer Research (1994).

Keyhanfar, M., et al., "Precise mapping of an IGF-1-binding site on IGF-1R," *Biochem. J.* 401:269-277, Portland Press (Jan. 2007).

Kopchick, J.J., et al., "Growth Hormone Receptor Antagonists: Discovery, Development, and Use in Patients with Acromegaly," *Endocr. Rev.* 23:623-646, Endocrine Society (2002).

Kull, F.C., et al., "Monoclonal Antibodies to Receptors for Insulin and Somatomedin-C," *J. Biol. Chem.* 258:6561-6566, American Society for Biochemistry and Molecular Biology (1983).

Letsch, M., et al., "Growth hormone-releasing hormone (GHRH) antagonists inhibit the proliferation of androgen-dependent and -independent prostate cancers," *Proc Natl. Acad. Sci. U.S.A.* 100:1250-1255, National Academy of Sciences (2003).

Lu, D., et al., "A Fully Human Recombinant IgG-like Bispecific Antibody to Both the Epidermal Growth Factor Receptor and the Insulin-like Growth Factor Receptor for Enhanced Antitumor Activity," *J. Biol. Chem.* 280: 19665-19672 (2005).

Ma, J., et al., "Prospective Study of Colorectal Cancer Risk in Men and Plasma Levels of Insulin-Like Growth Factor (IGF)-I and IGF-Binding Protein-3," *J. Natl. Cancer Inst.* 91:620-625, Oxford University Press (1999).

Maloney E.K., et al., "An Anti-Insulin-like Growth Factor I Receptor Antibody That Is a Potent Inhibitor of Cancer Cell Proliferation," *Cancer Research* 63:5073-5083, American Association for Cancer Research (2003).

Massagué, J. and Czech, M.P., "The Subunit Structures of Two Distinct Receptors for Insulin-like Growth Factors I and II and their Relationship to the Insulin Receptor," *J. Biol. Chem.* 257:5038-5045, American Society for Biochemistry and Molecular Biology (1992).

Mckern, N. M., et al., "Crystallization of the first three domains of the human insulin-like growth factor-1 receptor," *Protein Sci.* 6:2663-2666, Cold Spring Harbor Laboratory Press (1997).

Mckern, N. M., et al.,"Structure of the insulin receptor ectodomain reveals a folded-over conformation," *Nature* 443:218-221, Nature Publishing Group (Sep. 2006).

Miyamoto, S., et al., "Blockade of Paracrine Supply of Insulin-Like Growth Factors Using Neutralizing Antibodies Suppresses the Liver Metastasis of Human Colorectal Cancers," *Clin. Cancer Res.* 11:3494-3502, The Association for Cancer Research (May 2005).

Moschos, S., and Mantzoros, C.S., "The Role of the IGF System in Cancer: From Basic to Clinical Studies and Clinical Applications," *Oncology* 63:317-332, Karger (2002).

Nakamura, M., et al., "Low Levels of Insulin-Like Growth Factor Type 1 Receptor Expression at Cancer Cell Membrane Predict Liver Metastasis in Dukes' C Human Colorectal Cancers," *Clin. Cancer Res.* 10:8434-8441, The Association for Cancer Research (2004).

NCBI Entrez, GenBank Report, Accession No. NM_000875 (Entry Date 1999).

NCBI Entrez, GeneBank Report, Accession No. NP_000866 (Entry Date 1999).

Nolan, M.K., et al., "Differential Roles of IRS-1 and SHC Signaling Pathways in Breast Cancer Cells," *Int. J. Cancer* 72:828-834, Wiley-Liss (1997).

Nord, K., et al., "Binding proteins selected from combinatorial libraries of an α-helical bacterial receptor domain," *Nat. Biotechnol.* 15:772-777, Nature America Publishing (1997).

Oh, J.C., et al., "Increased Plasma Levels of Insulin-Like Growth Factor 2 and Insulin-Like Growth Factor Binding Protein 3 Are Associated with Endometrial Cancer Risk," *Cancer Epidemiol. Biomarkers. Prev.* 13:748-752, American Association for Cancer Research (2004).

Ouban, A., et al.,"Expression and Distribution of Insulin-Like Growth Factor-1 Receptor in Human Carcinomas," *Hum. Pathol.* 34:803-808, W.B. Saunders (2003).

Peters, G., et al., "IGF-1R, IGF-1 and IGF-2 expression as potential prognostic and predictive markers in colorectal-cancer," *Virchows Arch.* 443:139-145, Springer International (2003).

Peyrat, J.P., et al., "Plasma Insulin-like Growth Factor-1 (IGF-1) Concentrations in Human Breast Cancer," *Eur. J. Cancer* 4:492-497, Pergamon Press (1993).

Pietrzkowski, Z., et al., "Roles of Insulinlike Growth Factor 1 (IGF-1) and IGF-1 Receptor in Epidermal Growth Factor-Stimulated Growth of 3T3 Cells," *Mol. Cell. Biol.* 12:3883-3889, American Society for Micorbiology (1992).

Pollak, M.N., et al., "Insulin-Like Growth Factors and Neoplasia," *Nat. Rev. Cancer* 4:505-518, Nature Publishing Group (2004).

Prager, D., et al., "Dominant negative inhibition of tumorigenesis In vivo by human insulin-like growth factor I receptor mutant," *Proc. Natl. Acad. Sci.* 91:2181-2185, National Academy of Sciences (1994).

Railo, M.J., et al., "The Prognostic Value of Insulin-like Growth Factor-I in Breast Cancer Patients. Results of a Follow-up Study on 126 Patients," *Eur. J. Cancer* 30:307-311, Pergamon Press (1994).

Reiss, K., et al., "Mechanisms of regulation of cell adhesion and motility by insulin receptor substrate-1 in prostate cancer cells," *Oncogene* 20:490-500, Nature Publishing Group (2001).

Sachdev, D., et al., "A chimeric humanized single-chain antibody against the type I insulin-like growth factor (IGF) receptor renders breast cancer cells refractory to the mitogenic effects of IGF-I," *Cancer Res.* 63:627-635, American Association for Cancer Research (2003).

Schips, L., et al., "Analysis of Insulin-like Growth Factors and Insulin-like Growth Factor I Receptor Expression in Renal Cell Carcinoma," *Am. J. Pathol.* 122:931-937, American Society of Clinical Pathologists (2004).

Scotlandi, K., et al.,"Expression of an IGF-I Receptor Dominant Negative Mutant Induces Apoptosis, Inhibits Tumorigenesis and Enhances Chemosensitivity in Ewing's Sarcoma Cells," *Int. J Cancer* 101:11-16, Wiley-Liss (2002).

Scotlandi, K., et al., "Antitumor Activity of the Insulin-Like Growth Factor-I Receptor Kinase Inhibitor NVP-AEW541 in Musculoskeletal Tumors," *Cancer Res.* 65:3868-3876, American Association for Cancer Research (May 2005).

Scotlandi, K., et al., "Effectiveness of insulin-like growth factor I receptor antisense strategy against Ewing's sarcoma cells," *Cancer Gene Therapy* 9:296-307, Nature Publishing Group (2002).

Shapiro, D.N., et al., "Antisense -mediated Reduction in Insulin-like Growth Factor-I Receptor Expression Suppresses the Malignant Phenotype of a Human Alveolar Rhabdomyosarcoma, " *J. Clin. Invest.* 94:1235-1242, American Society for Clinical Investigation (1994).

Soos, M.A., et al., "A Panel of Monoclonal Antibodies for the Type I Insulin-like Growth Factor Receptor," *J. Biol. Chem.* 267:12955-12963, American Society for Biochemistry and Molecular Biology (1992).

Soos, M.A., et al., "Monoclonal antibodies reacting with multiple epitopes on the human insulin receptor," *Biochem. J.* 235:199-208, Portland Press (1986).

Sørensen, H., et al., "Mapping of the insulin-like growth factor II binding site of the Type I insulin-like growth factor receptor by alanine scanning mutagenesis," *FEBS Lett.* 565:19-22, Elsevier Science B.V. (2004).

Stracke, M., et al., "The Type I Insulin-Like Growth Factor Receptor Is a Motility Receptor in Human Melanoma Cells," *J. Biol. Chem.* 264:21544-21549, American Society for Biochemistry and Molecular Biology (1989).

Szereday, Z., et al., "Antagonists of Growth Hormone-Releasing Hormone Inhibit the Proliferation of Experimental Non-Small Cell Lung Carcinoma," *Cancer Res.* 63:7913-7919, American Association for Cancer Research (2003).

Ullrich, A., et al., "Insulin-like growth factor I receptor primary structure: comparison with insulin receptor suggests structural determinants that define functional specificity," *EMBO J.* 5:2503-2512, Oxford University Press (1986).

Ullrich, A., et al., "Signal Transduction by Receptors with Tyrosine Kinase Activity," *Cell* 61:203-212, Cell Press (1990).

Van Den Berg, C.L., et al., "Polyethylene Glycol Conjugated Insulin-like Growth Factor Binding Protein-1 (IGFBP-1) Inhibits Growth of Breast Cancer in Athymic Mice," *Eur. J. Cancer* 33:1108-1113, Pergamon Press (1997).

Whittaker, J., et al., "Alanine Scanning Mutagenesis of a Type 1 Insulin-Like Growth Factor Receptor Ligand Binding Site," *J. Biol. Chem.* 276:43980-43986, American Society for Biochemistry and Molecular Biology (2001).

Wraight, C.J., et al., "Reversal of epidermal hyperproliferation in psoriasis by insulin-like growth factor I receptor antisense oligonucleotides," *Nat. Biotechnol.* 18:521-526, Nature America Publishing (2000).

Wu, J.D., et al., "In vivo effects of the human type I insulin-like growth factor receptor antibody A12 on androgen-dependent and androgen-independent xenograft human prostate tumors," *Clin. Cancer Res.* 11:3065-74 (2005).

Yee, D., et al. "Insulin-like Growth Factor Binding Protein 1 Expression Inhibits Insulin-like Growth Factor I Action in MCF-7 Breast Cancer Cells," *Cell Growth Differ.* 5:73-77, American Association for Cancer Research (1994).

Yu, H., et al., "Plasma Levels of Insulin-Like Growth Factor-I and Lung Cancer Risk: a Case-Control Analysis," *J. Natl. Cancer Inst.* 91:151-156, Oxford University Press (1999).

Zhang, X., and Yee, D., "Tyrosine kinase signalling in breast cancer Insulin-like growth factors and their receptors in breast cancer," *Breast Cancer Res.* 2:170-175, BioMed Central Ltd. (2000).

International Search Report, International Application No. PCT/US07/07664, 1 page.

International Search Report and Written Opinion of the International Searching Authority, International Application No. PCT/US08/10176 (WO 2009/032145).

* cited by examiner (a)

Fig. 3
(a)
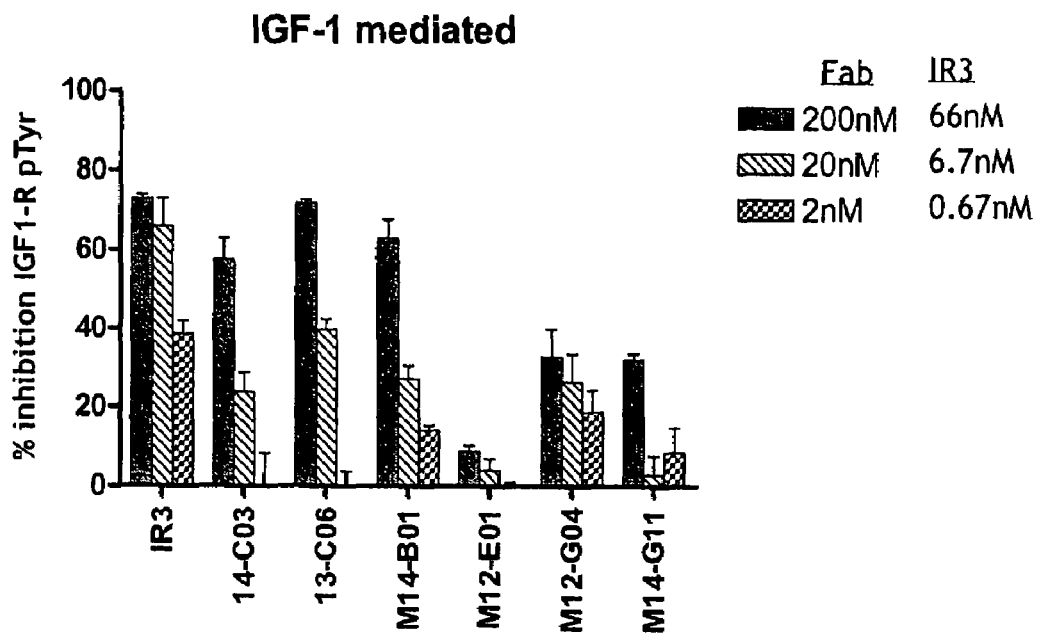
(b)
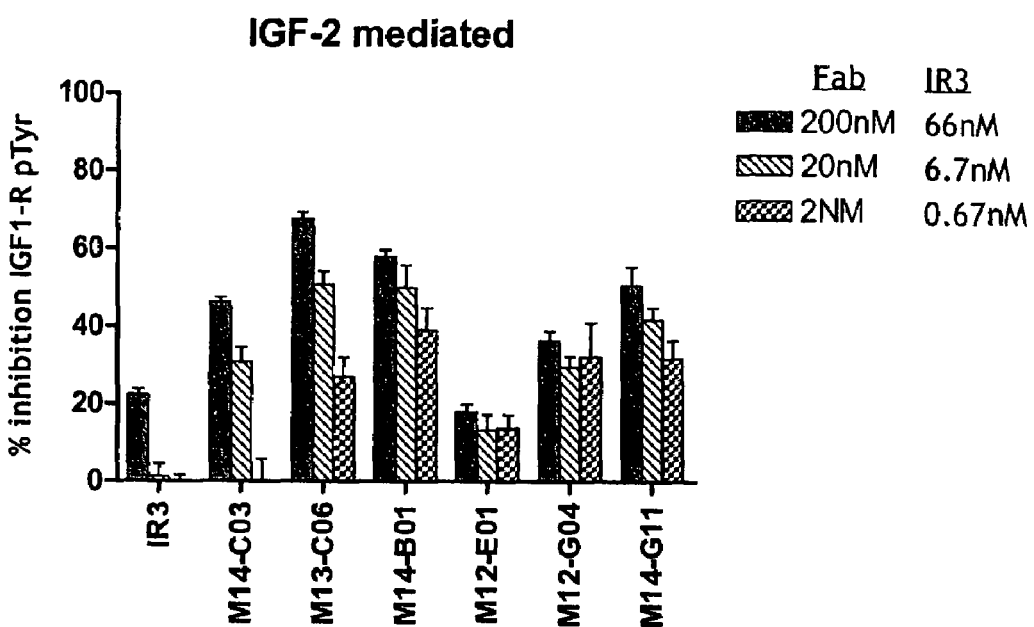

(a)
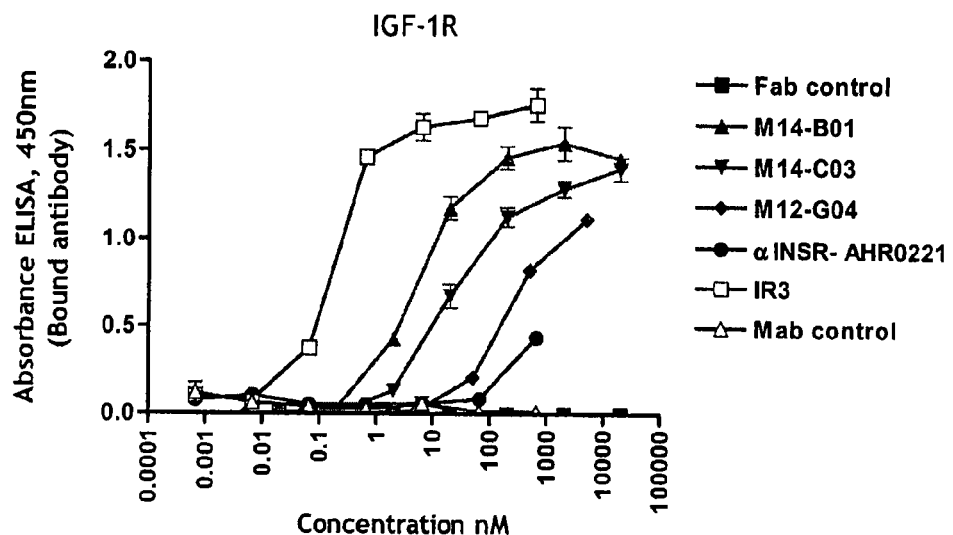
(b)
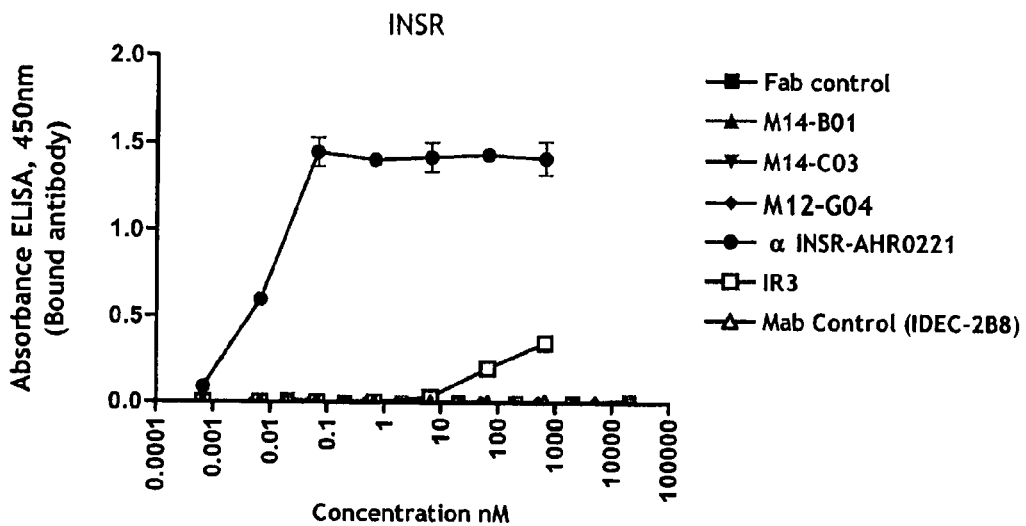
Fig. 4

FIG. 5A

SEQ ID NO 13:

GAAGTTCAATTGTTAGAGTCTGGTGGCGGTCTTGTTCAGCCTGGTGGTTCTTTACGTCTTT
CTTGCGCTGCTTCCGGATTCACTTTCTCTATTTACCGTATGCAGTGGGTTCGCCAAGCTCC
TGGTAAAGGTTTGGAGTGGGTTTCTGGTATCTCTCCTTCTGGTGGCACTACTTGGTATGCT
GACTCCGTTAAAGGTCGCTTCACTATCTCTAGAGACAACTCTAAGAATACTCTCTACTTG
CAGATGAACAGCTTAAGGGCTGAGGACACGGCCGTGTATTACTGTGCGAGATGGAGCGG
GGGTTCGGGCTATGCTTTTGATATCTGGGGCCAAGGGACAATGGTCACCGTCTCAAGC

FIG. 5B

SEQ ID NO 77:

GACATCCAGATGACCCAGTCTCCACTCTCCCTGTCTGCATCTGTAGGAGACAGAGTCACC
ATCACTTGCCAGGCGAGTCGGGACATTAGAAACTATTTAAATTGGTATCAACAAAAACC
AGGGAAAGCCCCGAAGCTCCTGATCTACGATGCATCCAGTTTGCAAACAGGGGTCCCAT
CAAGGTTCGGTGGCAGTGGATCTGGGACAGACTTTAGTTTCACCATCGGCAGCCTGCAGC
CTGAAGATATTGCAACATATTACTGTCAACAGTTTGATAGTCTCCCTCACACTTTTGGCCA
GGGGACCAAACTGGAGATCAAA

FIG. 5C

SEQ ID NO 14:

EVQLLESGGGLVQPGGSLRLSCAASGFTFSIYRMQWVRQAPGKGLEWVSGISPSGGTTWYA
DSVKGRFTISRDNSKNTLYLQMNSLRAEDTAVYYCARWSGGSGYAFDIWGQGTMVTVSS

FIG. 5D

SEQ ID NO 78:

DIQMTQSPLSLSASVGDRVTITCQASRDIRNYLNWYQQKPGKAPKLLIYDASSLQTGVPSRFG
GSGSGTDFSFTIGSLQPEDIATYYCQQFDSLPHTFGQGTKLEIK

FIG. 5E

SEQ ID NO 25:

GAAGTTCAATTGTTAGAGTCTGGTGGCGGTCTTGTTCAGCCTGGTGGTTCTTTACGTCTTT
CTTGCGCTGCTTCCGGATTCACTTTCTCTAAGTACATGATGTCTTGGGTTCGCCAAGCTCC
TGGTAAAGGTTTGGAGTGGGTTTCTTATATCTCTCCTTCTGGTGGCCTTACTTGGTATGCT
GACTCCGTTAAAGGTCGCTTCACTATCTCTAGAGACAACTCTAAGAATACTCTCTACTTG
CAGATGAACAGCTTAAGGGCTGAGGACACGGCCGTGTATTACTGTGCGAGAGATGGAGC
TAGAGGCTACGGTATGGACGTCTGGGGCCAAGGGACCACGGTCACCGTCTCAAGC

FIG. 5F
SEQ ID NO 87:

GACATCCAGATGACCCAGTCTCCAGCCACCCTGTCTTTGTCTCCAGGGGAAAGAGCCACC
CTCTCCTGCAGGGCCAGTCAGAGTGTTAGCAGCTACTTAGCCTGGTACCAACAGAAACCT
GGCCAGGCTCCCAGGCTCCTCATCTATGATGCATCCAACAGGGCCACTGGCATCCCAGCC
AGGTTCAGTGGCAGTGGGTCTGGGACAGACTTCACTCTCACCATCAGCAGCCTAGAGCCT
GAAGATTTTGCAGTTTATTACTGTCAGCAGCGTAGCAACTGGCCTCCGGAGGTCACTTTC
GGCCCTGGGACCAAAGTGGATATCAAA

FIG. 5G
SEQ ID NO 26:

EVQLLESGGGLVQPGGSLRLSCAASGFTFSKYMMSWVRQAPGKGLEWVSYISPSGGLTWYA
DSVKGRFTISRDNSKNTLYLQMNSLRAEDTAVYYCARDGARGYGMDVWGQGTTVTVSS

FIG. 5H
SEQ ID NO 88:

DIQMTQSPATLSLSPGERATLSCRASQSVSSYLAWYQQKPGQAPRLLIYDASNRATGIPARFS
GSGSGTDFTLTISSLEPEDFAVYYCQQRSNWPPEVTFGPGTKVDIK

FIG. 5I
SEQ ID NO 31:

GAAGTTCAATTGTTAGAGTCTGGTGGCGGTCTTGTTCAGCCTGGTGGTTCTTTACGTCTTT
CTTGCGCTGCTTCCGGATTCACTTTCTCTAATTACCCTATGTATTGGGTTCGCCAAGCTCC
TGGTAAAGGTTTGGAGTGGGTTTCTCGTATCTCTTCTTCTGGTGGCCGTACTGTTTATGCT
GACTCCGTTAAAGGTCGCTTCACTATCTCTAGAGACAACTCTAAGAATACTCTCTACTTG
CAGATGAACAGCTTAAGGGCTGAGGACACGGCCGTGTATTACTGTGCGAGAGATCGATG
GTCCAGATCTGCAGCTGAATATGGGTTGGGTGGCTACTGGGGCCAGGGAACCCTGGTCA
CCGTCTCAAGC

FIG. 5J
SEQ ID NO 92:

GACATCCAGATGACCCAGTCTCCAGACTCCCTGGCTGTGTCTCTGGGCGAGAGGGCCACC
ATCAACTGCAAGTCCAGCCAGAGTGTTTTATACAGCTCCAACAATAAGAACTACTTAGCT
TGGTACCAGCAGAAACCAGGACAGCCTCCTAAGCTGCTCATTTACTTGGCATCTACCCGG
GAATCCGGGGTCCCTGACCGATTCAGTGGCAGCGGGTCTGGGACAGATTTCACTCTCACC
ATCAGCAGCCTGCAGGCTGAAGATGTGGCAGTTTATTACTGTCAGCAATATTATAGTACT
TGGACGTTCGGCCAAGGGACCAAGGTGGAAATCAAA

FIG. 5K

SEQ ID NO 32:

EVQLLESGGGLVQPGGSLRLSCAASGFTFSNYPMYWVRQAPGKGLEWVSRISSSGGRTVYA
DSVKGRFTISRDNSKNTLYLQMNSLRAEDTAVYYCARDRWSRSAAEYGLGGYWGQGTLVT
VSS

FIG. 5L

SEQ ID NO 93:

DIQMTQSPDSLAVSLGERATINCKSSQSVLYSSNNKNYLAWYQQKPGQPPKLLIYLASTRESG
VPDRFSGSGSGTDFTLTISSLQAEDVAVYYCQQYYSTWTFGQGTKVEIK

FIG. 5M

SEQ ID NO 19:

GAAGTTCAATTGTTAGAGTCTGGTGGCGGTCTTGTTCAGCCTGGTGGTTCTTTACGTCTTT
CTTGCGCTGCTTCCGGATTCACTTTCTCTAATTACCATATGGCTTGGGTTCGCCAAGCTCC
TGGTAAAGGTTTGGAGTGGGTTTCTGTTATCTCTCCTACTGGTGGCCGTACTACTTATGCT
GACTCCGTTAAAGGTCGCTTCACTATCTCTAGAGACAACTCTAAGAATACTCTCTACTTG
CAGATGAACAGCTTAAGGGCTGAGGACACAGCCACATATTACTGTGCGAGAGCGGGGTA
CAGCTATGGTTATGGCTACTTTGACTACTGGGGCCAGGGAACCCTGGTCACCGTCTCAAG
C

FIG. 5N

SEQ ID NO 82:

GACATCCAGATGACCCAGTTTCCAGCCACCCTGTCTGTGTCTCCAGGGGAAAGAGCCACC
CTCTCCTGCAGGGCCAGTCAGAGTGTTATGAGGAACTTAGCCTGGTACCAGCAGAAACCT
GGCCAGCCTCCCAGGCTCCTCATCTATGGTGCATCCAAAAGGGCCACTGGCATCCCAGCC
AGGTTCAGTGGCAGTGGGTCTGGGACAGCCTTCACTCTCACCATCAGCAACCTAGAGCCT
GAAGATTTTGCAGTTTATTACTGTCACCAACGTAGCACCTGGCCTCTGGGGACTTTCGGC
CCTGGGACCAAACTGGAGGCCAAA

FIG. 5O

SEQ ID NO 20:

EVQLLESGGGLVQPGGSLRLSCAASGFTFSNYHMAWVRQAPGKGLEWVSVISPTGGRTTYA
DSVKGRFTISRDNSKNTLYLQMNSLRAEDTATYYCARAGYSYGYGYFDYWGQGTLVTVSS

FIG. 5P

SEQ ID NO 83:

DIQMTQFPATLSVSPGERATLSCRASQSVMRNLAWYQQKPGQPPRLLIYGASKRATGIPARFS
GSGSGTAFTLTISNLEPEDFAVYYCHQRSTWPLGTFGPGTKLEAK

FIG. 5Q

SEQ ID NO 18:

GAGGTCCAGCTGTTGGAGTCCGGCGGTGGCCTGGTGCAGCCTGGGGGGTCCCTGAGACT
CTCCTGCGCAGCTAGCGGCTTCACCTTCAGCATTTACCGTATGCAGTGGGTGCGCCAGGC
TCCTGGAAAGGGGCTGGAGTGGGTTTCCGGTATCTCTCCCTCTGGTGGCACGACGTGGTA
TGCTGACTCCGTGAAGGGCCGGTTCACAATCTCCAGAGACAATTCCAAGAACACTCTGTA
CCTGCAAATGAACAGCCTGAGAGCTGAGGATACTGCAGTGTACTACTGCGCCAGATGGT
CCGGGGGCTCCGGATACGCCTTCGACATCTGGGGACAGGGAACCATGGTCACCGTCTCA
AGC

FIG. 5R

SEQ ID NO 14:

EVQLLESGGGLVQPGGSLRLSCAASGFTFSIYRMQWVRQAPGKGLEWVSGISPSGGTTWYA
DSVKGRFTISRDNSKNTLYLQMNSLRAEDTAVYYCARWSGGSGYAFDIWGQGTMVTVSS

FIG. 5S

SEQ ID NO 30:

GAGGTCCAGCTGTTGGAGTCCGGCGGTGGCCTGGTGCAGCCTGGGGGGTCCCTGAGACT
CTCCTGCGCAGCTAGCGGCTTCACCTTCAGCAAGTACATGATGTCTTGGGTGCGCCAGGC
TCCTGGAAAGGGGCTGGAGTGGGTTTCCTATATCTCTCCCTCTGGTGGCCTGACGTGGTA
TGCTGACTCCGTGAAGGGCCGGTTCACAATCTCCAGAGACAATTCCAAGAACACTCTGTA
CCTGCAAATGAACAGCCTGAGAGCTGAGGATACTGCAGTGTACTACTGCGCCAGAGATG
GGGCTAGAGGATACGGAATGGACGTCTGGGGACAGGGAACCACCGTCACCGTCTCAAGC

FIG. 5T

SEQ ID NO 26:

EVQLLESGGGLVQPGGSLRLSCAASGFTFSKYMMSWVRQAPGKGLEWVSYISPSGGLTWYA
DSVKGRFTISRDNSKNTLYLQMNSLRAEDTAVYYCARDGARGYGMDVWGQGTTVTVSS

FIG. 5U

SEQ ID NO 36:

GAGGTCCAGCTGTTGGAGTCCGGCGGTGGCCTGGTGCAGCCTGGGGGGTCCCTGAGACT
CTCCTGCGCAGCTAGCGGCTTCACCTTCAGCAATTACCCCATGTACTGGGTGCGCCAGGC
TCCTGGAAAGGGGCTGGAGTGGGTTTCCAGGATCTCTAGCAGCGGTGGCAGGACCGTGT
ACGCTGACTCCGTGAAGGGCCGGTTCACAATCTCCAGAGACAATTCCAAGAACACTCTGT
ACCTGCAAATGAACAGCCTGAGAGCTGAGGATACTGCAGTGTACTACTGCGCCAGAGAT
AGGTGGTCCAGATCTGCAGCCGAGTACGGACTGGGGGGCTACTGGGGACAGGGAACCCT
GGTCACCGTCTCAAGC

FIG. 5V
SEQ ID NO 32:

EVQLLESGGGLVQPGGSLRLSCAASGFTFSNYPMYWVRQAPGKGLEWVSRISSSGGRTVYA
DSVKGRFTISRDNSKNTLYLQMNSLRAEDTAVYYCARDRWSRSAAEYGLGGYWGQGTLVT
VSS

FIG. 5W
SEQ ID NO 24:

GAGGTCCAGCTGTTGGAGTCCGGCGGTGGCCTGGTGCAGCCTGGGGGGTCCCTGAGACT
CTCCTGCGCAGCTAGCGGCTTCACCTTCAGCAATTACCACATGGCCTGGGTGCGCCAGGC
TCCTGGAAAGGGGCTGGAGTGGGTTTCCGTGATCTCTCCTACCGGTGGCAGGACCACTTA
CGCTGACTCCGTGAAGGGCCGGTTCACAATCTCCAGAGACAATTCCAAGAACACTCTGTA
CCTGCAAATGAACAGCCTGAGAGCTGAGGATACTGCAACATACTACTGCGCCAGAGCCG
GGTACTCCTACGGCTACGGATACTTCGACTACTGGGGACAGGGAACCCTGGTCACCGTCT
CAAGC

FIG. 5X
SEQ ID NO 20:

EVQLLESGGGLVQPGGSLRLSCAASGFTFSNYHMAWVRQAPGKGLEWVSVISPTGGRTTYA
DSVKGRFTISRDNSKNTLYLQMNSLRAEDTATYYCARAGYSYGYGYFDYWGQGTLVTVSS

FIG. 5Y
SEQ ID NO 153:

CGAACTGTGGCTGCACCATCTGTCTTCATCTTCCCGCCATCTGATGAGCAGTTGAAATCT
GGAACTGCCTCTGTTGTGTGCCTGCTGAATAACTTCTATCCCAGAGAGGCCAAAGTACAG
TGGAAGGTGGATAACGCCCTCCAATCGGGTAACTCCCAGGAGAGTGTCACAGAGCAGGA
CAGCAAGGACAGCACCTACAGCCTCAGCAGCACCCTGACGCTGAGCAAAGCAGACTACG
AGAAACACAAAGTCTACGCCTGCGAAGTCACCCATCAGGGCCTGAGCTCGCCCGTCACA
AAGAGCTTCAACAGGGGAGAGTGTTGA

FIG. 5Z
SEQ ID NO 154:

RTVAAPSVFIFPPSDEQLKSGTASVVCLLNNFYPREAKVQWKVDNALQSGNSQESVTEQDSK
DSTYSLSSTLTLSKADYEKHKVYACEVTHQGLSSPVTKSFNRGEC

FIG. 5AA
SEQ ID NO 155:

GCCTCAACGAAGGGGCCCAGCGTGTTCCCCCTGGCGCCCTGCTCCAGGAGCACCTCCGA
GAGCACAGCCGCCCTGGGCTGCCTGGTCAAGGACTACTTCCCCGAACCGGTGACGGTGT
CGTGGAACTCAGGCGCCCTGACCAGCGGCGTGCACACCTTCCCGGCTGTCCTACAGTCCT
CAGGACTCTACTCCCTCAGCAGCGTGGTGACCGTGCCCTCCAGCAGCTTGGGCACGAAG
ACCTACACCTGCAACGTAGATCACAAGCCCAGCAACACCAAGGTGGACAAGAGAGTTGA
GTCCAAATATGGTCCCCCATGCCCACCGTGCCCAGCACCTGAGTTCCTGGGGGGACCATC
AGTCTTCCTGTTCCCCCCAAAACCCAAGGACACTCTCATGATCTCCCGGACCCCTGAGGT
CACGTGCGTGGTGGTGGACGTGAGCCAGGAAGACCCCGAGGTCCAGTTCAACTGGTACG
TGGATGGCGTGGAGGTGCATAATGCCAAGACAAAGCCGCGGGAGGAGCAGTTCAACAG
CGCGTACCGTGTGGTCAGCGTCCTCACCGTCCTGCACCAGGACTGGCTGAACGGCAAGG
AGTACAAGTGCAAGGTCTCCAACAAAGGCCTCCCGTCCTCCATCGAGAAAACCATCTCC
AAAGCCAAAGGGCAGCCCCGAGAGCCACAAGTGTACACCCTGCCCCCATCCCAGGAGGA
GATGACCAAGAACCAGGTCAGCCTGACCTGCCTGGTCAAAGGCTTCTACCCCAGCGACA
TCGCCGTGGAGTGGGAGAGCAATGGGCAGCCGGAGAACAACTACAAGACCACGCCTCCC
GTCCTCGATTCCGACGGCTCCTTCTTCCTCTACAGCAGGCTAACCGTGGACAAGAGCAGG
TGGCAGGAGGGGAATGTCTTCTCATGCTCCGTGATGCATGAGGCTCTGCACAACCACTAC
ACACAGAAGAGCCTCTCCCTGTCTCTGGGTTGA

FIG. 5BB
SEQ ID NO 156:

ASTKGPSVFPLAPCSRSTSESTAALGCLVKDYFPEPVTVSWNSGALTSGVHTFPAVLQSSGLY
SLSSVVTVPSSSLGTKTYTCNVDHKPSNTKVDKRVESKYGPPCPPCPAPEFLGGPSVFLFPPKP
KDTLMISRTPEVTCVVVDVSQEDPEVQFNWYVDGVEVHNAKTKPREEQFNSAYRVVSVLTV
LHQDWLNGKEYKCKVSNKGLPSSIEKTISKAKGQPREPQVYTLPPSQEEMTKNQVSLTCLVK
GFYPSDIAVEWESNGQPENNYKTTPPVLDSDGSFFLYSRLTVDKSRWQEGNVFSCSVMHEAL
HNHYTQKSLSLSLG (a)
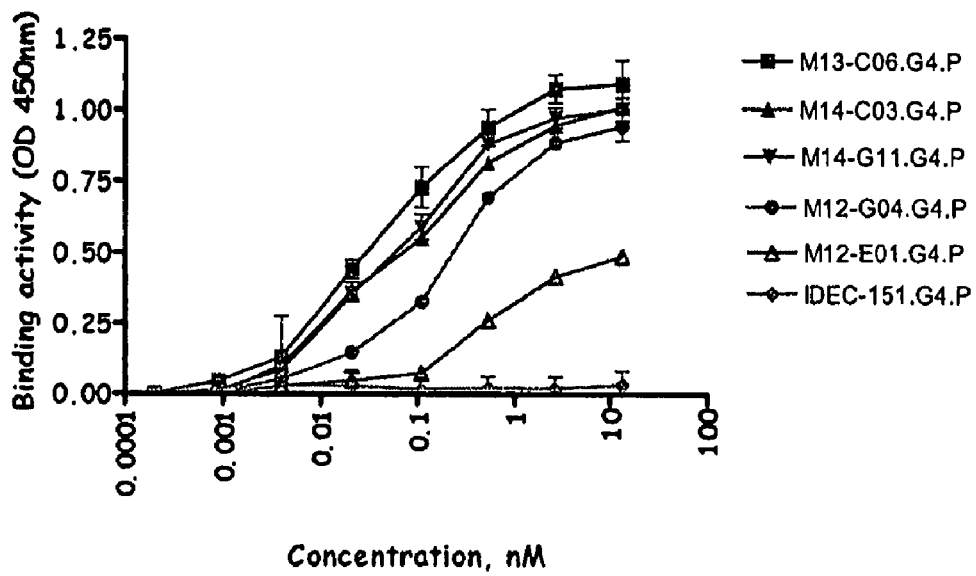
(b)
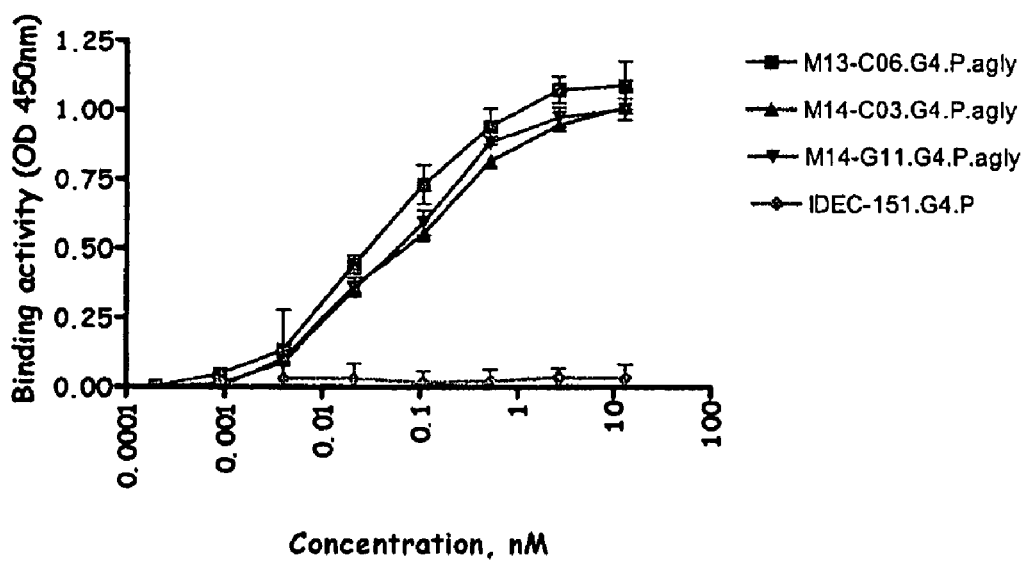
Fig. 7

(a)
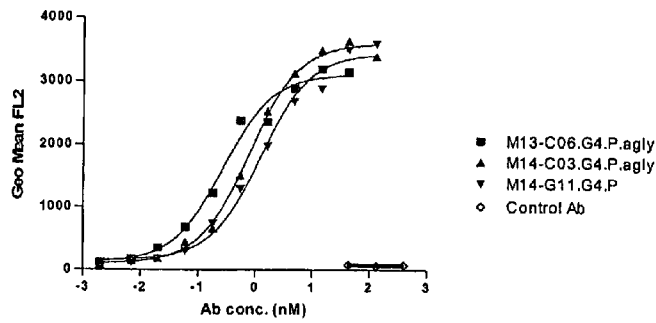
(b)
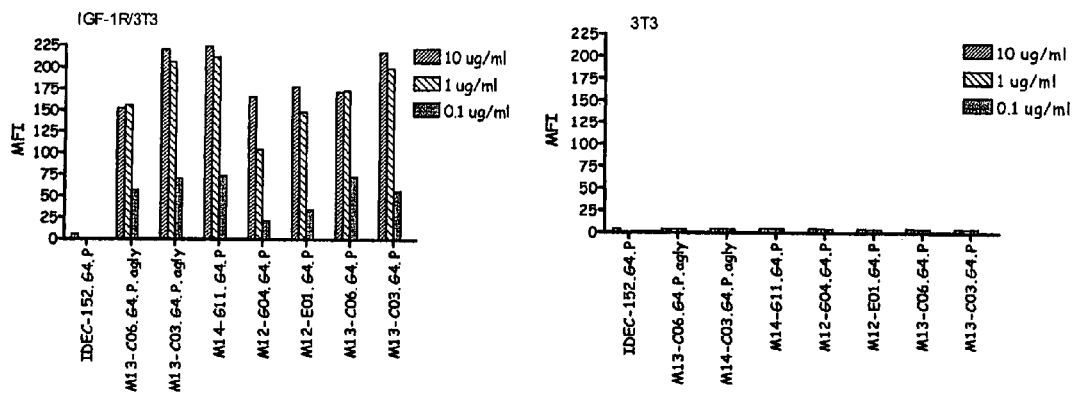
Fig. 8

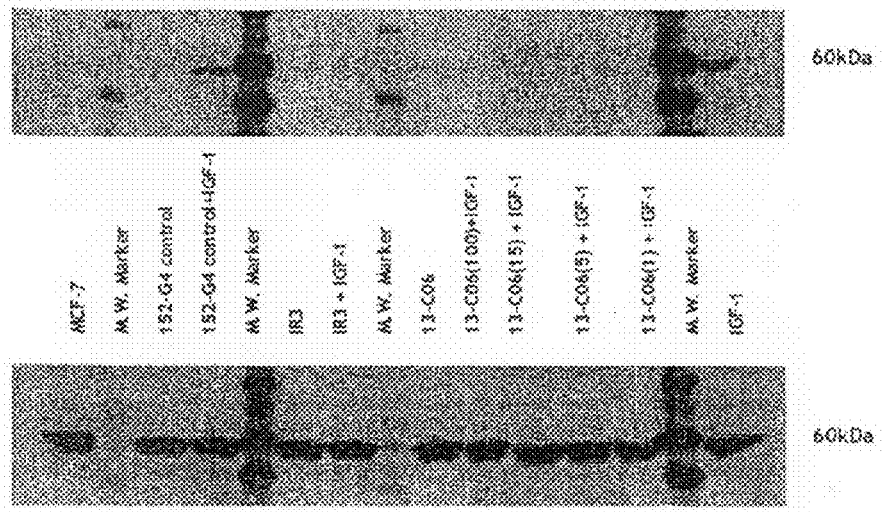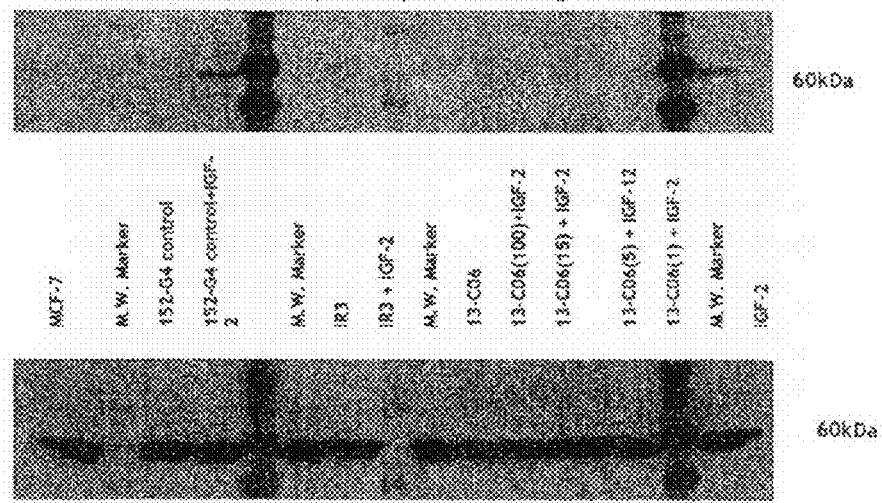
FIG. 12A

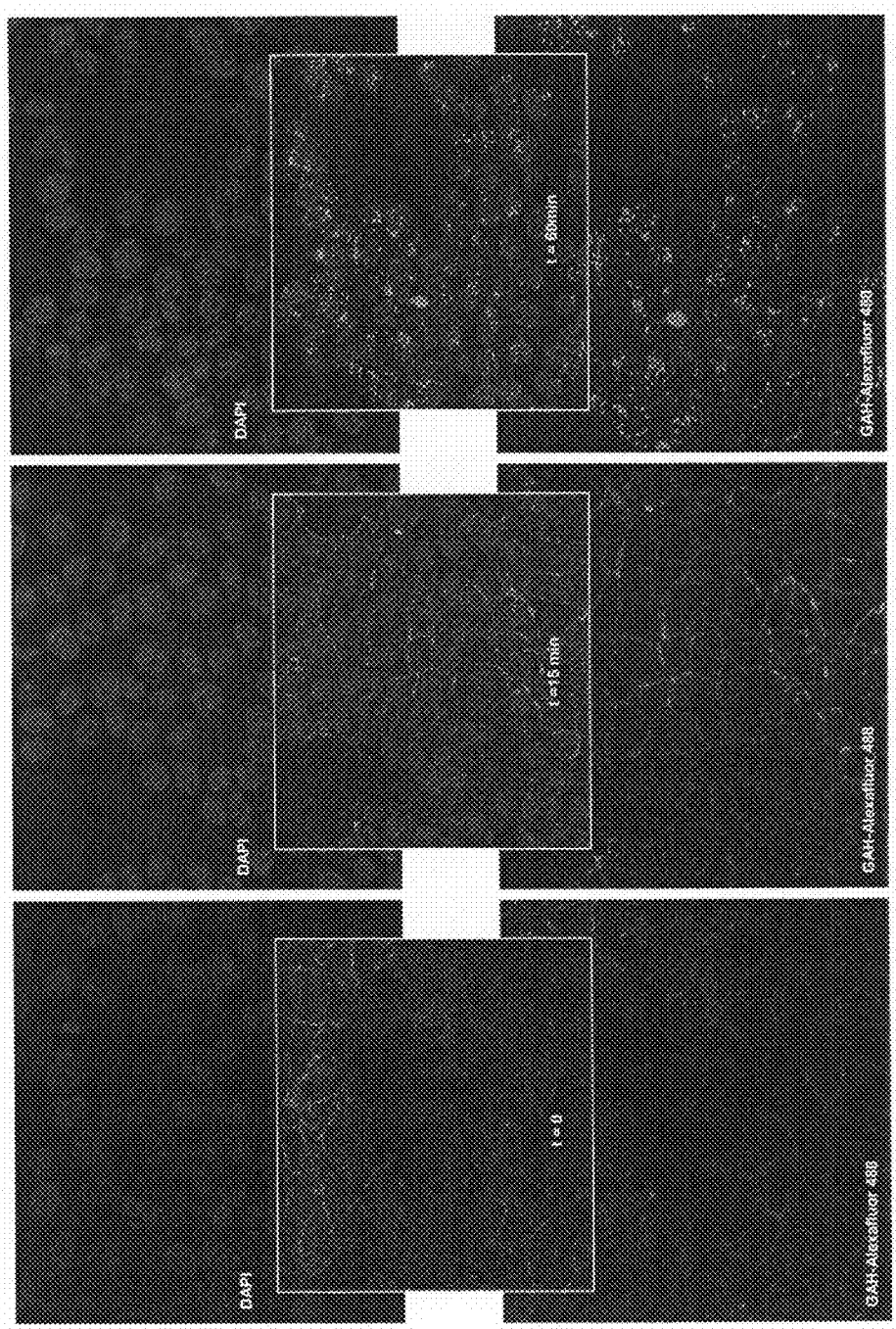
Figure 13.a

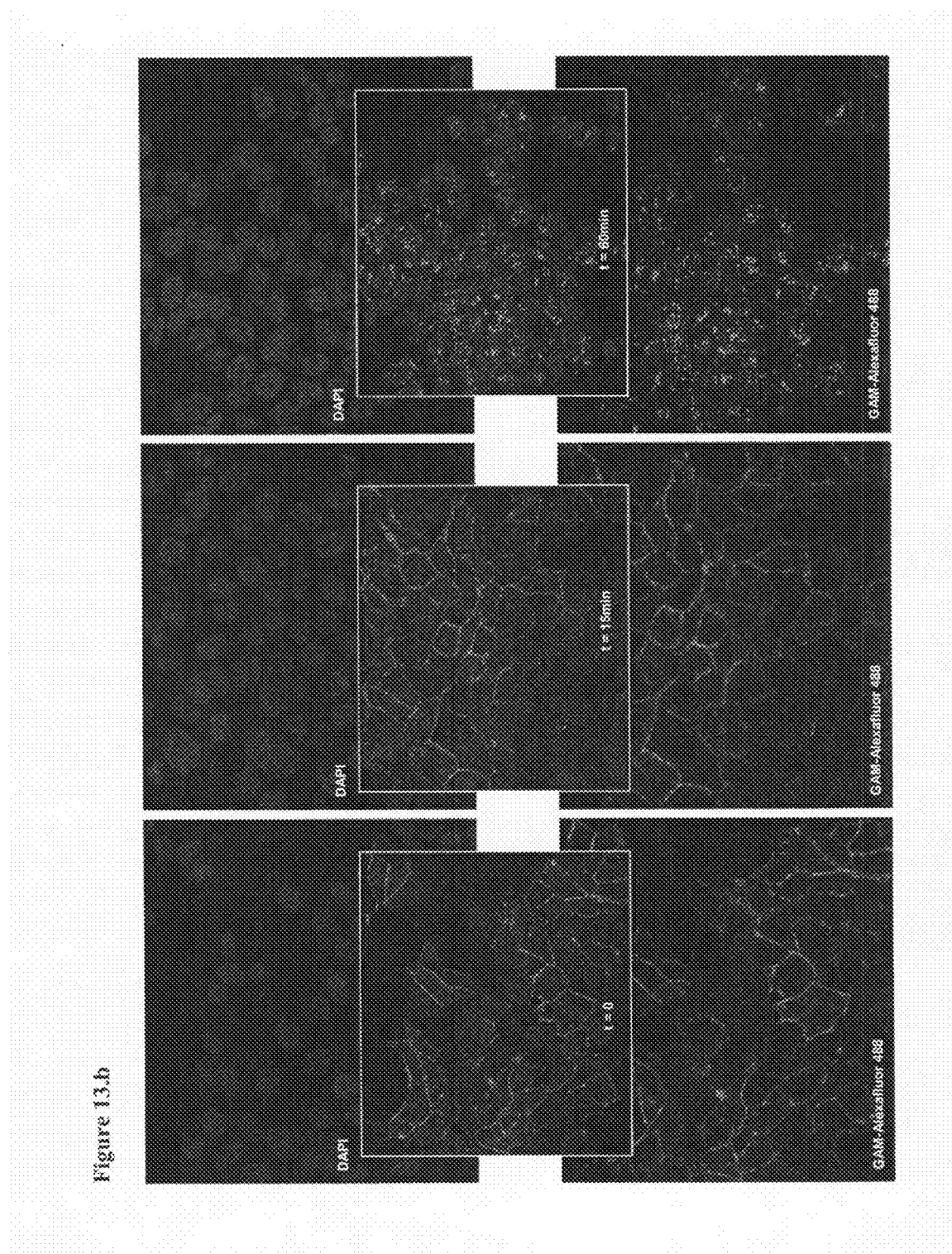

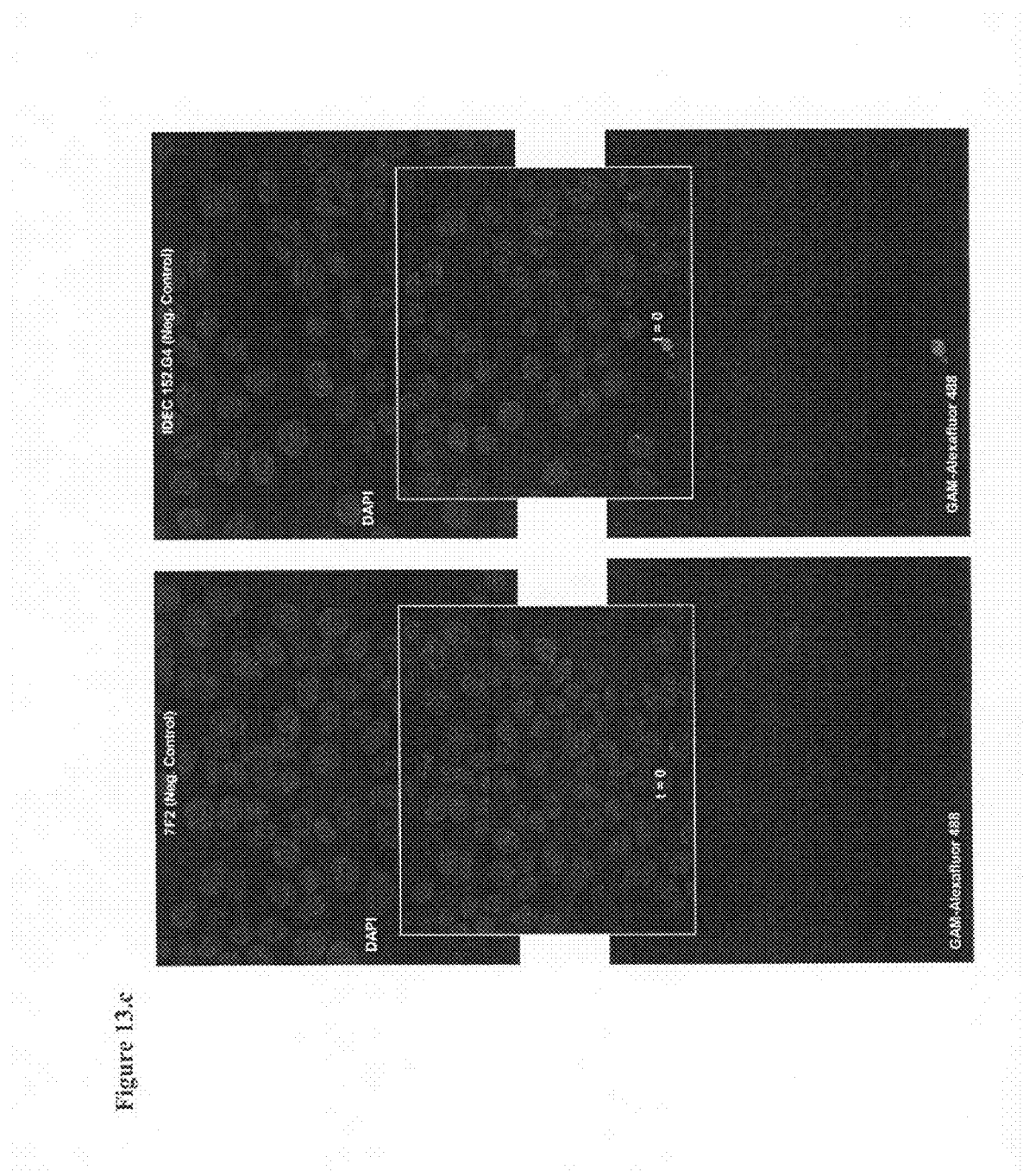
Figure 13.e

BxPC3 Tumor Cells

Fig. 17
NCI-H23 Tumor Cells
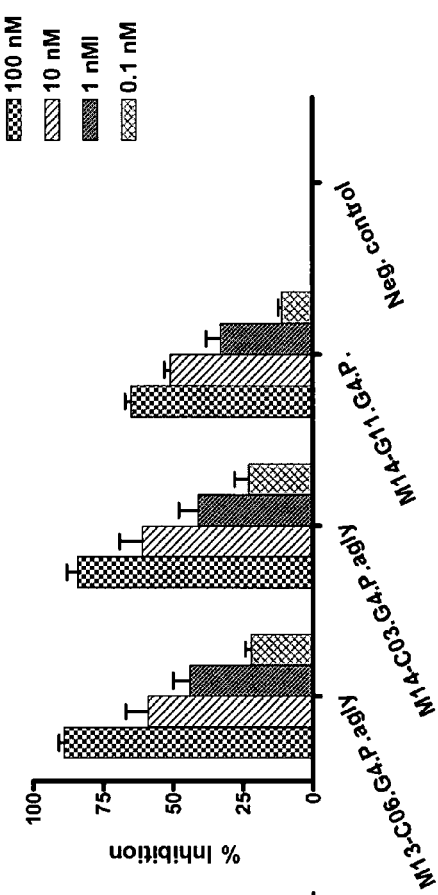
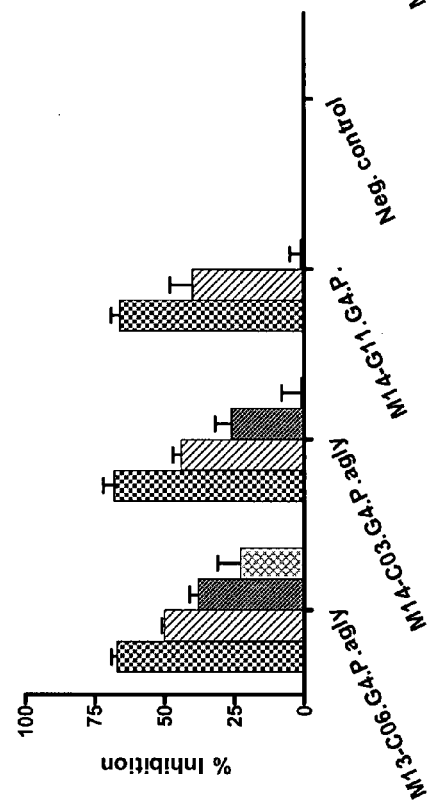

A549 Tumor Cells

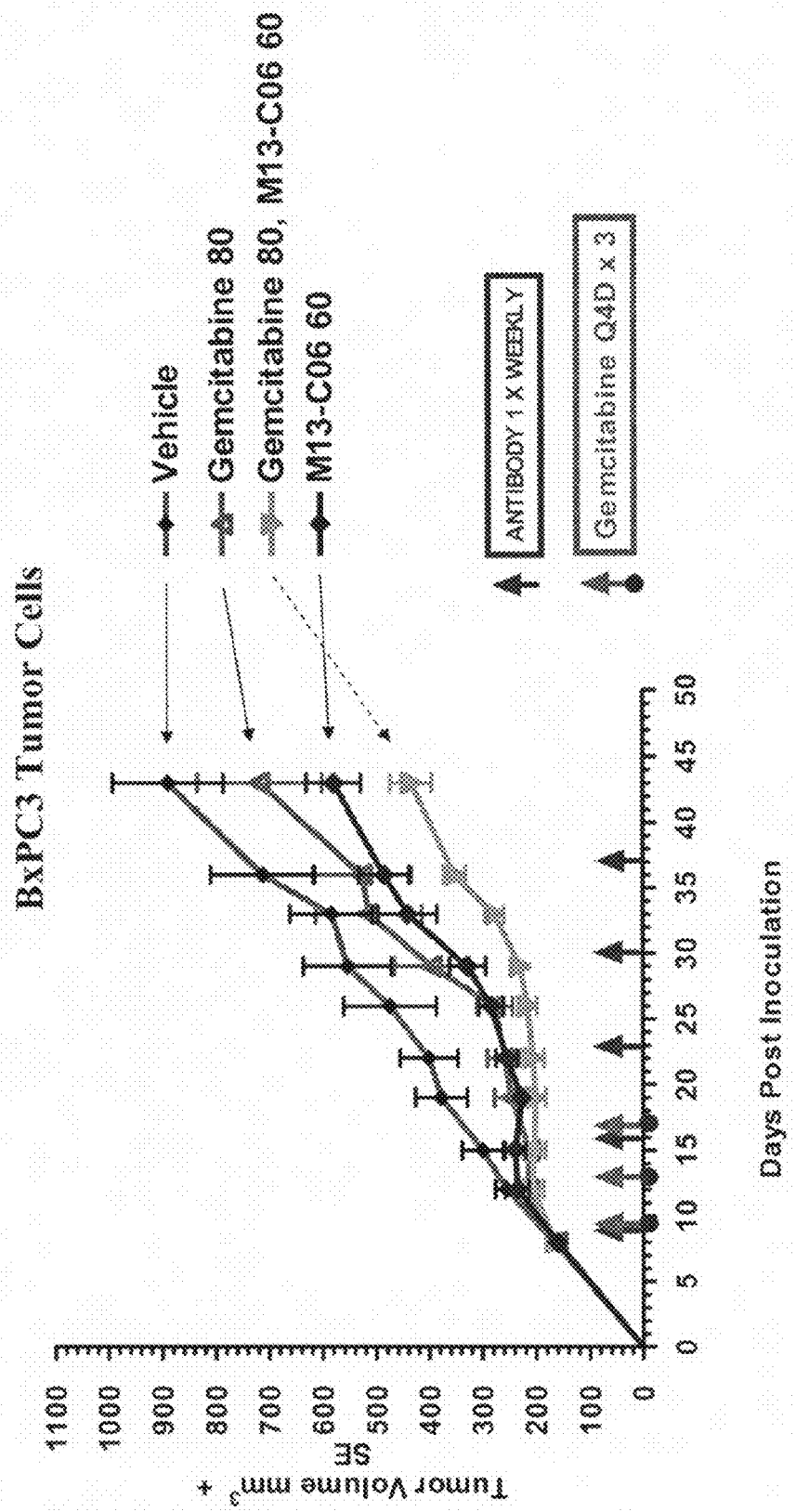

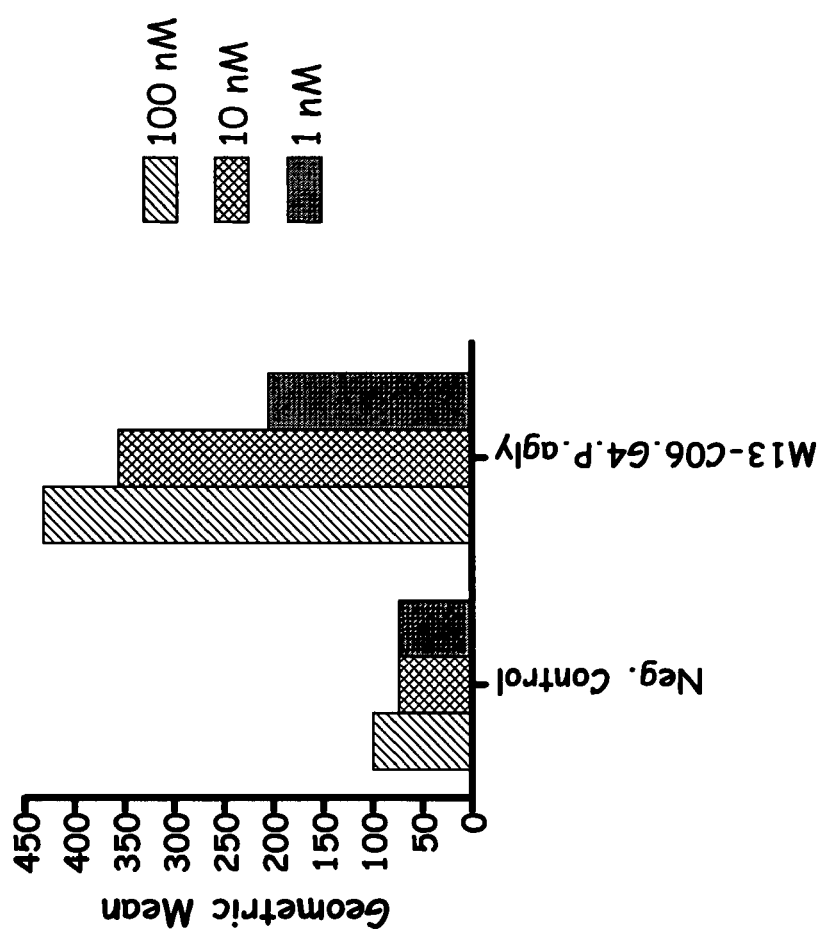

Fig. 24

| Unlabeled Competitor Antibodies: | | Labeled Antibodies: Biot-C06 | Biot-G11 | Zenon-O | Zenon-M | Zenon-IR3 |
|---|---|---|---|---|---|---|
| P3F9-A11 | A | - | + | +++++ | +++ | +++ |
| P1E2-3B12 | B | - | +++++ | +++++ | +++++ | +++++ |
| P4C5-F6 | C | - | +++++ | +++++ | +++++ | +++++ |
| P2A7-3E11 | D | - | +++++ | +++ | +++++ | N/A |
| P1B9-1H11 | E | - | +++++ | +++ | +++++ | +++++ |
| 20D8-23F5 | F | + | +++++ | +++++ | +++++ | +++++ |
| 20D8-24B11 | G | + | +++++ | + | +++++ | +++++ |
| 11B7-12D3 | H | - | ++++ | ++ | +++ | ++++ |
| 11B7-11E3 | I | - | ++++ | + | +++ | ++++ |
| 4D2-8G11 | J | - | +++++ | ++ | +++ | ++++ |
| 4D2-8B8 | K | - | +++++ | ++ | ++ | ++++ |
| 20C8-3B8 | L | N/A | N/A | N/A | N/A | N/A |
| 20C8-3B4 | M | + | +++++ | + | +++++ | +++++ |
| P1C4-3G4 | N | N/A | N/A | N/A | N/A | N/A |
| P1B10-1A10 | O | +/- | +/- | +++++ | +/- | +/- |
| P1A2-2B11 | P | + | +++++ | + | +++++ | +++++ |
| P1C10-2B8 | Q | + | +++++ | + | ++++ | +++++ |
| M13-C06 | C06 | +++++ | - | - | - | - |
| M14-C03 | C03 | +++++ | - | - | - | - |
| M14-G11 | G11 | ++ | +++++ | + | + | +++ |
| IR3 | IR3 | + | +++++ | +++ | +++ | +++++ |

ANTI-IGF-1R ANTIBODIES AND USES THEREOF

CROSS-REFERENCES TO RELATED APPLICATIONS

This is application claims benefit under 35 U.S.C. § 119(e) of U.S. provisional application No. 60/786,347, filed on Mar. 28, 2006 and of U.S. provisional application No. 60/876,554 filed on Dec. 22, 2006. Each of the above-referenced patent applications is hereby incorporated by reference in its entirety.

BACKGROUND OF THE INVENTION

A number of epidemiological studies have shown that higher than normal circulating levels of IGF-1 are associated with increased risk for several common cancers, including breast (Hankinson et al, Lancet 1998. 351:1393-6), prostate (Chan et al, Science. 1998. 279:563-6), lung (Yu et al, J. Natl. Cancer Inst. 1999. 91:151-6) and colorectal cancers (Ma et al, J. Natl. Cancer Inst. 1999. 91:620-5). Elevated circulating levels of IGF-2 also have been shown to be associated with increases risk for endometrial cancer (Jonathan et al, Cancer Biomarker & Prevention. 2004. 13:748-52). On the contrary, inverse correlation was observed with elevated levels of one of the IGF binding proteins, IGF-BP3, and cancer risk. Furthermore, elevated levels of IGFs have also been found in cancer patients (Peyrat et al Eur. J. Cancer. 1993. 351:1393-6; Jonathan et al, Cancer Biomarker & Prevention. 2004. 13:748-52).

IGF system plays an important role in regulating cell proliferation, differentiation, apoptosis and transformation (Jones et al, Endocrinology Rev. 1995. 16:3-34). The IGF system comprises of two types of unrelated receptors, the insulin like growth factor receptor 1 (IGF-1R; CD221) and insulin like growth factor receptor 2 (IGF-2R; CD222); two ligands, insulin like growth factor 1 (IGF-1 and IGF-2); several IGF binding proteins (IGFBP-1 to IGFBP-6). In addition, a large group of IGFBP proteases (e.g.: caspases, metalloproteinases, prostate-specific antigen) hydrolyze IGF bound IGFBP to release free IGFs, which then interact with IGF-1R and IGF-2R. The IGF system is also intimately connected to insulin and insulin receptor (InsR) (Moschos et al. Oncology 2002. 63:317-32; Baserga et al., Int J. Cancer. 2003. 107:873-77; Pollak et al., Nature Reviews Cancer. 2004. 4:505-516).

In a cancer cell, receptor tyrosine kinases (TK) play important role in connecting the extra-cellular tumor microenvironment to the intracellular signaling pathways that control diverse cellular functions, such as, cell division cycle, survival, apoptosis, gene expression, cytoskeletal architecture, cell adhesion, and cell migration. As the mechanisms controlling cell signaling are better understood, therapeutic strategies of disrupting one or more of these cellular functions could be developed by targeting at the level of ligand binding, receptor expression/recycling, receptor activation and the proteins involved in the signaling events (Hanahan and Weinberg, Cell 2000. 100:57-70).

The type I insulin like growth factor receptor (IGF-1R, CD221) belongs to receptor tyrosine kinase (RTK) family, (Ullrich et al., Cell. 1990, 61:203-12). IGF-1R is widely expressed and its ligands, IGF-1 and IGF-2 play a significant role in pre- and post-natal development, growth hormone responsiveness, cell transformation, survival, and have been implicated in the acquisition of an invasive and metastatic tumor phenotype (Baserga, Cell. 1994. 79:927-30; Baserga et al., Exp. Cell Res. 1999. 253:1-6, Baserga et al., Int J. Cancer. 2003. 107:873-77). Immunohistochemical studies have shown that a number of human tumors express higher levels of IGF-1R.

The molecular architecture of IGF-1R comprises, two extra-cellular $\alpha$ subunits (130-135 kD) and two membrane spanning $\beta$ subunits (95 kD) that contain the cytoplasmic catalytic kinase domain. IGF-1R, like the insulin receptor (InsR), differs from other RTK family members by having covalent dimeric ($\alpha 2\beta 2$) structures. Structurally, IGF-1R is highly related to InsR (Pierre De Meyts and Whittaker, Nature Reviews Drug Discovery. 2002, 1: 769-83). IGF-1R contains 84% sequence identity to InsR at the kinase domain, whereas the juxta-membrane and the c-terminal regions share 61% and 44% sequence identity, respectively (Ulrich et al., EMBO J., 1986, 5:2503-12; Blakesley et al., Cytokine Growth Factor Rev., 1996. 7:153-56).

The IGF-1 and IGF-2 are the two activating ligands of IGF-1R. The binding of IGF-1 and IGF-2 to the $\alpha$ chain induces conformational changes that result in auto-phosphorylation of each $\beta$-chain at specific tyrosine residues, converting the receptor from unphoshorylated state to the active state. The activation of three tyrosine residues in the activation loop (Tyr residues at 1131, 1135 and 1136) of the kinase domain leads to increase in catalytic activity that triggers docking and phosphorylation of the substrates such as IRS-1 and Shc adaptor proteins. Activation of these substrates leads to phosphorylation of additional proteins involved in the signaling cascade of survival (PI3K, AKT, TOR, S6) and/or proliferation (mitogen-activated protein kinase, p42/p44) (Pollak et al., Nature Reviews Cancer. 2004. 4:505-516; Baserga et al., Biochem Biophys Act. 1997. 1332:F105-F126; Baserga et al, Int. J. Cancer. 2003. 107:873-77).

Despite the high degree of homology between IGF-1R and InsR, evidence suggests that the two receptors have distinct biological roles; InsR is a key regulator of physiological functions such as glucose transport and biosynthesis of glycogen and fat, whereas the IGF-1R is a potent regulator of cell growth and differentiation. In contrast to InsR, IGF-1R is ubiquitously expressed in tissues where it plays a role in tissue growth, under the control of growth hormone (GH), which modulates IGF-1. Although IGF-1R activation has been shown to promote normal cell growth, experimental evidence suggests that IGF-1R is not an absolute requirement (Baserga et al, Exp Cell Res. 1999. 253:1-6; Baserga et al, Int. J. Cancer. 2003. 107:873-77).

IGFs play a crucial role in regulating cell proliferation, differentiation and apoptosis. Inhibition of IGF-1R mediated signaling has been shown to reduce tumor growth rate, increase apoptosis, increase killing of tumors by chemotherapy and other molecular target therapies (reviewed in Pollak et al., Nature Reviews Cancer. 2004. 4:505-516; Zhang et al., Breast Cancer Res. 2000. 2:170-75; Chakravarti et al, Cancer Res. 2002. 62:200-07).

Experimental approaches undertaken to inhibit IGF-1R function in tumors have provided encouraging but limited success, and their effectiveness in treating cancer is yet to be determined in the clinic. The experimental approaches include; antibodies to IGF-1R (Kull et al., J. Biol. Chem. 1983, 258:6561-66; Kalebic et al., Cancer Res. 1994. 54:5531-4), neutralizing antibodies to IGF-1 or IGF-2 (Fang et al, Mol. Cancer. Therapy. 2006. 5:114-20; Miyamoto et al, Clin. Cancer Res. 2005, 11:3494-502), small-molecule tyrosine kinase inhibitors (Garcia-Escheverria et al, Cancer Cell. 2004. 5:231-9; Scotlandi et al, Cancer Res. 2005. 65:3868-76), antisense oligonucleotides (Shapiro et al, J. Clin. Invest. 1994. 94:1235-42; Wraight et al. Nature Biotech. 2000. 18:521-26; Scotlandi et al, Cancer Gene Therapy. 2002.

9:296-07), dominant-negative mutants of IGF-1R (Prager et al, Proc. Natl. Acad. Sci. 1994, 91:2181-85; Kalebic et al., Int. J. Cancer 1998. 76:223-7; Scotlandi et al., Int J. Cancer. 2002:101:11-6), analogues of the IGF ligand (Pietrzkowski et al, Mol. Cell. Biol. 1992. 12:3883-89), recombinant IGF binding proteins (Yee et al. Cell growth Differ. 1994. 5:73-77; Van Den Berg et al, Eur. J. Cancer. 1997, 33:1108-1113; Jerome et al AACR 2004, Abstract #5334), antagonists of GH-releasing hormone, GHRH (Szereday et al, Cancer Res. 2003. 63:7913-19; Letsh et al, Proc Natl. Acad. Sci. USA. 2003. 100:1250-55) and GH (Kopchick et al, 2002. Endocr. Rev. 23, 623-46).

The ability of an antibody to inhibit IGF-1R function was first demonstrated with a mouse monoclonal antibody (α-IR3) targeting an unknown epitope in the α subunit of IGF-1R (Kull et al., J. Biol. Chem. 1983, 258:6561-66). Subsequently other antibodies developed to the α subunit of IGF-1R have been shown to inhibit IGF-1R function to varying degrees in different experimental cancer models (Maloney et al. Cancer Res. 2003. 63: 5073-83; Burtrum et al, Cancer Res. 2003. 63:8912-21; Sachdev D et al, Cancer Res. 2003. 63, 627-35; Cohen et al, Clin. Cancer Res. 2005. 11:3065-74; Goetsch et al, Intl. J. Cancer. 2005. 113:316-28. Lu et al, J. Biol. Chem. 2004. 280:19665-72).

In a cancer cell, in addition to pro-survival and proliferative signaling, activation of IGF-1R has also been shown to be involved in motility and invasion (Ress et al., Oncogene 2001. 20:490-00, Nolan et al, Int. J. Cancer. 1997.72:828-34, Stracke et al, J. Biol. Chem. 1989. 264:21544-49; Jackson et al, Oncogene, 2001. 20:7318-25).

Tumor cells have been shown to produce one or more of the components of the IGF system (IGF-1, IGF-2, IGF-1R, IGF-2R and IGF-BPs). Although in vitro studies have indicated that tumors can produce IGF-1 or IGF-2, translational studies indicate that IGF-2 is the more relevant and commonly expressed IGF in the tumors. This is due to loss of imprinting (LOI) of the silenced IGF-2 allele in the tumor by epigenetic alterations, resulting in biallelic expression of the IGF-2 gene (Fienberg et al., Nat. Rev. Cancer 2004. 4:143-53; Giovannucci et al, Horm. Metab. Res. 2003. 35:694-04; De Souza et al, FASEB J. et al, 1997. 11:60-7). This in turn results in increased IGF-2 supply to cancer cells and to the microenvironment supporting tumor growth.

IGF-1R sensitive tumors receive receptor activation signals of IGF-1 from the circulation (liver produced) and IGF-2 from the tumor, and thus approaches aimed at disrupting the biological activity mediated by both IGF-1 and IGF-2 should provide a better anti-tumor response. Therefore, anti-IGF-1R antibody methods that effectively block the biological functions mediated by both IGF-1 and IGF-2 may provide an improved efficacy over other approaches that do not efficiently block the biological functions of both IGF-1and IGF-2 mediated IGF-1R signaling in tumor microenvironment.

With regard to safety, IGF-1R is ubiquitously expressed and thus antibodies targeting IGF-1R should have minimal or no effector functions to avoid toxicities resulting from ADCC and CDC activities in normal tissues. One possibility of developing such antibodies is to have the non-glycosylated form of the human gamma 4 Fc region, which does not mediate ADCC or CDC functions.

IGF-1R is involved in oncogene mediated cellular transformation.

IGF/IGF-1R activation mediates mitogenic and pro-survival signaling in cancer cell.

IGF-1R activation also promotes cell motility and metastasis.

IGF-1R is over expressed in many cancers.

Individuals with higher than normal circulating IGF levels have increased risk for developing cancer.

Increased plasma levels of IGF 1 & 2 found in many cancer patients.

Human tumors produce IGF-2 as an autocrine growth factor.

Inhibition of tumor growth has been demonstrated as single agent and in combination with chemotherapeutic and biological agents.

There remains a need in the art for IGF-1R antibodies with different or improved binding, efficacy, and safety characteristics for the treatment of various neoplastic diseases including cancer and metastases thereof.

BRIEF SUMMARY OF THE INVENTION

The present invention is based on the important role of the IGF system in regulating cell proliferation, differentiation, apoptosis and transformation. In particular, type I insulin like growth factor receptor (IGF-1R) and its ligands, IGF-1 and IGF-2, play a significant role in pre- and post-natal development, growth hormone responsiveness, cell transformation, survival, and have been implicated in the acquisition of an invasive and metastatic tumor phenotype. The invention relates generally to IGF-1R antibodies, antigen binding fragments or derivatives thereof. Certain IGF-1R antibodies and antigen-binding fragments inhibit IGF-1R function or block the biological functions of IGF-1 and IGF-2 mediated IGF-1R signaling. Additionally, the invention generally relates to methods for treating various neoplastic diseases including cancer and metastases, as well as various hyperproliferative disease, disorders or injuries associated with IGF-1R signaling.

In some embodiments, the invention provides an isolated antibody or antigen-binding fragment thereof which specifically binds to the same IGF-R1 epitope as a reference monoclonal Fab antibody fragment selected from the group consisting of M13-C06, M14-G11, M14-C03, M14-B01, M12-E01, and M12-G04, or a reference monoclonal antibody produced by a hybridoma selected from the group consisting of P2A7.3E11, 20C8.3B8, P1A2.2B11, 20D8.24B11, P1E2.3B12, and P1G10.2B8.

In some embodiments, the invention provides an isolated antibody or antigen-binding fragment thereof which specifically binds to IGF-R1, where the antibody or fragment competitively inhibits a reference monoclonal Fab antibody fragment selected from the group consisting of M13-C06, M14-G11, M14-C03, M14-B01, M12-E01, and M12-G04, or a reference monoclonal antibody produced by a hybridoma selected from the group consisting of P2A7.3E11, 20C8.3B8, P1A2.2B11, 20D8.24B11, P1E2.3B12, and P1G10.2B8 from binding to IGF-R1.

In some embodiments, the invention provides an isolated antibody or antigen-binding fragment thereof which specifically binds to IGF-R1, where the antibody or fragment thereof comprises an antigen binding domain identical to that of a monoclonal Fab antibody fragment selected from the group consisting of M13-C06, M14-G11, M14-C03, M14-B01, M12-E01, and M12-G04, or a monoclonal antibody produced by a hybridoma selected from the group consisting of P2A7.3E11, 20C8.3B8, P1A2.2B11, 20D8.24B11, P1E2.3B12, and P1G10.2B8.

In some embodiments, the invention provides an isolated antibody or fragment thereof which specifically binds to IGF-R1, where the heavy chain variable region (VH) of the antibody or fragment thereof comprises an amino acid sequence at least 90% identical to a reference amino acid sequence selected from the group consisting of: SEQ ID NO: 4, SEQ ID NO: 9, SEQ ID NO: 14, SEQ ID NO: 20, SEQ ID NO: 26, SEQ ID NO: 32, SEQ ID NO: 38, SEQ ID NO: 43, SEQ ID NO: 48, SEQ ID NO: 53, SEQ ID NO: 58, and SEQ ID NO: 63.

In some embodiments, the invention provides an isolated antibody or fragment thereof which specifically binds to IGF-R1, where the light chain variable region (VL) of the antibody or fragment thereof comprises an amino acid sequence at least 90% identical to a reference amino acid sequence selected from the group consisting of: SEQ ID NO: 68, SEQ ID NO: 73, SEQ ID NO: 78, SEQ ID NO: 83, SEQ ID NO: 88, SEQ ID NO: 93, SEQ ID NO: 98, SEQ ID NO: 103, SEQ ID NO: 108, SEQ ID NO: 113, and SEQ ID NO: 118.

In some embodiments, the invention provides an isolated antibody or fragment thereof which specifically binds to IGF-R1, where the VH of the antibody or fragment thereof comprises an amino acid sequence identical, except for 20 or fewer conservative amino acid substitutions, to a reference amino acid sequence selected from the group consisting of: SEQ ID NO: 4, SEQ ID NO: 9, SEQ ID NO: 14, SEQ ID NO: 20, SEQ ID NO: 26, SEQ ID NO: 32, SEQ ID NO: 38, SEQ ID NO: 43, SEQ ID NO: 48, SEQ ID NO: 53, SEQ ID NO: 58, and SEQ ID NO: 63.

In some embodiments, the invention provides an isolated antibody or fragment thereof which specifically binds to IGF-R1, where the VL of the antibody or fragment thereof comprises an amino acid sequence identical, except for 20 or fewer conservative amino acid substitutions, to a reference amino acid sequence selected from the group consisting of: SEQ ID NO: 68, SEQ ID NO: 73, SEQ ID NO: 78, SEQ ID NO: 83, SEQ ID NO: 88, SEQ ID NO: 93, SEQ ID NO: 98, SEQ ID NO: 103, SEQ ID NO: 108, SEQ ID NO: 113, and SEQ ID NO: 118.

In some embodiments, the invention provides an isolated antibody or fragment thereof which specifically binds to IGF-R1, where the VH of the antibody or fragment thereof comprises an amino acid sequence selected from the group consisting of: SEQ ID NO: 4, SEQ ID NO: 9, SEQ ID NO: 14, SEQ ID NO: 20, SEQ ID NO: 26, SEQ ID NO: 32, SEQ ID NO: 38, SEQ ID NO: 43, SEQ ID NO: 48, SEQ ID NO: 53, SEQ ID NO: 58, and SEQ ID NO: 63.

In some embodiments, the invention provides an isolated antibody or fragment thereof which specifically binds to IGF-R1, where the VL of the antibody or fragment thereof comprises an amino acid sequence selected from the group consisting of: SEQ ID NO: 68, SEQ ID NO: 73, SEQ ID NO: 78, SEQ ID NO: 83, SEQ ID NO: 88, SEQ ID NO: 93, SEQ ID NO: 98, SEQ ID NO: 103, SEQ ID NO: 108, SEQ ID NO: 113, and SEQ ID NO: 118.

In some embodiments, the invention provides an isolated antibody or fragment thereof which specifically binds to IGF-R1, where the VH and VL of the antibody or fragment thereof comprise, respectively, amino acid sequences at least 90% identical to reference amino acid sequences selected from the group consisting of: SEQ ID NO: 4 and SEQ ID NO: 68; SEQ ID NO: 8 and SEQ ID NO: 73; SEQ ID NO: 14 and SEQ ID NO: 78; SEQ ID NO: 20 and SEQ ID NO: 83; SEQ ID NO: 26 and SEQ ID NO: 88; SEQ ID NO: 32 and SEQ ID NO: 93; SEQ ID NO: 38 and SEQ ID NO: 98; SEQ ID NO: 43 and SEQ ID NO: 103; SEQ ID NO: 48 and SEQ ID NO: 108; SEQ ID NO: 53 and SEQ ID NO: 103; SEQ ID NO: 58 and SEQ ID NO: 113; and SEQ ID NO: 63 and 118.

In some embodiments, the invention provides an isolated antibody or fragment thereof which specifically binds to IGF-R1, where the VH and VL of the antibody or fragment thereof comprise, respectively, amino acid sequences identical, except for 20 or fewer conservative amino acid substitutions each, to reference amino acid sequences selected from the group consisting of: SEQ ID NO: 4 and SEQ ID NO: 68; SEQ ID NO: 8 and SEQ ID NO: 73; SEQ ID NO: 14 and SEQ ID NO: 78; SEQ ID NO: 20 and SEQ ID NO: 83; SEQ ID NO: 26 and SEQ ID NO: 88; SEQ ID NO: 32 and SEQ ID NO: 93; SEQ ID NO: 38 and SEQ ID NO: 98; SEQ ID NO: 43 and SEQ ID NO: 103; SEQ ID NO: 48 and SEQ ID NO: 108; SEQ ID NO: 53 and SEQ ID NO: 103; SEQ ID NO: 58 and SEQ ID NO: 113; and SEQ ID NO: 63 and 118.

In some embodiments, the invention provides an isolated antibody or fragment thereof which specifically binds to IGF-R1, where the VH and VL of the antibody or fragment thereof comprise, respectively, amino acid sequences selected from the group consisting of: SEQ ID NO: 4 and SEQ ID NO: 68; SEQ ID NO: 8 and SEQ ID NO: 73; SEQ ID NO: 14 and SEQ ID NO: 78; SEQ ID NO: 20 and SEQ ID NO: 83; SEQ ID NO: 26 and SEQ ID NO: 88; SEQ ID NO: 32 and SEQ ID NO: 93; SEQ ID NO: 38 and SEQ ID NO: 98; SEQ ID NO: 43 and SEQ ID NO: 103; SEQ ID NO: 48 and SEQ ID NO: 108; SEQ ID NO: 53 and SEQ ID NO: 103; SEQ ID NO: 58 and SEQ ID NO: 113; and SEQ ID NO: 63 and 118.

In some embodiments, the invention provides an isolated antibody or fragment thereof which specifically binds to IGF-R1, where the VH of the antibody or fragment thereof comprises a Kabat heavy chain complementarity determining region-1 (VH-CDR1) amino acid sequence identical, except for two or fewer amino acid substitutions, to a reference VH-CDR1 amino acid sequence selected from the group consisting of: SEQ ID NO: 5, SEQ ID NO: 10, SEQ ID NO: 15, SEQ ID NO: 21, SEQ ID NO: 27, SEQ ID NO: 33, SEQ ID NO: 39, SEQ ID NO: 44, SEQ ID NO: 49, SEQ ID NO: 54, SEQ ID NO: 59, and SEQ ID NO: 64. In further embodiments, the VH-CDR1 amino acid sequence is selected from the group consisting of: SEQ ID NO: 5, SEQ ID NO: 10, SEQ ID NO: 15, SEQ ID NO: 21, SEQ ID NO: 27, SEQ ID NO: 33, SEQ ID NO: 39, SEQ ID NO: 44, SEQ ID NO: 49, SEQ ID NO: 54, SEQ ID NO: 59, and SEQ ID NO: 64.

In some embodiments, the invention provides an isolated antibody or fragment thereof which specifically binds to IGF-R1, where the VH of the antibody or fragment thereof comprises a Kabat heavy chain complementarity determining region-2 (VH-CDR2) amino acid sequence identical, except for four or fewer amino acid substitutions, to a reference VH-CDR2 amino acid sequence selected from the group consisting of: SEQ ID NO: 6, SEQ ID NO: 11, SEQ ID NO: 16, SEQ ID NO: 22, SEQ ID NO: 28, SEQ ID NO: 34, SEQ ID NO: 40, SEQ ID NO: 45, SEQ ID NO: 50, SEQ ID NO: 55, SEQ ID NO: 60, and SEQ ID NO: 65. In further embodiments, the VH-CDR2 amino acid sequence is selected from the group consisting of: SEQ ID NO: 6, SEQ ID NO: 11, SEQ ID NO: 16, SEQ ID NO: 22, SEQ ID NO: 28, SEQ ID NO: 34, SEQ ID NO: 40, SEQ ID NO: 45, SEQ ID NO: 50, SEQ ID NO: 55, SEQ ID NO: 60, and SEQ ID NO: 65.

In some embodiments, the invention provides an isolated antibody or fragment thereof which specifically binds to IGF-R1, where the VH of the antibody or fragment thereof comprises a Kabat heavy chain complementarity determining region-3 (VH-CDR3) amino acid sequence identical, except for four or fewer amino acid substitutions, to a reference VH-CDR3 amino acid sequence selected from the group consisting of: SEQ ID NO: 7, SEQ ID NO: 12, SEQ ID NO: 17, SEQ ID NO: 23, SEQ ID NO: 29, SEQ ID NO: 35, SEQ ID NO: 41, SEQ ID NO: 46, SEQ ID NO: 51, SEQ ID NO: 56, SEQ ID NO: 61, and SEQ ID NO: 66. In further embodiments, the VH-CDR3 amino acid sequence is selected from the group consisting of: SEQ ID NO: 7, SEQ ID NO: 12, SEQ ID NO: 17, SEQ ID NO: 23, SEQ ID NO: 29, SEQ ID NO: 35, SEQ ID NO: 41, SEQ ID NO: 46, SEQ ID NO: 51, SEQ ID NO: 56, SEQ ID NO: 61, and SEQ ID NO: 66.

In some embodiments, the invention provides an isolated antibody or fragment thereof which specifically binds to IGF-R1, where the VL of the antibody or fragment thereof comprises a Kabat light chain complementarity determining region-1 (VL-CDR1) amino acid sequence identical, except for four or fewer amino acid substitutions, to a reference VL-CDR1 amino acid sequence selected from the group consisting of: SEQ ID NO: 69, SEQ ID NO: 74, SEQ ID NO: 79, SEQ ID NO: 84, SEQ ID NO: 89, SEQ ID NO: 94, SEQ ID NO: 99, SEQ ID NO: 104, SEQ ID NO: 109, SEQ ID NO: 114, and SEQ ID NO: 119. In further embodiments, the VL-CDR1 amino acid sequence is selected from the group consisting of: SEQ ID NO: 69, SEQ ID NO: 74, SEQ ID NO: 79, SEQ ID NO: 84, SEQ ID NO: 89, SEQ ID NO: 94, SEQ ID NO: 99, SEQ ID NO: 104, SEQ ID NO: 109, SEQ ID NO: 114, and SEQ ID NO: 119.

In some embodiments, the invention provides an isolated antibody or fragment thereof which specifically binds to IGF-R1, where the VL of the antibody or fragment thereof comprises a Kabat light chain complementarity determining region-2 (VL-CDR2) amino acid sequence identical, except for two or fewer amino acid substitutions, to a reference VL-CDR2 amino acid sequence selected from the group consisting of: SEQ ID NO: 70, SEQ ID NO: 75, SEQ ID NO: 80, SEQ ID NO: 85, SEQ ID NO: 90, SEQ ID NO: 95, SEQ ID NO: 100, SEQ ID NO: 105, SEQ ID NO: 110, SEQ ID NO: 115, and SEQ ID NO: 120. In further embodiments, the VL-CDR2 amino acid sequence is selected from the group consisting of: SEQ ID NO: 70, SEQ ID NO: 75, SEQ ID NO: 80, SEQ ID NO: 85, SEQ ID NO: 90, SEQ ID NO: 95, SEQ ID NO: 100, SEQ ID NO: 105, SEQ ID NO: 110, SEQ ID NO: 115, and SEQ ID NO: 120.

In some embodiments, the invention provides an isolated antibody or fragment thereof which specifically binds to IGF-R1, where the VL of the antibody or fragment thereof comprises a Kabat light chain complementarity determining region-3 (VL-CDR3) amino acid sequence identical, except for four or fewer amino acid substitutions, to a reference VL-CDR3 amino acid sequence selected from the group consisting of: SEQ ID NO: 71, SEQ ID NO: 76, SEQ ID NO: 81, SEQ ID NO: 86, SEQ ID NO: 91, SEQ ID NO: 96, SEQ ID NO: 101, SEQ ID NO: 106, SEQ ID NO: 111, SEQ ID NO: 116, and SEQ ID NO: 121. In further embodiments, the VL-CDR3 amino acid sequence is selected from the group consisting of: SEQ ID NO: 71, SEQ ID NO: 76, SEQ ID NO: 81, SEQ ID NO: 86, SEQ ID NO: 91, SEQ ID NO: 96, SEQ ID NO: 101, SEQ ID NO: 106, SEQ ID NO:111, SEQ ID NO: 116, and SEQ ID NO: 121.

In some embodiments, the invention provides an isolated antibody or fragment thereof which specifically binds to IGF-R1, where the VH of the antibody or fragment thereof comprises VH-CDR1, VH-CDR2, and VH-CDR3 amino acid sequences selected from the group consisting of: SEQ ID NOs: 5, 6, and 7; SEQ ID NOs: 10, 11, and 12; SEQ ID NOs: 15, 16, and 17; SEQ ID NOs: 21, 22, and 23; SEQ ID NOs: 27, 28, and 29; SEQ ID NOs: 33, 34, and 35; SEQ ID NOs: 39, 40, and 41; SEQ ID NOs: 44, 45, and 46; SEQ ID NOs: 49, 50, and 51; SEQ ID NOs: 54, 55, and 56; SEQ ID NOs: 59, 60, and 61; and SEQ ID NOs: 64, 65, and 66, except for one, two, three, or four amino acid substitutions in at least one of said VH-CDRs.

In some embodiments, the invention provides an isolated antibody or fragment thereof which specifically binds to IGF-R1, where the VH of the antibody or fragment thereof comprises VH-CDR1, VH-CDR2, and VH-CDR3 amino acid sequences selected from the group consisting of: SEQ ID NOs: 5, 6, and 7; SEQ ID NOs: 10, 11, and 12; SEQ ID NOs: 15, 16, and 17; SEQ ID NOs: 21, 22, and 23; SEQ ID NOs: 27, 28, and 29; SEQ ID NOs: 33, 34, and 35; SEQ ID NOs: 39, 40, and 41; SEQ ID NOs: 44, 45, and 46; SEQ ID NOs: 49, 50, and 51; SEQ ID NOs: 54, 55, and 56; SEQ ID NOs: 59, 60, and 61; and SEQ ID NOs: 64, 65, and 66.

In some embodiments, the invention provides an isolated antibody or fragment thereof which specifically binds to IGF-R1, where the VL of the antibody or fragment thereof comprises VL-CDR1, VL-CDR2, and VL-CDR3 amino acid sequences selected from the group consisting of: SEQ ID NOs: 69, 70, and 71; SEQ ID NOs: 74, 75, and 76; SEQ ID NOs: 79, 80, and 81; SEQ ID NOs: 84, 85, and 86; SEQ ID NOs: 89, 90, and 91; SEQ ID NOs: 94, 95, and 96; SEQ ID NOs: 99, 100, and 101; SEQ ID NOs: 104, 105, and 106; SEQ ID NOs: 109, 110, and 111; SEQ ID NOs: 114, 115, and 116; and SEQ ID NOs: 119, 120, and 121, except for one, two, three, or four amino acid substitutions in at least one of said VL-CDRs.

In some embodiments, the invention provides an isolated antibody or fragment thereof which specifically binds to IGF-R1, where the VL of the antibody or fragment thereof comprises VL-CDR1, VL-CDR2, and VL-CDR3 amino acid sequences selected from the group consisting of: SEQ ID NOs: 69, 70, and 71; SEQ ID NOs: 74, 75, and 76; SEQ ID NOs: 79, 80, and 81; SEQ ID NOs: 84, 85, and 86; SEQ ID NOs: 89, 90, and 91; SEQ ID NOs: 94, 95, and 96; SEQ ID NOs: 99, 100, and 101; SEQ ID NOs: 104, 105, and 106; SEQ ID NOs: 109, 110, and 111; SEQ ID NOs: 114, 115, and 116; and SEQ ID NOs: 119, 120, and 121.

In various embodiments of the above-described antibodies or fragments thereof, the VH framework regions and/or VL framework regions are human, except for five or fewer amino acid substitutions.

In some embodiments, the above-described antibodies or fragments thereof bind to a linear epitope or a non-linear conformation epitope In some embodiments, the above-described antibodies or fragments thereof are multivalent, and comprise at least two heavy chains and at least two light chains.

In some embodiments, the above-described antibodies or fragments thereof are multispecific. In further embodiments, the above-described antibodies or fragments thereof are bispecific.

In various embodiments of the above-described antibodies or fragments thereof, the heavy and light chain variable domains are fully human. In further embodiments, the heavy and light chain variable domains are from a monoclonal Fab antibody fragment selected from the group consisting of M13-C06, M14-G11, M14-C03, M14-B01, M12-E01, and M12-G04.

In various embodiments of the above-described antibodies or fragments thereof, the heavy and light chain variable domains are murine. In further embodiments, the heavy and light chain variable domains are from a monoclonal antibody produced by a hybridoma selected from the group consisting of P2A7.3E11, 20C8.3B8, P1A2.2B11, 20D8.24B11, P1E2.3B12, and P1G10.2B8.

In various embodiments, the above-described antibodies or fragments thereof are humanized.

In various embodiments, the above-described antibodies or fragments thereof are chimeric.

In various embodiments, the above-described antibodies or fragments thereof are primatized.

In various embodiments, the above-described antibodies or fragments thereof are fully human.

In certain embodiments, the above-described antibodies or fragments thereof are Fab fragments, Fab' fragments, F(ab)$_2$ fragments, or Fv fragments.

In certain embodiments, the above-described antibodies are single chain antibodies.

In certain embodiments, the above-described antibodies or fragments thereof comprise light chain constant regions selected from the group consisting of a human kappa constant region and a human lambda constant region.

In certain embodiments, the above-described antibodies or fragments thereof comprise a heavy chain constant region or fragment thereof. In further embodiments, the heavy chain constant region or fragment thereof is human IgG4. In certain other embodiments, the IgG4 is mutagenized to remove glycosylation sites. In further embodiments, the IgG4 mutations comprise S241P and T318A, using the Kabat numbering system.

In some embodiments, the above-described antibodies or fragments thereof specifically bind to an IGF-R1 polypeptide or fragment thereof, or an IGF-R1 variant polypeptide, with an affinity characterized by a dissociation constant ($K_D$) which is less than the $K_D$ for said reference monoclonal antibody. In further embodiments, the dissociation constant ($K_D$) is no greater than $5\times10^{-2}$ M, $10^{-2}$ M, $5\times10^{-3}$ M, $10^{-3}$ M, $5\times10^{-4}$ M, $10^{-4}$ M, $5\times10^{-5}$ M, $10^{-5}$ M, $5\times10^{-6}$ M, $10^{-6}$ M, $5\times10^{-7}$ M, $10^{-7}$ M, $5\times10^{-8}$ M, $10^{-8}$ M, $5\times10^{-9}$ M, $10^{-9}$ M, $5\times10^{-10}$ M, $10^{-10}$ M, $5\times10^{-11}$ M, $10^{-11}$ M, $5\times10^{-12}$ M, $10^{-12}$ M, $5\times10^{-13}$ M, $10^{-13}$ M, $5\times10^{-14}$ M, $10^{-14}$ M, $5\times10^{-15}$ M, or $10^{-15}$ M.

In some embodiments, the above-described antibodies or fragments thereof preferentially bind to a human IGF-R1 polypeptide or fragment thereof, relative to a murine IGF-R1 polypeptide or fragment thereof or a non-human primate IGF-R1 polypeptide or fragment thereof.

In certain other embodiments, the above described antibodies or fragments thereof bind to human IGF-R1 polypeptide or fragment thereof, and also binds to a non-human primate IGF-R1 polypeptide or fragment thereof.

In some embodiments, the above described antibodies or fragments thereof bind to IGF-R1 expressed on the surface of a cell. In further embodiments, the cell is a malignant cell, a neoplastic cell, a tumor cell, or a metastatic cell.

In some embodiments, the above described antibodies or fragments thereof block insulin growth factor from binding to IGF-R1. In further embodiments, the insulin growth factor is insulin growth factor-1 (IGF-1) or insulin growth factor-2 (IGF-2). In certain embodiments, the above described antibodies or fragments thereof block both IGF-1 and IGF-2 from binding to IGF-R1.

In some embodiments, the above described antibodies or fragments thereof inhibit IGF-R1-mediated cell proliferation, IGF-1 or IGF-2-mediated IGF-R1 phosphorylation, tumor cell growth, or IGF-R1 internalization.

In further embodiments, the above described antibodies or fragments thereof further comprise a heterologous polypeptide fused thereto.

In some embodiments, the above described antibodies or fragments thereof are conjugated to an agent selected from the group consisting of cytotoxic agent, a therapeutic agent, cytostatic agent, a biological toxin, a prodrug, a peptide, a protein, an enzyme, a virus, a lipid, a biological response modifier, pharmaceutical agent, a lymphokine, a heterologous antibody or fragment thereof, a detectable label, polyethylene glycol (PEG), and a combination of two or more of any said agents. In further embodiments, the cytotoxic agent is selected from the group consisting of a radionuclide, a biotoxin, an enzymatically active toxin, a cytostatic or cytotoxic therapeutic agent, a prodrugs, an immunologically active ligand, a biological response modifier, or a combination of two or more of any said cytotoxic agents. In further embodiments, the detectable label is selected from the group consisting of an enzyme, a fluorescent label, a chemiluminescent label, a bioluminescent label, a radioactive label, or a combination of two or more of any said detectable labels.

In additional embodiments, the invention includes compositions comprising the above-described antibodies or fragments thereof, and a carrier.

Certain embodiments of the invention include an isolated polynucleotide comprising a nucleic acid which encodes an antibody VH polypeptide, where the amino acid sequence of the VH polypeptide is at least 90% identical to a reference amino acid sequence selected from the group consisting of: SEQ ID NO: 4, SEQ ID NO: 9, SEQ ID NO: 14, SEQ ID NO: 20, SEQ ID NO: 26, SEQ ID NO: 32, SEQ ID NO: 38, SEQ ID NO: 43, SEQ ID NO: 48, SEQ ID NO: 53, SEQ ID NO: 58, and SEQ ID NO: 63; and where an antibody or antigen binding fragment thereof comprising the VH polypeptide specifically binds to IGF-R1. In further embodiments, the amino acid sequence of the VH polypeptide is selected from the group consisting of: SEQ ID NO: 4, SEQ ID NO: 9, SEQ ID NO: 14, SEQ ID NO: 20, SEQ ID NO: 26, SEQ ID NO: 32, SEQ ID NO: 38, SEQ ID NO: 43, SEQ ID NO: 48, SEQ ID NO: 53, SEQ ID NO: 58, and SEQ ID NO: 63.

In certain embodiments, the nucleotide sequence encoding the VH polypeptide is optimized for increased expression without changing the amino acid sequence of the VH polypeptide. In further embodiments, the optimization comprises identification and removal of splice donor and splice acceptor sites and/or optimization of codon usage for the cells expressing the polynucleotide. In further embodiments, the nucleic acid comprises a nucleotide sequence selected from the group consisting of: SEQ ID NO: 3, SEQ ID NO: 8, SEQ ID NO: 13, SEQ ID NO: 18, SEQ ID NO: 19, SEQ ID NO: 24, SEQ ID NO: 25, SEQ ID NO: 30, SEQ ID NO: 31, SEQ ID NO: 36, SEQ ID NO: 37, SEQ ID NO: 42, SEQ ID NO: 47, SEQ ID NO: 52, SEQ ID NO: 57, and SEQ ID NO: 62.

In some embodiments, the invention provides an isolated polynucleotide comprising a nucleic acid which encodes an antibody VL polypeptide, where the amino acid sequence of the VL polypeptide is at least 90% identical to a reference amino acid sequence selected from the group consisting of: SEQ ID NO: 68, SEQ ID NO: 73, SEQ ID NO: 78, SEQ ID NO: 83, SEQ ID NO: 88, SEQ ID NO: 93, SEQ ID NO: 98, SEQ ID NO: 103, SEQ ID NO: 108, SEQ ID NO: 113, and SEQ ID NO: 118; and where an antibody or antigen binding fragment thereof comprising the VL polypeptide specifically binds to IGF-R1. In further embodiments, the amino acid sequence of the VL polypeptide is selected from the group consisting of: SEQ ID NO: 68, SEQ ID NO: 73, SEQ ID NO: 78, SEQ ID NO: 83, SEQ ID NO: 88, SEQ ID NO: 93, SEQ ID NO: 98, SEQ ID NO: 103, SEQ ID NO: 108, SEQ ID NO: 113, and SEQ ID NO: 118.

In certain embodiments, the nucleotide sequence encoding the VL polypeptide is optimized for increased expression without changing the amino acid sequence of said VL polypeptide. In further embodiments, the optimization comprises identification and removal of splice donor and splice acceptor sites and/or optimization of codon usage for the cells expressing the polynucleotide. In further embodiments, the nucleic acid comprises a nucleotide sequence selected from the group consisting of: SEQ ID NO: 67, SEQ ID NO: 72, SEQ ID NO: 77, SEQ ID NO: 82, SEQ ID NO: 87, SEQ ID NO: 92, SEQ ID NO: 97, SEQ ID NO: 102, SEQ ID NO: 107, SEQ ID NO: 112, and SEQ ID NO: 117.

In certain other embodiments, the invention provides an isolated polynucleotide comprising a nucleic acid which encodes an antibody VH polypeptide, where the amino acid sequence of the VH polypeptide is identical, except for 20 or fewer conservative amino acid substitutions, to a reference amino acid sequence selected from the group consisting of: SEQ ID NO: 4, SEQ ID NO: 9, SEQ ID NO: 14, SEQ ID NO: 20, SEQ ID NO: 26, SEQ ID NO: 32, SEQ ID NO: 38, SEQ ID NO: 43, SEQ ID NO: 48, SEQ ID NO: 53, SEQ ID NO: 58, and SEQ ID NO: 63; and where an antibody or antigen binding fragment thereof comprising said VH polypeptide specifically binds to IGF-R1.

In some embodiments, the invention provides an isolated polynucleotide comprising a nucleic acid which encodes an antibody VL polypeptide, where the amino acid sequence of the VL polypeptide is identical, except for 20 or fewer conservative amino acid substitutions, to a reference amino acid sequence selected from the group consisting of: SEQ ID NO: 68, SEQ ID NO: 73, SEQ ID NO: 78, SEQ ID NO: 83, SEQ ID NO: 88, SEQ ID NO: 93, SEQ ID NO: 98, SEQ ID NO: 103, SEQ ID NO: 108, SEQ ID NO: 113, and SEQ ID NO: 118; and wherein an antibody or antigen binding fragment thereof comprising said VL polypeptide specifically binds to IGF-R1.

In some embodiments, the invention provides an isolated polynucleotide comprising a nucleic acid which encodes a VH-CDR1 amino acid sequence identical, except for two or fewer amino acid substitutions, to a reference VH-CDR1 amino acid sequence selected from the group consisting of: SEQ ID NO: 5, SEQ ID NO: 10, SEQ ID NO: 15, SEQ ID NO: 21, SEQ ID NO: 27, SEQ ID NO: 33, SEQ ID NO: 39, SEQ ID NO: 44, SEQ ID NO: 49, SEQ ID NO: 54, SEQ ID NO: 59, and SEQ ID NO: 64; and where an antibody or antigen binding fragment thereof comprising the VH-CDR1 specifically binds to IGF-R1. In further embodiments, the VH-CDR1 amino acid sequence is selected from the group consisting of: SEQ ID NO: 5, SEQ ID NO: 10, SEQ ID NO: 15, SEQ ID NO: 21, SEQ ID NO: 27, SEQ ID NO: 33, SEQ ID NO: 39, SEQ ID NO: 44, SEQ ID NO: 49, SEQ ID NO: 54, SEQ ID NO: 59, and SEQ ID NO: 64.

In some embodiments, the invention provides an isolated polynucleotide comprising a nucleic acid which encodes a VH-CDR2 amino acid sequence identical, except for four or fewer amino acid substitutions, to a reference VH-CDR2 amino acid sequence selected from the group consisting of: SEQ ID NO: 6, SEQ ID NO: 11, SEQ ID NO: 16, SEQ ID NO: 22, SEQ ID NO: 28, SEQ ID NO: 34, SEQ ID NO: 40, SEQ ID NO: 45, SEQ ID NO: 50, SEQ ID NO: 55, SEQ ID NO: 60, and SEQ ID NO: 65; and where an antibody or antigen binding fragment thereof comprising the VH-CDR2 specifically binds to IGF-R1. In further embodiments, the VH-CDR2 amino acid sequence is selected from the group consisting of: SEQ ID NO: 6, SEQ ID NO: 11, SEQ ID NO: 16, SEQ ID NO: 22, SEQ ID NO: 28, SEQ ID NO: 34, SEQ ID NO: 40, SEQ ID NO: 45, SEQ ID NO: 50, SEQ ID NO: 55, SEQ ID NO: 60, and SEQ ID NO: 65.

In some embodiments, the invention provides an isolated polynucleotide comprising a nucleic acid which encodes a VH-CDR3 amino acid sequence identical, except for four or fewer amino acid substitutions, to a reference VH-CDR3 amino acid sequence selected from the group consisting of: SEQ ID NO: 7, SEQ ID NO: 12, SEQ ID NO: 17, SEQ ID NO: 23, SEQ ID NO: 29, SEQ ID NO: 35, SEQ ID NO: 41, SEQ ID NO: 46, SEQ ID NO: 51, SEQ ID NO: 56, SEQ ID NO: 61, and SEQ ID NO: 66; and where an antibody or antigen binding fragment thereof comprising the VH-CDR3 specifically binds to IGF-R1. In further embodiments, the VH-CDR3 amino acid sequence is selected from the group consisting of: SEQ ID NO: 7, SEQ ID NO: 12, SEQ ID NO: 17, SEQ ID NO: 23, SEQ ID NO: 29, SEQ ID NO: 35, SEQ ID NO: 41, SEQ ID NO: 46, SEQ ID NO: 51, SEQ ID NO: 56, SEQ ID NO: 61, and SEQ ID NO: 66.

In some embodiments, the invention provides an isolated polynucleotide comprising a nucleic acid which encodes a VL-CDR1 amino acid sequence identical, except for four or fewer amino acid substitutions, to a reference VL-CDR1 amino acid sequence selected from the group consisting of: SEQ ID NO: 69, SEQ ID NO: 74, SEQ ID NO: 79, SEQ ID NO: 84, SEQ ID NO: 89, SEQ ID NO: 94, SEQ ID NO: 99, SEQ ID NO: 104, SEQ ID NO: 109, SEQ ID NO: 114, and SEQ ID NO: 119; and where an antibody or antigen binding fragment thereof comprising the VL-CDR1 specifically binds to IGF-R1. In further embodiments, the VL-CDR1 amino acid sequence is selected from the group consisting of: SEQ ID NO: 69, SEQ ID NO: 74, SEQ ID NO: 79, SEQ ID NO: 84, SEQ ID NO: 89, SEQ ID NO: 94, SEQ ID NO: 99, SEQ ID NO: 104, SEQ ID NO: 109, SEQ ID NO: 114, and SEQ ID NO: 119.

In some embodiments, the invention provides an isolated polynucleotide comprising a nucleic acid which encodes a VL-CDR2 amino acid sequence identical, except for two or fewer amino acid substitutions, to a reference VL-CDR2 amino acid sequence selected from the group consisting of: SEQ ID NO: 70, SEQ ID NO: 75, SEQ ID NO: 80, SEQ ID NO: 85, SEQ ID NO: 90, SEQ ID NO: 95, SEQ ID NO: 100, SEQ ID NO: 105, SEQ ID NO: 110, SEQ ID NO: 115, and SEQ ID NO: 120; and wherein an antibody or antigen binding fragment thereof comprising said VL-CDR2 specifically binds to IGF-R1. In further embodiments, the VL-CDR2 amino acid sequence is selected from the group consisting of: SEQ ID NO: 70, SEQ ID NO: 75, SEQ ID NO: 80, SEQ ID NO: 85, SEQ ID NO: 90, SEQ ID NO: 95, SEQ ID NO: 100, SEQ ID NO: 105, SEQ ID NO: 110, SEQ ID NO: 115, and SEQ ID NO: 120.

In some embodiments, the invention provides an isolated polynucleotide comprising a nucleic acid which encodes a VL-CDR3 amino acid sequence identical, except for four or fewer amino acid substitutions, to a reference VL-CDR3 amino acid sequence selected from the group consisting of: SEQ ID NO: 71, SEQ ID NO: 76, SEQ ID NO: 81, SEQ ID NO: 86, SEQ ID NO: 91, SEQ ID NO: 96, SEQ ID NO: 101, SEQ ID NO: 106, SEQ ID NO: 111, SEQ ID NO: 116, and SEQ ID NO: 121; and wherein an antibody or antigen binding fragment thereof comprising said VL-CDR3 specifically binds to IGF-R1. In further embodiments, the VL-CDR3 amino acid sequence is selected from the group consisting of: SEQ ID NO: 71, SEQ ID NO: 76, SEQ ID NO: 81, SEQ ID NO: 86, SEQ ID NO: 91, SEQ ID NO: 96, SEQ ID NO: 101, SEQ ID NO: 106, SEQ ID NO:111, SEQ ID NO: 116, and SEQ ID NO: 121.

In some embodiments, the invention provides an isolated polynucleotide comprising a nucleic acid which encodes an antibody VH polypeptide, where the VH polypeptide comprises VH-CDR1, VH-CDR2, and VH-CDR3 amino acid sequences selected from the group consisting of: SEQ ID NOs: 5, 6, and 7; SEQ ID NOs: 10, 11, and 12; SEQ ID NOs: 15, 16, and 17; SEQ ID NOs: 21, 22, and 23; SEQ ID NOs: 27, 28, and 29; SEQ ID NOs: 33, 34, and 35; SEQ ID NOs: 39, 40, and 41; SEQ ID NOs: 44, 45, and 46; SEQ ID NOs: 49, 50, and 51; SEQ ID NOs: 54, 55, and 56; SEQ ID NOs: 59, 60, and 61; and SEQ ID NOs: 64, 65, and 66; and where an antibody or antigen binding fragment thereof comprising the VL-CDR3 specifically binds to IGF-R1.

In some embodiments, the invention provides an isolated polynucleotide comprising a nucleic acid which encodes an antibody VL polypeptide, wherein said VL polypeptide comprises VH-CDR1, VH-CDR2, and VH-CDR3 amino acid sequences selected from the group consisting of: SEQ ID NOs: 69, 70, and 71; SEQ ID NOs: 74, 75, and 76; SEQ ID NOs: 79, 80, and 81; SEQ ID NOs: 84, 85, and 86; SEQ ID NOs: 89, 90, and 91; SEQ ID NOs: 94, 95, and 96; SEQ ID NOs: 99, 100, and 101; SEQ ID NOs: 104, 105, and 106; SEQ ID NOs: 109, 110, and 111; SEQ ID NOs: 114, 115, and 116; and SEQ ID NOs: 119, 120, and 121; and wherein an antibody or antigen binding fragment thereof comprising said VL-CDR3 specifically binds to IGF-R1.

In some embodiments, the above-described polynucleotides further comprise a nucleic acid encoding a signal peptide fused to the antibody VH polypeptide or the antibody VL polypeptide.

In certain other embodiments, the above-described polynucleotides further comprise a nucleic acid encoding a heavy chain constant region CH1 domain fused to the VH polypeptide, encoding a heavy chain constant region CH2 domain fused to the VH polypeptide, encoding a heavy chain constant region CH3 domain fused to the VH polypeptide, or encoding a heavy chain hinge region fused to said VH polypeptide. In further embodiments, the heavy chain constant region is human IgG4. In certain other embodiments, the IgG4 is mutagenized to remove glycosylation sites. In further embodiments, the IgG4 mutations comprise S241P and T318A using the Kabat numbering system.

In some embodiments, the above-described polynucleotides comprise a nucleic acid encoding a light chain constant region domain fused to said VL polypeptide. In further embodiments, the light chain constant region is human kappa.

In various embodiments of the above-described polynucleotides, the antibody or antigen-binding fragment thereof comprising a polypeptide encoded by the nucleic acid specifically binds the same IGF-R1 epitope as a reference monoclonal Fab antibody fragment selected from the group consisting of M13-C06, M14-G11, M14-C03, M14-B0, M12-E01, and M12-G04, or a reference monoclonal antibody produced by a hybridoma selected from the group consisting of P2A7.3E11, 20C8.3B8, P1A2.2B11, 20D8.24B11, P1E2.3B12, and P1G10.2B8.

In various other embodiments of the above-described polynucleotides, the antibody or antigen-binding fragment thereof comprising a polypeptide encoded by the nucleic acid competitively inhibits a reference monoclonal Fab antibody fragment selected from the group consisting of M13-C06, M14-G11, M14-C03, M14-B01, M12-E01, and M12-G04, or a reference monoclonal antibody produced by a hybridoma selected from the group consisting of P2A7.3E11, 20C8.3B8, P1A2.2B11, 20D8.24B11, P1E2.3B12, and P1G10.2B8.

In various embodiments of the above-describe polynucleotides, the framework regions of the VH polypeptide or VL polypeptide are human, except for five or fewer amino acid substitutions.

In various embodiments of the above-described polynucleotides, the invention provides an antibody or antigen-binding fragment thereof comprising the polypeptide encoded by the nucleic acid, that binds to a linear epitope or a non-linear conformational epitope.

In various embodiments of the above-described polynucleotides, the antibody or antigen-binding fragment thereof comprising the polypeptide encoded by the nucleic acid is multivalent, and comprises at least two heavy chains and at least two light chains.

In certain embodiments of the above-described polynucleotides, the antibody or antigen-binding fragment thereof comprising the polypeptide encoded by the nucleic acid is multispecific. In further embodiments, the antibody or antigen-binding fragment thereof comprising the polypeptide encoded by the nucleic acid is bispecific.

In various embodiments of the above-described polynucleotides, the antibody or antigen-binding fragment thereof comprising the polypeptide encoded by the nucleic acid comprises heavy and light chain variable domains which are fully human. In further embodiments, the heavy and light chain variable domains are identical to those of a monoclonal Fab antibody fragment selected from the group consisting of M13-C06, M14-G11, M14-C03, M14-B01, M12-E01, and M12-G04.

In certain other embodiments of the above-described polynucleotides, the antibody or antigen-binding fragment thereof comprising the polypeptide encoded by the nucleic acid comprises heavy and light chain variable domains which are murine. In further embodiments, the heavy and light chain variable domains are identical to those of a monoclonal antibody produced by a hybridoma selected from the group consisting of P2A7.3E11, 20C8.3B8, P1A2.2B11, 20D8.24B11, P1E2.3B12, and P1G10.2B8.

In various embodiments of the above-described polynucleotides, the antibody or antigen-binding fragment thereof comprising the polypeptide encoded by the nucleic acid is humanized.

In various embodiments of the above-described polynucleotides, the antibody or antigen-binding fragment thereof comprising the polypeptide encoded by the nucleic acid is primatized.

In various embodiments of the above-described polynucleotides, the antibody or antigen-binding fragment thereof comprising the polypeptide encoded by the nucleic acid is chimeric.

In some embodiments of the above-described polynucleotides, the antibody or antigen-binding fragment thereof comprising the polypeptide encoded by the nucleic acid is fully human.

In various embodiments of the above-described polynucleotides, the antibody or antigen-binding fragment thereof comprising the polypeptide encoded by the nucleic acid is an Fab fragment, an Fab' fragment, an F(ab)$_2$ fragment, or an Fv fragment. In certain embodiments of the above-described polynucleotides, the antibody or antigen-binding fragment thereof comprising the polypeptide encoded by the nucleic acid is a single chain antibody.

In some embodiments of the above-described polynucleotides, the antibody or antigen-binding fragment thereof comprising the polypeptide encoded by the nucleic acid specifically binds to an IGF-R1 polypeptide or fragment thereof, or an IGF-R1 variant polypeptide, with an affinity characterized by a dissociation constant ($K_D$) no greater than $5 \times 10^{-2}$ M, $10^{-2}$ M, $5 \times 10^{-3}$ M, $10^{-3}$ M, $5 \times 10^{-4}$ M, $10^{-4}$ M, $5 \times 10^{-5}$ M, $10^{-5}$ M, $5 \times 10^{-6}$ M, $10^{-6}$ M, $5 \times 10^{-7}$ M, $10^{-7}$ M, $5 \times 10^{-8}$ M, $10^{-8}$ M, $5 \times 10^{-9}$ M, $10^{-9}$ M, $5 \times 10^{-10}$ M, $10^{-10}$ M, $5 \times 10^{-11}$ M, $10^{-11}$ M, $5 \times 10^{-12}$ M, $10^{-12}$ M, $5 \times 10^{-13}$ M, $10^{-13}$ M, $5 \times 10^{-14}$ M, $10^{-14}$ M, $5 \times 10^{-15}$ M, or $10^{-15}$ M.

In some embodiments of the above-described polynucleotides, the antibody or antigen-binding fragment thereof comprising the polypeptide encoded by the nucleic acid preferentially binds to a human IGF-R1 polypeptide or fragment thereof, relative to a murine IGF-R1 polypeptide or fragment thereof or a non-human primate IGF-R1 polypeptide or fragment thereof.

In some embodiments of the above-described polynucleotides, the antibody or antigen-binding fragment thereof comprising the polypeptide encoded by the nucleic acid binds to a human IGF-R1 polypeptide or fragment thereof, and also binds to a non-human primate IGF-R1 polypeptide or fragment thereof.

In some embodiments of the above-described polynucleotides, the antibody or antigen-binding fragment thereof comprising the polypeptide encoded by the nucleic acid binds to IGF-R1 expressed on the surface of a cell. In further embodiments, the cell is a malignant cell, a neoplastic cell, a tumor cell, or a metastatic cell.

In some embodiments of the above-described polynucleotides, the antibody or antigen-binding fragment thereof comprising the polypeptide encoded by said nucleic acid blocks insulin growth factor from binding to IGF-R1. In further embodiments, the insulin growth factor is insulin growth factor-1 (IGF-1) or insulin growth factor-2 (IGF-2). In certain other embodiments of the above-described polynucleotide, the antibody or antigen-binding fragment thereof blocks both IGF-1 and IGF-2 from binding to IGF-R1.

In some embodiments of the above-described polynucleotides, the an antibody or antigen-binding fragment thereof comprising the polypeptide encoded by the nucleic acid inhibits IGF-R1-mediated cell proliferation, inhibits IGF-1 or IGF-2-mediated IGF-R1 phosphorylation, inhibits tumor cell growth or inhibits IGF-R1 internalization.

In some embodiments, the above-described polynucleotides further comprise a nucleic acid encoding a heterologous polypeptide.

In some embodiments of the above-described polynucleotides, the antibody or antigen-binding fragment thereof comprising the polypeptide encoded by the nucleic acid is conjugated to an agent selected from the group consisting of cytotoxic agent, a therapeutic agent, cytostatic agent, a biological toxin, a prodrug, a peptide, a protein, an enzyme, a virus, a lipid, a biological response modifier, pharmaceutical agent, a lymphokine, a heterologous antibody or fragment thereof, a detectable label, polyethylene glycol (PEG), and a combination of two or more of any said agents. In further embodiments, the cytotoxic agent is selected from the group consisting of a radionuclide, a biotoxin, an enzymatically active toxin, a cytostatic or cytotoxic therapeutic agent, a prodrugs, an immunologically active ligand, a biological response modifier, or a combination of two or more of any said cytotoxic agents. In certain other embodiments, the detectable label is selected from the group consisting of an enzyme, a fluorescent label, a chemiluminescent label, a bioluminescent label, a radioactive label, or a combination of two or more of any said detectable labels.

In some embodiments, the invention provides compositions comprising the above-described polynucleotides.

In certain other embodiments, the invention provides vectors comprising the above-described polynucleotides. In further embodiments, the polynucleotides are operably associated with a promoter. In additional embodiments, the invention provides host cells comprising such vectors. In further embodiments, the invention provides vectors where the polynucleotide is operably associated with a promoter.

In additional embodiments, the invention provides a method of producing an antibody or fragment thereof which specifically binds IGF-1R, comprising culturing a host cell containing a vector comprising the above-described polynucleotides, and recovering said antibody, or fragment thereof. In further embodiments, the invention provides an isolated polypeptide produced by the above-described method.

In some embodiments, the invention provides isolated polypeptides encoded by the above-described polynucleotides.

In further embodiments of the above-described polypeptides, the antibody or fragment thereof comprising the polypeptide specifically binds to IGF-1R. Other embodiments include the isolated antibody or fragment thereof comprising the above-described polypeptides.

In some embodiments, the invention provides a composition comprising an isolated VH encoding polynucleotide and an isolated VL encoding polynucleotide, where the VH encoding polynucleotide and the VL encoding polynucleotide, respectively, comprise nucleic acids encoding amino acid sequences at least 90% identical to reference amino acid sequences selected from the group consisting of: SEQ ID NO: 4 and SEQ ID NO: 68; SEQ ID NO: 8 and SEQ ID NO: 73; SEQ ID NO: 14 and SEQ ID NO: 78; SEQ ID NO: 20 and SEQ ID NO: 83; SEQ ID NO: 26 and SEQ ID NO: 88; SEQ ID NO: 32 and SEQ ID NO: 93; SEQ ID NO: 38 and SEQ ID NO: 98; SEQ ID NO: 43 and SEQ ID NO: 103; SEQ ID NO: 48 and SEQ ID NO: 108; SEQ ID NO: 53 and SEQ ID NO: 103; SEQ ID NO: 58 and SEQ ID NO: 113; and SEQ ID NO: 63 and 118; and where an antibody or fragment thereof encoded by the VH and VL encoding polynucleotides specifically binds IGF-R1. In further embodiments, the VH encoding polynucleotide and said VL encoding polynucleotide, respectively, comprise nucleic acids encoding amino acid sequences selected from the group consisting of: SEQ ID NO: 4 and SEQ ID NO: 68; SEQ ID NO: 8 and SEQ ID NO: 73; SEQ ID NO: 14 and SEQ ID NO: 78; SEQ ID NO: 20 and SEQ ID NO: 83; SEQ ID NO: 26 and SEQ ID NO: 88; SEQ ID NO: 32 and SEQ ID NO: 93; SEQ ID NO: 38 and SEQ ID NO: 98; SEQ ID NO: 43 and SEQ ID NO: 103; SEQ ID NO: 48 and SEQ ID NO: 108; SEQ ID NO: 53 and SEQ ID NO: 103; SEQ ID NO:58 and SEQ ID NO: 113; and SEQ ID NO: 63 and 118.

In certain other embodiments, the invention provides a composition comprising an isolated VH encoding polynucleotide and an isolated VL encoding polynucleotide, where the VH encoding polynucleotide and the VL encoding polynucleotide, respectively, comprise nucleic acids encoding amino acid sequences identical, except for less than 20 conservative amino acid substitutions, to reference amino acid sequences selected from the group consisting of: SEQ ID NO: 4 and SEQ ID NO: 68; SEQ ID NO: 8 and SEQ ID NO: 73; SEQ ID NO: 14 and SEQ ID NO: 78; SEQ ID NO: 20 and SEQ ID NO: 83; SEQ ID NO: 26 and SEQ ID NO: 88; SEQ ID NO: 32 and SEQ ID NO: 93; SEQ ID NO: 38 and SEQ ID NO: 98; SEQ ID NO: 43 and SEQ ID NO: 103; SEQ ID NO: 48 and SEQ ID NO: 108; SEQ ID NO: 53 and SEQ ID NO: 103; SEQ ID NO: 58 and SEQ ID NO: 113; and SEQ ID NO: 63 and 118; and where an antibody or fragment thereof encoded by the VH and VL encoding polynucleotides specifically binds IGF-R1. In further embodiments, the VH encoding polynucleotide encodes a VH polypeptide comprising VH-CDR1, VH-CDR2, and VH-CDR3 amino acid sequences selected from the group consisting of: SEQ ID NOs: 5, 6, and 7; SEQ ID NOs: 10, 11, and 12; SEQ ID NOs: 15, 16, and 17; SEQ ID NOs: 21, 22, and 23; SEQ ID NOs: 27, 28, and 29; SEQ ID NOs: 33, 34, and 35; SEQ ID NOs: 39, 40, and 41; SEQ ID NOs: 44, 45, and 46; SEQ ID NOs: 49, 50, and 51; SEQ ID NOs: 54, 55, and 56; SEQ ID NOs: 59, 60, and 61; and SEQ ID NOs: 64, 65, and 66; where the VL encoding polynucleotide encodes a VL polypeptide comprising VL-CDR1, VL- CDR2, and VL-CDR3 amino acid sequences selected from the group consisting of: SEQ ID NOs: 69, 70, and 71; SEQ ID NOs: 74, 75, and 76; SEQ ID NOs: 79, 80, and 81; SEQ ID NOs: 84, 85, and 86; SEQ ID NOs: 89, 90, and 91; SEQ ID NOs: 94, 95, and 96; SEQ ID NOs: 99, 100, and 101; SEQ ID NOs: 104, 105, and 106; SEQ ID NOs: 109, 110, and 111; SEQ ID NOs: 114, 115, and 116; and SEQ ID NOs: 119, 120, and 121; and where an antibody or fragment thereof encoded by the VH and VL encoding polynucleotides specifically binds IGF-R1.

In various embodiments of the above-described compositions, the VH encoding polynucleotide further comprises a nucleic acid encoding a signal peptide fused to the antibody VH polypeptide.

In various embodiments of the above-described compositions, the VL encoding polynucleotide further comprises a nucleic acid encoding a signal peptide fused to the antibody VL polypeptide.

In some embodiments of the above-described compositions, the VH encoding polynucleotide further comprises a nucleic acid encoding a heavy chain constant region CH1 domain fused to the VH polypeptide, further comprises a nucleic acid encoding a heavy chain constant region CH2 domain fused to the VH polypeptide, further comprises a nucleic acid encoding a heavy chain constant region CH3 domain fused to the VH polypeptide, or further comprises a nucleic acid encoding a heavy chain hinge region fused to the VH polypeptide. In further embodiments, the heavy chain constant region is human IgG4. In certain other embodiments, the IgG4 is mutagenized to remove glycosylation sites. In further embodiments, the IgG4 mutations comprise S241P and T318A using the Kabat numbering system.

In some embodiments of the above-described compositions, the VL encoding polynucleotide further comprises a nucleic acid encoding a light chain constant region domain fused to the VL polypeptide. In further embodiments, the light chain constant region is human kappa.

In some embodiments of the above-described compositions, the antibody or fragment thereof encoded by the VH and VL encoding polynucleotides specifically binds the same IGF-R1 epitope as a reference monoclonal Fab antibody fragment selected from the group consisting of M13-C06, M14-G11, M14-C03, M14-B01, M12-E01, and M12-G04, or a reference monoclonal antibody produced by a hybridoma selected from the group consisting of P2A7.3E11, 20C8.3B8, P1A2.2B11, 20D8.24B11, P1E2.3B12, and P1G10.2B8.

In some embodiments of the above-described compositions, the antibody or fragment thereof encoded by the VH and VL encoding polynucleotides competitively inhibits a reference monoclonal Fab antibody fragment selected from the group consisting of M13-C06, M14-G11, M14-C03, M14-B01, M12-E01, and M12-G04, or a reference monoclonal antibody produced by a hybridoma selected from the group consisting of P2A7.3E11, 20C8.3B8, P1A2.2B11, 20D8.24B11, P1E2.3B12, and P1G10.2B8 from binding to IGF-R1.

In some embodiments of the above-described compositions, the framework regions of the VH and VL polypeptides are human, except for five or fewer amino acid substitutions.

In some embodiments of the above-described compositions, the antibody or fragment thereof encoded by the VH and VL encoding polynucleotides binds to a linear epitope or a non-linear conformational epitope.

In some embodiments of the above-described compositions, the antibody or fragment thereof encoded by the VH and VL encoding polynucleotides is multivalent, and comprises at least two heavy chains and at least two light chains.

In some embodiments of the above-described compositions, the antibody or fragment thereof encoded by the VH and VL encoding polynucleotides is multispecific. In further embodiments, the antibody or fragment thereof encoded by the VH and VL encoding polynucleotides is bispecific.

In some embodiments of the above-described compositions, the antibody or fragment thereof encoded by the VH and VL encoding polynucleotides comprises heavy and light chain variable domains which are fully human. In further embodiments, the heavy and light chain variable domains are identical to those of a monoclonal Fab antibody fragment selected from the group consisting of M13-C06, M14-G11, M14-C03, M14-B01, M12-E01, and M12-G04.

In some embodiments of the above-described compositions, the antibody or fragment thereof encoded by the VH and VL encoding polynucleotides comprises heavy and light chain variable domains which are murine. In further embodiments, the heavy and light chain variable domains are identical to those of a monoclonal antibody produced by a hybridoma selected from the group consisting of P2A7.3E11, 20C8.3B8, P1A2.2B11, 20D8.24B11, P1E2.3B12, and P1G10.2B8.

In various embodiments of the above-described compositions, the antibody or antigen-binding fragment thereof comprising the polypeptide encoded by the nucleic acid is humanized.

In various embodiments of the above-described compositions, the antibody or antigen-binding fragment thereof comprising the polypeptide encoded by the nucleic acid is primatized.

In various embodiments of the above-described compositions, the antibody or antigen-binding fragment thereof comprising the polypeptide encoded by the nucleic acid is chimeric.

In some embodiments of the above-described compositions, the antibody or antigen-binding fragment thereof comprising the polypeptide encoded by the nucleic acid is fully human.

In various embodiments of the above-described compositions, the antibody or antigen-binding fragment thereof comprising the polypeptide encoded by the nucleic acid is an Fab fragment, an Fab' fragment, an $F(ab)_2$ fragment, or an Fv fragment. In certain embodiments of the above-described compositions, the antibody or antigen-binding fragment thereof comprising the polypeptide encoded by the nucleic acid is a single chain antibody.

In some embodiments of the above-described compositions, the antibody or antigen-binding fragment thereof comprising the polypeptide encoded by the nucleic acid specifically binds to an IGF-R1 polypeptide or fragment thereof, or an IGF-R1 variant polypeptide, with an affinity characterized by a dissociation constant ($K_D$) no greater than $5 \times 10^{-2}$ M, $10^{-2}$ M, $5 \times 10^{-3}$ M, $10^{-3}$ M, $5 \times 10^{-4}$ M, $10^{-4}$ M, $5 \times 10^{-5}$ M, $10^{-5}$ M, $5 \times 10^{-6}$ M, $10^{-6}$ M, $5 \times 10^{-7}$ M, $10^{-7}$ M, $5 \times 10^{-8}$ M, $10^{-8}$ M, $5 \times 10^{-9}$ M, $10^{-9}$ M, $5 \times 10^{-10}$ M, $10^{-10}$ M, $5 \times 10^{-11}$ M, $10^{-11}$ M, $5 \times 10^{-12}$ M, $10^{-12}$ M, $5 \times 10^{-13}$ M, $10^{-13}$ M, $5 \times 10^{-14}$ M, $10^{-14}$ M, $5 \times 10^{-15}$ M, or $10^{-15}$ M.

In some embodiments of the above-described compositions, the antibody or antigen-binding fragment thereof comprising the polypeptide encoded by the nucleic acid preferentially binds to a human IGF-R1 polypeptide or fragment thereof, relative to a murine IGF-R1 polypeptide or fragment thereof or a non-human primate IGF-R1 polypeptide or fragment thereof.

In some embodiments of the above-described compositions, the antibody or antigen-binding fragment thereof comprising the polypeptide encoded by the nucleic acid binds to a human IGF-R1 polypeptide or fragment thereof, and also binds to a non-human primate IGF-R1 polypeptide or fragment thereof.

In some embodiments of the above-described compositions, the antibody or antigen-binding fragment thereof comprising the polypeptide encoded by the nucleic acid binds to IGF-R1 expressed on the surface of a cell. In further embodiments, the cell is a malignant cell, a neoplastic cell, a tumor cell, or a metastatic cell.

In some embodiments of the above-described compositions, the antibody or antigen-binding fragment thereof comprising the polypeptide encoded by said nucleic acid blocks insulin growth factor from binding to IGF-R1. In further embodiments, the insulin growth factor is insulin growth factor-1 (IGF-1) or insulin growth factor-2 (IGF-2). In certain other embodiments of the above-described compositions, the antibody or antigen-binding fragment thereof blocks both IGF-1 and IGF-2 from binding to IGF-R1.

In some embodiments of the above-described compositions, the an antibody or antigen-binding fragment thereof comprising the polypeptide encoded by the nucleic acid inhibits IGF-R1-mediated cell proliferation, inhibits IGF-1 or IGF-2-mediated IGF-R1 phosphorylation, inhibits tumor cell growth or inhibits IGF-R1 internalization.

In some embodiments, the above-described compositions, the VH encoding polynucleotide, the VL encoding polynucleotide, or both the VH and the VL encoding polynucleotides further comprise a nucleic acid encoding a heterologous polypeptide.

In some embodiments of the above-described compositions, the antibody or antigen-binding fragment thereof comprising the polypeptide encoded by the nucleic acid is conjugated to an agent selected from the group consisting of cytotoxic agent, a therapeutic agent, cytostatic agent, a biological toxin, a prodrug, a peptide, a protein, an enzyme, a virus, a lipid, a biological response modifier, pharmaceutical agent, a lymphokine, a heterologous antibody or fragment thereof, a detectable label, polyethylene glycol (PEG), and a combination of two or more of any said agents. In further embodiments, the cytotoxic agent is selected from the group consisting of a radionuclide, a biotoxin, an enzymatically active toxin, a cytostatic or cytotoxic therapeutic agent, a prodrugs, an immunologically active ligand, a biological response modifier, or a combination of two or more of any said cytotoxic agents. In certain other embodiments, the detectable label is selected from the group consisting of an enzyme, a fluorescent label, a chemiluminescent label, a bioluminescent label, a radioactive label, or a combination of two or more of any said detectable labels.

In some embodiments of the above-described compositions, the VH encoding polynucleotide is contained on a first vector and the VL encoding polynucleotide is contained on a second vector. In further embodiments, the VH encoding polynucleotide is operably associated with a first promoter and the VL encoding polynucleotide is operably associated with a second promoter. In certain other embodiments, the first and second promoters are copies of the same promoter. In further embodiments, the first and second promoters non-identical.

In various embodiments of the above-described compositions, the first vector and the second vector are contained in a single host cell.

In certain other embodiments of the above-described compositions, the first vector and the second vector are contained in a separate host cells.

In some embodiments, the invention provides a method of producing an antibody or fragment thereof which specifically binds IGF-1R, comprising culturing the above-described host cells, and recovering the antibody, or fragment thereof.

In other embodiments, the invention provides a method of producing an antibody or fragment thereof which specifically binds IGF-1R, comprising co-culturing separate host cells, and recovering the antibody, or fragment thereof. In further embodiments of the above-described method, the invention provides combining the VH and VL encoding polypeptides, and recovering the antibody, or fragment thereof.

In some embodiments, the invention provides an antibody or fragment thereof which specifically binds IGF-1R, produced by the above-described methods.

In some embodiments, the invention provides compositions, where the VH encoding polynucleotide and the VL encoding polynucleotide are on the same vector, as well as the vectors therein.

In various embodiments of the above described vectors, the VH encoding polynucleotide and the VL encoding polynucleotide are each operably associated with a promoter.

In various embodiments of the above described vectors, the VH encoding polynucleotide and the VL encoding polynucleotide are fused in frame, are co-transcribed from a single promoter operably associated therewith, and are cotranslated into a single chain antibody or antigen-binding fragment thereof.

In various embodiments of the above described vectors, the VH encoding polynucleotide and said VL encoding polynucleotide are co-transcribed from a single promoter operably associated therewith, but are separately translated. In further embodiments, the vectors further comprise an IRES sequence disposed between the VH encoding polynucleotide and the VL encoding polynucleotide. In certain other embodiments, the polynucleotide encoding a VH and the polynucleotide encoding a VL are separately transcribed, each being operably associated with a separate promoter. In further embodiments, the separate promoters are copies of the same promoter or the separate promoters are non-identical.

In some embodiments, the invention provides host cells comprising the above-described vectors.

In other embodiments, the invention provides a method of producing an antibody or fragment thereof which specifically binds IGF-1R, comprising culturing the above-described host cells, and recovering the antibody, or fragment thereof.

In some embodiments, the invention provides an antibody or fragment thereof which specifically binds IGF-1R, produced by the above-described methods.

In some embodiments, the invention provides a method for treating a hyperproliferative disorder in an animal, comprising administering to an animal in need of treatment a composition comprising: a) an isolated antibody or fragment as described above; and b) a pharmaceutically acceptable carrier. In further embodiments, the hyperproliferative disease or disorder is selected from the group consisting of cancer, a neoplasm, a tumor, a malignancy, or a metastasis thereof.

In various embodiments of the above-described methods, the antibody or fragment thereof specifically binds to IGF-1R expressed on the surface of a malignant cell. In further embodiments, the binding of the antibody or fragment thereof to the malignant cell results in growth inhibition of the malignant cell.

In various embodiments of the above-described methods, the antibody or fragment thereof inhibits IGF binding to the malignant cell. In further embodiments, the IGF is IGF-1 or IGF-2.

In various embodiments of the above-described methods, the antibody or fragment thereof inhibits IGF-1 from binding to said malignant cell but does not inhibit IGF-2. In certain other embodiments, the antibody or fragment thereof inhibits IGF-2 from binding to said malignant cell but does not inhibit IGF-1.

In various embodiments of the above-described methods, the antibody or fragment thereof promotes internalization of IGF-1R into the malignant cell.

In various embodiments of the above-described methods, the antibody or fragment thereof inhibits IGF-1R phosphorylation or inhibits tumor cell proliferation. In further embodiments, the tumor cell proliferation is inhibited through the prevention or retardation of metastatic growth.

In various embodiments of the above-described methods, the antibody or fragment thereof inhibits tumor cell migration. In further embodiments, the tumor cell proliferation is inhibited through the prevention or retardation of tumor spread to adjacent tissues.

In various embodiments of the above-described methods, the hyperproliferative disease or disorder is a neoplasm located in the: prostate, colon, abdomen, bone, breast, digestive system, liver, pancreas, peritoneum, adrenal gland, parathyroid gland, pituitary gland, testicles, ovary, thymus, thyroid, eye, head, neck, central nervous system, peripheral nervous system, lymphatic system, pelvis, skin, soft tissue, spleen, thoracic region, or urogenital tract.

In various embodiments of the above-described methods, the hyperproliferative disease is cancer, said cancer selected from the group consisting of: epithelial squamous cell cancer, melanoma, leukemia, myeloma, stomach cancer, brain cancer, lung cancer, pancreatic cancer, cervical cancer, ovarian cancer, liver cancer, bladder cancer, breast cancer, colon cancer, renal cancer, prostate cancer, testicular cancer, thyroid cancer, and head and neck cancer. In further embodiments, the cancer is selected from the group consisting of stomach cancer, renal cancer, brain cancer, bladder cancer, colon cancer, lung cancer, breast cancer, pancreatic cancer, ovarian cancer, and prostate cancer.

In various embodiments of the above-described methods, the animal is a mammal. In further embodiments, the mammal is a human.

BRIEF DESCRIPTION OF THE DRAWINGS

FIG. 3: Anti-IGF-1R Fabs inhibited the (a) IGF-1 and (b) IGF-2 induced phosphorylation in MCF7 cells FIG. 4: Binding of IGF-1R Fab fragment antibodies to soluble IGF-1R (a) and INSR (b) by ELISA.

FIG. 5: The nucleotide and the amino acid sequence of the original and the modified versions of VH and VL chains of M13-C06, M14-G11, M14-C03 and M14-B01. (a) (SEQ ID NO:13) shows the single-stranded DNA sequence of heavy chain M13-C06. (b) (SEQ ID NO:77) shows the single-stranded DNA sequence of light chain M13-C06. (c) (SEQ ID NO:14) shows the amino acid sequence of heavy chain M13-C06. (d) (SEQ ID NO:78) shows the amino acid sequence of light chain M13-C06. (e) (SEQ ID NO:25) shows the single-stranded DNA sequence of heavy chain M14-C03. (f) (SEQ ID NO:87) shows the single-stranded DNA sequence of light chain M14-C03. (g) (SEQ ID NO:26) shows the amino acid sequence of heavy chain M14-C03. (h) (SEQ ID NO:88) shows the amino acid sequence of light chain M14-C03. (i) (SEQ ID NO:31) shows the single-stranded DNA sequence of heavy chain M14-G11. (j) (SEQ ID NO:92) shows the single-stranded DNA sequence of light chain M14-G11. (k) (SEQ ID NO:32) shows the amino acid sequence of heavy chain M14-G11. (l) (SEQ ID NO:93) shows the amino acid sequence of light chain M14-G11. (m) (SEQ ID NO:19) shows the single-stranded DNA sequence of heavy chain M14-B01. (n) (SEQ ID NO:82) shows the single-stranded DNA sequence of light chain M14-B01. (o) (SEQ ID NO:20) shows the amino acid sequence of heavy chain M14-B01. (p) (SEQ ID NO:83) shows the amino acid sequence of light chain M14-B01. (q) (SEQ ID NO:18) shows the single-stranded DNA sequence of sequence optimized heavy chain M13-C06. (r) (SEQ ID NO:14) shows the amino acid sequence of sequence optimized heavy chain M13-C06. (s) (SEQ ID NO:30) shows the single-stranded DNA sequence of sequence optimized heavy chain M14-C03. (t) (SEQ ID NO:26) shows the amino acid sequence of sequence optimized heavy chain M14-C03. (u) (SEQ ID NO:36) shows the single-stranded DNA sequence of sequence optimized heavy chain M14-G11. (v) (SEQ ID NO:32) shows the amino acid sequence of sequence optimized heavy chain M14-G11. (w) (SEQ ID NO:24) shows the single-stranded DNA sequence of sequence optimized heavy chain M14-B01. (x) (SEQ ID NO:20) shows the amino acid sequence of sequence optimized heavy chain M14-B01. (y) (SEQ ID NO:153) shows the single-stranded DNA sequence of light chain constant domain. (z) (SEQ ID NO:154) shows the amino acid sequence of light chain constant domain. (aa) (SEQ ID NO:155) shows the single-stranded DNA sequence of heavy chain agly.IgG4.P constant domains. (bb) (SEQ ID NO:156) shows the amino acid sequence of heavy chain aglyIgG4.P constant domains.

FIG. 7: The binding activity of fully human G4.P (a) and G4.P.agly (b) versions of anti-IGF-1R antibodies as determined by ELISA.

FIG. 8: The binding of fully human antibodies to IGF-1R expressed on MCF-7 (8.a), IGF-1R/3T3 (8.b) cell was determined by flowcytometry. The binding EC50 on MCF-7 ranged between 2.7-12×10-10 nM.

FIG. 13: Internalization of IGF-1R by human anti-IGF-1R antibodies. The internalization of IGF-1R by M13-C06.G4.P.agly antibody (a) was observed at time 0, 15 and 60 min by confocal microscopy. Anti-mouse IGF-1R antibody clone 24-31 was the positive control (b) and mouse 7F2 antibody and a human G4.P antibody IDEC-151. G4.P were the isotype matched negative controls (c) for the experiment.

FIG. 17: Inhibition of NCI-H23 cell proliferation (driven with recombinant human IGF-1 and IGF-2) by M13-C06.G4.P.agly antibody.

FIG. 22: Fully human M13.C06.G4.P.agly antibody administered in combination with gemcitabine exhibits increased efficacy in inhibiting tumor growth.

FIG. 23: Fully human M13.C06.G4.P.agly antibody binds to IGF-1R expressed on an established cynomolgus fibroblast cell line.

FIG. 24: Cross-competition binding analysis of IGF-1R antibody binding epitopes.

DETAILED DESCRIPTION OF THE INVENTION

I. Definitions

Figure 1:
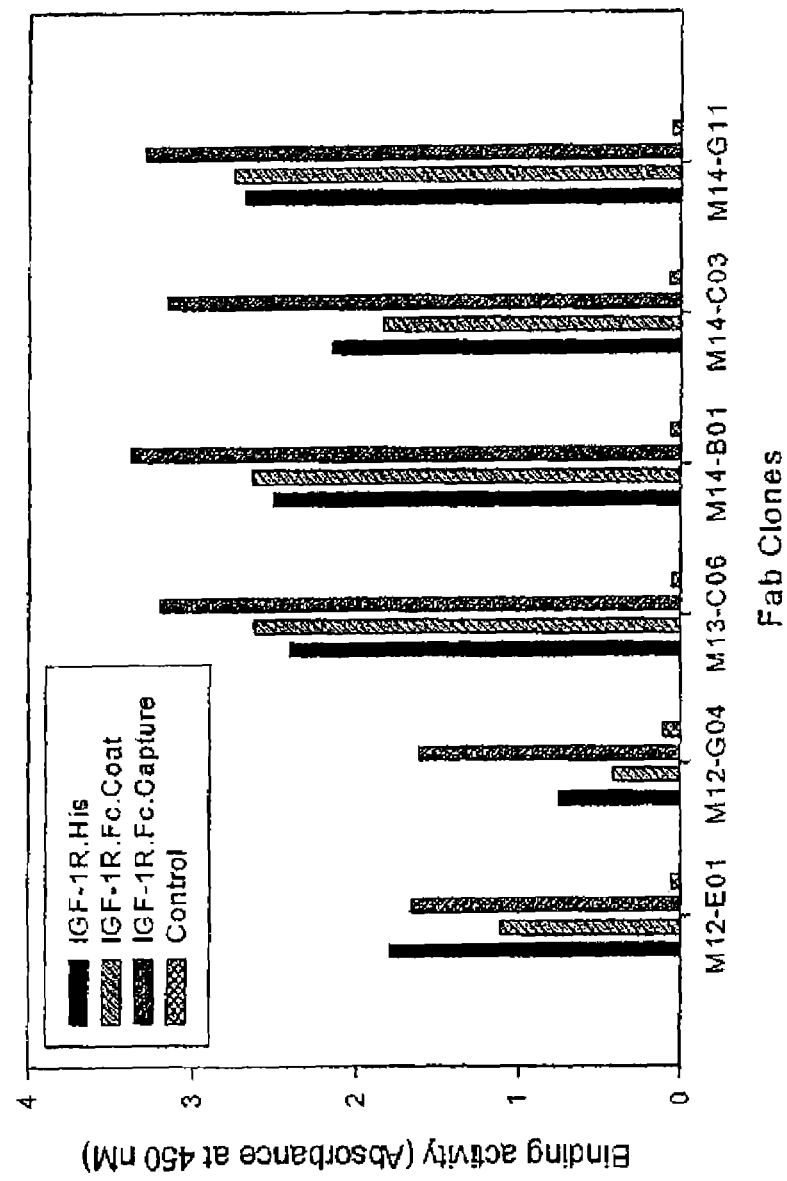
FIG. 1: Binding activity of IGF-1R specific Fabs. (a) Binding of purified anti-IGF1R Fab antibodies to recombinant IGF1R-his and IGF1R-Fc protein by ELISA. (b) Binding of purified anti-IGF1R Fab antibodies to human IGF1R expressed on 3T3 by flowcytometry.
Figure 1:
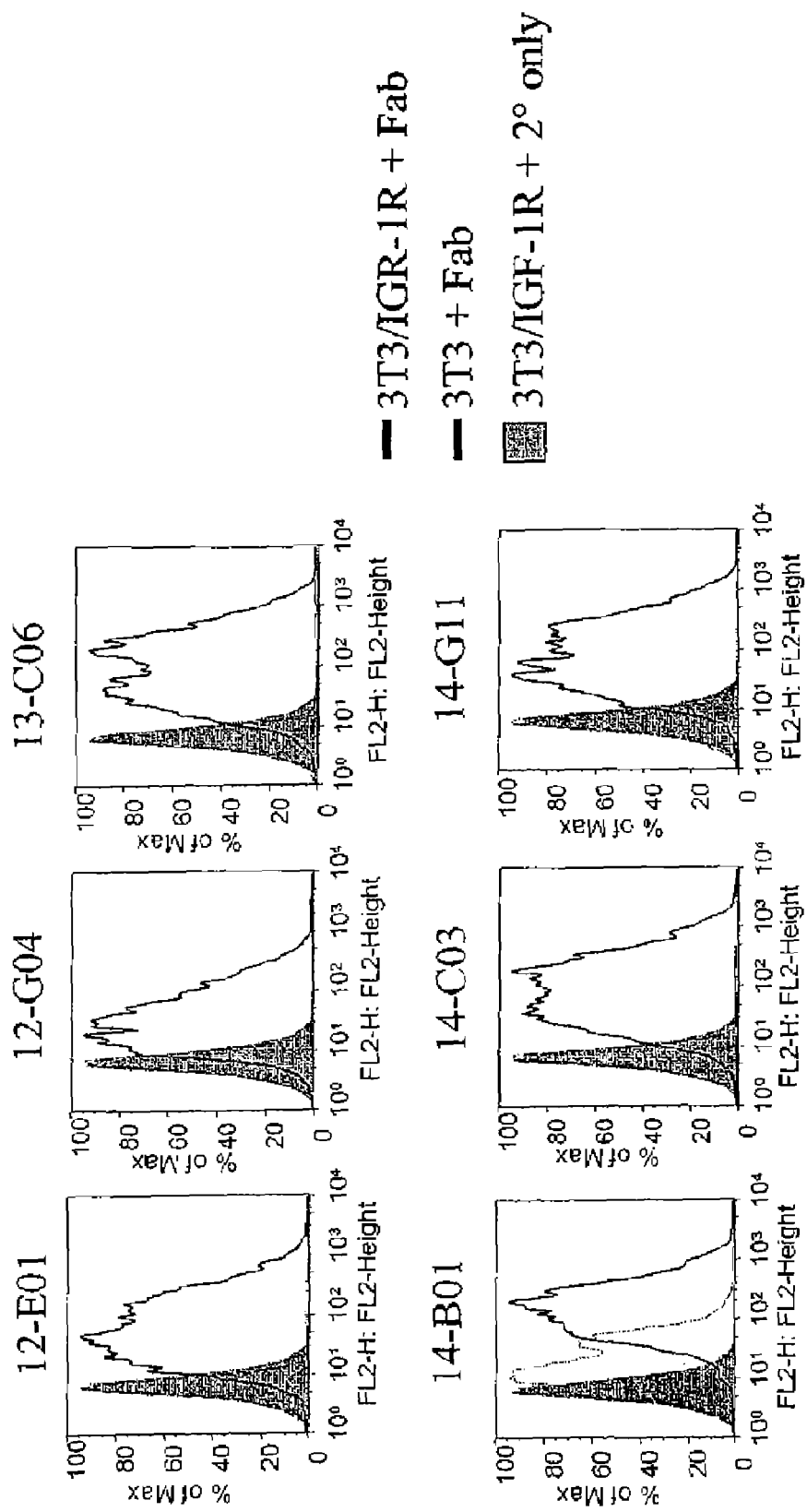

It is to be noted that the term "a" or "an" entity refers to one or more of that entity; for example, "an IGF-1R antibody," is understood to represent one or more IGF-1R antibodies. As such, the terms "a" (or "an"), "one or more," and "at least one" can be used interchangeably herein.

As used herein, the term "polypeptide" is intended to encompass a singular "polypeptide" as well as plural "polypeptides," and refers to a molecule composed of monomers (amino acids) linearly linked by amide bonds (also known as peptide bonds). The term "polypeptide" refers to any chain or chains of two or more amino acids, and does not refer to a specific length of the product. Thus, peptides, dipeptides, tripeptides, oligopeptides, "protein," "amino acid chain," or any other term used to refer to a chain or chains of two or more amino acids, are included within the definition of "polypeptide," and the term "polypeptide" may be used instead of, or interchangeably with any of these terms. The term "polypeptide" is also intended to refer to the products of post-expression modifications of the polypeptide, including without limitation glycosylation, acetylation, phosphorylation, amidation, derivatization by known protecting/blocking groups, proteolytic cleavage, or modification by non-naturally occurring amino acids. A polypeptide may be derived from a natural biological source or produced by recombinant technology, but is not necessarily translated from a designated nucleic acid sequence. It may be generated in any manner, including by chemical synthesis.

A polypeptide of the invention may be of a size of about 3 or more, 5 or more, 10 or more, 20 or more, 25 or more, 50 or more, 75 or more, 100 or more, 200 or more, 500 or more, 1,000 or more, or 2,000 or more amino acids. Polypeptides may have a defined three-dimensional structure, although they do not necessarily have such structure. Polypeptides with a defined three-dimensional structure are referred to as folded, and polypeptides which do not possess a defined three-dimensional structure, but rather can adopt a large number of different conformations, and are referred to as unfolded. As used herein, the term glycoprotein refers to a protein coupled to at least one carbohydrate moiety that is attached to the protein via an oxygen-containing or a nitrogen-containing side chain of an amino acid residue, e.g., a serine residue or an asparagine residue.

By an "isolated" polypeptide or a fragment, variant, or derivative thereof is intended a polypeptide that is not in its natural milieu. No particular level of purification is required. For example, an isolated polypeptide can be removed from its native or natural environment. Recombinantly produced polypeptides and proteins expressed in host cells are considered isolated for purposed of the invention, as are native or recombinant polypeptides which have been separated, fractionated, or partially or substantially purified by any suitable technique.

Also included as polypeptides of the present invention are fragments, derivatives, analogs, or variants of the foregoing polypeptides, and any combination thereof. The terms "fragment," "variant," "derivative" and "analog" when referring to IGF-1R antibodies or antibody polypeptides of the present invention include any polypeptides which retain at least some of the antigen-binding properties of the corresponding native antibody or polypeptide. Fragments of polypeptides of the present invention include proteolytic fragments, as well as deletion fragments, in addition to specific antibody fragments discussed elsewhere herein. Variants of IGF-1R antibodies and antibody polypeptides of the present invention include fragments as described above, and also polypeptides with altered amino acid sequences due to amino acid substitutions, deletions, or insertions. Variants may occur naturally or be non-naturally occurring Non-naturally occurring variants may be produced using art-known mutagenesis techniques. Variant polypeptides may comprise conservative or non-conservative amino acid substitutions, deletions or additions. Derivatives of IGF-1R antibodies and antibody polypeptides of the present invention, are polypeptides which have been altered so as to exhibit additional features not found on the native polypeptide. Examples include fusion proteins. Variant polypeptides may also be referred to herein as "polypeptide analogs." As used herein a "derivative" of an IGF-1R antibody or antibody polypeptide refers to a subject polypeptide having one or more residues chemically derivatized by reaction of a functional side group. Also included as "derivatives" are those peptides which contain one or more naturally occurring amino acid derivatives of the twenty standard amino acids. For example, 4-hydroxyproline may be substituted for proline; 5-hydroxylysine may be substituted for lysine; 3-methylhistidine may be substituted for histidine; homoserine may be substituted for serine; and ornithine may be substituted for lysine.

The term "polynucleotide" is intended to encompass a singular nucleic acid as well as plural nucleic acids, and refers to an isolated nucleic acid molecule or construct, e.g., messenger RNA (mRNA) or plasmid DNA (pDNA). A polynucleotide may comprise a conventional phosphodiester bond or a non-conventional bond (e.g., an amide bond, such as found in peptide nucleic acids (PNA)). The term "nucleic acid" refer to any one or more nucleic acid segments, e.g., DNA or RNA fragments, present in a polynucleotide. By "isolated" nucleic acid or polynucleotide is intended a nucleic acid molecule, DNA or RNA, which has been removed from its native environment. For example, a recombinant polynucleotide encoding an IGF-1R antibody contained in a vector is considered isolated for the purposes of the present invention. Further examples of an isolated polynucleotide include recombinant polynucleotides maintained in heterologous host cells or purified (partially or substantially) polynucleotides in solution. Isolated RNA molecules include in vivo or in vitro RNA transcripts of polynucleotides of the present invention. Isolated polynucleotides or nucleic acids according to the present invention further include such molecules produced synthetically. In addition, polynucleotide or a nucleic acid may be or may include a regulatory element such as a promoter, ribosome binding site, or a transcription terminator.

As used herein, a "coding region" is a portion of nucleic acid which consists of codons translated into amino acids. Although a "stop codon" (TAG, TGA, or TAA) is not translated into an amino acid, it may be considered to be part of a coding region, but any flanking sequences, for example promoters, ribosome binding sites, transcriptional terminators, introns, and the like, are not part of a coding region. Two or more coding regions of the present invention can be present in a single polynucleotide construct, e.g., on a single vector, or in separate polynucleotide constructs, e.g., on separate (different) vectors. Furthermore, any vector may contain a single coding region, or may comprise two or more coding regions, e.g., a single vector may separately encode an immunoglobulin heavy chain variable region and an immunoglobulin light chain variable region. In addition, a vector, polynucleotide, or nucleic acid of the invention may encode heterologous coding regions, either fused or unfused to a nucleic acid encoding an IGF-IR antibody or fragment, variant, or derivative thereof. Heterologous coding regions include without limitation specialized elements or motifs, such as a secretory signal peptide or a heterologous functional domain.

In certain embodiments, the polynucleotide or nucleic acid is DNA. In the case of DNA, a polynucleotide comprising a nucleic acid which encodes a polypeptide normally may include a promoter and/or other transcription or translation control elements operably associated with one or more coding regions. An operable association is when a coding region for a gene product, e.g., a polypeptide, is associated with one or more regulatory sequences in such a way as to place expression of the gene product under the influence or control of the regulatory sequence(s). Two DNA fragments (such as a polypeptide coding region and a promoter associated therewith) are "operably associated" if induction of promoter function results in the transcription of mRNA encoding the desired gene product and if the nature of the linkage between the two DNA fragments does not interfere with the ability of the expression regulatory sequences to direct the expression of the gene product or interfere with the ability of the DNA template to be transcribed. Thus, a promoter region would be operably associated with a nucleic acid encoding a polypeptide if the promoter was capable of effecting transcription of that nucleic acid. The promoter may be a cell-specific promoter that directs substantial transcription of the DNA only in predetermined cells. Other transcription control elements, besides a promoter, for example enhancers, operators, repressors, and transcription termination signals, can be operably associated with the polynucleotide to direct cell-specific transcription. Suitable promoters and other transcription control regions are disclosed herein.

A variety of transcription control regions are known to those skilled in the art. These include, without limitation, transcription control regions which function in vertebrate cells, such as, but not limited to, promoter and enhancer segments from cytomegaloviruses (the immediate early promoter, in conjunction with intron-A), simian virus 40 (the early promoter), and retroviruses (such as Rous sarcoma virus). Other transcription control regions include those derived from vertebrate genes such as actin, heat shock protein, bovine growth hormone and rabbit β-globin, as well as other sequences capable of controlling gene expression in eukaryotic cells. Additional suitable transcription control regions include tissue-specific promoters and enhancers as well as lymphokine-inducible promoters (e.g., promoters inducible by interferons or interleukins).

Similarly, a variety of translation control elements are known to those of ordinary skill in the art. These include, but are not limited to ribosome binding sites, translation initiation and termination codons, and elements derived from picornaviruses (particularly an internal ribosome entry site, or IRES, also referred to as a CITE sequence).

In other embodiments, a polynucleotide of the present invention is RNA, for example, in the form of messenger RNA (mRNA).

Polynucleotide and nucleic acid coding regions of the present invention may be associated with additional coding regions which encode secretory or signal peptides, which direct the secretion of a polypeptide encoded by a polynucleotide of the present invention. According to the signal hypothesis, proteins secreted by mammalian cells have a signal peptide or secretory leader sequence which is cleaved from the mature protein once export of the growing protein chain across the rough endoplasmic reticulum has been initiated. Those of ordinary skill in the art are aware that polypeptides secreted by vertebrate cells generally have a signal peptide fused to the N-terminus of the polypeptide, which is cleaved from the complete or "full length" polypeptide to produce a secreted or "mature" form of the polypeptide. In certain embodiments, the native signal peptide, e.g., an immunoglobulin heavy chain or light chain signal peptide is used, or a functional derivative of that sequence that retains the ability to direct the secretion of the polypeptide that is operably associated with it. Alternatively, a heterologous mammalian signal peptide, or a functional derivative thereof, may be used. For example, the wild-type leader sequence may be substituted with the leader sequence of human tissue plasminogen activator (TPA) or mouse β-glucuronidase.

The present invention is directed to certain IGF-1R antibodies, or antigen-binding fragments, variants, or derivatives thereof. Unless specifically referring to full-sized antibodies such as naturally-occurring antibodies, the term "IGF-1R antibodies" encompasses full-sized antibodies as well as antigen-binding fragments, variants, analogs, or derivatives of such antibodies, e.g., naturally occurring antibody or immunoglobulin molecules or engineered antibody molecules or fragments that bind antigen in a manner similar to antibody molecules.

The terms "antibody" and "immunoglobulin" are used interchangeably herein. An antibody or immunoglobulin comprises at least the variable domain of a heavy chain, and normally comprises at least the variable domains of a heavy chain and a light chain. Basic immunoglobulin structures in vertebrate systems are relatively well understood. See, e.g., Harlow et al., Antibodies: A Laboratory Manual, (Cold Spring Harbor Laboratory Press, 2nd ed. 1988).

As will be discussed in more detail below, the term "immunoglobulin" comprises various broad classes of polypeptides that can be distinguished biochemically. Those skilled in the art will appreciate that heavy chains are classified as gamma, mu, alpha, delta, or epsilon, (γ, μ, α, δ, ε) with some subclasses among them (e.g., γ1-γ4). It is the nature of this chain that determines the "class" of the antibody as IgG, IgM, IgA IgG, or IgE, respectively. The immunoglobulin subclasses (isotypes) e.g., IgG1, IgG2, IgG3, IgG4, IgA1, etc. are well characterized and are known to confer functional specialization. Modified versions of each of these classes and isotypes are readily discernable to the skilled artisan in view of the instant disclosure and, accordingly, are within the scope of the instant invention. All immunoglobulin classes are clearly within the scope of the present invention, the following discussion will generally be directed to the IgG class of immunoglobulin molecules. With regard to IgG, a standard immunoglobulin molecule comprises two identical light chain polypeptides of molecular weight approximately 23,000 Daltons, and two identical heavy chain polypeptides of molecular weight 53,000-70,000. The four chains are typically joined by disulfide bonds in a "Y" configuration wherein the light chains bracket the heavy chains starting at the mouth of the "Y" and continuing through the variable region.

Light chains are classified as either kappa or lambda (κ, λ). Each heavy chain class may be bound with either a kappa or lambda light chain. In general, the light and heavy chains are covalently bonded to each other, and the "tail" portions of the two heavy chains are bonded to each other by covalent disulfide linkages or non-covalent linkages when the immunoglobulins are generated either by hybridomas, B cells or genetically engineered host cells. In the heavy chain, the amino acid sequences run from an N-terminus at the forked ends of the Y configuration to the C-terminus at the bottom of each chain.

Both the light and heavy chains are divided into regions of structural and functional homology. The terms "constant" and "variable" are used functionally. In this regard, it will be appreciated that the variable domains of both the light (VL) and heavy (VH) chain portions determine antigen recognition and specificity. Conversely, the constant domains of the light chain (CL) and the heavy chain (CH1, CH2 or CH3) confer important biological properties such as secretion, transplacental mobility, Fc receptor binding, complement binding, and the like. By convention the numbering of the constant region domains increases as they become more distal from the antigen binding site or amino-terminus of the antibody. The N-terminal portion is a variable region and at the C-terminal portion is a constant region; the CH3 and CL domains actually comprise the carboxy-terminus of the heavy and light chain, respectively.

As indicated above, the variable region allows the antibody to selectively recognize and specifically bind epitopes on antigens. That is, the VL domain and VH domain, or subset of the complementarity determining regions (CDRs), of an antibody combine to form the variable region that defines a three dimensional antigen binding site. This quaternary antibody structure forms the antigen binding site present at the end of each arm of the Y. More specifically, the antigen binding site is defined by three CDRs on each of the VH and VL chains. In some instances, e.g., certain immunoglobulin molecules derived from camelid species or engineered based on camelid immunoglobulins, a complete immunoglobulin molecule may consist of heavy chains only, with no light chains. See, e.g., Hamers-Casterman et al., Nature 363:446-448 (1993).

In naturally occurring antibodies, the six "complementarity determining regions" or "CDRs" present in each antigen binding domain are short, non-contiguous sequences of amino acids that are specifically positioned to form the antigen binding domain as the antibody assumes its three dimensional configuration in an aqueous environment. The remainder of the amino acids in the antigen binding domains, referred to as "framework" regions, show less inter-molecular variability. The framework regions largely adopt a β-sheet conformation and the CDRs form loops which connect, and in some cases form part of, the β-sheet structure. Thus, framework regions act to form a scaffold that provides for positioning the CDRs in correct orientation by inter-chain, non-covalent interactions. The antigen binding domain formed by the positioned CDRs defines a surface complementary to the epitope on the immunoreactive antigen. This complementary surface promotes the non-covalent binding of the antibody to its cognate epitope. The amino acids comprising the CDRs and the framework regions, respectively, can be readily identified for any given heavy or light chain variable region by one of ordinary skill in the art, since they have been precisely defined (see, "Sequences of Proteins of Immunological Interest," Kabat, E., et al., U.S. Department of Health and Human Services, (1983); and Chothia and Lesk, J. Mol. Biol., 196: 901-917 (1987), which are incorporated herein by reference in their entireties).

In the case where there are two or more definitions of a term which is used and/or accepted within the art, the definition of the term as used herein is intended to include all such meanings unless explicitly stated to the contrary. A specific example is the use of the term "complementarity determining region" ("CDR") to describe the non-contiguous antigen combining sites found within the variable region of both heavy and light chain polypeptides. This particular region has been described by Kabat et al., U.S. Dept. of Health and Human Services, "Sequences of Proteins of Immunological Interest" (1983) and by Chothia et al., J. Mol. Biol. 196:901-917 (1987), which are incorporated herein by reference, where the definitions include overlapping or subsets of amino acid residues when compared against each other. Nevertheless, application of either definition to refer to a CDR of an antibody or variants thereof is intended to be within the scope of the term as defined and used herein. The appropriate amino acid residues which encompass the CDRs as defined by each of the above cited references are set forth below in Table I as a comparison. The exact residue numbers which encompass a particular CDR will vary depending on the sequence and size of the CDR. Those skilled in the art can routinely determine which residues comprise a particular CDR given the variable region amino acid sequence of the antibody.

TABLE 1

CDR Definitions[1]

| | Kabat | Chothia |
|---|---|---|
| VH CDR1 | 31-35 | 26-32 |
| VH CDR2 | 50-65 | 52-58 |
| VH CDR3 | 95-102 | 95-102 |
| VL CDR1 | 24-34 | 26-32 |
| VL CDR2 | 50-56 | 50-52 |
| VL CDR3 | 89-97 | 91-96 |

[1]Numbering of all CDR definitions in Table 1 is according to the numbering conventions set forth by Kabat et al. (see below).

Kabat et al. also defined a numbering system for variable domain sequences that is applicable to any antibody. One of ordinary skill in the art can unambigously assign this system of "Kabat numbering" to any variable domain sequence, without reliance on any experimental data beyond the sequence itself. As used herein, "Kabat numbering" refers to the numbering system set forth by Kabat et al., U.S. Dept. of Health and Human Services, "Sequence of Proteins of Immunological Interest" (1983). Unless otherwise specified, references to the numbering of specific amino acid residue positions in an IGF-IR antibody or antigen-binding fragment, variant, or derivative thereof of the present invention are according to the Kabat numbering system.

In camelid species, the heavy chain variable region, referred to as VHH, forms the entire antigen-binding domain. The main differences between camelid VHH variable regions and those derived from conventional antibodies (VH) include (a) more hydrophobic amino acids in the light chain contact surface of VH as compared to the corresponding region in VHH, (b) a longer CDR3 in VHH, and (c) the frequent occurrence of a disulfide bond between CDR1 and CDR3 in VHH.

Antibodies or antigen-binding fragments, variants, or derivatives thereof of the invention include, but are not limited to, polyclonal, monoclonal, multispecific, human, humanized, primatized, or chimeric antibodies, single chain antibodies, epitope-binding fragments, e.g., Fab, Fab' and F(ab')$_2$, Fd, Fvs, single-chain Fvs (scFv), single-chain antibodies, disulfide-linked Fvs (sdFv), fragments comprising either a VL or VH domain, fragments produced by a Fab expression library, and anti-idiotypic (anti-Id) antibodies (including, e.g., anti-Id antibodies to IGF-1R antibodies disclosed herein). ScFv molecules are known in the art and are described, e.g., in U.S. Pat. No. 5,892,019. Immunoglobulin or antibody molecules of the invention can be of any type (e.g., IgG, IgE, IgM, IgD, IgA, and IgY), class (e.g., IgG1, IgG2, IgG3, IgG4, IgA1 and IgA2) or subclass of immunoglobulin molecule.

Antibody fragments, including single-chain antibodies, may comprise the variable region(s) alone or in combination with the entirety or a portion of the following: hinge region, CH1, CH2, and CH3 domains. Also included in the invention are antigen-binding fragments also comprising any combination of variable region(s) with a hinge region, CH1, CH2, and CH3 domains. Antibodies or immunospecific fragments thereof of the present invention may be from any animal origin including birds and mammals. Preferably, the antibodies are human, murine, donkey, rabbit, goat, guinea pig, camel, llama, horse, or chicken antibodies. In another embodiment, the variable region may be condricthoid in origin (e.g., from sharks). As used herein, "human" antibodies include antibodies having the amino acid sequence of a human immunoglobulin and include antibodies isolated from human immunoglobulin libraries or from animals transgenic for one or more human immunoglobulins and that do not express endogenous immunoglobulins, as described infra and, for example in, U.S. Pat. No. 5,939,598 by Kucherlapati et al.

As used herein, the term "heavy chain portion" includes amino acid sequences derived from an immunoglobulin heavy chain. A polypeptide comprising a heavy chain portion comprises at least one of: a CH1 domain, a hinge (e.g., upper, middle, and/or lower hinge region) domain, a CH2 domain, a CH3 domain, or a variant or fragment thereof. For example, a binding polypeptide for use in the invention may comprise a polypeptide chain comprising a CH1 domain; a polypeptide chain comprising a CH1 domain, at least a portion of a hinge domain, and a CH2 domain; a polypeptide chain comprising a CH1 domain and a CH3 domain; a polypeptide chain comprising a CH1 domain, at least a portion of a hinge domain, and a CH3 domain, or a polypeptide chain comprising a CH1 domain, at least a portion of a hinge domain, a CH2 domain, and a CH3 domain. In another embodiment, a polypeptide of the invention comprises a polypeptide chain comprising a CH3 domain. Further, a binding polypeptide for use in the invention may lack at least a portion of a CH2 domain (e.g., all or part of a CH2 domain). As set forth above, it will be understood by one of ordinary skill in the art that these domains (e.g., the heavy chain portions) may be modified such that they vary in amino acid sequence from the naturally occurring immunoglobulin molecule.

In certain IGF-1R antibodies, or antigen-binding fragments, variants, or derivatives thereof disclosed herein, the heavy chain portions of one polypeptide chain of a multimer are identical to those on a second polypeptide chain of the multimer. Alternatively, heavy chain portion-containing monomers of the invention are not identical. For example, each monomer may comprise a different target binding site, forming, for example, a bispecific antibody.

The heavy chain portions of a binding polypeptide for use in the diagnostic and treatment methods disclosed herein may be derived from different immunoglobulin molecules. For example, a heavy chain portion of a polypeptide may comprise a CH1 domain derived from an IgG1 molecule and a hinge region derived from an IgG3 molecule. In another example, a heavy chain portion can comprise a hinge region derived, in part, from an IgG1 molecule and, in part, from an IgG3 molecule. In another example, a heavy chain portion can comprise a chimeric hinge derived, in part, from an IgG1 molecule and, in part, from an IgG4 molecule.

As used herein, the term "light chain portion" includes amino acid sequences derived from an immunoglobulin light chain. Preferably, the light chain portion comprises at least one of a VL or CL domain.

IGF-1R antibodies, or antigen-binding fragments, variants, or derivatives thereof disclosed herein may be described or specified in terms of the epitope(s) or portion(s) of an antigen, e.g., a target polypeptide (IGF-1R) that they recognize or specifically bind. The portion of a target polypeptide which specifically interacts with the antigen binding domain of an antibody is an "epitope," or an "antigenic determinant." A target polypeptide may comprise a single epitope, but typically comprises at least two epitopes, and can include any number of epitopes, depending on the size, conformation, and type of antigen. Furthermore, it should be noted that an "epitope" on a target polypeptide may be or include non-polypeptide elements, e.g., an "epitope may include a carbohydrate side chain.

The minimum size of a peptide or polypeptide epitope for an antibody is thought to be about four to five amino acids. Peptide or polypeptide epitopes preferably contain at least seven, more preferably at least nine and most preferably between at least about 15 to about 30 amino acids. Since a CDR can recognize an antigenic peptide or polypeptide in its tertiary form, the amino acids comprising an epitope need not be contiguous, and in some cases, may not even be on the same peptide chain. In the present invention, peptide or polypeptide epitope recognized by IGF-1R antibodies of the present invention contains a sequence of at least 4, at least 5, at least 6, at least 7, more preferably at least 8, at least 9, at least 10, at least 15, at least 20, at least 25, or between about 15 to about 30 contiguous or non-contiguous amino acids of IGF-1R.

By "specifically binds," it is generally meant that an antibody binds to an epitope via its antigen binding domain, and that the binding entails some complementarity between the antigen binding domain and the epitope. According to this definition, an antibody is said to "specifically bind" to an epitope when it binds to that epitope, via its antigen binding domain more readily than it would bind to a random, unrelated epitope. The term "specificity" is used herein to qualify the relative affinity by which a certain antibody binds to a certain epitope. For example, antibody "A" may be deemed to have a higher specificity for a given epitope than antibody "B," or antibody "A" may be said to bind to epitope "C" with a higher specificity than it has for related epitope "D."

By "preferentially binds," it is meant that the antibody specifically binds to an epitope more readily than it would bind to a related, similar, homologous, or analogous epitope. Thus, an antibody which "preferentially binds" to a given epitope would more likely bind to that epitope than to a related epitope, even though such an antibody may cross-react with the related epitope.

By way of non-limiting example, an antibody may be considered to bind a first epitope preferentially if it binds said first epitope with a dissociation constant ($K_D$) that is less than the antibody's $K_D$ for the second epitope. In another non-limiting example, an antibody may be considered to bind a first antigen preferentially if it binds the first epitope with an affinity that is at least one order of magnitude less than the antibody's $K_D$ for the second epitope. In another non-limiting example, an antibody may be considered to bind a first epitope preferentially if it binds the first epitope with an affinity that is at least two orders of magnitude less than the antibody's $K_D$ for the second epitope.

In another non-limiting example, an antibody may be considered to bind a first epitope preferentially if it binds the first epitope with an off rate (k(off)) that is less than the antibody's k(off) for the second epitope. In another non-limiting example, an antibody may be considered to bind a first epitope preferentially if it binds the first epitope with an affinity that is at least one order of magnitude less than the antibody's k(off) for the second epitope. In another non-limiting example, an antibody may be considered to bind a first epitope preferentially if it binds the first epitope with an affinity that is at least two orders of magnitude less than the antibody's k(off) for the second epitope.

An antibody or antigen-binding fragment, variant, or derivative disclosed herein may be said to bind a target polypeptide disclosed herein or a fragment or variant thereof with an off rate (k(off)) of less than or equal to $5 \times 10^{-2}$ sec$^{-1}$, $10^{-2}$ sec$^{-1}$, $5 \times 10^{-3}$ sec$^{-1}$ or $10^{-3}$ sec$^{-1}$. More preferably, an antibody of the invention may be said to bind a target polypeptide disclosed herein or a fragment or variant thereof with an off rate (k(off)) less than or equal to $5 \times 10^{-4}$ sec$^{-1}$, $10^{-4}$ sec$^{-1}$, $5 \times 10^{-5}$ sec$^{-1}$, or $10^{-5}$ sec$^{-1}$ $5 \times 10^{-6}$ sec$^{-1}$, $10^{-6}$ sec$^{-1}$, $5 \times 10^{-7}$ sec$^{-1}$ or $10^{-7}$ sec$^{-1}$.

An antibody or antigen-binding fragment, variant, or derivative disclosed herein may be said to bind a target polypeptide disclosed herein or a fragment or variant thereof with an on rate (k(on)) of greater than or equal to $10^3$ M$^{-1}$ sec$^{-1}$, $5 \times 10^3$ M$^{-1}$ sec$^{-1}$, $10^4$ M$^{-1}$ sec$^{-1}$ or $5 \times 10^4$ M$^{-1}$ sec$^{-1}$. More preferably, an antibody of the invention may be said to bind a target polypeptide disclosed herein or a fragment or variant thereof with an on rate (k(on)) greater than or equal to $10^5$ M$^{-1}$ sec$^{-1}$, $5 \times 10^5$ M$^{-1}$ sec$^{-1}$, $10^6$ M$^{-1}$ sec$^{-1}$, or $5 \times 10^6$ M$^{-1}$ sec$^{-1}$ or $10^7$ M$^{-1}$ sec$^{-1}$.

An antibody is said to competitively inhibit binding of a reference antibody to a given epitope if it preferentially binds to that epitope to the extent that it blocks, to some degree, binding of the reference antibody to the epitope. Competitive inhibition may be determined by any method known in the art, for example, competition ELISA assays. An antibody may be said to competitively inhibit binding of the reference antibody to a given epitope by at least 90%, at least 80%, at least 70%, at least 60%, or at least 50%.

As used herein, the term "affinity" refers to a measure of the strength of the binding of an individual epitope with the CDR of an immunoglobulin molecule. See, e.g., Harlow et al., Antibodies: A Laboratory Manual, (Cold Spring Harbor Laboratory Press, 2nd ed. 1988) at pages 27-28. As used herein, the term "avidity" refers to the overall stability of the complex between a population of immunoglobulins and an antigen, that is, the functional combining strength of an immunoglobulin mixture with the antigen. See, e.g., Harlow at pages 29-34. Avidity is related to both the affinity of individual immunoglobulin molecules in the population with specific epitopes, and also the valencies of the immunoglobulins and the antigen. For example, the interaction between a bivalent monoclonal antibody and an antigen with a highly repeating epitope structure, such as a polymer, would be one of high avidity.

IGF-1R antibodies or antigen-binding fragments, variants or derivatives thereof of the invention may also be described or specified in terms of their cross-reactivity. As used herein, the term "cross-reactivity" refers to the ability of an antibody, specific for one antigen, to react with a second antigen; a measure of relatedness between two different antigenic substances. Thus, an antibody is cross reactive if it binds to an epitope other than the one that induced its formation. The cross reactive epitope generally contains many of the same complementary structural features as the inducing epitope, and in some cases, may actually fit better than the original.

For example, certain antibodies have some degree of cross-reactivity, in that they bind related, but non-identical epitopes, e.g., epitopes with at least 95%, at least 90%, at least 85%, at least 80%, at least 75%, at least 70%, at least 65%, at least 60%, at least 55%, and at least 50% identity (as calculated using methods known in the art and described herein) to a reference epitope. An antibody may be said to have little or no cross-reactivity if it does not bind epitopes with less than 95%, less than 90%, less than 85%, less than 80%, less than 75%, less than 70%, less than 65%, less than 60%, less than 55%, and less than 50% identity (as calculated using methods known in the art and described herein) to a reference epitope. An antibody may be deemed "highly specific" for a certain epitope, if it does not bind any other analog, ortholog, or homolog of that epitope.

IGF-1R antibodies or antigen-binding fragments, variants or derivatives thereof of the invention may also be described or specified in terms of their binding affinity to a polypeptide of the invention. Preferred binding affinities include those with a dissociation constant or Kd less than $5 \times 10^{-2}$ M, $10^{-2}$ M, $5 \times 10^{-3}$ M, $10^{-3}$ M, $5 \times 10^{-4}$ M, $10^{-4}$ M, $5 \times 10^{-5}$ M, $10^{-5}$ M, $5 \times 10^{-6}$ M, $10^{-6}$ M, $5 \times 10^{-7}$ M, $10^{-7}$ M, $5 \times 10^{-8}$ M, $10^{-8}$ M, $5 \times 10^{-9}$ M, $10^{-9}$ M, $5 \times 10^{-10}$ M, $10^{-10}$ M, $5 \times 10^{-11}$ M, $10^{-11}$ M, $5 \times 10^{-12}$ M, $10^{-12}$ M, $5 \times 10^{-13}$ M, $10^{-13}$ M, $5 \times 10^{-14}$ M, $10^{-14}$ M, $5 \times 10^{-15}$ M, or $10^{-15}$ M.

IGF-1R antibodies or antigen-binding fragments, variants or derivatives thereof of the invention may be "multispecific," e.g., bispecific, trispecific or of greater multispecificity, meaning that it recognizes and binds to two or more different epitopes present on one or more different antigens (e.g., proteins) at the same time. Thus, whether an IGF-1R antibody is "monospecific" or "multispecific," e.g., "bispecific," refers to the number of different epitopes with which a binding polypeptide reacts. Multispecific antibodies may be specific for different epitopes of a target polypeptide described herein or may be specific for a target polypeptide as well as for a heterologous epitope, such as a heterologous polypeptide or solid support material.

As used herein the term "valency" refers to the number of potential binding domains, e.g., antigen binding domains, present in an IGF-1R antibody, binding polypeptide or antibody. Each binding domain specifically binds one epitope. When an IGF-1R antibody, binding polypeptide or antibody comprises more than one binding domain, each binding domain may specifically bind the same epitope, for an antibody with two binding domains, termed "bivalent monospecific," or to different epitopes, for an antibody with two binding domains, termed "bivalent bispecific." An antibody may also be bispecific and bivalent for each specificity (termed "bispecific tetravalent antibodies"). In another embodiment, tetravalent minibodies or domain deleted antibodies can be made.

Bispecific bivalent antibodies, and methods of making them, are described, for instance in U.S. Pat. Nos. 5,731,168; 5,807,706; 5,821,333; and U.S. Appl. Publ. Nos. 2003/0200734 and 2002/0155537, the disclosures of all of which are incorporated by reference herein. Bispecific tetravalent antibodies, and methods of making them are described, for instance, in WO 02/096948 and WO 00/44788, the disclosures of both of which are incorporated by reference herein. See generally, PCT publications WO 93/17715; WO 92/08802; WO 91/00360; WO 92/05793; Tutt et al., J. Immunol. 147:60-69 (1991); U.S. Pat. Nos. 4,474,893; 4,714,681; 4,925,648; 5,573,920; 5,601,819; Kostelny et al., J. Immunol. 148:1547-1553 (1992).

As previously indicated, the subunit structures and three dimensional configuration of the constant regions of the various immunoglobulin classes are well known. As used herein, the term "VH domain" includes the amino terminal variable domain of an immunoglobulin heavy chain and the term "CH1 domain" includes the first (most amino terminal) constant region domain of an immunoglobulin heavy chain. The CH1 domain is adjacent to the VH domain and is amino terminal to the hinge region of an immunoglobulin heavy chain molecule.

As used herein the term "CH2 domain" includes the portion of a heavy chain molecule that extends, e.g., from about residue 244 to residue 360 of an antibody using conventional numbering schemes (residues 244 to 360, Kabat numbering system; and residues 231-340, EU numbering system; see Kabat E A et al. op. cit. The CH2 domain is unique in that it is not closely paired with another domain. Rather, two N-linked branched carbohydrate chains are interposed between the two CH2 domains of an intact native IgG molecule. It is also well documented that the CH3 domain extends from the CH2 domain to the C-terminal of the IgG molecule and comprises approximately 108 residues.

As used herein, the term "hinge region" includes the portion of a heavy chain molecule that joins the CH1 domain to the CH2 domain. This hinge region comprises approximately 25 residues and is flexible, thus allowing the two N-terminal antigen binding regions to move independently. Hinge regions can be subdivided into three distinct domains: upper, middle, and lower hinge domains (Roux et al., J. Immunol. 161:4083 (1998)).

As used herein the term "disulfide bond" includes the covalent bond formed between two sulfur atoms. The amino acid cysteine comprises a thiol group that can form a disulfide bond or bridge with a second thiol group. In most naturally occurring IgG molecules, the CH1 and CL regions are linked by a disulfide bond and the two heavy chains are linked by two disulfide bonds at positions corresponding to 239 and 242 using the Kabat numbering system (position 226 or 229, EU numbering system).

As used herein, the term "chimeric antibody" will be held to mean any antibody wherein the immunoreactive region or site is obtained or derived from a first species and the constant region (which may be intact, partial or modified in accordance with the instant invention) is obtained from a second species. In preferred embodiments the target binding region or site will be from a non-human source (e.g. mouse or primate) and the constant region is human.

As used herein, the term "engineered antibody" refers to an antibody in which the variable domain in either the heavy and light chain or both is altered by at least partial replacement of one or more CDRs from an antibody of known specificity and, if necessary, by partial framework region replacement and sequence changing. Although the CDRs may be derived from an antibody of the same class or even subclass as the antibody from which the framework regions are derived, it is envisaged that the CDRs will be derived from an antibody of different class and preferably from an antibody from a different species. An engineered antibody in which one or more "donor" CDRs from a non-human antibody of known specificity is grafted into a human heavy or light chain framework region is referred to herein as a "humanized antibody." It may not be necessary to replace all of the CDRs with the complete CDRs from the donor variable region to transfer the antigen binding capacity of one variable domain to another. Rather, it may only be necessary to transfer those residues that are necessary to maintain the activity of the target binding site. Given the explanations set forth in, e.g., U.S. Pat. Nos. 5,585,089, 5,693,761, 5,693,762, and 6,180,370, it will be well within the competence of those skilled in the art, either by carrying out routine experimentation or by trial and error testing to obtain a functional engineered or humanized antibody.

As used herein the term "properly folded polypeptide" includes polypeptides (e.g., IGF-1R antibodies) in which all of the functional domains comprising the polypeptide are distinctly active. As used herein, the term "improperly folded polypeptide" includes polypeptides in which at least one of the functional domains of the polypeptide is not active. In one embodiment, a properly folded polypeptide comprises polypeptide chains linked by at least one disulfide bond and, conversely, an improperly folded polypeptide comprises polypeptide chains not linked by at least one disulfide bond.

As used herein the term "engineered" includes manipulation of nucleic acid or polypeptide molecules by synthetic means (e.g. by recombinant techniques, in vitro peptide synthesis, by enzymatic or chemical coupling of peptides or some combination of these techniques).

As used herein, the terms "linked," "fused" or "fusion" are used interchangeably. These terms refer to the joining together of two more elements or components, by whatever means including chemical conjugation or recombinant means. An "in-frame fusion" refers to the joining of two or more polynucleotide open reading frames (ORFs) to form a continuous longer ORF, in a manner that maintains the correct translational reading frame of the original ORFs. Thus, a recombinant fusion protein is a single protein containing two ore more segments that correspond to polypeptides encoded by the original ORFs (which segments are not normally so joined in nature.) Although the reading frame is thus made continuous throughout the fused segments, the segments may be physically or spatially separated by, for example, in-frame linker sequence. For example, polynucleotides encoding the CDRs of an immunoglobulin variable region may be fused, in-frame, but be separated by a polynucleotide encoding at least one immunoglobulin framework region or additional CDR regions, as long as the "fused" CDRs are co-translated as part of a continuous polypeptide.

In the context of polypeptides, a "linear sequence" or a "sequence" is an order of amino acids in a polypeptide in an amino to carboxyl terminal direction in which residues that neighbor each other in the sequence are contiguous in the primary structure of the polypeptide.

The term "expression" as used herein refers to a process by which a gene produces a biochemical, for example, an RNA or polypeptide. The process includes any manifestation of the functional presence of the gene within the cell including, without limitation, gene knockdown as well as both transient expression and stable expression. It includes without limitation transcription of the gene into messenger RNA (mRNA), transfer RNA (tRNA), small hairpin RNA (shRNA), small interfering RNA (siRNA) or any other RNA product, and the translation of such mRNA into polypeptide(s). If the final desired product is a biochemical, expression includes the creation of that biochemical and any precursors. Expression of a gene produces a "gene product." As used herein, a gene product can be either a nucleic acid, e.g., a messenger RNA produced by transcription of a gene, or a polypeptide which is translated from a transcript. Gene products described herein further include nucleic acids with post transcriptional modifications, e.g., polyadenylation, or polypeptides with post translational modifications, e.g., methylation, glycosylation, the addition of lipids, association with other protein subunits, proteolytic cleavage, and the like.

As used herein, the terms "treat" or "treatment" refer to both therapeutic treatment and prophylactic or preventative measures, wherein the object is to prevent or slow down (lessen) an undesired physiological change or disorder, such as the development or spread of cancer. Beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the condition or disorder is to be prevented.

By "subject" or "individual" or "animal" or "patient" or "mammal," is meant any subject, particularly a mammalian subject, for whom diagnosis, prognosis, or therapy is desired. Mammalian subjects include humans, domestic animals, farm animals, and zoo, sports, or pet animals such as dogs, cats, guinea pigs, rabbits, rats, mice, horses, cattle, cows, and so on.

As used herein, phrases such as "a subject that would benefit from administration of a binding molecule" and "an animal in need of treatment" includes subjects, such as mammalian subjects, that would benefit from administration of a binding molecule used, e.g., for detection of an antigen recognized by a binding molecule (e.g., for a diagnostic procedure) and/or from treatment, i.e., palliation or prevention of a disease such as cancer, with a binding molecule which specifically binds a given target protein. As described in more detail herein, the binding molecule can be used in unconjugated form or can be conjugated, e.g., to a drug, prodrug, or an isotope.

By "hyperproliferative disease or disorder" is meant all neoplastic cell growth and proliferation, whether malignant or benign, including all transformed cells and tissues and all cancerous cells and tissues. Hyperproliferative diseases or disorders include, but are not limited to, precancerous lesions, abnormal cell growths, benign tumors, malignant tumors, and "cancer." In certain embodiments of the present invention, the hyperproliferative disease or disorder, e.g., the precancerous lesion, abnormal cell growth, benign tumor, malignant tumor, or "cancer" comprises cells which express, over-express, or abnormally express IGF-1R.

Additional examples of hyperproliferative diseases, disorders, and/or conditions include, but are not limited to neoplasms, whether benign or malignant, located in the: prostate, colon, abdomen, bone, breast, digestive system, liver, pancreas, peritoneum, endocrine glands (adrenal, parathyroid, pituitary, testicles, ovary, thymus, thyroid), eye, head and neck, nervous (central and peripheral), lymphatic system, pelvic, skin, soft tissue, spleen, thoracic, and urogenital tract. Such neoplasms, in certain embodiments, express, over-express, or abnormally express IGF-1R.

Other hyperproliferative disorders include, but are not limited to: hypergammaglobulinemia, lymphoproliferative disorders, paraproteinemias, purpura, sarcoidosis, Sezary Syndrome, Waldenstron's macroglobulinemia, Gaucher's Disease, histiocytosis, and any other hyperproliferative disease, besides neoplasia, located in an organ system listed above. In certain embodiments of the present invention the diseases involve cells which express, over-express, or abnormally express IGF-1R.

As used herein, the terms "tumor" or "tumor tissue" refer to an abnormal mass of tissue that results from excessive cell division, in certain cases tissue comprising cells which express, over-express, or abnormally express IGF-1R. A tumor or tumor tissue comprises "tumor cells" which are neoplastic cells with abnormal growth properties and no useful bodily function. Tumors, tumor tissue and tumor cells may be benign or malignant. A tumor or tumor tissue may also comprise "tumor-associated non-tumor cells", e.g., vascular cells which form blood vessels to supply the tumor or tumor tissue. Non-tumor cells may be induced to replicate and develop by tumor cells, for example, the induction of angiogenesis in a tumor or tumor tissue.

As used herein, the term "malignancy" refers to a non-benign tumor or a cancer. As used herein, the term "cancer" connotes a type of hyperproliferative disease which includes a malignancy characterized by deregulated or uncontrolled cell growth. Examples of cancer include, but are not limited to, carcinoma, lymphoma, blastoma, sarcoma, and leukemia or lymphoid malignancies. More particular examples of such cancers are noted below and include: squamous cell cancer (e.g. epithelial squamous cell cancer), lung cancer including small-cell lung cancer, non-small cell lung cancer, adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial cancer or uterine carcinoma, salivary gland carcinoma, kidney or renal cancer, prostate cancer, vulval cancer, thyroid cancer, hepatic carcinoma, anal carcinoma, penile carcinoma, as well as head and neck cancer. The term "cancer" includes primary malignant cells or tumors (e.g., those whose cells have not migrated to sites in the subject's body other than the site of the original malignancy or tumor) and secondary malignant cells or tumors (e.g., those arising from metastasis, the migration of malignant cells or tumor cells to secondary sites that are different from the site of the original tumor). Cancers conducive to treatment methods of the present invention involves cells which express, over-express, or abnormally express IGF-1R.

Other examples of cancers or malignancies include, but are not limited to: Acute Childhood Lymphoblastic Leukemia, Acute Lymphoblastic Leukemia, Acute Lymphocytic Leukemia, Acute Myeloid Leukemia, Adrenocortical Carcinoma, Adult (Primary) Hepatocellular Cancer, Adult (Primary) Liver Cancer, Adult Acute Lymphocytic Leukemia, Adult Acute Myeloid Leukemia, Adult Hodgkin's Disease, Adult Hodgkin's Lymphoma, Adult Lymphocytic Leukemia, Adult Non-Hodgkin's Lymphoma, Adult Primary Liver Cancer, Adult Soft Tissue Sarcoma, AIDS-Related Lymphoma, AIDS-Related Malignancies, Anal Cancer, Astrocytoma, Bile Duct Cancer, Bladder Cancer, Bone Cancer, Brain Stem Glioma, Brain Tumors, Breast Cancer, Cancer of the Renal Pelvis and Ureter, Central Nervous System (Primary) Lymphoma, Central Nervous System Lymphoma, Cerebellar Astrocytoma, Cerebral Astrocytoma, Cervical Cancer, Childhood (Primary) Hepatocellular Cancer, Childhood (Primary) Liver Cancer, Childhood Acute Lymphoblastic Leukemia, Childhood Acute Myeloid Leukemia, Childhood Brain Stem Glioma, Childhood Cerebellar Astrocytoma, Childhood Cerebral Astrocytoma, Childhood Extracranial Germ Cell Tumors, Childhood Hodgkin's Disease, Childhood Hodgkin's Lymphoma, Childhood Hypothalamic and Visual Pathway Glioma, Childhood Lymphoblastic Leukemia, Childhood Medulloblastoma, Childhood Non-Hodgkin's Lymphoma, Childhood Pineal and Supratentorial Primitive Neuroectodermal Tumors, Childhood Primary Liver Cancer, Childhood Rhabdomyosarcoma, Childhood Soft Tissue Sarcoma, Childhood Visual Pathway and Hypothalamic Glioma, Chronic Lymphocytic Leukemia, Chronic Myelogenous Leukemia, Colon Cancer, Cutaneous T-Cell Lymphoma, Endocrine Pancreas Islet Cell Carcinoma, Endometrial Cancer, Ependymoma, Epithelial Cancer, Esophageal Cancer, Ewing's Sarcoma and Related Tumors, Exocrine Pancreatic Cancer, Extracranial Germ Cell Tumor, Extragonadal Germ Cell Tumor, Extrahepatic Bile Duct Cancer, Eye Cancer, Female Breast Cancer, Gaucher's Disease, Gallbladder Cancer, Gastric Cancer, Gastrointestinal Carcinoid Tumor, Gastrointestinal Tumors, Germ Cell Tumors, Gestational Trophoblastic Tumor, Hairy Cell Leukemia, Head and Neck Cancer, Hepatocellular Cancer, Hodgkin's Disease, Hodgkin's Lymphoma, Hypergammaglobulinemia, Hypopharyngeal Cancer, Intestinal Cancers, Intraocular Melanoma, Islet Cell Carcinoma, Islet Cell Pancreatic Cancer, Kaposi's Sarcoma, Kidney Cancer, Laryngeal Cancer, Lip and Oral Cavity Cancer, Liver Cancer, Lung Cancer, Lymphoproliferative Disorders, Macroglobulinemia, Male Breast Cancer, Malignant Mesothelioma, Malignant Thymoma, Medulloblastoma, Melanoma, Mesothelioma, Metastatic Occult Primary Squamous Neck Cancer, Metastatic Primary Squamous Neck Cancer, Metastatic Squamous Neck Cancer, Multiple Myeloma, Multiple Myeloma/Plasma Cell Neoplasm, Myelodysplastic Syndrome, Myelogenous Leukemia, Myeloid Leukemia, Myeloproliferative Disorders, Nasal Cavity and Paranasal Sinus Cancer, Nasopharyngeal Cancer, Neuroblastoma, Non-Hodgkin's Lymphoma During Pregnancy, Nonmelanoma Skin Cancer, Non-Small Cell Lung Cancer, Occult Primary Metastatic Squamous Neck Cancer, Oropharyngeal Cancer, Osteo-/Malignant Fibrous Sarcoma, Osteosarcoma/Malignant Fibrous Histiocytoma, Osteosarcoma/Malignant Fibrous Histiocytoma of Bone, Ovarian Epithelial Cancer, Ovarian Germ Cell Tumor, Ovarian Low Malignant Potential Tumor, Pancreatic Cancer, Paraproteinemias, Purpura, Parathyroid Cancer, Penile Cancer, Pheochromocytoma, Pituitary Tumor, Plasma Cell Neoplasm/Multiple Myeloma, Primary Central Nervous System Lymphoma, Primary Liver Cancer, Prostate Cancer, Rectal Cancer, Renal Cell Cancer, Renal Pelvis and Ureter Cancer, Retinoblastoma, Rhabdomyosarcoma, Salivary Gland Cancer, Sarcoidosis Sarcomas, Sezary Syndrome, Skin Cancer, Small Cell Lung Cancer, Small Intestine Cancer, Soft Tissue Sarcoma, Squamous Neck Cancer, Stomach Cancer, Supratentorial Primitive Neuroectodermal and Pineal Tumors, T-Cell Lymphoma, Testicular Cancer, Thymoma, Thyroid Cancer, Transitional Cell Cancer of the Renal Pelvis and Ureter, Transitional Renal Pelvis and Ureter Cancer, Trophoblastic Tumors, Ureter and Renal Pelvis Cell Cancer, Urethral Cancer, Uterine Cancer, Uterine Sarcoma, Vaginal Cancer, Visual Pathway and Hypothalamic Glioma, Vulvar Cancer, Waldenstrom's Macroglobulinemia, Wilms' Tumor, and any other hyperproliferative disease, besides neoplasia, located in an organ system listed above.

The method of the present invention may be used to treat premalignant conditions and to prevent progression to a neoplastic or malignant state, including but not limited to those disorders described above. Such uses are indicated in conditions known or suspected of preceding progression to neoplasia or cancer, in particular, where non-neoplastic cell growth consisting of hyperplasia, metaplasia, or most particularly, dysplasia has occurred (for review of such abnormal growth conditions, see Robbins and Angell, *Basic Pathology*, 2d Ed., W. B. Saunders Co., Philadelphia, pp. 68-79 (1976). Such conditions in which cells begin to express, over-express, or abnormally express IGF-1R, are particularly treatable by the methods of the present invention.

Hyperplasia is a form of controlled cell proliferation, involving an increase in cell number in a tissue or organ, without significant alteration in structure or function. Hyperplastic disorders which can be treated by the method of the invention include, but are not limited to, angiofollicular mediastinal lymph node hyperplasia, angiolymphoid hyperplasia with eosinophilia, atypical melanocytic hyperplasia, basal cell hyperplasia, benign giant lymph node hyperplasia, cementum hyperplasia, congenital adrenal hyperplasia, congenital sebaceous hyperplasia, cystic hyperplasia, cystic hyperplasia of the breast, denture hyperplasia, ductal hyperplasia, endometrial hyperplasia, fibromuscular hyperplasia, focal epithelial hyperplasia, gingival hyperplasia, inflammatory fibrous hyperplasia, inflammatory papillary hyperplasia, intravascular papillary endothelial hyperplasia, nodular hyperplasia of prostate, nodular regenerative hyperplasia, pseudoepitheliomatous hyperplasia, senile sebaceous hyperplasia, and verrucous hyperplasia.

Metaplasia is a form of controlled cell growth in which one type of adult or fully differentiated cell substitutes for another type of adult cell. Metaplastic disorders which can be treated by the method of the invention include, but are not limited to, agnogenic myeloid metaplasia, apocrine metaplasia, atypical metaplasia, autoparenchymatous metaplasia, connective tissue metaplasia, epithelial metaplasia, intestinal metaplasia, metaplastic anemia, metaplastic ossification, metaplastic polyps, myeloid metaplasia, primary myeloid metaplasia, secondary myeloid metaplasia, squamous metaplasia, squamous metaplasia of amnion, and symptomatic myeloid metaplasia.

Dysplasia is frequently a forerunner of cancer, and is found mainly in the epithelia; it is the most disorderly form of non-neoplastic cell growth, involving a loss in individual cell uniformity and in the architectural orientation of cells. Dysplastic cells often have abnormally large, deeply stained nuclei, and exhibit pleomorphism. Dysplasia characteristically occurs where there exists chronic irritation or inflammation. Dysplastic disorders which can be treated by the method of the invention include, but are not limited to, anhidrotic ectodermal dysplasia, anterofacial dysplasia, asphyxiating thoracic dysplasia, atriodigital dysplasia, bronchopulmonary dysplasia, cerebral dysplasia, cervical dysplasia, chondroectodermal dysplasia, cleidocranial dysplasia, congenital ectodermal dysplasia, craniodiaphysial dysplasia, craniocarpotarsal dysplasia, craniometaphysial dysplasia, dentin dysplasia, diaphysial dysplasia, ectodermal dysplasia, enamel dysplasia, encephalo-ophthalmic dysplasia, dysplasia epiphysialis hemimelia, dysplasia epiphysialis multiplex, dysplasia epiphysialis punctata, epithelial dysplasia, faciodigitogenital dysplasia, familial fibrous dysplasia of jaws, familial white folded dysplasia, fibromuscular dysplasia, fibrous dysplasia of bone, florid osseous dysplasia, hereditary renal-retinal dysplasia, hidrotic ectodermal dysplasia, hypohidrotic ectodermal dysplasia, lymphopenic thymic dysplasia, mammary dysplasia, mandibulofacial dysplasia, metaphysial dysplasia, Mondini dysplasia, monostotic fibrous dysplasia, mucoepithelial dysplasia, multiple epiphysial dysplasia, oculoauriculovertebral dysplasia, oculodentodigital dysplasia, oculovertebral dysplasia, odontogenic dysplasia, opthalmomandibulomelic dysplasia, periapical cemental dysplasia, polyostotic fibrous dysplasia, pseudoachondroplastic spondyloepiphysial dysplasia, retinal dysplasia, septo-optic dysplasia, spondyloepiphysial dysplasia, and ventriculoradial dysplasia.

Additional pre-neoplastic disorders which can be treated by the method of the invention include, but are not limited to, benign dysproliferative disorders (e.g., benign tumors, fibrocystic conditions, tissue hypertrophy, intestinal polyps, colon polyps, and esophageal dysplasia), leukoplakia, keratoses, Bowen's disease, Farmer's Skin, solar cheilitis, and solar keratosis.

In preferred embodiments, the method of the invention is used to inhibit growth, progression, and/or metastasis of cancers, in particular those listed above.

Additional hyperproliferative diseases, disorders, and/or conditions include, but are not limited to, progression, and/or metastases of malignancies and related disorders such as leukemia (including acute leukemias (e.g., acute lymphocytic leukemia, acute myelocytic leukemia (including myeloblastic, promyelocytic, myelomonocytic, monocytic, and erythroleukemia)) and chronic leukemias (e.g., chronic myelocytic (granulocytic) leukemia and chronic lymphocytic leukemia)), polycythemia vera, lymphomas (e.g., Hodgkin's disease and non-Hodgkin's disease), multiple myeloma, Waldenstrom's macroglobulinemia, heavy chain disease, and solid tumors including, but not limited to, sarcomas and carcinomas such as fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, emangioblastoma, acoustic neuroma, oligodendroglioma, menangioma, melanoma, neuroblastoma, and retinoblastoma.

II. IGF-1R

Naturally occurring insulin-like growth factor receptor-1 (IGF-1R) IGF-1R is a heterotetrameric plasma membrane glycoprotein composed of two α-subunits (130 kDa each) and two β-subunits (90 kDa each) linked by disulfide bonds. Massagué, J. and Czech, M. P. *J. Biol. Chem.* 257:5038-5045 (1992). IGF-1R is also known in the art by the names CD221 and JTK13. The nucleic acid sequence of the human IGF-1R mRNA is available under GenBank Accession Number NM_000875, and is presented herein as SEQ ID NO:1.

```
                                              SEQ ID NO: 1
>gi|11068002|ref|NM_000875.2| Homo sapiens insulin-
like growth factor 1 receptor (IGF1R), mRNA
TTTTTTTTTTTTTTGAGAAAGGGAATTTCATCCCAAATAAAAGGAATGAA

GTCTGGCTCCGGAGGAGGGTCCCCGACCTCGCTGTGGGGGCTCCTGTTTC

TCTCCGCCGCGCTCTCGCTCTGGCCGACGAGTGGAGAAATCTGCGGGCCA

GGCATCGACATCCGCAACGACTATCAGCAGCTGAAGCGCCTGGAGAACTG
```

-continued

CACGGTGATCGAGGGCTACCTCCACATCCTGCTCATCTCCAAGGCCGAGG
ACTACCGCAGCTACCGCTTCCCCAAGCTCACGGTCATTACCGAGTACTTG
CTGCTGTTCCGAGTGGCTGGCCTGAGAGCCTCGGAGACCTCTTCCCCAA
CCTCACGGTCATCCGCGGCTGGAAACTCTTCTACAACTACGCCCTGGTCA
TCTTCGAGATGACCAATCTCAAGGATATTGGGCTTTACAACCTGAGGAAC
ATTACTCGGGGGGCCATCAGGATTGAGAAAAATGCTGACCTCTGTTACCT
CTCCACTGTGGACTGGTCCCTGATCCTGGATGCGGTGTCCAATAACTACA
TTGTGGGGAATAAGCCCCCAAAGGAATGTGGGGACCTGTGTCCAGGGACC
ATGGAGGAGAAGCCGATGTGTGAGAAGACCACCATCAACAATGAGTACAA
CTACCGCTGCTGGACCACAAACCGCTGCCAGAAAATGTGCCCAAGCACGT
GTGGGAAGCGGGCGTGCACCGAGAACAATGAGTGCTGCCACCCCGAGTGC
CTGGGCAGCTGCAGCGCGCCTGACAACGACACGGCCTGTGTAGCTTGCCG
CCACTACTACTATGCCGGTGTCTGTGTGCCTGCCTGCCCGCCCAACACCT
ACAGGTTTGAGGGCTGGCGCTGTGTGGACCGTGACTTCTGCGCCAACATC
CTCAGCGCCGAGAGCAGCGACTCCGAGGGGTTTGTGATCCACGACGGCGA
GTGCATGCAGGAGTGCCCCTCGGGCTTCATCCGCAACGGCAGCCAGAGCA
TGTACTGCATCCCTTGTGAAGGTCCTTGCCCGAAGGTCTGTGAGGAAGAA
AAGAAAACAAAGACCATTGATTCTGTTACTTCTGCTCAGATGCTCCAAGG
ATGCACCATCTTCAAGGGCAATTTGCTCATTAACATCCGACGGGGAATA
ACATTGCTTCAGAGCTGGAGAACTTCATGGGGCTCATCGAGGTGGTGACG
GGCTACGTGAAGATCCGCCATTCTCATGCCTTGGTCTCCTTGTCCTTCCT
AAAAAAACCTTCGCCTCATCCTAGGAGAGGAGCAGCTAGAAGGGAATTACT
CCTTCTACGTCCTCGACAACCAGAACTTGCAGCAACTGTGGGACTGGGAC
CACCGCAACCTGACCATCAAAGCAGGGAAAATGTACTTTGCTTTCAATCC
CAAATTATGTGTTTCCGAAATTTACCGCATGGAGGAAGTGACGGGGACTA
AAGGGCGCCAAAGCAAAGGGGACATAAACACCAGGAACAACGGGGAGAGA
GCCTCCTGTGAAAGTGACGTCCTGCATTTCACCTCCACCACCACGTCGAA
GAATCGCATCATCATAACCTGGCACCGGTACCGGCCCCCTGACTACAGGG
ATCTCATCAGCTTCACCGTTTACTACAAGGAAGCACCCTTTAAGAATGTC
ACAGAGTATGATGGGCAGGATGCCTGCGCTCCAACAGCTGGAACATGGT
GGACGTGGACCTCCCGCCCAACAAGGACGTGGAGCCCGGCATCTTACTAC
ATGGGCTGAAGCCCTGGACTCAGTACGCCGTTTACGTCAAGGCTGTGACC
CTCACCATGGTGGAGAACGACCATATCCGTGGGGCCAAGAGTGAGATCTT
GTACATTCGCACCAATGCTTCAGTTCCTTCCATTCCCTTGGACGTTCTTT
CAGCATCGAACTCCTCTTCTCAGTTAATCGTGAAGTGGAACCCTCCCTCT
CTGCCCAACGGCAACCTGAGTTACTACATTGTGCGCTGGCAGCGGCAGCC
TCAGGACGGCTACCTTTACCGGCACAATTACTGCTCCAAAGACAAAATCC
CCATCAGGAAGTATGCCGACGGCACCATCGACATTGAGGAGGTCACAGAG
AACCCCAAGACTGAGGTGTGTGGTGGGGAGAAAGGGCCTTGCTGCGCCTG
CCCCAAAACTGAAGCCGAGAAGCAGGCCGAGAAGGAGGAGGCTGAATACC

-continued

GCAAAGTCTTTGAGAATTTCCTGCACAACTCCATCTTCGTGCCCAGACCT
GAAAGGAAGCGGAGAGATGTCATGCAAGTGGCCAACACCACCATGTCCAG
CCGAAGCAGGAACACCACGGCCGCAGACACCTACAACATCACCGACCCGG
AAGAGCTGGAGACAGAGTACCCTTTCTTTGAGAGCAGAGTGGATAACAAG
GAGAGAACTGTCATTTCTAACCTTCGGCCTTTCACATTGTACCGCATCGA
TATCCACAGCTGCAACCACGAGGCTGAGAAGCTGGGCTGCAGCGCCTCCA
ACTTCGTCTTTGCAAGGACTATGCCCGCAGAAGGAGCAGATGACATTCCT
GGGCCAGTGACCTGGGAGCCAAGGCCTGAAAACTCCATCTTTTTTAAAGTG
GCCGGAACCTGAGAATCCCAATGGATTGATTCTAATGTATGAAATAAAAT
ACGGATCACAAGTTGAGGATCAGCGAGAATGTGTGTCCAGACAGGAATAC
AGGAAGTATGGAGGGCCAAGCTAAACCGGCTAAACCCGGGGAACTACAC
AGCCCGGATTCAGGCCACATCTCTCTGGGAATGGGTCGTGGACAGATC
CTGTGTTCTTCTATGTCCAGGCCAAAACAGGATATGAAAACTTCATCCAT
CTGATCATCGCTCTGCCCGTCGCTGTCCTGTTGATCGTGGGAGGGTTGGT
GATTATGCTGTACGTCTTCCATAGAAAGAGAAATAACAGCAGGCTGGGGA
ATGGAGTGCTGTATGCCTCTGTGAACCCGGAGTACTTCAGCGCTGCTGAT
GTGTACGTTCCTGATGAGTGGGAGGTGGCTCGGGAGAAGATCACCATGAG
CCGGGAACTTGGGCAGGGGTCGTTTGGGATGGTCTATGAAGGAGTTGCCA
AGGGTGTGGTGAAAGATGAACCTGAAACCAGAGTGGCCATTAAAACAGTG
AACGAGGCCGCAAGCATGCGTGAGAGGATTGAGTTTCTCAACGAAGCTTC
TGTGATGAAGGAGTTCAATTGTCACCATGTGGTGCGATTGCTGGGTGTGG
TGTCCCAAGGCCAGCCAACACTGGTCATCATGGAACTGATGACACGGGC
GATCTCAAAAGTTATCTCCGGTCTCTGAGGCCAGAAATGGAGAATAATCC
AGTCCTAGCACCTCCAAGCCTGAGCAAGATGATTCAGATGGCCGGAGAGA
TTGCAGACGGCATGGCATACCTCAACGCCAATAAGTTCGTCCACAGAGAC
CTTGCTGCCCGGAATTGCATGGTAGCCGAAGATTTCACAGTCAAAATCGG
AGATTTTGGTATGACGCGAGATATCTATGAGACAGACTATTACCGGAAAG
GAGGCAAAGGGCTGCTGCCCGTGCGCTGGATGTCTCCTGAGTCCCTCAAG
GATGGAGTCTTCACCACTTACTCGGACGTCTGGTCCTTCGGGGTCGTCCT
CTGGGAGATCGCCACACTGGCCGAGCAGCCCTACCAGGGCTTGTCCAACG
AGCAAGTCCTTCGCTTCGTCATGGAGGCGGCCTTCTGGACAAGCCAGAC
AACTGTCCTGACATGCTGTTTGAACTGATGCGCATGTGCTGGCAGTATAA
CCCCCAAGATGAGGCCTTCCTTCCTGGAGATCATCAGCAGCATCAAAGAGG
AGATGGAGCCTGGCTTCCGGGAGGTCTCCTTCTACTACAGCGAGGAGAAC
AAGCTGCCCGAGCGGAGGAGCTGGACCTGGAGCCAGAGAACATGGAGAG
CGTCCCCCTGGACCCCTCGGCCTCCTCGTCCTCCCTGCCACTGCCCGACA
GACACTCAGGACAAGGCCGAGAACGGCCCCGGCCCTGGGGTGCTGGTC
CTCCGCGCCAGCTTCGACGAGAGACAGCCTTACGCCCACATGAACGGGGG
CCGCAAGAACGAGCGGGCCTTGCCGCTGCCCCAGTCTTCGACCTGCTGAT
CCTTGGATCCTGAATCTGTGCAAACAGTAACGTGTGCGCACGCGCAGCGG

-continued

```
GGTGGGGGGGAGAGAGAGTTTTAACAATCCATTCACAAGCCTCCTGTAC

CTCAGTGGATCTTCAGTTCTGCCCTTGCTGCCCGCGGGAGACAGCTTCTC

TGCAGTAAAACACATTTGGGATGTTCCTTTTTTCAATATGCAAGCAGCTT

TTTATTCCCTGCCCAAACCCTTAACTGACATGGGCCTTTAAGAACCTTAA

TGACAACACTTAATAGCAACAGAGCACTTGAGAACCAGTCTCCTCACTCT

GTCCCTGTCCTTCCCTGTTCTCCCTTTCTCTCTCCTCTCTGCTTCATAAC

GGAAAAATAATTGCCACAAGTCCAGCTGGGAAGCCCTTTTTATCAGTTTG

AGGAAGTGGCTGTCCCTGTGGCCCCATCCAACCACTGTACACACCCGCCT

GACACCGTGGGTCATTACAAAAAAACACGTGGAGATGGAAATTTTTACCT

TTATCTTTCACCTTTCTAGGGACATGAAATTTACAAAGGGCCATCGTTCA

TCCAAGGCTGTTACCATTTTAACGCTGCCTAATTTTGCCAAAATCCTGAA

CTTTCTCCCTCATCGGCCCGGCGCTGATTCCTCGTGTCCGGAGGCATGGG

TGAGCATGGCAGCTGGTTGCTCCATTTGAGAGACACGCTGGCGACACACT

CCGTCCATCCGACTGCCCCTGCTGTGCTGCTCAAGGCCACAGGCACACAG

GTCTCATTGCTTCTGACTAGATTATTATTTGGGGAACTGGACACAATAG

GTCTTTCTCTCAGTGAAGGTGGGGAGAAGCTGAACCGGC
```

The precursor polypeptide sequence is available under GenBank Accession Number NP_000866, and is presented herein as SEQ ID NO:2.

```
                                    SEQ ID NO: 2
>gi|4557665|ref|NP_000866.1| insulin-like growth
factor 1 receptor precursor [Homo sapiens]
MKSGSGGGSPTSLWGLLFLSAALSLWPTSGEICGPGIDIRNDYQQLKRLE

NCTVIEGYLHILLISKAEDYRSYRFPKLTVITEYLLLFRVAGLESLGDLF

PNLTVIRGWKLFYNYALVIFEMTNLKDIGLYNLRNITRGAIRIEKNADLC

YLSTVDWSLILDAVSNNYIVGNKPPKECGDLCPGTMEEKPMCEKTTINNE

YNYRCWTTNRCQKMCPSTCGKRACTENNECCHPECLGSCSAPDNDTACVA

CRHYYYAGVCVPACPPNTYRFEGWRCVDRDFCANILSAESSDSEGFVIHD

GECMQECPSGFIRNGSQSMYCIPCEGPCPKVCEEEKKTKTIDSVTSAQML

QGCTIFKGNLLINIRRGNNIASELENFMGLIEVVTGYVKIRHSHALVSLS

FLKNLRLILGEEQLEGNYSFYVLDNQNLQQLWDWDHRNLTIKAGKMYFAF

NPKLCVSEIYRMEEVTGTKGRQSKGDINTRNNGERASCESDVLHFTSTTT

SKNRIIITWHRYRPPDYRDLISFTVYYKEAPFKNVTEYDGQDACGSNSWN

MVDVDLPPNKDVEPGILLHGLKPWTQYAVYVKAVTLTMVENDHIRGAKSE

ILYIRTNASVPSIPLDVLSASNSSSQLIVKWNPPSLPNGNLSYYIVRWQR

QPQDGYLYRHNYCSKDKIPIRKYADGTIDIEEVTENPKTEVCGGEKGPCC

ACPKTEAEKQAEKEEAEYRKVFENFLHNSIFVPRPERKRRDVMQVANTTM

SSRSRNTTAADTYNITDPEELETEYPFFESRVDNKERTVISNLRPFTLYR

IDIHSCNHEAEKLGCSASNFVFARTMPAEGADDIPGPVTWEPRPENSIFL

KWPEPENPNGLILMYEIKYGSQVEDQRECVSRQEYRKYGGAKLNRLNPGN

YTARIQATSLSGNGSWTDPVFFYVQAKTGYENFIHLIIALPVAVLLIVGG

LVIMLYVFHRKRNNSRLGNGVLYASVNPEYFSAADVYVPDEWEVAREKIT

MSRELGQGSFGMVYEGVAKGVVKDEPETRVAIKTVNEAASMRERIEFLNE

ASVMKEFNCHHVVRLLGVVSQGQPTLVIMELMTRGDLKSYLRSLRPEMEN

NPVLAPPSLSKMIQMAGEIADGMAYLNANKFVHRDLAARNCMVAEDFTVK

IGDFGMTRDIYETDYYRKGGKGLLPVRWMSPESLKDGVFTTYSDVWSFGV

VLWEIATLAEQPYQGLSNEQVLRFVMEGGLLDKPDNCPDMLFELMRMCWQ

YNPKMRPSFLEIISSIKEEMEPGFREVSFYYSEENKLPEPEELDLEPENM

ESVPLDPSASSSSLPLPDRHSGHKAENGPGPGVLVLRASFDERQPYAHMN

GGRKNERALPLPQSSTC
```

Amino acids 1 to 30 of SEQ ID NO:2 are reported to encode the IGF-1R signal peptide, amino acids 31 to 740 of SEQ ID NO:2 are reported to encode the IGF-1R α-subunit, and amino acids 741 to 1367 of SEQ ID NO:2 are reported to encode the IGF-1R β-subunit. These and other features of human IGF-1R reported in the NP_000866 GenBank entry are presented in Table 2.

TABLE 2

| SEQ ID NO: 2 | Feature (from NP_000866) |
|---|---|
| 1 to 30 | signal peptide |
| 31 to 740 | insulin-like growth factor 1 receptor alpha chain |
| 51 to 161 | Receptor L domain |
| 230 to 277 | Furin-like repeats |
| 372 to 467 | Receptor L domain |
| 494 to 606 | Fibronectin type 3 domain |
| 611 to >655 | Fibronectin type 3 domain |
| 741 to 1367 | insulin-like growth factor 1 receptor beta |
| 835 to 924 | Fibronectin type 3 domain |
| 931 to 955 | transmembrane region |
| 973 | Phosphorylation |
| 980 | Phosphorylation |
| 991 to 1268 | Tyrosine kinase, catalytic domain |
| 1161 | Phosphorylation |
| 1165 | Phosphorylation |
| 1166 | Phosphorylation |

The present invention is also directed to IGF-1R antibodies, or antigen-binding fragments, variants, or derivatives thereof which bind specifically, preferentially, or competitively to non-human IGF-1R proteins, e.g., IGF-1R from rodents or non-human primates.

IGF-1R is expressed in a large number of tumor cells, including, but not limited to certain of the following: bladder tumors (Hum. Pathol. 34:803 (2003)); brain tumors (Clinical Cancer Res. 8:1822 (2002)); breast tumors (Eur. J. Cancer 30:307 (1994) and Hum Pathol. 36:448-449 (2005)); colon tumors, e.g., adenocarcinomas, metastases, and adenomas (Human Pathol. 30:1128 (1999), Virchows. Arc. 443:139 (2003), and Clinical Cancer Res. 10:843 (2004)); gastric tumors (Clin. Exp. Metastasis 21:755 (2004)); kidney tumors, e.g., clear cell, chromophobe and papillary RCC (Am. J. Clin. Pathol. 122:931-937 (2004)); lung tumors (Hum. Pathol. 34:803-808 (2003) and J. Cancer Res. Clinical Oncol. 119:665-668 (1993)); ovarian tumors (Hum. Pathol. 34:803-808 (2003)); pancreatic tumors, e.g., ductal adenocarcinoma (Digestive Diseases. Sci. 48:1972-1978 (2003) and Clinical Cancer Res. 11:3233-3242 (2005)); and prostate tumors (Cancer Res. 62:2942-2950 (2002)).

III. IGF-1R Antibodies

In one embodiment, the present invention is directed to IGF-1R antibodies, or antigen-binding fragments, variants, or derivatives thereof. For example, the present invention includes at least the antigen-binding domains of certain monoclonal antibodies, and fragments, variants, and derivatives thereof shown in Tables 3 and 4. Table 3 lists human anti-human IGF-1R Fab regions identified from a phage display library and various binding properties of the antibodies, described in more detail in the Examples. Table 4 lists murine anti-human IGF-1R monoclonal antibodies identified by hybridoma technology, and various binding properties of the antibodies, described in more detail in the Examples.

TABLE 3

Functional properties of IGF-1R specific Fabs.

| | Fabs | ELISA Binding | | | FACS Binding | | IGF Blocking | | Inhibition of IGF-1R Phosphorylation | |
|---|---|---|---|---|---|---|---|---|---|---|
| | | IGF-1R-His | IGF-1R-Fc | InsR | IGF-1R3T3 | MCF-7 EC50nM | IGF-1 | IGF-2 | IGF-1 | IGF-2 |
| 1 | M13-C06 | + | +++ | − | +++ | 8.8 | + | ++ | ++ | ++ |
| 2 | M14-G11 | ++ | +++ | − | +++ | 39.8 | ++ | ++ | + | +++ |
| 3 | M14-C03 | ++ | +++ | − | +++ | 25.4 | − | + | ++ | ++ |
| 4 | M14-B01 | +++ | +++ | − | +++ | 29.4 | ++ | ++ | ++ | ++ |
| 5 | M12-E01 | +++ | +++ | − | +++ | 7.4 | − | ++ | ++ | + |
| 6 | M12-G04 | + | ++ | − | ++ | 25.0 | + | + | + | + | pTy-IGF-1R

| | |
|---|---|
| >30% @0.1 µg/ml | +++ |
| >30% @1 µg/ml | ++ |
| >30% @10 µg/ml | + |
| >OD 2x bkg ELISA | |
| @0.1 µg/ml | +++ |
| >OD 2x bkg @1 µg/ml | ++ |
| >OD 2x bkg @10 µg/ml | + |
| Ligand Blocking | |
| >30% @0.1 µg/ml | +++ |
| >30% @1 µg/ml | ++ |
| >30% @10 µg/ml | + |

TABLE 4

Functional properties of murine monoclonal antibodies

| | Hybridoma # | Isotype | Binding (EC$_{50}$nM) | | InsR ELISA | IGF Blocking | | Inhibition of IGF-1R.pTy | | Proliferation of Tumor Cells 1 | | | | |
|---|---|---|---|---|---|---|---|---|---|---|---|---|---|---|
| | | | Protein ELISA | Tumor MCF-7 | | IGF-1 | IGF-2 | IGF-1 | IGF-2 | MCF-7* | H-23 | Calu-6 | Panc-1 | Colo205 |
| 1 | P2A7.3E11 | IgG2a/k | 0.011 | 0.447 | − | +++ | − | +++ | ++ | ++ | ++++ | +++ | ++++ | +++ |
| 2 | 20C8.3B8 | IgG1/k | 0.085 | 1.228 | − | +++ | +++ | +++ | ++ | +++ | +++ | +++ | +++ | +++ |
| 3 | P1A2.2B11 | IgG2b/k | 0.023 | 1.103 | − | +++ | − | +++ | +++ | ++ | +++ | ++ | +++ | +++ |
| 4 | 20D8.24B11 | IgG1/k | 0.042 | 1.296 | − | +++ | +++ | +++ | ++ | ++ | ++++ | +++ | +++ | +++ |
| 5 | P1E2.3B12 | IgG2b/k | 0.016 | 0.391 | − | +++ | − | +++ | +++ | ++ | ++++ | ++ | ++ | ++ |
| 6 | P1G10.2B8 | IgG1/k | 0.075 | 2.059 | − | +++ | − | +++ | +++ | +++ | +++ | ++ | + | ++ |

1MCF-1 = breast cancer cell; H-23 and Calu-6 = lung cancer cells; Panc-1 = pancreatic cancer cell; Colo205 = colon cancer cell pTy-IGF-1R

| | |
|---|---|
| >30% @0.1 µg/ml | +++ |
| >30% @1 µg/ml | ++ |
| >30% @10 µg/ml | + |
| Ligand Blocking | |
| >40% @0.1 µg/ml | +++ |
| >40% @1 µg/ml | ++ |
| >40% @10 µg/ml | + |
| *Ki67 Inhibit. (MCF-7) | |
| >50% @0.01 µg/ml | ++++ |
| >50% @0.1 µg/ml | +++ |

TABLE 4-continued

| | |
|---|---|
| >50% @1 µg/ml | ++ |
| >50% @10 µg/ml | + |
| Prolif. Inhibition | |
| | |
| >30% @0.01 µg/ml | ++++ |
| >30% @0.1 µg/ml | +++ |
| >30% @1 µg/ml | ++ |
| >30% @10 µg/ml | + |

Chinese Hamster Ovary cell lines which express full-length antibody of M13-C06 and M14-C03 were deposited with the American Type Culture Collection ("ATCC") on Mar. 28, 2006, and were given ATCC Deposit Numbers PTA-7444 and PTA-7445, respectively. Chinese Hamster Ovary cell lines which express Fab antibody fragment M14-G11 were deposited with the American Type Culture Collection ("ATCC") on Aug. 29, 2006, and were given ATCC Deposit Number PTA-7855.

The ATCC is located at 10801 University Boulevard, Manassas, Va. 20110-2209, USA. The ATCC deposits were made pursuant to the terms of the Budapest Treaty on the international recognition of the deposit of microorganisms for purposes of patent procedure.

Certain embodiments of the invention were deposited with the American Type Culture Collection as shown in the following table ("ATCC Deposit Table").

ATCC DEPOSIT TABLE

| Chinese Hamster Ovary (CHO) Cells | | | |
|---|---|---|---|
| Name of cell line ("as indicated on ATCC deposit receipt"): | Date of deposit (ATCC deposit number) | Cell line referred to herein as: | Antibody produced: |
| "Chinese Hamster Ovary (CHO): C06-40B5; CHO DG44Biogen Idec EA03.14.06" | Mar. 28, 2006 (PTA-7444) | M13-C06 | M13-C06.G4.P.agly |
| "Chinese Hamster Ovary (CHO): C03-2 CHO DG44Biogen Idec DA 03.14.06" | Mar. 28, 2006 (PTA-7445) | M14-C03 | M14-C03.G4.P.agly |
| "Chinese hamster ovary cell line: G11 70 8e6 cells 08.09.2006" | Aug. 29, 2006 (PTA-7855) | M14-G11 | M14-G11.G4.P.agly |

| Hybridomas | | | |
|---|---|---|---|
| Name of cell line ("as indicated on ATCC deposit receipt"): | Date of deposit (ATCC deposit number) | Cell line referred to herein as: | Antibody isotype: |
| "Hybridoma 8.P2A7.3D11" | Mar. 28, 2006 (PTA-7458) | P2A7.3E11 | IgG2a/k |
| "Hybridoma cell line: 7.20C8.3B8" | Jun. 13, 2006 (PTA-7732) | 20C8.3B8 | IgG1/k |
| "Hybridoma: 5.P1A2.2B11" | Mar. 28, 2006 (PTA-7457) | P1A2.2B11 | IgG2b/k |
| "Hybridoma: 7.20D8.24.B11" | Mar. 28, 2006 (PTA-7456) | 20D8.24B11 | IgG1/k |
| "Hybridoma Cell Line: 9.P1E2.3B12" | Jul. 11, 2006 (PTA-7730) | P1E2.3B12 | IgG2b/k |
| "Hybridoma Cell Line: 5P1G10.2B8" | Jul. 11, 2006 (PTA-7731) | P1G10.2B8 | IgG1/k |

Hybridoma cell line which express full-length human antibodies P2A7.3E11, 20C8.3B8, and P1A2.2B11 were deposited with the ATCC on Mar. 28, 2006, Jun. 13, 2006, and Mar. 28, 2006, respectively, and were given the ATCC Deposit Numbers PTA-7458, PTA-7732, and, PTA-7457, respectively. Hybridoma cell lines which express full-length human antibodies 20D8.24B11, P1E2.3B12, and P1G10.2B8 were deposited with the ATCC on Mar. 28, 2006, Jul. 11, 2006, and Jul. 11, 2006, respectively, and were given the ATCC Deposit Numbers PTA-7456, PTA-7730, and PTA-7731, respectively. See, ATCC Deposit Table (below) for correlation of antibodies and deposited cell lines.

As used herein, the term "antigen binding domain" includes a site that specifically binds an epitope on an antigen (e.g., an epitope of IGF-1R). The antigen binding domain of an antibody typically includes at least a portion of an immunoglobulin heavy chain variable region and at least a portion of an immunoglobulin light chain variable region. The binding site formed by these variable regions determines the specificity of the antibody.

The present invention is more specifically directed to an IGF-1R antibody, or antigen-binding fragment, variant or derivatives thereof, where the IGF-1R antibody specifically binds to the same IGF-R1 epitope as a reference monoclonal Fab antibody fragment selected from the group consisting of M13-C06, M14-G11, M14-C03, M14-B01, M12-E01, and M12-G04, or a reference monoclonal antibody produced by a hybridoma selected from the group consisting of P2A7.3E11, 20C8.3B8, P1A2.2B11, 20D8.24B11, P1E2.3B12, and P1G10.2B8.

The invention is further drawn to an IGF-1R antibody, or antigen-binding fragment, variant or derivatives thereof, where the IGF-1R antibody competitively inhibits a reference monoclonal Fab antibody fragment selected from the group consisting of M13-C06, M14-G11, M14-C03, M14-B01, M12-E01, and M12-G04, or a reference monoclonal antibody produced by a hybridoma selected from the group consisting of P2A7.3E11, 20C8.3B8, P1A2.2B11, 20D8.24B11, P1E2.3B12, and P1G10.2B8 from binding to IGF-1R.

The invention is also drawn to an IGF-1R antibody, or antigen-binding fragment, variant or derivatives thereof, where the IGF-1R antibody comprises an antigen binding domain identical to that of a monoclonal Fab antibody fragment selected from the group consisting of M13-C06, M14-G11, M14-C03, M14-B01, M12-E01, and M12-G04, or a monoclonal antibody produced by a hybridoma selected from the group consisting of P2A7.3E11, 20C8.3B8, P1A2.2B11, 20D8.24B11, P1E2.3B12, and P1G10.2B8.

Methods of making antibodies are well known in the art and described herein. Once antibodies to various fragments of, or to the full-length IGF-1R without the signal sequence, have been produced, determining which amino acids, or epitope, of IGF-1R to which the antibody or antigen binding fragment binds can be determined by epitope mapping protocols as described herein as well as methods known in the art (e.g. double antibody-sandwich ELISA as described in "Chapter 11—Immunology," *Current Protocols in Molecular Biology*, Ed. Ausubel et al., v.2, John Wiley & Sons, Inc. (1996)). Additional epitope mapping protocols may be found in Morris, G. *Epitope Mapping Protocols*, New Jersey: Humana Press (1996), which are both incorporated herein by reference in their entireties. Epitope mapping can also be performed by commercially available means (i.e. Proto-PROBE, Inc. (Milwaukee, Wis.)).

Additionally, antibodies produced which bind to any portion of IGF-1R can then be screened for their ability to act as an antagonist of IGF-1R for example, to inhibit binding of insulin growth factor, e.g., IGF-1, IGF-2, or both IGF-1 and IGF-2 to IGF-1R, to promote internalization of IGF-1R, to inhibit phosphorylation of IGF-1R, to inhibit downstream phosphorylation, e.g., of Akt or p42/44 MAPK, or to inhibit tumor cell proliferation, motility or metastasis. Antibodies can be screened for these and other properties according to methods described in detail in the Examples. Other functions of antibodies of the present invention can be tested using other assays as described in the Examples herein.

In other embodiments, the present invention includes an antibody, or antigen-binding fragment, variant, or derivative thereof which specifically or preferentially binds to at least one epitope of IGF-1R, where the epitope comprises, consists essentially of, or consists of at least about four to five amino acids of SEQ ID NO:2, at least seven, at least nine, or between at least about 15 to about 30 amino acids of SEQ ID NO:2. The amino acids of a given epitope of SEQ ID NO:2 as described may be, but need not be contiguous or linear. In certain embodiments, at least one epitope of IGF-1R comprises, consists essentially of, or consists of a non-linear epitope formed by the extracellular domain of IGF-1R as expressed on the surface of a cell or as a soluble fragment, e.g., fused to an IgG Fc region. Thus, in certain embodiments at least one epitope of IGF-1R comprises, consists essentially of, or consists of at least 4, at least 5, at least 6, at least 7, at least 8, at least 9, at least 10, at least 15, at least 20, at least 25, between about 15 to about 30, or at least 10, 15, 20, 25, 30, 35, 40, 45, 50, 55, 60, 65, 70, 75, 80, 85, 90, 95, or 100 contiguous or non-contiguous amino acids of SEQ ID NO:2, where non-contiguous amino acids form an epitope through protein folding.

In other embodiments, the present invention includes an antibody, or antigen-binding fragment, variant, or derivative thereof which specifically or preferentially binds to at least one epitope of IGF-1R, where the epitope comprises, consists essentially of, or consists of, in addition to one, two, three, four, five, six or more contiguous or non-contiguous amino acids of SEQ ID NO:2 as described above, and an additional moiety which modifies the protein, e.g., a carbohydrate moiety may be included such that the IGF-1R antibody binds with higher affinity to modified target protein than it does to an unmodified version of the protein. Alternatively, the IGF-1R antibody does not bind the unmodified version of the target protein at all.

In certain aspects, the present invention is directed to an antibody, or antigen-binding fragment, variant, or derivative thereof which specifically binds to a IGF-1R polypeptide or fragment thereof, or an IGF-1R variant polypeptide, with an affinity characterized by a dissociation constant ($K_D$) which is less than the $K_D$ for a given reference monoclonal antibody.

In certain embodiments, an antibody, or antigen-binding fragment, variant, or derivative thereof of the invention binds specifically to at least one epitope of IGF-1R or fragment or variant described above, i.e., binds to such an epitope more readily than it would bind to an unrelated, or random epitope; binds preferentially to at least one epitope of IGF-1R or fragment or variant described above, i.e., binds to such an epitope more readily than it would bind to a related, similar, homologous, or analogous epitope; competitively inhibits binding of a reference antibody which itself binds specifically or preferentially to a certain epitope of IGF-1R or fragment or variant described above; or binds to at least one epitope of IGF-1R or fragment or variant described above with an affinity characterized by a dissociation constant $K_D$ of less than about $5 \times 10^{-2}$ M, about $10^{-2}$ M, about $5 \times 10^{-3}$ M, about $10^{-3}$ M, about $5 \times 10^{-4}$ M, about $10^{-4}$ M, about $5 \times 10^{-5}$ M, about $10^{-5}$ M, about $5 \times 10^{-6}$ M, about $10^{-6}$ M, about $5 \times 10^{-7}$ M, about $10^{-7}$ M, about $5 \times 10^{-8}$ M, about $10^{-8}$ M, about $5 \times 10^{-9}$ M, about $10^{-9}$ M, about $5 \times 10^{-10}$ M, about $10^{-10}$ M, about $5 \times 10^{-11}$ M, about $10^{-11}$ M, about $5 \times 10^{-12}$ M, about $10^{-12}$ M, about $5 \times 10^{-13}$ M, about $10^{-13}$ M, about $5 \times 10^{-14}$ M, about $10^{-14}$ M, about $5 \times 10^{-15}$ M, or about $10^{-15}$ M. In a particular aspect, the antibody or fragment thereof preferentially binds to a human IGF-1R polypeptide or fragment thereof, relative to a murine IGF-1R polypeptide or fragment thereof. In another particular aspect, the antibody or fragment thereof preferentially binds to one or more IGF-1R polypeptides or fragments thereof, e.g., one or more mammalian IGF-1R polypeptides, but does not bind to insulin receptor (InsR) polypeptides. While not being bound by theory, insulin receptor polypeptides are known to have some sequence similarity with IGF-1R polypeptides, and antibodies which cross react with InsR may produce unwanted side effects in vivo, e.g., interfering with glucose metabolism.

As used in the context of antibody binding dissociation constants, the term "about" allows for the degree of variation inherent in the methods utilized for measuring antibody affinity. For example, depending on the level of precision of the instrumentation used, standard error based on the number of samples measured, and rounding error, the term "about $10^{-2}$ M" might include, for example, from 0.05 M to 0.005 M.

In specific embodiments, an antibody, or antigen-binding fragment, variant, or derivative thereof of the invention binds IGF-1R polypeptides or fragments or variants thereof with an off rate (k(off)) of less than or equal to $5 \times 10^{-2}$ sec$^{-1}$, $10^{-2}$ sec$^{-1}$, $5 \times 10^{-3}$ sec$^{-1}$ or $10^{-3}$ sec$^{-1}$. Alternatively, an antibody, or antigen-binding fragment, variant, or derivative thereof of the invention binds IGF-1R polypeptides or fragments or variants thereof with an off rate (k(off)) of less than or equal to $5 \times 10^{-4}$ sec$^{-1}$, $10^{-4}$ sec$^{1}$, $5 \times 10^{-5}$ sec$^{-1}$, or $10^{-5}$ sec$^{-1}$ $5 \times 10^{-6}$ sec$^{-1}$, $10^{-6}$ sec$^{-1}$, $5 \times 10^{-7}$ sec$^{-7}$ or $10^{-7}$ sec$^{-1}$.

In other embodiments, an antibody, or antigen-binding fragment, variant, or derivative thereof of the invention binds IGF-1R polypeptides or fragments or variants thereof with an on rate (k(on)) of greater than or equal to $10^3$ M$^{-1}$ sec$^{1}$, $5 \times 10^3$ M$^{-1}$ sec$^{-1}$, $10^4$ M$^{-1}$ sec$^{1}$ or $5 \times 10^4$ M$^{-1}$ sec$^{-1}$. Alternatively, an antibody, or antigen-binding fragment, variant, or derivative thereof of the invention binds IGF-1R polypeptides or fragments or variants thereof with an on rate (k(on)) greater than or equal to $10^5$ M$^{-1}$ sec$^{-1}$, $5 \times 10^{-5}$ M$^{-1}$ sec$^{-1}$, $10^6$ M$^{-1}$ sec$^{-1}$, or $5 \times 10^6$ M$^{-1}$ sec$^{-1}$ or $10^7$ M$^{-1}$ sec$^{-1}$.

In various embodiments, an IGF-1R antibody, or antigen-binding fragment, variant, or derivative thereof as described herein is an antagonist of IGF-1R activity. In certain embodiments, for example, binding of an antagonist IGF-1R antibody to IGF-1R as expressed on a tumor cell inhibits binding of insulin growth factor, e.g., IGF-1, IGF-2, or both IGF-1 and IGF-2 to IGF-1R, promotes internalization of IGF-1R thereby inhibiting its signal transduction capability, inhibits phosphorylation of IGF-1R, inhibits phosphorylation of molecules downstream in the signal transduction pathway, e.g., Akt or p42/44 MAPK, or inhibits tumor cell proliferation, motility or metastasis.

Unless it is specifically noted, as used herein a "fragment thereof" in reference to an antibody refers to an antigen-binding fragment, i.e., a portion of the antibody which specifically binds to the antigen. In one embodiment, an IGF-1R antibody, e.g., an antibody of the invention is a bispecific IGF-1R antibody, e.g., a bispecific antibody, minibody, domain deleted antibody, or fusion protein having binding specificity for more than one epitope, e.g., more than one antigen or more than one epitope on the same antigen. In one embodiment, a bispecific IGF-1R antibody has at least one binding domain specific for at least one epitope on a target polypeptide disclosed herein, e.g., IGF-1R. In another embodiment, a bispecific IGF-1R antibody has at least one binding domain specific for an epitope on a target polypeptide and at least one target binding domain specific for a drug or toxin. In yet another embodiment, a bispecific IGF-1R antibody has at least one binding domain specific for an epitope on a target polypeptide disclosed herein, and at least one binding domain specific for a prodrug. A bispecific IGF-1R antibody may be a tetravalent antibody that has two target binding domains specific for an epitope of a target polypeptide disclosed herein and two target binding domains specific for a second target. Thus, a tetravalent bispecific IGF-1R antibody may be bivalent for each specificity.

IGF-1R antibodies, or antigen-binding fragments, variants, or derivatives thereof of the invention, as known by those of ordinary skill in the art, can comprise a constant region which mediates one or more effector functions. For example, binding of the C1 component of complement to an antibody constant region may activate the complement system. Activation of complement is important in the opsonisation and lysis of cell pathogens. The activation of complement also stimulates the inflammatory response and may also be involved in autoimmune hypersensitivity. Further, antibodies bind to receptors on various cells via the Fc region, with a Fc receptor binding site on the antibody Fc region binding to a Fc receptor (FcR) on a cell. There are a number of Fc receptors which are specific for different classes of antibody, including IgG (gamma receptors), IgE (epsilon receptors), IgA (alpha receptors) and IgM (mu receptors). Binding of antibody to Fc receptors on cell surfaces triggers a number of important and diverse biological responses including engulfment and destruction of antibody-coated particles, clearance of immune complexes, lysis of antibody-coated target cells by killer cells (called antibody-dependent cell-mediated cytotoxicity, or ADCC), release of inflammatory mediators, placental transfer and control of immunoglobulin production.

Accordingly, certain embodiments of the invention include an IGF-1R antibody, or antigen-binding fragment, variant, or derivative thereof, in which at least a fraction of one or more of the constant region domains has been deleted or otherwise altered so as to provide desired biochemical characteristics such as reduced effector functions, the ability to non-covalently dimerize, increased ability to localize at the site of a tumor, reduced serum half-life, or increased serum half-life when compared with a whole, unaltered antibody of approximately the same immunogenicity. For example, certain antibodies for use in the diagnostic and treatment methods described herein are domain deleted antibodies which comprise a polypeptide chain similar to an immunoglobulin heavy chain, but which lack at least a portion of one or more heavy chain domains. For instance, in certain antibodies, one entire domain of the constant region of the modified antibody will be deleted, for example, all or part of the CH2 domain will be deleted. In other embodiments, certain antibodies for use in the diagnostic and treatment methods described herein have s constant region, e.g., an IgG4 heavy chain constant region, which is altered to eliminate glycosylation, referred to elsewhere herein as "agly" antibodies. While not being bound by theory, it is believed that "agly" antibodies may have an improved safety and stability profile in vivo.

In certain IGF-1R antibodies, or antigen-binding fragments, variants, or derivatives thereof described herein, the Fc portion may be mutated to decrease effector function using techniques known in the art. For example, the deletion or inactivation (through point mutations or other means) of a constant region domain may reduce Fc receptor binding of the circulating modified antibody thereby increasing tumor localization. In other cases it may be that constant region modifications consistent with the instant invention moderate complement binding and thus reduce the serum half life and nonspecific association of a conjugated cytotoxin. Yet other modifications of the constant region may be used to modify disulfide linkages or oligosaccharide moieties that allow for enhanced localization due to increased antigen specificity or antibody flexibility. The resulting physiological profile, bioavailability and other biochemical effects of the modifications, such as tumor localization, biodistribution and serum half-life, may easily be measured and quantified using well know immunological techniques without undue experimentation.

Modified forms of IGF-1R antibodies, or antigen-binding fragments, variants, or derivatives thereof of the invention can be made from whole precursor or parent antibodies using techniques known in the art. Exemplary techniques are discussed in more detail herein.

In certain embodiments both the variable and constant regions of IGF-1R antibodies, or antigen-binding fragments, variants, or derivatives thereof are fully human. Fully human antibodies can be made using techniques that are known in the art and as described herein. For example, fully human antibodies against a specific antigen can be prepared by administering the antigen to a transgenic animal which has been modified to produce such antibodies in response to antigenic challenge, but whose endogenous loci have been disabled. Exemplary techniques that can be used to make such antibodies are described in U.S. Pat. Nos. 6,150,584; 6,458,592; 6,420,140. Other techniques are known in the art. Fully human antibodies can likewise be produced by various display technologies, e.g., phage display or other viral display systems, as described in more detail elsewhere herein.

IGF-1R antibodies, or antigen-binding fragments, variants, or derivatives thereof of the invention can be made or manufactured using techniques that are known in the art. In certain embodiments, antibody molecules or fragments thereof are "recombinantly produced," i.e., are produced using recombinant DNA technology. Exemplary techniques for making antibody molecules or fragments thereof are discussed in more detail elsewhere herein.

IGF-1R antibodies, or antigen-binding fragments, variants, or derivatives thereof of the invention also include derivatives that are modified, e.g., by the covalent attachment of any type of molecule to the antibody such that covalent attachment does not prevent the antibody from specifically binding to its cognate epitope. For example, but not by way of limitation, the antibody derivatives include antibodies that have been modified, e.g., by glycosylation, acetylation, pegylation, phosphorylation, amidation, derivatization by known protecting/blocking groups, proteolytic cleavage, linkage to a cellular ligand or other protein, etc. Any of numerous chemical modifications may be carried out by known techniques, including, but not limited to specific chemical cleavage, acetylation, formylation, metabolic synthesis of tunicamycin, etc. Additionally, the derivative may contain one or more non-classical amino acids.

In certain embodiments, IGF-1R antibodies, or antigen-binding fragments, variants, or derivatives thereof of the invention will not elicit a deleterious immune response in the animal to be treated, e.g., in a human. In one embodiment, IGF-1R antibodies, or antigen-binding fragments, variants, or derivatives thereof of the invention are modified to reduce their immunogenicity using art-recognized techniques. For example, antibodies can be humanized, primatized, deimmunized, or chimeric antibodies can be made. These types of antibodies are derived from a non-human antibody, typically a murine or primate antibody, that retains or substantially retains the antigen-binding properties of the parent antibody, but which is less immunogenic in humans. This may be achieved by various methods, including (a) grafting the entire non-human variable domains onto human constant regions to generate chimeric antibodies; (b) grafting at least a part of one or more of the non-human complementarity determining regions (CDRs) into a human framework and constant regions with or without retention of critical framework residues; or (c) transplanting the entire non-human variable domains, but "cloaking" them with a human-like section by replacement of surface residues. Such methods are disclosed in Morrison et al., *Proc. Natl. Acad. Sci.* 81:6851-6855 (1984); Morrison et al., *Adv. Immunol.* 44:65-92 (1988); Verhoeyen et al., *Science* 239:1534-1536 (1988); Padlan, *Molec. Immun.* 28:489-498 (1991); Padlan, *Molec. Immun.* 31:169-217 (1994), and U.S. Pat. Nos. 5,585,089, 5,693,761, 5,693,762, and 6,190,370, all of which are hereby incorporated by reference in their entirety.

De-immunization can also be used to decrease the immunogenicity of an antibody. As used herein, the term "de-immunization" includes alteration of an antibody to modify T cell epitopes (see, e.g., WO9852976A1, WO0034317A2). For example, VH and VL sequences from the starting antibody are analyzed and a human T cell epitope "map" from each V region showing the location of epitopes in relation to complementarity-determining regions (CDRs) and other key residues within the sequence. Individual T cell epitopes from the T cell epitope map are analyzed in order to identify alternative amino acid substitutions with a low risk of altering activity of the final antibody. A range of alternative VH and VL sequences are designed comprising combinations of amino acid substitutions and these sequences are subsequently incorporated into a range of binding polypeptides, e.g., IGF-1R-specific antibodies or immunospecific fragments thereof for use in the diagnostic and treatment methods disclosed herein, which are then tested for function. Typically, between 12 and 24 variant antibodies are generated and tested. Complete heavy and light chain genes comprising modified V and human C regions are then cloned into expression vectors and the subsequent plasmids introduced into cell lines for the production of whole antibody. The antibodies are then compared in appropriate biochemical and biological assays, and the optimal variant is identified.

IGF-1R antibodies, or antigen-binding fragments, variants, or derivatives thereof of the invention may be generated by any suitable method known in the art. Polyclonal antibodies to an antigen of interest can be produced by various procedures well known in the art. For example, an IGF-1R antibody, e.g., a binding polypeptide, e.g., an IGF-1R-specific antibody or immunospecific fragment thereof can be administered to various host animals including, but not limited to, rabbits, mice, rats, chickens, hamsters, goats, donkeys, etc., to induce the production of sera containing polyclonal antibodies specific for the antigen. Various adjuvants may be used to increase the immunological response, depending on the host species, and include but are not limited to, Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *Corynebacterium parvum*. Such adjuvants are also well known in the art.

Monoclonal antibodies can be prepared using a wide variety of techniques known in the art including the use of hybridoma, recombinant, and phage display technologies, or a combination thereof. For example, monoclonal antibodies can be produced using hybridoma techniques including those known in the art and taught, for example, in Harlow et al., *Antibodies: A Laboratory Manual*, Cold Spring Harbor Laboratory Press, 2nd ed. (1988); Hammerling et al., in: *Monoclonal Antibodies and T-Cell Hybridomas* Elsevier, N.Y., 563-681 (1981) (said references incorporated by reference in their entireties). The term "monoclonal antibody" as used herein is not limited to antibodies produced through hybridoma technology. The term "monoclonal antibody" refers to an antibody that is derived from a single clone, including any eukaryotic, prokaryotic, or phage clone, and not the method by which it is produced. Thus, the term "monoclonal antibody" is not limited to antibodies produced through hybridoma technology. Monoclonal antibodies can be prepared using IGF-1R knockout mice to increase the regions of epitope recognition. Monoclonal antibodies can be prepared using a wide variety of techniques known in the art including the use of hybridoma and recombinant and phage display technology as described elsewhere herein.

Using art recognized protocols, in one example, antibodies are raised in mammals by multiple subcutaneous or intraperitoneal injections of the relevant antigen (e.g., purified IGF-1R or cells or cellular extracts comprising IGF-1R) and an adjuvant. This immunization typically elicits an immune response that comprises production of antigen-reactive antibodies from activated splenocytes or lymphocytes. While the resulting antibodies may be harvested from the serum of the animal to provide polyclonal preparations, it is often desirable to isolate individual lymphocytes from the spleen, lymph nodes or peripheral blood to provide homogenous preparations of monoclonal antibodies (MAbs). Preferably, the lymphocytes are obtained from the spleen.

In this well known process (Kohler et al., *Nature* 256:495 (1975)) the relatively short-lived, or mortal, lymphocytes from a mammal which has been injected with antigen are fused with an immortal tumor cell line (e.g. a myeloma cell line), thus, producing hybrid cells or "hybridomas" which are both immortal and capable of producing the genetically coded antibody of the B cell. The resulting hybrids are segregated into single genetic strains by selection, dilution, and regrowth with each individual strain comprising specific genes for the formation of a single antibody. They produce antibodies which are homogeneous against a desired antigen and, in reference to their pure genetic parentage, are termed "monoclonal."

Hybridoma cells thus prepared are seeded and grown in a suitable culture medium that preferably contains one or more substances that inhibit the growth or survival of the unfused, parental myeloma cells. Those skilled in the art will appreciate that reagents, cell lines and media for the formation, selection and growth of hybridomas are commercially available from a number of sources and standardized protocols are well established. Generally, culture medium in which the hybridoma cells are growing is assayed for production of monoclonal antibodies against the desired antigen. Preferably, the binding specificity of the monoclonal antibodies produced by hybridoma cells is determined by in vitro assays such as immunoprecipitation, radioimmunoassay (RIA) or enzyme-linked immunoabsorbent assay (ELISA). After hybridoma cells are identified that produce antibodies of the desired specificity, affinity and/or activity, the clones may be subcloned by limiting dilution procedures and grown by standard methods (Goding, *Monoclonal Antibodies: Principles and Practice*, Academic Press, pp 59-103 (1986)). It will further be appreciated that the monoclonal antibodies secreted by the subclones may be separated from culture medium, ascites fluid or serum by conventional purification procedures such as, for example, protein-A, hydroxylapatite chromatography, gel electrophoresis, dialysis or affinity chromatography.

Antibody fragments that recognize specific epitopes may be generated by known techniques. For example, Fab and F(ab')$_2$ fragments may be produced recombinantly or by proteolytic cleavage of immunoglobulin molecules, using enzymes such as papain (to produce Fab fragments) or pepsin (to produce F(ab')$_2$ fragments). F(ab')$_2$ fragments contain the variable region, the light chain constant region and the CH1 domain of the heavy chain.

Those skilled in the art will also appreciate that DNA encoding antibodies or antibody fragments (e.g., antigen binding sites) may also be derived from antibody libraries, such as phage display libraries. In a particular, such phage can be utilized to display antigen-binding domains expressed from a repertoire or combinatorial antibody library (e.g., human or murine). Phage expressing an antigen binding domain that binds the antigen of interest can be selected or identified with antigen, e.g., using labeled antigen or antigen bound or captured to a solid surface or bead. Phage used in these methods are typically filamentous phage including fd and M13 binding domains expressed from phage with Fab, Fv OE DAB (individual Fv region from light or heavy chains) or disulfide stabilized Fv antibody domains recombinantly fused to either the phage gene III or gene VIII protein. Exemplary methods are set forth, for example, in EP 368 684 B1; U.S. Pat. No. 5,969,108, Hoogenboom, H. R. and Chames, *Immunol. Today* 21:371 (2000); Nagy et al. *Nat. Med.* 8:801 (2002); Huie et al., *Proc. Natl. Acad. Sci. USA* 98:2682 (2001); Lui et al., *J. Mol. Biol.* 315:1063 (2002), each of which is incorporated herein by reference. Several publications (e.g., Marks et al., *Bio/Technology* 10:779-783 (1992)) have described the production of high affinity human antibodies by chain shuffling, as well as combinatorial infection and in vivo recombination as a strategy for constructing large phage libraries. In another embodiment, Ribosomal display can be used to replace bacteriophage as the display platform (see, e.g., Hanes et al., *Nat. Biotechnol.* 18:1287 (2000); Wilson et al., *Proc. Natl. Acad. Sci. USA* 98:3750 (2001); or Irving et al., *J. Immunol. Methods* 248:31 (2001)). In yet another embodiment, cell surface libraries can be screened for antibodies (Boder et al., *Proc. Natl. Acad. Sci. USA* 97:10701 (2000); Daugherty et al., *J. Immunol. Methods* 243: 211 (2000)). Such procedures provide alternatives to traditional hybridoma techniques for the isolation and subsequent cloning of monoclonal antibodies.

In phage display methods, functional antibody domains are displayed on the surface of phage particles which carry the polynucleotide sequences encoding them. For example, DNA sequences encoding VH and VL regions are amplified or otherwise isolated from animal cDNA libraries (e.g., human or murine cDNA libraries of lymphoid tissues) or synthetic cDNA libraries. In certain embodiments, the DNA encoding the VH and VL regions are joined together by an scFv linker by PCR and cloned into a phagemid vector (e.g., p CANTAB 6 or pComb 3 HSS). The vector is electroporated in *E. coli* and the *E. coli* is infected with helper phage. Phage used in these methods are typically filamentous phage including fd and M13 and the VH or VL regions are usually recombinantly fused to either the phage gene III or gene VIII. Phage expressing an antigen binding domain that binds to an antigen of interest (i.e., an IGF-1R polypeptide or a fragment thereof) can be selected or identified with antigen, e.g., using labeled antigen or antigen bound or captured to a solid surface or bead.

Additional examples of phage display methods that can be used to make the antibodies include those disclosed in Brinkman et al., *J. Immunol. Methods* 182:41-50 (1995); Ames et al., *J. Immunol. Methods* 184:177-186 (1995); Kettleborough et al., *Eur. J. Immunol.* 24:952-958 (1994); Persic et al., *Gene* 187:9-18 (1997); Burton et al., *Advances in Immunology* 57:191-280 (1994); PCT Application No. PCT/GB91/01134; PCT publications WO 90/02809; WO 91/10737; WO 92/01047; WO 92/18619; WO 93/11236; WO 95/15982; WO 95/20401; and U.S. Pat. Nos. 5,698,426; 5,223,409; 5,403, 484; 5,580,717; 5,427,908; 5,750,753; 5,821,047; 5,571,698; 5,427,908; 5,516,637; 5,780,225; 5,658,727; 5,733,743 and 5,969,108; each of which is incorporated herein by reference in its entirety.

As described in the above references, after phage selection, the antibody coding regions from the phage can be isolated and used to generate whole antibodies, including human antibodies, or any other desired antigen binding fragment, and expressed in any desired host, including mammalian cells, insect cells, plant cells, yeast, and bacteria. For example, techniques to recombinantly produce Fab, Fab' and F(ab')$_2$ fragments can also be employed using methods known in the art such as those disclosed in PCT publication WO 92/22324; Mullinax et al., *BioTechniques* 12(6):864-869 (1992); and Sawai et al., *AJRI* 34:26-34 (1995); and Better et al., *Science* 240:1041-1043 (1988) (said references incorporated by reference in their entireties).

Examples of techniques which can be used to produce single-chain Fvs and antibodies include those described in U.S. Pat. Nos. 4,946,778 and 5,258,498; Huston et al., *Methods in Enzymology* 203:46-88 (1991); Shu et al., *PNAS* 90:7995-7999 (1993); and Skerra et al., *Science* 240:1038-1040 (1988). For some uses, including in vivo use of antibodies in humans and in vitro detection assays, it may be preferable to use chimeric, humanized, or human antibodies. A chimeric antibody is a molecule in which different portions of the antibody are derived from different animal species, such as antibodies having a variable region derived from a murine monoclonal antibody and a human immunoglobulin constant region. Methods for producing chimeric antibodies are known in the art. See, e.g., Morrison, *Science* 229:1202 (1985); Oi et al., *BioTechniques* 4:214 (1986); Gillies et al., *J. Immunol. Methods* 125:191-202 (1989); U.S. Pat. Nos. 5,807,715; 4,816,567; and 4,816,397, which are incorporated herein by reference in their entireties. Humanized antibodies are antibody molecules from non-human species antibody that binds the desired antigen having one or more complementarity determining regions (CDRs) from the non-human species and framework regions from a human immunoglobulin molecule. Often, framework residues in the human framework regions will be substituted with the corresponding residue from the CDR donor antibody to alter, preferably improve, antigen binding. These framework substitutions are identified by methods well known in the art, e.g., by modeling of the interactions of the CDR and framework residues to identify framework residues important for antigen binding and sequence comparison to identify unusual framework residues at particular positions. (See, e.g., Queen et al., U.S. Pat. No. 5,585,089; Riechmann et al., *Nature* 332:323 (1988), which are incorporated herein by reference in their entireties.) Antibodies can be humanized using a variety of techniques known in the art including, for example, CDR-grafting (EP 239,400; PCT publication WO 91/09967; U.S. Pat. Nos. 5,225,539; 5,530,101; and 5,585,089), veneering or resurfacing (EP 592,106; EP 519,596; Padlan, *Molecular Immunology* 28(4/5):489-498 (1991); Studnicka et al., *Protein Engineering* 7(6):805-814 (1994); Roguska. et al., *PNAS* 91:969-973 (1994)), and chain shuffling (U.S. Pat. No. 5,565,332).

Completely human antibodies are particularly desirable for therapeutic treatment of human patients. Human antibodies can be made by a variety of methods known in the art including phage display methods described above using antibody libraries derived from human immunoglobulin sequences. See also, U.S. Pat. Nos. 4,444,887 and 4,716,111; and PCT publications WO 98/46645, WO 98/50433, WO 98/24893, WO 98/16654, WO 96/34096, WO 96/33735, and WO 91/10741; each of which is incorporated herein by reference in its entirety.

Human antibodies can also be produced using transgenic mice which are incapable of expressing functional endogenous immunoglobulins, but which can express human immunoglobulin genes. For example, the human heavy and light chain immunoglobulin gene complexes may be introduced randomly or by homologous recombination into mouse embryonic stem cells. Alternatively, the human variable region, constant region, and diversity region may be introduced into mouse embryonic stem cells in addition to the human heavy and light chain genes. The mouse heavy and light chain immunoglobulin genes may be rendered non-functional separately or simultaneously with the introduction of human immunoglobulin loci by homologous recombination. In particular, homozygous deletion of the JH region prevents endogenous antibody production. The modified embryonic stem cells are expanded and microinjected into blastocysts to produce chimeric mice. The chimeric mice are then bred to produce homozygous offspring that express human antibodies. The transgenic mice are immunized in the normal fashion with a selected antigen, e.g., all or a portion of a desired target polypeptide. Monoclonal antibodies directed against the antigen can be obtained from the immunized, transgenic mice using conventional hybridoma technology. The human immunoglobulin transgenes harbored by the transgenic mice rearrange during B-cell differentiation, and subsequently undergo class switching and somatic mutation. Thus, using such a technique, it is possible to produce therapeutically useful IgG, IgA, IgM and IgE antibodies. For an overview of this technology for producing human antibodies, see Lonberg and Huszar *Int. Rev. Immunol.* 13:65-93 (1995). For a detailed discussion of this technology for producing human antibodies and human monoclonal antibodies and protocols for producing such antibodies, see, e.g., PCT publications WO 98/24893; WO 96/34096; WO 96/33735; U.S. Pat. Nos. 5,413,923; 5,625,126; 5,633,425; 5,569,825; 5,661,016; 5,545,806; 5,814,318; and 5,939,598, which are incorporated by reference herein in their entirety. In addition, companies such as Abgenix, Inc. (Freemont, Calif.) and GenPharm (San Jose, Calif.) can be engaged to provide human antibodies directed against a selected antigen using technology similar to that described above.

Completely human antibodies which recognize a selected epitope can be generated using a technique referred to as "guided selection." In this approach a selected non-human monoclonal antibody, e.g., a mouse antibody, is used to guide the selection of a completely human antibody recognizing the same epitope. (Jespers et al., *Bio/Technology* 12:899-903 (1988). See also, U.S. Pat. No. 5,565,332.)

Further, antibodies to target polypeptides of the invention can, in turn, be utilized to generate anti-idiotype antibodies that "mimic" target polypeptides using techniques well known to those skilled in the art. (See, e.g., Greenspan & Bona, *FASEB J.* 7(5):437-444 (1989) and Nissinoff, *J. Immunol.* 147(8):2429-2438 (1991)). For example, antibodies which bind to and competitively inhibit polypeptide multimerization and/or binding of a polypeptide of the invention to a ligand can be used to generate anti-idiotypes that "mimic" the polypeptide multimerization and/or binding domain and, as a consequence, bind to and neutralize polypeptide and/or its ligand. Such neutralizing anti-idiotypes or Fab fragments of such anti-idiotypes can be used in therapeutic regimens to neutralize polypeptide ligand. For example, such anti-idiotypic antibodies can be used to bind a desired target polypeptide and/or to bind its ligands/receptors, and thereby block its biological activity.

In another embodiment, DNA encoding desired monoclonal antibodies may be readily isolated and sequenced using conventional procedures (e.g., by using oligonucleotide probes that are capable of binding specifically to genes encoding the heavy and light chains of murine antibodies). The isolated and subcloned hybridoma cells serve as a preferred source of such DNA. Once isolated, the DNA may be placed into expression vectors, which are then transfected into prokaryotic or eukaryotic host cells such as, but not limited to, *E. coli* cells, simian COS cells, Chinese Hamster Ovary (CHO) cells or myeloma cells that do not otherwise produce immunoglobulins. More particularly, the isolated DNA (which may be synthetic as described herein) may be used to clone constant and variable region sequences for the manufacture antibodies as described in Newman et al., U.S.

Pat. No. 5,658,570, filed Jan. 25, 1995, which is incorporated by reference herein. Essentially, this entails extraction of RNA from the selected cells, conversion to cDNA, and amplification by PCR using Ig specific primers. Suitable primers for this purpose are also described in U.S. Pat. No. 5,658,570. As will be discussed in more detail below, transformed cells expressing the desired antibody may be grown up in relatively large quantities to provide clinical and commercial supplies of the immunoglobulin.

In one embodiment, an IGF-1R antibody of the invention comprises at least one heavy or light chain CDR of an antibody molecule. In another embodiment, an IGF-1R antibody of the invention comprises at least two CDRs from one or more antibody molecules. In another embodiment, an IGF-1R antibody of the invention comprises at least three CDRs from one or more antibody molecules. In another embodiment, an IGF-IR antibody of the invention comprises at least four CDRs from one or more antibody molecules. In another embodiment, an IGF-1R antibody of the invention comprises at least five CDRs from one or more antibody molecules. In another embodiment, an IGF-IR antibody of the invention comprises at least six CDRs from one or more antibody molecules. Exemplary antibody molecules comprising at least one CDR that can be included in the subject IGF-1R antibodies are described herein.

In a specific embodiment, the amino acid sequence of the heavy and/or light chain variable domains may be inspected to identify the sequences of the complementarity determining regions (CDRs) by methods that are well know in the art, e.g., by comparison to known amino acid sequences of other heavy and light chain variable regions to determine the regions of sequence hypervariability. Using routine recombinant DNA techniques, one or more of the CDRs may be inserted within framework regions, e.g., into human framework regions to humanize a non-human antibody. The framework regions may be naturally occurring or consensus framework regions, and preferably human framework regions (see, e.g., Chothia et al., *J. Mol. Biol.* 278:457-479 (1998) for a listing of human framework regions). Preferably, the polynucleotide generated by the combination of the framework regions and CDRs encodes an antibody that specifically binds to at least one epitope of a desired polypeptide, e.g., IGF-1R. Preferably, one or more amino acid substitutions may be made within the framework regions, and, preferably, the amino acid substitutions improve binding of the antibody to its antigen. Additionally, such methods may be used to make amino acid substitutions or deletions of one or more variable region cysteine residues participating in an intrachain disulfide bond to generate antibody molecules lacking one or more intrachain disulfide bonds. Other alterations to the polynucleotide are encompassed by the present invention and within the skill of the art.

In addition, techniques developed for the production of "chimeric antibodies" (Morrison et al., *Proc. Natl. Acad. Sci.* 81:851-855 (1984); Neuberger et al., *Nature* 312:604-608 (1984); Takeda et al., *Nature* 314:452-454 (1985)) by splicing genes from a mouse antibody molecule of appropriate antigen specificity together with genes from a human antibody molecule of appropriate biological activity can be used. As used herein, a chimeric antibody is a molecule in which different portions are derived from different animal species, such as those having a variable region derived from a murine monoclonal antibody and a human immunoglobulin constant region, e.g., humanized antibodies.

Alternatively, techniques described for the production of single chain antibodies (U.S. Pat. No. 4,694,778; Bird, *Science* 242:423-442 (1988); Huston et al., *Proc. Natl. Acad. Sci. USA* 85:5879-5883 (1988); and Ward et al., *Nature* 334:544-554 (1989)) can be adapted to produce single chain antibodies. Single chain antibodies are formed by linking the heavy and light chain fragments of the Fv region via an amino acid bridge, resulting in a single chain antibody. Techniques for the assembly of functional Fv fragments in *E coli* may also be used (Skerra et al., *Science* 242:1038-1041 (1988)).

Yet other embodiments of the present invention comprise the generation of human or substantially human antibodies in transgenic animals (e.g., mice) that are incapable of endogenous immunoglobulin production (see e.g., U.S. Pat. Nos. 6,075,181, 5,939,598, 5,591,669 and 5,589,369 each of which is incorporated herein by reference). For example, it has been described that the homozygous deletion of the antibody heavy-chain joining region in chimeric and germ-line mutant mice results in complete inhibition of endogenous antibody production. Transfer of a human immunoglobulin gene array to such germ line mutant mice will result in the production of human antibodies upon antigen challenge. Another preferred means of generating human antibodies using SCID mice is disclosed in U.S. Pat. No. 5,811,524 which is incorporated herein by reference. It will be appreciated that the genetic material associated with these human antibodies may also be isolated and manipulated as described herein.

Yet another highly efficient means for generating recombinant antibodies is disclosed by Newman, *Biotechnology* 10: 1455-1460 (1992). Specifically, this technique results in the generation of primatized antibodies that contain monkey variable domains and human constant sequences. This reference is incorporated by reference in its entirety herein. Moreover, this technique is also described in commonly assigned U.S. Pat. Nos. 5,658,570, 5,693,780 and 5,756,096 each of which is incorporated herein by reference.

In another embodiment, lymphocytes can be selected by micromanipulation and the variable genes isolated. For example, peripheral blood mononuclear cells can be isolated from an immunized mammal and cultured for about 7 days in vitro. The cultures can be screened for specific IgGs that meet the screening criteria. Cells from positive wells can be isolated. Individual Ig-producing B cells can be isolated by FACS or by identifying them in a complement-mediated hemolytic plaque assay. Ig-producing B cells can be micromanipulated into a tube and the VH and VL genes can be amplified using, e.g., RT-PCR. The VH and VL genes can be cloned into an antibody expression vector and transfected into cells (e.g., eukaryotic or prokaryotic cells) for expression.

Alternatively, antibody-producing cell lines may be selected and cultured using techniques well known to the skilled artisan. Such techniques are described in a variety of laboratory manuals and primary publications. In this respect, techniques suitable for use in the invention as described below are described in *Current Protocols in Immunology*, Coligan et al., Eds., Green Publishing Associates and Wiley-Interscience, John Wiley and Sons, New York (1991) which is herein incorporated by reference in its entirety, including supplements.

Antibodies of the present invention can be produced by any method known in the art for the synthesis of antibodies, in particular, by chemical synthesis or preferably, by recombinant expression techniques as described herein.

In one embodiment, an IGF-1R antibody, or antigen-binding fragment, variant, or derivative thereof of the invention comprises a synthetic constant region wherein one or more domains are partially or entirely deleted ("domain-deleted antibodies"). In certain embodiments compatible modified antibodies will comprise domain deleted constructs or variants wherein the entire CH2 domain has been removed (ΔCH2 constructs). For other embodiments a short connecting peptide may be substituted for the deleted domain to provide flexibility and freedom of movement for the variable region. Those skilled in the art will appreciate that such constructs are particularly preferred due to the regulatory properties of the CH2 domain on the catabolic rate of the antibody. Domain deleted constructs can be derived using a vector encoding an IgG$_1$ human constant domain (see, e.g., WO 02/060955A2 and WO02/096948A2). This vector is engineered to delete the CH2 domain and provide a synthetic vector expressing a domain deleted IgG$_1$ constant region.

In certain embodiments, IGF-1R antibodies, or antigen-binding fragments, variants, or derivatives thereof of the invention are minibodies. Minibodies can be made using methods described in the art (see e.g., U.S. Pat. No. 5,837,821 or WO 94/09817A1).

In one embodiment, an IGF-1R antibody, or antigen-binding fragment, variant, or derivative thereof of the invention comprises an immunoglobulin heavy chain having deletion or substitution of a few or even a single amino acid as long as it permits association between the monomeric subunits. For example, the mutation of a single amino acid in selected areas of the CH2 domain may be enough to substantially reduce Fc binding and thereby increase tumor localization. Similarly, it may be desirable to simply delete that part of one or more constant region domains that control the effector function (e.g. complement binding) to be modulated. Such partial deletions of the constant regions may improve selected characteristics of the antibody (serum half-life) while leaving other desirable functions associated with the subject constant region domain intact. Moreover, as alluded to above, the constant regions of the disclosed antibodies may be synthetic through the mutation or substitution of one or more amino acids that enhances the profile of the resulting construct. In this respect it may be possible to disrupt the activity provided by a conserved binding site (e.g. Fc binding) while substantially maintaining the configuration and immunogenic profile of the modified antibody. Yet other embodiments comprise the addition of one or more amino acids to the constant region to enhance desirable characteristics such as effector function or provide for more cytotoxin or carbohydrate attachment. In such embodiments it may be desirable to insert or replicate specific sequences derived from selected constant region domains.

The present invention also provides antibodies that comprise, consist essentially of, or consist of, variants (including derivatives) of antibody molecules (e.g., the VH regions and/or VL regions) described herein, which antibodies or fragments thereof immunospecifically bind to an IGF-1R polypeptide or fragment or variant thereof. Standard techniques known to those of skill in the art can be used to introduce mutations in the nucleotide sequence encoding an IGF-1R antibody, including, but not limited to, site-directed mutagenesis and PCR-mediated mutagenesis which result in amino acid substitutions. Preferably, the variants (including derivatives) encode less than 50 amino acid substitutions, less than 40 amino acid substitutions, less than 30 amino acid substitutions, less than 25 amino acid substitutions, less than 20 amino acid substitutions, less than 15 amino acid substitutions, less than 10 amino acid substitutions, less than 5 amino acid substitutions, less than 4 amino acid substitutions, less than 3 amino acid substitutions, or less than 2 amino acid substitutions relative to the reference VH region, VH-CDR1, VH-CDR2, VH-CDR3, VL region, VL-CDR1, VL-CDR2, or VL-CDR3. A "conservative amino acid substitution" is one in which the amino acid residue is replaced with an amino acid residue having a side chain with a similar charge. Families of amino acid residues having side chains with similar charges have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Alternatively, mutations can be introduced randomly along all or part of the coding sequence, such as by saturation mutagenesis, and the resultant mutants can be screened for biological activity to identify mutants that retain activity (e.g., the ability to bind an IGF-1R polypeptide).

For example, it is possible to introduce mutations only in framework regions or only in CDR regions of an antibody molecule. Introduced mutations may be silent or neutral missense mutations, i.e., have no, or little, effect on an antibody's ability to bind antigen, indeed some such mutations do not alter the amino acid sequence whatsoever. These types of mutations may be useful to optimize codon usage, or improve a hybridoma's antibody production. Codon-optimized coding regions encoding IGF-1R antibodies of the present invention are disclosed elsewhere herein. Alternatively, non-neutral missense mutations may alter an antibody's ability to bind antigen. The location of most silent and neutral missense mutations is likely to be in the framework regions, while the location of most non-neutral missense mutations is likely to be in CDR, though this is not an absolute requirement. One of skill in the art would be able to design and test mutant molecules with desired properties such as no alteration in antigen binding activity or alteration in binding activity (e.g., improvements in antigen binding activity or change in antibody specificity). Following mutagenesis, the encoded protein may routinely be expressed and the functional and/or biological activity of the encoded protein, (e.g., ability to immunospecifically bind at least one epitope of an IGF-1R polypeptide) can be determined using techniques described herein or by routinely modifying techniques known in the art.

IV. Polynucleotides Encoding IGF-1R Antibodies

The present invention also provides for nucleic acid molecules encoding IGF-1R antibodies, or antigen-binding fragments, variants, or derivatives thereof of the invention.

In one embodiment, the present invention provides an isolated polynucleotide comprising, consisting essentially of, or consisting of a nucleic acid encoding an immunoglobulin heavy chain variable region (VH), where at least one of the CDRs of the heavy chain variable region or at least two of the VH-CDRs of the heavy chain variable region are at least 80%, 85%, 90% or 95% identical to reference heavy chain VH-CDR1, VH-CDR2, or VH-CDR3 amino acid sequences from monoclonal IGF-1R antibodies disclosed herein. Alternatively, the VH-CDR1, VH-CDR2, and VH-CDR3 regions of the VH are at least 80%, 85%, 90% or 95% identical to reference heavy chain VH-CDR1, VH-CDR2, and VH-CDR3 amino acid sequences from monoclonal IGF-1R antibodies disclosed herein. Thus, according to this embodiment a heavy chain variable region of the invention has VH-CDR1, VH-CDR2, or VH-CDR3 polypeptide sequences related to the polypeptide sequences shown in Table 5:

TABLE 5

Reference VH-CDR1, VH-CDR2, and VH-CDR3 amino acid sequences*

| Antibody | SEQUENCE PN/PP (VH-CDR1, VH-CDR2, and VH-CDR3 underlined) | VH CDR1 | VH CDR2 | VH CDR3 |
|---|---|---|---|---|
| M12-E01 | GAAGTTCAATTGTTAGAGTCTGGTGGCGGTCT TGTTCAGCCTGGTGGTTCTTTACGTCTTTCTT GCGCTGCTTCCGGATTCACTTTCTCTCCTTAC TCTATGCTTTGGGTTCGCCAAGCTCCTGGTAA AGGTTTGGAGTGGGTTTCTTCTATCGGTTCTT CTGGTGGCTCTACTCGTTATGCTGACTCCGTT AAAGGTCGCTTCACTATCTCTAGAGACAACTC TAAGAATACTCTACTTGCAGATGAACAGCT TAAGGGCTGAGGACACCGCCATGTATTACTGT GCACGGGTACGGGGGATCCTTCATTACGATAT TTTGATTGGTAGAAATCTCTACTACTACTACA TGGACGTCTGGGGCAAAGGGACCACGGTCACC GTCTCAAGC (SEQ ID NO: 3)<br><br>EVQLLESGGGLVQPGGSLRLSCAASGFTFS<u>PY SML</u>WVRQAPGKGLEWVS<u>SIGSSGGSTRYADSV KG</u>RFTISRDNSKNTLYLQMNSLRAEDTAMYYC AR<u>VRGILHYDILIGRNLYYYMDV</u>WGKGTTVT VSS (SEQ ID NO: 4) | PYSML (SEQ ID NO: 5) | SIGSSGGS TRYADSVK G (SEQ ID NO: 6) | VRGILHYD ILIGRNLY YYYMDV (SEQ ID NO: 7) |
| M12-G04 | GAAGTTCAATTGTTAGAGTCTGGTGGCGGTCT TGTTCAGCCTGGTGGTTCTTTACGTCTTTCTT GCGCTGCTTCCGGATTCACTTTCTCTAAGTAC ACTATGCATTGGGTTCGCCAAGCTCCTGGTAA AGGTTTGGAGTGGGTTTCTTCTATCGTTTCTT CTGGTGGCTGGACTGATTATGCTGACTCCGTT AAAGGTCGCTTCACTATCTCTAGAGACAACTC TAAGAATACTCTACTTGCAGATGAACAGCT TAAGGGCTGAGGACACGGCCGTGTATTACTGT GCGAGAGATCGGAGTATAGCAGCAGCTGGTAC CGGTTGGTCTGTGAGTTTTGTGGACTGGTTCG ACCCCTGGGGCCAGGGAACCCTGGTCACCGTC TCAAGC (SEQ ID NO: 8)<br><br>EVQLLESGGGLVQPGGSLRLSCAASGFTFS<u>KY TMH</u>WVRQAPGKGLEWVS<u>SIVSSGGWTDYADSV KG</u>RFTISRDNSKNTLYLQMNSLRAEDTAVYYC ARD<u>RSIAAAGTGWSVSFVDWFDP</u>WGQGTLVTV SS (SEQ ID NO: 9) | KYTMH (SEQ ID NO: 10) | SIVSSGGW TDYADSVK G (SEQ ID NO: 11) | DRSIAAAG TGWSVSFV DWFDP (SEQ ID NO: 12) |
| M13-C06 | GAAGTTCAATTGTTAGAGTCTGGTGGCGGTCT TGTTCAGCCTGGTGGTTCTTTACGTCTTTCTT GCGCTGCTTCCGGATTCACTTTCTCTATTTAC CGTATGCAGTGGGTTCGCCAAGCTCCTGGTAA AGGTTTGGAGTGGGTTTCTGGTATCTCTCCTT CTGGTGGCACTACTTGGTATGCTGACTCCGTT AAAGGTCGCTTCACTATCTCTAGAGACAACTC TAAGAATACTCTACTTGCAGATGAACAGCT TAAGGGCTGAGGACACGGCCGTGTATTACTGT GCGAGATGGAGCGGGGGTTCGGGCTATGCTTT TGATATCTGGGGCCAAGGGACAATGGTCACCG TCTCAAGC (SEQ ID NO: 13)<br><br>EVQLLESGGGLVQPGGSLRLSCAASGFTFS<u>IY RMQ</u>WVRQAPGKGLEWVS<u>GISPSGGTTWYADSV KG</u>RFTISRDNSKNTLYLQMNSLRAEDTAVYYC AR<u>WSGGSGYAFDI</u>WGQGTMVTVSS (SEQ ID NO: 14) | IYRMQ (SEQ ID NO: 15) | GISPSGGT TWYADSVK G (SEQ ID NO: 16) | WSGGSGYA FDI (SEQ ID NO: 17) |
| M13-C06 Optimized | GAGGTCCAGCTGTTGGAGTCCGGCGGTGGCCT GGTGCAGCCTGGGGGGTCCCTGAGACTCTCCT GCGCAGCTAGCGGCTTCACCTTCAGCATTTAC CGTATGCAGTGGGTGCGCCAGGCTCCTGGAAA GGGGCTGGAGTGGGTTTCCGGTATCTCTCCCT CTGGTGGCACGACGTGGTATGCTGACTCCGTG AAGGGCCGGTTCACAATCTCCAGAGACAATTC CAAGAACACTCTGTACCTGCAAATGAACAGCC TGAGAGCTGAGGATACTGCAGTGTACTACTGC | IYRMQ (SEQ ID NO: 15) | GISPSGGT TWYADSVK G (SEQ ID NO: 16) | WSGGSGYA FDI (SEQ ID NO: 17) |

TABLE 5-continued

Reference VH-CDR1, VH-CDR2, and VH-CDR3 amino acid sequences*

| Antibody | SEQUENCE PN/PP (VH-CDR1, VH-CDR2, and VH-CDR3 underlined) | VH CDR1 | VH CDR2 | VH CDR3 |
|---|---|---|---|---|
| | GCCAGATGGTCCGGGGGCTCCGGATACGCCTT<br>CGACATCTGGGGACAGGGAACCATGGTCACCG<br>TCTCAAGC<br>(SEQ ID NO: 18)<br><br>EVQLLESGGGLVQPGGSLRLSCAASGFTFS<u>IY<br>RM</u>QWVRQAPGKGLEWVS<u>GISPSGGTTWYADSV<br>KG</u>RFTISRDNSKNTLYLQMNSLRAEDTAVYYC<br>AR<u>WSGGSGYAFDI</u>WGQGTMVTVSS<br>(SEQ ID NO: 14) | | | |
| M14-B01 | GAAGTTCAATTGTTAGAGTCTGGTGGCGGTCT<br>TGTTCAGCCTGGTGGTTCTTTACGTCTTTCTT<br>GCGCTGCTTCCGGATTCACTTTCTCTAATTAC<br>CATATGGCTTGGGTTCGCCAAGCTCCTGGTAA<br>AGGTTTGGAGTGGGTTTCTGTTATCTCTCCTA<br>CTGGTGGCCGTACTACTTATGCTGACTCCGTT<br>AAAGGTCGCTTCACTATCTCTAGAGACAACTC<br>TAAGAATACTCTCTACTTGCAGATGAACAGCT<br>TAAGGGCTGAGGACACAGCCACATATTACTGT<br>GCGAGAGCGGGGTACAGCTATGGTTATGGCTA<br>CTTTGACTACTGGGGCCAGGGAACCCTGGTCA<br>CCGTCTCAAGC<br>(SEQ ID NO: 19)<br><br>EVQLLESGGGLVQPGGSLRLSCAASGFTFS<u>NY<br>HMA</u>WVRQAPGKGLEWVS<u>VISPTGGRTTYADSV<br>KG</u>RFTISRDNSKNTLYLQMNSLRAEDTATYYC<br>AR<u>AGYSYGYGYFDY</u>WGQGTLVTVSS<br>(SEQ ID NO: 20) | NYHMA<br>(SEQ ID<br>NO: 21) | VISPTGGR<br>TTYADSVK<br>G<br>(SEQ ID<br>NO: 22) | AGYSYGYG<br>YFDY<br>(SEQ ID<br>NO: 23) |
| M14-B01 Optimized | GAGGTCCAGCTGTTGGAGTCCGGCGGTGGCCT<br>GGTGCAGCCTGGGGGGTCCCTGAGACTCTCCT<br>GCGCAGCTAGCGGCTTCACCTTCAGCAATTAC<br>CACATGGCCTGGGTGCGCCAGGCTCCTGGAAA<br>GGGGCTGGAGTGGGTTTCCGTGATCTCTCCTA<br>CCGGTGGCAGGACCACTTACGCTGACTCCGTG<br>AAGGGCCGGTTCACAATCTCCAGAGACAATTC<br>CAAGAACACTCTGTACCTGCAAATGAACAGCC<br>TGAGAGCTGAGGATACTGCAACATACTACTGC<br>GCCAGAGCCGGGTACTCCTACGGCTACGGATA<br>CTTCGACTACTGGGGACAGGGAACCCTGGTCA<br>CCGTCTCAAGC<br>(SEQ ID NO: 24)<br><br>EVQLLESGGGLVQPGGSLRLSCAASGFTFS<u>NY<br>HMA</u>WVRQAPGKGLEWVS<u>VISPTGGRTTYADSV<br>KG</u>RFTISRDNSKNTLYLQMNSLRAEDTATYYC<br>AR<u>AGYSYGYGYFDY</u>WGQGTLVTVSS<br>(SEQ ID NO: 20) | NYHMA<br>(SEQ ID<br>NO: 21) | VISPTGGR<br>TTYADSVK<br>G<br>(SEQ ID<br>NO: 22) | AGYSYGYG<br>YFDY<br>(SEQ ID<br>NO: 23) |
| M14-C03 | GAAGTTCAATTGTTAGAGTCTGGTGGCGGTCT<br>TGTTCAGCCTGGTGGTTCTTTACGTCTTTCTT<br>GCGCTGCTTCCGGATTCACTTTCTCTAAGTAC<br>ATGATGTCTTGGGTTCGCCAAGCTCCTGGTAA<br>AGGTTTGGAGTGGGTTTCTTATATCTCTCCTT<br>CTGGTGGCCTTACTTGGTATGCTGACTCCGTT<br>AAAGGTCGCTTCACTATCTCTAGAGACAACTC<br>TAAGAATACTCTCTACTTGCAGATGAACAGCT<br>TAAGGGCTGAGGACACAGCCGTGTATTACTGT<br>GCGAGAGATGGAGCTAGAGGCTACGGTATGGA<br>CGTCTGGGGCCAAGGGACCACGGTCACCGTCT<br>CAAGC<br>(SEQ ID NO: 25)<br><br>EVQLLESGGGLVQPGGSLRLSCAASGFTFS<u>KY<br>MMS</u>WVRQAPGKGLEWVS<u>YISPSGGLTWYADSV<br>KG</u>RFTISRDNSKNTLYLQMNSLRAEDTAVYYC<br>AR<u>DGARGYGMDV</u>WGQGTTVTVSS<br>(SEQ ID NO: 26) | KYMMS<br>(SEQ ID<br>NO: 27) | YISPSGGL<br>TWYADSVK<br>G<br>(SEQ ID<br>NO: 28) | DGARGYGM<br>DV<br>(SEQ ID<br>NO: 29) |

TABLE 5-continued

Reference VH-CDR1, VH-CDR2, and VH-CDR3 amino acid sequences*

| Antibody | SEQUENCE PN/PP (VH-CDR1, VH-CDR2, and VH-CDR3 underlined) | VH CDR1 | VH CDR2 | VH CDR3 |
|---|---|---|---|---|
| M14-C03 Optimized | GAGGTCCAGCTGTTGGAGTCCGGCGGTGGCCT GGTGCAGCCTGGGGGGTCCCTGAGACTCTCCT GCGCAGCTAGCGGCTTCACCTTCAGCAAGTAC ATGATGTCTTGGGTGCGCCAGGCTCCTGGAAA GGGGCTGGAGTGGGTTTCCTATATCTCTCCCT CTGGTGGCCTGACGTGGTATGCTGACTCCGTG AAGGGCCGGTTCACAATCTCCAGAGACAATTC CAAGAACACTCTGTACCTGCAAATGAACAGCC TGAGAGCTGAGGATACTGCAGTGTACTACTGC GCCAGAGATGGGGCTAGAGGATACGGAATGGA CGTCTGGGGACAGGGAACCACCGTCACCGTCT CAAGC (SEQ ID NO: 30)<br><br>EVQLLESGGGLVQPGGSLRLSCAASGFTFS<u>KY MMS</u>WVRQAPGKGLEWVS<u>YISPSGGLTWYADSV KG</u>RFTISRDNSKNTLYLQMNSLRAEDTAVYYC ARD<u>GARGYGMDV</u>WGQGTTVTVSS (SEQ ID NO: 26) | KYMMS (SEQ ID NO: 27) | YISPSGGL TWYADSVK G (SEQ ID NO: 28) | DGARGYGM DV (SEQ ID NO: 29) |
| M14-G11 | GAAGTTCAATTGTTAGAGTCTGGTGGCGGTCT TGTTCAGCCTGGTGGTTCTTTACGTCTTTCTT GCGCTGCTTCCGGATTCACTTTCTCTAATTAC CCTATGTATTGGGTTCGCCAAGCTCCTGGTAA AGGTTTGGAGTGGGTTTCTCGTATCTCTTCTT CTGGTGGCCGTACTGTTTATGCTGACTCCGTT AAAGGTCGCTTCACTATCTCTAGAGACAACTC TAAGAATACTCTCTACTTGCAGATGAACAGCT TAAGGGCTGAGGACACGGCCGTGTATTACTGT GCGAGAGATCGATGGTCCAGATCTGCAGCTGA ATATGGTTGGGTGGCTACTGGGGCCAGGGAA CCCTGGTCACCGTCTCAAGC (SEQ ID NO: 31)<br><br>EVQLLESGGGLVQPGGSLRLSCAASGFTFS<u>NY PMY</u>WVRQAPGKGLEWVS<u>RISSSGGRTVYADSV KG</u>RFTISRDNSKNTLYLQMNSLRAEDTAVYYC ARD<u>RWSRSAAEYGLGGY</u>WGQGTLVTVSS (SEQ ID NO: 32) | NYPMY (SEQ ID NO: 33) | RISSSGGR TVYADSVK G (SEQ ID NO: 34) | DRWSRSAA EYGLGGY (SEQ ID NO: 35) |
| M14-G11 Optimized | GAGGTCCAGCTGTTGGAGTCCGGCGGTGGCCT GGTGCAGCCTGGGGGGTCCCTGAGACTCTCCT GCGCAGCTAGCGGCTTCACCTTCAGCAATTAC CCCATGTACTGGGTGCGCCAGGCTCCTGGAAA GGGGCTGGAGTGGGTTTCCAGGATCTCTAGCA GCGGTGGCAGGACCGTGTACGCTGACTCCGTG AAGGGCCGGTTCACAATCTCCAGAGACAATTC CAAGAACACTCTGTACCTGCAAATGAACAGCC TGAGAGCTGAGGATACTGCAGTGTACTACTGC GCCAGAGATAGGTGGTCCAGATCTGCAGCCGA GTACGGACTGGGGGGCTACTGGGGACAGGGAA CCCTGGTCACCGTCTCAAGC (SEQ ID NO: 36)<br><br>EVQLLESGGGLVQPGGSLRLSCAASGFTFS<u>NY PMY</u>WVRQAPGKGLEWVS<u>RISSSGGRTVYADSV KG</u>RFTISRDNSKNTLYLQMNSLRAEDTAVYYC ARD<u>RWSRSAAEYGLGGY</u>WGQGTLVTVSS (SEQ ID NO: 32) | NYPMY (SEQ ID NO: 33) | RISSSGGR TVYADSVK G (SEQ ID NO: 34) | DRWSRSAA EYGLGGY (SEQ ID NO: 35) |
| P2A7.3E11 | CAGGTTCAGCTGCAGCAGTCTGGACCTGAGCT AGTGAAGCCTGGGGCTTCAGTGAAGATGTCCT GCAAGGCTTCTGGAAACACATTCACTGACTAT GTTATAAACTGGGTGAAGCAGAGAACTGGACA GGGCCTTGAGTGGATTGGAGAGATTTATCCTG GAAATGAAAATACTTATTACAATGAGAAGTTC AAGGGCAAGGCCACACTGACTGCAGACAAATC CTCCAACACAGCCTACATGCAGCTCAGTAGCC TGACATCTGAGGACTCTGCGGTCTATTTCTGT GCAAGAGGGATTTATTACTACGGTAGTAGGAC | DYVIN (SEQ ID NO: 39) | IYPGNENT YYNEKFKG (SEQ ID NO: 40) | GIYYYGSR TRTMDY (SEQ ID NO: 41) |

TABLE 5-continued

Reference VH-CDR1, VH-CDR2, and VH-CDR3 amino acid sequences*

| Antibody | SEQUENCE PN/PP (VH-CDR1, VH-CDR2, and VH-CDR3 underlined) | VH CDR1 | VH CDR2 | VH CDR3 |
|---|---|---|---|---|
| | GAGGACTATGGACTACTGGGGTCAAGGAACCT<br>CAGTCACCGTCTCCTCA<br>(SEQ ID NO: 37)<br><br>QVQLQQSGPELVKPGASVKMSCKASGNTFTDY<br>VINWVKQRTGQGLEWIGEIYPGNENTYYNEKF<br>KGKATLTADKSSNTAYMQLSSLTSEDSAVYFC<br>ARGIYYYGSRTRTMDYWGQGTSVTVSS<br>(SEQ ID NO: 38) | | | |
| 20C8.3B8 | GACGTCCAACTGCAGGAGTCTGGACCTGACCT<br>GGTGAAACCTTCTCAGTCACTTTCACTCACCT<br>GCACTGTCACTGGCTACTCCATCACCAGTGGT<br>TATAGCTGGCACTGGATCCGGCAGTTTCCAGG<br>AAACAAACTGGAATGGATGGGCTACATACACT<br>ACAGTGGTGGCACTAACTACAACCCATCTCTC<br>AAAAGTCGAATCTCTATCACTCGAGACACATC<br>CAAGAACCAGTTCTTCCTCCAGTTGAATTCTG<br>TGACTACTGAGGACACAGCCACATATTACTGT<br>GCAAGATCGGGGTACGGCTACAGGAGTGCGTA<br>CTATTTTGACTACTGGGGCCAAGGGACCACGG<br>TCACCGTCTCCTCA<br>(SEQ ID NO: 42)<br><br>DVQLQESGPDLVKPSQSLSLTCTVTGYSITSG<br>YSWHWIRQFPGNKLEWMGYIHYSGGTNYNPSL<br>KSRISITRDTSKNQFFLQLNSVTTEDTATYYC<br>ARSGYGYRSAYYFDYWGQGTTVTVSS<br>(SEQ ID NO: 43) | SGYSWH<br>(SEQ ID<br>NO: 44) | YIHYSGGT<br>NYNPSLKS<br>(SEQ ID<br>NO: 45) | SGYGYRSA<br>YYFDY<br>(SEQ ID<br>NO: 46) |
| P1A2.2B11 | CAAATACAGTTGGTTCAGAGCGGACCTGAGCT<br>GAAGAAGCCTGGAGAGACAGTCAAGATCTCCT<br>GCAAGGCTTCTGGGTATACCTTCACAAACCAT<br>GGAATGAACTGGGTGAAGCAGGCTCCAGGAAA<br>GGGTTTAAAGTGGATGGGCTGGATAAACACCT<br>CCACTGGAGAGCCAACATATGCTGATGACTTC<br>AAGGGACGTTTTGCCTTCTCTTTGGAAACCTC<br>TGCCAGCACTGCCTTTTTGCAGATCAACAACC<br>TCAAAAATGAGGACACGGCTTCATATTTCTGT<br>GCAAGTCCCCTCTACTATATGTACGGGCGGTA<br>TATCGATGTCTGGGGCGCAGGGACCGCGGTCA<br>CCGTCTCCTCA<br>(SEQ ID NO: 47)<br><br>QIQLVQSGPELKKPGETVKISCKASGYTFTNH<br>GMNWVKQAPGKGLKWMGWNTSTGEPTYADDFK<br>GRFAFSLETSASTAFLQINNLKNEDTASYFCA<br>SPLYYMYGRYIDVWGAGTAVTVSS<br>(SEQ ID NO: 48) | NHGMN<br>(SEQ ID<br>NO: 49) | NTSTGEPT<br>YADDFKG<br>(SEQ ID<br>NO: 50) | PLYYMYGR<br>YIDV<br>(SEQ ID<br>NO: 51) |
| 20D8.24B11 | ACGTCCAACTGCAGGAGTCTGGACCTGACCTG<br>GTGAAACCTTCTCAGTCACTTTCACTCACCTG<br>CACTGTCACTGGCTACTCCATCACCAGTGGTT<br>ATAGCTGGCACTGGATCCGGCAGTTTCCAGGA<br>AACAAACTGGAATGGATGGGCTACATACACTA<br>CAGTGGTGGCACTAACTACAACCCATCTCTCA<br>AAAGTCGAATCTCTATCACTCGAGACACATCC<br>AAGAACCAGTTCTTCCTCCAGTTGAATTCTGT<br>GACTACTGAGGACACAGCCACATATTACTGTG<br>CAAGATCGGGGTACGGCTACAGGAGTG<br>(SEQ ID NO: 52)<br><br>DVQLQESGPDLVKPSQSLSLTCTVTGYSITSG<br>YSWHWIRQFPGNKLEWMGYIHYSGGTNYNPSL<br>KSRISITRDTSKNQFFLQLNSVTTEDTATYYC<br>ARSGYGYRSAYYFDYWGQGTTLTVSS<br>(SEQ ID NO: 53) | SGYSWH<br>(SEQ ID<br>NO: 54) | YIHYSGGT<br>NYNPSLKS<br>(SEQ ID<br>NO: 55) | SGYGYRSA<br>YYFDY<br>(SEQ ID<br>NO: 56) |
| P1G10.2B8 | CAGATCCAGTTGGTGCAGTCTGGACCTGACCT<br>GAAGAAGCCTGGAGAGACAGTCAAGATCTCCT<br>GCAAGGCTTCTGGGTATACCTTCACAAACCAT<br>GGAATGAACTGGGTGAAGCAGGCTCCAGGAAA<br>GGATTTAAAGTGGATGGGCTGGATAAACACCA | NHGMN<br>(SEQ ID<br>NO: 59) | WINTNTGE<br>PTYADDFK<br>(SEQ ID<br>NO: 60) | PLYYRNGR<br>YFDV<br>(SEQ ID<br>NO: 61) |

TABLE 5-continued

Reference VH-CDR1, VH-CDR2, and VH-CDR3 amino acid sequences*

| Antibody | SEQUENCE PN/PP (VH-CDR1, VH-CDR2, and VH-CDR3 underlined) | VH CDR1 | VH CDR2 | VH CDR3 |
|---|---|---|---|---|
| | ACACTGGAGAGCCAACATATGCTGATGACTTC<br>AAGGGACGGTTTGCCTTCTCTTTGGAAACCTC<br>TGCCAGCACTGCCTATTTGCAGATCAACAACC<br>TCAAAAATGAGGACACGGCTACATATTTCTGT<br>GCAAGTCCCCTCTACTATAGGAACGGGCGATA<br>CTTCGATGTCTGGGGCGCAGGGACCACGGTCA<br>CCGTCTCC<br>(SEQ ID NO: 57)<br>QIQLVQSGPDLKKPGETVKISCKASGYTFTNH<br>GMNWVKQAPGKDLKWMGWINTNTGEPTYADDF<br>KGRFAFSLETSASTAYLQINNLKNEDTATYFC<br>ASPLYYRNGRYFDVWGAGTTVTSS<br>(SEQ ID NO: 58) | | | |
| P1E2.3B12 | CAGGTCCAACTGCAGCAGCCTGGGGCTGAACT<br>GGTGAAGCCTGGGGCTTCAGTGAAGCTGTCCT<br>GTAAGGCTTCTGGCTACACCTTCACCAGCTAC<br>TGGATGCACTGGGTGAAGCAGAGGCCTGGACA<br>AGGCCTTGAGTGGATTGGAGAGATTAATCCTA<br>CCTACGGTCGTAGTAATTACAATGAGAAGTTC<br>AAGAGTAAGGCCACACTGACTGTAGACAAATC<br>CTCCAGCACAGCCTACATGCAACTCAGCAGCC<br>TGACATCTGAGGACTCTGCGGTCTATTACTGT<br>GCAAGATTAGTACGCCTACGGTACTTCGATGT<br>CTGGGGCGCAGGGACCACGGTCACCGTCTCCT<br>CA<br>(SEQ ID NO: 62)<br><br>QVQLQQPGAELVKPGASVKLSCKASGYTFTSY<br>WMHWVKQRPGQGLEWIGEINPTYGRSNYNEKF<br>KSKATLTVDKSSSTAYMQLSSLTSEDSAVYYC<br>ARLVRLRYFDVWGAGTTVTSS<br>(SEQ ID NO: 63) | SYWMH<br>(SEQ ID<br>NO: 64) | EINPTYGR<br>SNYNEKFK<br>S<br>(SEQ ID<br>NO: 65) | LVRLRYFD<br>V<br>(SEQ ID<br>NO: 66) |

*Determined by the Kabat system (see supra).
N= nucleotide sequence, P= polypeptide sequence.

As known in the art, "sequence identity" between two polypeptides or two polynucleotides is determined by comparing the amino acid or nucleic acid sequence of one polypeptide or polynucleotide to the sequence of a second polypeptide or polynucleotide. When discussed herein, whether any particular polypeptide is at least about 40%, 45%, 50%, 55%, 60%, 65%, 70%, 75%, 80%, 85%, 90% or 95% identical to another polypeptide can be determined using methods and computer programs/software known in the art such as, but not limited to, the BESTFIT program (Wisconsin Sequence Analysis Package, Version 8 for Unix, Genetics Computer Group, University Research Park, 575 Science Drive, Madison, Wis. 53711). BESTFIT uses the local homology algorithm of Smith and Waterman, Advances in Applied Mathematics 2:482-489 (1981), to find the best segment of homology between two sequences. When using BESTFIT or any other sequence alignment program to determine whether a particular sequence is, for example, 95% identical to a reference sequence according to the present invention, the parameters are set, of course, such that the percentage of identity is calculated over the full length of the reference polypeptide sequence and that gaps in homology of up to 5% of the total number of amino acids in the reference sequence are allowed.

In certain embodiments, an antibody or antigen-binding fragment comprising the VH encoded by the polynucleotide specifically or preferentially binds to IGF-1R. In certain embodiments the nucleotide sequence encoding the VH polypeptide is altered without altering the amino acid sequence encoded thereby. For instance, the sequence may be altered for improved codon usage in a given species, to remove splice sites, or the remove restriction enzyme sites. Sequence optimizations such as these are described in the examples and are well known and routinely carried out by those of ordinary skill in the art.

In another embodiment, the present invention provides an isolated polynucleotide comprising, consisting essentially of, or consisting of a nucleic acid encoding an immunoglobulin heavy chain variable region (VH) in which the VH-CDR1, VH-CDR2, and VH-CDR3 regions have polypeptide sequences which are identical to the VH-CDR1, VH-CDR2, and VH-CDR3 groups shown in Table 5. In certain embodiments, an antibody or antigen-binding fragment comprising the VH encoded by the polynucleotide specifically or preferentially binds to IGF-1R.

In certain embodiments, an antibody or antigen-binding fragment thereof comprising, consisting essentially of, or consisting of a VH encoded by one or more of the polynucleotides described above specifically or preferentially binds to the same IGF-R1 epitope as a reference monoclonal Fab antibody fragment selected from the group consisting of M13-C06, M14-G11, M14-C03, M14-B01, M12-E01, and M12-G04, or a reference monoclonal antibody produced by a hybridoma selected from the group consisting of P2A7.3E11, 20C8.3B8, P1A2.2B11, 20D8.24B11, P1E2.3B12, and P1G10.2B8, or will competitively inhibit such a monoclonal antibody or fragment from binding to IGF-1R.

In certain embodiments, an antibody or antigen-binding fragment thereof comprising, consisting essentially of, or consisting of a VH encoded by one or more of the polynucleotides described above specifically or preferentially binds to an IGF-1R polypeptide or fragment thereof, or a IGF-1R variant polypeptide, with an affinity characterized by a dissociation constant ($K_D$) no greater than $5 \times 10^{-2}$ M, $10^{-2}$ M, $5 \times 10^{-3}$ M, $10^{-3}$ M, $5 \times 10^{-4}$ M, $10^{-4}$ M, $5 \times 10^{-5}$ M, $10^{-5}$ M, $5 \times 10^{-6}$ M, $10^{-6}$ M, $5 \times 10^{-7}$ M, $10^{-7}$ M, $5 \times 10^{-8}$ M, $10^{-8}$ M, $5 \times 10^{-9}$ M, $10^{-9}$ M, $5 \times 10^{-10}$ M, $10^{-10}$ M, $5 \times 10^{-11}$ M, $10^{-11}$ M, $5 \times 10^{-12}$ M, $10^{-12}$ M, $5 \times 10^{-13}$ M, $10^{-13}$ M, $5 \times 10^{-14}$ M, $10^{-14}$ M, $5 \times 10^{-15}$ M, or $10^{-15}$ M.

In another embodiment, the present invention provides an isolated polynucleotide comprising, consisting essentially of, or consisting of a nucleic acid encoding an immunoglobulin light chain variable region (VL), where at least one of the VL-CDRs of the light chain variable region or at least two of the VL-CDRs of the light chain variable region are at least 80%, 85%, 90% or 95% identical to reference light chain VL-CDR1, VL-CDR2, or VL-CDR3 amino acid sequences from monoclonal IGF-1R antibodies disclosed herein. Alternatively, the VL-CDR1, VL-CDR2, and VL-CDR3 regions of the VL are at least 80%, 85%, 90% or 95% identical to reference light chain VL-CDR1, VL-CDR2, and VL-CDR3 amino acid sequences from monoclonal IGF-1R antibodies disclosed herein. Thus, according to this embodiment a light chain variable region of the invention has VL-CDR1, VL-CDR2, or VL-CDR3 polypeptide sequences related to the polypeptide sequences shown in Table 6:

TABLE 6

Reference VL-CDR1, VL-CDR2, and VL-CDR3 amino acid sequences*

| Antibody | VL SEQUENCE PN/PP (VL-CDR1, VL-CDR2, and VL-CDR3 sequence underlined) | VL CDR1 | VL CDR2 | VL CDR3 |
|---|---|---|---|---|
| M12-E01 | CAGTACGAATTGACTCAGCCGCCCTCGGTGT CTGAGGCCCCCCGGCAGAGGGTCACCATCTC CTGTTCTGGAAGCAGCTCCAACATCGGAAAT AATGCTATAAACTGGTACCAGCAACTCCCAG GAAAGCCTCCCAAACTCCTCATCTATTATGA TGATCTGTTGCCCTCAGGGGTCTCTGACCGA TTCTCTGGCTCCAAGTCTGGCACCTCAGGCT CCCTGGCCATCAGTGGGCTGCAGTCTGAGGA TGAGGCTGATTATTACTGTGCAGCATGGGAT GACAACCTGAATGGTGTGATTTTCGGCGGAG GGACCAAGCTGACCGTCCTA (SEQ ID NO: 67)<br><br>QYELTQPPSVSEAPRQRVTISC<u>SGSSSNIGN NAIN</u>WYQQLPGKPPKLLIY<u>YDDLLPS</u>GVSDR FSGSKSGTSGSLAISGLQSEDEADYYC<u>AAWD DNLNGVI</u>FGGGTKLTVL (SEQ ID NO: 68) | SGSSSNIGN NAIN (SEQ ID NO: 69) | YDDLLPS (SEQ ID NO: 70) | AAWDDNLN GVI (SEQ ID NO: 71) |
| M12-G04 | GACATCCAGATGACCCAGTCTCCACTCTCCC TGTCTGCATCTGTAGGAGACAGAGTCACCAT CACTTGCCGGGCAAGTCAGAGCATTAACGGC TACTTAAATTGGTATCAGCAGAAACCAGGGA AAGCCCCTAACCTCCTGATCTACGCTACATC CAGTTTGCAAAGTGGGGTCCCATCAAGGTTC AGTGGCAGTGGATCTGGGACAGATTTCACTC TCACCATCAGCAGTCTGCAACCTGAAGATTT TGCAACTTACTACTGTCAACAGAGTTACAGT ACCCCCCCGTACACTTTTGGCCAGGGGACCA AGCTGGAGATCAAA (SEQ ID NO: 72)<br><br>DIQMTQSPLSLSASVGDRVTITC<u>RASQSING YLN</u>WYQQKPGKAPNLLIY<u>ATSSLQS</u>GVPSRF SGSGSGTDFTLTISSLQPEDFATYYC<u>QQSYS TPPYT</u>FGQGTKLEIK (SEQ ID NO: 73) | RASQSINGY LN (SEQ ID NO: 74) | ATSSLQS (SEQ ID NO: 75) | QQSYSTPP YT (SEQ ID NO: 76) |
| M13-C06 | GACATCCAGATGACCCAGTCTCCACTCTCCC TGTCTGCATCTGTAGGAGACAGAGTCACCAT CACTTGCCAGGCGAGTCGGGACATTAGAAAC TATTTAAATTGGTATCAACAAAAACCAGGGA AAGCCCCGAAGCTCCTGATCTACGATGCATC CAGTTTGCAAACAGGGGTCCCATCAAGGTTC GGTGGCAGTGGATCTGGGACAGACTTTAGTT TCACCATCGGCAGCCTGCAGCCTGAAGATAT TGCAACATATTACTGTCAACAGTTTGATAGT CTCCCTCACACTTTTGGCCAGGGGACCAAAC TGGAGATCAAA (SEQ ID NO: 77) | QASRDIRNY LN (SEQ ID NO: 79) | DASSLQT (SEQ ID NO: 80) | QQFDSLPH T (SEQ ID NO: 81) |

TABLE 6-continued

Reference VL-CDR1, VL-CDR2, and VL-CDR3 amino acid sequences*

| Antibody | VL SEQUENCE PN/PP (VL-CDR1, VL-CDR2, and VL-CDR3 sequence underlined) | VL CDR1 | VL CDR2 | VL CDR3 |
|---|---|---|---|---|
| | DIQMTQSPLSLSASVGDRVTITC<u>QASRDIRN YLN</u>WYQQKPGKAPKLLIY<u>DASSLQT</u>GVPSRF GGSGSGTDFSFTIGSLQPEDIATYYC<u>QQFDS LPHT</u>FGQGTKLEIK (SEQ ID NO: 78) | | | |
| M14-B01 | GACATCCAGATGACCCAGTTTCCAGCCACCC TGTCTGTGTCTCCAGGGGAAAGAGCCACCCT CTCCTGCAGGGCCAGTCAGAGTGTTATGAGG AACTTAGCCTGGTACCAGCAGAAACCTGGCC AGCCTCCCAGGCTCCTCATCTATGGTGCATC CAAAAGGGCCACTGGCATCCCAGCCAGGTTC AGTGGCAGTGGGTCTGGGACAGCCTTCACTC TCACCATCAGCAACCTAGAGCCTGAAGATTT TGCAGTTTATTACTGTCACCAACGTAGCACC TGGCCTCTGGGGACTTTCGGCCCTGGGACCA AACTGGAGGCCAAA (SEQ ID NO: 82) | RASQSVMRN LA (SEQ ID NO: 84) | GASKRAT (SEQ ID NO: 85) | HQRSTWPL GT (SEQ ID NO: 86) |
| | DIQMTQFPATLSVSPGERATLSC<u>RASQSVMR NLA</u>WYQQKPGQPPRLLIY<u>GASKRAT</u>GIPARF SGSGSGTAFTLTISNLEPEDFAVYYC<u>HQRST WPLGT</u>FGPGTKLEAK (SEQ ID NO: 83) | | | |
| M14-C03 | GACATCCAGATGACCCAGTCTCCAGCCACCC TGTCTTTGTCTCCAGGGGAAAGAGCCACCCT CTCCTGCAGGGCCAGTCAGAGTGTTAGCAGC TACTTAGCCTGGTACCAACAGAAACCTGGCC AGGCTCCCAGGCTCCTCATCTATGATGCATC CAACAGGGCCACTGGCATCCCAGCCAGGTTC AGTGGCAGTGGGTCTGGGACAGACTTCACTC TCACCATCAGCAGCCTAGAGCCTGAAGATTT TGCAGTTTATTACTGTCAGCAGCGTAGCAAC TGGCCTCCGGAGGTCACTTTCGGCCCTGGGA CCAAAGTGGATATCAAA (SEQ ID NO: 87) | RASQSVSSY LA (SEQ ID NO: 89) | DASNRAT (SEQ ID NO: 90) | QQRSNWPP EVT (SEQ ID NO: 91) |
| | DIQMTQSPATLSLSPGERATLSC<u>RASQSVSS YLA</u>WYQQKPGQAPRLLIY<u>DASNRAT</u>GIPARF SGSGSGTDFTLTISSLEPEDFAVYYC<u>QQRSN WPPEVT</u>FGPGTKVDIK (SEQ ID NO: 88) | | | |
| M14-G11 | GACATCCAGATGACCCAGTCTCCAGACTCCC TGGCTGTGTCTCTGGGCGAGAGGGCCACCAT CAACTGCAAGTCCAGCCAGAGTGTTTTATAC AGCTCCAACAATAAGAACTACTTAGCTTGGT ACCAGCAGAAACCAGGACAGCCTCCTAAGCT GCTCATTTACTTGGCATCTACCCGGGAATCC GGGGTCCCTGACCGATTCAGTGGCAGCGGGT CTGGGACAGATTTCACTCTCACCATCAGCAG CCTGCAGGCTGAAGATGTGGCAGTTTATTAC TGTCAGCAATATTATAGTACTTGGACGTTCG GCCAAGGGACCAAGGTGGAAATCAAA (SEQ ID NO: 92) | KSSQSVLYS SNNKNYLA (SEQ ID NO: 94) | LASTRES (SEQ ID NO: 95) | QQYYSTWT (SEQ ID NO: 96) |
| | DIQMTQSPDSLAVSLGERATINC<u>KSSQSVLY SSNNKNYLA</u>WYQQKPGQPPKLLIY<u>LASTRES</u> GVPDRFSGSGSGTDFTLTISSLQAEDVAVYY C<u>QQYYSTWT</u>FGQGTKVEIK (SEQ ID NO: 93) | | | |
| P2A7.3E11 | GAAGTTGTGCTCACCCAGTCTCCAACCGCCA TGGCTGCATCTCCCGGGGAGAAGATCACTAT CACCTGCAGTGCCAGCTCAACTTTAAGTTCC AATTACTTGCATTGGTATCAGCAGAAGCCAG GATTCTCCCCTAAACTCTTGATTTATAGGAC ATCCAATCTGGCCTCTGGAGTCCCAGGTCGC TTCAGTGGCAGTGGGTCTGGGACCTCTTACT CTCTCACAATTGGCACCATGGAGGCTGAAGA | <u>SASSTLSSN YLH</u> (SEQ ID NO: 99) | RTSNLAS (SEQ ID NO: 100) | QQGSSIPL T (SEQ ID NO: 101) |

TABLE 6-continued

Reference VL-CDR1, VL-CDR2, and VL-CDR3
amino acid sequences*

| Antibody | VL SEQUENCE PN/PP (VL-CDR1, VL-CDR2, and VL-CDR3 sequence underlined) | VL CDR1 | VL CDR2 | VL CDR3 |
|---|---|---|---|---|
| | TGTTGCCACTTACTACTGCCAGCAGGGTAGT<br>AGTATACCGCTCACGTTCGGTGCTGGGACCA<br>AGCTGGAGCTGAAG<br>(SEQ ID NO: 97)<br><br>EVVLTQSPTAMAASPGEKITITCSASSTLSS<br>NYLHWYQQKPGFSPKLLIYRTSNLASGVPGR<br>FSGSGSGTSYSLTIGTMEAEDVATYYCQQGS<br>SIPLTFGAGTKLELK<br>(SEQ ID NO: 98) | | | |
| 20C8.3B8 | GACATTGTGCTGACACAGTCTCCTGCTTCCT <u>RASKSVSTS</u><br>TAGCTGTATCTCTGGGGCAGAGGGCCACCAT <u>AYSYMH</u><br>CTCATGCAGGGCCAGCAAAAGTGTCAGTACA (SEQ ID<br>TCTGCCTATAGTTATATGCACTGGTACCAAC NO: 104)<br>AGAAACCAGGACAGCCACCCAAACTCCTCAT<br>CTATCTTGCATCCAACCTAGAATCTGGGGTC<br>CCTGCCAGGTTCAGTGGCAGTGGGTCTGGGA<br>CAGACTTCACCCTCAACATCCATCCTGTGGA<br>GGAGGAGGATGCTGCAACCTATTACTGTCAG<br>CACAGTAGGGAGCTTCCGTATACGTTCGGAG<br>GGGGGACCAAGCTGGAAATC<br>(SEQ ID NO: 102)<br><br>DIVLTQSPASLAVSLGQPATISCRASKSVST<br>SAYSYMHWYQQKPGQPPKLLIYLASNLESGV<br>PARFSGSGSGTDFTLNIHPVEEEDAATYYCQ<br>HSRELPYTFGGGTKLEIK<br>(SEQ ID NO: 103) | <u>RASKSVSTS</u><br><u>AYSYMH</u><br>(SEQ ID NO: 104) | <u>LASNLES</u><br>(SEQ ID NO: 105) | <u>QHSRELPY</u><br><u>T</u><br>(SEQ ID NO: 106) |
| P1A2.2B11 | GATATCCAGATGACACAGACTACATCCTCCC <u>RASQDISNY</u><br>TATCTGCCTCTCTGGGAGACAGAGTCACCAT <u>LN</u><br>CAGTTGCAGGGCAAGTCAGGACATTAGCAAT (SEQ ID<br>TATTTAAACTGGTATCAGCAGAAACCAGATG NO: 109)<br>GAACTATTAAACTCCTGATCTACTACACATC<br>AAGATTACACTCAGGAGTCCCATCAAGGTTC<br>AGTGGCAGTGGGTCTGGAACAGATTATTCTC<br>TCACCATTAGCAACCTGGAACAAGAAGATTT<br>TGCCACTTACTTTTGCCAACAGGGTAAAACG<br>CTTCCGTGGACGTTCGGTGGAGGCACCAAGC<br>TGGAAATCAAA<br>(SEQ ID NO: 107)<br><br>DIQMTQTTSSLSASLGDRVTISCRASQDISN<br>YLNWYQQKPDGTIKLLIYYTSRLHSGVPSRF<br>SGSGSGTDYSLTISNLEQEDFATYFCQQGKT<br>LPWTFGGGTKLEIK<br>(SEQ ID NO: 108) | <u>RASQDISNY</u><br><u>LN</u><br>(SEQ ID NO: 109) | <u>TSRLHS</u><br>(SEQ ID NO: 110) | <u>QQGKTLPW</u><br><u>T</u><br>(SEQ ID NO: 111) |
| 20D8.24B11 | SAME AS 20C8 | | | |
| P1G10.2B8 | GATATCCAGATGACACAGACTACATCCTCCC <u>RASQDISNY</u><br>TGTCTGCCTCTCTGGGAGACAGAGTCACCAT <u>LN</u><br>CAGTTGCAGGGCAAGTCAGGACATTAGTAAT (SEQ ID<br>TATTTAAATTGGTATCAGCAGAAACCAGATG NO: 114)<br>GATCTGTTAAACTCCTGATCTACTACACATC<br>AAGATTACACTCAGGAGTCCCATCAAGGTTC<br>AGTGGCAGTGGGTCTGGAACAGATTATTCTC<br>TCACCATTAGCAACCTGGAACAAGAAGATAT<br>TGCCACTTACTTTTGCCAACAGGGAAAGACG<br>CTTCCGTGGACGTTCGGTGGAGGCACCAAGC<br>TGGAAATCAAA<br>(SEQ ID NO: 112)<br><br>DIQMTQTTSSLSASLGDRVTISCRASQDISN<br>YLNWYQQKPDGSVKLLIYYTSRLHSGVPSRF<br>SGSGSGTDYSLTISNLEQEDIATYFCQQGKT<br>LPWTFGGGTKLEIK<br>(SEQ ID NO: 113) | <u>RASQDISNY</u><br><u>LN</u><br>(SEQ ID NO: 114) | <u>TSRLH</u><br>(SEQ ID NO: 115) | <u>QQGKTLPW</u><br><u>T</u><br>(SEQ ID NO: 116) |
| P1E2.3B12 | GATATTGTGATGACGCAGGCTGCATTCTCCA <u>RSSKSLLHS</u><br>ATCCAGTCACTCTTGGAACATCAGCTTCAT <u>NGITYLY</u> | <u>RSSKSLLHS</u><br><u>NGITYLY</u> | <u>QMSNLAS</u><br>(SEQ ID | <u>AQNLELPY</u><br><u>T</u> |

TABLE 6-continued

Reference VL-CDR1, VL-CDR2, and VL-CDR3
amino acid sequences*

| Antibody | VL SEQUENCE PN/PP (VL-CDR1, VL-CDR2, and VL-CDR3 sequence underlined) | VL CDR1 | VL CDR2 | VL CDR3 |
|---|---|---|---|---|
| | CTCCTGCAGGTCTAGTAAGAGTCTCCTACAT AGTAATGGCATCACTTATTTGTATTGGTATC TGCAGAAGCCAGGCCAGTCTCCTCAGCTCCT GATTTATCAGATGTCCAACCTTGCCTCAGGA GTCCCAGACAGGTTCAGTAGCAGTGGGTCAG GAACTGATTTCACACTGAGAATCAGCAGAGT GGAGGCTGAGGATGTGGGTGTTTATTACTGT GCTCAAAATCTAGAACTTCCGTACACGTTCG GAGGGGGGACCAAGCTGGAAATCAAA (SEQ ID NO: 117) DIVMTQAAFSNPVTLGTSASISCRSSKSLLH SNGITYLYWYLQKPGQSPQLLIYQMSNLASG VPDRFSSSGSGTDFTLRISRVEAEDVGVYYC AQNLELPYTFGGGTKLEIK (SEQ ID NO: 118) | (SEQ ID NO: 119) | (SEQ ID NO: 120) | (SEQ ID NO: 121) |

*Determined by the Kabat system (see supra).
PN = nucleotide sequence, PP = polypeptide sequence.

In certain embodiments, an antibody or antigen-binding fragment comprising the VL encoded by the polynucleotide specifically or preferentially binds to IGF-1R.

In another embodiment, the present invention provides an isolated polynucleotide comprising, consisting essentially of, or consisting of a nucleic acid encoding an immunoglobulin light chain variable region (VL) in which the VL-CDR1, VL-CDR2, and VL-CDR3 regions have polypeptide sequences which are identical to the VL-CDR1, VL-CDR2, and VL-CDR3 groups shown in Table 6. In certain embodiments, an antibody or antigen-binding fragment comprising the VL encoded by the polynucleotide specifically or preferentially binds to IGF-1R.

In a further aspect, the present invention provides an isolated polynucleotide comprising, consisting essentially of, or consisting of a nucleic acid encoding an immunoglobulin light chain variable region (VL) in which the VL-CDR1, VL-CDR2, and VL-CDR3 regions are encoded by nucleotide sequences which are identical to the nucleotide sequences which encode the VL-CDR1, VL-CDR2, and VL-CDR3 groups shown in Table 6. In certain embodiments, an antibody or antigen-binding fragment comprising the VL encoded by the polynucleotide specifically or preferentially binds to IGF-1R.

In certain embodiments, an antibody or antigen-binding fragment thereof comprising, consisting essentially of, or consisting of a VL encoded by one or more of the polynucleotides described above specifically or preferentially binds to the same IGF-R1 epitope as a reference monoclonal Fab antibody fragment selected from the group consisting of M13-C06, M14-G11, M14-C03, M14-B01, M12-E01, and M12-G04, or a reference monoclonal antibody produced by a hybridoma selected from the group consisting of P2A7.3E11, 20C8.3B8, P1A2.2B11, 20D8.24B11, P1E2.3B12, and P1G10.2B8, or will competitively inhibit such a monoclonal antibody or fragment from binding to IGF-1R.

In certain embodiments, an antibody or antigen-binding fragment thereof comprising, consisting essentially of, or consisting of a VL encoded by one or more of the polynucleotides described above specifically or preferentially binds to an IGF-1R polypeptide or fragment thereof, or a IGF-1R variant polypeptide, with an affinity characterized by a dissociation constant ($K_D$) no greater than $5 \times 10^{-2}$ M, $10^{-2}$ M, $5 \times 10^{-3}$ M, $10^{-3}$ M, $5 \times 10^{-4}$ M, $10^{-4}$ M, $5 \times 10^{-5}$ M, $10^{-5}$ M, $5 \times 10^{-6}$ M, $10^{-6}$ M, $5 \times 10^{-7}$ M, $10^{-7}$ M, $5 \times 10^{-8}$ M, $10^{-8}$ M, $5 \times 10^{-9}$ M, $10^{-9}$ M, $5 \times 10^{-10}$ M, $10^{-10}$ M, $5 \times 10^{-11}$ M, $10^{-11}$ M, $5 \times 10^{-12}$ M, $10^{-12}$ M, $5 \times 10^{-13}$ M, $10^{-13}$ M, $5 \times 10^{-14}$ M, $10^{-14}$ M, $5 \times 10^{-15}$ M, or $10^{-15}$ M.

In a further embodiment, the present invention includes an isolated polynucleotide comprising, consisting essentially of, or consisting of a nucleic acid encoding a VH at least 80%, 85%, 90% 95% or 100% identical to a reference VH polypeptide sequence selected from the group consisting of SEQ ID NOs: 4, 9, 14, 20, 26, 32, 38, 43, 48, 53, 58, and 63. In certain embodiments, an antibody or antigen-binding fragment comprising the VH encoded by the polynucleotide specifically or preferentially binds to IGF-1R.

In another aspect, the present invention includes an isolated polynucleotide comprising, consisting essentially of, or consisting of a nucleic acid sequence encoding a VH having a polypeptide sequence selected from the group consisting of SEQ ID NOs: 4, 9, 14, 20, 26, 32, 38, 43, 48, 53, 58, and 63. In certain embodiments, an antibody or antigen-binding fragment comprising the VH encoded by the polynucleotide specifically or preferentially binds to IGF-1R.

In a further embodiment, the present invention includes an isolated polynucleotide comprising, consisting essentially of, or consisting of a VH-encoding nucleic acid at least 80%, 85%, 90% 95% or 100% identical to a reference nucleic acid sequence selected from the group consisting of SEQ ID NOs: 3, 8, 13, 18, 19, 24, 25, 30, 31, 36, 37, 42, 47, 52, 57, and 62. In certain embodiments, an antibody or antigen-binding fragment comprising the VH encoded by such polynucleotides specifically or preferentially binds to IGF-1R.

In another aspect, the present invention includes an isolated polynucleotide comprising, consisting essentially of, or consisting of a nucleic acid sequence encoding a VH of the invention, where the amino acid sequence of the VH is selected from the group consisting of SEQ ID NOs: 4, 9, 14, 20, 26, 32, 38, 43, 48, 53, 58, and 63. The present invention further includes an isolated polynucleotide comprising, consisting essentially of, or consisting of a nucleic acid sequence encoding a VH of the invention, where the sequence of the nucleic acid is selected from the group consisting of SEQ ID NOs: 3, 8, 13, 18, 19, 24, 25, 30, 31, 36, 37, 42, 47, 52, 57, and 62. In certain embodiments, an antibody or antigen-binding fragment comprising the VH encoded by such polynucleotides specifically or preferentially binds to IGF-1R.

In certain embodiments, an antibody or antigen-binding fragment thereof comprising, consisting essentially of, or consisting of a VH encoded by one or more of the polynucleotides described above specifically or preferentially binds to the same IGF-R1 epitope as a reference monoclonal Fab antibody fragment selected from the group consisting of M13-C06, M14-G11, M14-C03, M14-B01, M12-E01, and M12-G04, or a reference monoclonal antibody produced by a hybridoma selected from the group consisting of P2A7.3E11, 20C8.3B8, P1A2.2B11, 20D8.24B11, P1E2.3B12, and P1G10.2B8, or will competitively inhibit such a monoclonal antibody or fragment from binding to IGF-1R, or will competitively inhibit such a monoclonal antibody from binding to IGF-1R.

In certain embodiments, an antibody or antigen-binding fragment thereof comprising, consisting essentially of, or consisting of a VH encoded by one or more of the polynucleotides described above specifically or preferentially binds to an IGF-1R polypeptide or fragment thereof, or a IGF-1R variant polypeptide, with an affinity characterized by a dissociation constant ($K_D$) no greater than $5 \times 10^{-2}$ M, $10^{-2}$ M, $5 \times 10^{-3}$ M, $10^{-3}$ M, $5 \times 10^{-4}$ M, $10^{-4}$ M, $5 \times 10^{-5}$ M, $10^{-5}$ M, $5 \times 10^{-6}$ M, $10^{-6}$ M, $5 \times 10^{-7}$ M, $10^{-7}$ M, $5 \times 10^{-8}$ M, $10^{-8}$ M, $5 \times 10^{-9}$ M, $10^{-9}$ M, $5 \times 10^{-10}$ M, $10^{-10}$ M, $5 \times 10^{-11}$ M, $10^{-11}$ M, $5 \times 10^{-12}$ M, $10^{-12}$ M, $5 \times 10^{-13}$ M, $10^{-13}$ M, $5 \times 10^{-14}$ M, $10^{-14}$ M, $5 \times 10^{-15}$ M, or $10^{-15}$ M.

In a further embodiment, the present invention includes an isolated polynucleotide comprising, consisting essentially of, or consisting of a nucleic acid encoding a VL at least 80%, 85%, 90% 95% or 100% identical to a reference VL polypeptide sequence having an amino acid sequence selected from the group consisting of SEQ ID NOs: 68, 73, 78, 83, 88, 93, 98, 103, 108, 113, and 118. In a further embodiment, the present invention includes an isolated polynucleotide comprising, consisting essentially of, or consisting of a VL-encoding nucleic acid at least 80%, 85%, 90% 95% or 100% identical to a reference nucleic acid sequence selected from the group consisting of SEQ ID NOs: 67, 72, 77, 82, 87, 92, 97, 102, 107, 112, and 117. In certain embodiments, an antibody or antigen-binding fragment comprising the VL encoded by such polynucleotides specifically or preferentially binds to IGF-1R.

In another aspect, the present invention includes an isolated polynucleotide comprising, consisting essentially of, or consisting of a nucleic acid sequence encoding a VL having a polypeptide sequence selected from the group consisting of SEQ ID NOs: 68, 73, 78, 83, 88, 93, 98, 103, 108, 113, and 118. The present invention further includes an isolated polynucleotide comprising, consisting essentially of, or consisting of a nucleic acid sequence encoding a VL of the invention, where the sequence of the nucleic acid is selected from the group consisting of SEQ ID NOs: 67, 72, 77, 82, 87, 92, 97, 102, 107, 112, and 117. In certain embodiments, an antibody or antigen-binding fragment comprising the VL encoded by such polynucleotides specifically or preferentially binds to IGF-1R.

In certain embodiments, an antibody or antigen-binding fragment thereof comprising, consisting essentially of, or consisting of a VL encoded by one or more of the polynucleotides described above specifically or preferentially binds to the same IGF-R1 epitope as a reference monoclonal Fab antibody fragment selected from the group consisting of M13-C06, M14-G11, M14-C03, M14-B01, M12-E01, and M12-G04, or a reference monoclonal antibody produced by a hybridoma selected from the group consisting of P2A7.3E11, 20C8.3B8, P1A2.2B11, 20D8.24B11, P1E2.3B12, and P1G10.2B8, or will competitively inhibit such a monoclonal antibody or fragment from binding to IGF-1R.

In certain embodiments, an antibody or antigen-binding fragment thereof comprising, consisting essentially of, or consisting of a VL encoded by one or more of the polynucleotides described above specifically or preferentially binds to an IGF-1R polypeptide or fragment thereof, or a IGF-1R variant polypeptide, with an affinity characterized by a dissociation constant ($K_D$) no greater than $5 \times 10^{-2}$ M, $10^{-2}$ M, $5 \times 10^{-3}$ M, $10^{-3}$ M, $5 \times 10^{-4}$ M, $10^{-4}$ M, $5 \times 10^{-5}$ M, $10^{-5}$ M, $5 \times 10^{-6}$ M, $10^{-6}$ M, $5 \times 10^{-7}$ M, $10^{-7}$ M, $5 \times 10^{-8}$ M, $10^{-8}$ M, $5 \times 10^{-9}$ M, $10^{-9}$ M, $5 \times 10^{-10}$ M, $10^{-10}$ M, $5 \times 10^{-11}$ M, $10^{-11}$ M, $5 \times 10^{-12}$ M, $10^{-12}$ M, $5 \times 10^{-13}$ M, $10^{-13}$ M, $5 \times 10^{-14}$ M, $10^{-14}$ M, $5 \times 10^{-15}$ M, or $10^{-14}$ M.

Any of the polynucleotides described above may further include additional nucleic acids, encoding, e.g., a signal peptide to direct secretion of the encoded polypeptide, antibody constant regions as described herein, or other heterologous polypeptides as described herein.

Also, as described in more detail elsewhere herein, the present invention includes compositions comprising the polynucleotides comprising one or more of the polynucleotides described above. In one embodiment, the invention includes compositions comprising a first polynucleotide and second polynucleotide wherein said first polynucleotide encodes a VH polypeptide as described herein and wherein said second polynucleotide encodes a VL polypeptide as described herein. Specifically a composition which comprises, consists essentially of, or consists of a VH polynucleotide, and a VL polynucleotide, wherein the VH polynucleotide and the VL polynucleotide encode polypeptides, respectively at least 80%, 85%, 90% 95% or 100% identical to reference VL and VL polypeptide amino acid sequences selected from the group consisting of SEQ ID NOs: 4 and 68, 8 and 73, 14 and 78, 20 and 83, 26 and 88, 32 and 93, 38 and 98, 43 and 103, 48 and 108, 53 and 103, 58 and 113, and 63 and 118. Or alternatively, a composition which comprises, consists essentially of, or consists of a VH polynucleotide, and a VL polynucleotide at least 80%, 85%, 90% 95% or 100% identical, respectively, to reference VL and VL nucleic acid sequences selected from the group consisting of SEQ ID NOs: 3 and 67, 8 and 72, 13 and 77, 18 and 77, 19 and 82, 24 and 82, 25 and 87, 30 and 87, 31 and 92, 36 and 92, 37 and 97, 42 and 102, 47 and 107, 58 and 102, 57 and 112, and 62 and 117. In certain embodiments, an antibody or antigen-binding fragment comprising the VH and VL encoded by the polynucleotides in such compositions specifically or preferentially binds to IGF-1R.

The present invention also includes fragments of the polynucleotides of the invention, as described elsewhere. Additionally polynucleotides which encode fusion polynucleotides, Fab fragments, and other derivatives, as described herein, are also contemplated by the invention.

The polynucleotides may be produced or manufactured by any method known in the art. For example, if the nucleotide sequence of the antibody is known, a polynucleotide encoding the antibody may be assembled from chemically synthesized oligonucleotides (e.g., as described in Kutmeier et al., *BioTechniques* 17:242 (1994)), which, briefly, involves the synthesis of overlapping oligonucleotides containing portions of the sequence encoding the antibody, annealing and ligating of those oligonucleotides, and then amplification of the ligated oligonucleotides by PCR.

Alternatively, a polynucleotide encoding an IGF-1R antibody, or antigen-binding fragment, variant, or derivative thereof may be generated from nucleic acid from a suitable source. If a clone containing a nucleic acid encoding a particular antibody is not available, but the sequence of the antibody molecule is known, a nucleic acid encoding the antibody may be chemically synthesized or obtained from a suitable source (e.g., an antibody cDNA library, or a cDNA library generated from, or nucleic acid, preferably poly A+RNA, isolated from, any tissue or cells expressing the antibody or other IGF-1R antibody, such as hybridoma cells selected to express an antibody) by PCR amplification using synthetic primers hybridizable to the 3' and 5' ends of the sequence or by cloning using an oligonucleotide probe specific for the particular gene sequence to identify, e.g., a cDNA clone from a cDNA library that encodes the antibody or other IGF-1R antibody. Amplified nucleic acids generated by PCR may then be cloned into replicable cloning vectors using any method well known in the art.

Once the nucleotide sequence and corresponding amino acid sequence of the IGF-1R antibody, or antigen-binding fragment, variant, or derivative thereof is determined, its nucleotide sequence may be manipulated using methods well known in the art for the manipulation of nucleotide sequences, e.g., recombinant DNA techniques, site directed mutagenesis, PCR, etc. (see, for example, the techniques described in Sambrook et al., *Molecular Cloning, A Laboratory Manual*, 2d Ed., Cold Spring Harbor Laboratory, Cold Spring Harbor, N.Y. (1990) and Ausubel et al., eds., *Current Protocols in Molecular Biology*, John Wiley & Sons, NY (1998), which are both incorporated by reference herein in their entireties), to generate antibodies having a different amino acid sequence, for example to create amino acid substitutions, deletions, and/or insertions.

A polynucleotide encoding an IGF-1R antibody, or antigen-binding fragment, variant, or derivative thereof can be composed of any polyribonucleotide or polydeoxyribonucleotide, which may be unmodified RNA or DNA or modified RNA or DNA. For example, a polynucleotide encoding IGF-1R antibody, or antigen-binding fragment, variant, or derivative thereof can be composed of single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, a polynucleotide encoding an IGF-1R antibody, or antigen-binding fragment, variant, or derivative thereof can be composed of triple-stranded regions comprising RNA or DNA or both RNA and DNA. A polynucleotide encoding an IGF-1R antibody, or antigen-binding fragment, variant, or derivative thereof may also contain one or more modified bases or DNA or RNA backbones modified for stability or for other reasons. "Modified" bases include, for example, tritylated bases and unusual bases such as inosine. A variety of modifications can be made to DNA and RNA; thus, "polynucleotide" embraces chemically, enzymatically, or metabolically modified forms.

An isolated polynucleotide encoding a non-natural variant of a polypeptide derived from an immunoglobulin (e.g., an immunoglobulin heavy chain portion or light chain portion) can be created by introducing one or more nucleotide substitutions, additions or deletions into the nucleotide sequence of the immunoglobulin such that one or more amino acid substitutions, additions or deletions are introduced into the encoded protein. Mutations may be introduced by standard techniques, such as site-directed mutagenesis and PCR-mediated mutagenesis. Preferably, conservative amino acid substitutions are made at one or more non-essential amino acid residues.

V. IGF-1R Antibody Polypeptides

The present invention is further directed to isolated polypeptides which make up IGF-1R antibodies, and polynucleotides encoding such polypeptides. IGF-1R antibodies of the present invention comprise polypeptides, e.g., amino acid sequences encoding IGF-IR-specific antigen binding regions derived from immunoglobulin molecules. A polypeptide or amino acid sequence "derived from" a designated protein refers to the origin of the polypeptide having a certain amino acid sequence. In certain cases, the polypeptide or amino acid sequence which is derived from a particular starting polypeptide or amino acid sequence has an amino acid sequence that is essentially identical to that of the starting sequence, or a portion thereof, wherein the portion consists of at least 10-20 amino acids, at least 20-30 amino acids, at least 30-50 amino acids, or which is otherwise identifiable to one of ordinary skill in the art as having its origin in the starting sequence.

In one embodiment, the present invention provides an isolated polypeptide comprising, consisting essentially of, or consisting of an immunoglobulin heavy chain variable region (VH), where at least one of VH-CDRs of the heavy chain variable region or at least two of the VH-CDRs of the heavy chain variable region are at least 80%, 85%, 90% or 95% identical to reference heavy chain VH-CDR1, VH-CDR2 or VH-CDR3 amino acid sequences from monoclonal IGF-1R antibodies disclosed herein. Alternatively, the VH-CDR1, VH-CDR2 and VH-CDR3 regions of the VH are at least 80%, 85%, 90% or 95% identical to reference heavy chain VH-CDR1, VH-CDR2 and VH-CDR3 amino acid sequences from monoclonal IGF-1R antibodies disclosed herein. Thus, according to this embodiment a heavy chain variable region of the invention has VH-CDR1, VH-CDR2 and VH-CDR3 polypeptide sequences related to the groups shown in Table 5, supra. While Table 5 shows VH-CDRs defined by the Kabat system, other CDR definitions, e.g., VH-CDRs defined by the Chothia system, are also included in the present invention. In certain embodiments, an antibody or antigen-binding fragment comprising the VH specifically or preferentially binds to IGF-1R.

In another embodiment, the present invention provides an isolated polypeptide comprising, consisting essentially of, or consisting of an immunoglobulin heavy chain variable region (VH) in which the VH-CDR1, VH-CDR2 and VH-CDR3 regions have polypeptide sequences which are identical to the VH-CDR1, VH-CDR2 and VH-CDR3 groups shown in Table 5. In certain embodiments, an antibody or antigen-binding fragment comprising the VH specifically or preferentially binds to IGF-1R.

In another embodiment, the present invention provides an isolated polypeptide comprising, consisting essentially of, or consisting of an immunoglobulin heavy chain variable region (VH) in which the VH-CDR1, VH-CDR2 and VH-CDR3 regions have polypeptide sequences which are identical to the VH-CDR1, VH-CDR2 and VH-CDR3 groups shown in Table 5, except for one, two, three, four, five, or six amino acid substitutions in any one VH-CDR. In larger CDRs, e.g., VH-CDR-3, additional substitutions may be made in the CDR, as long as the a VH comprising the VH-CDR specifically or preferentially binds to IGF-1R. In certain embodiments the amino acid substitutions are conservative. In certain embodiments, an antibody or antigen-binding fragment comprising the VH specifically or preferentially binds to IGF-1R.

In a further embodiment, the present invention includes an isolated polypeptide comprising, consisting essentially of, or consisting of a VH polypeptide at least 80%, 85%, 90% 95% or 100% identical to a reference VH polypeptide amino acid sequence selected from the group consisting of SEQ ID NOs: SEQ ID NOs: 4, 9, 14, 20, 26, 32, 38, 43, 48, 53, 58, and 63. In certain embodiments, an antibody or antigen-binding fragment comprising the VH polypeptide specifically or preferentially binds to IGF-1R.

In another aspect, the present invention includes an isolated polypeptide comprising, consisting essentially of, or consisting of a VH polypeptide selected from the group consisting of SEQ ID NOs: SEQ ID NOs: 4, 9, 14, 20, 26, 32, 38, 43, 48, 53, 58, and 63. In certain embodiments, an antibody or antigen-binding fragment comprising the VH polypeptide specifically or preferentially binds to IGF-1R.

In certain embodiments, an antibody or antigen-binding fragment thereof comprising, consisting essentially of, or consisting of a one or more of the VH polypeptides described above specifically or preferentially binds to the same IGF-R1 epitope as a reference monoclonal Fab antibody fragment selected from the group consisting of M13-C06, M14-G11, M14-C03, M14-B01, M12-E01, and M12-G04, or a reference monoclonal antibody produced by a hybridoma selected from the group consisting of P2A7.3E11, 20C8.3B8, P1A2.2B11, 20D8.24B11, P1E2.3B12, and P1G10.2B8, or will competitively inhibit such a monoclonal antibody or fragment from binding to IGF-1R In certain embodiments, an antibody or antigen-binding fragment thereof comprising, consisting essentially of, or consisting of one or more of the VH polypeptides described above specifically or preferentially binds to an IGF-1R polypeptide or fragment thereof, or a IGF-1R variant polypeptide, with an affinity characterized by a dissociation constant ($K_D$) no greater than $5 \times 10^{-2}$ M, $10^{-2}$ M, $5 \times 10^{-3}$ M, $10^{-3}$ M, $5 \times 10^{-4}$ M, $10^{-4}$ M, $5 \times 10^{-5}$ M, $10^{-5}$ M, $5 \times 10^{-6}$ M, $10^{-6}$ M, $5 \times 10^{-7}$ M, $10^{-7}$ M, $5 \times 10^{-8}$ M, $10^{-8}$ M, $5 \times 10^{-9}$ M, $10^{-9}$ M, $5 \times 10^{-10}$ M, $10^{-10}$ M, $5 \times 10^{-11}$ M, $10^{-11}$ M, $5 \times 10^{-12}$ M, $10^{-12}$ M, $5 \times 10^{-13}$ M, $10^{-13}$ M, $5 \times 10^{-14}$ M, $10^{-14}$ M, $5 \times 10^{-15}$ M, or $10^{-15}$ M.

In another embodiment, the present invention provides an isolated polypeptide comprising, consisting essentially of, or consisting of an immunoglobulin light chain variable region (VL), where at least one of the VL-CDRs of the light chain variable region or at least two of the VL-CDRs of the light chain variable region are at least 80%, 85%, 90% or 95% identical to reference light chain VL-CDR1, VL-CDR2 or VL-CDR3 amino acid sequences from monoclonal IGF-1R antibodies disclosed herein. Alternatively, the VL-CDR1, VL-CDR2 and VL-CDR3 regions of the VL are at least 80%, 85%, 90% or 95% identical to reference light chain VL-CDR1, VL-CDR2 and VL-CDR3 amino acid sequences from monoclonal IGF-1R antibodies disclosed herein. Thus, according to this embodiment a light chain variable region of the invention has VL-CDR1, VL-CDR2 and VL-CDR3 polypeptide sequences related to the polypeptides shown in Table 6, supra. While Table 6 shows VL-CDRs defined by the Kabat system, other CDR definitions, e.g., VL-CDRs defined by the Chothia system, are also included in the present invention. In certain embodiments, an antibody or antigen-binding fragment comprising the VL polypeptide specifically or preferentially binds to IGF-1R.

In another embodiment, the present invention provides an isolated polypeptide comprising, consisting essentially of, or consisting of an immunoglobulin light chain variable region (VL) in which the VL-CDR1, VL-CDR2 and VL-CDR3 regions have polypeptide sequences which are identical to the VL-CDR1, VL-CDR2 and VL-CDR3 groups shown in Table 6. In certain embodiments, an antibody or antigen-binding fragment comprising the VL polypeptide specifically or preferentially binds to IGF-1R.

In another embodiment, the present invention provides an isolated polypeptide comprising, consisting essentially of, or consisting of an immunoglobulin heavy chain variable region (VL) in which the VL-CDR1, VL-CDR2 and VL-CDR3 regions have polypeptide sequences which are identical to the VL-CDR1, VL-CDR2 and VL-CDR3 groups shown in Table 6, except for one, two, three, four, five, or six amino acid substitutions in any one VL-CDR. In larger CDRs, additional substitutions may be made in the VL-CDR, as long as the a VL comprising the VL-CDR specifically or preferentially binds to IGF-1R. In certain embodiments the amino acid substitutions are conservative. In certain embodiments, an antibody or antigen-binding fragment comprising the VL specifically or preferentially binds to IGF-1R.

In a further embodiment, the present invention includes an isolated polypeptide comprising, consisting essentially of, or consisting of a VL polypeptide at least 80%, 85%, 90% 95% or 100% identical to a reference VL polypeptide sequence selected from the group consisting of SEQ ID NOs: 68, 73, 78, 83, 88, 93, 98, 103, 108, 113, and 118. In certain embodiments, an antibody or antigen-binding fragment comprising the VL polypeptide specifically or preferentially binds to IGF-1R.

In another aspect, the present invention includes an isolated polypeptide comprising, consisting essentially of, or consisting of a VL polypeptide selected from the group consisting of S SEQ ID NOs: 68, 73, 78, 83, 88, 93, 98, 103, 108, 113, and 118. In certain embodiments, an antibody or antigen-binding fragment comprising the VL polypeptide specifically or preferentially binds to IGF-1R.

In certain embodiments, an antibody or antigen-binding fragment thereof comprising, consisting essentially of, one or more of the VL polypeptides described above specifically or preferentially binds to the same IGF-R1 epitope as a reference monoclonal Fab antibody fragment selected from the group consisting of M13-C06, M14-G11, M14-C03, M14-B01, M12-E01, and M12-G04, or a reference monoclonal antibody produced by a hybridoma selected from the group consisting of P2A7.3E11, 20C8.3B8, P1A2.2B11, 20D8.24B11, P1E2.3B12, and P1G10.2B8, or will competitively inhibit such a monoclonal antibody or fragment from binding to IGF-1R In certain embodiments, an antibody or antigen-binding fragment thereof comprising, consisting essentially of, or consisting of a one or more of the VL polypeptides described above specifically or preferentially binds to an IGF-1R polypeptide or fragment thereof, or a IGF-1R variant polypeptide, with an affinity characterized by a dissociation constant ($K_D$) no greater than $5 \times 10^{-2}$ M, $10^{-2}$ M, $5 \times 10^{-3}$ M, $10^{-3}$ M, $5 \times 10^{-4}$ M, $10^{-4}$ M, $5 \times 10^{-5}$ M, $10^{-5}$ M, $5 \times 10^{-6}$ M, $10^{-6}$ M, $5 \times 10^{-7}$ M, $10^{-7}$ M, $5 \times 10^{-8}$ M, $10^{-8}$ M, $5 \times 10^{-9}$ M, $10^{-9}$ M, $5 \times 10^{-10}$ M, $10^{-10}$ M, $5 \times 10^{-11}$ M, $10^{-11}$ M, $5 \times 10^{-12}$ M, $10^{-12}$ M, $5 \times 10^{-13}$ M, $10^{-13}$ M, $5 \times 10^{-14}$ M, $10^{-14}$ M, $5 \times 10^{-15}$ M, or $10^{-15}$ M.

In other embodiments, an antibody or antigen-binding fragment thereof comprises, consists essentially of or consists of a VH polypeptide, and a VL polypeptide, where the VH polypeptide and the VL polypeptide, respectively are at least 80%, 85%, 90% 95% or 100% identical to reference VL and VL polypeptide amino acid sequences selected from the group consisting of SEQ ID NOs: 4 and 68, 8 and 73, 14 and 78, 20 and 83, 26 and 88, 32 and 93, 38 and 98, 43 and 103, 48 and 108, 53 and 103, 58 and 113, and 63 and 118. In certain embodiments, an antibody or antigen-binding fragment comprising these VH and VL polypeptides specifically or preferentially binds to IGF-1R.

Any of the polypeptides described above may further include additional polypeptides, e.g., a signal peptide to direct secretion of the encoded polypeptide, antibody constant regions as described herein, or other heterologous polypeptides as described herein. Additionally, polypeptides of the invention include polypeptide fragments as described elsewhere. Additionally polypeptides of the invention include fusion polypeptide, Fab fragments, and other derivatives, as described herein.

Also, as described in more detail elsewhere herein, the present invention includes compositions comprising the polypeptides described above.

It will also be understood by one of ordinary skill in the art that IGF-1R antibody polypeptides as disclosed herein may be modified such that they vary in amino acid sequence from the naturally occurring binding polypeptide from which they were derived. For example, a polypeptide or amino acid sequence derived from a designated protein may be similar, e.g., have a certain percent identity to the starting sequence, e.g., it may be 60%, 70%, 75%, 80%, 85%, 90%, or 95% identical to the starting sequence.

Furthermore, nucleotide or amino acid substitutions, deletions, or insertions leading to conservative substitutions or changes at "non-essential" amino acid regions may be made. For example, a polypeptide or amino acid sequence derived from a designated protein may be identical to the starting sequence except for one or more individual amino acid substitutions, insertions, or deletions, e.g., one, two, three, four, five, six, seven, eight, nine, ten, fifteen, twenty or more individual amino acid substitutions, insertions, or deletions. a polypeptide or amino acid sequence derived from a designated protein may be identical to the starting sequence except for one or more individual amino acid substitutions, insertions, or deletions, e.g., one, two, three, four, five, six, seven, eight, nine, ten, fifteen, twenty or more individual amino acid substitutions, insertions, or deletions. In other embodiments, a polypeptide or amino acid sequence derived from a designated protein may be identical to the starting sequence except for two or fewer, three or fewer, four or fewer, five or fewer, six or fewer, seven or fewer, eight or fewer, nine or fewer, ten or fewer, fifteen or fewer, or twenty or fewer individual amino acid substitutions, insertions, or deletions. In certain embodiments, a polypeptide or amino acid sequence derived from a designated protein has one to five, one to ten, one to fifteen, or one to twenty individual amino acid substitutions, insertions, or deletions relative to the starting sequence.

Certain IGF-1R antibody polypeptides of the present invention comprise, consist essentially of, or consist of an amino acid sequence derived from a human amino acid sequence. However, certain IGF-1R antibody polypeptides comprise one or more contiguous amino acids derived from another mammalian species. For example, an IGF-IR antibody of the present invention may include a primate heavy chain portion, hinge portion, or antigen binding region. In another example, one or more murine-derived amino acids may be present in a non-murine antibody polypeptide, e.g., in an antigen binding site of an IGF-1R antibody. In another example, the antigen binding site of an IGF-1R antibody is fully murine. In certain therapeutic applications, IGF-1R-specific antibodies, or antigen-binding fragments, variants, or analogs thereof are designed so as to not be immunogenic in the animal to which the antibody is administered.

In certain embodiments, an IGF-1R antibody polypeptide comprises an amino acid sequence or one or more moieties not normally associated with an antibody. Exemplary modifications are described in more detail below. For example, a single-chain fv antibody fragment of the invention may comprise a flexible linker sequence, or may be modified to add a functional moiety (e.g., PEG, a drug, a toxin, or a label).

An IGF-1R antibody polypeptide of the invention may comprise, consist essentially of, or consist of a fusion protein. Fusion proteins are chimeric molecules which comprise, for example, an immunoglobulin antigen-binding domain with at least one target binding site, and at least one heterologous portion, i.e., a portion with which it is not naturally linked in nature. The amino acid sequences may normally exist in separate proteins that are brought together in the fusion polypeptide or they may normally exist in the same protein but are placed in a new arrangement in the fusion polypeptide. Fusion proteins may be created, for example, by chemical synthesis, or by creating and translating a polynucleotide in which the peptide regions are encoded in the desired relationship.

The term "heterologous" as applied to a polynucleotide or a polypeptide, means that the polynucleotide or polypeptide is derived from a distinct entity from that of the rest of the entity to which it is being compared. For instance, as used herein, a "heterologous polypeptide" to be fused to an IGF-1R antibody, or an antigen-binding fragment, variant, or analog thereof is derived from a non-immunoglobulin polypeptide of the same species, or an immunoglobulin or non-immunoglobulin polypeptide of a different species.

A "conservative amino acid substitution" is one in which the amino acid residue is replaced with an amino acid residue having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a non-essential amino acid residue in an immunoglobulin polypeptide is preferably replaced with another amino acid residue from the same side chain family. In another embodiment, a string of amino acids can be replaced with a structurally similar string that differs in order and/or composition of side chain family members.

Alternatively, in another embodiment, mutations may be introduced randomly along all or part of the immunoglobulin coding sequence, such as by saturation mutagenesis, and the resultant mutants can be incorporated into IGF-1R antibodies for use in the diagnostic and treatment methods disclosed herein and screened for their ability to bind to the desired antigen, e.g., IGF-1R.

VI. Fusion Proteins and Antibody Conjugates

As discussed in more detail elsewhere herein, IGF-1R antibodies, or antigen-binding fragments, variants, or derivatives thereof of the invention may further be recombinantly fused to a heterologous polypeptide at the N- or C-terminus or chemically conjugated (including covalent and non-covalent conjugations) to polypeptides or other compositions. For example, IGF-1R-specific IGF-1R antibodies may be recombinantly fused or conjugated to molecules useful as labels in detection assays and effector molecules such as heterologous polypeptides, drugs, radionuclides, or toxins. See, e.g., PCT publications WO 92/08495; WO 91/14438; WO 89/12624; U.S. Pat. No. 5,314,995; and EP 396,387.

IGF-1R antibodies, or antigen-binding fragments, variants, or derivatives thereof of the invention include derivatives that are modified, i.e., by the covalent attachment of any type of molecule to the antibody such that covalent attachment does not prevent the antibody binding IGF-1R. For example, but not by way of limitation, the antibody derivatives include antibodies that have been modified, e.g., by glycosylation, acetylation, pegylation, phosphylation, phosphorylation, amidation, derivatization by known protecting/blocking groups, proteolytic cleavage, linkage to a cellular ligand or other protein, etc. Any of numerous chemical modifications may be carried out by known techniques, including, but not limited to specific chemical cleavage, acetylation, formylation, metabolic synthesis of tunicamycin, etc. Additionally, the derivative may contain one or more non-classical amino acids.

IGF-1R antibodies, or antigen-binding fragments, variants, or derivatives thereof of the invention can be composed of amino acids joined to each other by peptide bonds or modified peptide bonds, i.e., peptide isosteres, and may contain amino acids other than the 20 gene-encoded amino acids. IGF-1R-specific antibodies may be modified by natural processes, such as posttranslational processing, or by chemical modification techniques which are well known in the art. Such modifications are well described in basic texts and in more detailed monographs, as well as in a voluminous research literature. Modifications can occur anywhere in the IGF-1R-specific antibody, including the peptide backbone, the amino acid side-chains and the amino or carboxyl termini, or on moieties such as carbohydrates. It will be appreciated that the same type of modification may be present in the same or varying degrees at several sites in a given IGF-1R-specific antibody. Also, a given IGF-1R-specific antibody may contain many types of modifications. IGF-1R-specific antibodies may be branched, for example, as a result of ubiquitination, and they may be cyclic, with or without branching. Cyclic, branched, and branched cyclic IGF-1R-specific antibodies may result from posttranslation natural processes or may be made by synthetic methods. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristoylation, oxidation, pegylation, proteolytic processing, phosphorylation, prenylation, racemization, selenoylation, sulfation, transfer-RNA mediated addition of amino acids to proteins such as arginylation, and ubiquitination. (See, for instance, *Proteins—Structure And Molecular Properties*, T. E. Creighton, W. H. Freeman and Company, New York 2nd Ed., (1993); *Posttranslational Covalent Modification Of Proteins*, B. C. Johnson, Ed., Academic Press, New York, pgs. 1-12 (1983); Seifter et al., *Meth Enzymol* 182:626-646 (1990); Rattan et al., *Ann NY Acad Sci* 663:48-62 (1992)).

The present invention also provides for fusion proteins comprising an IGF-1R antibody, or antigen-binding fragment, variant, or derivative thereof, and a heterologous polypeptide. The heterologous polypeptide to which the antibody is fused may be useful for function or is useful to target the IGF-1R polypeptide expressing cells. In one embodiment, a fusion protein of the invention comprises, consists essentially of, or consists of, a polypeptide having the amino acid sequence of any one or more of the VH regions of an antibody of the invention or the amino acid sequence of any one or more of the VL regions of an antibody of the invention or fragments or variants thereof, and a heterologous polypeptide sequence. In another embodiment, a fusion protein for use in the diagnostic and treatment methods disclosed herein comprises, consists essentially of, or consists of a polypeptide having the amino acid sequence of any one, two, three of the VH-CDRs of an IGF-1R-specific antibody, or fragments, variants, or derivatives thereof, or the amino acid sequence of any one, two, three of the VL-CDRs of an IGF-1R-specific antibody, or fragments, variants, or derivatives thereof, and a heterologous polypeptide sequence. In one embodiment, the fusion protein comprises a polypeptide having the amino acid sequence of a VH-CDR3 of an IGF-1R-specific antibody of the present invention, or fragment, derivative, or variant thereof, and a heterologous polypeptide sequence, which fusion protein specifically binds to at least one epitope of IGF-1R. In another embodiment, a fusion protein comprises a polypeptide having the amino acid sequence of at least one VH region of an IGF-1R-specific antibody of the invention and the amino acid sequence of at least one VL region of an IGF-1R-specific antibody of the invention or fragments, derivatives or variants thereof, and a heterologous polypeptide sequence. Preferably, the VH and VL regions of the fusion protein correspond to a single source antibody (or scFv or Fab fragment) which specifically binds at least one epitope of IGF-1R. In yet another embodiment, a fusion protein for use in the diagnostic and treatment methods disclosed herein comprises a polypeptide having the amino acid sequence of any one, two, three or more of the VH CDRs of an IGF-1R-specific antibody and the amino acid sequence of any one, two, three or more of the VL CDRs of an IGF-IR-specific antibody, or fragments or variants thereof, and a heterologous polypeptide sequence. Preferably, two, three, four, five, six, or more of the VH-CDR(s) or VL-CDR(s) correspond to single source antibody (or scFv or Fab fragment) of the invention. Nucleic acid molecules encoding these fusion proteins are also encompassed by the invention.

Exemplary fusion proteins reported in the literature include fusions of the T cell receptor (Gascoigne et al., *Proc. Natl. Acad. Sci. USA* 84:2936-2940 (1987)); CD4 (Capon et al., *Nature* 337:525-531 (1989); Traunecker et al., *Nature* 339:68-70 (1989); Zettmeissl et al., *DNA Cell Biol. USA* 9:347-353 (1990); and Byrn et al., *Nature* 344:667-670 (1990)); L-selectin (homing receptor) (Watson et al., *J. Cell. Biol.* 110:2221-2229 (1990); and Watson et al., *Nature* 349: 164-167 (1991)); CD44 (Aruffo et al., *Cell* 61:1303-1313 (1990)); CD28 and B7 (Linsley et al., *J. Exp. Med.* 173:721-730 (1991)); CTLA-4 (Lisley et al., *J. Exp. Med.* 174:561-569 (1991)); CD22 (Stamenkovic et al., *Cell* 66:1133-1144 (1991)); TNF receptor (Ashkenazi et al., *Proc. Natl. Acad. Sci. USA* 88:10535-10539 (1991); Lesslauer et al., *Eur. J. Immunol.* 27:2883-2886 (1991); and Peppel et al., *J. Exp. Med.* 174:1483-1489 (1991)); and IgE receptor a (Ridgway and Gorman, *J. Cell. Biol. Vol.* 115, Abstract No. 1448 (1991)).

As discussed elsewhere herein, IGF-1R antibodies, or antigen-binding fragments, variants, or derivatives thereof of the invention may be fused to heterologous polypeptides to increase the in vivo half life of the polypeptides or for use in immunoassays using methods known in the art. For example, in one embodiment, PEG can be conjugated to the IGF-1R antibodies of the invention to increase their half-life in vivo. Leong, S. R., et al., *Cytokine* 16:106 (2001); *Adv. in Drug Deliv. Rev.* 54:531 (2002); or Weir et al., *Biochem. Soc. Transactions* 30:512 (2002).

Moreover, IGF-1R antibodies, or antigen-binding fragments, variants, or derivatives thereof of the invention can be fused to marker sequences, such as a peptide to facilitate their purification or detection. In preferred embodiments, the marker amino acid sequence is a hexa-histidine peptide, such as the tag provided in a pQE vector (QIAGEN, Inc., 9259 Eton Avenue, Chatsworth, Calif., 91311), among others, many of which are commercially available. As described in Gentz et al., *Proc. Natl. Acad. Sci. USA* 86:821-824 (1989), for instance, hexa-histidine provides for convenient purification of the fusion protein. Other peptide tags useful for purification include, but are not limited to, the "HA" tag, which corresponds to an epitope derived from the influenza hemagglutinin protein (Wilson et al., *Cell* 37:767 (1984)) and the "flag" tag.

Fusion proteins can be prepared using methods that are well known in the art (see for example U.S. Pat. Nos. 5,116,964 and 5,225,538). The precise site at which the fusion is made may be selected empirically to optimize the secretion or binding characteristics of the fusion protein. DNA encoding the fusion protein is then transfected into a host cell for expression.

IGF-1R antibodies of the present invention may be used in non-conjugated form or may be conjugated to at least one of a variety of molecules, e.g., to improve the therapeutic properties of the molecule, to facilitate target detection, or for imaging or therapy of the patient. IGF-1R antibodies, or antigen-binding fragments, variants, or derivatives thereof of the invention can be labeled or conjugated either before or after purification, when purification is performed.

In particular, IGF-1R antibodies, or antigen-binding fragments, variants, or derivatives thereof of the invention may be conjugated to therapeutic agents, prodrugs, peptides, proteins, enzymes, viruses, lipids, biological response modifiers, pharmaceutical agents, or PEG.

Those skilled in the art will appreciate that conjugates may also be assembled using a variety of techniques depending on the selected agent to be conjugated. For example, conjugates with biotin are prepared e.g. by reacting a binding polypeptide with an activated ester of biotin such as the biotin N-hydroxysuccinimide ester. Similarly, conjugates with a fluorescent marker may be prepared in the presence of a coupling agent, e.g. those listed herein, or by reaction with an isothiocyanate, preferably fluorescein-isothiocyanate. Conjugates of the IGF-1R antibodies, or antigen-binding fragments, variants, or derivatives thereof of the invention are prepared in an analogous manner.

The present invention further encompasses IGF-1R antibodies, or antigen-binding fragments, variants, or derivatives thereof of the invention conjugated to a diagnostic or therapeutic agent. The IGF-1R antibodies can be used diagnostically to, for example, monitor the development or progression of a neurological disease as part of a clinical testing procedure to, e.g., determine the efficacy of a given treatment and/or prevention regimen. Detection can be facilitated by coupling the IGF-1R antibody, or antigen-binding fragment, variant, or derivative thereof to a detectable substance. Examples of detectable substances include various enzymes, prosthetic groups, fluorescent materials, luminescent materials, bioluminescent materials, radioactive materials, positron emitting metals using various positron emission tomographies, and nonradioactive paramagnetic metal ions. See, for example, U.S. Pat. No. 4,741,900 for metal ions which can be conjugated to antibodies for use as diagnostics according to the present invention. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin; and examples of suitable radioactive material include $^{125}$I, $^{131}$I, $^{111}$In or $^{99}$Tc.

An IGF-1R antibody, or antigen-binding fragment, variant, or derivative thereof also can be detectably labeled by coupling it to a chemiluminescent compound. The presence of the chemiluminescent-tagged IGF-1R antibody is then determined by detecting the presence of luminescence that arises during the course of a chemical reaction. Examples of particularly useful chemiluminescent labeling compounds are luminol, isoluminol, theromatic acridinium ester, imidazole, acridinium salt and oxalate ester.

One of the ways in which an IGF-1R antibody, or antigen-binding fragment, variant, or derivative thereof can be detectably labeled is by linking the same to an enzyme and using the linked product in an enzyme immunoassay (EIA) (Voller, A., "The Enzyme Linked Immunosorbent Assay (ELISA)" Microbiological Associates Quarterly Publication, Walkersville, Md., *Diagnostic Horizons* 2:1-7 (1978)); Voller et al., *J. Clin. Pathol.* 31:507-520 (1978); Butler, J. E., *Meth. Enzymol.* 73:482-523 (1981); Maggio, E. (ed.), *Enzyme Immunoassay*, CRC Press, Boca Raton, Fla., (1980); Ishikawa, E. et al., (eds.), *Enzyme Immunoassay*, Kgaku Shoin, Tokyo (1981). The enzyme, which is bound to the IGF-1R antibody will react with an appropriate substrate, preferably a chromogenic substrate, in such a manner as to produce a chemical moiety which can be detected, for example, by spectrophotometric, fluorimetric or by visual means. Enzymes which can be used to detectably label the antibody include, but are not limited to, malate dehydrogenase, staphylococcal nuclease, delta-5-steroid isomerase, yeast alcohol dehydrogenase, alpha-glycerophosphate, dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase and acetylcholinesterase. Additionally, the detection can be accomplished by colorimetric methods which employ a chromogenic substrate for the enzyme. Detection may also be accomplished by visual comparison of the extent of enzymatic reaction of a substrate in comparison with similarly prepared standards.

Detection may also be accomplished using any of a variety of other immunoassays. For example, by radioactively labeling the IGF-1R antibody, or antigen-binding fragment, variant, or derivative thereof, it is possible to detect the antibody through the use of a radioimmunoassay (RIA) (see, for example, Weintraub, B., *Principles of Radioimmunoassays, Seventh Training Course on Radioligand Assay Techniques*, The Endocrine Society, (March, 1986)), which is incorporated by reference herein). The radioactive isotope can be detected by means including, but not limited to, a gamma counter, a scintillation counter, or autoradiography.

An IGF-1R antibody, or antigen-binding fragment, variant, or derivative thereof can also be detectably labeled using fluorescence emitting metals such as 152Eu, or others of the lanthanide series. These metals can be attached to the antibody using such metal chelating groups as diethylenetriaminepentacetic acid (DTPA) or ethylenediaminetetraacetic acid (EDTA).

Techniques for conjugating various moieties to an IGF-1R antibody, or antigen-binding fragment, variant, or derivative thereof are well known, see, e.g., Arnon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. (1985); Hellstrom et al., "Antibodies For Drug Delivery", in *Controlled Drug Delivery* (2nd Ed.), Robinson et al. (eds.), Marcel Dekker, Inc., pp. 623-53 (1987); Thorpe, "Antibody Carriers Of Cytotoxic Agents In Cancer Therapy: A Review", in *Monoclonal Antibodies '84: Biological And Clinical Applications*, Pinchera et al. (eds.), pp. 475-506 (1985); "Analysis, Results, And Future Prospective Of The Therapeutic Use Of Radiolabeled Antibody In Cancer Therapy", in *Monoclonal Antibodies For Cancer Detection And Therapy*, Baldwin et al. (eds.), Academic Press pp. 303-16 (1985), and Thorpe et al., "The Preparation And Cytotoxic Properties Of Antibody-Toxin Conjugates", *Immunol. Rev.* 62:119-58 (1982).

In particular, binding molecules, e.g., binding polypeptides, e.g., IGF-1R-specific antibodies or immunospecific fragments thereof for use in the diagnostic and treatment methods disclosed herein may be conjugated to cytotoxins (such as radioisotopes, cytotoxic drugs, or toxins) therapeutic agents, cytostatic agents, biological toxins, prodrugs, peptides, proteins, enzymes, viruses, lipids, biological response modifiers, pharmaceutical agents, immunologically active ligands (e.g., lymphokines or other antibodies wherein the resulting molecule binds to both the neoplastic cell and an effector cell such as a T cell), or PEG. In another embodiment, a binding molecule, e.g., a binding polypeptide, e.g., a IGF-1R-specific antibody or immunospecific fragment thereof for use in the diagnostic and treatment methods disclosed herein can be conjugated to a molecule that decreases vascularization of tumors. In other embodiments, the disclosed compositions may comprise binding molecules, e.g., binding polypeptides, e.g., IGF-1R-specific antibodies or immunospecific fragments thereof coupled to drugs or prodrugs. Still other embodiments of the present invention comprise the use of binding molecules, e.g., binding polypeptides, e.g., IGF-1R-specific antibodies or immunospecific fragments thereof conjugated to specific biotoxins or their cytotoxic fragments such as ricin, gelonin, pseudo monas exotoxin or diphtheria toxin. The selection of which conjugated or unconjugated binding molecule to use will depend on the type and stage of cancer, use of adjunct treatment (e.g., chemotherapy or external radiation) and patient condition. It will be appreciated that one skilled in the art could readily make such a selection in view of the teachings herein.

It will be appreciated that, in previous studies, anti-tumor antibodies labeled with isotopes have been used successfully to destroy cells in solid tumors as well as lymphomas/leukemias in animal models, and in some cases in humans. Exemplary radioisotopes include: $^{90}$Y, $^{125}$I, $^{131}$I, $^{123}$I, $^{111}$In, $^{105}$Rh, $^{153}$Sm, $^{67}$Cu, $^{67}$Ga, $^{166}$Ho, $^{177}$Lu, $^{186}$Re and $^{188}$Re. The radionuclides act by producing ionizing radiation which causes multiple strand breaks in nuclear DNA, leading to cell death. The isotopes used to produce therapeutic conjugates typically produce high energy α- or β-particles which have a short path length. Such radionuclides kill cells to which they are in close proximity, for example neoplastic cells to which the conjugate has attached or has entered. They have little or no effect on non-localized cells. Radionuclides are essentially non-immunogenic.

With respect to the use of radiolabeled conjugates in conjunction with the present invention, binding molecules, e.g., binding polypeptides, e.g., IGF-1R-specific antibodies or immunospecific fragments thereof may be directly labeled (such as through iodination) or may be labeled indirectly through the use of a chelating agent. As used herein, the phrases "indirect labeling" and "indirect labeling approach" both mean that a chelating agent is covalently attached to a binding molecule and at least one radionuclide is associated with the chelating agent. Such chelating agents are typically referred to as bifunctional chelating agents as they bind both the polypeptide and the radioisotope. Particularly preferred chelating agents comprise 1-isothiocycmatobenzyl-3-methyldiothelene triaminepentaacetic acid ("MX-DTPA") and cyclohexyl diethylenetriamine pentaacetic acid ("CHX-DTPA") derivatives. Other chelating agents comprise P-DOTA and EDTA derivatives. Particularly preferred radionuclides for indirect labeling include $^{111}$In and $^{90}$Y.

As used herein, the phrases "direct labeling" and "direct labeling approach" both mean that a radionuclide is covalently attached directly to a polypeptide (typically via an amino acid residue). More specifically, these linking technologies include random labeling and site-directed labeling. In the latter case, the labeling is directed at specific sites on the polypeptide, such as the N-linked sugar residues present only on the Fc portion of the conjugates. Further, various direct labeling techniques and protocols are compatible with the instant invention. For example, Technetium-99 labeled polypeptides may be prepared by ligand exchange processes, by reducing pertechnate (TcO$_4^-$) with stannous ion solution, chelating the reduced technetium onto a Sephadex column and applying the binding polypeptides to this column, or by batch labeling techniques, e.g. by incubating pertechnate, a reducing agent such as SnCl$_2$, a buffer solution such as a sodium-potassium phthalate-solution, and the antibodies. In any event, preferred radionuclides for directly labeling antibodies are well known in the art and a particularly preferred radionuclide for direct labeling is $^{131}$I covalently attached via tyrosine residues. Binding molecules, e.g., binding polypeptides, e.g., IGF-1R-specific antibodies or immunospecific fragments thereof for use in the diagnostic and treatment methods disclosed herein may be derived, for example, with radioactive sodium or potassium iodide and a chemical oxidizing agent, such as sodium hypochlorite, chloramine T or the like, or an enzymatic oxidizing agent, such as lactoperoxidase, glucose oxidase and glucose.

Patents relating to chelators and chelator conjugates are known in the art. For instance, U.S. Pat. No. 4,831,175 of Gansow is directed to polysubstituted diethylenetriaminepentaacetic acid chelates and protein conjugates containing the same, and methods for their preparation. U.S. Pat. Nos. 5,099,069, 5,246,692, 5,286,850, 5,434,287 and 5,124,471 of Gansow also relate to polysubstituted DTPA chelates. These patents are incorporated herein by reference in their entireties. Other examples of compatible metal chelators are ethylenediaminetetraacetic acid (EDTA), diethylenetriaminepentaacetic acid (DPTA), 1,4,8,11-tetraazatetradecane, 1,4,8,11-tetraazatetradecane-1,4,8,11-tetraacetic acid, 1-oxa-4,7,12,15-tetraazaheptadecane-4,7,12,15-tetraacetic acid, or the like. Cyclohexyl-DTPA or CHX-DTPA is particularly preferred and is exemplified extensively below. Still other compatible chelators, including those yet to be discovered, may easily be discerned by a skilled artisan and are clearly within the scope of the present invention.

Compatible chelators, including the specific bifunctional chelator used to facilitate chelation U.S. Pat. Nos. 6,682,134, 6,399,061, and 5,843,439, incorporated herein by reference in their entireties, are preferably selected to provide high affinity for trivalent metals, exhibit increased tumor-to-non-tumor ratios and decreased bone uptake as well as greater in vivo retention of radionuclide at target sites, i.e., B-cell lymphoma tumor sites. However, other bifunctional chelators that may or may not possess all of these characteristics are known in the art and may also be beneficial in tumor therapy.

It will also be appreciated that, in accordance with the teachings herein, binding molecules may be conjugated to different radiolabels for diagnostic and therapeutic purposes. To this end the aforementioned U.S. Pat. Nos. 6,682,134, 6,399,061, and 5,843,439 disclose radiolabeled therapeutic conjugates for diagnostic "imaging" of tumors before administration of therapeutic antibody. "In2B8" conjugate comprises a murine monoclonal antibody, 2B8, specific to human CD20 antigen, that is attached to $^{111}$In via a bifunctional chelator, i.e., MX-DTPA (diethylenetriaminepentaacetic acid), which comprises a 1:1 mixture of 1-isothiocyanatobenzyl-3-methyl-DTPA and 1-methyl-3-isothiocyanatobenzyl-DTPA. $^{111}$In is particularly preferred as a diagnostic radionuclide because between about 1 to about 10 mCi can be safely administered without detectable toxicity; and the imaging data is generally predictive of subsequent $^{90}$Y-labeled antibody distribution. Most imaging studies utilize 5 mCi $^{111}$In-labeled antibody, because this dose is both safe and has increased imaging efficiency compared with lower doses, with optimal imaging occurring at three to six days after antibody administration. See, for example, Murray, J. Nuc. Med. 26: 3328 (1985) and Carraguillo et al., J. Nuc. Med. 26: 67 (1985).

As indicated above, a variety of radionuclides are applicable to the present invention and those skilled in the can readily determine which radionuclide is most appropriate under various circumstances. For example, $^{131}$I is a well known radionuclide used for targeted immunotherapy. However, the clinical usefulness of $^{131}$I can be limited by several factors including: eight-day physical half-life; dehalogenation of iodinated antibody both in the blood and at tumor sites; and emission characteristics (e.g., large gamma component) which can be suboptimal for localized dose deposition in tumor. With the advent of superior chelating agents, the opportunity for attaching metal chelating groups to proteins has increased the opportunities to utilize other radionuclides such as $^{111}$In and $^{90}$Y. $^{90}$Y provides several benefits for utilization in radioimmunotherapeutic applications: the 64 hour half-life of $^{90}$Y is long enough to allow antibody accumulation by tumor and, unlike e.g., $^{131}$I, $^{90}$Y is a pure beta emitter of high energy with no accompanying gamma irradiation in its decay, with a range in tissue of 100 to 1,000 cell diameters. Furthermore, the minimal amount of penetrating radiation allows for outpatient administration of $^{90}$Y-labeled antibodies. Additionally, internalization of labeled antibody is not required for cell killing, and the local emission of ionizing radiation should be lethal for adjacent tumor cells lacking the target molecule.

Additional preferred agents for conjugation to binding molecules, e.g., binding polypeptides, e.g., IGF-1R-specific antibodies or immunospecific fragments thereof are cytotoxic drugs, particularly those which are used for cancer therapy. As used herein, "a cytotoxin or cytotoxic agent" means any agent that is detrimental to the growth and proliferation of cells and may act to reduce, inhibit or destroy a cell or malignancy. Exemplary cytotoxins include, but are not limited to, radionuclides, biotoxins, enzymatically active toxins, cytostatic or cytotoxic therapeutic agents, prodrugs, immunologically active ligands and biological response modifiers such as cytokines. Any cytotoxin that acts to retard or slow the growth of immunoreactive cells or malignant cells is within the scope of the present invention.

Exemplary cytotoxins include, in general, cytostatic agents, alkylating agents, anti-metabolites, anti-proliferative agents, tubulin binding agents, hormones and hormone antagonists, and the like. Exemplary cytostatics that are compatible with the present invention include alkylating substances, such as mechlorethamine, triethylenephosphoramide, cyclophosphamide, ifosfamide, chlorambucil, busulfan, melphalan or triaziquone, also nitrosourea compounds, such as carmustine, lomustine, or semustine. Other preferred classes of cytotoxic agents include, for example, the maytansinoid family of drugs. Other preferred classes of cytotoxic agents include, for example, the anthracycline family of drugs, the vinca drugs, the mitomycins, the bleomycins, the cytotoxic nucleosides, the pteridine family of drugs, diynenes, and the podophyllotoxins. Particularly useful members of those classes include, for example, adriamycin, caminomycin, daunorubicin (daunomycin), doxorubicin, aminopterin, methotrexate, methopterin, mithramycin, streptonigrin, dichloromethotrexate, mitomycin C, actinomycin-D, porfiromycin, 5-fluorouracil, floxuridine, ftorafur, 6-mercaptopurine, cytarabine, cytosine arabinoside, podophyllotoxin, or podophyllotoxin derivatives such as etoposide or etoposide phosphate, melphalan, vinblastine, vincristine, leurosidine, vindesine, leurosine and the like. Still other cytotoxins that are compatible with the teachings herein include taxol, taxane, cytochalasin B, gramicidin D, ethidium bromide, emetine, tenoposide, colchicin, dihydroxy anthracin dione, mitoxantrone, procaine, tetracaine, lidocaine, propranolol, and puromycin and analogs or homologs thereof. Hormones and hormone antagonists, such as corticosteroids, e.g. prednisone, progestins, e.g. hydroxyprogesterone or medroprogesterone, estrogens, e.g. diethylstilbestrol, antiestrogens, e.g. tamoxifen, androgens, e.g. testosterone, and aromatase inhibitors, e.g. aminogluthetimide are also compatible with the teachings herein. One skilled in the art may make chemical modifications to the desired compound in order to make reactions of that compound more convenient for purposes of preparing conjugates of the invention.

One example of particularly preferred cytotoxins comprise members or derivatives of the enediyne family of anti-tumor antibiotics, including calicheamicin, esperamicins or dynemicins. These toxins are extremely potent and act by cleaving nuclear DNA, leading to cell death. Unlike protein toxins which can be cleaved in vivo to give many inactive but immunogenic polypeptide fragments, toxins such as calicheamicin, esperamicins and other enediynes are small molecules which are essentially non-immunogenic. These non-peptide toxins are chemically-linked to the dimers or tetramers by techniques which have been previously used to label monoclonal antibodies and other molecules. These linking technologies include site-specific linkage via the N-linked sugar residues present only on the Fc portion of the constructs. Such site-directed linking methods have the advantage of reducing the possible effects of linkage on the binding properties of the constructs.

As previously alluded to, compatible cytotoxins for preparation of conjugates may comprise a prodrug. As used herein, the term "prodrug" refers to a precursor or derivative form of a pharmaceutically active substance that is less cytotoxic to tumor cells compared to the parent drug and is capable of being enzymatically activated or converted into the more active parent form. Prodrugs compatible with the invention include, but are not limited to, phosphate-containing prodrugs, thiophosphate-containing prodrugs, sulfate containing prodrugs, peptide containing prodrugs, β-lactam-containing prodrugs, optionally substituted phenoxyacetamide-containing prodrugs or optionally substituted phenylacetamide-containing prodrugs, 5-fluorocytosine and other 5-fluorouridine prodrugs that can be converted to the more active cytotoxic free drug. Further examples of cytotoxic drugs that can be derivatized into a prodrug form for use in the present invention comprise those chemotherapeutic agents described above.

Among other cytotoxins, it will be appreciated that binding molecules, e.g., binding polypeptides, e.g., IGF-1R-specific antibodies or immunospecific fragments thereof disclosed herein can also be associated with or conjugated to a biotoxin such as ricin subunit A, abrin, diptheria toxin, botulinum, cyanginosins, saxitoxin, shigatoxin, tetanus, tetrodotoxin, trichothecene, verrucologen or a toxic enzyme. Preferably, such constructs will be made using genetic engineering techniques that allow for direct expression of the antibody-toxin construct. Other biological response modifiers that may be associated with the binding molecules, e.g., binding polypeptides, e.g., IGF-1R-specific antibodies or immunospecific fragments thereof disclosed herein comprise cytokines such as lymphokines and interferons. In view of the instant disclosure it is submitted that one skilled in the art could readily form such constructs using conventional techniques.

Another class of compatible cytotoxins that may be used in association with or conjugated to the disclosed binding molecules, e.g., binding polypeptides, e.g., IGF-1R-specific antibodies or immunospecific fragments thereof, are radiosensitizing drugs that may be effectively directed to tumor or immunoreactive cells. Such drugs enhance the sensitivity to ionizing radiation, thereby increasing the efficacy of radiotherapy. An antibody conjugate internalized by the tumor cell would deliver the radiosensitizer nearer the nucleus where radiosensitization would be maximal. The unbound radiosensitizer linked binding molecules of the invention would be cleared quickly from the blood, localizing the remaining radiosensitization agent in the target tumor and providing minimal uptake in normal tissues. After rapid clearance from the blood, adjunct radiotherapy would be administered in one of three ways: 1.) external beam radiation directed specifically to the tumor, 2.) radioactivity directly implanted in the tumor or 3.) systemic radioimmunotherapy with the same targeting antibody. A potentially attractive variation of this approach would be the attachment of a therapeutic radioisotope to the radiosensitized immunoconjugate, thereby providing the convenience of administering to the patient a single drug.

In certain embodiments, a moiety that enhances the stability or efficacy of a binding molecule, e.g., a binding polypeptide, e.g., a IGF-1R-specific antibody or immunospecific fragment thereof can be conjugated. For example, in one embodiment, PEG can be conjugated to the binding molecules of the invention to increase their half-life in vivo. Leong, S. R., et al., *Cytokine* 16:106 (2001); *Adv. in Drug Deliv. Rev.* 54:531 (2002); or Weir et al., *Biochem. Soc. Transactions* 30:512 (2002).

The present invention further encompasses the use of binding molecules, e.g., binding polypeptides, e.g., IGF-1R-specific antibodies or immunospecific fragments conjugated to a diagnostic or therapeutic agent. The binding molecules can be used diagnostically to, for example, monitor the development or progression of a tumor as part of a clinical testing procedure to, e.g., determine the efficacy of a given treatment and/or prevention regimen. Detection can be facilitated by coupling the binding molecule, e.g., binding polypeptide, e.g., IGF-1R-specific antibody or immunospecific fragment thereof to a detectable substance. Examples of detectable substances include various enzymes, prosthetic groups, fluorescent materials, luminescent materials, bioluminescent materials, radioactive materials, positron emitting metals using various positron emission tomographies, and nonradioactive paramagnetic metal ions. See, for example, U.S. Pat. No. 4,741,900 for metal ions which can be conjugated to antibodies for use as diagnostics according to the present invention. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin; and examples of suitable radioactive material include $^{125}$I, $^{113}$I, $^{111}$In or $^{99}$Tc.

A binding molecule, e.g., a binding polypeptide, e.g., a IGF-1R-specific antibody or immunospecific fragment thereof also can be detectably labeled by coupling it to a chemiluminescent compound. The presence of the chemiluminescent-tagged binding molecule is then determined by detecting the presence of luminescence that arises during the course of a chemical reaction. Examples of particularly useful chemiluminescent labeling compounds are luminol, isoluminol, theromatic acridinium ester, imidazole, acridinium salt and oxalate ester.

One of the ways in which a binding molecule, e.g., a binding polypeptide, e.g., a IGF-1R-specific antibody or immunospecific fragment thereof can be detectably labeled is by linking the same to an enzyme and using the linked product in an enzyme immunoassay (EIA) (Voller, A., "The Enzyme Linked Immunosorbent Assay (ELISA)" Microbiological Associates Quarterly Publication, Walkersville, Md., *Diagnostic Horizons* 2:1-7 (1978)); Voller et al., *J. Clin. Pathol.* 31:507-520 (1978); Butler, J. E., *Meth. Enrymol.* 73:482-523 (1981); Maggio, E. (ed.), *Enzyme Immunoassay*, CRC Press, Boca Raton, Fla., (1980); Ishikawa, E. et al., (eds.), *Enzyme Immunoassay*, Kgaku Shoin, Tokyo (1981). The enzyme, which is bound to the binding molecule will react with an appropriate substrate, preferably a chromogenic substrate, in such a manner as to produce a chemical moiety which can be detected, for example, by spectrophotometric, fluorimetric or by visual means. Enzymes which can be used to detectably label the antibody include, but are not limited to, malate dehydrogenase, staphylococcal nuclease, delta-5-steroid isomerase, yeast alcohol dehydrogenase, alpha-glycerophosphate, dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase and acetylcholinesterase. Additionally, the detection can be accomplished by colorimetric methods which employ a chromogenic substrate for the enzyme. Detection may also be accomplished by visual comparison of the extent of enzymatic reaction of a substrate in comparison with similarly prepared standards.

Detection may also be accomplished using any of a variety of other immunoassays. For example, by radioactively labeling the binding molecule, e.g., binding polypeptide, e.g., IGF-1R-specific antibody or immunospecific fragment thereof, it is possible to detect cancer antigens through the use of a radioimmunoassay (RIA) (see, for example, Weintraub, B., *Principles of Radioimmunoassays, Seventh Training Course on Radioligand Assay Techniques*, The Endocrine Society, (March, 1986)), which is incorporated by reference herein). The radioactive isotope can be detected by means including, but not limited to, a gamma counter, a scintillation counter, or autoradiography.

A binding molecule, e.g., a binding polypeptide, e.g., a IGF-1R-specific antibody or immunospecific fragment thereof can also be detectably labeled using fluorescence emitting metals such as 152Eu, or others of the lanthanide series. These metals can be attached to the antibody using such metal chelating groups as diethylenetriaminepentacetic acid (DTPA) or ethylenediaminetetraacetic acid (EDTA).

Techniques for conjugating various moieties to a binding molecule, e.g., a binding polypeptide, e.g., a IGF-1R-specific antibody or immunospecific fragment thereof are well known, see, e.g., Arnon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. (1985); Hellstrom et al., "Antibodies For Drug Delivery", in Controlled Drug Delivery (2nd Ed.), Robinson et al. (eds.), Marcel Dekker, Inc., pp. 623-53 (1987); Thorpe, "Antibody Carriers Of Cytotoxic Agents In Cancer Therapy: A Review", in *Monoclonal Antibodies '84: Biological And Clinical Applications*, Pinchera et al. (eds.), pp. 475-506 (1985); "Analysis, Results, And Future Prospective Of The Therapeutic Use Of Radiolabeled Antibody In Cancer Therapy", in *Monoclonal Antibodies For Cancer Detection And Therapy*, Baldwin et al. (eds.), Academic Press pp. 303-16 (1985), and Thorpe et al., "The Preparation And Cytotoxic Properties Of Antibody-Toxin Conjugates", *Immunol. Rev.* 62:119-58 (1982).

VII. Expression of Antibody Polypeptides

As is well known, RNA may be isolated from the original hybridoma cells or from other transformed cells by standard techniques, such as guanidinium isothiocyanate extraction and precipitation followed by centrifugation or chromatography. Where desirable, mRNA may be isolated from total RNA by standard techniques such as chromatography on oligo dT cellulose. Suitable techniques are familiar in the art.

In one embodiment, cDNAs that encode the light and the heavy chains of the antibody may be made, either simultaneously or separately, using reverse transcriptase and DNA polymerase in accordance with well known methods. PCR may be initiated by consensus constant region primers or by more specific primers based on the published heavy and light chain DNA and amino acid sequences. As discussed above, PCR also may be used to isolate DNA clones encoding the antibody light and heavy chains. In this case the libraries may be screened by consensus primers or larger homologous probes, such as mouse constant region probes.

DNA, typically plasmid DNA, may be isolated from the cells using techniques known in the art, restriction mapped and sequenced in accordance with standard, well known techniques set forth in detail, e.g., in the foregoing references relating to recombinant DNA techniques. Of course, the DNA may be synthetic according to the present invention at any point during the isolation process or subsequent analysis.

Following manipulation of the isolated genetic material to provide IGF-1R antibodies, or antigen-binding fragments, variants, or derivatives thereof of the invention, the polynucleotides encoding the IGF-1R antibodies are typically inserted in an expression vector for introduction into host cells that may be used to produce the desired quantity of IGF-1R antibody.

Recombinant expression of an antibody, or fragment, derivative or analog thereof, e.g., a heavy or light chain of an antibody which binds to a target molecule described herein, e.g., IGF-1R, requires construction of an expression vector containing a polynucleotide that encodes the antibody. Once a polynucleotide encoding an antibody molecule or a heavy or light chain of an antibody, or portion thereof (preferably containing the heavy or light chain variable domain), of the invention has been obtained, the vector for the production of the antibody molecule may be produced by recombinant DNA technology using techniques well known in the art. Thus, methods for preparing a protein by expressing a polynucleotide containing an antibody encoding nucleotide sequence are described herein. Methods which are well known to those skilled in the art can be used to construct expression vectors containing antibody coding sequences and appropriate transcriptional and translational control signals. These methods include, for example, in vitro recombinant DNA techniques, synthetic techniques, and in vivo genetic recombination. The invention, thus, provides replicable vectors comprising a nucleotide sequence encoding an antibody molecule of the invention, or a heavy or light chain thereof, or a heavy or light chain variable domain, operably linked to a promoter. Such vectors may include the nucleotide sequence encoding the constant region of the antibody molecule (see, e.g., PCT Publication WO 86/05807; PCT Publication WO 89/01036; and U.S. Pat. No. 5,122,464) and the variable domain of the antibody may be cloned into such a vector for expression of the entire heavy or light chain.

The host cell may be co-transfected with two expression vectors of the invention, the first vector encoding a heavy chain derived polypeptide and the second vector encoding a light chain derived polypeptide. The two vectors may contain identical selectable markers which enable equal expression of heavy and light chain polypeptides. Alternatively, a single vector may be used which encodes both heavy and light chain polypeptides. In such situations, the light chain is advantageously placed before the heavy chain to avoid an excess of toxic free heavy chain (Proudfoot, *Nature* 322:52 (1986); Kohler, *Proc. Natl. Acad. Sci. USA* 77:2197 (1980)). The coding sequences for the heavy and light chains may comprise cDNA or genomic DNA.

The term "vector" or "expression vector" is used herein to mean vectors used in accordance with the present invention as a vehicle for introducing into and expressing a desired gene in a host cell. As known to those skilled in the art, such vectors may easily be selected from the group consisting of plasmids, phages, viruses and retroviruses. In general, vectors compatible with the instant invention will comprise a selection marker, appropriate restriction sites to facilitate cloning of the desired gene and the ability to enter and/or replicate in eukaryotic or prokaryotic cells.

For the purposes of this invention, numerous expression vector systems may be employed. For example, one class of vector utilizes DNA elements which are derived from animal viruses such as bovine papilloma virus, polyoma virus, adenovirus, vaccinia virus, baculovirus, retroviruses (RSV, MMTV or MOMLV) or SV40 virus. Others involve the use of polycistronic systems with internal ribosome binding sites. Additionally, cells which have integrated the DNA into their chromosomes may be selected by introducing one or more markers which allow selection of transfected host cells. The marker may provide for prototrophy to an auxotrophic host, biocide resistance (e.g., antibiotics) or resistance to heavy metals such as copper. The selectable marker gene can either be directly linked to the DNA sequences to be expressed, or introduced into the same cell by cotransformation. Additional elements may also be needed for optimal synthesis of mRNA.

These elements may include signal sequences, splice signals, as well as transcriptional promoters, enhancers, and termination signals.

In particularly preferred embodiments the cloned variable region genes are inserted into an expression vector along with the heavy and light chain constant region genes (preferably human) synthetic as discussed above. In one embodiment, this is effected using a proprietary expression vector of Biogen IDEC, Inc., referred to as NEOSPLA (disclosed in U.S. Pat. No. 6,159,730). This vector contains the cytomegalovirus promoter/enhancer, the mouse beta globin major promoter, the SV40 origin of replication, the bovine growth hormone polyadenylation sequence, neomycin phosphotransferase exon 1 and exon 2, the dihydrofolate reductase gene and leader sequence. This vector has been found to result in very high level expression of antibodies upon incorporation of variable and constant region genes, transfection in CHO cells, followed by selection in G418 containing medium and methotrexate amplification. Of course, any expression vector which is capable of eliciting expression in eukaryotic cells may be used in the present invention. Examples of suitable vectors include, but are not limited to plasmids pcDNA3, pHCMV/Zeo, pCR3.1, pEF1/His, pIND/GS, pRc/HCMV2, pSV40/Zeo2, pTRACER-HCMV, pUB6/V5-His, pVAX1, and pZeoSV2 (available from Invitrogen, San Diego, Calif.), and plasmid pCI (available from Promega, Madison, Wis.). In general, screening large numbers of transformed cells for those which express suitably high levels if immunoglobulin heavy and light chains is routine experimentation which can be carried out, for example, by robotic systems. Vector systems are also taught in U.S. Pat. Nos. 5,736,137 and 5,658,570, each of which is incorporated by reference in its entirety herein. This system provides for high expression levels, e.g., >30 pg/cell/day. Other exemplary vector systems are disclosed e.g., in U.S. Pat. No. 6,413,777.

In other preferred embodiments the IGF-1R antibodies, or antigen-binding fragments, variants, or derivatives thereof of the invention may be expressed using polycistronic constructs such as those disclosed in United States Patent Application Publication No. 2003-0157641 A1, filed Nov. 18, 2002 and incorporated herein in its entirety. In these novel expression systems, multiple gene products of interest such as heavy and light chains of antibodies may be produced from a single polycistronic construct. These systems advantageously use an internal ribosome entry site (IRES) to provide relatively high levels of IGF-1R antibodies, e.g., binding polypeptides, e.g., IGF-IR-specific antibodies or immunospecific fragments thereof in eukaryotic host cells. Compatible IRES sequences are disclosed in U.S. Pat. No. 6,193,980 which is also incorporated herein. Those skilled in the art will appreciate that such expression systems may be used to effectively produce the full range of IGF-1R antibodies disclosed in the instant application.

More generally, once the vector or DNA sequence encoding a monomeric subunit of the IGF-1R antibody has been prepared, the expression vector may be introduced into an appropriate host cell. Introduction of the plasmid into the host cell can be accomplished by various techniques well known to those of skill in the art. These include, but are not limited to, transfection (including electrophoresis and electroporation), protoplast fusion, calcium phosphate precipitation, cell fusion with enveloped DNA, microinjection, and infection with intact virus. See, Ridgway, A. A. G. "*Mammalian Expression Vectors*" Vectors, Rodriguez and Denhardt, Eds., Butterworths, Boston, Mass., Chapter 24.2, pp. 470-472 (1988). Typically, plasmid introduction into the host is via electroporation. The host cells harboring the expression construct are grown under conditions appropriate to the production of the light chains and heavy chains, and assayed for heavy and/or light chain protein synthesis. Exemplary assay techniques include enzyme-linked immunosorbent assay (ELISA), radioimmunoassay (RIA), or fluorescence-activated cell sorter analysis (FACS), immunohistochemistry and the like.

The expression vector is transferred to a host cell by conventional techniques and the transfected cells are then cultured by conventional techniques to produce an antibody for use in the methods described herein. Thus, the invention includes host cells containing a polynucleotide encoding an antibody of the invention, or a heavy or light chain thereof, operably linked to a heterologous promoter. In preferred embodiments for the expression of double-chained antibodies, vectors encoding both the heavy and light chains may be co-expressed in the host cell for expression of the entire immunoglobulin molecule, as detailed below.

As used herein, "host cells" refers to cells which harbor vectors constructed using recombinant DNA techniques and encoding at least one heterologous gene. In descriptions of processes for isolation of antibodies from recombinant hosts, the terms "cell" and "cell culture" are used interchangeably to denote the source of antibody unless it is clearly specified otherwise. In other words, recovery of polypeptide from the "cells" may mean either from spun down whole cells, or from the cell culture containing both the medium and the suspended cells.

A variety of host-expression vector systems may be utilized to express antibody molecules for use in the methods described herein. Such host-expression systems represent vehicles by which the coding sequences of interest may be produced and subsequently purified, but also represent cells which may, when transformed or transfected with the appropriate nucleotide coding sequences, express an antibody molecule of the invention in situ. These include but are not limited to microorganisms such as bacteria (e.g., *E. coli, B. subtilis*) transformed with recombinant bacteriophage DNA, plasmid DNA or cosmid DNA expression vectors containing antibody coding sequences; yeast (e.g., *Saccharomyces, Pichia*) transformed with recombinant yeast expression vectors containing antibody coding sequences; insect cell systems infected with recombinant virus expression vectors (e.g., baculovirus) containing antibody coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing antibody coding sequences; or mammalian cell systems (e.g., COS, CHO, BLK, 293, 3T3 cells) harboring recombinant expression constructs containing promoters derived from the genome of mammalian cells (e.g., metallothionein promoter) or from mammalian viruses (e.g., the adenovirus late promoter; the vaccinia virus 7.5K promoter). Preferably, bacterial cells such as *Escherichia coli*, and more preferably, eukaryotic cells, especially for the expression of whole recombinant antibody molecule, are used for the expression of a recombinant antibody molecule. For example, mammalian cells such as Chinese hamster ovary cells (CHO), in conjunction with a vector such as the major intermediate early gene promoter element from human cytomegalovirus is an effective expression system for antibodies (Foecking et al., *Gene* 45:101 (1986); Cockett et al., *Bio/Technology* 8:2 (1990)).

The host cell line used for protein expression is often of mammalian origin; those skilled in the art are credited with ability to preferentially determine particular host cell lines which are best suited for the desired gene product to be expressed therein. Exemplary host cell lines include, but are not limited to, CHO (Chinese Hamster Ovary), DG44 and DUXB11 (Chinese Hamster Ovary lines, DHFR minus), HELA (human cervical carcinoma), CVI (monkey kidney line), COS (a derivative of CVI with SV40 T antigen), VERY, BHK (baby hamster kidney), MDCK, 293, WI38, R1610 (Chinese hamster fibroblast) BALBC/3T3 (mouse fibroblast), HAK (hamster kidney line), SP2/O (mouse myeloma), P3x63-Ag3.653 (mouse myeloma), BFA-1c1BPT (bovine endothelial cells), RAJI (human lymphocyte) and 293 (human kidney). CHO cells are particularly preferred. Host cell lines are typically available from commercial services, the American Tissue Culture Collection or from published literature.

In addition, a host cell strain may be chosen which modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used.

For long-term, high-yield production of recombinant proteins, stable expression is preferred. For example, cell lines which stably express the antibody molecule may be engineered. Rather than using expression vectors which contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells may be allowed to grow for 1-2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which stably express the antibody molecule.

A number of selection systems may be used, including but not limited to the herpes simplex virus thymidine kinase (Wigler et al., *Cell* 11:223 (1977)), hypoxanthine-guanine phosphoribosyltransferase (Szybalska & Szybalski, *Proc. Natl. Acad. Sci. USA* 48:202 (1992)), and adenine phosphoribosyltransferase (Lowy et al., *Cell* 22:817 1980) genes can be employed in tk-, hgprt- or aprt-cells, respectively. Also, anti-metabolite resistance can be used as the basis of selection for the following genes: dhfr, which confers resistance to methotrexate (Wigler et al., *Natl. Acad. Sci. USA* 77:357 (1980); O'Hare et al., *Proc. Natl. Acad. Sci. USA* 78:1527 (1981)); gpt, which confers resistance to mycophenolic acid (Mulligan & Berg, *Proc. Natl. Acad. Sci. USA* 78:2072 (1981)); neo, which confers resistance to the aminoglycoside G-418 *Clinical Pharmacy* 12:488-505; Wu and Wu, *Biotherapy* 3:87-95 (1991); Tolstoshev, *Ann. Rev. Pharmacol. Toxicol.* 32:573-596 (1993); Mulligan, *Science* 260:926-932 (1993); and Morgan and Anderson, *Ann. Rev. Biochem.* 62:191-217 (1993); *TIB TECH* 11(5):155-215 (May, 1993); and hygro, which confers resistance to hygromycin (Santerre et al., *Gene* 30:147 (1984). Methods commonly known in the art of recombinant DNA technology which can be used are described in Ausubel et al. (eds.), *Current Protocols in Molecular Biology*, John Wiley & Sons, NY (1993); Kriegler, *Gene Transfer and Expression*, A Laboratory Manual, Stockton Press, NY (1990); and in Chapters 12 and 13, Dracopoli et al. (eds), *Current Protocols in Human Genetics*, John Wiley & Sons, NY (1994); Colberre-Garapin et al., *J. Mol. Biol.* 150:1 (1981), which are incorporated by reference herein in their entireties.

The expression levels of an antibody molecule can be increased by vector amplification (for a review, see Bebbington and Hentschel, *The use of vectors based on gene amplification for the expression of cloned genes in mammalian cells in DNA cloning*, Academic Press, New York, Vol. 3. (1987)). When a marker in the vector system expressing antibody is amplifiable, increase in the level of inhibitor present in culture of host cell will increase the number of copies of the marker gene. Since the amplified region is associated with the antibody gene, production of the antibody will also increase (Crouse et al., *Mol. Cell. Biol.* 3:257 (1983)).

In vitro production allows scale-up to give large amounts of the desired polypeptides. Techniques for mammalian cell cultivation under tissue culture conditions are known in the art and include homogeneous suspension culture, e.g. in an airlift reactor or in a continuous stirrer reactor, or immobilized or entrapped cell culture, e.g. in hollow fibers, microcapsules, on agarose microbeads or ceramic cartridges. If necessary and/or desired, the solutions of polypeptides can be purified by the customary chromatography methods, for example gel filtration, ion-exchange chromatography, chromatography over DEAE-cellulose or (immuno-)affinity chromatography, e.g., after preferential biosynthesis of a synthetic hinge region polypeptide or prior to or subsequent to the HIC chromatography step described herein.

Genes encoding IGF-1R antibodies, or antigen-binding fragments, variants, or derivatives thereof of the invention can also be expressed non-mammalian cells such as bacteria or insect or yeast or plant cells. Bacteria which readily take up nucleic acids include members of the enterobacteriaceae, such as strains of *Escherichia coli* or *Salmonella*; Bacillaceae, such as *Bacillus subtilis*; Pneumococcus; *Streptococcus*, and *Haemophilus influenzae*. It will further be appreciated that, when expressed in bacteria, the heterologous polypeptides typically become part of inclusion bodies. The heterologous polypeptides must be isolated, purified and then assembled into functional molecules. Where tetravalent forms of antibodies are desired, the subunits will then self-assemble into tetravalent antibodies (WO02/096948A2).

In bacterial systems, a number of expression vectors may be advantageously selected depending upon the use intended for the antibody molecule being expressed. For example, when a large quantity of such a protein is to be produced, for the generation of pharmaceutical compositions of an antibody molecule, vectors which direct the expression of high levels of fusion protein products that are readily purified may be desirable. Such vectors include, but are not limited, to the *E. coli* expression vector pUR278 (Ruther et al., *EMBO J.* 2:1791 (1983)), in which the antibody coding sequence may be ligated individually into the vector in frame with the lacZ coding region so that a fusion protein is produced; pIN vectors (Inouye & Inouye, *Nucleic Acids Res.* 13:3101-3109 (1985); Van Heeke & Schuster, *J. Biol. Chem.* 24:5503-5509 (1989)); and the like. pGEX vectors may also be used to express foreign polypeptides as fusion proteins with glutathione S-transferase (GST). In general, such fusion proteins are soluble and can easily be purified from lysed cells by adsorption and binding to a matrix glutathione-agarose beads followed by elution in the presence of free glutathione. The pGEX vectors are designed to include thrombin or factor Xa protease cleavage sites so that the cloned target gene product can be released from the GST moiety.

In addition to prokaryotes, eukaryotic microbes may also be used. *Saccharomyces cerevisiae*, or common baker's yeast, is the most commonly used among eukaryotic microorganisms although a number of other strains are commonly available, e.g., *Pichia pastoris*.

For expression in *Saccharomyces*, the plasmid YRp7, for example, (Stinchcomb et al., Nature 282:39 (1979); Kingsman et al., *Gene* 7:141 (1979); Tschemper et al., *Gene* 10:157 (1980)) is commonly used. This plasmid already contains the TRP1 gene which provides a selection marker for a mutant strain of yeast lacking the ability to grow in tryptophan, for example ATCC No. 44076 or PEP4-1 (Jones, *Genetics* 85:12 (1977)). The presence of the trpl lesion as a characteristic of the yeast host cell genome then provides an effective environment for detecting transformation by growth in the absence of tryptophan.

In an insect system, *Autographa californica* nuclear polyhedrosis virus (AcNPV) is typically used as a vector to express foreign genes. The virus grows in *Spodoptera frugiperda* cells. The antibody coding sequence may be cloned individually into non-essential regions (for example the polyhedrin gene) of the virus and placed under control of an AcNPV promoter (for example the polyhedrin promoter).

Once an antibody molecule of the invention has been recombinantly expressed, it may be purified by any method known in the art for purification of an immunoglobulin molecule, for example, by chromatography (e.g., ion exchange, affinity, particularly by affinity for the specific antigen after Protein A, and sizing column chromatography), centrifugation, differential solubility, or by any other standard technique for the purification of proteins. Alternatively, a preferred method for increasing the affinity of antibodies of the invention is disclosed in US 2002 0123057 A1.

VIII. Treatment Methods Using Therapeutic IGF-1R-Specific Antibodies, or Immunospecific Fragments Thereof One embodiment of the present invention provides methods for treating a hyperproliferative disease or disorder, e.g., cancer, a malignancy, a tumor, or a metastasis thereof, in an animal suffering from such disease or predisposed to contract such disease, the method comprising, consisting essentially of, or consisting of administering to the animal an effective amount of an antibody or immunospecific fragment thereof, that binds to IGF-1R or a variant of IGF-1R. Suitable antibodies include all antibodies and antigen-specific fragments thereof described herein. Examples include, but are not limited to, an isolated antibody or antigen-binding fragment thereof which specifically binds to the same IGF-R1 epitope as a reference monoclonal Fab antibody fragment selected from the group consisting of M13-C06, M14-G11, M14-C03, M14-B01, M12-E01, and M12-G04, or a reference monoclonal antibody produced by a hybridoma selected from the group consisting of P2A7.3E11, 20C8.3B8, P1A2.2B11, 20D8.24B11, P1E2.3B12, and P1G10.2B8, an isolated antibody or antigen-binding fragment thereof which specifically binds to IGF-R1, where the antibody or fragment thereof competitively inhibits a reference monoclonal Fab antibody fragment selected from the group consisting of M13-C06, M14-G11, M14-C03, M14-B01, M12-E01, and M12-G04, or a reference monoclonal antibody produced by a hybridoma selected from the group consisting of P2A7.3E11, 20C8.3B8, P1A2.2B11, 20D8.24B11, P1E2.3B12, and P1G10.2B8 from binding to IGF-R1, or an isolated antibody or antigen-binding fragment thereof which specifically binds to IGF-R1, where the antibody or fragment thereof comprises an antigen binding domain identical to that of a monoclonal Fab antibody fragment selected from the group consisting of M13-C06, M14-G11, M14-C03, M14-B01, M12-E01, and M12-G04, or a monoclonal antibody produced by a hybridoma selected from the group consisting of P2A7.3E11, 20C8.3B8, P1A2.2B11, 20D8.24B11, P1E2.3B12, and P1G10.2B8.

In certain embodiments an antibody of the present invention which specifically binds to IGF-1R or a variant thereof inhibits one or more insulin growth factors, e.g., IGF-1, IGF-2 or both IGF-1 and IGF-1 from binding to IGF-1R. In other embodiments, an antibody of the present invention which specifically binds to IGF-1R or a variant thereof inhibits phosphorylation of IGF-1R upon binding of one or more insulin growth factors. In a further embodiment, an antibody of the present invention which specifically binds to IGF-1R or a variant thereof expressed on a cell, in particular, a tumor cell. inhibits phosphorylation of downstream signal transduction molecules involved in cell proliferation, motility and/or metastasis. Such molecules include, but are not limited to Akt and p42/44 MAPK. In a further embodiment, an antibody of the present invention which specifically binds to IGF-1R or a variant thereof expressed on a cell promotes internalization of surface-expressed IGF-1R, limiting its availability to interact with IGF. In yet a further embodiment, an antibody of the present invention which specifically binds to IGF-1R or a variant thereof expressed on a cell, in particular, a tumor cell, inhibits cell proliferation, motility, and/or metastasis.

An antibody of the present invention which specifically binds to IGF-1R or a variant thereof, to be used in treatment methods disclosed herein can be prepared and used as a therapeutic agent that stops, reduces, prevents, or inhibits cellular activities involved in cellular hyperproliferation, e.g., cellular activities that induce the altered or abnormal pattern of vascularization that is often associated with hyperproliferative diseases or disorders.

Antibodies or immunospecific fragments thereof of the present invention include, but are not limited to monoclonal, chimeric or humanized antibodies, and fragments of antibodies that bind specifically to tumor-associated proteins such as IGF-1R. The antibodies may be monovalent, bivalent, polyvalent, or bifunctional antibodies, and the antibody fragments include Fab F(ab')$_2$, and Fv.

Therapeutic antibodies according to the invention can be used in unlabeled or unconjugated form, or can be coupled or linked to cytotoxic moieties such as radiolabels and biochemical cytotoxins to produce agents that exert therapeutic effects.

In certain embodiments, an antibody, or immunospecific fragment thereof of the invention includes an antigen binding domain. An antigen binding domain is formed by antibody variable regions that vary from one antibody to another. Naturally occurring antibodies comprise at least two antigen binding domains, i.e., they are at least bivalent. As used herein, the term "antigen binding domain" includes a site that specifically binds an epitope on an antigen (e.g., a cell surface or soluble antigen). The antigen binding domain of an antibody typically includes at least a portion of an immunoglobulin heavy chain variable region and at least a portion of an immunoglobulin light chain variable region. The binding site formed by these variable regions determines the specificity of the antibody.

The present invention provides methods for treating various hyperproliferative disorders, e.g., by inhibiting tumor growth, in a mammal, comprising, consisting essentially of, or consisting of administering to the mammal an effective amount of a antibody or antigen-binding fragment thereof which specifically or preferentially binds to IGF-R1, e.g., human IGF-R1.

The present invention is more specifically directed to a method of treating a hyperproliferative disease, e.g., inhibiting or preventing tumor formation, tumor growth, tumor invasiveness, and/or metastasis formation, in an animal, e.g., a mammal, e.g., a human, comprising, consisting essentially of, or consisting of administering to an animal in need thereof an effective amount of a an antibody or immunospecific fragment thereof, which specifically or preferentially binds to one or more epitopes of IGF-1R.

In other embodiments, the present invention includes a method for treating a hyperproliferative disease, e.g., inhibiting tumor formation, tumor growth, tumor invasiveness, and/or metastasis formation in an animal, e.g., a human patient, where the method comprises administering to an animal in need of such treatment an effective amount of a composition comprising, consisting essentially of, or consisting of, in addition to a pharmaceutically acceptable carrier, an antibody, or immunospecific fragment thereof, which specifically binds to at least one epitope of IGF-1R, where the epitope comprises, consists essentially of, or consists of at least about four to five amino acids amino acids of SEQ ID NO:2, at least seven, at least nine, or between at least about 15 to about 30 amino acids of SEQ ID NO:2. The amino acids of a given epitope of SEQ ID NO:2 as described may be, but need not be contiguous. In certain embodiments, the at least one epitope of IGF-1R comprises, consists essentially of, or consists of a non-linear epitope formed by the extracellular domain of IGF-1R as expressed on the surface of a cell. Thus, in certain embodiments the at least one epitope of IGF-1R comprises, consists essentially of, or consists of at least 4, at least 5, at least 6, at least 7, at least 8, at least 9, at least 10, at least 15, at least 20, at least 25, between about 15 to about 30, or at least 10, 15, 20, 25, 30, 35, 40, 45, 50, 55, 60, 65, 70, 75, 80, 85, 90, 95, or 100 contiguous or non-contiguous amino acids of SEQ ID NO:2, where non-contiguous amino acids form an epitope through protein folding.

In other embodiments, the present invention includes a method for treating a hyperproliferative disease, e.g., inhibiting tumor formation, tumor growth, tumor invasiveness, and/or metastasis formation in an animal, e.g., a human patient, where the method comprises administering to an animal in need of such treatment an effective amount of a composition comprising, consisting essentially of, or consisting of, in addition to a pharmaceutically acceptable carrier, an antibody, or immunospecific fragment thereof, which specifically binds to at least one epitope of IGF-1R, where the epitope comprises, consists essentially of, or consists of, in addition to one, two, three, four, five, six or more contiguous or non-contiguous amino acids of SEQ ID NO:2 as described above, and an additional moiety which modifies the protein, e.g., a carbohydrate moiety may be included such that the binding molecule binds with higher affinity to modified target protein than it does to an unmodified version of the protein. Alternatively, the binding molecule does not bind the unmodified version of the target protein at all.

More specifically, the present invention provides a method of treating cancer in a human, comprising administering to a human in need of treatment a composition comprising an effective amount of an IGF-1R-specific antibody or immunospecific fragment thereof, and a pharmaceutically acceptable carrier. Types of cancer to be treated include, but are not limited to, stomach cancer, renal cancer, brain cancer, bladder cancer, colon cancer, lung cancer, breast cancer, pancreatic cancer, ovarian cancer, and prostate cancer.

In certain embodiments, an antibody or fragment thereof binds specifically to at least one epitope of IGF-1R or fragment or variant described above, i.e., binds to such an epitope more readily than it would bind to an unrelated, or random epitope; binds preferentially to at least one epitope of IGF-1R or fragment or variant described above, i.e., binds to such an epitope more readily than it would bind to a related, similar, homologous, or analogous epitope; competitively inhibits binding of a reference antibody which itself binds specifically or preferentially to a certain epitope of IGF-1R or fragment or variant described above; or binds to at least one epitope of IGF-1R or fragment or variant described above with an affinity characterized by a dissociation constant $K_D$ of less than about $5\times10^{-2}$ M, about $10^{-2}$ M, about $5\times10^{-3}$ M, about $10^{-3}$ M, about $5\times10^{-4}$ M, about $10^{-4}$ M, about $5\times10^{-5}$ M, about $10^{-5}$ M, about $5\times10^{-6}$ M, about $10^{-6}$ M, about $5\times10^{-7}$ M, about $10^{-7}$ M, about $5\times10^{-8}$ M, about $10^{-8}$ M, about $5\times10^{-9}$ M, about $10^{-9}$ M, about $5\times10^{-10}$ M, about $10^{-10}$ M, about $5\times10^{-11}$ M, about $10^{-11}$ M, about $5\times10^{-12}$ M, about $10^{-12}$ M, about $5\times10^{-13}$ M, about $10^{-13}$ M, about $5\times10^{-14}$ M, about $10^{-14}$ M, about $5\times10^{-15}$ M, or about $10^{-15}$ M. As used in the context of antibody binding dissociation constants, the term "about" allows for the degree of variation inherent in the methods utilized for measuring antibody affinity. For example, depending on the level of precision of the instrumentation used, standard error based on the number of samples measured, and rounding error, the term "about $10^{-2}$ M" might include, for example, from 0.05 M to 0.005 M. In certain embodiments, antibodies and fragments thereof of the present invention cross-react with IGF-1R proteins of other species from which they were raised, e.g., an antibody or fragment thereof which specifically binds to human IGF-1R also binds to primate IGF-1R and/or murine IGF-1R. Other suitable antibodies or fragments thereof of the present invention include those that are highly species specific.

In specific embodiments, antibodies or immunospecific fragments thereof disclosed herein bind IGF-1R polypeptides or fragments or variants thereof with an off rate (k(off)) of less than or equal to $5\times10^{-2}$ sec$^{-1}$, $10^{-2}$ sec$^{-1}$, $5\times10^{-3}$ sec$^{-1}$ or $10^{-3}$ sec$^{-1}$. Other antibodies or immunospecific fragments thereof disclosed herein bind IGF-1R polypeptides or fragments or variants thereof with an off rate (k(off)) of less than or equal to $5\times10^{-4}$ sec$^{-1}$, $10^{-4}$ sec$^{-1}$, $5\times10^{-5}$ sec$^{-1}$, or $10^{-5}$ sec$^1$ $5\times10^{-6}$ sec$^{-1}$, $10^{-6}$ sec$^{-1}$, $5\times10^{-7}$ sec$^{-1}$ or $10^{-7}$ sec$^{-1}$.

In other embodiments, antibodies or immunospecific fragments thereof disclosed herein bind IGF-1R polypeptides or fragments or variants thereof with an on rate (k(on)) of greater than or equal to $10^3$ M$^{-1}$ sec$^{-1}$, $5\times10^3$ M$^{-1}$ sec$^{-1}$, $10^4$ M$^{-1}$ sec$^{-1}$ or $5\times10^4$ M$^{-1}$ sec$^{-1}$. Other antibodies or immunospecific fragments thereof for use in the diagnostic and treatment methods disclosed herein bind IGF-1R polypeptides or fragments or variants thereof with an on rate (k(on)) greater than or equal to $10^5$ M$^{-1}$ sec$^{-1}$, $5\times10^5$ M$^{-1}$ sec$^{-1}$, $10^6$ M$^{-1}$ sec$^{-1}$, or $5\times10^6$ M$^{-1}$ sec$^{-1}$ or $10^7$ M$^{-1}$ sec$^{-1}$.

In various embodiments, one or more binding molecules as described above is an antagonist of IGF-1R activity, for example, binding of an antagonist IGF-1R antibody to IGF-1R as expressed on a tumor cell inhibits binding of insulin growth factor, e.g., IGF-1, IGF-2, or both IGF-1 and IGF-2 to IGF-1R, promotes internalization of IGF-1R thereby inhibiting its signal transduction capability, inhibits phosphorylation of IGF-1R, inhibits phosphorylation of molecules downstream in the signal transduction pathway, e.g., Akt or p42/44 MAPK, or inhibits tumor cell proliferation, motility or metastasis.

IX. Diagnostic or Prognostic Methods Using IGF-1R-Specific Binding Molecules and Nucleic Acid Amplification Assays IGF-1R-specific antibodies, or fragments, derivatives, or analogs thereof, can be used for diagnostic purposes to detect, diagnose, or monitor diseases, disorders, and/or conditions associated with the aberrant expression and/or activity of IGF-1R. IGF-1R expression is increased in tumor tissue and other neoplastic conditions.

IGF-1R-specific antibodies or fragments thereof, are useful for diagnosis, treatment, prevention and/or prognosis of hyperproliferative disorders in mammals, preferably humans. Such disorders include, but are not limited to, cancer, neoplasms, tumors and/or as described under elsewhere herein, especially IGF-1R-associated cancers such as stomach cancer, renal cancer, brain cancer, bladder cancer, colon cancer, lung cancer, breast cancer, pancreatic cancer, ovarian cancer, and prostate cancer.

For example, as disclosed herein, IGF-1R expression is associated with at least stomach, renal, brain, bladder, colon, lung, breast, pancreatic, ovarian, and prostate tumor tissues. Accordingly, antibodies (and antibody fragments) directed against IGF-1R may be used to detect particular tissues expressing increased levels of IGF-1R. These diagnostic assays may be performed in vivo or in vitro, such as, for example, on blood samples, biopsy tissue or autopsy tissue.

Thus, the invention provides a diagnostic method useful during diagnosis of a cancers and other hyperproliferative disorders, which involves measuring the expression level of IGF-1R protein or transcript in tissue or other cells or body fluid from an individual and comparing the measured expression level with a standard IGF-1R expression levels in normal tissue or body fluid, whereby an increase in the expression level compared to the standard is indicative of a disorder.

One embodiment provides a method of detecting the presence of abnormal hyperproliferative cells, e.g., precancerous or cancerous cells, in a fluid or tissue sample, comprising assaying for the expression of IGF-1R in tissue or body fluid samples of an individual and comparing the presence or level of IGF-1R expression in the sample with the presence or level of IGF-1R expression in a panel of standard tissue or body fluid samples, where detection of IGF-1R expression or an increase in IGF-1R expression over the standards is indicative of aberrant hyperproliferative cell growth.

More specifically, the present invention provides a method of detecting the presence of abnormal hyperproliferative cells in a body fluid or tissue sample, comprising (a) assaying for the expression of IGF-1R in tissue or body fluid samples of an individual using IGF-1R-specific antibodies or immunospecific fragments thereof of the present invention, and (b) comparing the presence or level of IGF-1R expression in the sample with a the presence or level of IGF-1R expression in a panel of standard tissue or body fluid samples, whereby detection of IGF-1R expression or an increase in IGF-1R expression over the standards is indicative of aberrant hyperproliferative cell growth.

With respect to cancer, the presence of a relatively high amount of IGF-1R protein in biopsied tissue from an individual may indicate the presence of a tumor or other malignant growth, may indicate a predisposition for the development of such malignancies or tumors, or may provide a means for detecting the disease prior to the appearance of actual clinical symptoms. A more definitive diagnosis of this type may allow health professionals to employ preventative measures or aggressive treatment earlier thereby preventing the development or further progression of the cancer.

IGF-1R-specific antibodies of the present invention can be used to assay protein levels in a biological sample using classical immunohistological methods known to those of skill in the art (e.g., see Jalkanen, et al., *J. Cell. Biol.* 101:976-985 (1985); Jalkanen, et al., *J. Cell Biol.* 105:3087-3096 (1987)). Other antibody-based methods useful for detecting protein expression include immunoassays, such as the enzyme linked immunosorbent assay (ELISA) and the radioimmunoassay (RIA). Suitable antibody assay labels are known in the art and include enzyme labels, such as, glucose oxidase; radioisotopes, such as iodine ($^{125}$I, $^{121}$I), carbon ($^{14}$C), sulfur ($^{35}$S), tritium ($^{3}$H), indium ($^{112}$In), and technetium ($^{99}$Tc); luminescent labels, such as luminol; and fluorescent labels, such as fluorescein and rhodamine, and biotin. Suitable assays are described in more detail elsewhere herein.

One aspect of the invention is a method for the in vivo detection or diagnosis of a hyperproliferative disease or disorder associated with aberrant expression of IGF-1R in an animal, preferably a mammal and most preferably a human. In one embodiment, diagnosis comprises: a) administering (for example, parenterally, subcutaneously, or intraperitoneally) to a subject an effective amount of a labeled antibody or fragment thereof of the present invention, which specifically binds to IGF-1R; b) waiting for a time interval following the administering for permitting the labeled binding molecule to preferentially concentrate at sites in the subject where IGF-1R is expressed (and for unbound labeled molecule to be cleared to background level); c) determining background level; and d) detecting the labeled molecule in the subject, such that detection of labeled molecule above the background level indicates that the subject has a particular disease or disorder associated with aberrant expression of IGF-1R. Background level can be determined by various methods including comparing the amount of labeled molecule detected to a standard value previously determined for a particular system.

It will be understood in the art that the size of the subject and the imaging system used will determine the quantity of imaging moiety needed to produce diagnostic images. In the case of a radioisotope moiety, for a human subject, the quantity of radioactivity injected will normally range from about 5 to 20 millicuries of, e.g., $^{99}$Tc. The labeled binding molecule, e.g., antibody or antibody fragment, will then preferentially accumulate at the location of cells which contain the specific protein. In vivo tumor imaging is described in S. W. Burchiel et al., "Immunopharmacokinetics of Radiolabeled Antibodies and Their Fragments." (Chapter 13 in Tumor Imaging: *The Radiochemical Detection of Cancer*, S. W. Burchiel and B. A. Rhodes, eds., Masson Publishing Inc. (1982).

Depending on several variables, including the type of label used and the mode of administration, the time interval following the administration for permitting the labeled molecule to preferentially concentrate at sites in the subject and for unbound labeled molecule to be cleared to background level is 6 to 48 hours or 6 to 24 hours or 6 to 12 hours. In another embodiment the time interval following administration is 5 to 20 days or 7 to 10 days.

Presence of the labeled molecule can be detected in the patient using methods known in the art for in vivo scanning. These methods depend upon the type of label used. Skilled artisans will be able to determine the appropriate method for detecting a particular label. Methods and devices that may be used in the diagnostic methods of the invention include, but are not limited to, computed tomography (CT), whole body scan such as position emission tomography (PET), magnetic resonance imaging (MRI), and sonography.

In a specific embodiment, the binding molecule is labeled with a radioisotope and is detected in the patient using a radiation responsive surgical instrument (Thurston et al., U.S. Pat. No. 5,441,050). In another embodiment, the binding molecule is labeled with a fluorescent compound and is detected in the patient using a fluorescence responsive scanning instrument. In another embodiment, the binding molecule is labeled with a positron emitting metal and is detected in the patent using positron emission-tomography. In yet another embodiment, the binding molecule is labeled with a paramagnetic label and is detected in a patient using magnetic resonance imaging (MRI).

Antibody labels or markers for in vivo imaging of IGF-1R expression include those detectable by X-radiography, nuclear magnetic resonance imaging (NMR), MRI, CAT-scans or electron spin resonance imaging (ESR). For X-radiography, suitable labels include radioisotopes such as barium or cesium, which emit detectable radiation but are not overtly harmful to the subject. Suitable markers for NMR and ESR. include those with a detectable characteristic spin, such as deuterium, which may be incorporated into the antibody by labeling of nutrients for the relevant hybridoma. Where in vivo imaging is used to detect enhanced levels of IGF-1R expression for diagnosis in humans, it may be preferable to use human antibodies or "humanized" chimeric monoclonal antibodies as described elsewhere herein.

In a related embodiment to those described above, monitoring of an already diagnosed disease or disorder is carried out by repeating any one of the methods for diagnosing the disease or disorder, for example, one month after initial diagnosis, six months after initial diagnosis, one year after initial diagnosis, etc.

Where a diagnosis of a disorder, including diagnosis of a tumor, has already been made according to conventional methods, detection methods as disclosed herein are useful as a prognostic indicator, whereby patients continuing to exhibiting enhanced IGF-1R expression will experience a worse clinical outcome relative to patients whose expression level decreases nearer the standard level.

By "assaying the expression level of the tumor associated IGF-1R polypeptide" is intended qualitatively or quantitatively measuring or estimating the level of IGF-1R polypeptide in a first biological sample either directly (e.g., by determining or estimating absolute protein level) or relatively (e.g., by comparing to the cancer associated polypeptide level in a second biological sample). Preferably, IGF-1R polypeptide expression level in the first biological sample is measured or estimated and compared to a standard IGF-1R polypeptide level, the standard being taken from a second biological sample obtained from an individual not having the disorder or being determined by averaging levels from a population of individuals not having the disorder. As will be appreciated in the art, once the "standard" IGF-1R polypeptide level is known, it can be used repeatedly as a standard for comparison.

By "biological sample" is intended any biological sample obtained from an individual, cell line, tissue culture, or other source of cells potentially expressing IGF-1R. As indicated, biological samples include body fluids (such as sera, plasma, urine, synovial fluid and spinal fluid), and other tissue sources which contain cells potentially expressing IGF-1R. Methods for obtaining tissue biopsies and body fluids from mammals are well known in the art.

In an additional embodiment, antibodies, or immunospecific fragments of antibodies directed to a conformational epitope of IGF-1R may be used to quantitatively or qualitatively detect the presence of IGF-1R gene products or conserved variants or peptide fragments thereof. This can be accomplished, for example, by immunofluoresence techniques employing a fluorescently labeled antibody coupled with light microscopic, flow cytometric, or fluorimetric detection.

Cancers that may be diagnosed, and/or prognosed using the methods described above include but are not limited to, stomach cancer, renal cancer, brain cancer, bladder cancer, colon cancer, lung cancer, breast cancer, pancreatic cancer, ovarian cancer, and prostate cancer.

X. Immunoassays

IGF-1R-specific antibodies or immunospecific fragments thereof disclosed herein may be assayed for immunospecific binding by any method known in the art. The immunoassays which can be used include but are not limited to competitive and non-competitive assay systems using techniques such as western blots, radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, protein A immunoassays, to name but a few. Such assays are routine and well known in the art (see, e.g., Ausubel et al., eds, *Current Protocols in Molecular Biology*, John Wiley & Sons, Inc., New York, Vol. 1 (1994), which is incorporated by reference herein in its entirety). Exemplary immunoassays are described briefly below (but are not intended by way of limitation).

Immunoprecipitation protocols generally comprise lysing a population of cells in a lysis buffer such as RIPA buffer (1% NP-40 or Triton X-100, 1% sodium deoxycholate, 0.1% SDS, 0.15 M NaCl, 0.01 M sodium phosphate at pH 7.2, 1% Trasylol) supplemented with protein phosphatase and/or protease inhibitors (e.g., EDTA, PMSF, aprotinin, sodium vanadate), adding the antibody of interest to the cell lysate, incubating for a period of time (e.g., 1-4 hours) at 4.degree. C., adding protein A and/or protein G sepharose beads to the cell lysate, incubating for about an hour or more at 4.degree. C., washing the beads in lysis buffer and resuspending the beads in SDS/sample buffer. The ability of the antibody of interest to immunoprecipitate a particular antigen can be assessed by, e.g., western blot analysis. One of skill in the art would be knowledgeable as to the parameters that can be modified to increase the binding of the antibody to an antigen and decrease the background (e.g., pre-clearing the cell lysate with sepharose beads). For further discussion regarding immunoprecipitation protocols see, e.g., Ausubel et al., eds, *Current Protocols in Molecular Biology*, John Wiley & Sons, Inc., New York, Vol. 1 (1994) at 10.16.1.

Western blot analysis generally comprises preparing protein samples, electrophoresis of the protein samples in a polyacrylamide gel (e.g., 8%-20% SDS-PAGE depending on the molecular weight of the antigen), transferring the protein sample from the polyacrylamide gel to a membrane such as nitrocellulose, PVDF or nylon, blocking the membrane in blocking solution (e.g., PBS with 3% BSA or non-fat milk), washing the membrane in washing buffer (e.g., PBS-Tween 20), blocking the membrane with primary antibody (the antibody of interest) diluted in blocking buffer, washing the membrane in washing buffer, blocking the membrane with a secondary antibody (which recognizes the primary antibody, e.g., an anti-human antibody) conjugated to an enzymatic substrate (e.g., horseradish peroxidase or alkaline phosphatase) or radioactive molecule (e.g., 32P or 125I) diluted in blocking buffer, washing the membrane in wash buffer, and detecting the presence of the antigen. One of skill in the art would be knowledgeable as to the parameters that can be modified to increase the signal detected and to reduce the background noise. For further discussion regarding western blot protocols see, e.g., Ausubel et al., eds, *Current Protocols in Molecular Biology*, John Wiley & Sons, Inc., New York Vol. 1 (1994) at 10.8.1.

ELISAs comprise preparing antigen, coating the well of a 96 well microtiter plate with the antigen, adding the antibody of interest conjugated to a detectable compound such as an enzymatic substrate (e.g., horseradish peroxidase or alkaline phosphatase) to the well and incubating for a period of time, and detecting the presence of the antigen. In ELISAs the antibody of interest does not have to be conjugated to a detectable compound; instead, a second antibody (which recognizes the antibody of interest) conjugated to a detectable compound may be added to the well. Further, instead of coating the well with the antigen, the antibody may be coated to the well. In this case, a second antibody conjugated to a detectable compound may be added following the addition of the antigen of interest to the coated well. One of skill in the art would be knowledgeable as to the parameters that can be modified to increase the signal detected as well as other variations of ELISAs known in the art. For further discussion regarding ELISAs see, e.g., Ausubel et al., eds, *Current Protocols in Molecular Biology*, John Wiley & Sons, Inc., New York, Vol. 1 (1994) at 11.2.1.

The binding affinity of an antibody to an antigen and the off-rate of an antibody-antigen interaction can be determined by competitive binding assays. One example of a competitive binding assay is a radioimmunoassay comprising the incubation of labeled antigen (e.g., $^3$H or $^{125}$I) with the antibody of interest in the presence of increasing amounts of unlabeled antigen, and the detection of the antibody bound to the labeled antigen. The affinity of the antibody of interest for a particular antigen and the binding off-rates can be determined from the data by Scatchard plot analysis. Competition with a second antibody can also be determined using radioimmunoassays. In this case, the antigen is incubated with antibody of interest is conjugated to a labeled compound (e.g., $^3$H or $^{125}$I) in the presence of increasing amounts of an unlabeled second antibody.

IGF-1R-specific antibodies may, additionally, be employed histologically, as in immunofluorescence, immunoelectron microscopy or non-immunological assays, for in situ detection of cancer antigen gene products or conserved variants or peptide fragments thereof. In situ detection may be accomplished by removing a histological specimen from a patient, and applying thereto a labeled IGF-1R-specific antibody or fragment thereof, preferably applied by overlaying the labeled antibody (or fragment) onto a biological sample. Through the use of such a procedure, it is possible to determine not only the presence of IGF-1R protein, or conserved variants or peptide fragments, but also its distribution in the examined tissue. Using the present invention, those of ordinary skill will readily perceive that any of a wide variety of histological methods (such as staining procedures) can be modified in order to achieve such in situ detection.

Immunoassays and non-immunoassays for IGF-1R gene products or conserved variants or peptide fragments thereof will typically comprise incubating a sample, such as a biological fluid, a tissue extract, freshly harvested cells, or lysates of cells which have been incubated in cell culture, in the presence of a detectably labeled antibody capable of binding to IGF-1R or conserved variants or peptide fragments thereof, and detecting the bound antibody by any of a number of techniques well-known in the art.

The biological sample may be brought in contact with and immobilized onto a solid phase support or carrier such as nitrocellulose, or other solid support which is capable of immobilizing cells, cell particles or soluble proteins. The support may then be washed with suitable buffers followed by treatment with the detectably labeled IGF-1R-specific antibody. The solid phase support may then be washed with the buffer a second time to remove unbound antibody. Optionally the antibody is subsequently labeled. The amount of bound label on solid support may then be detected by conventional means.

By "solid phase support or carrier" is intended any support capable of binding an antigen or an antibody. Well-known supports or carriers include glass, polystyrene, polypropylene, polyethylene, dextran, nylon, amylases, natural and modified celluloses, polyacrylamides, gabbros, and magnetite. The nature of the carrier can be either soluble to some extent or insoluble for the purposes of the present invention. The support material may have virtually any possible structural configuration so long as the coupled molecule is capable of binding to an antigen or antibody. Thus, the support configuration may be spherical, as in a bead, or cylindrical, as in the inside surface of a test tube, or the external surface of a rod. Alternatively, the surface may be flat such as a sheet, test strip, etc. Preferred supports include polystyrene beads. Those skilled in the art will know many other suitable carriers for binding antibody or antigen, or will be able to ascertain the same by use of routine experimentation.

The binding activity of a given lot of IGF-1R-specific antibody may be determined according to well known methods. Those skilled in the art will be able to determine operative and optimal assay conditions for each determination by employing routine experimentation.

There are a variety of methods available for measuring the affinity of an antibody-antigen interaction, but relatively few for determining rate constants. Most of the methods rely on either labeling antibody or antigen, which inevitably complicates routine measurements and introduces uncertainties in the measured quantities.

Surface plasmon resonance (SPR) as performed on BIAcore offers a number of advantages over conventional methods of measuring the affinity of antibody-antigen interactions: (i) no requirement to label either antibody or antigen; (ii) antibodies do not need to be purified in advance, cell culture supernatant can be used directly; (iii) real-time measurements, allowing rapid semi-quantitative comparison of different monoclonal antibody interactions, are enabled and are sufficient for many evaluation purposes; (iv) biospecific surface can be regenerated so that a series of different monoclonal antibodies can easily be compared under identical conditions; (v) analytical procedures are fully automated, and extensive series of measurements can be performed without user intervention. BIAapplications Handbook, version AB (reprinted 1998), BIACORE code No. BR-1001-86; BIAtechnology Handbook, version AB (reprinted 1998), BIACORE code No. BR-1001-84.

SPR based binding studies require that one member of a binding pair be immobilized on a sensor surface. The binding partner immobilized is referred to as the ligand. The binding partner in solution is referred to as the analyte. In some cases, the ligand is attached indirectly to the surface through binding to another immobilized molecule, which is referred as the capturing molecule. SPR response reflects a change in mass concentration at the detector surface as analytes bind or dissociate.

Based on SPR, real-time BIAcore measurements monitor interactions directly as they happen. The technique is well suited to determination of kinetic parameters. Comparative affinity ranking is extremely simple to perform, and both kinetic and affinity constants can be derived from the sensorgram data.

When analyte is injected in a discrete pulse across a ligand surface, the resulting sensorgram can be divided into three essential phases: (i) Association of analyte with ligand during sample injection; (ii) Equilibrium or steady state during sample injection, where the rate of analyte binding is balanced by dissociation from the complex; (iii) Dissociation of analyte from the surface during buffer flow.

The association and dissociation phases provide information on the kinetics of analyte-ligand interaction ($k_a$ and $k_d$, the rates of complex formation and dissociation, $k_d/k_a=K_D$). The equilibrium phase provides information on the affinity of the analyte-ligand interaction ($K_D$).

BIAevaluation software provides comprehensive facilities for curve fitting using both numerical integration and global fitting algorithms. With suitable analysis of the data, separate rate and affinity constants for interaction can be obtained from simple BIAcore investigations. The range of affinities measurable by this technique is very broad ranging from mM to pM.

Epitope specificity is an important characteristic of a monoclonal antibody. Epitope mapping with BIAcore, in contrast to conventional techniques using radioimmunoassay, ELISA or other surface adsorption methods, does not require labeling or purified antibodies, and allows multi-site specificity tests using a sequence of several monoclonal antibodies. Additionally, large numbers of analyses can be processed automatically.

Pair-wise binding experiments test the ability of two MAbs to bind simultaneously to the same antigen. MAbs directed against separate epitopes will bind independently, whereas MAbs directed against identical or closely related epitopes will interfere with each other's binding. These binding experiments with BIAcore are straightforward to carry out.

For example, one can use a capture molecule to bind the first Mab, followed by addition of antigen and second MAb sequentially. The sensorgrams will reveal: 1. how much of the antigen binds to first Mab, 2. to what extent the second MAb binds to the surface-attached antigen, 3. if the second MAb does not bind, whether reversing the order of the pair-wise test alters the results.

Peptide inhibition is another technique used for epitope mapping. This method can complement pair-wise antibody binding studies, and can relate functional epitopes to structural features when the primary sequence of the antigen is known. Peptides or antigen fragments are tested for inhibition of binding of different MAbs to immobilized antigen. Peptides which interfere with binding of a given MAb are assumed to be structurally related to the epitope defined by that MAb.

XI. Pharmaceutical Compositions and Administration Methods

Methods of preparing and administering IGF-1R-specific antibodies or immunospecific fragments thereof to a subject in need thereof are well known to or are readily determined by those skilled in the art. The route of administration of the binding molecule, e.g., binding polypeptide, e.g., IGF-1R-specific antibody or immunospecific fragment thereof may be, for example, oral, parenteral, by inhalation or topical. The term parenteral as used herein includes, e.g., intravenous, intraarterial, intraperitoneal, intramuscular, subcutaneous, rectal or vaginal administration. While all these forms of administration are clearly contemplated as being within the scope of the invention, a form for administration would be a solution for injection, in particular for intravenous or intraarterial injection or drip. Usually, a suitable pharmaceutical composition for injection may comprise a buffer (e.g. acetate, phosphate or citrate buffer), a surfactant (e.g. polysorbate), optionally a stabilizer agent (e.g. human albumin), etc. However, in other methods compatible with the teachings herein, binding molecules, e.g., binding polypeptides, e.g., IGF-1R-specific antibodies or immunospecific fragments thereof can be delivered directly to the site of the adverse cellular population thereby increasing the exposure of the diseased tissue to the therapeutic agent.

Preparations for parenteral administration includes sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. In the subject invention, pharmaceutically acceptable carriers include, but are not limited to, 0.01-0.1M and preferably 0.05M phosphate buffer or 0.8% saline. Other common parenteral vehicles include sodium phosphate solutions, Ringer's dextrose, dextrose and sodium chloride, lactated Ringer's, or fixed oils. Intravenous vehicles include fluid and nutrient replenishers, electrolyte replenishers, such as those based on Ringer's dextrose, and the like. Preservatives and other additives may also be present such as for example, antimicrobials, antioxidants, chelating agents, and inert gases and the like.

More particularly, pharmaceutical compositions suitable for injectable use include sterile aqueous solutions (where water soluble) or dispersions and sterile powders for the extemporaneous preparation of sterile injectable solutions or dispersions. In such cases, the composition must be sterile and should be fluid to the extent that easy syringability exists. It should be stable under the conditions of manufacture and storage and will preferably be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Suitable formulations for use in the therapeutic methods disclosed herein are described in Remington's Pharmaceutical Sciences, Mack Publishing Co., 16th ed. (1980).

Prevention of the action of microorganisms can be achieved by various antibacterial and antifungal agents, for example, parabens, chlorobutanol, phenol, ascorbic acid, thimerosal and the like. In many cases, it will be preferable to include isotonic agents, for example, sugars, polyalcohols, such as mannitol, sorbitol, or sodium chloride in the composition. Prolonged absorption of the injectable compositions can be brought about by including in the composition an agent which delays absorption, for example, aluminum monostearate and gelatin.

In any case, sterile injectable solutions can be prepared by incorporating an active compound (e.g., a binding molecule, e.g., a binding polypeptide, e.g., a IGF-1R-specific antibody or immunospecific fragment thereof, by itself or in combination with other active agents) in the required amount in an appropriate solvent with one or a combination of ingredients enumerated herein, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, the preferred methods of preparation are vacuum drying and freeze-drying, which yields a powder of an active ingredient plus any additional desired ingredient from a previously sterile-filtered solution thereof. The preparations for injections are processed, filled into containers such as ampoules, bags, bottles, syringes or vials, and sealed under aseptic conditions according to methods known in the art. Further, the preparations may be packaged and sold in the form of a kit such as those described in co-pending U.S. Ser. No. 09/259,337 (US-2002-0102208 A1), which is incorporated herein by reference in its entirety. Such articles of manufacture will preferably have labels or package inserts indicating that the associated compositions are useful for treating a subject suffering from, or predisposed to autoimmune or neoplastic disorders.

Effective doses of the compositions of the present invention, for treatment of hyperproliferative disorders as described herein vary depending upon many different factors, including means of administration, target site, physiological state of the patient, whether the patient is human or an animal, other medications administered, and whether treatment is prophylactic or therapeutic. Usually, the patient is a human but non-human mammals including transgenic mammals can also be treated. Treatment dosages may be titrated using routine methods known to those of skill in the art to optimize safety and efficacy.

For treatment of hyperproliferative disorders with an antibody or fragment thereof, the dosage can range, e.g., from about 0.0001 to 100 mg/kg, and more usually 0.01 to 5 mg/kg (e.g., 0.02 mg/kg, 0.25 mg/kg, 0.5 mg/kg, 0.75 mg/kg, 1 mg/kg, 2 mg/kg, etc.), of the host body weight. For example dosages can be 1 mg/kg body weight or 10 mg/kg body weight or within the range of 1-10 mg/kg, preferably at least 1 mg/kg. Doses intermediate in the above ranges are also intended to be within the scope of the invention. Subjects can be administered such doses daily, on alternative days, weekly or according to any other schedule determined by empirical analysis. An exemplary treatment entails administration in multiple dosages over a prolonged period, for example, of at least six months. Additional exemplary treatment regimes entail administration once per every two weeks or once a month or once every 3 to 6 months. Exemplary dosage schedules include 1-10 mg/kg or 15 mg/kg on consecutive days, 30 mg/kg on alternate days or 60 mg/kg weekly. In some methods, two or more monoclonal antibodies with different binding specificities are administered simultaneously, in which case the dosage of each antibody administered falls within the ranges indicated.

IGF-1R-specific antibodies or immunospecific fragments thereof disclosed herein can be administered on multiple occasions. Intervals between single dosages can be weekly, monthly or yearly. Intervals can also be irregular as indicated by measuring blood levels of target polypeptide or target molecule in the patient. In some methods, dosage is adjusted to achieve a plasma polypeptide concentration of 1-1000 µg/ml and in some methods 25-300 µg/ml. Alternatively, binding molecules can be administered as a sustained release formulation, in which case less frequent administration is required. Dosage and frequency vary depending on the half-life of the antibody in the patient. The half-life of a binding molecule can also be prolonged via fusion to a stable polypeptide or moiety, e.g., albumin or PEG. In general, humanized antibodies show the longest half-life, followed by chimeric antibodies and nonhuman antibodies. In one embodiment, the binding molecules of the invention can be administered in unconjugated form, In another embodiment, the binding molecules, e.g., binding polypeptides, e.g., IGF-1R-specific antibodies or immunospecific fragments thereof for use in the methods disclosed herein can be administered multiple times in conjugated form. In still another embodiment, the binding molecules of the invention can be administered in unconjugated form, then in conjugated form, or vise versa.

The dosage and frequency of administration can vary depending on whether the treatment is prophylactic or therapeutic. In prophylactic applications, compositions comprising antibodies or a cocktail thereof are administered to a patient not already in the disease state or in a pre-disease state to enhance the patient's resistance. Such an amount is defined to be a "prophylactic effective dose." In this use, the precise amounts again depend upon the patient's state of health and general immunity, but generally range from 0.1 to 25 mg per dose, especially 0.5 to 2.5 mg per dose. A relatively low dosage is administered at relatively infrequent intervals over a long period of time. Some patients continue to receive treatment for the rest of their lives.

In therapeutic applications, a relatively high dosage (e.g., from about 1 to 400 mg/kg of binding molecule, e.g., antibody per dose, with dosages of from 5 to 25 mg being more commonly used for radioimmunoconjugates and higher doses for cytotoxin-drug conjugated molecules) at relatively short intervals is sometimes required until progression of the disease is reduced or terminated, and preferably until the patient shows partial or complete amelioration of symptoms of disease. Thereafter, the patent can be administered a prophylactic regime.

In one embodiment, a subject can be treated with a nucleic acid molecule encoding an IGF-1R-specific antibody or immunospecific fragment thereof (e.g., in a vector). Doses for nucleic acids encoding polypeptides range from about 10 ng to 1 g, 100 ng to 100 mg, 1 µg to 10 mg, or 30-300 µg DNA per patient. Doses for infectious viral vectors vary from 10-100, or more, virions per dose.

Therapeutic agents can be administered by parenteral, topical, intravenous, oral, subcutaneous, intraarterial, intracranial, intraperitoneal, intranasal or intramuscular means for prophylactic and/or therapeutic treatment. In some methods, agents are injected directly into a particular tissue where IGF-1R-expressing cells have accumulated, for example intracranial injection. Intramuscular injection or intravenous infusion are preferred for administration of antibody. In some methods, particular therapeutic antibodies are injected directly into the cranium. In some methods, antibodies are administered as a sustained release composition or device, such as a Medipad™ device.

IGF-1R antibodies or fragments thereof of the invention can optionally be administered in combination with other agents that are effective in treating the disorder or condition in need of treatment (e.g., prophylactic or therapeutic).

Effective single treatment dosages (i.e., therapeutically effective amounts) of $^{90}$Y-labeled binding polypeptides range from between about 5 and about 75 mCi, more preferably between about 10 and about 40 mCi. Effective single treatment non-marrow ablative dosages of $^{131}$I-labeled antibodies range from between about 5 and about 70 mCi, more preferably between about 5 and about 40 mCi. Effective single treatment ablative dosages (i.e., may require autologous bone marrow transplantation) of $^{131}$I-labeled antibodies range from between about 30 and about 600 mCi, more preferably between about 50 and less than about 500 mCi. In conjunction with a chimeric antibody, owing to the longer circulating half life vis-á-vis murine antibodies, an effective single treatment non-marrow ablative dosages of iodine-131 labeled chimeric antibodies range from between about 5 and about 40 mCi, more preferably less than about 30 mCi. Imaging criteria for, e.g., the $^{111}$In label, are typically less than about 5 mCi.

While a great deal of clinical experience has been gained with $^{131}$I and $^{90}$Y, other radiolabels are known in the art and have been used for similar purposes. Still other radioisotopes are used for imaging. For example, additional radioisotopes which are compatible with the scope of the instant invention include, but are not limited to, $^{123}$I, $^{125}$I, $^{32}$P, $^{57}$Co, $^{64}$Cu, $^{67}$CU, $^{77}$Br, $^{81}$Rb, $^{81}$Kr, $^{87}$Sr, $^{113}$In, $^{127}$Cs, $^{129}$Cs, $^{132}$I, $^{197}$H, $^{203}$Pb, $^{206}$Bi, $^{177}$Lu, $^{186}$Re, $^{212}$Pb, $^{212}$Bi, 47Sc, $^{105}$Rh, $^{109}$Pd, $^{153}$Sm, $^{188}$Re, $^{199}$Au, $^{225}$Ac, $^{211}$At, and $^{213}$Bi. In this respect alpha, gamma and beta emitters are all compatible with in the instant invention. Further, in view of the instant disclosure it is submitted that one skilled in the art could readily determine which radionuclides are compatible with a selected course of treatment without undue experimentation. To this end, additional radionuclides which have already been used in clinical diagnosis include $^{125}$I, $^{123}$I, $^{99}$Tc, $^{43}$K, $^{52}$Fe, $^{67}$Ga, $^{68}$Ga, as well as $^{111}$In. Antibodies have also been labeled with a variety of radionuclides for potential use in targeted immunotherapy (Peirersz et al. *Immunol. Cell Biol.* 65: 111-125 (1987)). These radionuclides include $^{188}$Re and $^{186}$Re as well as $^{199}$Au and $^{67}$Cu to a lesser extent. U.S. Pat. No. 5,460,785 provides additional data regarding such radioisotopes and is incorporated herein by reference.

Whether or not IGF-1R-specific antibodies or immunospecific fragments thereof disclosed herein are used in a conjugated or unconjugated form, it will be appreciated that a major advantage of the present invention is the ability to use these molecules in myelosuppressed patients, especially those who are undergoing, or have undergone, adjunct therapies such as radiotherapy or chemotherapy. That is, the beneficial delivery profile (i.e. relatively short serum dwell time, high binding affinity and enhanced localization) of the molecules makes them particularly useful for treating patients that have reduced red marrow reserves and are sensitive to myelotoxicity. In this regard, the unique delivery profile of the molecules make them very effective for the administration of radiolabeled conjugates to myelosuppressed cancer patients. As such, the IGF-1R-specific antibodies or immunospecific fragments thereof disclosed herein are useful in a conjugated or unconjugated form in patients that have previously undergone adjunct therapies such as external beam radiation or chemotherapy. In other preferred embodiments, binding molecules, e.g., binding polypeptides, e.g., IGF-1R-specific antibodies or immunospecific fragments thereof (again in a conjugated or unconjugated form) may be used in a combined therapeutic regimen with chemotherapeutic agents. Those skilled in the art will appreciate that such therapeutic regimens may comprise the sequential, simultaneous, concurrent or coextensive administration of the disclosed antibodies or other binding molecules and one or more chemotherapeutic agents. Particularly preferred embodiments of this aspect of the invention will comprise the administration of a radiolabeled binding polypeptide.

While IGF-1R-specific antibodies or immunospecific fragments thereof may be administered as described immediately above, it must be emphasized that in other embodiments conjugated and unconjugated binding molecules may be administered to otherwise healthy patients as a first line therapeutic agent. In such embodiments binding molecules may be administered to patients having normal or average red marrow reserves and/or to patients that have not, and are not, undergoing adjunct therapies such as external beam radiation or chemotherapy.

However, as discussed above, selected embodiments of the invention comprise the administration of IGF-1R-specific antibodies or immunospecific fragments thereof to myelosuppressed patients or in combination or conjunction with one or more adjunct therapies such as radiotherapy or chemotherapy (i.e. a combined therapeutic regimen). As used herein, the administration of IGF-1R-specific antibodies or immunospecific fragments thereof in conjunction or combination with an adjunct therapy means the sequential, simultaneous, coextensive, concurrent, concomitant or contemporaneous administration or application of the therapy and the disclosed binding molecules. Those skilled in the art will appreciate that the administration or application of the various components of the combined therapeutic regimen may be timed to enhance the overall effectiveness of the treatment. For example, chemotherapeutic agents could be administered in standard, well known courses of treatment followed within a few weeks by radioimmunoconjugates described herein. Conversely, cytotoxin-conjugated binding molecules could be administered intravenously followed by tumor localized external beam radiation. In yet other embodiments, binding molecules may be administered concurrently with one or more selected chemotherapeutic agents in a single office visit. A skilled artisan (e.g. an experienced oncologist) would be readily be able to discern effective combined therapeutic regimens without undue experimentation based on the selected adjunct therapy and the teachings of the instant specification.

In this regard it will be appreciated that the combination of a binding molecule (with or without cytotoxin) and the chemotherapeutic agent may be administered in any order and within any time frame that provides a therapeutic benefit to the patient. That is, the chemotherapeutic agent and IGF-1R-specific antibody or immunospecific fragment thereof, may be administered in any order or concurrently. In selected embodiments IGF-IR-specific antibodies or immunospecific fragments thereof of the present invention will be administered to patients that have previously undergone chemotherapy. In yet other embodiments, IGF-1R-specific antibodies or immunospecific fragments thereof of the present invention will be administered substantially simultaneously or concurrently with the chemotherapeutic treatment. For example, the patient may be given the binding molecule while undergoing a course of chemotherapy. In preferred embodiments the binding molecule will be administered within 1 year of any chemotherapeutic agent or treatment. In other preferred embodiments the polypeptide will be administered within 10, 8, 6, 4, or 2 months of any chemotherapeutic agent or treatment. In still other preferred embodiments the binding molecule will be administered within 4, 3, 2 or 1 week of any chemotherapeutic agent or treatment. In yet other embodiments the binding molecule will be administered within 5, 4, 3, 2 or 1 days of the selected chemotherapeutic agent or treatment. It will further be appreciated that the two agents or treatments may be administered to the patient within a matter of hours or minutes (i.e. substantially simultaneously).

Moreover, in accordance with the present invention a myelosuppressed patient shall be held to mean any patient exhibiting lowered blood counts. Those skilled in the art will appreciate that there are several blood count parameters conventionally used as clinical indicators of myelosuppression and one can easily measure the extent to which myelosuppression is occurring in a patient. Examples of art accepted myelosuppression measurements are the Absolute Neutrophil Count (ANC) or platelet count. Such myelosuppression or partial myeloablation may be a result of various biochemical disorders or diseases or, more likely, as the result of prior chemotherapy or radiotherapy. In this respect, those skilled in the art will appreciate that patients who have undergone traditional chemotherapy typically exhibit reduced red marrow reserves. As discussed above, such subjects often cannot be treated using optimal levels of cytotoxin (i.e. radionuclides) due to unacceptable side effects such as anemia or immunosuppression that result in increased mortality or morbidity.

More specifically conjugated or unconjugated IGF-1R-specific antibodies or immunospecific fragments thereof of the present invention may be used to effectively treat patients having ANCs lower than about 2000/mm$^3$ or platelet counts lower than about 150,000/mm$^3$. More preferably IGF-1R-specific antibodies or immunospecific fragments thereof of the present invention may be used to treat patients having ANCs of less than about 1500/mm$^3$, less than about 1000/mm$^3$ or even more preferably less than about 500/mm$^3$. Similarly, IGF-1R-specific antibodies or immunospecific fragments thereof of the present invention may be used to treat patients having a platelet count of less than about 75,000/mm$^3$, less than about 50,000/mm$^3$ or even less than about 10,000/mm$^3$. In a more general sense, those skilled in the art will easily be able to determine when a patient is myelosuppressed using government implemented guidelines and procedures.

As indicated above, many myelosuppressed patients have undergone courses of treatment including chemotherapy, implant radiotherapy or external beam radiotherapy. In the case of the latter, an external radiation source is for local irradiation of a malignancy. For radiotherapy implantation methods, radioactive reagents are surgically located within the malignancy, thereby selectively irradiating the site of the disease. In any event, IGF-1R-specific antibodies or immunospecific fragments thereof of the present invention may be used to treat disorders in patients exhibiting myelosuppression regardless of the cause.

In this regard it will further be appreciated that IGF-1R-specific antibodies or immunospecific fragments thereof of the present invention may be used in conjunction or combination with any chemotherapeutic agent or agents (e.g. to provide a combined therapeutic regimen) that eliminates, reduces, inhibits or controls the growth of neoplastic cells in vivo. As discussed, such agents often result in the reduction of red marrow reserves. This reduction may be offset, in whole or in part, by the diminished myelotoxicity of the compounds of the present invention that advantageously allow for the aggressive treatment of neoplasias in such patients. In other embodiments, radiolabeled immunoconjugates disclosed herein may be effectively used with radiosensitizers that increase the susceptibility of the neoplastic cells to radionuclides. For example, radiosensitizing compounds may be administered after the radiolabeled binding molecule has been largely cleared from the bloodstream but still remains at therapeutically effective levels at the site of the tumor or tumors.

With respect to these aspects of the invention, exemplary chemotherapeutic agents that are compatible with the instant invention include alkylating agents, vinca alkaloids (e.g., vincristine and vinblastine), procarbazine, methotrexate and prednisone. The four-drug combination MOPP (mechlethamine (nitrogen mustard), vincristine (Oncovin), procarbazine and prednisone) is very effective in treating various types of lymphoma and comprises a preferred embodiment of the present invention. In MOPP-resistant patients, ABVD (e.g., adriamycin, bleomycin, vinblastine and dacarbazine), ChlVPP (chlorambucil, vinblastine, procarbazine and prednisone), CABS (lomustine, doxorubicin, bleomycin and streptozotocin), MOPP plus ABVD, MOPP plus ABV (doxorubicin, bleomycin and vinblastine) or BCVPP (carmustine, cyclophosphamide, vinblastine, procarbazine and prednisone) combinations can be used. Arnold S. Freedman and Lee M. Nadler, *Malignant Lymphomas*, in Harrison's Principles of Internal Medicine 1774-1788 (Kurt J. Isselbacher et al., eds., 13$^{th}$ ed. 1994) and V. T. DeVita et al., (1997) and the references cited therein for standard dosing and scheduling. These therapies can be used unchanged, or altered as needed for a particular patient, in combination with one or more IGF-1R-specific antibodies or immunospecific fragments thereof of the present invention.

Additional regimens that are useful in the context of the present invention include use of single alkylating agents such as cyclophosphamide or chlorambucil, or combinations such as CVP (cyclophosphamide, vincristine and prednisone), CHOP (CVP and doxorubicin), C-MOPP (cyclophosphamide, vincristine, prednisone and procarbazine), CAP-BOP (CHOP plus procarbazine and bleomycin), m-BACOD (CHOP plus methotrexate, bleomycin and leucovorin), ProMACE-MOPP (prednisone, methotrexate, doxorubicin, cyclophosphamide, etoposide and leucovorin plus standard MOPP), ProMACE-CytaBOM (prednisone, doxorubicin, cyclophosphamide, etoposide, cytarabine, bleomycin, vincristine, methotrexate and leucovorin) and MACOP-B (methotrexate, doxorubicin, cyclophosphamide, vincristine, fixed dose prednisone, bleomycin and leucovorin). Those skilled in the art will readily be able to determine standard dosages and scheduling for each of these regimens. CHOP has also been combined with bleomycin, methotrexate, procarbazine, nitrogen mustard, cytosine arabinoside and etoposide. Other compatible chemotherapeutic agents include, but are not limited to, 2-chlorodeoxyadenosine (2-CDA), 2'-deoxycoformycin and fludarabine.

For patients with intermediate- and high-grade malignancies, who fail to achieve remission or relapse, salvage therapy is used. Salvage therapies employ drugs such as cytosine arabinoside, cisplatin, carboplatin, etoposide and ifosfamide given alone or in combination. In relapsed or aggressive forms of certain neoplastic disorders the following protocols are often used: IMVP-16 (ifosfamide, methotrexate and etoposide), MIME (methyl-gag, ifosfamide, methotrexate and etoposide), DHAP (dexamethasone, high dose cytarabine and cisplatin), ESHAP (etoposide, methylpredisolone, HD cytarabine, cisplatin), CEPP(B) (cyclophosphamide, etoposide, procarbazine, prednisone and bleomycin) and CAMP (lomustine, mitoxantrone, cytarabine and prednisone) each with well known dosing rates and schedules.

The amount of chemotherapeutic agent to be used in combination with the IGF-1R-specific antibodies or immunospecific fragments thereof of the present invention may vary by subject or may be administered according to what is known in the art. See for example, Bruce A Chabner et al., Antineoplastic *Agents, in* Goodman & Gilman's The Pharmacological Basis of Therapeutics 1233-1287 (Joel G. Hardman et al., eds., 9$^{th}$ ed. (1996)).

In another embodiment, an IGF-1R-specific antibody or immunospecific fragment thereof of the present invention is administered in conjunction with a biologic. Biologics useful in the treatment of cancers are known in the art and a binding molecule of the invention may be administered, for example, in conjunction with such known biologics.

For example, the FDA has approved the following biologics for the treatment of breast cancer: Herceptin® (trastuzumab, Genentech Inc., South San Francisco, Calif.; a humanized monoclonal antibody that has anti-tumor activity in HER2-positive breast cancer); Faslodex® (fulvestrant, AstraZeneca Pharmaceuticals, LP, Wilmington, Del.; an estrogen-receptor antagonist used to treat breast cancer); Arimidex® (anastrozole, AstraZeneca Pharmaceuticals, LP; a nonsteroidal aromatase inhibitor which blocks aromatase, an enzyme needed to make estrogen); Aromasin® (exemestane, Pfizer Inc., New York, N.Y.; an irreversible, steroidal aromatase inactivator used in the treatment of breast cancer); Femara® (letrozole, Novartis Pharmaceuticals, East Hanover, N.J.; a nonsteroidal aromatase inhibitor approved by the FDA to treat breast cancer); and Nolvadex® (tamoxifen, AstraZeneca Pharmaceuticals, LP; a nonsteroidal antiestrogen approved by the FDA to treat breast cancer). Other biologics with which the binding molecules of the invention may be combined include: Avastin™ (bevacizumab, Genentech Inc.; the first FDA-approved therapy designed to inhibit angiogenesis); and Zevalin® (ibritumomab tiuxetan, Biogen Idec, Cambridge, Mass.; a radiolabeled monoclonal antibody currently approved for the treatment of B-cell lymphomas).

In addition, the FDA has approved the following biologics for the treatment of colorectal cancer: Avastin™; Erbitux™ (cetuximab, ImClone Systems Inc., New York, N.Y., and Bristol-Myers Squibb, New York, N.Y.; is a monoclonal antibody directed against the epidermal growth factor receptor (EGFR)); Gleevec® (imatinib mesylate; a protein kinase inhibitor); and Ergamisol® (levamisole hydrochloride, Janssen Pharmaceutica Products, LP, Titusville, N.J.; an immunomodulator approved by the FDA in 1990 as an adjuvant treatment in combination with 5-fluorouracil after surgical resection in patients with Dukes' Stage C colon cancer).

For use in treatment of Non-Hodgkin's Lymphomas currently approved therapies include: Bexxar® (tositumomab and iodine I-131 tositumomab, GlaxoSmithKline, Research Triangle Park, N.C.; a multi-step treatment involving a mouse monoclonal antibody (tositumomab) linked to a radioactive molecule (iodine I-131)); Intron® A (interferon alfa-2b, Schering Corporation, Kenilworth, N.J.; a type of interferon approved for the treatment of follicular non-Hodgkin's lymphoma in conjunction with anthracycline-containing combination chemotherapy (e.g., cyclophosphamide, doxorubicin, vincristine, and prednisone [CHOP])); Rituxan® (rituximab, Genentech Inc., South San Francisco, Calif., and Biogen Idec, Cambridge, Mass.; a monoclonal antibody approved for the treatment of non-Hodgkin's lymphoma; Ontak® (denileukin diftitox, Ligand Pharmaceuticals Inc., San Diego, Calif.; a fusion protein consisting of a fragment of diphtheria toxin genetically fused to interleukin-2); and Zevalin® (ibritumomab tiuxetan, Biogen Idec; a radiolabeled monoclonal antibody approved by the FDA for the treatment of B-cell non-Hodgkin's lymphomas).

For treatment of Leukemia, exemplary biologics which may be used in combination with the binding molecules of the invention include Gleevec®; Campath®-1H (alemtuzumab, Berlex Laboratories, Richmond, Calif.; a type of monoclonal antibody used in the treatment of chronic Lymphocytic leukemia). In addition, Genasense (oblimersen, Genta Corporation, Berkley Heights, N.J.; a BCL-2 antisense therapy under development to treat leukemia may be used (e.g., alone or in combination with one or more chemotherapy drugs, such as fludarabine and cyclophosphamide) may be administered with the claimed binding molecules.

For the treatment of lung cancer, exemplary biologics include Tarceva™ (erlotinib HCL, OSI Pharmaceuticals Inc., Melville, N.Y.; a small molecule designed to target the human epidermal growth factor receptor 1 (HER1) pathway).

For the treatment of multiple myeloma, exemplary biologics include Velcade® Velcade (bortezomib, Millennium Pharmaceuticals, Cambridge Mass.; a proteasome inhibitor). Additional biologics include Thalidomid® (thalidomide, Clegene Corporation, Warren, N.J.; an immunomodulatory agent and appears to have multiple actions, including the ability to inhibit the growth and survival of myeloma cells and anti-angiogenesis).

Other exemplary biologics include the MOAB IMC-C225, developed by ImClone Systems, Inc., New York, N.Y.

As previously discussed, IGF-1R-specific antibodies or immunospecific fragments thereof of the present invention, or recombinants thereof may be administered in a pharmaceutically effective amount for the in vivo treatment of mammalian hyperproliferative disorders. In this regard, it will be appreciated that the disclosed antibodies will be formulated so as to facilitate administration and promote stability of the active agent. Preferably, pharmaceutical compositions in accordance with the present invention comprise a pharmaceutically acceptable, non-toxic, sterile carrier such as physiological saline, non-toxic buffers, preservatives and the like. For the purposes of the instant application, a pharmaceutically effective amount of IGF-1R-specific antibodies or immunospecific fragments thereof of the present invention, or recombinant thereof, conjugated or unconjugated to a therapeutic agent, shall be held to mean an amount sufficient to achieve effective binding to a target and to achieve a benefit, e.g., to ameliorate symptoms of a disease or disorder or to detect a substance or a cell. In the case of tumor cells, the binding molecule will be preferably be capable of interacting with selected immunoreactive antigens on neoplastic or immunoreactive cells, or on non neoplastic cells, e.g., vascular cells associated with neoplastic cells. and provide for an increase in the death of those cells. Of course, the pharmaceutical compositions of the present invention may be administered in single or multiple doses to provide for a pharmaceutically effective amount of the binding molecule.

In keeping with the scope of the present disclosure, IGF-1R-specific antibodies or immunospecific fragments thereof of the present invention may be administered to a human or other animal in accordance with the aforementioned methods of treatment in an amount sufficient to produce a therapeutic or prophylactic effect. The IGF-1R-specific antibodies or immunospecific fragments thereof of the present invention can be administered to such human or other animal in a conventional dosage form prepared by combining the antibody of the invention with a conventional pharmaceutically acceptable carrier or diluent according to known techniques. It will be recognized by one of skill in the art that the form and character of the pharmaceutically acceptable carrier or diluent is dictated by the amount of active ingredient with which it is to be combined, the route of administration and other well-known variables. Those skilled in the art will further appreciate that a cocktail comprising one or more species of binding molecules according to the present invention may prove to be particularly effective.

The practice of the present invention will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, Molecular Cloning A Laboratory Manual, 2nd Ed., Sambrook et al., ed., Cold Spring Harbor Laboratory Press: (1989); *Molecular Cloning: A Laboratory Manual*, Sambrook et al., ed., Cold Springs Harbor Laboratory, New York (1992), *DNA Cloning*, D. N. Glover ed., Volumes I and II (1985); *Oligonucleotide Synthesis*, M. J. Gait ed., (1984); Mullis et al. U.S. Pat. No. 4,683,195; *Nucleic Acid Hybridization*, B. D. Hames & S. J. Higgins eds. (1984); *Transcription And Translation*, B. D. Hames & S. J. Higgins eds. (1984); *Culture Of Animal Cells*, R. I. Freshney, Alan R. Liss, Inc., (1987); *Immobilized Cells And Enzymes*, IRL Press, (1986); B. Perbal, *A Practical Guide To Molecular Cloning* (1984); the treatise, *Methods In Enzymology*, Academic Press, Inc., N.Y.; *Gene Transfer Vectors For Mammalian Cells*, J. H. Miller and M. P. Calos eds., Cold Spring Harbor Laboratory (1987); *Methods In Enzymology*, Vols. 154 and 155 (Wu et al. eds.); *Immunochemical Methods In Cell And Molecular Biology*, Mayer and Walker, eds., Academic Press, London (1987); *Handbook Of Experimental Immunology*, Volumes I-IV, D. M. Weir and C. C. Blackwell, eds., (1986); *Manipulating the Mouse Embryo*, Cold Spring Harbor Laboratory Press, Cold Spring Harbor, N.Y., (1986); and in Ausubel et al., *Current Protocols in Molecular Biology*, John Wiley and Sons, Baltimore, Md. (1989).

General principles of antibody engineering are set forth in *Antibody Engineering*, 2nd edition, C. A. K. Borrebaeck, Ed., Oxford Univ. Press (1995). General principles of protein engineering are set forth in *Protein Engineering, A Practical Approach*, Rickwood, D., et al., Eds., IRL Press at Oxford Univ. Press, Oxford, Eng. (1995). General principles of antibodies and antibody-hapten binding are set forth in: Nisonoff, A., *Molecular Immunology*, 2nd ed., Sinauer Associates, Sunderland, Mass. (1984); and Steward, M. W., *Antibodies, Their Structure and Function*, Chapman and Hall, New York, N.Y. (1984). Additionally, standard methods in immunology known in the art and not specifically described are generally followed as in *Current Protocols in Immunology*, John Wiley & Sons, New York; Stites et al. (eds), *Basic and Clinical—Immunology* (8th ed.), Appleton & Lange, Norwalk, Conn. (1994) and Mishell and Shiigi (eds), *Selected Methods in Cellular Immunology*, W.H. Freeman and Co., New York (1980).

Standard reference works setting forth general principles of immunology include *Current Protocols in Immunology*, John Wiley & Sons, New York; Klein, J., Immunology: *The Science of Self-Nonself Discrimination*, John Wiley & Sons, New York (1982); Kennett, R., et al., eds., *Monoclonal Antibodies, Hybridoma: A New Dimension in Biological Analyses*, Plenum Press, New York (1980); Campbell, A., "Monoclonal Antibody Technology" in Burden, R., et al., eds., *Laboratory Techniques in Biochemistry and Molecular Biology*, Vol. 13, Elsevere, Amsterdam (1984), *Kuby Immunology* 4$^{th}$ ed. Richard A. Goldsby, Thomas J. Kindt and Barbara A. Osborne, H. Freemand & Co. (2000); Roitt, I., Brostoff, J. and Male D., *Immunology* 6$^{th}$ ed. London: Mosby (2001); Abbas A., Abul, A. and Lichtman, A., *Cellular and Molecular Immunology* Ed. 5, Elsevier Health Sciences Division (2005); Kontermann and Dubel, *Antibody Engineering*, Springer Verlan (2001); Sambrook and Russell, *Molecular Cloning: A Laboratory Manual*. Cold Spring Harbor Press (2001); Lewin, *Genes VIII*, Prentice Hall (2003); Harlow and Lane, *Antibodies: A Laboratory Manual*, Cold Spring Harbor Press (1988); Dieffenbach and Dveksler, *PCR Primer* Cold Spring Harbor Press (2003).

All of the references cited above, as well as all references cited herein, are incorporated herein by reference in their entireties.

EXAMPLES

Example 1

Selection of IGF-1R Specific Fabs from Phage Libraries

Recombinant human IGF-1R ectodomain was used to screen a human naïve phagemid Fab library containing 3.5× $10^{10}$ unique clones (Hoet, R. M., et al. *Nat Biotechnol*. 23(3): 344-8 (2005), ("Hoet et al.") which is incorporated herein by reference in its entirety). Two distinct panning arms were followed using biotinylated IGF1R-his and IGF1R-Fc protein. Proteins were captured on steptavidin-coated magnetic beads prior to incubation with the phage library. In the case of IGF1R-Fc, a biotinylated anti-Fc antibody was captured on the magnetic beads, followed by captured of the Fc fusion protein. Selections were performed as described in Hoet et al. After 3 rounds of panning, the 479 bp gene III stump was removed by MluI digestion, and the vector was religated for soluble Fab expression in TG1 cells. ELISA analysis of 920 clones from the biotinylated IGF1R-his arm yielded 593 positive clones, containing 33 unique sequences. ELISA analysis of 920 clones from the IGF1R-Fc arm yielded 163 positive clones, containing 12 unique sequences. Sequence analysis of all clones determined 12 clones were isolated in both arms of the panning strategy. Unique clones were purified and binding was reconfirmed to recombinant human IGF-1R ectodomain by ELISA as well as 3T3 cells stably transfected with full-length human IGF-1R (FIGS. 1A & 1B). Based on binding data, 6 of the 12 unique clones isolated in both arms were selected for further analysis.

Example 2

Binding Activity of Fabs to IGF-1R Expressed on Tumor Cells

The ability of Fabs to bind to the wild type IGF-1R was determined by flowcytometry using MCF-7 tumor cell line.

MCF-7 cells (Human Breast Adenocarcinoma from NCI) were split 24 hours prior to the setup of the assay to obtain 70% confluent monolayer. Routinely, MCF-7 cell line was maintained within 20 passages. Cells were lifted with cell dissociation buffer (Gibco catalog #13151-014), counted, washed and adjusted to 1×10$^6$ cells/ml and one ml of cells were then added to each tube (12×75 mm tube Falcon catalog#352054). Cells were pelleted and supernatant removed by centrifugation at 1200 rpm for 5 min and 100 µl of diluted antibodies were then added to the cell pellet. Purified Fabs were tested at a starting concentration of either 210 or 60 µg/ml with 1:3 dilutions in FACS buffer, down to 0.001 µg/ml. FACS buffer used throughout the assay was PBS (without Ca++/Mg++) containing 1% BSA (Sigma catalog#A-7906) and 0.1% Sodium Azide (Sigma catalog #S2002). As a positive control IR3 a murine antibody (Ab-1; Calbiochem #GR11L) was used. Samples were allowed to incubate on ice for 1 hour and 15 minutes then were washed with 2 ml FACS buffer and centrifuged at 1200 rpm for 5 minutes at 4° C. The supernatant was aspirated and 100 µl of the secondary detection antibody was added to each corresponding tube in FACS buffer. Samples were then incubated for 30 minutes on ice, in the dark. Cells were washed as described above, then, re-suspended in 250 µl FACS buffer per tube/sample.

Cell bound Fabs were detected using FITC-conjugated affinity-purified F(ab')$_2$ Fragment specific goat anti-human-IgG (Jackson ImmunoResearch Lab catalog #109-096-006; use at 5 µg/ml), while positive murine control antibody was detected using the F(ab')$_2$ FITC conjugated goat anti-mouse IgG (H+L) (Jackson ImmunoResearch, catalog#115-096-062; used at 5 µg/ml). Cells were stained for live cell determination with Propidium Iodide staining solution (PI for dead cell exclusion; BD Pharmingen catalog#51-66211E or 556463; use at 1:500 final in FACS buffer). Samples were run on the FACSCalibur instrument (Becton Dickinson) with 10,000 live events collected per sample. Data analysis was done using GraphPad Prism version 4.0 software (www.graphpad.com) (GraphPad Software, Inc., 11452 El Camino Real, #215, San Diego, Calif. 92130 USA).

Once samples have been run and geometric means determined, antibody concentration (X axis) vs. geometric mean (Y axis) was graphed to the log 10, using Graphpad Prism (Prism Graph) graphing program. Data sets were then transformed (X value data set=antibody concentration) to X=Log (X) and graphed using a nonlinear regression curve fit, Sigmoidal dose-response. $EC_{50}$ values and $R^2$ values were generated using the Prism Graph software.

Figure 2:
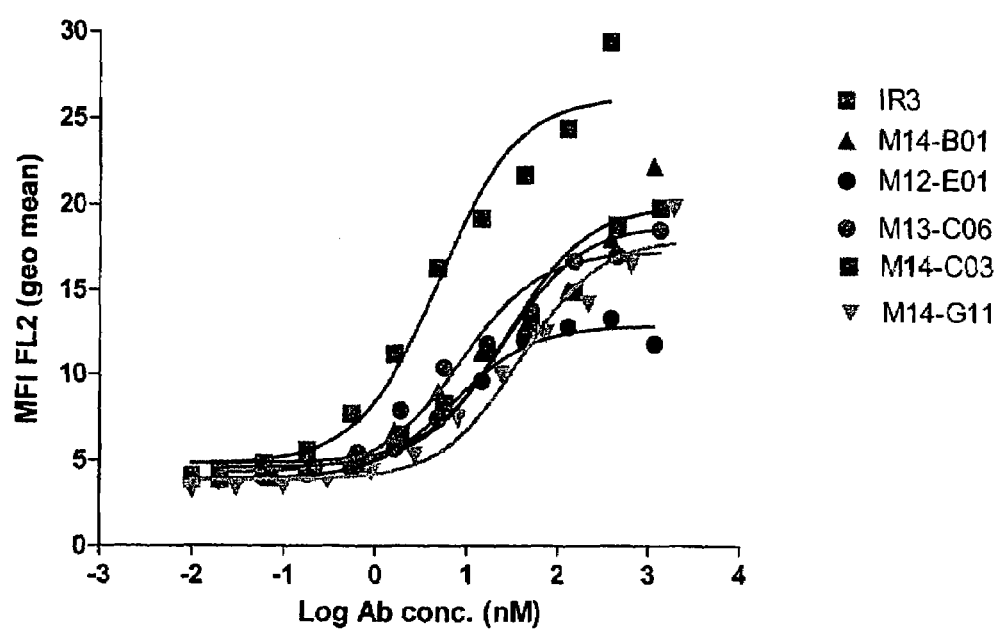
FIG. 2: Binding activity of Fabs to IGF-1R expressed on MCF-7 cells.

All 6 Fabs showed good binding activity to wild type IGF-1R expressed on MCF-7 tumor cells (FIG. 2). The $EC_{50}$ of binding ranged between 9 to 42 nM (Table 3).

Example 3

Inhibition of Ligand Binding to IGF-1R by Fabs

The ability of Fabs to block the binding of IGF-1 and IGF-2 ligands to IGF-1R was determined using a radioimmunoassay (RIA).

Ligand blocking assay (RIA). Recombinant human IGF-1 (Cat #291-G1), IGF-2 (Cat #292-G2), insulin (Cat #Custom02) human Insulin Receptor (Cat #1544-1R) were purchased from R&D Systems, Inc., Minneapolis, Minn. Insulin (Arg-Insulin, Cat #01-207) was purchased from Upstate Cell Signaling Solutions (Lake Placid, N.Y. (now part of Millipore, Concord, Mass. (USA)). $^{125}$I-rhIGF-1 (Cat #IM172), $^{125}$I-rhIGF-2 (Cat#IM238) and $^{125}$I-rhInsulin (Cat#IM166) were purchased from Amersham Biosciences (Piscataway, N.J.). AffiPure goat anti-human IgG, Fcγ fragment specific antibodies (Cat #109-005-098, Jackson ImmunoResearch, West Grove, Pa.) was used for IGF-1R-Fc capture. As detection antibody, goat anti-mouse IgG HRP (Cat #1030-05, Southern Biotech Birmingham, Ala.) was used.

As positive controls for IGF-1 and IGF-2 blocking, IR3 (Ab-1, Cat. #GR11LSP5, Calbiochem, La Jolla, Calif.) and 1H7 (Mouse Monoclonal specific to IGF-1R α-chain, sc-461, $IgG_1$ Santa Cruz Biotechnology, Santa Cruz, Calif.) were used respectively. Human insulin receptor α-subunit specific antibodies, Clone 83-14, (Cat #AHR0221, Biosource International, Inc., Camarillo, Calif.) and the 47-9 (Cat #E55502M, Biodesign International, Saco, Me.) were used as positive controls blocking of insulin-insulin receptor binding experiments. Recombinant IGF-1R-Fc fusion protein was produced at Biogen Idec (Cambridge, Mass.).

As isotype matched mouse negative control antibodies, 2B8 (murine α-CD20.$IgG_1$) and 2B8 mkm.$G_{2a}$ (murine α-CD20 MAb, $IgG_{2a}$, Biogen Idec, Lot #NB3304-87, San Diego, Calif.) were used. The negative control for Fabs was R001-1B provided by Christilyn Graff (Biogen Idec, Cambridge, Mass.). PBS used in buffers was from BioWhittaker (Cat. #17-513F, Walkersville, Md.).

Recombinant human IGF-1R (Histidine tagged version) or IGF-1R-Fc was coated onto IMMULON2 HB (high binding) Removawell strips (Dynex Technologies, Inc., cat. #6302) diluted with carbonate coating buffer pH 9.5 to a concentration of 250 ng/well. After overnight incubation at 4° C., the wells were washed three times with washing buffer (0.05% Tween 20/PBS) then blocked with blocking buffer (3% BSA/PBS) for one hour at room temperature. The blocking buffer was removed and the wells washed three more times. Antibody, Fab, or ligand preparations were diluted to desired concentration with dilution buffer (1% BSA/0.05% Tween 20/PBS) and plated at 50 µl per well in duplicate. After 45 minutes at room temperature, 100,000 cpm of either [125I] rhIGF-1 or [125I] rhIGF-2 in 50 µl dilution buffer was added per well. This was incubated at room temperature for one more hour. The wells were washed again three more times and left liquid free after the last wash. The air-dried wells were counted with the Isodata Gamma Counter.

Alternatively, Fabs were evaluated by a modified capture assay, where the IGF-1R-Fc was captured using anti-human IgG immobilized to a plate. Immobilization was carried out by overnight incubation of goat anti-human IgG, Fcγ fragment specific antibody (200 ng/well) in carbonate coating buffer. The wells were washed, blocked and 250 ng of IGF-1R-Fc was added per well.

The ability of 6 different Fabs to block the binding of IGF-1 or IGF-2, or both ligands is shown in Table 3. The top 6 Fabs with different blocking activity were selected for further analysis.

Example 4

Fabs Inhibited IGF-1 and IGF-2 Mediated IGF-1R Phosphorylation

Cell lines: IGF1R expressing human breast carcinoma cell line MCF-7 (NCI) were maintained at 37° C. and 5% $CO_2$ in MEM eagle (ATCC) containing 10% FBS, 1× non-essential amino acids, 2 mM L-glutamine, 1 mM sodium pyruvate and 1000 U/ml penicillin and streptomycin. Cells were sub-cultured twice weekly for maintenance and assay, and used with a maximum of 12 passages.

MCF-7 cells were plated in 2 ml growth media at $2 \times 10^5$ to $4.0 \times 10^5$ cells/well in Ploy-D-Lysine coated 12 well plates (BD Biosciences, #35-6470) and cultured at 37° C., 5% $CO_2$. At 48 hours, media removed and cells serum starved overnight at 37° C., 5% $CO_2$. Serum free media was removed and control or test antibodies at indicated concentration were added in 350 ul of fresh serum free media and incubated for 1 hour at room temperature, or alternately at 37° C. Fabs were tested at 200 nM, 20 nM and 2 nM concentration and the mAbs were tested at 67, 6.7 and 0.67 nM. The commercial anti-IGF-1R control antibody used was αIR3 (EMD biosciences, Oncogene Research products, #D27249). Human recombinant IGF-1 at 13 nM or IGF-2 at 27 nM (R & D Systems, #291-G1, #292-G2) added to wells in 35 ul serum free media and incubated at 37° C. for 15 minutes. Ligand was incubated at room temperature for 37° C. antibody experiments. Cells were lysed in 1× cell lysis buffer (Cell Signal technologies, #9803) with 1 mM PMSF for 1 hour at room temperature.

Cell lysates were added to ELISA plates pre-coated with IGF-1Rβ antibody (Clone 1-2, Biosource International, #AHR0361) and incubated for 2 hours. Following which plates were washed and the plate bound phosphorylated receptor was detected with the biotin labeled anti-phosphotyrosine antibody 4G10 (Catalog #16-103, Upstate Cell Signaling Solutions (Lake Placid, N.Y. (now part of Millipore, Concord, Mass. (USA)) and streptavidin-HRP (BD Pharmingen, #554066). Assay is developed by addition of TMB substrate (Kierkegaard & Perry, #50-76-00) and color stopped by addition of 4N $H_2SO_4$ (LabChem, Cat#LC25830-1). Optical density is measured at 450 nm using a Molecular Devices plate reader and percent inhibition over the ligand control is calculated for each antibody-ligand sample.

Table 3 summarizes the inhibition of IGF-1 and IGF-2 mediated phosphorylation of IGF-1R in MCF-7 cells by Fabs. A total of 16 IGF-1R Fabs were screened for inhibition of receptor phosphorylation by ELISA. Nine antibodies showed positive response of "+" or better at a concentration of 200 nM against IGF-1, IGF-2 or both. These antibodies were selected for scale up quantities and tested again for dose dependent inhibitory response. Based on the ability to inhibit ligand binding and receptor phosphorylation, four Fabs were selected as lead candidates for full-length antibody conversion (see, Example 6).

FIGS. 3 (A & B), shows the Inhibition of IGF-1R phosphorylation of the scaled up material of the top 6 IGF-1R Fabs.

Example 5

Binding Specificities and Affinities for IGF-1R Versus INSR

Part I: Analysis of Antibody Binding to Soluble IGF-1R Versus Soluble INSR Using Enzyme-Linked Immunosorbent Assays (ELISA)

ELISA assays were performed to determine specific binding of the Fab fragment antibodies to soluble IGF-1R over the insulin receptor. Plates were coated with 10 ug/ml of rh-IGF-1R (R & D Systems, #305-GR) or rh-INSR (R & D Systems, #1544-IR) overnight and blocked with 5% milk. The antibodies were added at a range of 2 µM-0.2 nM for Fabs or 667-0.067 nM for murine MAbs in a 1:10 serial dilution and incubated 1 hour at room temperature. Bound antibody was detected with HRPO labeled goat α-human kappa (Southern Biotechnology Associates, #2060-05) for Fabs and goat α-mouse IgG Fcγ (Jackson Immunoresearch, #115-035-164) for murine MAbs. Color development was stopped by addition of 4N $H_2SO_4$ and optical density is measured at 450 nm using a Molecular Devices plate reader and binding curves are generated.

IGF-1R Fabs showed no specific binding to soluble insulin receptor at any concentration (Table 3) while, as expected they showed good binding to IGF-1R-Fc.

FIGS. 4 (A & B) illustrates the representative binding curves obtained with Fabs M14-B01, M14-C03 and M12-G04. Similar binding patterns were observed for M13-C06, M14-G11 and M12-E01 (data not shown).

Part II: Analysis of Antibody Binding to Soluble IGF-1R Versus Soluble INSR Using Surface Plasmon Resonance (SPR) and Time-Resolved Fuorescence Resonance Energy Transfer (tr-FRET)

Binding affinities of M13-C06, M14-C03, and M14-G11 antibodies to soluble human IGF-1R and insulin receptor ectodomains were compared using surface plasmon resonance (Biacore) and time-resolved fluorescence resonance energy transfer (tr-FRET); further demonstrating that M13-C06 antibody does not exhibit significant cross-reactivity with insulin receptor, murine IGF-1R, or a truncated version of human IGF-1R (i.e., hIGF-1R amino acid residues 1-462 containing only the first and second leucine rich repeat domains as well as the cysteine rich repeat domain, but lacking IGF-1R's three fibronectin type III domains).

Surface Plasmon Resonance (SPR) Analyses

SPR analyses were performed using a Biacore3000. The instrument was set to 25° C. and assays performed with running buffer HBS-EP pH 7.2 purchased from Biacore (Biacore, Cat. No. BR-1001-88). The fully human antibodies, M13-C06, M14-C03, and M14-G11 were immobilized to ~10,000 RU on Biacore CM5 Research Grade Sensor Chip surfaces using the standard NHS/EDC-amine reactive chemistry according to protocols supplied by Biacore. For immobilization, the antibodies were diluted to 40 µg/mL in a 10 mM Acetate pH 4.0 buffer. To investigate the relative kinetics of association and dissociation of the full-length ectodomains of human IGF-1R(1-902)-$His_{10}$ (hIGF-1R-$His_{10}$ (R&D systems)) and human INSR(28-956)-$His_{10}$ (INSR(R&D systems)) to each of the human antibodies, increasing concentrations of hIGF-1R-$His_{10}$ or INSR were injected over the sensorchip surfaces. The hIGF-1R-$His_{10}$ concentration series ranged from 1.0 nM to 250 nM while the INSR concentrations ranged from 1.0 nM to 2 µM. All antibody surfaces were reliably regenerated with 100 mM Glycine, pH 2.0. Repeated regenerations did not lead to activity losses for any of the antibody surfaces. Flow rates were 20 µl/min. ("$His_{10}$" denotes a 10-residue histidine tag on the C-terminus of the constructs.)

Time-Resolved Fluorescence Resonance Energy Transfer (tr-FRET) Assay hIGF-1R-$His_{10}$ and M13-C06 were covalently conjugated to Cy5 and a Europium chelate, respectively, using standard NHS chemistry according to the dye manufacturer's protocols. Serial dilutions of several unlabeled soluble ectodomain receptor competitors, (1) hIGF-1R-$His_{10}$, (2) human IGF-1R (1-903)-Flag$His_{10}$ (hIGF-1R-Flag$His_{10}$, Biogen Idec), (3) human IGF-1R(1-903)-Fc (hIGF-1R-Fc, Biogen Idec), (4) human IGF-1R(1-462)-Fc (hIGF-1R(1-462)-Fc, Biogen Idec), (5) murine IGF-1R(1-903)-Fc (mIGF-1R-Fc, Biogen Idec) or (6) INSR, starting at 6.25 µg (50 µl of 125 µg/ml stock solution) were mixed with 0.1 µg hIGF1R-$His_{10}$-Cy5 (25 µl of 4 µg/ml stock solution) and 0.075 µg Eu-C06 (25 µl of 3 µg/ml stock solution) in 96-well microtiter plates (black from Costar). The conjugation levels for hIGF-1R-$His_{10}$-Cy5 were 6.8:1 (Cy5:IGF-1R-$His_{10}$), and for Eu-C06 were 10.3:1 (Eu:C06) as determined by the absorbance of each dye with respect to the protein concentration. The total volume was 100 µl for each sample. Plates were incubated for 1 hr at room temperature on a plate agitator. Fluorescence measurements were carried out on a Wallac Victor$^2$ fluorescent plate reader (Perkin Elmer) using the LANCE protocol with the excitation wavelength at 340 nm and emission wavelength at 665 nm. All constructs were sampled with at least two replicates.

All Biogen Idec derived soluble IGF-1R receptor ectodomain constructs were subcloned into Biogen Idec PV-90 vectors for CHO expression using described methodology (Brezinsky et al., 2003). Each receptor containing a C-terminal IgG-Fc tag was affinity purified using a single protein A SEPHAROSE FF™ (GE Heathcare) step as described previously. hIGF-1R-Flag$His_{10}$ was purified using $Ni^{2+}$-agarose (Qiagen) as described previously (Demarest et al., 2006).

Results:

The fully human anti-IGF-1R antibodies, M13-C06, M14-C03, and M14-G11, were evaluated for their comparative binding activities towards soluble IGF-1R and INSR ectodomain constructs using surface plasmon resonance (SPR). hIGF-1R-$His_{10}$ and INSR were injected over immobilized antibody surfaces using identical protocols. hIGF-1R-$His_{10}$ demonstrated binding to all three anti-IGF-1R antibodies even at the lowest concentration, 0.5 nM (data not shown: concentrations ranged from 1 to 250 nM and the receptor injection phase was 400-2200 seconds followed by a buffer dissociation phase and subsequent regeneration with glycine, pH 2.0). hIGF-1R-$His_{10}$ binding was strongest for the M13-C06 surface. In contrast, INSR demonstrated little activity towards the M13-C06 surface even at a concentration as high as 2 µM receptor (>1000 higher than what was observed for IGF-1R binding (data not shown: concentrations ranged from 1.0 nM to 2 µM and the receptor injection phase was 500-1000 seconds followed by a buffer dissociation phase). The M14-C03 and M14-G11 surfaces also demonstrated little binding activity towards INSR.

Next, the affinities of various recombinant IGF-1R and INSR constructs for M13-C06 were determined using a competition-based tr-FRET assay. Best fit binding curves for all recombinant receptor constructs (described below) were determined (data not shown). All data were fitted to a one-site binding model from which the corresponding $IC_{50}$ values were determined. The three full-length human IGF-1R ectodomain constructs (hIGF-1R-Fc, hIGF-1R-His$_{10}$, and hIGF-1R-FlagHis$_{10}$) all competed in a concentration dependent manner with $IC_{50}$ values of 2.9, 2.0, 5.2 μg/ml, respectively. The truncated human IGF-1R(1-462)-Fc construct, the full-length mouse IGF-1R-Fc construct, and the full-length human INSR-His$_{10}$ construct did not inhibit Cy5-labeled hIGF-1R-His$_{10}$ at concentrations 100-fold above the $IC_{50}$ of the recombinant full-length human IGF-1R constructs, suggesting these former constructs do not exhibit significant binding reactivity for M13-C06 compared to the latter full-length human IGF-1R.

Part III: Relative Binding Affinity of M13-C06 Antibody for Soluble Human Versus Murine IGF-1R.

The relative binding affinity of M13-C06 for murine versus human IGF-1R were compared. Surface plasmon resonance (SPR) was used to determine the affinity of M13-C06 for murine IGF-1R Fc and human IGF-1R Fc. Experiments were performed on a Biacore 3000 set to 25° C. using HBS-EP (Biacore, Cat. No. BR-1001-88) as the running buffer. An anti-human IgG-Fc antibody (2C11 from Biogenesis, Cat. No. 5218-9850) was immobilized to saturation on a Biacore CM5 chip (Cat. No. BR-1000-14) surface by injection at 500 nM in HBS-EP buffer. mIGF-1R-Fc or hIGF-1R-Fc was captured on the chip surface by injecting 40 μL of 20 nM receptor at 3 μL/min. Following capture of receptor, 40 μL of M13-C06 Fab was injected at 3 μL/min. Dissociation of Fab was measured for ~27 minutes. Fab was serially diluted from 25 to 0.4 nM to obtain concentration dependent kinetic binding curves. Regeneration of the surface chip between each injection series was performed using 3×10 μL injections of 100 mM glycine pH 2.0 at 60 μL/min. Each curve was double referenced using (1) data obtained from a CM5 chip surface devoid of the anti-IgG antibody 2C11 and (2) data from a primary injection of receptor followed by a secondary injection of HBS-EP buffer. The concentration series of M13-C06 Fab for each receptor was fit to the 1:1 binding model provided within the BiaEvaluation software of the manufacturer. To obtain the $k_d$ of M13-C06 binding to mIGF-1R-Fc, the experiment was repeated with M13-C06 Fab at 25 nM and mIGF-1R-Fc at 20 nM with the only change in the original protocol being an extension of the dissociation period to three hours.

Figure 27:
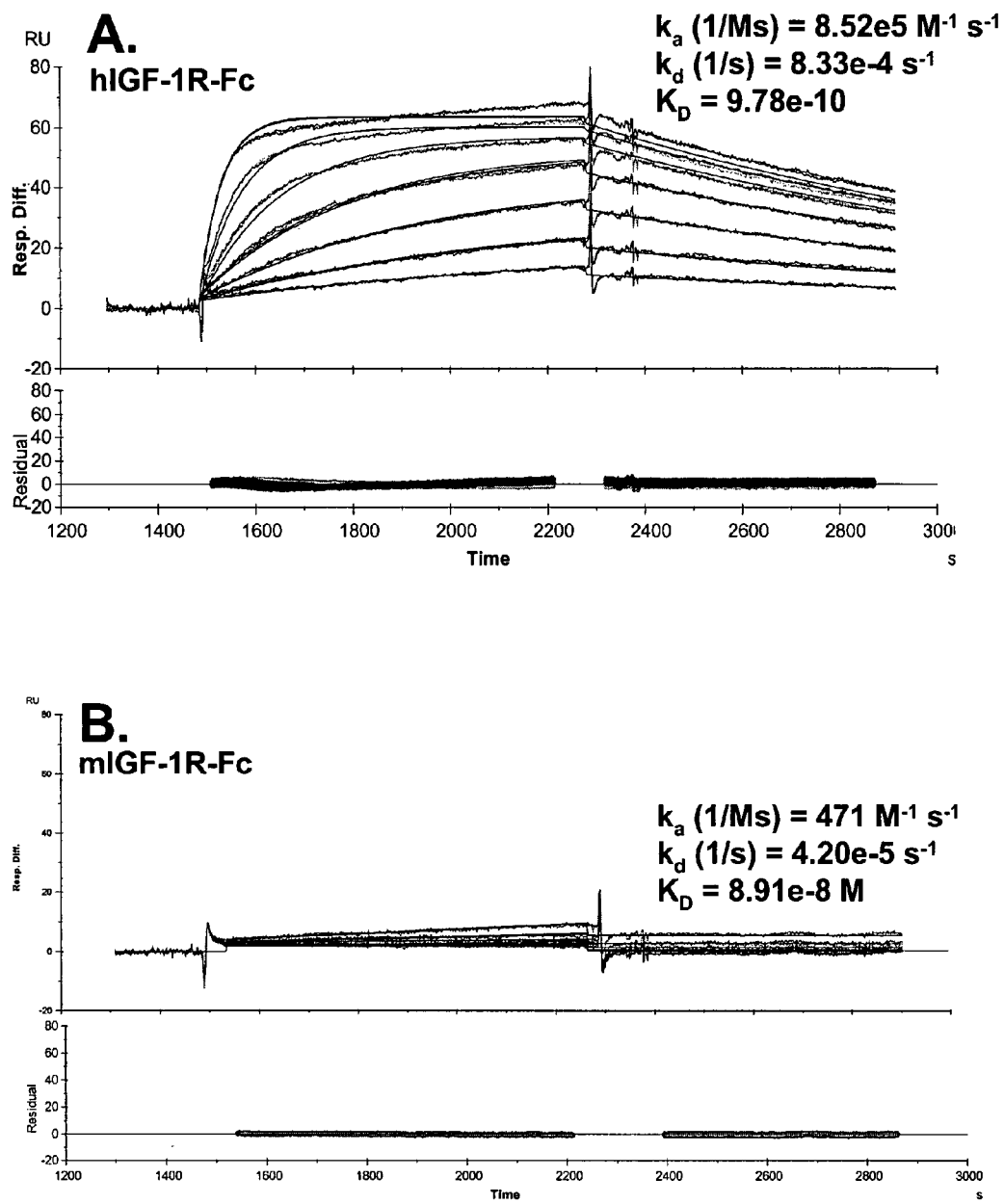
FIG. 27. Relative binding affinity measurements of M13-C06 Fab for (A) hIGF-1R-Fc and (B) mIGF-1R-Fc. The x- and y-axis scales are identical for (A) and (B). Residuals for the binding fits are shown at the bottom of each panel to indicate the applicability of the 1:1 binding model in determining relative affinities of M13-C06 for each receptor.

Results:

M13-C06 Fab was applied to Biacore surfaces containing hIGF-1R-Fc or mIGF-1R-Fc to determine the relative affinity of the antibody to the two species of receptor. The presence of the C-terminal IgG1-Fc tag results in additional multimerization of the IGF-1R-Fc receptor constructs (data not shown); therefore, the binding model fits provide a measure of the relative or apparent affinities of M13-C06 for each receptor. The affinity of M13-C06 Fab for human and murine IGF-1R Fc was found to be 0.978 nM and 89.1 nM, respectively. The 100-fold decrease in binding to murine IGF-1R is readily apparent when comparing FIGS. 27 A & B, which display the association and dissociation curves, kinetic rate constants, and equilibrium dissociation constants. FIG. 27A shows the concentration dependent binding characteristics of M13-C06 Fab for human IGF-1R ($k_a$ (1/Ms)=8.52e5 M$^{-1}$ s$^{-1}$; $k_d$ (1/s) =8.33e−4 s$^{-1}$; and, $K_D$=9.78e−10 M). FIG. 27B shows the slow association and dissociation binding characteristics of M13-C06 for mIGF-1R-Fc ($k_a$ (1/Ms)=471 M$^{-1}$ s$^{-1}$; $k_d$ (1/s) =4.20e−5 s$^{-1}$; $K_D$=8.91e−8 M). Due to the extremely slow dissociation of M13-C06 Fab from mIGF-1R-Fc, the kinetic dissociation rate constant, $k_d$, could not be determined using the initial data set. A second experiment was performed using a 3 hr dissociation period to obtain the dissociation rate constant, $k_d$ of 4.20e−5 s$^{-1}$ which was used to obtain the equilibrium dissociation constant, $K_D$, (described above) from the original dataset. The presence of the C-terminal IgG1-Fc tag results in additional multimerization of the IGF-1R-Fc receptor constructs (data not shown); therefore, the binding model fits provide a measure of the relative or apparent affinities of M13-C06 for each receptor.

Part IV: M13-C06 Full-Length Antibody Specifically Binds IGF-1R but not INSR Expressed in Mammalian Cells.

Figure 26:
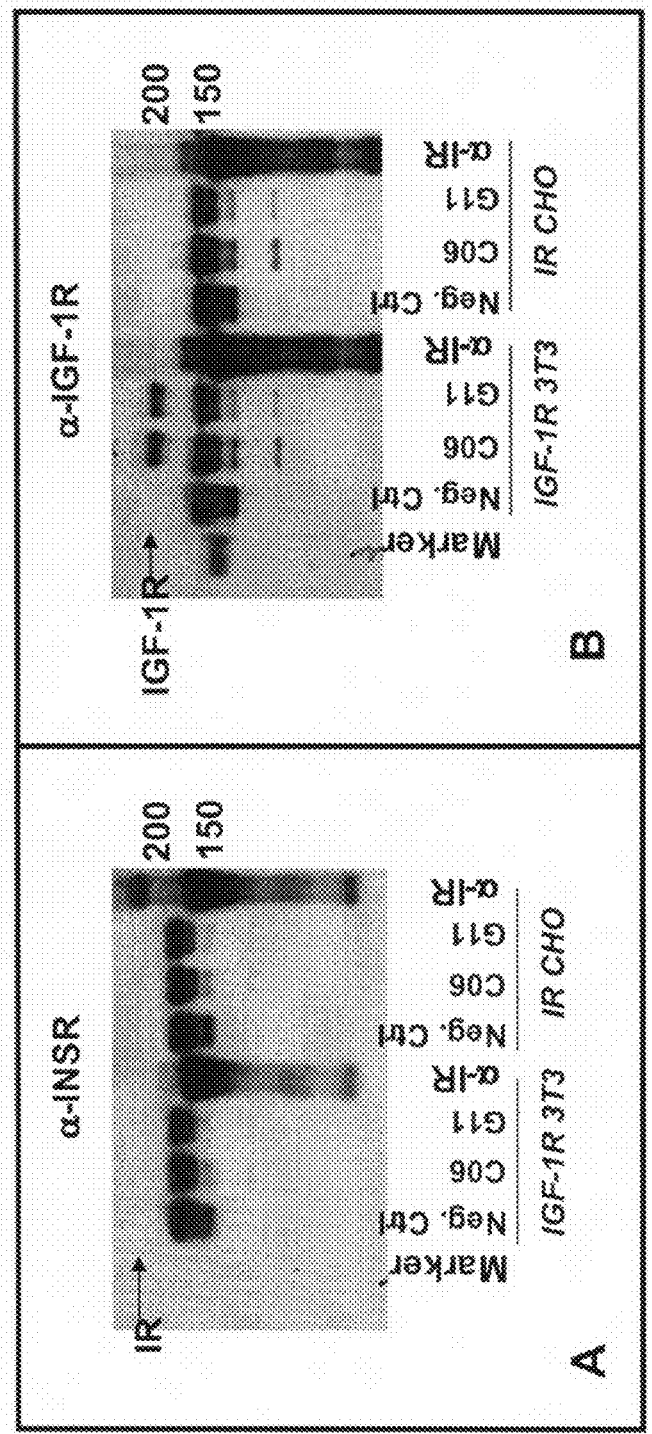
FIG. 26: Immunoprecipitation of IGF-1R and INSR in mammalian cells demonstrates M13.C06.G4.P.agly antibody binding to IGF-1R but not insulin receptor. IGF-1 R and INSR proteins were detected by immunoblot (Western blot) analysis with mouse anti-human IR (A) or mouse anti-human IGF-1R (B).

Recombinant IGF-1R and insulin receptor (IR) were independently expressed in mammalian cells (3T3 or CHO). Cells were solubilized with 1% Triton X-100 and the receptor was immunoprecipitated with protein-A/G beads coupled to a negative control antibody (IDEC-151), M13.C06.G4.P.agly antibody (C06), M14-G11.G4.P.agly antibody (G11), or an INSR antibody (α-IR). Antibody/antigen complexes were released from the beads by acid treatment, applied to Tris-Glycine SDS-PAGE gels and blotted to nitrocellulose membranes. Detection was performed using mouse anti-human IR (FIG. 26A) or mouse anti-human IGF-1R (FIG. 26B) and goat α-mouse IgG. Results: M13.C06.G4.P.agly antibody binds to IGF-1R but not to INSR expressed in mammalian cells.

Example 6

Construction of Full-Length Anti-IGF-1R IgGs

Four Fabs were converted to IgG4.P.agly version and expressed in CHO cells. DNA sequences encoding four distinct anti-IGF-1R Fabs-M13-C06 (FIGS. 5 (A)-(D)), M14-C03 (FIGS. 5(E)-(H)), M14-G11 (FIGS. 5(I)-(L)), and M14-B01 (FIGS. 5(M)-(P)) were selected from a human antibody phage library (Dyax Corp) by biopanning against a recombinant human IGF-1R ectodomain-Fc fusion protein. Each of the four anti-IGF-1R Fabs contained the V$_H$3-23 human heavy chain germline framework and were kappa light chains. The Fab gene sequences were used to construct expression plasmids encoding full-length anti-IGF-R1 antibodies using the pV90AS expression vector system for antibody production in mammalian cells. pV90AS is a modified pV90 expression vector designed to generate two transcripts from a single promoter through alternate splicing of a primary transcript (Reference: USPTO Application WO2005/ 089285). The natural CMV splice donor is spliced either to a partially impaired splice acceptor to generate an antibody light chain-encoding transcript, or to a natural CMV splice acceptor to generate the antibody heavy chain-coding transcript. The partially impaired splice acceptor has been engineered to result in similar amounts of both heavy and light chain transcripts. Light chain Variable (VL) and Constant (CL) regions (SEQ ID NOs:153 and 154, FIG. 5(Y)-(Z)) of each anti-IGF-1R Fab (M13-C06; M14-C03; M14-G11 and M14-B01) were amplified by PCR. (Table 7). The 5' light chain PCR primer IGF1R-FK included a Sfi I restriction endonuclease site followed by sequence encoding an immunoglobulin light chain signal peptide MDMRV-PAQLLGLLLLWLPGARC (SEQ ID NO:157) in frame to sequences corresponding to the amino-terminus of the VL region according to the methods described in Nakamura T, et al., *Int J Immunopharmacol.* 22:131-41 (2000), which is incorporated herein by reference in its entirety. All four of the mature IGF1R light chain sequences had identical amino-termini. The 3' light chain PCR primer IGF1R-RK included sequence corresponding to the carboxyl-terminus of the CL region and an Asc I site. The PCR product was purified by agarose gel electrophoresis and extraction using the QIAquick GelExtration kit protocol (QIAGEN CA), digested with restriction endonucleases Sfi I and Asc I and ligated with the Sfi I/Asc I digested pHLP025 vector (Holly Prentice). The pHLP025 vector contains Sfi I/Asc I restriction endonuclease sites for receiving antibody light chain (signal peptide-VL-CL) as a Sfi I/Asc I digested PCR fragment in addition to the natural CMV splice donor site sequence, a partially impaired splice acceptor site sequence, and a poly A signal sequence (Reference: USPTO Application WO2005/089285).

The heavy chain Variable (VH) region of each anti-IGF-1R Fab (M13-C06; M14-C03; M14-G11 and M14-B01) was amplified by PCR. The 5' heavy chain VH PCR primer IGF1R-FH included a Nco I restriction endonuclease site followed by sequence encoding synthetic heavy chain signal peptide MGWSLILLFLVAVATRVLS (SEQ ID NO:122)) in frame to sequences corresponding to the amino-terminus of the VH region as described above. The 3' heavy chain VH PCR primer IGF1R-RH included sequence corresponding to the carboxyl-terminus of the VH region and an Sfi I site. The PCR product was purified by agarose gel electrophoresis and extraction using the QIAquick GelExtration kit protocol (QIAGEN, CA), digested with restriction endonucleases Nco I and Sfi I and ligated with the Nco I/Sfi I digested pHLP029 vector (Holly Prentice). The pHLP029 vector contains Nco I/Sfi I sites for receiving the antibody signal peptide-VH sequence as a Nco I/Sfi I digested PCR fragment in addition to an upstream poly A signal sequence, a natural CMV splice acceptor site sequence, and a downstream poly A signal sequence (Reference: USPTO Application WO2005/089285).

The gene sequences coding for (Sfi I site-light chain signal peptide-anti-IGF-1R VL and CL) in pHLP025 and (heavy chain signal peptide-anti-IGF-1R VH-Sfi I site) in pHLP029 were assembled into a single DNA fragment by PCR amplification through common overlapping sequences present in both vectors using the 5' light chain IGF1R-FK and 3' heavy chain VH IGF1R-RH PCR primers described above. The resulting PCR product was purified by agarose gel electrophoresis and extraction using the QIAquick GelExtration kit protocol (QIAGEN, CA), digested with restriction endonuclease Sfi I and ligated with the Dra III digested pXWU007 vector. Briefly, pXWU007 was first constructed by subcloning an Age I/BamHI human IgG4 constant region fragment containing a S228P mutation in the IgG4 hinge region and a T299A mutation in the $C_H2$ domain, EU numbering system (Kabat, E, Wu, T T, Perry, H M, Gottesman, K S, Foeller, C: Sequences of Proteins of Immunological Interest. Bethesda, US Department of Health and Human Services, NIH, 1991) (SEQ ID NOs:155 and 156, FIG. 5 (AA)-(BB)) from plasmid pEAG1808 (provided by Ellen Garber) into Age I/BamHI digested pHLP028 vector. pHLP028 is a pV90 IgG4 vector modified to contain a Dra III site for receiving the single Sfi I-digested PCR product described above (Reference: USPTO Application WO2005/089285).

The resulting plasmid produces a bi-cistronic precursor transcript that upon alternative splicing results in translationally active antibody heavy and light chain mRNAs in approximately stoichiometric quantities. Intermediate and expression vectors for producing full-length aglycosylated human anti-IGF-1R IgG4.P antibodies are shown in Table 8. Correct sequences were confirmed by DNA sequence analysis. Expression of full-length antibodies from plasmids pXWU020, pXWU022, pXWU024, and pXWU025 in mammalian cells results in production of stable, aglycosylated human IgG4.P antibodies.

TABLE 7

Oligonucleotides for PCR amplification of human antibody domains.

LC Primers

IGF1R-FK    5'-CGAACAGGCCCAGCTGGCCACCATGGACATGAGGGT
            CCCCGCTCAGCTCCTGGGGCTCCTTCTGCTCTGGCTCCC
            AGGTGCCAGATGTGACATCCAGATGACCCAG-3'
            (SEQ ID NO: 123)

IGF1R-RK    5'-TCGCACGGCGCGCCTCAACACTCTCCCCTGTTGAAG
            C-3'
            (SEQ ID NO: 124)

VH Primers

IGF1R-FH    5'-CGGCCACCATGGGTTGGAGCCTCATCTTGCTCTTCC
            TTGTCGCTGTTGCTACGCGTGTCCTGTCCGAAGTTCAAT
            TGTTAGAG-3'
            (SEQ ID NO: 125)

IGF1R-RH    5'-GGGATCGGCCAGCTGGGCCCCTTCGTTGAGGCGCTT
            GAGACGGTGAC-3'
            (SEQ ID NO: 126)

Forward 5' light chain PCR primer includes a Sfi I restriction endonuclease site (underlined) and sequence encoding the light chain signal peptide; Reverse 3' light chain PCR primer includes an Asc I site (underlined).
Forward 5' heavy chain variable PCR primer includes a Nco I restriction endonuclease site (underlined) and sequence encoding the heavy chain signal peptide.
Reverse 3' heavy chain variable PCR primer includes an Sfi I site (underlined).

TABLE 8

Intermediate and expression plasmids encoding anti-IGF-1R antibodies.

| Vector | Composition | Antibody chain (s) |
|---|---|---|
| pXWU008 | pHLP025 + C03 L | C03 VL-CL |
| pXWU010 | pHLP025 + C06 L | C06 VL-CL |
| pXWU012 | pHLP025 + G11 L | G11 VL-CL |
| pXWU013 | pHLP025 + B01 L | B01 VL-CL |
| pXWU014 | pHLP029 + C03 VH | C03 VH |
| pXWU016 | pHLP029 + C06 VH | C06 VH |
| pXWU018 | pHLP029 + G11 VH | G11 VH |
| pXWU019 | pHLP029 + B01 VH | B01 VH |
| pXWU020 | pXWU007 + C03 L-VH | C03 VL-CL + C03 VH-agly γ4.P |
| pXWU022 | pXWU007 + C06 L-VH | C06 VL-CL + C06 VH-agly γ4.P |
| pXWU024 | pXWU007 + G11 L-VH | G11 VL-CL + G11 VH-agly γ4.P |
| pXWU025 | pXWU007 + B01 L-VH | B01 VL-CL + B01 VH-agly γ4.P |

Example 7

Construction of Full-Length Anti-IGF-1R IgGs for Improved Expression in Mammalian Cells To improve antibody expression yields and product quality the original VH gene sequences from anti-IGF-1R Fabs M13-C06, M14-C03, M14-G11, and M14-B01 were modified. First, anti-IGF-1R VH sequences were analyzed for sequences containing putative splice sites with public sequence recognition programs (www.tigr.org/tdb/GeneSplicer/gene_spl.html (The Institute for Genomic Research, 9712 Medical Center Drive, Rockville, Md. 20850), www.fruitfly.org/seq_tools/splice.html (Martin G. Reese and Frank H. Eeckman, Lawrence Berkeley National Laboratory, Genome Informatics Group, 1 Cyclotron Road, Berkeley, Calif., 94720; see also, Reese M G, Eeckman, F H, Kulp, D, Haussler, D, 1997. "Improved Splice Site Detection in Genie". J Comp Biol 4(3), 311-23.). Second, codons in the heavy chain variable region of the anti-IGF-1R Fabs were replaced with codons corresponding to the identical Kabat positions from antibodies that have been successfully expressed in CHO cells without encountering any changes in the original anti-IGF-1R VH polypeptide sequence. This second step mostly removes putative splice sites but an additional splice site analysis followed by synonymous codon exchange was performed to reduce the predicted likelihood of a putative splice site being present.

DNA fragments encoding synthetic heavy chain leader in frame with sequence-optimized VH sequences of anti-IGF-1R Fabs-M13-C06 (SEQ ID NO:18, FIG. 5(Q)), M14-C03 (SEQ ID NO:30, FIG. 5(S)), M14-G11 (SEQ ID NO:36, FIG. 5(U)), and M14-B01 (SEQ ID NO:24, FIG. 5(W)) were obtained as chemically synthesized double-stranded DNA sequences from a commercial provider (Blue Heron Biotechnology, Inc. Bothell Wash.). The Nco I and Sfi I restriction endonuclease sites at 5' and 3' were included in the synthesized fragments. The leader and anti-IGF1R sequence-optimized VH region fragments were cloned into the Nco I/Sfi I digested the pHLP029 vector as described in Example 6 above. Recombination with the appropriate corresponding light chains in pHLP025 and subsequent cloning of the single fragment into pXWU007 is as described in Example 6 above. Expression constructs producing the sequence-optimized full-length aglycosylated human anti-IGF-1R IgG4.P antibodies are shown in Table 9. Correct sequences were confirmed by DNA sequence analysis. Expression of full-length antibodies from the plasmid series pXWU029-pXWU032 in mammalian cells results in production of stable, aglycosylated human IgG4.P antibodies.

TABLE 9

Sequence-optimized expression plasmids encoding anti-IGF-1R antibodies. Optimized heavy chain sequences are preceded with an "m".

| Vector | Composition | Antibody chain (s) |
|---|---|---|
| pXWU029 | pXWU007 + C03 L-mVH | C03 VL-CL + mC03 VH-agly γ4.P |
| pXWU030 | pXWU007 + C06 L-mVH | C06 VL-CL + mC06 VH-agly γ4.P |
| pXWU031 | pXWU007 + G11 L-mVH | G11 VL-CL + mG11 VH-agly γ4.P |
| pXWU032 | pXWU007 + B01 L-mVH | B01 VL-CL + mB01 VH-agly γ4.P |

Example 8

Transient Expression and Characterization of IGF-1R Antibodies

Plasmid DNAs were used to transform CHO DG44 cells for transient production of antibody protein. 20 µg of plasmid DNA was combined with 4×10$^6$ cells in a volume of 0.4 mL of 1×PBS. The mixture was added to a 0.4 cm cuvette (Bio-Rad) and placed on ice for 15 min. The cells were electroporated at 600 uF and 350 volts with a Gene Pulser electroporator (BioRad). The cells were placed into a T-25 flask containing CHO-SSFM II media plus 100 uM Hypoxanthine and 16 uM Thymidine and incubated at 37° for 4 days. Supernatants were harvested and biochemically characterized by Western Blot and tested for antigen binding by ELISA.

Alternatively, selected Fabs also converted to full-length human IgG4.P version and expressed using a different vector system by a method described below. DNA sequences encoding five distinct anti-IGF1R Fab antibodies, M12-E01, M12-G04, M13-C06, M14-C03, and M14-G11 were transferred into vectors for expression of full-length human IgG4.P. All five antibodies use the $V_H3$-23 human heavy chain germline fragment. The variable heavy chain was removed from the soluble Fab expression vector by digestion with restriction enzymes MfeI and BstEII. The resulting fragment was purified by agarose gel electrophoresis using the QIAquick Gel Extraction Kit (Qiagen, CA) and ligated into the MfeI/BstEII digested pRR253 vector (Rachel Rennard). The resulting plasmid contains the heavy chain signal peptide (MGWSCI-ILFLVATATGAHS, SEQ ID NO:127) followed by the anti-IGF1R VH and constant regions for human IgG4.P.

Four of the five antibodies, M12-G04, M13-C06, M14-C03, and M14-G11, contain kappa light chains. The variable light chain was amplified by PCR with primers to introduce an EcoRV site 5' and a BsgI 3' to the variable region. The resulting PCR fragment was purified by agarose gel electrophoresis using the QIAquick Gel Extraction Kit (Qiagen, CA) and ligated into TOPO2.1 TA vector (Invitrogen, CA). The variable kappa light chain was removed from the TOPO vector by digestion with restriction enzymes EcoRV and BsgI and purified. The fragment was ligated into EcoRV/BsgI digested pRR237 vector, which contains the immunoglobulin light chain signal peptide (MDMRVPAQLLGLLLLWLR-GARC, SEQ ID NO:128) and the constant kappa domain. The resulting vector was digested with BamHI and NotI and the entire expression cassette (signal sequence, variable and constant kappa domains) was purified and ligated into BamHI/NotI digested pRR223.

The M12-E01 antibody contains a lambda light chain. The variable light chain was amplified by PCR with primers to introduce an AgeI site 5' of the variable region. The resulting PCR fragment was purified by agarose gel electrophoresis using the QIAquick Gel Extraction Kit (Qiagen, CA) and ligated into TOPO2.1 TA vector (Invitrogen, CA). The variable lambda light chain was removed from the TOPO vector by digestion with restriction enzymes AgeI and AvrII and purified. The fragment was ligated into AgeI/AvrII digested pXW347 vector (Xin Wang), which contains the immunoglobulin light chain signal peptide (METDTLLLWVLLL-WVPGSTG, SEQ ID NO:129) and the constant lambda domain. The resulting vector was digested with NotI and the entire expression cassette (signal sequence, variable and constant lambda domains) was purified and ligated into NotI digested pRR223.

Plasmid DNA was used to transfect 293E cells for transient expression of antibody protein. 1.2 µg of each (heavy and light) plasmid DNA was transfected into 2×10$^6$ cells with Qiagen's Effectene Transfection Protocol (Qiagen, CA). Cells were incubated at 37° C. for 3 days. Supernatant was harvested and full-length antibody confirmed by both Western Blot and ELISA methods. The ability of full.IgG4.P to bind to IGF-1R was confirmed by ELISA.

Example 9

Development of Anti-IGF-1R Antibody Producing CHO Cell Line

This example gives a detailed description of expression of the anti-IGF-1R antibody comprising the binding domain of the Fab M13-C06 as full-length hinged-modified agly gamma 4, kappa (referred to herein as "agly.IgG4.P" or "G4.P.agly") antibody. The other Fabs described herein, i.e., those listed Table 3, were expressed in a similar manner. The variable and constant regions of M13-C06 are of human sequence origin. The entire light chain and heavy chain variable regions are derived from a Fab generated against human IGF-1R by the DYAX phage display technology. The variable, as well as the light chain constant regions were subcloned into an alternate splice expression vector. The alternate splice configuration links the light and heavy chain through the usage of a single splice donor with two splice acceptors where each splice acceptor generates a transcript encoding one of the two chains. The expression vector DNA encoding the immunoglobulin genes was electroporated into insulin independent Chinese hamster ovary cells (CHO DG44i). A CHO transfectoma (cell line 40B5) was selected for production purposes.

pXWU007—an "empty" expression vector contains a human gamma 4 constant region (heavy chain) as well as separate promoter-enhancers and polyadenylation regions for gene expression in mammalian cells, but does not contain variable domains. When expressed and translated the heavy chain polypeptide contains two amino acid substitutions, S228P and T299A, to reduce "half-antibody" formation and eliminate N-linked glycosylation, respectively.

Complementary DNA from the corresponding variable (VL) and constant (CL) domains of the light chain gene of M13-C06 and the variable (VH) domain of the heavy chain gene of M13-C06 was cloned into the expression vector pXWU007. The pXWU007 vector contains cloning sites for inserting the entire light chain and variable heavy cDNAs directly upstream of the human heavy chain constant region. In addition to the Ig genes, this expression vector contains a dihydrofolate reductase (DHFR) gene that can be used for selection in mammalian cells.

The resulting expression vector was then transfected into CHO cells to initiate the generation of the anti-IGF-1R secreting CHO cell lines (40B5).

PXWU022 was electroporated into CHO cells. Immunoglobulin light chain specific PCR primers were used to PCR amplify the Fab light chain cDNA. The 5' specific oligo sequence included the native signal peptide from the light chain of the Biogen Idec anti-CD23 molecule. The 5' and 3' oligos contain Sfi I and Asc I restriction endonuclease recognition sequences, respectively, for subcloning into an intermediate vector (pHLP025). The VH cDNA was PCR amplified using a 5' oligo that included a synthetic heavy chain signal peptide. The 5' and 3' oligos contain Nco I and Sfi I restriction endonuclease recognition sequences, respectively, for subcloning into an intermediate vector (pHLP029).

Overlapping PCR using the light chain 5' and VH 3' oligos and pHLP025 and pHLP029 as templates was employed to combine the light chain and the VH region as one cDNA segment. The resultant product was subcloned into the Dra III site of pXWU007 thus creating the final alternate splice expression vector, pXWU022. The alternate splice configuration generates two transcripts from a single promoter through alternate splicing of the primary transcript. The natural CMV splice donor is spliced either to a suboptimal splice acceptor to generate a light chain-encoding transcript, or to a natural CMV splice acceptor to generate the heavy chain-coding transcript. The sub-optimal splice acceptor has been designed to generate similar amounts of both transcripts.

The DNA vector (pXWU022) was prepared in HEBS buffer at a concentration of ~700 ng/μL prior to electroporation in to CHO cells. Five electroporations were performed using various concentrations of DNA (15, 20, 30, 40, and 45 μg). Each electroporation was done in a disposable 0.4 cm cuvette (Invitrogen) containing $4 \times 10^6$ log phase CHO cells in 0.7 ml sterile HEBS buffer and DNA in 0.1 mL HEBS (0.8 mL total volume). Cells were shocked using a Bio-Rad Gene Pulser XCELL, set at 290 volts, 950 micro Faradays. Shocked cells were then allowed to stand at room temperature for 10 minutes then mixed with 10 mL room temp insulin free CHOM16 medium, centrifuged (3' @ 1000 rpm), and aspirated. Cells were then resuspended in 12 mL (room temp.) insulin free CHOM16 medium and transferred to a T-75 tissue culture flask.

Cells and Media: prior to electroporation the CHO cells were grown in serum free media (CHOM24) with the addition of 1× nucleosides. CHOM24 is a chemically defined in-house media formulation that does not contain any animal components. Methotrexate selection was performed in nucleoside free CHOM16 and CHOM24 chemically defined media.

Following electroporation, $4 \times 10^6$ CHO cells were pooled into a T-75 flask. Selection for DHFR expression began immediately as the cells were inoculated in nucleoside free medium. Cells were eventually expanded to 125 mL shake flasks in CHOM24 (~3 weeks). To isolate clonal cell lines, the transfected stable pools were diluted and plated at 1 cell/well in 200 μL CHOM16 on four 96-well plates. Plates were maintained at 36° C. until they were screened for antibody titer.

CHO colonies were screened for immunoglobulin production by assaying cell supernatants using an ELISA specific for the human kappa chain (day 21 to day 28 after plating). The capture antibody used in the ELISA was a polyclonal goat anti-human IgG (SouthernBiotech) and the detection antibody was a polyclonal goat anti-human kappa conjugated to horseradish peroxidase (SouthernBiotech). Colonies secreting the highest amount of immunoglobulin were expanded.

A total of 381 nearly confluent wells of the 1920 wells seeded were assayed. Of the 381 wells, 60 were expanded for further study and of these 60, 4 were selected for amplification (15A7, 40B3, 40B5, 40F6).

Example 10

Purification and Characterization of Fully Human Anti-IGF-1R IgG4.P.agly Antibodies The antibody produced in CHO cells were purified and characterized by methods described below.

Protein A Capture: Pre-equilibrate the Protein A column with 1×PBS (equilibration buffer) at 100-150 cm/hr with 3 column volumes. Load the supernatant at 150 cm/hr with a maximum of 10 mg of αIGF-1R per milliliter of resin. After loading, wash the column with 5 column volumes of equilibration buffer. Then, step elute in an upflow direction with 100 mM Glycine, pH 3.0. Collect desired fractions and titrate to neutral pH with 2M Tris base. Dialyze collected fractions against 1×PBS and concentrate material to prepare for the size exclusion step.

SUPERDEX™ 200 (Size Exclusion) aggregate removal step involved equilibration of SUPERDEX™ 200 with 1×PBS with 1.5 column volumes at a flow rate of 36 cm/hr followed by loading of protein and collecting desired fractions.

Identity testing performed as follows

1). Intact mass analysis by mass spectrometry where molecular mass measurements were performed on an electrospray mass spectrometer (ESI-MSD). Prior to analysis, the sample was reduced to remove disulfide bonds. The deconvoluted mass spectrum represents the masses of the heavy and light chains.

2). N-terminal sequence analysis was performed by Edman degradation using an ABI protein sequencer equipped with an on-line PTH analyzer. The sequences for the initial amino acids of the light chain and heavy chain were identified.

3). Peptide mapping with mass spectrometric analysis: tryptic or/and EndoLysC peptide maps were performed to obtain complete sequence coverage by analysis of the LC/MS data generated from each peptide. In addition, determination of sites and amounts of oxidation and deamidation were detected.

Purity testing was performed by; 1) SDS-Page or CE-SDS: Reduced and non-reduced samples, this technique is used to measure antibody fragmentation, aggregation and impurities, 2) SEC-HPLC with LS and RI technique was used to measure aggregation and fragmentation and light scattering determines the molar mass of sample components. 3) SDS gel or capillary IEF method was used to determine the isoelectric focusing pattern and pI distribution of charge isoforms that can result from C- and N-terminal heterogeneity and/or deamidation.

Finally, endotoxin concentrations were measured by the *Limulus* amoebocyte lysate (LAL) kinetic turbidometric method.

Figure 6:
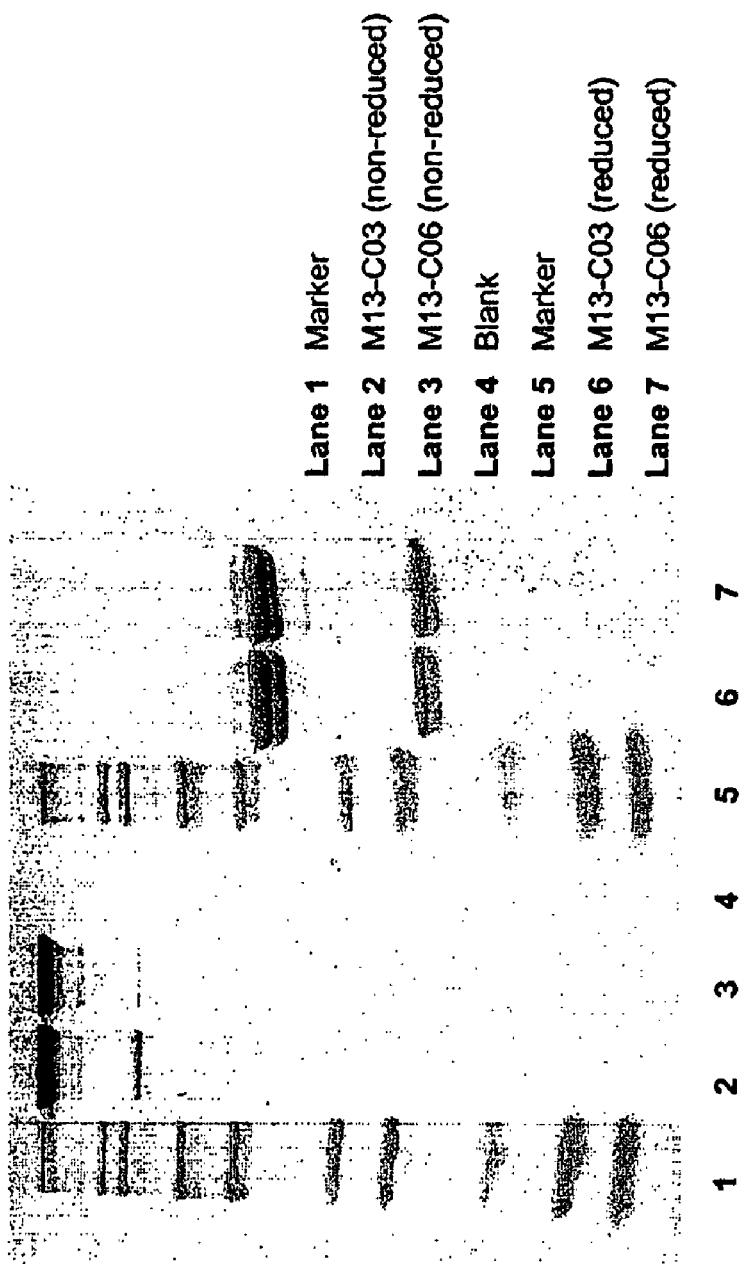
FIG. 6: Non-reduced and reduced SDA PAGE analysis of G4.P.agly versions of fully human M13-C06 and M14-C03 antibodies.

FIG. 6 shows non-reduced and reduced SDS PAGE analysis of G4.P.agly versions of fully human M13-C06 and M14-C03 antibodies. Both G4.P and G4.P.agly versions of antibodies M13-C06, M14-C03, M14-B01, and M14-G11 were produced. M12-E01 and M12-G04 were produced on as the G4.P version.

Example 11

Binding Activity of Fully Human Anti-IGF-1R Antibodies

The binding activity to soluble IGF-1R of the G4.P.agly and G4.P versions of antibodies tested by ELISA. Soluble IGF-1 receptor fusion protein (Biogen Idec) at 2.5 µg/ml in 0.025 M carbonate buffer, pH 9.6 was coated at 50 µl/well in a 96-well (IMMULON2 HB, Dynex Technologies, Inc., Cat. #3455) plate and incubated overnight at 4° C. The plate was washed with phosphate-buffered saline (PBS, Irvine Scientific, Cat#9240), pH 7.4 plus 0.025% Tween 20 in the Skan Washer 300 (Skatron Instruments), blocked with buffer containing 1% nonfat milk, 0.05% Tween 20 in PBS, pH 7.4, and then incubated at room temperature for 1 hour. After incubation plate was washed with PBS plus 0.025% Tween 20 in the Skan Washer 300. For the assay, the soluble IGF-1 receptor-coated plate was next incubated with the control and test antibodies of varied concentrations, diluted in 1% nonfat milk, 0.05% Tween 20 in PBS at 50 µl/well. Following a one hour incubation at room temperature, plate was washed with PBS plus 0.025% Tween 20 in the Skan Washer 300. A 2000-fold dilution in 1% nonfat milk, 0.05% Tween 20 in PBS of goat anti-human Kappa—HRP (Southern Biotech Cat#2060-05) was added 50 µl/well to detect bound antibody. Plate incubated for 1 hour at room temperature was washed with PBS plus 0.025% Tween 20 in the Skan Washer 300. TMB solution (KIRKEGAARD & PERRY LABS, INC. cat: 50-76-00) was added 100 µl/well, and the reaction was stopped with 50 ul/well of 4N $H_2SO_4$ (LabChem, Cat#LC25830-1) after two minutes. The absorbance was measured at 450 nm, background 540 nm for TMB using the Molecular Devices plate reader. Data was analyzed using the SOFTMAX PRO software package version 4.3 LS (Molecular Devices Corp.).

FIG. 7 (A) shows the concentration dependent binding of G4 version of M13-C06, M14-C03, M14-G11, M12-E01 and M12-G04, whereas the control antibody, IDEC-151 (G4.P) again did not show any binding to IGF-1R.Fc.

FIG. 7 (B) shows the concentration dependent binding of G4.P.agly version of M13-C06, M14-C03 and M14-B01 to soluble IGF-1R.Fc by ELISA. A G4.P antibody of irrelevant specificity (IDEC-151) used as a negative control did not show any binding to IGF-1R.Fc.

The binding activity of human antibodies to wild type IGF-1R expressed on tumor cells was determined by flow cytometry. Tumor cell lines MCF-7 and Calu-6 were cultured in Minimum Essential Medium Eagle (ATCC, Cat#30-2003) supplemented with 10% fetal bovine serum (FBS) (Irvine Scientific, Cat#3000A) and 50 µ/ml gentamicin (Gibco Invitrogen, Cat#15750-060). Panc-1, Colo-205, NCI-H23 and ZR-75 were cultured in RPMI-1640 (ATCC, Cat#30-2001) supplemented with 10% FBS and 50 µg/ml gentamicin. Trypsin-EDTA (Sigma, Cat#T4049) solution was used for removal of adherent cells from culture vessels.

Cells were rinsed twice with phosphate buffered saline (PBS) (Irvine Scientific, Cat#9240), pH 7.4, trypsinized and washed once in PBS and 10% FBS. Cells were adjusted to $10^7$ cells/ml in FACS buffer (0.05% sodium azide, 2% FBS, 10% normal goat serum and 100 µg/ml normal goat IgG in PBS) and put on ice for at least 15 minutes. Control and test antibodies were aliquoted into a Corning 3790 plate. Cells at 50 µl/well were added to a Corning 3799 plate. Primary antibodies from Corning 3790 plate were added at 50 µl/well to respective wells of Corning 3799 plate. Next, cells (0.5×$10^6$ cells/sample) were incubated 45 min on ice. Following incubation plates were centrifuged at 1500 rpm for 4 minutes and then supernatants were aspirated. Cells were resuspended in 150 µl of FACS buffer. Plates were centrifuged at 1500 rpm for 4 minutes and supernatants were aspirated. A 750-fold dilution in FACS buffer of goat anti-human IgG-RPE (Southern Biotech Cat#2040-09) was added 100 µl/well. Next, cells (0.5×$10^6$ cells/secondary antibody) were incubated 45 min on ice. A 500-fold dilution in FACS buffer of 7AAD (Molecular Probes, Cat#A1310) was added 50 µl/well and incubated for 5 minutes on ice. Following incubation plates are spun at 1500 rpm for 4 minutes and then supernatants were aspirated. Cells were resuspended in 150 µl of FACS buffer. Plates were centrifuged at 1500 rpm for 4 minutes and supernatants were aspirated. Cells were resuspended in 100 µl/well of FACS buffer. Cells were transferred to 12×75 mm FACS tubes with 200 µl of FACS buffer. Finally, cells were examined for fluorescence intensity on a FACSCalibur using CellQuest software (both from Becton Dickinson).

FIG. 8 shows the concentration dependent binding of M13-C06.G4.P.agly, M14-C03.G4.P.agly and M14-G11.G4.P to IGF-1R expressed on MCF-7 cells (FIG. 8(A)). The cell-surface binding specificity of antibodies was confirmed by testing binding to IGF-1R/3T3 transfectants and 3T3 parent cells. All of the lead antibodies showed specific reactivity to IGF-1R expressing 3T3 but not to 3T3 cells (FIG. 8(B)).

Example 12

Inhibition of Ligand Binding to IGF-1R by Fully Human Antibodies

Figure 9:
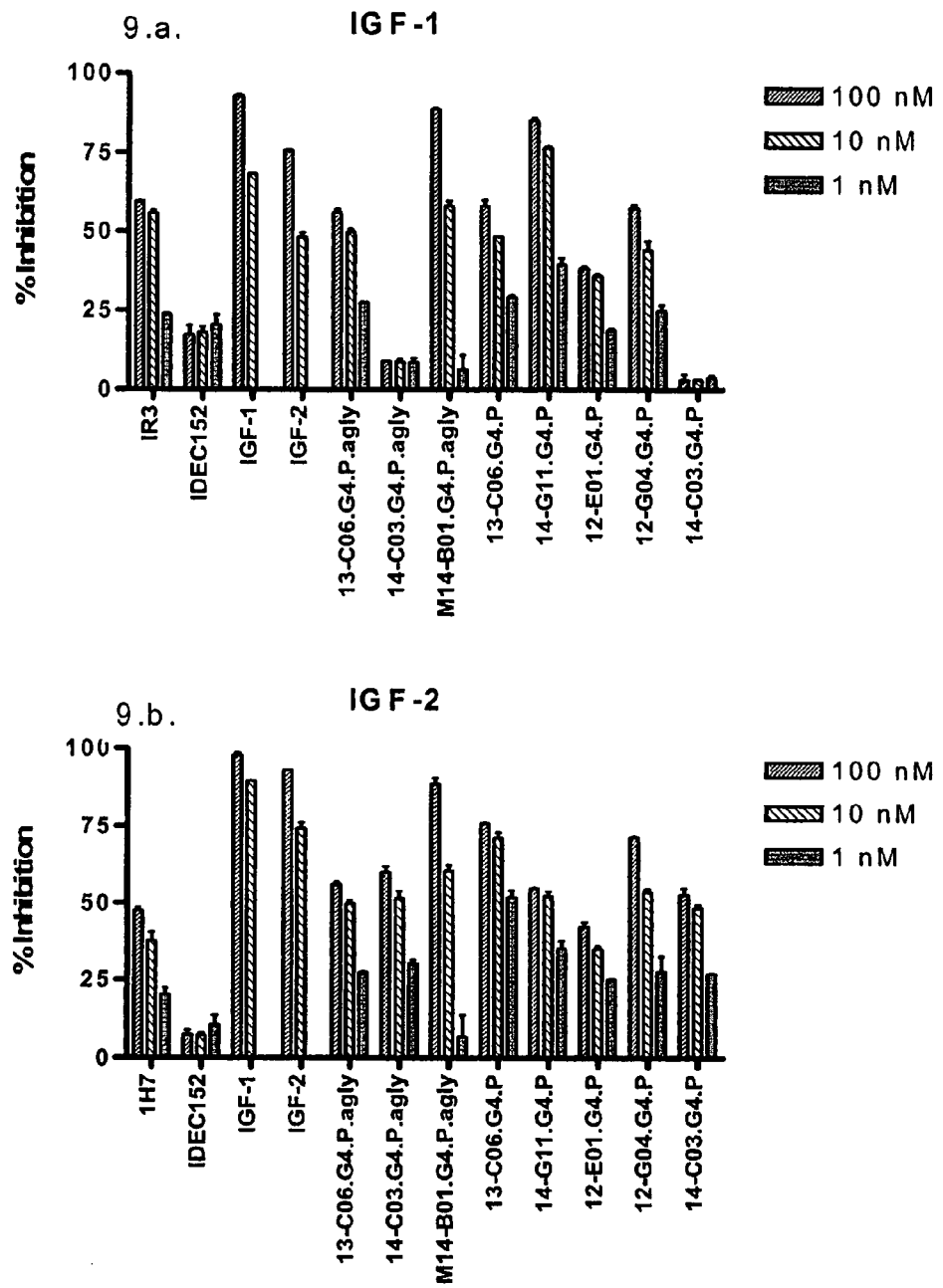
FIG. 9: The ability of G4 versions of fully human antibodies to block IGF-1 (a) and IGF-2 (b) binding to IGF-1R was determined by an RIA.

The ability of the G4.P.agly and G4.P versions of human antibodies to block IGF-1 and IGF-2 binding to soluble IGF-1R-Fc was determined. The IgG4 versions of M13-C06, M14-G11, M14-B01, M12-E01 and M12-G04 blocked both IGF-1 and IGF-2 binding to IGF-1R, whereas M14-C03 only blocked IGF-2 (FIGS. 9 (A) and (B)).

The ligand blocking ability of the anti-IGF-1R antibody was determined by a solid phase RIA capture method as described in Example 3. Briefly, the antibodies at varying concentrations were (100 nM-0.01 nM) co-incubated with 100,000 cpm of $^{125}$I-labeled IGF-1 or 125I-IGF-2 in the wells of a 96-well IMMULON2 plate, wherein human IGF-1R-Fc was previously immobilized (200 ng/well). After 1 hour of incubation at room temperature, the wells were washed and counted for bound radioactivity by a Gamma Counter. An isotype matched negative antibody control, IDEC-151 (human G4), was used. Percent (%) inhibition was calculated as =[1−(Ave.CPM with Ab)/(Ave.CPM with buffer)]×100%.

The result demonstrate that fully human antibodies M13-C06.G4.P, M13-C06.G4.P.agly, M14-G11.G4.P, M14-G11.G4.P.agly, M14-B01.G4.P.agly, M12-E01.G4.P, and M12-G04.G4.P block both IGF-1 and IGF-2 binding to IGF-1R, whereas, the antibodies M14-C03.G4.P and M14-C03.G4.P.agly block only IGF-2 binding to IGF-1R. See, FIG. 9(A)-(B).

Example 13

Inhibition of Tumor Cell Growth by Fully Human Anti-IGF-1R Antibodies

The ability of antibodies to block IGF-1 and IGF-2 driven tumor cell growth was tested using a cell viability assay.

NCI-H23, Calu-6, Colo-205, Panc-1, BxPC-3 (ATCC) tumor lines were purchased from ATCC. Cell lines were grown in complete growth medium containing RPMI-1640 (ATCC), 10% fetal bovine serum (Irvine Scientific Inc.) and 50 μg/ml of Gentamycin (Gibco, Invitrogen). Trypsin-EDTA solution (Sigma) was used for removal of adherent cells from culture vessels. Phosphate buffered saline, pH 7.2, was from MediaTech Inc The 96-well clear bottom plates for luminescent assay was purchased from Wallac Inc.

Cells grown to 80% monolayers were, trypsinized, washed, resuspended and plated into 96-well plates in 200 μl of 2% growth medium at 8×10$^3$ cells/well for NCI-H23 and Colo-205 cells; and 5×10$^3$ cells/well for Calu-6, Panc-1 and BxPC-3 cells. After 24 hours, the culture medium was replaced with 100 μl of serum free medium (SFM), and 50 μl of serially diluted antibodies at 4× concentration was added. Following another hour of incubation at 37° C., 50 μl of IGF-1 or IGF-2 at 4× concentration was added and incubated at 37° C. until 48 hours to measure cell growth. All treatments were done in triplicates. Cell growth was measured using the CELL TITER-GLO™ Luminescent Cell Viability Assay (Promega, Madison, Wis.). The 1:1 mixture of reagent and SFM was added at 200 μl/well. Luminescence was detected on Wallac (Boston, Mass.) plate reader.

Figure 10A:
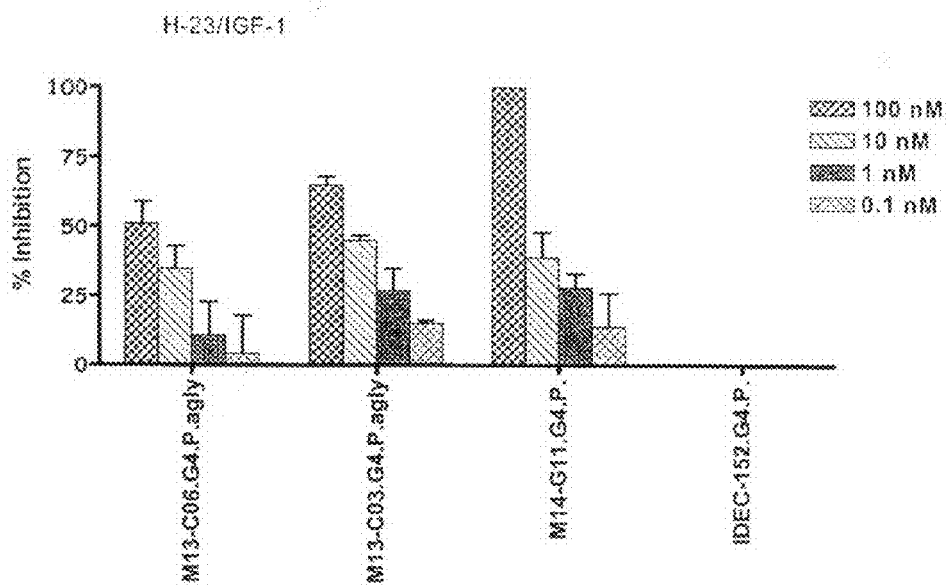
FIG. 10: (a) Inhibition of H-23 tumor cell proliferation in response to IGF-1 by G4 versions of fully human antibodies; (b) Inhibition of H-23 tumor cell proliferation in response to IGF-2 by G4 versions of fully human antibodies; (c) Inhibition of Calu-6 tumor cell proliferation in response to IGF-1 by G4 versions of fully human antibodies.
Figure 10B:
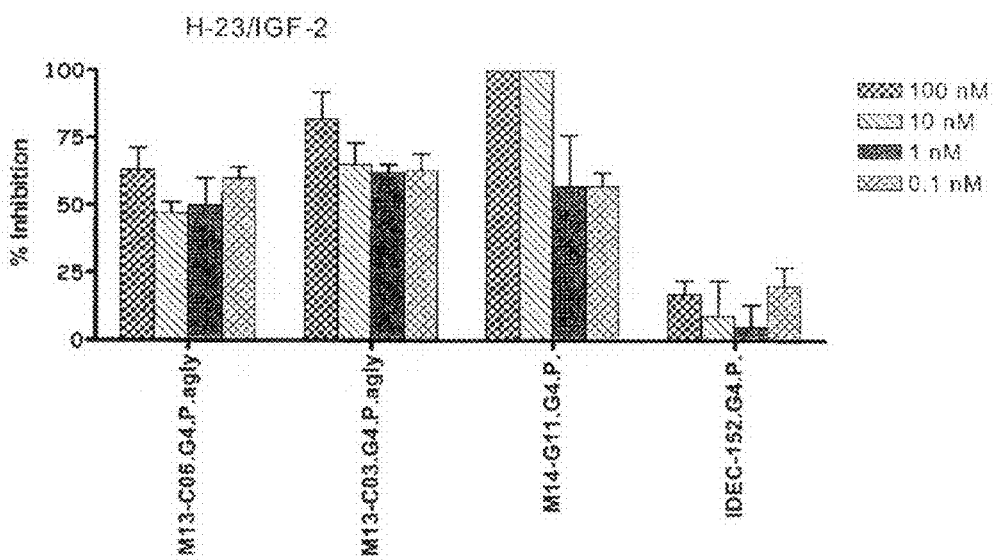
Figure 10C:
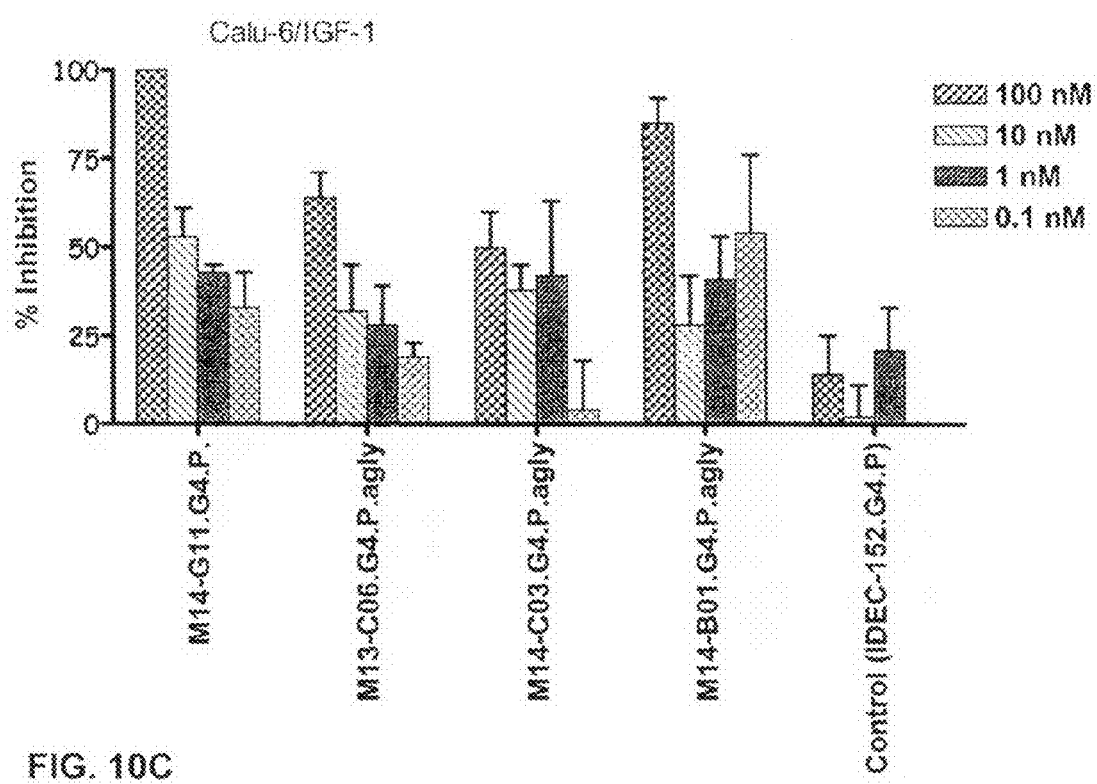

The various human IgG4 versions of the anti-IGF-1R antibodies exhibited inhibition of IGF-1 and IGF-2 driven cell proliferation in H-23 (IGF-1 and IGF-2) Calu-6 (IGF-2) cells (FIG. 10(A)-(C)). Other cell lines exhibited comparable trends (see e.g., Example 20).

Example 14

Internalization of IGF-1R by Fully Human Anti-IGF-1R Antibodies

MCF-7 cells were seeded at 50,000 cells per well into 8 well chamber slides (Becton Dickinson Collagen Type 1 coated culture slides, BD BioCoat™ #354630) 48 hours prior to staining procedures. Cells were routinely maintained below 20 passages. On day of staining procedures, culture media was discarded from each well and replaced with 500 μl cold incubation buffer (MEM Eagle ATCC #30-2003+1% BSA). Cells were washed 2× with this buffer for 3 min each wash. 250 μl of each mAb or human G4.P.agly antibody to be tested was then added to the appropriate well at a concentration of 10 μg/ml, diluted in incubation media, and incubated on ice for 1 hour. A murine anti-human-IGF-1R antibody (Lab Vision/NeoMarkers, clone 24-31 cat#MS-641) was used as a positive control antibody to compare degree of internalization. After the 1 hour incubation on ice, the time zero (t=0') slide was washed 3× with 500 μl of cold wash buffer (PBS+1% BSA+2% Goat serum) for 3 min each wash (slides always kept on ice!). The t=0 slide was then fixed with 500 μl 4% paraformaldehyde (diluted with PBS from 16% stock; EMS #15710) for 15 minutes at room temperature. The t=0 slide was then washed again 3× with cold wash buffer for 3 minutes each wash, then left on ice. Meanwhile, the remaining slides were put into a 37° C. incubator for their designated time points (15 and 60 minutes). At the end of their incubation time each slide followed the same procedures as above—washes and fixation, and put on ice. All slides were then permeabilized with 200 μl cold permeabilization buffer (Wash buffer+0.5% Triton-X) for 10 minutes on ice. All slides were then washed 3× with 500 μl cold wash buffer for 3 minutes each wash. The secondary antibody was prepared at a 1:1000 dilution (AlexaFluor 488 Goat-anti-mouse IgG (H+L), Molecular Probes #A11029 for the mAbs and AlexaFluor 488 Goat-anti-human IgG (H+L), Molecular Probes #A11013 for G4 antibodies) in wash buffer, after an initial spin of the stock vial at 10,000 rpm for 10 min at 4° C. 250 μl of the diluted secondary antibody was added to each well and incubated for 40 min at room temperature in the dark (covered). Slides were again washed 3× with 500 μl cold wash buffer. On the final wash, the buffer was discarded and all wells were left empty. The chambers were then disassembled from the slide using the provided disassembly tool, and cover slips were mounted with Vectashield mounting medium containing DAPI (Vector #H-1500, Hard Set™). Slides were stored at 4° C. in the dark overnight to allow the mounting medium to dry.

Pictures of the slides were taken with a confocal microscope using the LaserSharp 2000 program (BioRad v5.2) and represented as a merge of blue and green components from Kalman 10 average.

M13-C06.G4.P.agly showed rapid internalization of IGF-1R in 60 min as shown in FIG. 13A. Both M14-C03.G4.P.agly and M14-G11.4.P all showed internalization property similar to M13-C06.G4.P.agly antibody (data not shown). As expected the positive control, clone 24-31, also internalized the receptor whereas isotype matched negative controls (mouse 7F2 and human G4, IDEC-152.G.P (primatized antibody)) did not bind or internalize (FIG. 13(B)-(C)).

In addition, the rate of receptor internalization was measured by a FACS based method for certain of the murine monoclonal antibodies. MCF-7 cells grown to 70% confluent monolayers were lifted off the flask with cell dissociation buffer (Gibco catalog #13151-014). Cells resuspended in media and $5\times10^6$ cells were added into 12×75 mm tube (Falcon catalog#352054), where each tube represents a different mAb to be tested. 10 µg/ml mAb was added to its corresponding tube in 0.5 ml FACS buffer containing no azide (PBS+1% BSA) as well as a control tube with no antibody for measuring experimental internalization error. Tubes were incubated on ice for 1 hour 15 minutes then washed and reconstituted in 1 ml FACS buffer. 100 µl of each sample was removed into 1 well of a 96 well u-bottom plate (NUNC #163320) kept on ice to prevent internalization and termed time zero (t=0). This was used as a 100% Ab bound control. Tubes were then transferred to a 37° C. water bath and 100 µl samples removed at time (t)=5, 10, 20, 40, and 60 minutes (later changed to 5, 10, 15, 30 and 60 minutes) and placed into separate wells of a 96 well u-bottom plate on ice. Once all samples were collected, the plates were spun at 1200 rpm in a 4° C. centrifuge to pellet cells. Antibody added to detect internalization of receptor was either anti-CD221-PE (BD Pharmingen cat#555999-anti-IGF-1R; 10µ/100 µl sample) to detect receptors remaining on cell surface, or Goat-anti-mouse-PE (Jackson ImmunoResearch Lab cat#115-116-146; 5 µg/ml) to detect antibody remaining on cell surface. Samples were incubated 1 hour in FACS buffer containing 0.1% Sodium Azide, washed ×1, and brought to a final volume of 200 l in FACS buffer containing azide. Samples were then run and collected using a FACSArray (BD) and geometric means determined. Also run PE-labeled Quantibrite beads (BD #340495) to quantitate the number of PE molecules bound to the cell surface, where the Quantibrite bead are run on the same FL2 setting as samples. The number of PE molecules bound to the bead is given in their packaging, allowing the quantitation of the number of PE molecules bound to the cell surface using geometric means of the sample and of the beads. The FACS assay showed that the murine monoclonal antibodies tested promoted internalization of IGF-1R (data not shown).

Example 15

Inhibition of IGF-1R Mediated Signaling by Fully Human Antibodies

Part I: Inhibition of Signal Transduction in MCF-7 Cells

Figure 11:
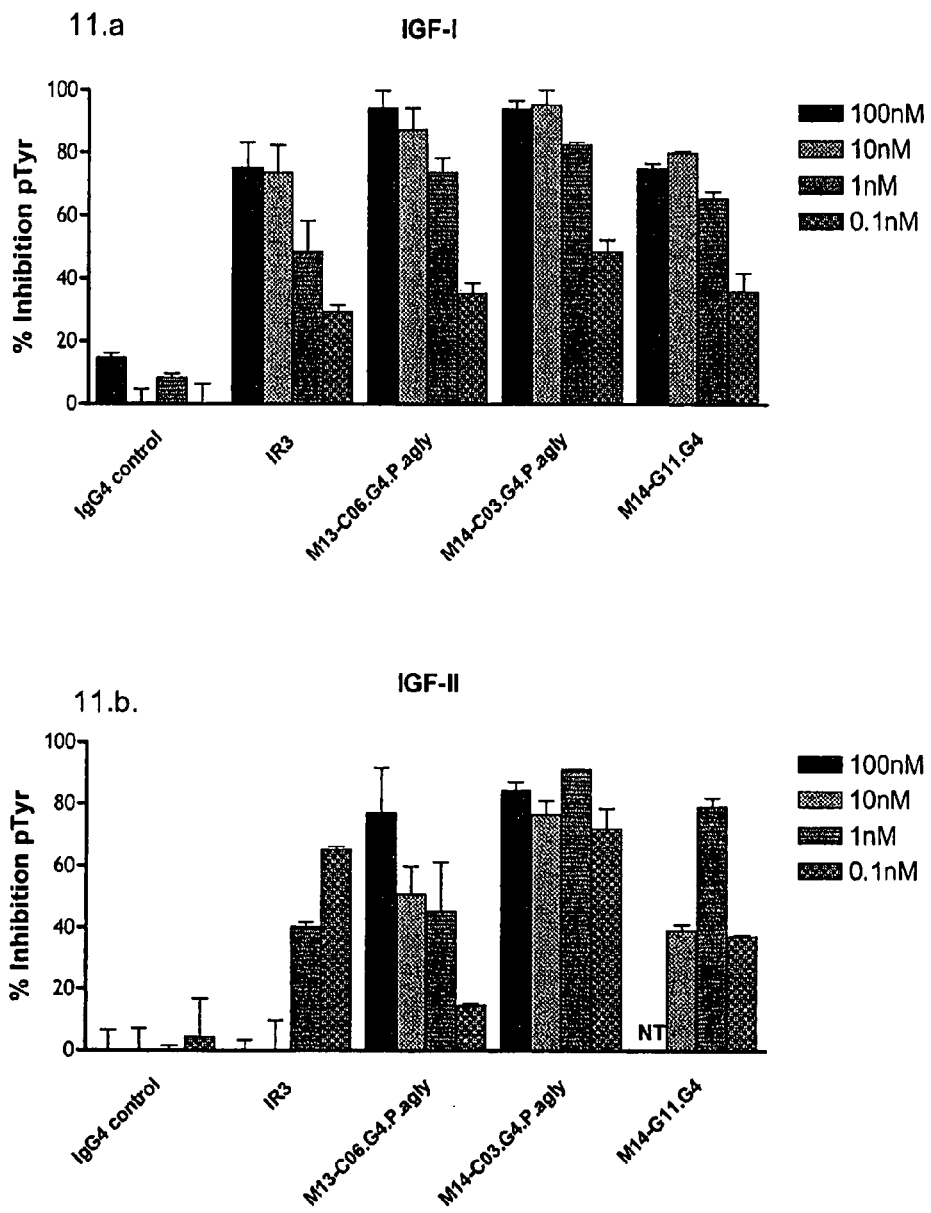
FIG. 11: Inhibition of IGF-1 (a) and IGF-2 (b) driven receptor phosphorylation by M13.C06.G4.P.agly, M14.C03.G4.P.agly and M14.G11.P antibodies.

The effect of human anti-IGF-1R antibodies on IGF-1R signaling was evaluated using MCF-7 cells (human breast adenocarcinoma cells). The ability of antibodies to block IGF-1 and IGF-2 mediated IGF-1R receptor phosphorylation was determined as described in Example 4. All of the IgG4 versions of the fully human antibodies showed good inhibition ($EC_{50}$<1 nM) and inhibited the phosphorylation of IGF-1R (FIGS. 11 (A & B).

To detect the effect on downstream signaling, cell lysates were generated as described in Example 4. For signaling experiments control and test antibodies were added after serum starvation at 100 nM, 15 nM, 5 nM and 1 nM in 350 µl of fresh serum free media and incubated for 1 hour at 37° C. Human recombinant IGF-1 at 13 nM or IGF-II at 27 nM (R & D Systems, #291-G1 and #292-G2) was added to wells in 35 µl serum free media and incubated at room temperature for 15 minutes. Cells were lysed and recovered sample separated using a 4-12% Bis-Tris gel and immobilized to nitrocellulose (Invitrogen Corp.). The IGF-1R signaling pathway was detected with phospho-Akt at site Thr308 (Cell signaling Technologies, #4056) and phospho-p44/42 MAPK at site Thr202/Tyr204 (Cell signaling Technologies, #9101) and anti-rabbit IgG-HRP (Cell Signaling Technologies, #7071). Bands were visualized using ECL luminol reagent (Amersham Biosciences, #RPN2109) and autoradiography. Each blot was stripped of antibody and re-probed respectively for total Akt (Cell signaling Technologies, #9272) or total p44/42 MAPK (Cell signaling Technologies, #9102) and anti-rabbit IgG-HRP. Bands visualized using ECL luminol reagent and autoradiography.

Figure 12B:
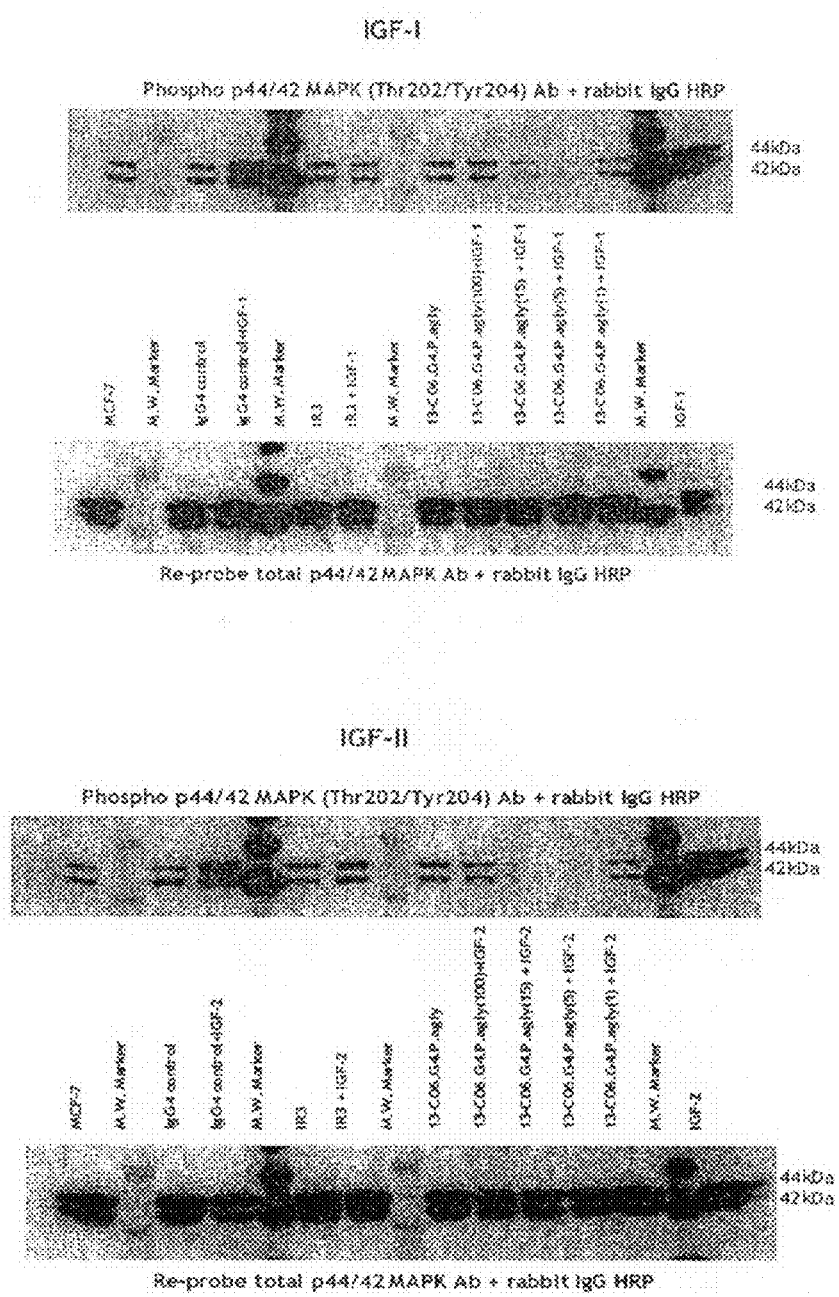
FIG. 12: Inhibition of downstream signaling by M13.C06.G4.P.agly. (a). Phospho Akt (Thr308) and total Akt have been shown in top and bottom rows respectively. (b) Top Phospho p44/42 MAPK and total p44/42 MAPK shown in top and bottom rows respectively.
Figure 14:
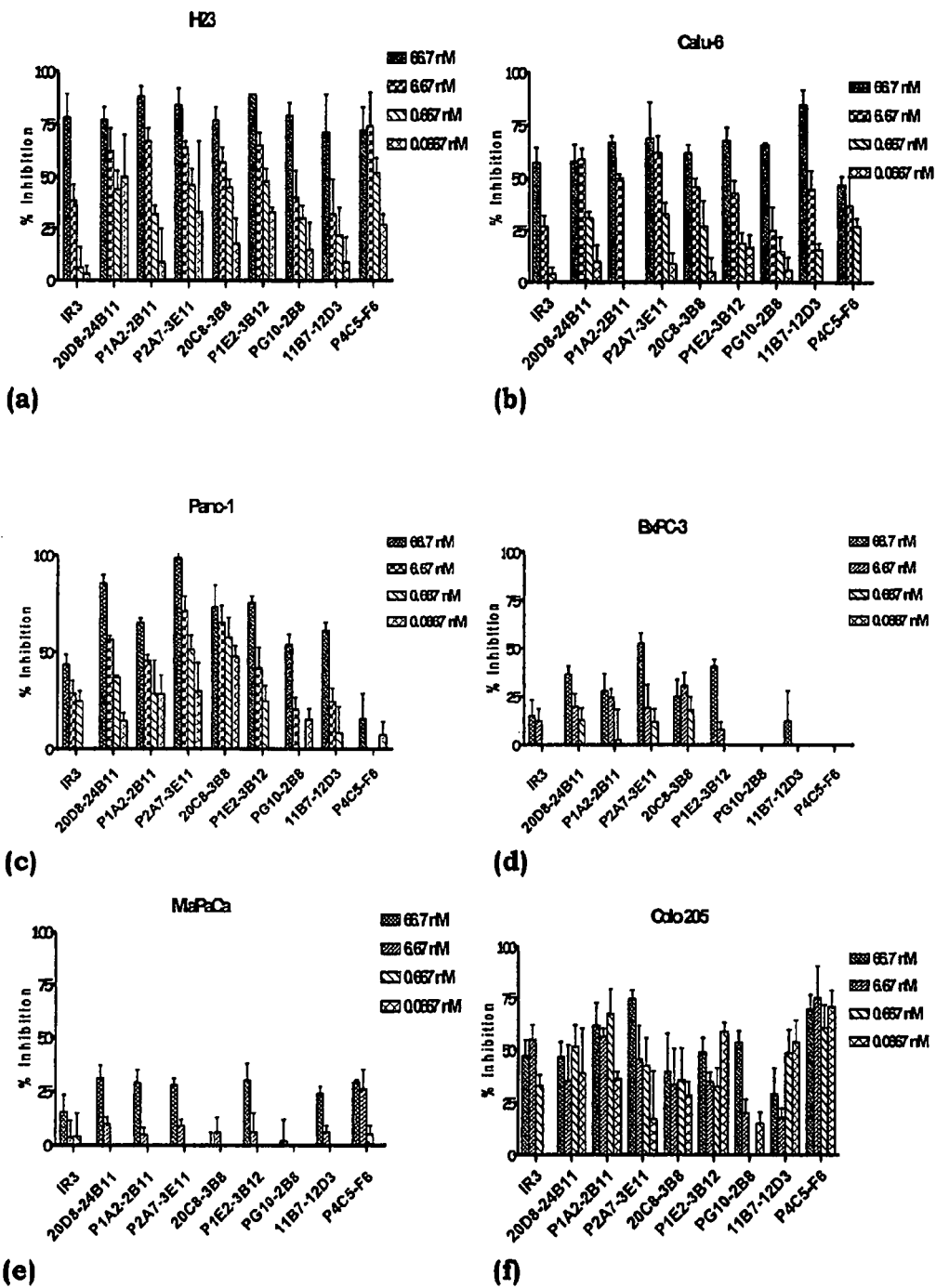
FIG. 14: Inhibition of IGF-1 mediated tumor cell growth by selected IGF-1R mAbs. (a) H23; (b) Calu-6; (c) Panc-1; (d) BxPC3; (e) MaPaCa; and (f) Colo205. Bars show means and SD.

The effect of antibody on down stream signaling events such as Akt and MAPK phosphorylation was determined. Cell lysates from autophosphorylation were immunoprecipitated with polyclonal IGF-1RP antibody-agarose conjugate (Santa Cruz Biotechnology, #SC-713). Recovered receptor protein was separated using a 4-12% Tris-Glycine gel and immobilized to nitrocellulose (Invitrogen Corp.). Receptor was detected with anti-phospho-IGF-1R site Tyr1131 (Cell Signaling Technologies, #3021) or anti-IGF-1RP (Santa Cruz Biotechnology, #SC-9038) and anti-rabbit IgG-HRP (Cell Signaling Technologies, #7071). Bands were visualized using ECL luminol reagent (Amersham Biosciences, #RPN2109) and autoradiography. (FIGS. 12A and 12B).

Figure 19:
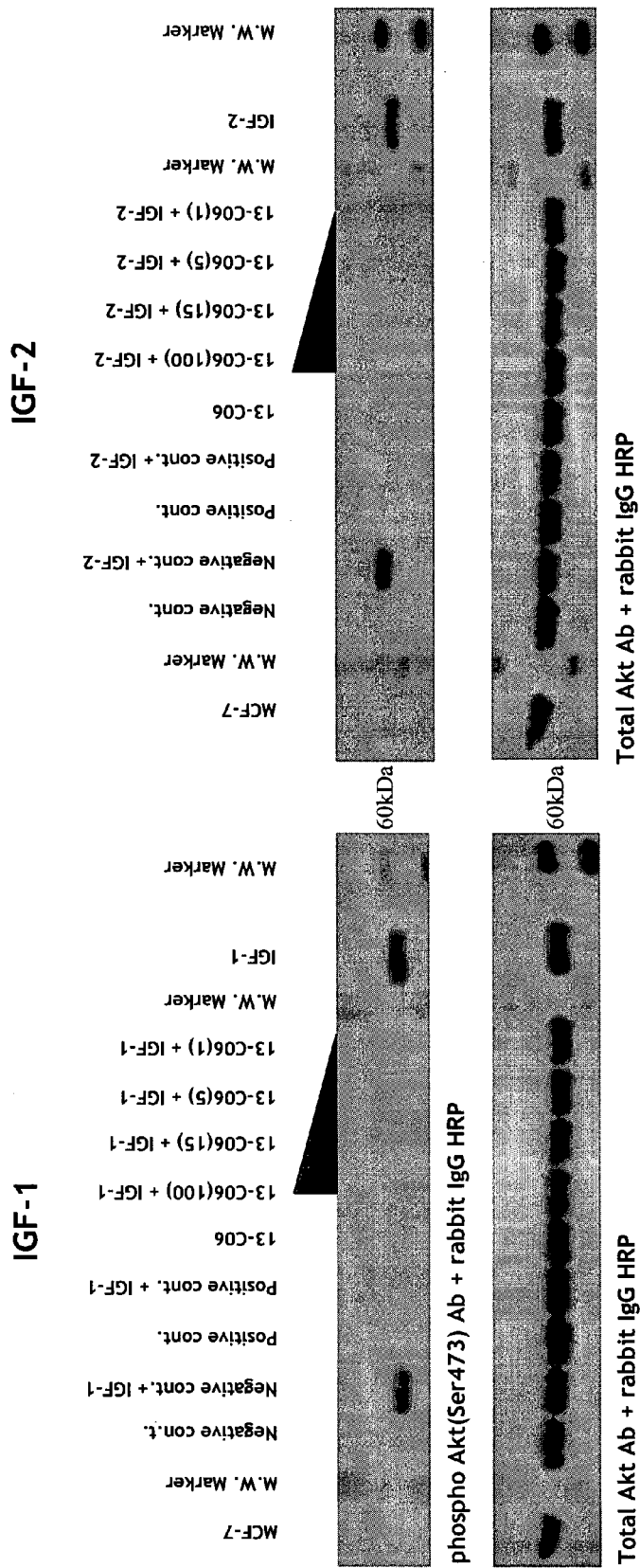
FIG. 19: Inhibition of IGF-1 and IGF-2 induced phosphorylation of Akt at amino acid residue Ser473 by a fully human IGF-1R antibody.

FIGS. 12 A & B show that M13.C06.G4.P.agly inhibited IGF-1 and IGF-2 mediated phosphorylation of Akt and p42/44 MAPK in a dose dependent manner. In particular, the M13-C06.G4.P.agly IGF-1R antibody inhibited ligand induced Akt signaling in MCF7 cells at all concentrations tested (i.e., 1-100 nM), as demonstrated by inhibition of IGF-1 and IGF-2 induced phosphorylation of Akt at amino acid residue Ser473 (FIG. 19). Control antibodies were tested at 100 nM, whereas M13-C06.G4.p.agly was tested at 100, 15, 5 and 1 nM. Antibody IDEC-152, a human G4 version of an antibody of irrelevant specificity, was used as a negative control. Antibody IR3, a murine monoclonal antibody to IGF-1R, was used as a positive control. In addition, M14-C03.G4.P.agly and M14.G11.G4.P full-length antibodies also inhibited IGF-1 and IGF-2 driven signaling of Akt and p42/44 MAPK activation (data not shown).

Part II: Inhibition of Signal Transduction in A549, Calu-6, and H1299 Cells

The ability of M13-C06.G4.P.agly to disrupt the association of insulin receptor substrate (IRS-1) with p85 the regulatory subunit of phosphoinositide 3-kinase (PI3K) was determined in tumor cell lines by a co-immunoprecipitation assay. In particular, IRS-1 binds to PI3K subunit p85 in an IGF-1R-dependent manner in NSCLC cell lines sensitive to M13-C06.G4.P.agly antibody. Thus, two non-small cell lung carcinoma cell lines (NSCLC) A549 and H1299 (responsive to M13-C06.G4.P.agly) and one NSCLC cell line, Calu-6 (less responsive to M13-C06.G4.P.agly) were grown in the presence of M13.C06.G4.P.agly or control antibody (IDEC-151) for 24 hours. Cell lysates were immunoprecipitated with an anti-p85 antibody and subjected to western blot analysis with anti-IRS-1 (top blot) and anti-p85 (bottom blot) antibodies (FIG. 25).

For this assay, human lung tumor cell lines A549, Calu-6, and NCI-1299 cells were purchased from ATCC and maintained in RPMI medium 1640 containing 10% fetal bovine serum (FBS). Cells were seeded at $3\times10^6$ cells per dish in 100 mm dishes, cultured for 24 hours, and then treated with 100 nM of M13-C06.G4.P.agly or IDEC-151 (human G4.β isotype matched negative control antibody) for 24 hours in the presence of 5% FBS. Cell lysates were prepared in 1% Triton X-100 lysis buffer from Cell Signaling Technology, Inc. (Danvers, Mass. USA)). For immunoprecipitation, anti-p85 antibody (Cat #06-649, Upstate Cell Signaling Solutions (now part of Millipore, Concord, Mass. (USA) was added to the lysate (4 ug of antibody per 1-2 mg of lysate) and incubated at 4° C. overnight. The immunocomplex was then captured by mixing with protein-G agarose beads for 2 hours at 4° C. The immunoprecipitates were washed with ice-cold lysis buffer and boiled in 2×LDS (Lithium Dodecyl Sulfate) sample buffer before separation by NuPAGE® Novex 4-12% Bis-Tris Gel electrophoresis (Invitrogen Corp., Carlsbad, Calif. (USA)), and transfer to nitrocellulose membranes. IRS-1 (Cat #06-248, Upstate) and p85 (Cat #06-649, Upstate) antibodies were purchased from Millipore and immunoblotting was performed according to the manufacturer's protocols.

Figure 25:
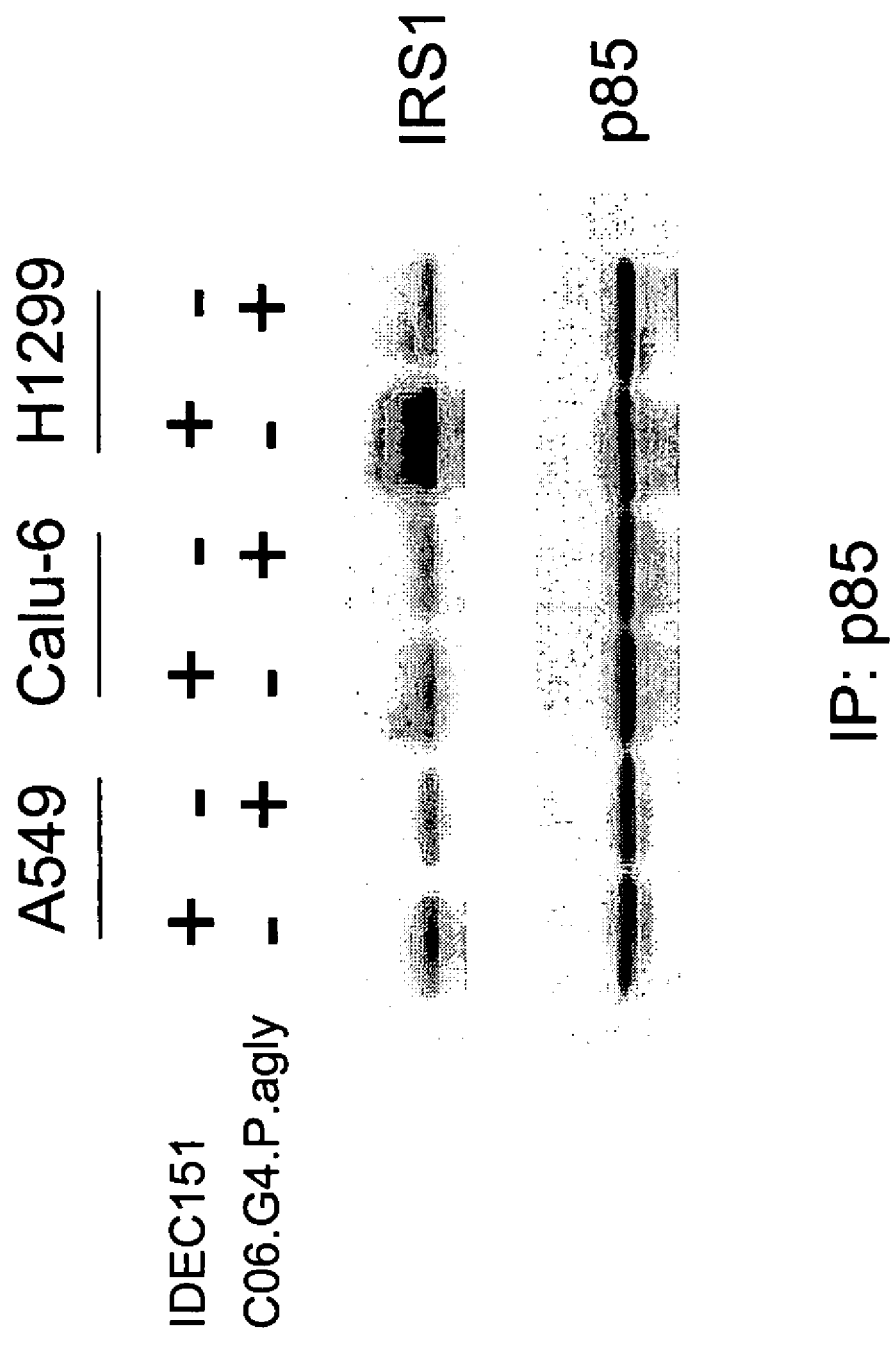
FIG. 25: Co-immunoprecipitation of IRS-1 and p85 (regulatory subunit of PI3K) demonstrates M13-C06.G4.P.agly mediated inhibition of IGF-1R signal transduction.

Result:

M13-C06.G4.P.agly inhibited the association of IRS-1 with the p85 regulatory subunit of PI3K in the presence of serum in A549 and H1299 cell lines but not in Calu-6 (FIG. 25).

Example 16

Antibody Cross-Reactivity to Non-Human Primate IGF-1R

The ability of anti-human IGF-IR antibodies to recognize the IGF-IR from non-human primates was tested. First Rhesus and cynomolgus monkey IGF-IR was cloned and expressed in CHO cells. The binding of all antibodies was determined by flow cytometry and confirmed by confocal microscopy. M13.C06.G4.P.agly, M14.C03.G4.P.agly and M14.G11.G4.P all showed specific binding activity to both Rhesus and cynomolgus IGF-1R (data not shown). Further species cross-reactivity studies showed binding of M14.G11.G4.P and M14.C03.G4.P.agly to murine IGF-1R expressing CHO cells (data not shown).

In addition to cynomolgus IGF-1R expressed on CHO cells, the M13.C06.G4.P.agly antibody also cross-reacts with cynomolgus macaque IGF-1R expressed on granulocytes and monocytes from this species. (Specificity of binding was demonstrated by the ability of soluble recombinant human IGF-1R to block M13.C06.G4.P.agly antibody binding (data not shown)). Similarly, the M13.C06.G4.P.agly antibody also binds to an established cynomolgus fibroblast cell line. (See, Example 26, FIG. 23). These results indicate that cynomolgus macaque is an ideal non-rodent species in which toxicity testing has been performed.

In contrast to results with the IGF-1R receptor in primates, M13.C06.G4.P.agly did not show cross-reactivity to rat or mouse IGF-1R expressed on immune cells (granulocytes, monocytes, lymphocytes) as assessed by FACS analysis.

Example 17

Generation of IGF-1R Specific Murine Mabs

Murine monoclonal antibodies specific to human IGF-1R were generated by standard hybridoma technology. Splenocytes from Balb/c mice were immunized with IGF-1R expressing NIH 3T3 fibroblast and IGF-1R.Ig fusion protein were used for PEG induced somatic cell fusion. Table 4 summarizes the properties of the anti-IGF-1R murine monoclonal antibodies.

The ability of the selected murine antibodies to inhibit IGF/IGF-1R dependent in vitro growth of several human tumor lines (Lung, H-23, Calu-6; Pancreas, BxPc-3, Panc-1, MiaPaCa and Colon Colo205) was measured by a proliferation as described in Example 13. FIG. 14(A)-(F) shows the antibody concentration dependent inhibitory effects of eight of the murine antibodies on tumor cell growth in the presence of IGF-1 at 100 ng/ml.

Figure 15:
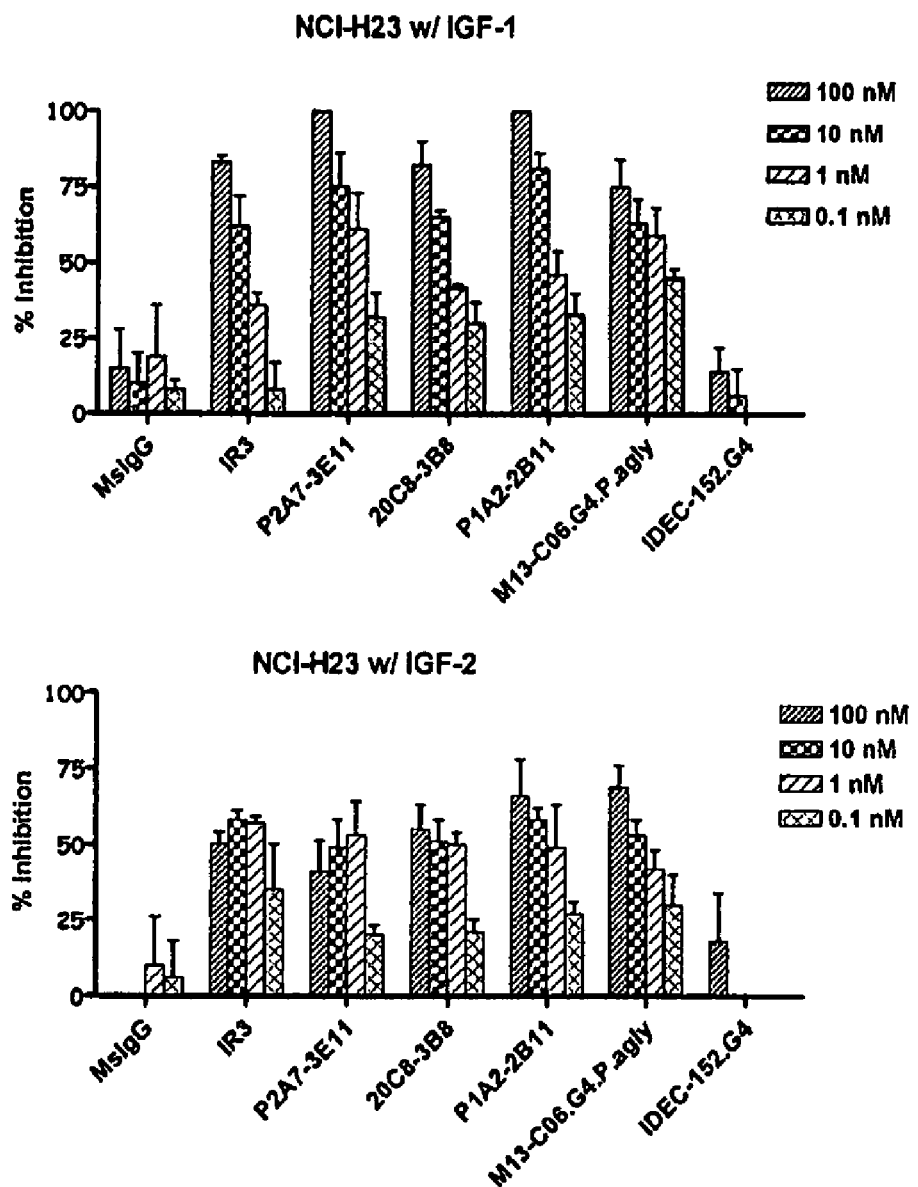
FIG. 15: Inhibition of IGF-1 and IGF-2 driven proliferation of H-23 cells by anti-IGF-1R antibodies.

The ability of antibodies to block IGF-1 and IGF-2 driven tumor cell growth was compared using the NCI-H23 lung tumor cell line. FIG. 15 gives an example of the growth inhibitory effects seen with three of the murine MAbs' (P2A7-3E11, 20C8-3E8, P1A2-2B11) and one of the fully human antibody, M13-C06.G4.P.agly. All of the antibodies showed inhibition of IGF-1 and IGF-2 driven tumor growth. As positive control IR3, a commercially available anti-IGF-1R antibody was used. The mouse IgG (anti-IDectin, IgG1) and human gamma 4 version of IDEC-152 antibody of irrelevant specificity were used as isotype matched controls for the experiments.

Example 18

Cloning of Murine Anti-Human IGF-1R mAbs

Cloning of Anti-IGF-1R Murine Hybridoma P2A7.3E11 Immunoglobulin Variable Regions Total cellular RNA from murine hybridoma cells was prepared using a Qiagen RNeasy mini kit following the manufacturer's recommended protocol. cDNAs encoding the variable regions of the heavy and light chains were cloned by RT-PCR from total cellular RNA using the Pharmacia Biotech First Strand cDNA Synthesis kit following the manufacturer's recommended protocol using random hexamers for priming.

The cloning and chimerization of the P2A7.3E11 variable domains will be described in detail as an example (other mAb variable domains were cloned and chimerized by similar methods, but will not be described in detail for the sake of brevity, since standard molecular biology techniques familiar to those skilled in the art of antibody engineering were used). For PCR amplification of the murine immunoglobulin variable domains with intact signal sequences, a cocktail of degenerate forward primers hybridizing to multiple murine immunoglobulin gene family signal sequences and a single back primer specific for 5' end of the murine constant domain as described in Current Protocols in Immunology (Wiley and Sons, 1999) were used. PCR conditions using Clontech's Advantage Taq polymerase were: initial denaturation for 2 min at 94°, followed by 30 cycles of denature 1 min at 94°, anneal 1 min at 45°, and elongate 1 min at 72°. The P2A7 heavy chain variable domain was amplified with the following primers: 5' GGG GAT ATC CAC CAT GGR ATG SAG CTG KGT MAT SCT CTT 3' (M=A/C, K=G/T, R=A/G, and S=C/G) (SEQ ID NO:130) and 5' AGG TCT AGA AYC TCC ACA CAC AGG RRC CAG TGG ATA GAC 3' (R=A/G, and Y=C/T). (SEQ ID NO:131) The P2A7 light chain variable domain with its signal sequence was amplified with the following primers: 5' GGG GAT ATC CAC CAT GGA TTT TCA GGT GCA GAT TTT CAG 3' (SEQ ID NO:132) and 5' GCG TCT AGA ACT GGA TGG TGG GAG ATG GA 3'. (SEQ ID NO:133) The PCR products were gel-purified using a Qiagen Qiaquick gel extraction kit following the manufacturer's recommended protocol. Purified PCR products were subcloned into Invitrogen's pCR2.1TOPO vector using their TOPO cloning kit following the manufacturer's recommended protocol. Inserts from multiple independent subclones were sequenced to guard against PCR errors.

Blast analyses of the variable domain sequences confirmed their immunoglobulin identity. The P2A7 heavy chain variable domain is a member of murine subgroup II(A). The sequence of the P2A7 mature heavy chain variable domain, with its CDRs underlined (with the CDRs, complementarity determining regions, based upon the Kabat designations) is shown below:

```
                                                            (SEQ ID NO: 38)
  1 QVQLQQSGPE LVKPGASVKM SCKASGNTFT DYVINWVKQR TGQGLEWIGE

51 IYPGNENTYY NEKFKGKATL TADKSSNTAY MQLSSLTSED SAVYFCARGI

101 YYYGSRTRTM DYWGQGTSVT VSS
```

The P2A7 light chain variable region is a member of murine kappa subgroup IV. The sequence of the P2A7 mature light chain variable domain, with its CDRs underlined, is shown below:

```
                                                            (SEQ ID NO: 98)
  1 EVVLTQSPTA MAASPGEKIT ITCSASSTLS SNYLHWYQQK PGFSPKLLIY

51 RTSNLASGVP GRFSGSGSGT SYSLTIGTME AEDVATYYCQ QGSSIPLTFG

101 AGTKLELK
```

Construction and Expression of chP2A7 cDNAs encoding the murine P2A7 variable regions of the heavy and light chains were used to construct vectors for expression of murine-human chimeras (chP2A7) in which the muP2A7 variable regions were linked to human IgG4 and kappa constant regions. For construction of the heavy chain chimera, a 0.47 kb NotI-BsmBI fragment from the P2A7 heavy chain subclone pCN363 and the 1.0 kb BsmBI-NotI fragment from pEAG1995 (a plasmid containing a sequence-confirmed aglycosylated S228P/T299A (Kabat EU nomenclature) variant huIgG4 heavy chain constant domain cDNA with the C-terminal lysine residue genetically removed) were subcloned into the phosphatased 6.1 kb NotI-linearized vector backbone of pV90 (a sequence-confirmed pUC-based Biogen Idec proprietary expression vector containing a SV40 early promoter-driven dhfr selectable marker in which heterologous gene expression is controlled by a CMV-IE promoter and a human growth hormone polyadenylation signal). The heavy chain cDNA sequence in the resultant plasmid pEAG2045 was confirmed by DNA sequencing. The sequence of the chimeric P2A7 heavy chain cDNA insert (from the signal sequence's initiator ATG through the terminator TGA) is shown below as SEQ ID NO:134:

```
  1 ATGGAATGGA GCTGTGTCAT GCTCTTCATC CTGTCAGGAA CTGCAGGTGT

51 CCACTCCCAG GTTCAGCTGC AGCAGTCTGG ACCTGAGCTA GTGAAGCCTG

101 GGGCTTCAGT GAAGATGTCC TGCAAGGCTT CTGGAAACAC ATTCACTGAC

151 TATGTTATAA ACTGGGTGAA GCAGAGAACT GGACAGGGCC TTGAGTGGAT

201 TGGAGAGATT TATCCTGGAA ATGAAAATAC TTATTACAAT GAGAAGTTCA

251 AGGGCAAGGC CACACTGACT GCAGACAAAT CCTCCAACAC AGCCTACATG

301 CAGCTCAGTA GCCTGACATC TGAGGACTCT GCGGTCTATT TCTGTGCAAG

351 AGGGATTTAT TACTACGGTA GTAGGACGAG GACTATGGAC TACTGGGGTC

401 AAGGAACCTC AGTCACCGTC TCCTCAGCCT CCACCAAGGG CCCATCCGTC

451 TTCCCCCTGG CGCCCTGCTC CAGATCTACC TCCGAGAGCA CAGCCGCCCT

501 GGGCTGCCTG GTCAAGGACT ACTTCCCCGA ACCGGTGACG GTGTCGTGGA

551 ACTCAGGCGC CCTGACCAGC GGCGTGCACA CCTTCCCGGC TGTCCTACAG

601 TCCTCAGGAC TCTACTCCCT CAGCAGCGTG GTGACCGTGC CCTCCAGCAG

651 CTTGGGCACG AAGACCTACA CCTGCAACGT AGATCACAAG CCCAGCAACA

701 CCAAGGTGGA CAAGAGAGTT GAGTCCAAAT ATGGTCCCCC ATGCCCACCG

751 TGCCCAGCAC CTGAGTTCCT GGGGGGACCA TCAGTCTTCC TGTTCCCCCC

801 AAAACCCAAG GACACTCTCA TGATCTCCCG GACCCCTGAG GTCACGTGCG

851 TGGTGGTGGA CGTGAGCCAG GAAGACCCCG AGGTCCAGTT CAACTGGTAC

901 GTGGATGGCG TGGAGGTGCA TAATGCCAAG ACAAAGCCGC GGGAGGAGCA
```

```
-continued
 951 GTTCAACAGC GCGTACCGTG TGGTCAGCGT CCTCACCGTC CTGCACCAGG

1001 ACTGGCTGAA CGGCAAGGAG TACAAGTGCA AGGTCTCCAA CAAAGGCCTC

1051 CCGTCCTCCA TCGAGAAAAC CATCTCCAAA GCCAAGGGC AGCCCCGAGA

1101 GCCACAAGTG TACACCCTGC CCCCATCCCA GGAGGAGATG ACCAAGAACC

1151 AGGTCAGCCT GACCTGCCTG GTCAAAGGCT TCTACCCCAG CGACATCGCC

1201 GTGGAGTGGG AGAGCAATGG GCAGCCGGAG AACAACTACA AGACCACGCC

1251 TCCCGTCCTC GATTCCGACG GCTCCTTCTT CCTCTACAGC AGGCTAACCG

1301 TGGACAAGAG CAGGTGGCAG GAGGGGAATG TCTTCTCATG CTCCGTGATG

1351 CATGAGGCTC TGCACAACCA CTACACACAG AAGAGCCTCT CCCTGTCTCT

1401 GGGTTGA
```

The predicted mature chP2A7 heavy chain protein sequence is shown below as SEQ ID NO:135:

```
  1 QVQLQQSGPE LVKPGASVKM SCKASGNTFT DYVINWVKQR TGQGLEWIGE

51 IYPGNENTYY NEKFKGKATL TADKSSNTAY MQLSSLTSED SAVYFCARGI

101 YYYGSRTRTM DYWGQGTSVT VSSASTKGPS VFPLAPCSRS TSESTAALGC

151 LVKDYFPEPV TVSWNSGALT SGVHTFPAVL QSSGLYSLSS VVTVPSSSLG

201 TKTYTCNVDH KPSNTKVDKR VESKYGPPCP PCPAPEFLGG PSVFLFPPKP

251 KDTLMISRTP EVTCVVVDVS QEDPEVQFNW YVDGVEVHNA KTKPREEQFN

301 SAYRVVSVLT VLHQDWLNGK EYKCKVSNKG LPSSIEKTIS KAKGQPREPQ

351 VYTLPPSQEE MTKNQVSLTC LVKGFYPSDI AVEWESNGQP ENNYKTTPPV

401 LDSDGSFFLY SRLTVDKSRW QEGNVFSCSV MHEALHNHYT QKSLSLSLG
```

The murine variable domain is residues 1-122, the human IgG4 heavy chain constant domain is residues 123-459. The Kabat EU-designated S228P hinge substitution (to correct the propensity of IgG4 to form half-antibodies) is residue 231 above, while the T299A substitution in CH2 to genetically remove N-linked glycosylation is residue 302 in the above sequence.

For construction of the light chain chimera, the PCR-amplified P2A7 light chain was subjected to site-directed mutagenesis using a STRATAGENE® Quick-Change mutagenesis kit following the manufacturer's recommended protocol, with the mutagenic primers 5' CGC CAG TGT GCG GCC GCT GGA ATT CGC CCT TG 3' (SEQ ID NO:136) and its reverse complement, which introduced a unique NotI site 5' of the heavy chain signal sequence, and 5' GGA CCA AGC TGG AGC TGA AGC GTA CGG ATG CTG CAC CAA CTG TAT CC 3' (SEQ ID NO:137) and its reverse complement, which introduced a unique BsiWI site immediately downstream of the light chain variable/kappa constant domain junction. Mutated plasmids were identified by screening for the introduced NotI and BsiWI site changes. The light chain sequence was confirmed by DNA sequencing. The 0.42 kb NotI-BsiWI light chain variable domain fragment produced as described above, and the 0.34 kb BsiWI-NotI fragment from the plasmid pEAG1572, containing a sequence-confirmed humanized anti-LTbR kappa light chain constant domain cDNA were subcloned into the NotI site of the expression vector pEAG1256 (a sequence-confirmed pUC-based expression vector containing a phosphoglycerokinase promoter-driven neo selectable marker in which heterologous gene expression is controlled by a CMV-IE promoter and a human growth hormone polyadenylation signal). The light chain cDNA sequence in the resultant plasmid was confirmed by DNA sequencing. The sequence of the chimeric P2A7 light chain cDNA insert (from the signal sequence's initiator ATG through the terminator TAG) is shown below (SEQ ID NO:138):

```
  1 ATGGATTTTC AGGTGCAGAT TTTCAGCTTG CTGCTAATCA GTGTCACAGT

51 CATAGTGTCT AATGGAGAAG TTGTGCTCAC CCAGTCTCCA ACCGCCATGG

101 CTGCATCTCC CGGGGAGAAG ATCACTATCA CCTGCAGTGC CAGCTCAACT

151 TTAAGTTCCA ATTACTTGCA TTGGTATCAG CAGAAGCCAG GATTCTCCCC
```

```
201 TAAACTCTTG ATTTATAGGA CATCCAATCT GGCCTCTGGA GTCCCAGGTC

251 GCTTCAGTGG CAGTGGGTCT GGGACCTCTT ACTCTCTCAC AATTGGCACC

301 ATGGAGGCTG AAGATGTTGC CACTTACTAC TGCCAGCAGG GTAGTAGTAT

351 ACCGCTCACG TTCGGTGCTG GGACCAAGCT GGAGCTGAAG CGTACGGTGG

401 CTGCACCATC TGTCTTCATC TTCCCGCCAT CTGATGAGCA GTTGAAATCT

451 GGAACTGCCT CTGTTGTGTG CCTGCTGAAT AACTTCTATC CCAGAGAGGC

501 CAAAGTACAG TGGAAGGTGG ATAACGCCCT CCAATCGGGT AACTCCCAGG

551 AGAGTGTCAC AGAGCAGGAC AGCAAGGACA GCACCTACAG CCTCAGCAGC

601 ACCCTGACGC TGAGCAAAGC AGACTACGAG AAACACAAAG TCTACGCCTG

651 CGAAGTCACC CATCAGGGCC TGAGCTCGCC CGTCACAAAG AGCTTCAACA

701 GGGGAGAGTG TTAG
```

The predicted mature chP2A7 light chain protein sequence is shown below (SEQ ID NO:139):

```
  1 EVVLTQSPTA MAASPGEKIT ITCSASSTLS SNYLHWYQQK PGFSPKLLIY
 51 RTSNLASGVP GRFSGSGSGT SYSLTIGTME AEDVATYYCQ QGSSIPLTFG
101 AGTKLELKRT VAAPSVFIFP PSDEQLKSGT ASVVCLLNNF YPREAKVQWK
151 VDNALQSGNS QESVTEQDSK DSTYSLSSTL TLSKADYEKH KVYACEVTHQ
201 GLSSPVTKSF NRGEC
```

The murine variable domain is residues 1-108 above, while the human kappa constant domain is residues 109-215 in the above sequence.

The chP2A7 heavy chain expression vector and the chP2A7 light chain expression vector were co-transfected into 293-EBNA cells and transfected cells were tested for antibody secretion and specificity. Empty vector- and hu5c8-S228P/T299A IgG4 (a molecularly cloned CD40L-specific mAb)-transfected cells served as controls. Western blot analysis (developed with anti-human heavy and light chain antibodies) of conditioned medium indicated that chP2A7-transfected cells synthesized and efficiently secreted heavy and light chains. FACS analysis of IGF-1R-expressing MCF7 human mammary adenocarcinoma cells stained with conditioned medium from transfected cells indicated that the chP2A7 antibody bound and produced staining patterns similar to those of muP2A7, while conditioned medium from mock- and hu5c8-transfected cells failed to stain MCF7 cells (detected with PE-conjugated anti-human heavy and light chain antibodies). Dilution titration indicated that specific staining with the conditioned medium containing chP2A7 mAb demonstrated a dose response. CHO cells were co-transfected with the chP2A7 heavy chain expression vector and the chP2A7 light chain expression vector to generate stable lines expressing chimeric P2A7-aglycosylated huIgG4, kappa mAb.

Cloning of Anti-IGF-1R Murine Hybridoma 20C8.3B8 Immunoglobulin Variable Regions Variable domains of other anti-IGF-1R mAbs were cloned and chimerized by standard recombinant DNA techniques similar to those described for the P2A7 mAb.

The predicted mature sequence of the 20C8.3B8 mAb heavy chain variable domain, belonging to murine subgroup I(A), is shown below with its CDRs underlined:

(SEQ ID NO: 43)
```
  1 DVQLQESGPD LVKPSQSLSL TCTVTGYSIT SGYSWHWIRQ FPGNKLEWMG
 51 YIHYSGGTNY NPSLKSRISI TRDTSKNQFF LQLNSVTTED TATYYCARSG
101 YGYRSAYYFD YWGQGTTVTV SS
```

The predicted mature sequence of the 20C8 light chain variable domain, belonging to murine kappa subgroup III, is shown below:

(SEQ ID NO: 103)
```
  1 DIVLTQSPAS LAVSLGQRAT ISCRASKSVS TSAYSYMHWY QQKPGQPPKL
 51 LIYLASNLES GVPARFSGSG SGTDFTLNIH PVEEEDAATY YCQHSRELPY
101 TFGGGTKLEI K
```

Expression vectors for chimeric 20C8 heavy and light chain cDNAs were constructed as described above. The immunoglobulin cDNA sequence in the plasmids' inserts were confirmed by DNA sequencing. The sequence of the chimeric 20C8 heavy chain cDNA insert (from the signal sequence's initiator ATG through the terminator TGA) is shown below as SEQ ID NO:140:

```
   1 ATGGACTGGA CCTGGAGGGT CTTCTGCTTG CTGGCTGTAG CACCAGGTGC
  51 CCACTCCGAC GTCCAACTGC AGGAGTCTGG ACCTGACCTG GTGAAACCTT
 101 CTCAGTCACT TTCACTCACC TGCACTGTCA CTGGCTACTC CATCACCAGT
 151 GGTTATAGCT GGCACTGGAT CCGGCAGTTT CCAGGAAACA AACTGGAATG
 201 GATGGGCTAC ATACACTACA GTGGTGGCAC TAACTACAAC CCATCTCTCA
 251 AAAGTCGAAT CTCTATCACT CGAGACACAT CCAAGAACCA GTTCTTCCTC
 301 CAGTTGAATT CTGTGACTAC TGAGGACACA GCCACATATT ACTGTGCAAG
 351 ATCGGGGTAC GGCTACAGGA GTGCGTACTA TTTTGACTAC TGGGGCCAAG
 401 GGACCACGGT CACCGTCTCC TCAGCTTCCA CCAAGGGCCC ATCCGTCTTC
 451 CCCCTGGCGC CCTGCTCCAG ATCTACCTCC GAGAGCACAG CCGCCCTGGG
 501 CTGCCTGGTC AAGGACTACT TCCCCGAACC GGTGACGGTG TCGTGGAACT
 551 CAGGCGCCCT GACCAGCGGC GTGCACACCT TCCCGGCTGT CCTACAGTCC
 601 TCAGGACTCT ACTCCCTCAG CAGCGTGGTG ACCGTGCCCT CCAGCAGCTT
 651 GGGCACGAAG ACCTACACCT GCAACGTAGA TCACAAGCCC AGCAACACCA
 701 AGGTGGACAA GAGAGTTGAG TCCAAATATG GTCCCCCATG CCCACCGTGC
 751 CCAGCACCTG AGTTCCTGGG GGGACCATCA GTCTTCCTGT TCCCCCCAAA
 801 ACCCAAGGAC ACTCTCATGA TCTCCCGGAC CCCTGAGGTC ACGTGCGTGG
 851 TGGTGGACGT GAGCCAGGAA GACCCCGAGG TCCAGTTCAA CTGGTACGTG
 901 GATGGCGTGG AGGTGCATAA TGCCAAGACA AAGCCGCGGG AGGAGCAGTT
 951 CAACAGCGCG TACCGTGTGG TCAGCGTCCT CACCGTCCTG CACCAGGACT
1001 GGCTGAACGG CAAGGAGTAC AAGTGCAAGG TCTCCAACAA AGGCCTCCCG
1051 TCCTCCATCG AGAAAACCAT CTCCAAAGCC AAAGGGCAGC CCCGAGAGCC
1101 ACAAGTGTAC ACCCTGCCCC CATCCCAGGA GGAGATGACC AAGAACCAGG
1151 TCAGCCTGAC CTGCCTGGTC AAAGGCTTCT ACCCCAGCGA CATCGCCGTG
1201 GAGTGGGAGA GCAATGGGCA GCCGGAGAAC AACTACAAGA CCACGCCTCC
1251 CGTCCTCGAT TCCGACGGCT CCTTCTTCCT CTACAGCAGG CTAACCGTGG
1301 ACAAGAGCAG GTGGCAGGAG GGGAATGTCT TCTCATGCTC CGTGATGCAT
1351 GAGGCTCTGC ACAACCACTA CACACAGAAG AGCCTCTCCC TGTCTCTGGG
1401 TTGA
```

The predicted mature ch20C8 heavy chain protein sequence is shown below as SEQ ID NO:141:

```
  1 DVQLQESGPD LVKPSQSLSL TCTVTGYSIT SGYSWHWIRQ FPGNKLEWMG

51 YIHYSGGTNY NPSLKSRISI TRDTSKNQFF LQLNSVTTED TATYYCARSG

101 YGYRSAYYFD YWGQGTTVTV SSASTKGPSV FPLAPCSRST SESTAALGCL

151 VKDYFPEPVT VSWNSGALTS GVHTFPAVLQ SSGLYSLSSV VTVPSSSLGT

201 KTYTCNVDHK PSNTKVDKRV ESKYGPPCPP CPAPEFLGGP SVFLFPPKPK

251 DTLMISRTPE VTCVVVDVSQ EDPEVQFNWY VDGVEVHNAK TKPREEQFNS

301 AYRVVSVLTV LHQDWLNGKE YKCKVSNKGL PSSIEKTISK AKGQPREPQV

351 YTLPPSQEEM TKNQVSLTCL VKGFYPSDIA VEWESNGQPE NNYKTTPPVL

401 DSDGSFFLYS RLTVDKSRWQ EGNVFSCSVM HEALHNHYTQ KSLSLSLG
```

The murine variable domain is residues 1-122, the human IgG4 heavy chain constant domain is residues 123-459.

The sequence of the chimeric 20C8 light chain cDNA insert (from the signal sequence's initiator ATG through the terminator TAG) is shown below as SEQ ID NO:142:

```
  1 ATGGAGACAG ACACACTCCT GTTATGGGTA CTGCTGCTCT GGGTTCCAGG

51 TTCCACTGGT GACATTGTGC TGACACAGTC TCCTGCTTCC TTAGCTGTAT

101 CTCTGGGGCA GAGGGCCACC ATCTCATGCA GGGCCAGCAA AAGTGTCAGT

151 ACATCTGCCT ATAGTTATAT GCACTGGTAC CAACAGAAAC CAGGACAGCC

201 ACCCAAACTC CTCATCTATC TTGCATCCAA CCTAGAATCT GGGGTCCCTG

251 CCAGGTTCAG TGGCAGTGGG TCTGGGACAG ACTTCACCCT CAACATCCAT

301 CCTGTGGAGG AGGAGGATGC TGCAACCTAT TACTGTCAGC ACAGTAGGGA

351 GCTTCCGTAT ACGTTCGGAG GGGGGACCAA GCTGGAAATC AAACGTACGG

401 TGGCTGCACC ATCTGTCTTC ATCTTCCCGC CATCTGATGA GCAGTTGAAA

451 TCTGGAACTG CCTCTGTTGT GTGCCTGCTG AATAACTTCT ATCCCAGAGA

501 GGCCAAAGTA CAGTGGAAGG TGGATAACGC CCTCCAATCG GGTAACTCCC

551 AGGAGAGTGT CACAGAGCAG GACAGCAAGG ACAGCACCTA CAGCCTCAGC

601 AGCACCCTGA CGCTGAGCAA AGCAGACTAC GAGAAACACA AAGTCTACGC

651 CTGCGAAGTC ACCCATCAGG GCCTGAGCTC GCCCGTCACA AAGAGCTTCA

701 ACAGGGGAGA GTGTTAG
```

The predicted mature ch20C8 light chain protein sequence is shown below as SEQ ID NO:143:

```
  1 DIVLTQSPAS LAVSLGQRAT ISCRASKSVS TSAYSYMHWY QQKPGQPPKL

51 LIYLASNLES GVPARFSGSG SGTDFTLNIH PVEEEDAATY YCQHSRELPY

101 TFGGGTKLEI KRTVAAPSVF IFPPSDEQLK SGTASVVCLL NNFYPREAKV

151 QWKVDNALQS GNSQESVTEQ DSKDSTYSLS STLTLSKADY EKHKVYACEV

201 THQGLSSPVT KSFNRGEC
```

The murine variable domain is residues 1-111 above, while the human kappa constant domain is residues 112-218 in the above sequence.

The ch20C8 heavy chain expression vector and ch20C8 light chain expression vector were co-transfected into 293-EBNA cells and transfected cells were tested for antibody secretion and specificity. Empty vector- and hu5c8-S228P/

T299A IgG4 (a molecularly cloned CD40L-specific mAb)-transfected cells served as controls. Western blot analysis (developed with anti-human heavy and light chain antibodies) of conditioned medium indicated that ch20C8-transfected cells synthesized and efficiently secreted heavy and light chains. FACS analysis of IGF-1R-expressing MCF7 human mammary adenocarcinoma cells stained with conditioned medium from transfected cells indicated that the ch20C8 antibody bound with a titratable dose response, while conditioned medium from mock- and hu5c8-transfected cells failed to stain MCF7 cells (detected with PE-conjugated anti-human heavy and light chain antibodies). CHO cells were co-transfected with the ch20C8 heavy chain expression vector and ch20C8 light chain expression vector to generate stable lines expressing chimeric 20C8-aglycosylated huIgG4, kappa mAb.

Cloning of Anti-IGF-1R mAb 20D8.24B11 Immunoglobulin Variable Regions

The mAb 20D8.24B11 appears to be a sister clone of 20C8.3B8 (both were derived from fusion 7): sharing a common light chain and having a heavy chain that differs from that of 20C8 by a single residue in FR4. The predicted mature sequence of the 20D8.24B11 mAb heavy chain variable domain, belonging to murine subgroup I(A), is shown below with its CDRs underlined:

```
                                                        (SEQ ID NO: 53)
  1 DVQLQESGPD LVKPSQSLSL TCTVTGYSIT SGYSWHWIRQ FPGNKLEWMG

51 YIHYSGGTNY NPSLKSRISI TRDTSKNQFF LQLNSVTTED TATYYCARSG

101 YGYRSAYYFD YWGQGTTLTV SS
```

An alignment of the 20D8 (upper) and 20C8 (lower) heavy chain variable domains, highlighting the single conservative difference corresponding to FR4 Kabat residue 109 (residue 118 below) is shown below:

```
  1 DVQLQESGPDLVKPSQSLSLTCTVTGYSITSGYSWHWIRQFPGNKLEWMG    50   (SEQ ID NO:53)
    |||||||||||||||||||||||||||||||||||||||||||||||||
  1 DVQLQESGPDLVKPSQSLSLTCTVTGYSITSGYSWHWIRQFPGNKLEWMG    50   (SEQ ID NO:43)

51 YIHYSGGTNYNPSLKSRISITRDTSKNQFFLQLNSVTTEDTATYYCARSG   100   (SEQ ID NO:53)
    |||||||||||||||||||||||||||||||||||||||||||||||||
 51 YIHYSGGTNYNPSLKSRISITRDTSKNQFFLQLNSVTTEDTATYYCARSG   100   (SEQ ID NO:43)

101 YGYRSAYYFDYWGQGTTLTVSS   122   (SEQ ID NO:53)
    |||||||||||||||||||.|||
101 YGYRSAYYFDYWGQGTTVTVSS   122   (SEQ ID NO:43)
```

An expression vector for chimeric 20D8 heavy chain cDNA was constructed and the heavy chain cDNA insert in plasmid pCN380 was confirmed by DNA sequencing. The sequence of the chimeric 20D8 heavy chain cDNA insert (from the signal sequence's initiator ATG through the terminator TGA) is shown below as SEQ ID NO:144:

```
  1 ATGGACTGGA CCTGGAGGGT CTTCTGCTTG CTGGCTGTAG CACCAGGTGC

51 CCACTCCGAC GTCCAACTGC AGGAGTCTGG ACCTGACCTG GTGAAACCTT

101 CTCAGTCACT TTCACTCACC TGCACTGTCA CTGGCTACTC CATCACCAGT

151 GGTTATAGCT GGCACTGGAT CCGGCAGTTT CCAGGAAACA AACTGGAATG

201 GATGGGCTAC ATACACTACA GTGGTGGCAC TAACTACAAC CCATCTCTCA

251 AAAGTCGAAT CTCTATCACT CGAGACACAT CCAAGAACCA GTTCTTCCTC

301 CAGTTGAATT CTGTGACTAC TGAGGACACA GCCACATATT ACTGTGCAAG

351 ATCGGGGTAC GGCTACAGGA GTGCGTACTA TTTTGACTAC TGGGGCCAAG

401 GGACCACGTT GACAGTCTCC TCAGCTTCCA CCAAGGGCCC ATCCGTCTTC

451 CCCCTGGCGC CCTGCTCCAG ATCTACCTCC GAGAGCACAG CCGCCCTGGG

501 CTGCCTGGTC AAGGACTACT TCCCCGAACC GGTGACGGTG TCGTGGAACT
```

```
551 CAGGCGCCCT GACCAGCGGC GTGCACACCT TCCCGGCTGT CCTACAGTCC

601 TCAGGACTCT ACTCCCTCAG CAGCGTGGTG ACCGTGCCCT CCAGCAGCTT

651 GGGCACGAAG ACCTACACCT GCAACGTAGA TCACAAGCCC AGCAACACCA

701 AGGTGGACAA GAGAGTTGAG TCCAAATATG GTCCCCCATG CCCACCGTGC

751 CCAGCACCTG AGTTCCTGGG GGGACCATCA GTCTTCCTGT TCCCCCCAAA

801 ACCCAAGGAC ACTCTCATGA TCTCCCGGAC CCCTGAGGTC ACGTGCGTGG

851 TGGTGGACGT GAGCCAGGAA GACCCCGAGG TCCAGTTCAA CTGGTACGTG

901 GATGGCGTGG AGGTGCATAA TGCCAAGACA AAGCCGCGGG AGGAGCAGTT

951 CAACAGCGCG TACCGTGTGG TCAGCGTCCT CACCGTCCTG CACCAGGACT

1001 GGCTGAACGG CAAGGAGTAC AAGTGCAAGG TCTCCAACAA AGGCCTCCCG

1051 TCCTCCATCG AGAAAACCAT CTCCAAAGCC AAAGGGCAGC CCCGAGAGCC

1101 ACAAGTGTAC ACCCTGCCCC CATCCCAGGA GGAGATGACC AAGAACCAGG

1151 TCAGCCTGAC CTGCCTGGTC AAAGGCTTCT ACCCCAGCGA CATCGCCGTG

1201 GAGTGGGAGA GCAATGGGCA GCCGGAGAAC AACTACAAGA CCACGCCTCC

1251 CGTCCTCGAT TCCGACGGCT CCTTCTTCCT CTACAGCAGG CTAACCGTGG

1301 ACAAGAGCAG GTGGCAGGAG GGGAATGTCT TCTCATGCTC CGTGATGCAT

1351 GAGGCTCTGC ACAACCACTA CACACAGAAG AGCCTCTCCC TGTCTCTGGG

1401 TTGA
```

The predicted mature ch20D8 heavy chain protein sequence encoded by the above sequence is shown below as SEQ ID NO:145:

```
  1 DVQLQESGPD LVKPSQSLSL TCTVTGYSIT SGYSWHWIRQ FPGNKLEWMG

51 YIHYSGGTNY NPSLKSRISI TRDTSKNQFF LQLNSVTTED TATYYCARSG

101 YGYRSAYYFD YWGQGTTLTV SSASTKGPSV FPLAPCSRST SESTAALGCL

151 VKDYFPEPVT VSWNSGALTS GVHTFPAVLQ SSGLYSLSSV VTVPSSSLGT

201 KTYTCNVDHK PSNTKVDKRV ESKYGPPCPP CPAPEFLGGP SVFLFPPKPK

251 DTLMISRTPE VTCVVVDVSQ EDPEVQFNWY VDGVEVHNAK TKPREEQFNS

301 AYRVVSVLTV LHQDWLNGKE YKCKVSNKGL PSSIEKTISK AKGQPREPQV

351 YTLPPSQEEM TKNQVSLTCL VKGFYPSDIA VEWESNGQPE NNYKTTPPVL

401 DSDGSFFLYS RLTVDKSRWQ EGNVFSCSVM HEALHNHYTQ KSLSLSLG
```

The murine variable domain is residues 1-122, the human S228P/T299A IgG4 heavy chain constant domain is residues 123-458.

The 20D8 light chain variable sequence is identical to that of 20C8: please see the information previously described for 20C8.

Cloning of Anti-IGF-1R mAb P1G10.2B8 Immunoglobulin Variable Regions

The predicted sequence of the mature P1G10 heavy chain variable domain is shown below as SEQ ID NO:58, with its CDRs underlined:

```
  1 QIQLVQSGPD LKKPGETVKI SCKASGYTFT NHGMNWVKQA PGKDLKWMGW

51 INTNTGEPTY ADDFKGRFAF SLETSASTAY LQINNLKNED TATYFCASPL

101 YYRNGRYFDV WGAGTTVTVS S
```

P1G10 appears to belong to the murine heavy chain variable domain subgroup II(A), but with only 55% identity to the heavy II(A) consensus sequence.

An expression vector for the chimeric P1G10 heavy chain cDNA was constructed and its cDNA insert was sequence confirmed. The sequence of the chimeric P1G10 heavy chain cDNA insert (from the signal sequence's initiator ATG through the terminator TGA is shown below as SEQ ID NO:146:

```
   1 ATGGGTTGGA TCTGTATCTT TCTATTCTTG GTGGCAGCTG CCCAAAGTGC
  51 CCAAGCACAG ATCCAGTTGG TGCAGTCTGG ACCTGACCTG AAGAAGCCTG
 101 GAGAGACAGT CAAGATCTCC TGCAAGGCTT CTGGGTATAC CTTCACAAAC
 151 CATGGAATGA ACTGGGTGAA GCAGGCTCCA GGAAAGGATT TAAAGTGGAT
 201 GGGCTGGATA AACACCAACA CTGGAGAGCC AACATATGCT GATGACTTCA
 251 AGGGACGGTT TGCCTTCTCT TTGGAAACCT CTGCCAGCAC TGCCTATTTG
 301 CAGATCAACA ACCTCAAAAA TGAGGACACG GCTACATATT TCTGTGCAAG
 351 TCCCCTCTAC TATAGGAACG GGCGATACTT CGATGTCTGG GGCGCAGGGA
 401 CCACGGTCAC CGTCTCCTCA GCTTCCACCA AGGGCCCATC CGTCTTCCCC
 451 CTGGCGCCCT GCTCCAGATC TACCTCCGAG AGCACAGCCG CCCTGGGCTG
 501 CCTGGTCAAG GACTACTTCC CCGAACCGGT GACGGTGTCG TGGAACTCAG
 551 GCGCCCTGAC CAGCGGCGTG CACACCTTCC CGGCTGTCCT ACAGTCCTCA
 601 GGACTCTACT CCCTCAGCAG CGTGGTGACC GTGCCCTCCA GCAGCTTGGG
 651 CACGAAGACC TACACCTGCA ACGTAGATCA CAAGCCCAGC AACACCAAGG
 701 TGGACAAGAG AGTTGAGTCC AAATATGGTC CCCCATGCCC ACCGTGCCCA
 751 GCACCTGAGT TCCTGGGGGG ACCATCAGTC TTCCTGTTCC CCCCAAAACC
 801 CAAGGACACT CTCATGATCT CCCGGACCCC TGAGGTCACG TGCGTGGTGG
 851 TGGACGTGAG CCAGGAAGAC CCCGAGGTCC AGTTCAACTG GTACGTGGAT
 901 GGCGTGGAGG TGCATAATGC CAAGACAAAG CCGCGGGAGG AGCAGTTCAA
 951 CAGCGCGTAC CGTGTGGTCA GCGTCCTCAC CGTCCTGCAC CAGGACTGGC
1001 TGAACGGCAA GGAGTACAAG TGCAAGGTCT CCAACAAAGG CCTCCCGTCC
1051 TCCATCGAGA AAACCATCTC CAAAGCCAAA GGGCAGCCCC GAGAGCCACA
1101 AGTGTACACC CTGCCCCCAT CCCAGGAGGA GATGACCAAG AACCAGGTCA
1151 GCCTGACCTG CCTGGTCAAA GGCTTCTACC CCAGCGACAT CGCCGTGGAG
1201 TGGGAGAGCA ATGGGCAGCC GGAGAACAAC TACAAGACCA CGCCTCCCGT
1251 CCTCGATTCC GACGGCTCCT TCTTCCTCTA CAGCAGGCTA ACCGTGGACA
1301 AGAGCAGGTG GCAGGAGGGG AATGTCTTCT CATGCTCCGT GATGCATGAG
1351 GCTCTGCACA ACCACTACAC ACAGAAGAGC CTCTCCCTGT CTCTGGGTTG
1401 A
```

The predicted mature chP1G10 heavy chain protein sequence encoded the sequence above is shown below as SEQ ID NO:147:

```
  1 QIQLVQSGPD LKKPGETVKI SCKASGYTFT NHGMNWVKQA PGKDLKWMGW

51 INTNTGEPTY ADDFKGRFAF SLETSASTAY LQINNLKNED TATYFCASPL

101 YYRNGRYFDV WGAGTTVTVS SASTKGPSVF PLAPCSRSTS ESTAALGCLV

151 KDYFPEPVTV SWNSGALTSG VHTFPAVLQS SGLYSLSSVV TVPSSSLGTK

201 TYTCNVDHKP SNTKVDKRVE SKYGPPCPPC PAPEFLGGPS VFLFPPKPKD

251 TLMISRTPEV TCVVVDVSQE DPEVQFNWYV DGVEVHNAKT KPREEQFNSA

301 YRVVSVLTVL HQDWLNGKEY KCKVSNKGLP SSIEKTISKA KGQPREPQVY

351 TLPPSQEEMT KNQVSLTCLV KGFYPSDIAV EWESNGQPEN NYKTTPPVLD

401

SDGSFFLYSR LTVDKSRWQE GNVFSCSVMH EALHNHYTQK SLSLSLG
```

The murine variable domain is residues 1-121, the human S228P/T299A IgG4 heavy chain constant domain is residues 122-457.

The predicted sequence of the mature P1G10 light chain variable domain, belonging to murine kappa subgroup V, is shown below as SEQ ID NO:113, with its CDRs underlined:

```
  1 DIQMTQTTSS LSASLGDRVT ISCRASQDIS NYLNWYQQKP DGSVKLLIYY

51 TSRLHSGVPS RFSGSGSGTD YSLTISNLEQ EDIATYFCQQ GKTLPWTFGG

101 GTKLEIK
```

An expression vector for the chimeric P1G10 light chain cDNA was constructed and its cDNA insert was sequence confirmed. The sequence of the chimeric P1G10 light chain cDNA insert (from the signal sequence's initiator ATG through the terminator TAG) is shown below as SEQ ID NO:148:

```
  1 ATGAGGTCCC CTGCTCAGTT TCTTGGTCTC CTGTTGCTCT GTTTTCAAGG

51 TGCCAGATGT GATATCCAGA TGACACAGAC TACATCCTCC CTGTCTGCCT

101 CTCTGGGAGA CAGAGTCACC ATCAGTTGCA GGGCAAGTCA GGACATTAGT

151 AATTATTTAA ATTGGTATCA GCAGAAACCA GATGGATCTG TTAAACTCCT

201 GATCTACTAC ACATCAAGAT TACACTCAGG AGTCCCATCA AGGTTCAGTG

251 GCAGTGGGTC TGGAACAGAT TATTCTCTCA CCATTAGCAA CCTGGAACAA

301 GAAGATATTG CCACTTACTT TTGCCAACAG GGAAAGACGC TTCCGTGGAC

351 GTTCGGTGGA GGCACCAAGC TGGAAATCAA ACGTACGGTG GCTGCACCAT

401 CTGTCTTCAT CTTCCCGCCA TCTGATGAGC AGTTGAAATC TGGAACTGCC

451 TCTGTTGTGT GCCTGCTGAA TAACTTCTAT CCCAGAGAGG CCAAAGTACA

501 GTGGAAGGTG GATAACGCCC TCCAATCGGG TAACTCCCAG GAGAGTGTCA

551 CAGAGCAGGA CAGCAAGGAC AGCACCTACA GCCTCAGCAG CACCCTGACG

601 CTGAGCAAAG CAGACTACGA GAAACACAAA GTCTACGCCT GCGAAGTCAC
```

```
651 CCATCAGGGC CTGAGCTCGC CCGTCACAAA GAGCTTCAAC AGGGGAGAGT

701 GTTAG
```

The predicted mature chP1G10 light chain protein sequence encoded by the sequence above is shown below as SEQ ID NO:149:

```
  1 DIQMTQTTSS LSASLGDRVT ISCRASQDIS NYLNWYQQKP DGSVKLLIYY

51 TSRLHSGVPS RFSGSGSGTD YSLTISNLEQ EDIATYFCQQ GKTLPWTFGG

101 GTKLEIKRTV AAPSVFIFPP SDEQLKSGTA SVVCLLNNFY PREAKVQWKV

151 DNALQSGNSQ ESVTEQDSKD STYSLSSTLT LSKADYEKHK VYACEVTHQG

201

LSSPVTKSFN RGEC
```

The murine variable domain is residues 1-107 above, while the human kappa constant domain is residues 108-214 in the above sequence.

The chP1G10 heavy chain expression vector and chP1G10 light chain expression vector were co-transfected into 293-EBNA cells and transfected cells were tested for antibody secretion and specificity (empty vector- and hu5c8-S228P/T299A IgG4 (a molecularly cloned CD40L-specific mAb)-transfected cells served as controls). Western blot analysis (developed with anti-human heavy and light chain antibodies) of conditioned medium indicated that chP1G10-transfected cells synthesized and efficiently secreted heavy and light chains. FACS analysis of IGF-1R-expressing MCF7 human mammary adenocarcinoma cells stained with conditioned medium from transfected cells indicated that the chP1G10 antibody bound with a titratable dose response, while conditioned medium from mock- and hu5c8-transfected cells failed to stain MCF7 cells (detected with PE-conjugated anti-human heavy and light chain antibodies). CHO cells were co-transfected with the chP1G10 heavy chain expression vector and chP1G10 light chain expression vector to generate stable lines expressing chimeric P1G10-aglycosylated huIgG4, kappa mAb.

Cloning of Anti-IGF-1R mAb P1A2.2B11 Immunoglobulin Variable Regions

The predicted sequence of the mature P1A2 heavy chain variable domain, belonging to murine subgroup II(A) is shown below as SEQ ID NO:48:

```
  1 QIQLVQSGPE LKKPGETVKI SCKASGYTFT NHGMNWVKQA PGKGLKWMGW

51 NTSTGEPTYA DDFKGRFAFS LETSASTAFL QINNLKNEDT ASYFCASPLY

101 YMYGRYIDVW GAGTAVTVSS
```

The P1A2 heavy chain is 92.6% identical to that of P1G10 (both were derived from fusion 5), with one FR1, one FR2, two CDR2, two FR3, two CDR3, and 1 FR4 differences. The alignment of the P1A2 (upper line) and P1G10 (lower line) heavy chain variable domains is shown below:

```
  1   QIQLVQSGPELKKPGETVKISCKASGYTFTNHGMNWVKQAPGKGLKWMGW    50   (SEQ ID NO:48)
      ||||||||:||||||||||||||||||||||||||||||||||| ||||||
  1   QIQLVQSGPDLKKPGETVKISCKASGYTFTNHGMNWVKQAPGKDLKWMGW    50   (SEQ ID NO:58)

51   .NTSTGEPTYADDFKGRFAFSLETSASTAFLQINNLKNEDTASYFCASPL    99   (SEQ ID NO:48)
      ||.|||||||||||||||||||||||||:|||||||||||.|||||||||
 51   INTNTGEPTYADDFKGRFAFSLETSASTAYLQINNLKNEDTATYFCASPL   100   (SEQ ID NO:58)

100   YYMYGRYIDVWGAGTAVTVSS   120   (SEQ ID NO:48)
      || ||| |||||||| |||||
101   YYRNGRYFDVWGAGTTVTVSS   121   (SEQ ID NO:58)
```

An expression vector for the chimeric P1A2 heavy chain is constructed by the methods described above. The predicted sequence of the chP1A2 heavy chain encoded by that plasmid (SEQ ID NO:150) is:

```
  1  QIQLVQSGPE LKKPGETVKI SCKASGYTFT NHGMNWVKQA PGKGLKWMGW

51  NTSTGEPTYA DDFKGRFAFS LETSASTAFL QINNLKNEDT ASYFCASPLY

101  YMYGRYIDVW GAGTAVTVSS ASTKGPSVFP LAPCSRSTSE STAALGCLVK

151  DYFPEPVTVS WNSGALTSGV HTFPAVLQSS GLYSLSSVVT VPSSSLGTKT

201  YTCNVDHKPS NTKVDKRVES KYGPPCPPCP APEFLGGPSV FLFPPKPKDT

251  KNUSRTPEVT CVVVDVSQED PEVQFNWYVD GVEVHNAKTK PREEQFNSAY

301  RVVSVLTVLH QDWLNGKEYK CKVSNKGLPS SIEKTISKAK GQPREPQVYT

351  LPPSQEEMTK NQVSLTCLVK GFYPSDIAVE WESNGQPENN YKTTPPVLDS

401  DGSFFLYSRL TVDKSRWQEG NVFSCSVMHE ALHNHYTQKS LSLSLG
```

The murine variable domain is residues 1-120, the human S228P/T299A IgG4 heavy chain constant domain is residues 121-456.

The predicted sequence of the mature P1A2 light chain variable domain, belonging to murine kappa subgroup V, is shown below as SEQ ID NO:108, with its CDRs underlined:

```
  1  DIQMTQTTSS LSASLGDRVT ISCRASQDIS NYLNWYQQKP DGTIKLLIYY

51  TSRLHSGVPS RFSGSGSGTD YSLTISNLEQ EDFATYFCQQ GKTLPWTFGG

101  GTKLEIK
```

The P1A2 light chain is 97.2% identical to that of P1G10 (both were derived from fusion 5), with two FR2 and one FR3 difference, but sharing identical CDRs. The alignment of the P1A2 (upper line) and P1G10 (lower line) light chain variable domains is shown below:

```
  1 DIQMTQTTSSLSASLGDRVTISCRASQDISNYLNWYQQKPDGTIKLLIYY   50 (SEQ ID NO:108)
    ||||||||||||||||||||||||||||||||||||||||||::||||||
  1 DIQMTQTTSSLSASLGDRVTISCRASQDISNYLNWYQQKPDGSVKLLIYY   50 (SEQ ID NO:113)

51 TSRLHSGVPSRFSGSGSGTDYSLTISNLEQEDFATYFCQQGKTLPWTFGG  100 (SEQ ID NO:108)
    |||||||||||||||||||||||||||||||| |||||||||||||||||
 51 TSRLHSGVPSRFSGSGSGTDYSLTISNLEQEDIATYFCQQGKTLPWTFGG  100 (SEQ ID NO:113)

101 GTKLEIK  107 (SEQ ID NO:108)
    |||||||
101 GTKLEIK  107 (SEQ ID NO:113)
```

An expression vector for the chimeric P1A2 light chain cDNA was constructed and its cDNA insert was sequence confirmed. The sequence of the chimeric P1A2 light chain cDNA insert (from the signal sequence's initiator ATG through the terminator TAG) is shown below as SEQ ID NO:151:

```
  1 ATGAGGTCCC CTGCTCAGTT TCTTGGAGAC CTGTTGCTCT GTTTTCAAGG
 51 TACCAGATGT GATATCCAGA TGACACAGAC TACATCCTCC CTATCTGCCT
101 CTCTGGGAGA CAGAGTCACC ATCAGTTGCA GGGCAAGTCA GGACATTAGC
151 AATTATTTAA ACTGGTATCA GCAGAAACCA GATGGAACTA TTAAACTCCT
201 GATCTACTAC ACATCAAGAT TACACTCAGG AGTCCCATCA AGGTTCAGTG
251 GCAGTGGGTC TGGAACAGAT TATTCTCTCA CCATTAGCAA CCTGGAACAA
301 GAAGATTTTG CCACTTACTT TTGCCAACAG GGTAAAACGC TTCCGTGGAC
351 GTTCGGTGGA GGCACCAAGC TGGAAATCAA ACGTACGGTG GCTGCACCAT
401 CTGTCTTCAT CTTCCCGCCA TCTGATGAGC AGTTGAAATC TGGAACTGCC
451 TCTGTTGTGT GCCTGCTGAA TAACTTCTAT CCCAGAGAGG CCAAAGTACA
501 GTGGAAGGTG GATAACGCCC TCCAATCGGG TAACTCCCAG GAGAGTGTCA
551 CAGAGCAGGA CAGCAAGGAC AGCACCTACA GCCTCAGCAG CACCCTGACG
601 CTGAGCAAAG CAGACTACGA GAAACACAAA GTCTACGCCT GCGAAGTCAC
651 CCATCAGGGC CTGAGCTCGC CCGTCACAAA GAGCTTCAAC AGGGGAGAGT
701 GTTAG
```

The predicted mature chP1A2 light chain protein sequence encoded by pCN379 is shown below as SEQ ID NO:152:

```
  1 DIQMTQTTSS LSASLGDRVT ISCRASQDIS NYLNWYQQKP DGTIKLLIYY
 51 TSRLHSGVPS RFSGSGSGTD YSLTISNLEQ EDFATYFCQQ GKTLPWTFGG
101 GTKLEIKRTV AAPSVFIFPP SDEQLKSGTA SVVCLLNNFY PREAKVQWKV
151 DNALQSGNSQ ESVTEQDSKD STYSLSSTLT LSKADYEKHK VYACEVTHQG
201 LSSPVTKSFN RGEC
```

The murine variable domain is residues 1-107 above, while the human kappa constant domain is residues 108-214 in the above sequence.

Cloning of Anti-IGF-1R mAb P1E2.3B12 Immunoglobulin Variable Regions

Cloning of the P1E2 variable domains is carried out by the methods described above.

Example 19

IGF-1R Fab Antibodies Bind Soluble IGF-1R with High Affinity

Method: The binding activity of M13-C06, M14-C03, and M14-G11 Fabs to soluble IGF-1R was measured using surface plasmon resonance. Biotinylated PENTA-His Antibody (Qiagen, Inc.) was immobilized onto a Streptavidin coated Sensor Chip. Soluble/Dimeric IGF-1R-His ectodomain (R&D systems, Inc.) was captured on the surface via the PENTA-His antibody. Secondary injections of M13-C06, M14-C03, or M14-G11 Fabs (0.5 nM-1000 nM) were performed. The surfaces were regenerated with three short injections of acetate, pH 4.0.

Results: The M13-C06 Fab bound recombinant IGF-1R with the highest affinity at KD=1.3 nM, whereas M14-G11 Fab bound with a $K_D$=4.0 nM, and M14-C03 Fab bound with a $K_D$=4.9 nM (data not shown).

Example 20

Inhibition of IGF-1 and IGF-2 Stimulated Tumor Cell Growth by Fully Human IGF-1R Antibodies Method: The effect of antibody on tumor growth in vitro was measured using a CELL TITER-GLO™ assay (Promega Corporation, 2800 Woods Hollow Rd., Madison, Wis. 53711 USA). BxPC3 cells in 10% FBS containing RPMI medium were cultured in Wallac 96-well clear bottom TC-treated plates (8000 cell/well). After 24 hours, culture medium was changed to serum free condition and antibodies at different concentrations (100 nM, 10 nM, 1 nM, and 0.1 nM) were added. Following 30 minute incubation, IGF-1 or IGF-2 was added at 100 ng/ml. The cells were incubated for another 48 hours until lysed to determine the amount of ATP present using the CELL TITER-GLO™ reagent. Inhibition was calculated as [1−(Ab−SFM)/(IGF−SFM)]×100%. An isotype matched antibody, IDEC-151 (human G4), antibody was used as a negative control.

Figure 16:
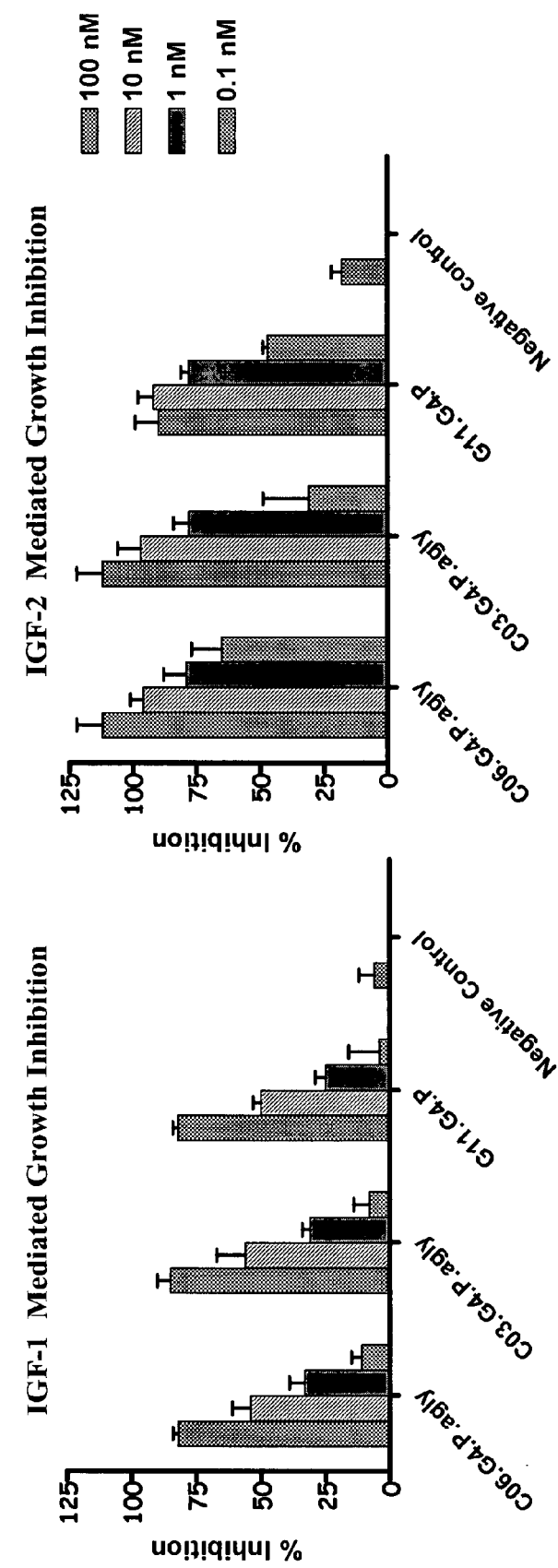
FIG. 16: Inhibition of BxPC3 cell proliferation (driven with recombinant human IGF-1 and IGF-2) by M13-C06.G4.P.agly antibody.
Figure 18:
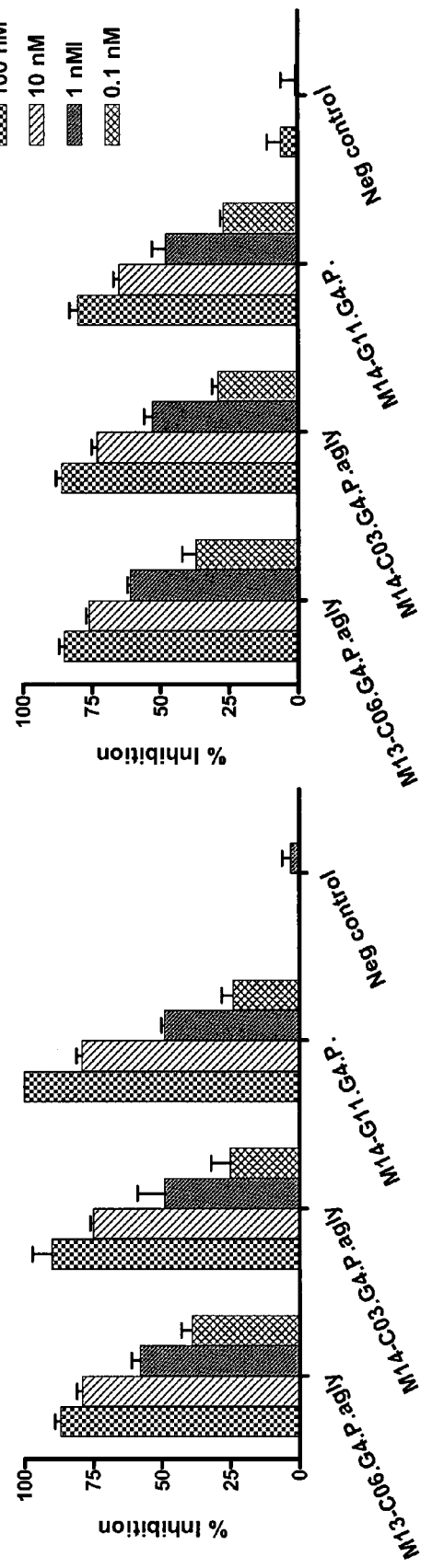
FIG. 18: Inhibition of A549 cell proliferation (driven with recombinant human IGF-1 and IGF-2) by M13-C06.G4.P.agly antibody.

Results: Fully human antibodies M13-C06.G4.P.agly, M14-G11.G4.P and M14-C03.G4.P.agly inhibited BxPC3 (human pancreas adenocarcinoma) cell proliferation driven with recombinant human IGF-1 and IGF-2 (FIG. 16). Similar growth inhibition results were obtained with these antibodies against cell proliferation driven with recombinant human IGF-1 and IGF-2 in human lung cancer cell line NCI-H23 (FIG. 17; M13-C06.G4.P.agly antibody) and human lung cancer cell line A549 (FIG. 18; M13-C06.G4.P.agly antibody). In all three cell lines M14-G11.G4.P, agly showed similar results as M14.G11.G4.P version (data not shown).

Example 21

Cell-Cycle Arrest of Tumor Cell Growth In Vitro by Fully Human IGF-1R Antibodies Method: The ability of fully human IGF-1R antibodies to arrest cell cycle progression was assessed by FACS analysis; monitoring incorporation of propidium iodide in cultured BxPC3 cells. BxPC3 cells ($4 \times 10^5$ cells/well) were plated into 6 well plates. After 24 hours, cells were changed to serum-free media (SFM) for the following 24 hours. Next the IGF-1R antibodies at a final concentration of 133.3 nM (20 micrograms/ml) and IGF-1 at 200 ng/ml was added to the media. After 24 hours, the cells were trypsinized and fixed with ethanol. DNA content was stained with propidium iodide (PI) prior to FACS analysis. An isotype matched antibody, IDEC-151 (human G4), was used as a negative control.

Results: Fully human antibodies M13-C06.G4.P.agly (Table 11), M14-G11.G4.P.agly and M14-C03.G4.P.agly arrested the BxPC3 tumor cells at the G0/G1 phase of the cell cycle.

TABLE 11

| Antibody (µg/mL) | Non-IGF Treated Cells | | | IGF-1 Treated Cells | | |
| --- | --- | --- | --- | --- | --- | --- |
| | G1/O phase (% cells) | S phase (% cells) | G2/M phase (% cells) | G1/O phase (% cells) | S phase (% cells) | G2/M phase (% cells) |
| SFM | 70.76 | 24.69 | 7.76 | 37.53 | 55.96 | 11.04 |
| IDEC141 (20) | 69.44 | 23.14 | 9.21 | 36.11 | 57.71 | 11.1 |
| CO3 (20) | 64.71 | 32.94 | 3.68 | 56.95 | 31.42 | 21.75 |
| CO6 (20) | 68.87 | 28.53 | 3.82 | 57.08 | 38.16 | 8.33 |
| G11 (20) | 68.59 | 25.87 | 7.66 | 58.83 | 36.16 | 9.06 |

Example 22

In Vivo Inhibition of Tumor Growth in a Pancreatic Cancer Model

Methods: Single agent in vivo efficacy of M13.C06.G4.P.agly antibody was evaluated in a xenograft pancreatic cancer model system using BxPC3 (pancreatic cancer) cells. CB17 SCID mice were inoculated with $2 \times 10^6$ cells and monitored for tumor growth. Mean tumor volume at the start of the therapy was ~200 mm³. The M13.C06.G4.P.agly antibody was administered intraperitoneally (i.p.) at 60, 30 and 15 mg/kg administered one time per week for 5 weeks. An isotype matched antibody, IDEC-151 (human G4), was administered as a negative control at 60 mg/kg one time per week for 5 weeks. Tumors were extracted at the indicated intervals post-inoculation (FIG. 20) and total tumor volume was measured.

Figure 20:
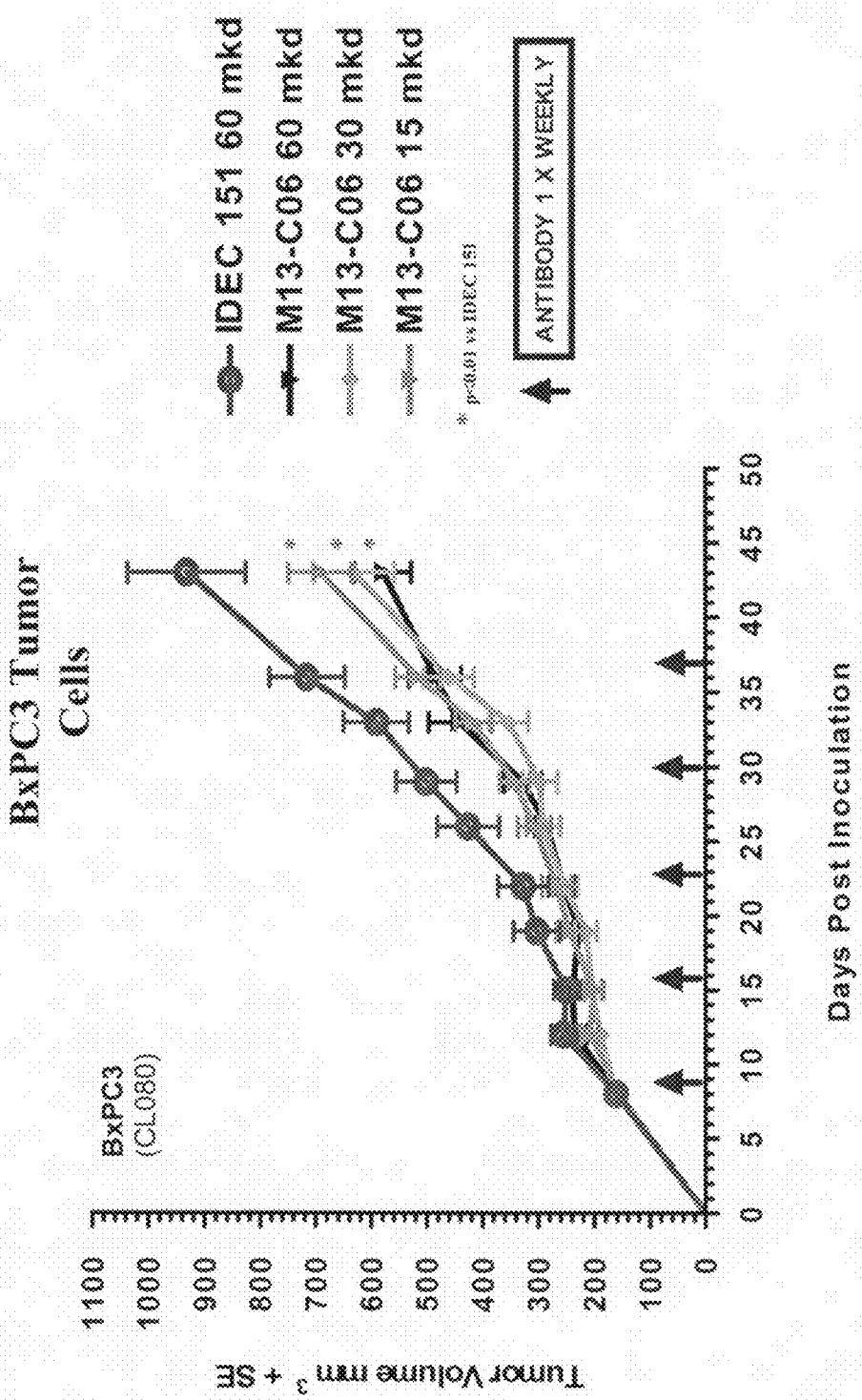
FIG. 20: Fully human M13.C06.G4.P.agly antibody exhibits in vivo dose dependent inhibition of tumor growth in a pancreatic cancer model.

Results: The fully human M13.C06.G4.P.agly antibody inhibited tumor growth in a dose dependent manner (FIG. 20). The antibody demonstrated statistically significant single agent efficacy at 60, 30 and 15 mg/kg administered weekly for 5 weeks. Moreover, the antibody was efficacious at doses as low as 15 mg/kg administered once a week (FIG. 20).

Example 23

In Vivo Inhibition of Tumor Growth in a Lung Cancer Model

Methods: Single agent in vivo efficacy of M13.C06.G4.P.agly antibody was evaluated in a xenograft lung cancer model system using A549 (lung cancer) cells. CB17 SCID mice were inoculated with 3-5×10$^6$ cells and monitored for tumor growth. Mean tumor volume at the start of the therapy was ~150 mm$^3$. The M13.C06.G4.P.agly antibody was administered intraperitoneally (i.p.) at 30 and 15 mg/kg administered two times per week per week for 4 weeks. An isotype matched antibody, IDEC-151 (human G4), was administered as a negative control at 30 mg/kg. Tumors were extracted at the indicated intervals post-inoculation (FIG. 21) and total tumor volume was measured.

Figure 21:
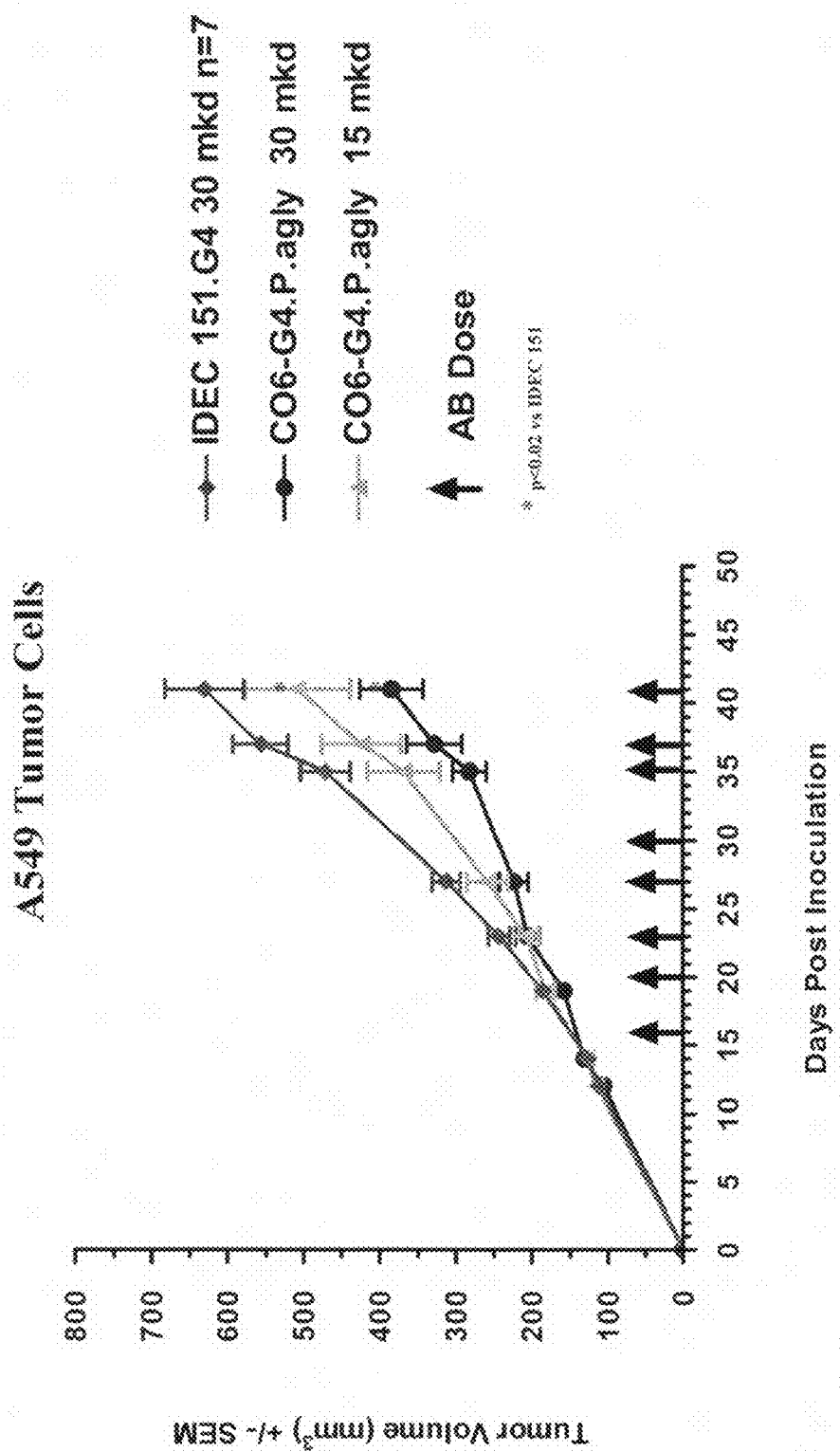
FIG. 21: Fully human M13.C06.G4.P.agly antibody exhibits in vivo dose dependent inhibition of tumor growth in a lung cancer model.

Results: The fully human M13.C06.G4.P.agly antibody inhibited tumor growth in a dose dependent manner (FIG. 21). The antibody demonstrated statistically significant single agent efficacy at 30 and 15 mg/kg doses administered over a 4 week period (FIG. 21). Additional studies performed in this model showed that C06 is efficacious at doses as low as 7.5 mg/kg weekly injections (data not shown).

Example 24

In Vivo Inhibition of Tumor Growth Using Combination Therapy

Method: The efficacy of M13.C06.G4.P.agly antibody in inhibiting tumor growth in combination with gemcitabine (a drug commonly used to treat non-small cell lung cancer, pancreatic, bladder and breast cancer) was tested in a BxPC3 xenograft model. The efficacy of M13.C06.G4.P.agly antibody administered intraperitoneally (i.p.) two times per week at 30 mg/kg for 7 weeks (data not shown) or one time per week at 60 mg/kg for 5 weeks (FIG. 22) was evaluated in combination with gemcitabine administered according to the current standard of care (i.e., 80 mg/kg every 3 days for 4 weeks). Gemcitabine alone, M13.C06.G4.P.agly antibody alone, and sham injections of the delivery vehicle alone were administered as negative controls. Tumor volume at the start of the therapy was approximately 200 mm$^3$.

Results: M13-C06.G4.P.agly antibody and gemcitabine as a single agent (i.e., administered alone) showed similar efficacy. In combination with Gemcitabine, the M13-C06.G4.P.agly antibody at 30 mg/kg on twice a week schedule (data not shown) or 60 mg/kg on a weekly schedule (FIG. 22) showed additive efficacy compared to the single agent treatments. In addition, combination with 15 mg/kg also showed additive efficacy (data not shown)

Example 25

Fully Human IGF-1R Antibody Binds to Cynomolgus Macaque Fibroblast Cell Line

Methods: The M13.C06.G4.P.agly antibody binds to a fibroblast cell line established from cynomolgus macaque. The fibroblast cell line was generated from a skin biopsy. Antibody binding was assessed by lifting the fibroblast cells with cell disassociation buffer and incubating with biotinylated M13.C06.G4.P.agly for 45 minutes at 4° C. After washing the cells, streptavidin-PE was added and incubated for additional 30 minutes at 4° C. in the dark. The cells were then washed and 200 ul cold PBS was added followed by fixation with 1% formaldehyde and gentle vortexing. Antibody binding was assessed by FACS analysis.

Results: The M13-C06.G4.P.agly antibody binds to IGF-1R expressed on the cynomolgus fibroblast cell line in a concentration dependent manner (FIG. 23).

Example 26

Part I: Summary of Biological Characteristics of Fully Human M13.C06.G4.P.agly Antibody Biological characteristics assessed for fully human M13.C06.G4.P.agly antibody are presented in Tables 11 and 12. These characteristics were ascertained by methods, experiments, and examples described herein and/or as may be routinely determined via methods and experiments known and performed by those of ordinary skill in the art.

TABLE 11

Biological characteristics of M13.C06.G4.P.agly antibody (human, non-glycosylated, IgG4)

| Properties Assessed: | Results Obtained: |
|---|---|
| IGF-1R Binding (EC50)* | Solube IGF-1R Protein: $4.22 \times 10^{-11}$ M |
|  | Tumor cell IGF-1R: $2.2 \times 10^{-10}$ M |
|  | (M13.C06 Fab affinity for IGF-1R = 1.3 nM) |
| Cyno IGF-1R | Cyno IGF-1R/CHO = $4.7 \times 10^{-10}$ M |
| Rhesus IGF-1R | Rhesus IGF-1R/CHO = $2.7 \times 10^{-10}$ M |
| Ligand Blocking (IC50 nM) | IGF-1 blocking: 0.979 nM |
|  | IGF-2 blocking: 0.525 nM |
| Inhibition of IGF-1 & IGF-2 stimulated phosphorylation of IGF-1R (IC50 nM) | IGF-1 < 0.13 nM |
|  | IGF-2 < 0.63 nM |
| Inhibition of IGF-1 & IGF-2 mediated phosphorylation of Akt (Thr308, Ser473) and pErk | Positive for IGF-1 and IGF-2 at: >1 nM >1 nM |
| IGF-1R down regulation (internalization) | >60% down regulation in 1 hour in MCF-7 cells |
| In vitro inhibition of IGF-1 & IGF-2 driven tumor cell line growth: | Inhibition observed in ~70% cell lines (15 of 21 cell lines) |
| In vivo efficacy of antibody in reducing tumor size: | Activity in 3 mouse models at doses as low as 7.5 mg/Kg × 1 week |

M13. C06. G4.P.agly Antibody Serum Half-Life

A pharmacokinetic (PK) study in non-tumor bearing mice was performed using 3 mg/kg of M13.C06.G4.P.agly antibody (one dose level, intraperitoneal injections) in SCID mice. M13.C06.G4.P.agly antibody in SCID mouse serum was detected using IgG specific ELISA. Goat anti-human IgG (100 ng/well) was immobilized on immulon plates. Serums were titrated in triplicate starting at 1:25 with two fold serial dilutions. Binding was determined using Goat anti-human Kappa-HRP. Results of this study indicate a serum-half life of ~11.5 days in this mouse model system (data not shown).

Serum concentrations of M13.C06.G4.P.agly were assessed after intraperitoneal injections in MCF-7 tumor bearing animals (antibody at 30 ug/kg) and BxPC3 tumor bearing animals (antibody at 15 ug/kg). Binding of M13.C06.G4.P.agly antibody to Goat anti-Human IgG (100 ng/well) immobilized on 96-well (IMMULON2 HB, Dynax Technologies, Inc., Cat. #3455) was measured via ELISA. Standard curves were titrated starting at 10 ug/ml with 3 fold serial dilutions. Serum was titrated starting at 1:25 dilutions with 2 fold serial dilutions. M13.C06.G4.P.agly antibody was detected using Goat anti-human Kappa-HRP. SOFTMAX PRO software package version 4.3 LS (Molecular Devices Corp.) was used to determine antibody concentrations.

Average serum concentrations were observed as shown below:

| Bleed Time Points (hrs) | Average serum concentraion (μg/mL) |
|---|---|
| MCF-7 Tumor Bearing Mice | |
| 0 | 0 |
| 2 | 213 |
| 6 | 253 |
| 12 | 189 |
| 24 | 224 |
| 48 | 137 |
| BxPC3 Tumor Bearing Mice | |
| 0 | 0 |
| 2 | 102 |
| 6 | 145 |
| 12 | 122 |
| 24 | 115 |
| 48 | 79 |

The pharmocokinetics of M13.C06.G4.P.agly antibody has also been investigated in cynomolgus monkeys after 10 mg/kg and 25 mg/kg dose injections, where the serum half-life was observed to be ~10 to 12 days (data not shown).

Tables 12 and 13 show the dose dependent inhibition (percent inhibition) of in vitro cell growth observed for various lung, pancreas, and colon tumor cell lines when M13-C06.G4.P.agly antibody is added to cell culture media supplemented with IGF-1 or IGF-2 (Table 12) or supplemented with 10% fetal calf serum (FCS) or fetal bovine serum (FBS) (Table 13).

TABLE 12

| Cell | | IGF-1 in Media | | | | IGF-2 in Media | | | |
|---|---|---|---|---|---|---|---|---|---|
| | | Dose dependent cell growth inhibition with increasing M13-C06.G4.P.agly antibody concentration (% = percent growth inhibition; nM = antibody concentration) | | | | | | | |
| Type: | Cell Line: | 0.1 nM | 1 nM | 10 nM | 100 nM | 0.1 nM | 1 nM | 10 nM | 100 nM |
| Lung | NCI-H23 | 12% | 32% | 61% | 84% | 2% | 32% | 61% | 85% |
| | A549 | 39% | 58% | 79% | 87% | 37% | 61% | 76% | 85% |
| | Calu-6 | 12% | 15% | 19% | 53% | −4% | 16% | 27% | 62% |
| | SK-MES-1 | −30% | −15% | 5% | 46% | ND | ND | ND | ND |
| Pancreas | BXPC3 | 12% | 34% | 54% | 82% | 63% | 79% | 96% | 99% |
| | Panc-1 | 0% | 0% | 18% | 60% | 0% | 12% | 35% | 62% |
| | Capan-1 | 2% | 0% | 20% | 17% | 19% | 12% | 12% | 31% |
| | Capan-2 | 14% | 22% | 36% | 49% | ND | ND | ND | ND |
| Colon | Colo 205 | 15% | 37% | 56% | 76% | 18% | 30% | 45% | ND |
| | SW620 | 10% | 12% | 13% | 27% | ND | ND | ND | ND |

TABLE 13

| Cell | | 10% Serum in Media Dose dependent cell growth inhibition with increasing M13-C06.G4.P.agly antibody concentration (% = percent growth inhibition; nM = antibody concentration) | | | |
|---|---|---|---|---|---|
| Type: | Cell Line: | 0.2 nM | 2 nM | 20 nM | 200 nM |
| Lung | NCI-H23 | 5% | 12% | 21% | 47% |
| | A549 | 2% | 12% | 22% | 41% |
| | Calu-6 | 0% | 0% | 0% | 9% |
| | SK-MES-1 | 12% | 10% | 6% | 7% |
| Pancreas | BXPC3 | 6% | 3% | 9% | 26% |
| | Panc-1 | 6% | 11% | 12% | 30% |
| | Capan-1 | 0% | 0% | 0% | 0% |
| | Capan-2 | 41% | 45% | 47% | 38% |
| Colon | Colo 205 | 0% | 0% | 11% | 28% |
| | SW620 | 0% | 4% | 6% | 20% |
| | HT-29 | 21% | 21% | 23% | 37% |
| | WiDr | 35% | 45% | 51% | 57% |

Part II: Antibody Affinity Measurements

Objective:

The objective was to measure the binding affinity of IGF-1R antibodies.

Methods:

Preparation of M13-C06, M14-C03, and M14-G11 Fabs

M13-C06, M14-C03, and M14-G11 Fab antibodies were prepared by digestion with immobilized papain (Pierce Cat. No. 20341). The papain resin was washed with 20 mM sodium phosphate pH 7.0; 10 mM EDTA; 20 mM Cysteine. Antibodies were mixed with the papain resin in 500 mM EDTA, 100 mM Cysteine pH 7.0 and digested for three hours in a 37° C. water bath followed by mixing on an inverting shaker overnight at room temperature. Completion of each digestion was determined by analytical size exclusion chromatography (SEC). The resin was removed from the digested protein with a sintered glass funnel filter and washed with 20 mM acetate pH 5.0. The flowthrough was collected and diluted 10-fold with 20 mM acetate pH 5.0. Fab fragments were purified by S-SEPHAROSE™ cation exchange chromatography using a linear salt gradient. Analytical SEC was performed on the eluted fractions and the desired fractions were pooled and dialyzed into PBS. The Fabs were subsequently alkylated to inhibit the re-formation of hinge disulfides resulting in (Fab)$_2$ production. Alkylation was carried out by diluting 1M Tris; 200 mM Iodoacetate pH 8.5 10-fold into the Fab solutions. The mixtures were incubated on an inverting shaker for twenty minutes at room temperature followed by exhaustive dialysis into 1×PBS. Final purification of each Fab was performed using preparative size exclusion chromatography.

Surface Plasmon Resonance (SPR) Affinity Measurements

All surface plasmon resonance (SPR) experiments were performed on a Biacore 3000 set to 25° C. using HBS-EP (Biacore, Cat. No. BR-1001-88) as the running buffer. A biotin-labeled anti-HisTag antibody (biotin-PENTA-His, Qiagen Cat. No. 34440) was immobilized to saturation on a Biacore SA chip (Cat. No. BR-1000-32) surface by injection at 500 nM in HBS-EP buffer. Recombinant human IGF-1R-10His (R&D Systems, Cat. No. 305-GR-050) was captured on the biotin-PENTA-His surface by injecting 20 µL of 40 nM protein at 2 µL/min. Subsequent to IGF-1R injections, flow rates were increased to 20 µL/min. A second, 130 µL injection of anti-IGF-1R antibody or Fab was performed to investigate interactions with the receptor. Each antibody and Fab was serially diluted from 64 nM to 0.5 nM to obtain concentration dependent kinetic binding curves. Each injection series was regenerated using 3×10 µL injections of 10 mM Acetate, pH 4.0, at 20 µL/min. Each curve was double referenced using (1) data obtained from a streptavidin surface devoid of IGF-1R and (2) data from a primary injection of IGF-1R followed by a secondary injection of HBS-EP buffer. The concentration series for each antibody and Fab was fit to the 1:1 binding model provided within the BiaEvaluation software of the manufacturer.

Results

Three recombinant anti-IGF-1R antibodies, M13-C06, M14-C03, and M14-G11, were tested for binding to IGF-1R using surface plasmon resonance as described above. All three antibodies demonstrated strong binding to the receptor. Concentration dependent binding of each antibody (64 nM serially diluted to 0.5 nM) to immobilized recombinant human IGF-1R was observed (data not shown). The rates at which the antibodies accumulate on the IGF-1R coated surface when applied at various concentrations as well as the rates at which they dissociated during applications of pure buffer were investigated by fitting the data to a 1:1 binding model. Approximate kinetic rate constants and equilibrium dissociation constant were calculated (Table 14).

TABLE 14

| Antibody/Fab | $K_D$ (M) | $k_d$ (s$^{-1}$) | $k_a$ (M$^{-1}$ s$^{-1}$) |
|---|---|---|---|
| M13-C06_Ab | 1.3e−10 | 2.5e−4 | 1.8e6 |
| M14-C03_Ab | 3.6e−10 | 2.0e−4 | 5.7e5 |
| M14-G11_Ab | 1.1e−10 | 1.1e−4 | 1.0e6 |

TABLE 15

| Antibody/Fab | $K_D$ (M) | $k_d$ (s$^{-1}$) | $k_a$ (M$^{-1}$ s$^{-1}$) |
|---|---|---|---|
| M13-C06_Fab | 1.3e−9 | 1.2e−3 | 8.8e5 |
| M14-C03_Fab | 4.9e−9 | 9.4e−4 | 1.9e5 |
| M14-G11_Fab | 4.0e−9 | 1.2e−3 | 3.0e5 |

To obtain discrete affinities, Fab fragments of each antibody were generated using papain digestion as described above. Due to the presence of a single antigen binding site, the Fabs uniformly demonstrated monophasic binding and dissociation curves when applied to the IGF-1R receptor in an identical fashion as described for the full-length antibodies (data not shown). The affinities of each Fab for IGF-1R are provided in Table 15.

Example 27

Part I: M13.C06.G4.P.agly Antibody has Unique Epitope Binding Characteristics Compared to Other IGF-1R Antibodies A cross-competition antibody binding study was performed to compare the IGF-1R antibody binding epitopes of M13.C06.G4.P.agly and other IGF-1R antibodies. See, FIG. 24. Unlabeled competitor antibodies were analyzed for their ability to cross-compete with five different labeled antibodies for binding to soluble IGF-1R. The five labeled antibodies used were biotin-labeled M13.C06.G4.P.agly ("Biotin-C06"), biotin labeled M14-G11 ("Biotin-G11"), zenon-labeled P1B10-1A10 ("Zenon-O"), zenon-labeled 20C8-3B4 ("Zenon-M"), or zenon-labeled IR3 antibody ("Zenon-IR3"). See, FIG. 24.

Antibodies were labeled with Biotin using a Biotinylation kit from Pierce Chemical (#21335).

Zenon labeling was performed using Zenon mouse IgG labeling kit from Molecular Probes (Z25000).

+++++=antibody binding competition relative to itself (90-100%)
++++=70-90% competition
+++=50-70% competition
++=30-50% competition
+=10-30% competition
+/−=0-10% competition
N/A=results not available.

The results of this analysis indicate that M13.C06.G4.P.agly and M14.C03.G4.P.agly antibodies bind to the same or a similar region of IGF-1R, which is distinct from all other antibodies tested. In particular, only biotin-labeled M13.C06.G4.P.agly antibody was effectively competed from IGF-1R binding by unlabeled M13.C06.G4.P.agly or by unlabeled M4.C3.G4.P.agly. It is also notable that M13.C06.G4.P.agly does not cross-compete with the well-studied IR3 antibody. Hence, these two antibodies, in particular, bind to different IGF-1R epitopes.

Part II: M13-C06 Allosterically Decreases the Binding Affinity of IGF-1 for IGF-1R Via Antibody Binding to the N-Terminal Region of the FnIII-1 Domain Objective:
The objective was to elucidate the binding epitope of M13-C06 antibody on IGF-IR and the mechanism behind inhibition of IGF-1/IGF-2 binding to IGF-1R.

Background:
IGF-1R consists of 6 domains (FIG. 29A). It has been published that mutations in the first three domains of IGF-1R, denoted L1 (leucine rich repeat domain 1), CR (cysteine rich repeat domain), and L2, as well as a peptidic loop region in domain 5 (FnIII-2, Fibronectin type III domain 2) have a negative impact on IGF-1 and IGF-2 binding (Whittaker 2001; Sorensen 2004). Here, we demonstrate that M13-C06 antibody does not block IGF-1 and IGF-2 binding to IGF-1R by competitively interacting with the growth factor binding site, but instead binds to FnIII-1 and allosterically inhibits IGF-1/IGF-2 signaling. FnIII-1 is believed to facilitate receptor homodimerization of both IGF-1R and INSR (McKern 2006) and, upon binding ligand, transmit an activating signal through the transmembrane region to the C-terminal tyrosine kinase domains via a quarternary structure change. The data from this example suggests M13-C06 antibody inhibits conformational changes induced by IGF-1/IGF-2 that lead to downstream receptor signaling.

Methods:

IGF-1/IGF-1R Binding Experiments in the Presence and Absence of M13-C06 Antibody Several constructs were used to investigate antibody/IGF-1 binding to the IGF-1R receptor or insulin receptor: human IGF-1R(1-902)-His$_{10}$ (denoted hIGF-1R-His$_{10}$, from R&D systems), human INSR(28-956)-His$_{10}$ (denoted INSR, from R&D systems), human IGF-1R(1-903)-Fc (denoted hIGF-1R-Fc, generated by Biogen Idec), human IGF-1R(1-462)-Fc (denoted hIGF-1R(1-462)-Fc, generated by Biogen Idec), and murine IGF-1R(1-903)-Fc (denoted mIGF-1R-Fc, generated by Biogen Idec). "His$_{10}$" denotes a 10-residue histidine tag on the C-terminus of the constructs. "Fc" denotes a C-terminal human IgG1-Fc tag.

Human IGF-1 was purchased from Millipore. The affinity of IGF-1 for hIGF-1R-His$_{10}$ was determined using surface plasmon resonance (SPR). A biotin-labeled anti-H HisTag antibody (biotin-PENTA-His, Qiagen Cat. No. 34440) was immobilized to saturation on a Biacore SA chip (Cat. No. BR-1000-32) surface by injection at 500 nM in HBS-EP buffer. For each sensorgram, hIGF-1R-His$_{10}$ (described in Example 5 (Part II)) was captured on the biotin-PENTA-His surface by injecting 20 µL of 40 nM protein at 2 µL/min. Subsequent to hIGF-1R-His$_{10}$ injection, the flow rate was increased to 20 µL/min. A second, 130 µL injection containing IGF-1 was performed to investigate interaction of the growth hormone with its receptor. IGF-1 was serially diluted from 64 nM to 0.125 nM to obtain concentration dependent kinetic binding curves. Each injection series was regenerated using 3×10 µL injections of 10 mM Acetate, pH 4.0, at 20 µL/min. Each curve was double referenced using (1) data obtained from a streptavidin surface devoid of PENTA-His antibody and (2) data from a primary injection of hIGF-1R-His$_{10}$ followed by a secondary injection of HBS-EP buffer. The concentration series for IGF-1 was fit to the 1:1 binding model provided within the BiaEvaluation software of the manufacturer. Two sets of data were obtained, one in the absence and another in the presence of 400 nM M13-C06 in the running buffer, hIGF-1R-His$_{10}$ injection buffer, and IGF-1 injection buffer.

Pull-Down and Western Blot Analysis of IGF-1/IGF-1R/M13-C06 Antibody Ternary Complexes Resuspended Protein A/G beads (300 µl, Pierce Cat. No. 20422) were washed with 1×PBS and mixed with 1.0 mg M13-C06 in a 1.5 ml Eppendorf tube on a rotary shaker for two hours at room temperature. In a separate tube, 12 µg hIGF-1R-His$_{10}$ (R&D systems) and 460 ng human IGF-1 (Chemicon International Cat. No. GF006) were mixed (1:1 protein:protein ratio) for one hour at room temperature. Protein A/G with bound M13-C06 was washed with PBS and incubated with the hIGF-1R-His$_{10}$/IGF-1 mixture for 30 minutes at room temperature. Protein A/G with bound protein was washed with PBS followed by elution of bound protein with 300 µL 100 mM glycine, pH 3.0. For the negative control, the addition of 12 µg human IGF-1R(1-902)-His$_{10}$ was omitted. Eluted proteins were detected by Western Blot with an anti-human IGF-1 antibody (Rabbit anti-Human IGF-1 Biotin, USBiological Cat. No. 17661-01B) and an anti-human IGF-1R antibody (IGF-1Rα1H7, Santa Cruz Biotechnology Cat. No. sc-461) as primary antibodies followed by HRP-labeled streptavidin (Southern Biotech Cat. No. 7100-05) and HRP-labeled goat anti-mouse IgG (USBiological Cat. No. 11904-40J) as secondary antibodies. To demonstrate the ability of IGF-1/IGF-1R/M13-C06 to form a ternary complex the concentrations of the IGF-1 and IGF-1R used in this experiment were well in excess (>15-fold above) the normal physiological levels of these proteins (particularly IGF-1 in the serum) as well as the measured equilibrium dissociation constant for IGF-1R/IGF-1. See, for example, Hankinson et al., 1997.

Construction of IGF-1R(1-462)-Fc and Comparative Antibody Binding Studies Versus the Full-Length Receptor Ectodomain Construction of the IGF-1/IGF-2 binding domains, L1-CR-L2 (residues 1-462), of human IGF-1R was published previously (McKern 1997). Utilizing this information, we subcloned human IGF-1R residues 1-462 (along with the N-terminal signal sequence) into the same in-house PV90 vector that was used to produce the full-length human ectodomain (residues 1-903, hIGF-1R-Fc). Expression in CHO was facilitated using methods described previously (Brezinsky 2003). The protein was purified from CHO supernatants by passage over a protein A affinity column as described previously for other Fc-fusion proteins (Demarest 2006). The protein construct is denoted hIGF-1R(1-462)-Fc.

The ability of M13-C06, M14-C03, and M14-G11 antibodies to bind hIGF-IR(1-462)-Fc and the full-length ectodomain construct, hIGF-1R-Fc, was determined by SPR using a Biacore3000. The instrument was set to 25° C. and the running buffer was HBS-EP, pH 7.2 (Biacore, Cat. No. BR-1001-88). The fully human antibodies, M13-C06, M14-C03, and M14-G11, were immobilized to 10,000 RU on Biacore CM5 Research Grade Sensor Chip (Cat. No. BR-1000-14) surfaces using the standard NHS/EDC-amine reactive chemistry according to protocols supplied by Biacore. For immobilization, the antibodies were diluted to 40 µg/mL in a 10 mM Acetate pH 4.0 buffer. To investigate the relative kinetics of association and dissociation of hIGF-1R-Fc and hIGF-1R(1-462)-Fc to each of the human antibodies, increasing concentrations of each receptor construct were injected over the sensorchip surfaces. The hIGF-1R-Fc concentration series ranged from 1.0 nM to 100 nM while the hIGF-1R(1-462)-Fc concentration series ranged from 1.0 nM to 2 µM. All antibody surfaces were reliably regenerated with 100 mM Glycine, pH 2.0. Repeated regenerations did not lead to activity losses for any of the antibody surfaces. Flow rates were 20 µl/min.

Epitope Mapping Mutations

The choice of mutants to probe for the epitope of M13-C06 antibody on IGF-1R were based on the observation that the binding affinity of M13-C06 to mouse IGF-1R was significantly reduced or non-detectable in Biacore and FRET binding experiments (Example 5 (Part III)). Mouse and human IGF-1R share 95% primary amino acid sequence identity. Human IGF-1R and human INSR share 57% identity (73% similarity). We identified 33 residues that differ between mouse and human IGF-1R in the ectodomain (Table 16). Twenty of these residues were targeted for mutation because the homologous positions within the INSR ectodomain were exposed to solvent based on the recent INSR crystal structure (pdb code 2DTG, McKern 2006). Accessible surface areas were calculated using StrucTools (http://molbio.info.nih.gov/structbio/basic.html) with a 1.4 Å probe radius. Four additional residues not in the structure of INSR were also chosen for mutagenesis as they resided in the unstructured loop region of the FnIII-2 domain that has been demonstrated to be important for IGF-1/IGF-2 binding (Whittaker 2001; Sorensen 2004). The list of the 24 mutations chosen for the epitope mapping study are shown in Table 17.

TABLE 16

Amino acid differences between human and mouse IGF-1R. Solvent accessibility of each residue position was determined based on the publicly available structure of the homologous INSR ectodomain. Residues shown in bold/italics exposed greater than 30% of their surface area to solvent and were mutagenized to screen for the IGF-1R epitope of M13-C06.

| Residue # | Human IGF1R | Mouse IGF1R | Human INSR | IR pdb # | % Solvent Accessibility |
|---|---|---|---|---|---|
| 28 | Y | F | H | 32 | 33.3 |
| 125 | V | I | I | 131 | 0 |
| 156 | M | L | A | 163 | 73.9 |
| 188 | T | V | I | 195 | 89.3 |
| 210 | S | H | S | 217 | 56.1 |
| 211 | A | T | Q | 218 | 54 |
| 214 | N | D | D | 221 | 25.7 |
| 215 | D | N | P | 222 | 20.4 |
| 217 | A | T | K | 224 | 57.3 |
| 227 | A | K | D | 234 | 78.9 |
| 237 | N | G | P | 244 | 90.1 |
| 257 | L | P | H | 263 | 19.2 |
| 258 | S | N | H | 264 | 56.5 |
| 264 | E | D | N | 275 | 38.3 |
| 271 | G | D | N | 282 | 72.5 |
| 285 | G | S | S | 296 | 100 |
| 286 | S | T | S | 297 | 67.2 |
| 303 | E | G | H | 313 | 64.5 |
| 326 | F | L | I | 335 | 25.5 |
| 405 | D | N | S | 415 | 67.9 |
| 411 | I | V | T | 421 | 0.5 |
| 412 | K | R | T | 422 | 34.7 |
| 413 | A | S | Q | 423 | 58.2 |
| 464 | H | R | K | 474 | 76.3 |
| 471 | S | W | S | 481 | 26.4 |
| 531 | D | E | Q | 541 | N/A |
| 532 | V | G | N | 542 | N/A |
| 605 | S | T | S | 615 | N/A |
| 650 | I | V | S | N/A | N/A |
| 665 | E | D | INSERT | N/A | N/A |
| 739 | A | V | F | N/A | N/A |
| 741 | L | F | P | N/A | N/A |

The 24 mutant epitope mapping library was constructed by mutagenizing the wild-type hIGF-1R-Fc PV-90 plasmid using the Stratagene site-directed mutagenesis kit following the manufacturer's protocols. Incorporation of each mutant (or double mutant in the case of the SD004, SD011, SD014, SD016, and SD019 library members) into the PV-90 vector was confirmed by our in-house DNA sequencing facility. Plasmids were miniprepped and maxiprepped using the Qiagen Miniprep Kit and Qiagen Endotoxin-Free Maxikits, respectively. 200 µg of each mutant plasmid was transiently tranfected into 100 mL HEK293 T cells at $2 \times 10^6$ cells/mL using the PolyFect transfection kit (Qiagen) for soluble protein secretion into the media. Cells were cultured in DMEM (IvrineScientific), 10% FBS (low IgG bovine serum, Invitrogen—further depleted of bovine IgG by passage over a 20 mL protein A column) at 37° C. in a $CO_2$ incubator. After 7 days, supernatants containing each IGF-1R-Fc mutant were collected by centrifugation at 1200 rpm and filtration through a 0.2 µm filter. Each mutant was affinity purified by passage of the supernatants over a 1.2 mL protein A Sepharose FF column pre-equilibrated with 1×PBS. The mutants were eluted from the column using 0.1 M glycine, pH 3.0, neutralized with 1 M Tris, pH 8.5, 0.1% Tween-80, and concentrated to ~300 µL using VivaSpin 6 MWCO 30,000 centrifugal concentration devices (Sartorius, Cat. No. VS0621).

Western Blot Analysis of IGF-1R Mutants hIGF-1R-Fc mutant samples were run on 4-20% Tris-Glycine gels (Invitrogen Cat. No. EC6028) using Xcell SureLock Mini Cell (Invitrogen Cat. No. EI0001) following standard manufacturer protocol. Samples were transferred to nitrocellulose using the iBlot Dry Blotting System (Invitrogen Cat. No. IB1001) and Transfer Stacks (Invitrogen Cat. No. IB3010-01 or 3010-02) following standard manufacturer protocol. Membranes were blocked overnight at 4° C. in 25 ml of PBST; 5 mg/ml non-fat dry milk. After blocking, membranes were washed once with 25 ml PBST for 5 min at room temperature. Membranes were incubated with a primary anti-IGF-1Rβ antibody (Santa Cruz Biotechnology Cat. No. sc-9038) at 1:100 in 10 ml PBST for 1 hr at room temperature. The membranes were subsequently washed three times in 25 ml PBST for 5 min. For detection, membranes were incubated with a secondary HRP-conjugated Goat anti-Rabbit IgG-Fc antibody (US Biological Cat. No. I1904-40J) at a 1:1000 dilution in 10 ml PBST for 1 hr at room temperature. Membranes were washed three times in 25 ml PBST for 5 min followed by one wash in 25 ml PBST for 20 min. Protein bands were detected using the Amersham ECL Western Blotting Analysis System (GE Healthcare Cat. No. RPN2108) following standard manufacturer protocol.

Biacore Analysis of the IGF-1R-Fc Mutant Library

Both mIGF-1R-Fc and hIGF-1R-Fc bind with high apparent affinity to the M13-C06, M14-C03, and M14-G11 sensorchip surfaces described above due to their highly multivalent nature induced by the incorporation of two separate homodimeric regions (IGF-1R and IgG1-Fc). To distinguish between the actual high affinity binding hIGF-1R-Fc to M13-C06 and the low affinity binding of mIGF-1R-Fc to M13-C06, the receptor-Fc fusions were captured on the M13-C06 sensorchip surface followed by an additional soluble M13-C06 Fab binding event. Receptor-Fc constructs were captured to the M13-C06 chip surface (prepared as described above) by injection of 60 µL of the affinity purified, concentrated material at a 1 µl/min flow rate. After, completion of the receptor-Fc loading step, flow rates were elevated to 5 µl/min. 10 nM, 3 nM, and 1 nM M13-C06 Fab concentrations were injected (50 µL) subsequent to the loading of each receptor-Fc construct. At the end of each sensorgram, the flow rate was elevated to 30 µl/min and the chip surface was regenerated by 2×10 µL injections of 0.1 M glycine, pH 2.

Time-Resolved Fluorescence Resonance Energy Transfer (tr-FRET) Assay for IGF-1R-Fc Mutant Screening Serial dilutions of mutant receptor, starting at 0.25-0.5 µg (25 µl) were mixed with 0.05 µg IGF1R-$His_{10}$-Cy5 (12.5 µl) and 0.00375 µg Eu:C06 (12.5 µl) in 384-well microtiter plates (white from Costar). The conjugation levels for IGF1R-$His_{10}$-Cy5 were 6.8:1 Cy5:IGF1R-$His_{10}$, and for Eu-C06 were 10.3:1 Eu:C06. The total volume was 50 µl for each sample. Plates were incubated for 1 hr at room temperature on a plate agitator. Fluorescence measurements were carried out on a Wallac Victor$^2$ fluorescent plate reader (Perkin Elmer) using the LANCE protocol with the excitation wavelength at 340 nm and emission wavelength at 665 nm. All data were fitted to a one-site binding model from which the corresponding $IC_{50}$ values were determined.

Results

Inhibition of IGF-1 and/or IGF-2 binding to hIGF-1R-Fc by M13-C06 was demonstrated as previously described in Example 3. Even at saturating conditions, most antibodies do not fully inhibit IGF-1 or IGF-2 binding to hIGF-1R-Fc. Particularly for M13-C06, we hypothesized that inhibition of ligand binding might be non-competitive or allosteric. To test this hypothesis, we determined the affinity of IGF-1 for hIGF-1R-His$_{10}$ in the presence and absence of 400 nM M13-C06 antibody (4000-fold above the affinity of the antibody for hIGF-1R-His$_{10}$). Using SPR hIGF-1R-His$_{10}$ was immobilized to chip surfaces using an anti-Histag antibody followed by injection of increasing concentrations of IGF-1 (up to 64 nM). IGF-1 binding to hIGF-1R-His$_{10}$ was evident in the absence and presence of 400 nM M13-C06. (Data not shown: Surface plasmon resonance demonstrating binding of IGF-1 to hIGF-1R-His$_{10}$ in the absence and presence of 400 nM M13-C06. The SPR association phase was between 1400-1800 seconds while the dissociation phase was between 1800-3000 seconds. In the absence of M13-C06, IGF-1 bound to hIGF-1R-His$_{10}$ with $K_D$=17 nM ($k_a$=2.4×10$^{-5}$/ M*s). In the presence, of 400 nM M13-C06, IGF-1 bound to hIGF-1R-His$_{10}$ with $K_D$=59 nM ($k_a$=7.1×10$^{-4}$/M*s).) The kinetic association rate constant of IGF-1 binding to hIGF-1R-His$_{10}$ was reduced approximately 3-fold in the presence of M13-C06, suggesting that M13-C06 allosterically reduces the affinity of the ligand for the receptor.

Supporting evidence that M13-C06 does not directly compete with IGF-1 for binding to hIGF-1R-His$_{10}$ was generated by performing a co-immunoprecipitation of hIGF-1R-His$_{10}$ and IGF-1 using M13-C06 at concentrations well above the apparent affinities of both IGF-1 and M13-C06 for hIGF-1R-His$_{10}$. Western blot analysis demonstrated that ~70-100% of the IGF-1 material mixed with hIGF-1R-His$_{10}$ was pulled down with M13-C06, thereby demonstrating that co-engagement of M13-C06 and IGF-1 with hIGF-1R-His$_{10}$ to form the ternary complex is possible (data not shown). These results demonstrate the allosteric nature of M13-C06 inhibition of IGF-1 binding at normal IGF-1 serum concentrations and suggest that the binding site of M13-C06 does not overlap with the IGF-1R ligand-binding pocket.

Next, we investigated whether M13-C06 binds the putative ligand binding domains of IGF-1R (L1-CR-L2). We generated a truncated version of the receptor containing the N-terminal three domains (residues 1-462) fused to an IgG1-Fc and compared its ability to bind M13-C06, M14-C03, and M14-G11 to that of the full-length receptor ectodomain construct, hIGF-1R-Fc, using surface plasmon resonance (SPR). M14-G11 demonstrated equivalent binding to the truncated version of the receptor, while the binding of M13-C06 and M14-C03 was dramatically reduced. (Data not shown: Surface immobilized M13-C06, M14-C03, and M14-G11 antibodies were tested for binding to hIGF-1R(1-903)Fc and truncated hIGF-1R(1-462)-Fc at concentrations ranging from 2 µM, 100 nM, 30 nM, 10 nM, 5 nM and 1 nM. The SPR association phase was between 480-960 seconds while the dissociation phase was between 960-1170 seconds.) Residual binding was apparent for both M13-C06 and M14-C03; however, the data suggests that at least a good portion of the epitopes of these antibodies resides in an IGF-1R region outside the ligand binding domains.

We utilized the fact that murine IGF-1R does not bind M13-C06 antibody to design a library of mouse mutations within hIGF-1R-Fc to assess the location of the M13-C06 binding site on IGF-1R. The various mutations in hIGF-1R tested are shown in Table 17. Western blot analysis was used to confirm expression of each hIGF-1R-Fc mutant and to develop a standard curve to approximate the relative concentration of each mutant protein; using purified hIGF-1R-Fc as a positive control (data not shown).

TABLE 17

Affect of mutations on IGF-1R binding to M13-C06. SD015 is bold-faced as it was the only residue to demonstrate little to no binding to M13-C06 in the two assay formats. ND = not determined.

| Mutation Number | Individual Mutants | Biacore Relative RUmax | IC50 values (µg/ml) |
|---|---|---|---|
| SDWT | Wild-type | 1.0 | 1.5 |
| mIGF1R | — | 0.0 | >100 |
| SD001 | Y28A | 0.6 | 1.0 |
| SD002 | M156A | 1.2 | 0.3 |
| SD003 | T188F | 1.0 | 0.2 |
| SD004 | S210H_A211Q | 0.8 | ND |
| SD005 | A217T | 0.9 | ND |
| SD006 | A227K | 1.7 | 0.2 |
| SD007 | N237G | 1.3 | <0.1 |
| SD008 | S258F | 1.5 | <0.1 |
| SD009 | E264K | 0.6 | 7.7 |
| SD010 | G271D | 0.8 | 0.1 |
| SD011 | G285S_S286T | 1.8 | <0.1 |
| SD012 | E303G | 0.3 | 0.9 |
| SD013 | D405K | 0.7 | <0.1 |
| SD014 | K412A_A413Q | 0.6 | <0.1 |
| SD015 | H464E | 0.04 | >100 |
| SD016 | D531Q_V532N | 2.0 | 0.1 |
| SD017 | I650S | 2.0 | 0.2 |
| SD018 | E665A | 1.7 | <0.1 |
| SD019 | A739W_I741F | 1.9 | 0.2 |

Figure 28:
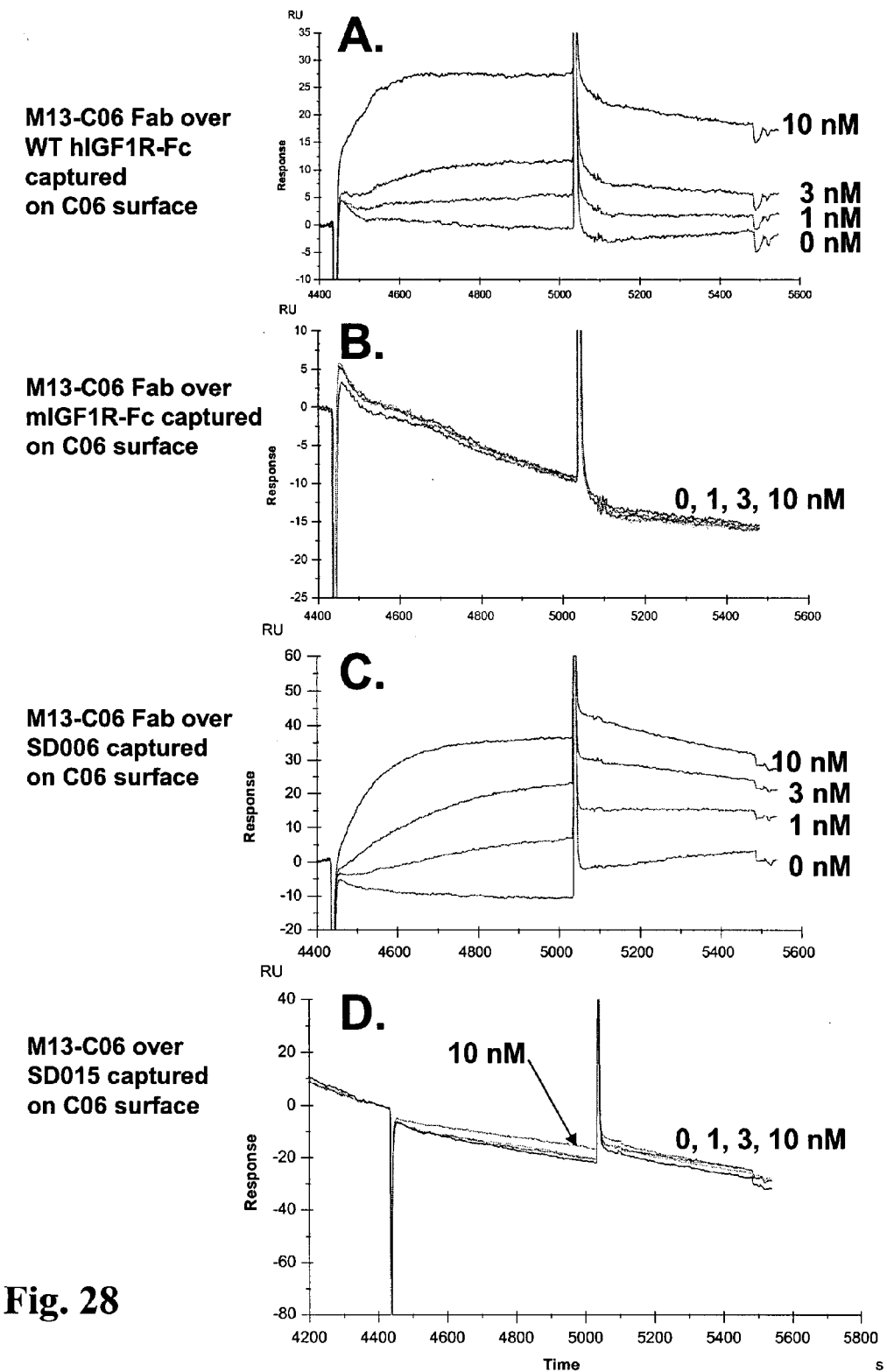
FIG. 28: Examples of M13.C06 antibody binding to hIGF-1R-Fc and mIGF-1R-Fc controls in the SPR assay compared to antibody binding to IGF-1R mutant proteins SD006 (binding positive) and SD015 (binding negative).

SPR and tr-FRET was used to screen for mutations that inhibit the binding of IGF-1R-Fc to M13-C06. Except for the SD015 mutant, all mutant IGF-1R constructs demonstrated M13-C06 binding activity, or M13-C06 Fab binding activity in the SPR experiments. See: FIG. 28; Table 17; and, data not shown (competitive inhibition analysis was used to establish binding curves for displacement of Eu-M13-C06 bound to Cy5-labeled IGF1R by increasing concentrations of unlabeled hIGF1R-Fc (SDWT), mouse IGF1R-Fc (mIGF1R-Fc) and mutant hIGF1R-Fc constructs).

Figure 29:
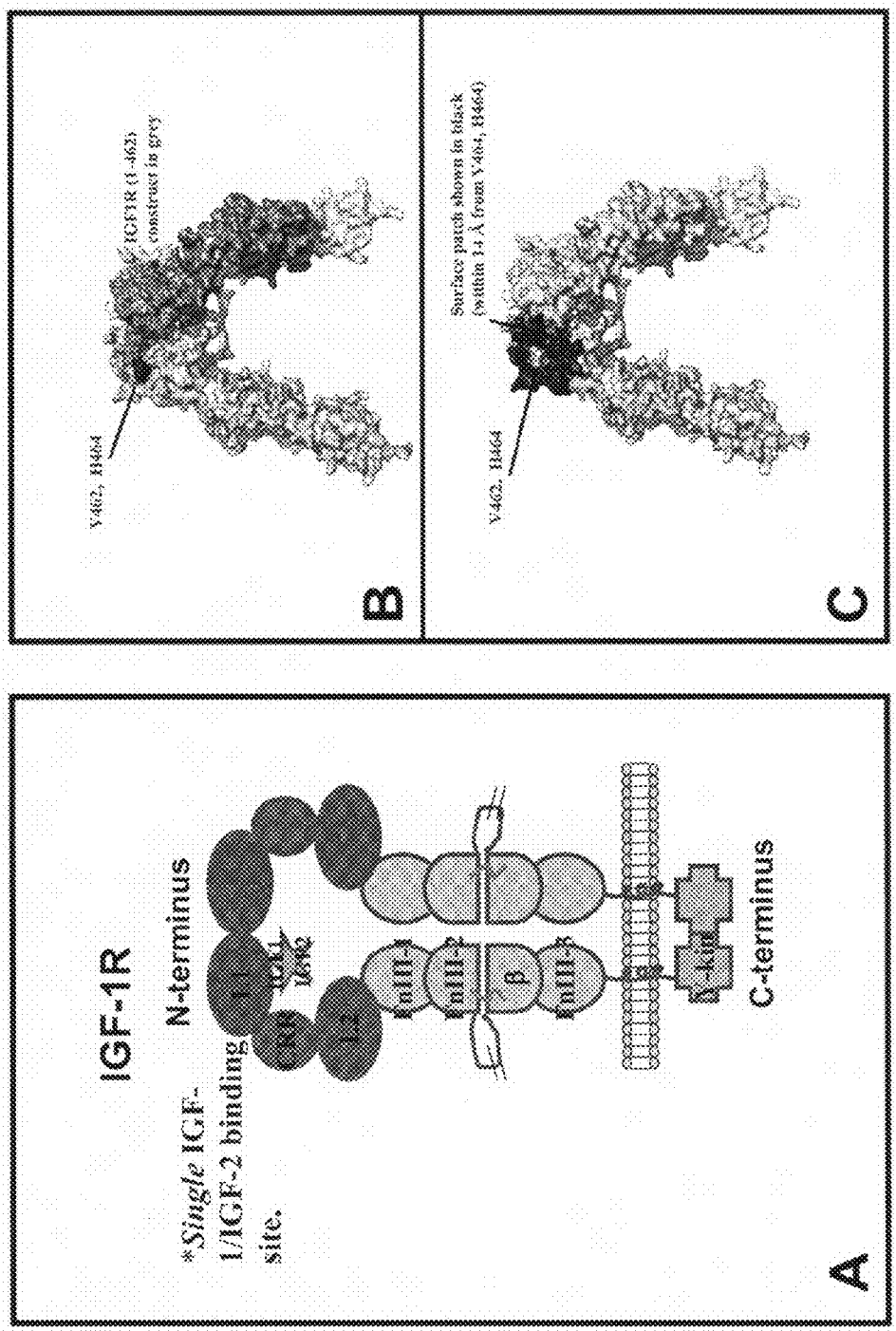
FIG. 29: Structural representations of IGF-1R and INSR: A) Schematic diagram of the structure of IGF-1R. A) FnIII-2 contains loop structure that is proteolytically processed in vivo as shown on the diagram. The transmembrane region is shown as a helical loop that traverses a schematic of a phospholipid bilayer. The location of the IGF-1/IGF-2 binding site within IGF-1R is shown by a star. It has been demonstrated that only one IGF-1/IGF-2 molecule binds to each IGF-1R heterodimeric molecule. B & C) M13-C06 IGF-1R binding epitope mapped to the surface of the structure of the homologous INSR. The M13-C06 IGF-1R binding epitope was modeled based on the highly homologous INSR crystal structure. B) Surface representation of the INSR structure with amino acid residue positions corresponding to the homologous positions of V462-H464 in IGF-1R (i.e., L472-K474 in INSR) are shaded black. The first three domains corresponding to IGF-1R (i.e., L1-CR-L2) (such as are included in the truncated IGF-1R(1-462)-Fc construct described herein) are shaded grey. C) Surface representation of the INSR structure with those residues that expose surface area to solvent and that are within a 14 Å (angstrom) radius (or 28 Å diameter) of residues corresponding to 462-464 of IGF-1R (i.e., 472-474 of INSR) are shaded black. Residues corresponding to IGF-1R amino acids 462-464 are shaded grey to indicate the experimentally confirmed surface area of the proposed epitope.

There was some deviation in the IC$_{50}$ values determined using tr-FRET and relative binding strengths determined using SPR due to natural variations in expression and quantitation by Western Blot; however, SD015 was the only mutant to demonstrate virtually no binding activity toward M13-C06 in both assays and to parallel the results determined for the mIGF-1R-Fc control. His464 is located 2 amino acids C-terminal in primary amino acid sequence to the C-terminus of the truncated version of hIGF-1R-Fc construct (i.e., hIGF-1R(1-462)-Fc). The residual binding activity of M13-C06 to truncated hIGF-1R(1-462) suggests that the M13-C06 binding epitope minimally encompasses residues Val462-His464. Additional residues are likely involved in the antibody-epitope binding interaction as evidence indicates that M13-C06's epitope is conformationally dependent. Notably, however, residues Val462 and His464 are predicted to reside on the exterior surface of the FnIII-1 domain (FIG. 29).

In an attempt to characterize the extent of the M13-C06 epitope (i.e., what residues periperhal to 462-464 are important for antibody binding and activity), we took a structural modeling approach. Human IGF-1R and human INSR share 57% identity (73% similarity) and a similar tertiary structure. Previous analyses of X-ray crystal structure protein antigen: antibody binding surfaces has suggested an average binding surface of 700 A2 (angstroms-squared) with an approximate radius of 14 Å from the center of the binding epitope (Davies 1996). Using the X-ray crystal structure of the homologous ectodomain of INSR (pdb code 2DTG, (McKern 2006)), we calculated the residues on the surface of the FnIII-1 domain within a 14 Å radius of residues 462-464 by mapping the IGF-1R residues V462 through H464 to INSR residues L472 and K474. The distances cut-off was applied for any atom-to-atom distance within 14 Å, while the average distance was calculated from the Cα to Cα distance of L472 and K474 to each residue within the surface patch. The average distance calculated is listed as 14 Å for residues for which the Cα to Cα distance was greater than 14 Å but in which the sidechains are within the 14 Å cut-off. Residues of likely importance for M13-C06 binding and activity are listed in Table 18.

Table 18. Residues within IGF-1R predicted to be important for M13-C06 binding and activity. Residues 462 and 464 are italicized as these represent the predicted center of the IGF-1R binding epitope and experimental data demonstrates the importance of these residues in M13-C06 binding.

TABLE 18

| IR AA residue # (2DTG) | Surface accessibility | IGF1R AA | IGF1R residue # | Distance to 472 (Å) (Cα to Cα) | Distance to 474 (Å) (Cα to Cα) | Average distance (Å) |
|---|---|---|---|---|---|---|
| S437 | 0.477792 | S | 427 | 13.785 | 14 | 13.8925 |
| E438 | 0.337716 | E | 428 | 14 | 14 | 14 |
| E469 | 0.320544 | E | 459 | 9.95 | 14 | 11.975 |
| N470 | 0.8196 | S | 460 | 6.29 | 12.42 | 9.355 |
| E471 | 0.349164 | D | 461 | 3.79 | 9.57 | 6.68 |
| *L472* | *0.475107* | *V* | *462* |  | 6.25 | 6.25 |
| *K474* | *0.646513* | *H* | *464* | 6.25 | 14 | 10.125 |
| S476 | 0.477792 | T | 466 | 12.45 | 6.43 | 9.44 |
| Y477 | 0.524048 | S | 467 | 14 | 9.15 | 11.575 |
| I478 | 0.5405 | T | 468 | 14 | 11.03 | 12.515 |
| R479 | 0.362378 | T | 469 | 14 | 14 | 14 |
| R488 | 0.375476 | T | 478 | 13.98 | 8.75 | 11.365 |
| E490 | 0.37206 | H | 480 | 9.18 | 5.84 | 7.51 |
| Y492 | 0.313493 | Y | 482 | 10.45 | 11.24 | 10.845 |
| W493 | 0.87318 | R | 483 | 11.17 | 13.03 | 12.1 |
| P495 | 0.824499 | P | 485 | 14 | 14 | 14 |
| D496 | 1 | D | 486 | 14 | 14 | 14 |
| E509 | 0.520884 | E | 499 | 14 | 14 | 14 |
| Q513 | 0.515108 | K | 503 | 14 | 14 | 14 |
| N514 | 0.68983 | N | 504 | 14 | 14 | 14 |
| V515 | 0.644094 | V | 505 | 14 | 14 | 14 |
| K544 | 0.865258 | N | 529 | 14 | 14 | 14 |
| S545 | 0.699624 | K | 530 | 14 | 14 | 14 |
| Q546 | 1 | D | 531 | 14 | 14 | 14 |
| N547 | 0.87424 | V | 532 | 14 | 14 | 14 |
| H548 | 0.406778 | E | 533 | 14 | 10.89 | 12.445 |
| W551 | 0.523908 | I | 536 | 14 | 14 | 14 |
| R577 | 0.41477 | H | 563 | 14 | 14 | 14 |
| T578 | 0.43254 | I | 564 | 13.19 | 14 | 13.595 |
| Y579 | 0.603591 | R | 565 | 9.54 | 14 | 11.77 |
| K582 | 0.34027 | K | 568 | 5.54 | 8.98 | 7.26 |
| D584 | 0.602475 | E | 570 | 7.01 | 7.4 | 7.205 |
| I585 | 0.340515 | I | 571 | 10.79 | 10 | 10.395 |
| I586 | 0.308085 | L | 572 | 13.04 | 10.49 | 11.765 |
| Y587 | 0.580196 | Y | 573 | 14 | 13.65 | 13.825 |

Published work has shown that antibodies that recognize residues 440-586 can be both inhibitory and agonistic to IGF-1 binding (Soos 1992; Keynhanfar 2007). 440-586 represents all of L2 and FnIII-1 with many potential non-overlapping surfaces accessible to anti-IGF-1R antibodies. Our study is the first study that we are aware of where the inhibitory epitope of IGF-1R has been mapped to a particular residue(s). A recent structure of INSR was co-crystallized with anti-INSR antibody known to inhibit insulin binding to its receptor (Soos 1986; McKern 2006). The homologous residue to His464 of IGF-1R (K474 of INSR) is part of the binding surface of this antibody with INSR. It is possible that M13-C06 shares a similar inhibitory mechanism for inhibiting IGF-1 binding to IGF-1R as the antagonistic anti-INSR antibody.

Example 28

M13.C06.G4.P.agly Antibody Effectively Localizes In Vivo to Tumor Cells, Inhibits Ki67 Expression, and Downregulates Expression of IGF-1R M13. C06. G4.P.agly Antibody Effectively Localizes to Tumor Cells In Vivo Methods: SCID Beige mice were injected with $2 \times 10^6$ MCF-7 cells (in matrigel) in the presence of estrogen (0.36 mg pellet, 90 day release (Innovative Research of America)). Tumors were grown to 300-500 mm³ then mice were injected intraperitoneally with 30 mg/kg of M13.C06.G4.P.agly antibody. Mice were sacrificed and tumors were removed at 2, 6, 12, 24, and 48 hours post injection frozen in OCT and sectioned at 6 μm for immunohistochemical analysis (IHC). A tumor with no antibody injection was excised as a control. Tumors were frozen in OCT and sectioned at 6 μm for IHC. Substrate is Vector VIP, a purple stain. Bound antibody was detected using goat anti-human IgG H+L (Human Elite ABC kit, Vector Labs) on M13.C06.G4.P.agly or IDEC151 (negative control antibody) treated tumors. IGF-1R expression was detected using an α-IGF-1R Mab (clone 24-31, NeoMarkers/Lab Vision) on M13.C06.G4.P.agly or IDEC151 treated tumors. Similar studies were conducted in BxPC3 pancreatic cancer xenograft model.

Results (data not shown): In vivo efficacy experiments using a mouse MCF-7 breast or BxPC3 pancreatic tumor xenograft models revealed that intraperitoneal injection of M13.C06.G4.P.agly was effective at inhibiting tumor cell growth at 30 and 15 mg/kg. A time-course experiment was performed to study the pharmacodynamics of a single 30 mg/kg or 15 mg/kg dose of M13.C06.G4.P.agly in either MCF-7 or BX-Pc3 tumor-bearing mice, respectively. M13.C06.G4.P.agly localized to tumors as early as 6 hours post treatment, with maximum localization at 48 hours as determined by immunohistochemical analysis (IHC). The expression of IGF-1R as determined by Western and IHC analysis showed significant loss of IGF-1R in M13.C06.G4.P.agly treated tumors 6 hours post-treatment, with almost complete loss of IGF-1R at 24 hours. No change was observed in tumors treated with isotype-matched control antibody. Analysis of tumor lysates for signaling pathways revealed transient reduction of phosphorylated Erk and Akt in 2-12 hours.

M13.C06.G4.P.agly Antibody Inhibits Ki67 Expression

Ki67 staining of M13.C06.G4.P.agly treated tumors also showed a reduced number of proliferating cells compared to control antibody treated tumors (data not shown). These data indicate that M13.C06.G4.P.agly effectively localizes to tumors in vivo, and inhibits tumor growth by downregulation of IGF-1R and inhibition of IGF-1R mediated signaling.

M13.C06.G4.P.agly Downregulates and Degrades IGF-1R in Tumors

Figure 30:
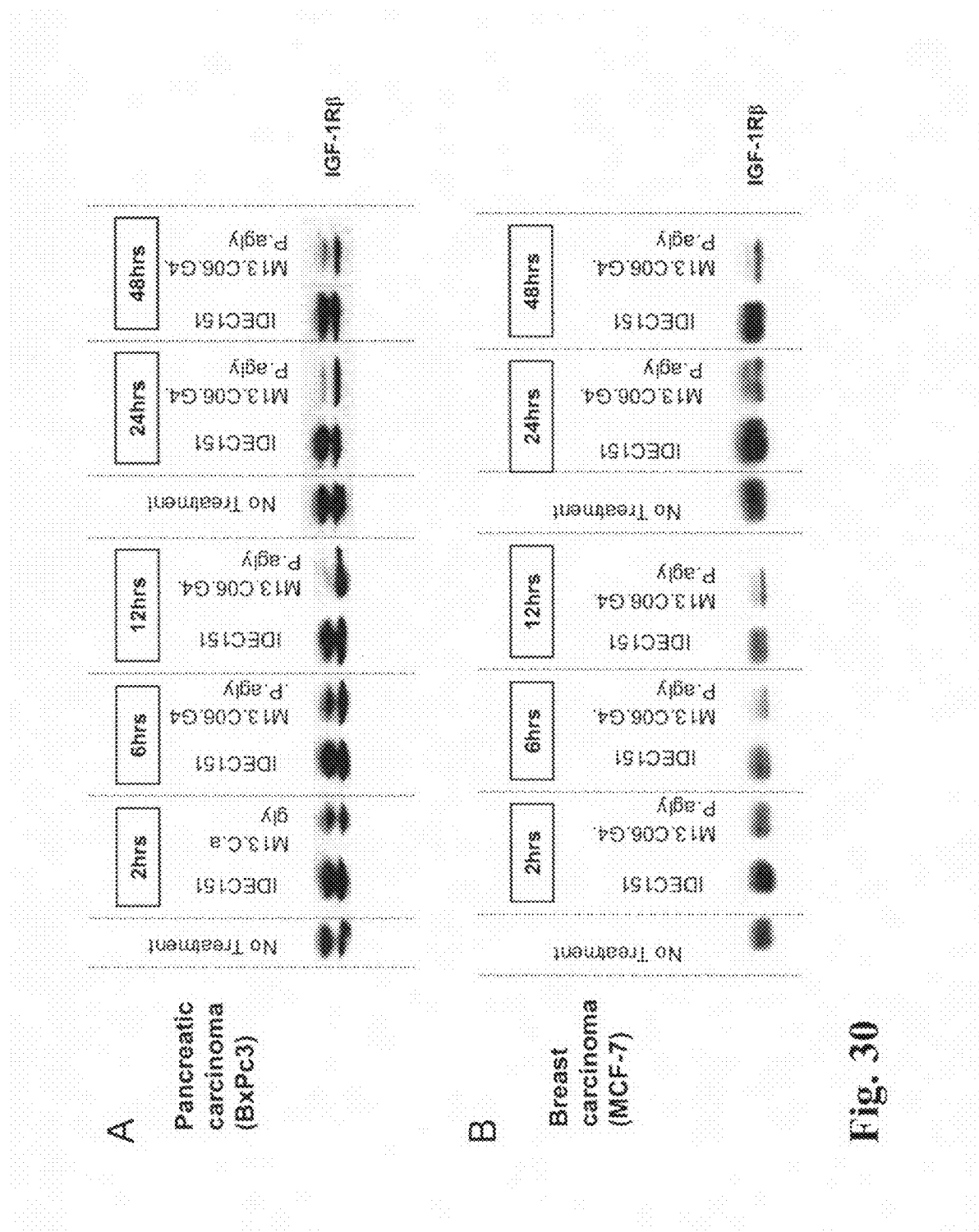
FIG. 30: Immunoblot (Western blot) analysis of in vivo IGF-1R expression in mouse tumors treated with M13.C06.G4.P.agly antibody.

IGF-1R was immunoblotted from lysates of SCID mouse tumors generated with human pancreatic cells (BxPC3; FIG. 30(A)) and breast cancer cells (MCF-7; FIG. 30(B)). Tumors were excised at designated time points after treatment with M13.C06.G4.P.agly or IDEC-151 negative control antibody. Tumors were snap frozen, pulverized and lysed. Protein concentration of tumor cell lysates were normalized and separated on 4-12% NuPAGE® gel (Invitrogen Inc., SD, CA). The gel was blotted to nitrocellulose filter, probed with polyclonal anti-IGF-1RP and detected by enzymatic reaction with anti-rabbit-horse radish peroxidase antibody. Results show that M13.C06.G4.P.agly resulted in down-regulation and degradation of IGF-1R compared to negative control antibody.

Example 29

M13.C06.G4.P.agly Antibody Demonstrates In Vivo Anti-Tumor Activity in a Variety of Tumor Model Systems In addition to the in vivo inhibition of tumor growth demonstrated for M13.C06.G4.P.agly in lung and pancreatic model systems as described in previous examples, the following experiments further demonstrate the diversity of tumor cell models in which M13.C06.G4.P.agly exhibits activity.

Anti-Tumor Activity of M13.C06.G4.P.agly in Tumors Generated with MiaPaCa2 Pancreatic Carcinoma Cells.

Female SCID mice were innoculated in the right flank with $2 \times 10^6$ MiaPaCa2 pancreatic carcinoma cells in 50% Matrigel (BD Biosciences)/PBS. Tumors were allowed to reach a volume of 150 mm³ (L×W2/2) and mice were sorted and dosed intraperitoneally with single agent (antibody alone) and combination treatments (M13.C06.G4.P.agly antibody and gemcitabine). Gemcitabine alone (20 mg/kg, Q4D×3) and in combination with M13.C06.G4.P.agly (30 mg/kg) as well as M13.C06.G4.P.agly alone (at both 15 mg/kg and 30 mg/kg; 1×week×6) inhibited tumor growth.

In addition to gemcitabine, many other combination therapies could also be tested and used in conjunction with antibodies of the present invention. For example, combination therapies of compounds in the following categories, to list a small exemplary sampling, could be utilized with antibodies of the present invention:

EGFR tyrosine kinase inhibitors, for example:
  Tarceva (Erlotinib)
  Iressa (Gefitinib)
EGFR antibodies, for example:
  Erbitux (cetuximab)
  Victibix (panitumumab)
mTOR inhibitors, for example:
  temsirolimus
  rapamycin
and other anti-cancer compounds, for example:
  Gleevec (Imatinib)
  Sutent (Sunitinib)
  Sorafenib (Bay-439006)
  SAHA (HDAC inhibitor)
  HSP90 inhibitors
  M200 (Volociximab).

Figure 31:
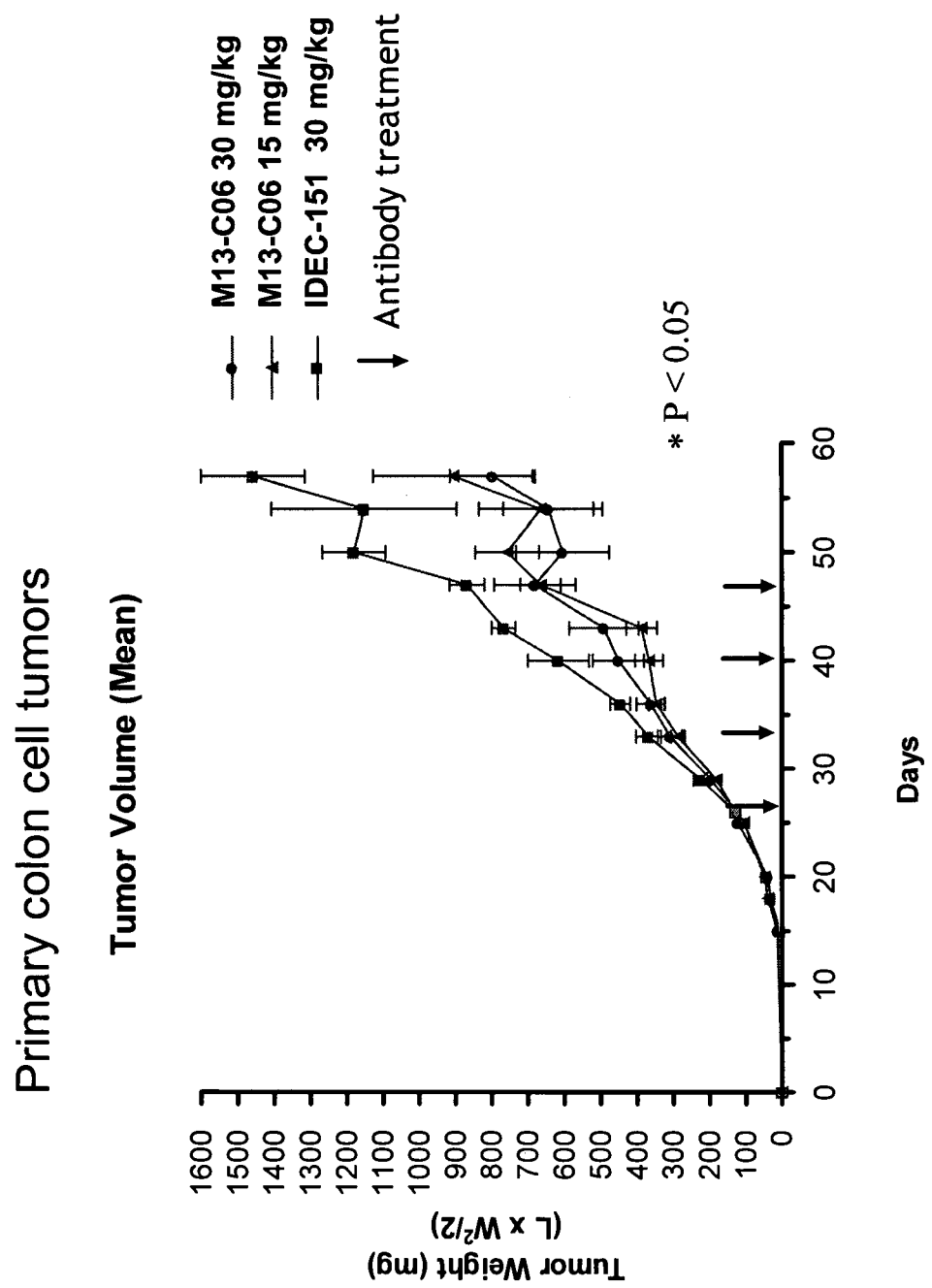
FIG. 31: In vivo anti-tumor activity of M13-C06.G4.P.agly in tumors generated from a primary human colon tumor.

Anti-Tumor Activity of M13.C06.G4.P.agly in Tumors Generated with Cells Derived from a Primary Human Colon Adenocarcinoma Female SCID mice were innoculated in the right flank with 1 mm³ of colon tumor fragments. The tumor fragment was derived by serial passage (5×) of colon tumor tissue obtained following surgical resection of a tumor from a patient with colon adenocarcinoma. Tumors were allowed to reach a volume of 150 mm³ (L×W2/2) and mice were sorted and dosed with the indicated treatments (n=6) (FIG. 31). Antibodies at 15 mg/kg or 30 mg/kg were dosed intraperitoneally 1× weekly.

Results: M13.C06.G4.P.agly effectively inhibited primary colon tumor (CT3) growth in SCID mice (FIG. 31).

Anti-Tumor Activity of M13.C06.G4.P.agly in Tumors Generated with MCF-7 Breast Carcinoma Cells.

Figure 32:
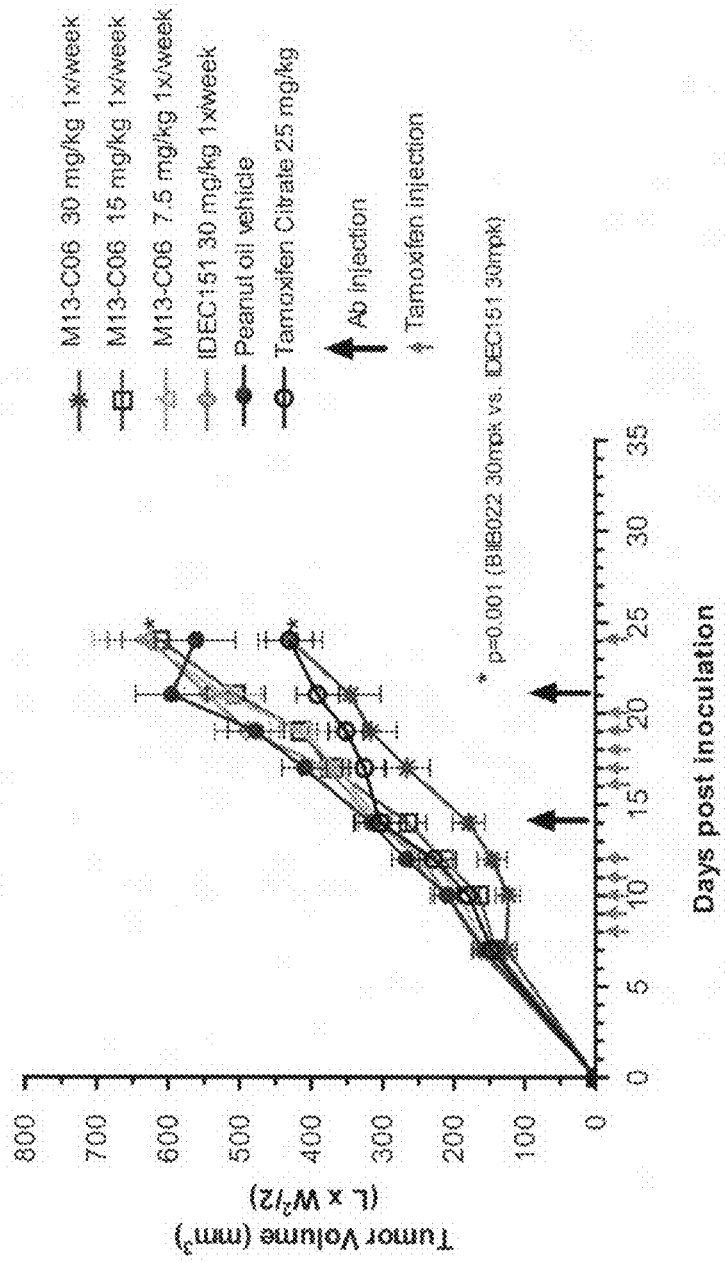
FIG. 32: In vivo anti-tumor activity of M13-C06.G4.P.agly in tumors generated from breast carcinoma (MCF-7) cells.

Female SCID Beige mice were innoculated in the right flank with $2 \times 10^6$ MCF-7 cells (estrogen dependent) in 50% Matrigel/PBS. An estradiol pellet was implanted in the left flank 24 hours prior to cell inoculation (0.36 mg pellet estradiol, 90 day release (Innovative Research of America)). Tumors were allowed to reach a volume of 150 mm³ (L×W2/2) and mice were sorted and dosed with the indicated treatments (n=10) (FIG. 32). Antibodies were dosed intraperitoneally 1×/week, while Tamoxifen Citrate (Sigma Inc.) in peanut oil was dosed sub-cutaneously 5 times a week for each regimen. Statistical analysis was performed using a paired student t test.

Results: M13.C06.G4.P.agly effectively inhibited growth of MCF-7 breast carcinoma tumors (FIG. 32).

Of course, the tumor inhibiting efficacy antibodies of the invention could also be readily tested in numerous other cancer cell types (such as: lung cancer cell lines H-1299, H-460, H-23; colon cancer cell lines Colo205 and HT-29; pancreatic cancer cell lines such as Panc-1; and, prostate cancer cell lines such as PC-3 to name a small exemplary sampling).

Example 30

M13.C06.G4.P.agly Antibody does not Exhibit In Vitro ADCC Activity

Method:

Human peripheral blood mononuclear cells were purified from heparinized whole blood by standard Ficoll-paque separation. The cells were resuspended in GIBCO™ RPMI1640 media containing 10% FBS and 200 U/ml of human IL-2 and incubated overnight at 37° C. The following day, the cells were collected and washed once in culture media and resuspended at $1 \times 10^7$ cells/ml.

Target cells (MCF-7, breast carcinoma cells) were incubated with 100 µCi $^{51}$Cr for 1 hour at 37° C. The target cells were washed once to remove the unincorporated $^{51}$Cr, and plated at a volume of $1 \times 10^4$ cells/well. Target cells were incubated with 50 µl of effector cells and 50 µl of antibody. A target to effector ratio of 1:50 was used throughout the experiments. Controls included were incubated with and without antibodies, these include M13.C06.G4.P.agly, Herceptin (positive control) and IDEC-151 (negative control—macaque/human chimeric IgG1 monoclonal antibody specific to CD4). Following a 4-hour incubation at 37° C., the supernatants were collected and counted on a gamma counter (Isodata Gamma Counter, Packard Instruments). The % lysis was determined using the following calculation:

% Lysis=[Sample Release (CPM)−spontaneous release (CPM)]÷[Maximum release (CPM)−spontaneous release (CPM)]×100%

Figure 33:
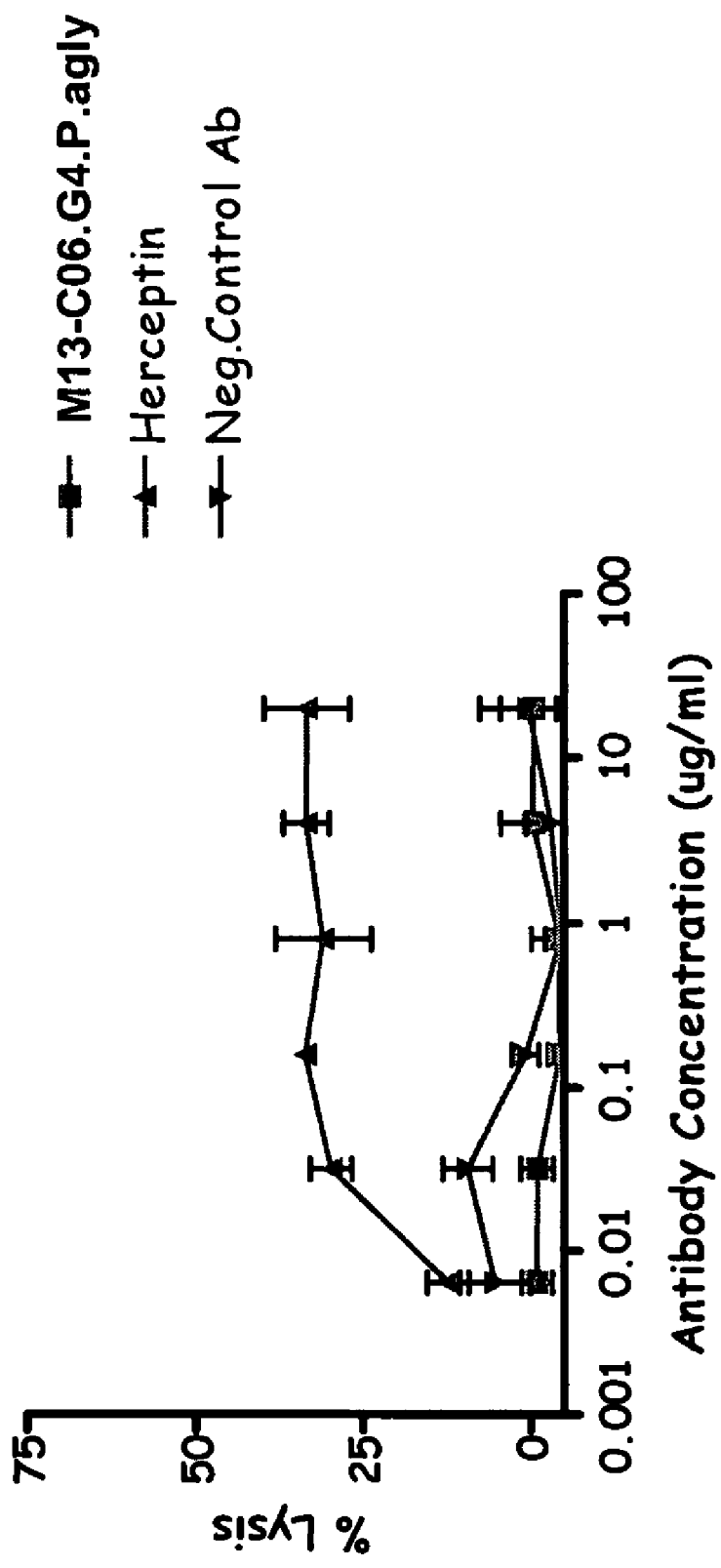
FIG. 33: M13-C06 antibody does not exhibit in vitro ADCC activity.

Results: In contrast to the Herceptin antibody positive control, neither M13-C06 or IDEC-151 antibodies exhibited ADCC activity, thereby indicating a lack of effector function for these latter antibodies (FIG. 33).

Example 31

Treatment of Human Cancer Using Anti-IGF-1R Antibodies

This example describes methods for treating cancer using antibodies against IGF-IR to target malignant cells, for example, hyperproliferating cells in which IGF-1R expression has been detected.

In certain embodiments, M13.C06.G4.P.agly antibody (or another antibody of the present invention) is purified and formulated with a suitable pharmaceutical vehicle for injection. A human patient with a hyperproliferative disorder is given multiple doses of M13.C06.G4.P.agly antibody (or another antibody of the present invention) by intravenous infusion at about 1 mg/kg body weight to about 100 mg/kg body weight, e.g., once per every two weeks or once a month, for at least six months. Intervals can also be irregular as indicated by measuring prognostic indicators in the patient.

Antibodies can be administered prior to, concurrently with, or after standard radiotherapy regimens as described herein. The patient is monitored to determine whether treatment has resulted in an anti-tumor response, for example, based on tumor regression, reduction in the incidences of new tumors, lower tumor antigen expression, or other means of evaluating disease prognosis.

REFERENCES

Brezinsky, S. C. G., Chiang, G. G., Szilvasi, A., Mohan, S., Shapiro, R. I., MacLean, A., Sisk, W., and Thill, G. (2003). "A simple method for enriching populations of transfected CHO cells for cells of higher specific productivity." *J. Immunol. Methods* 277: 141-155.

Davies, D. R., and Cohen, G. H. (1996). "Interactions of protein antigens with antibodies." *Proc. Natl. Acad. Sci. USA* 93: 7-12.

Demarest, S. J., Chen, G., Kimmel, B. E., Gustafson, D., Wu, J., Salbato, J., Poland, J., Short, J., Hansen, G. (2006) *Protein Engng. Des. Select.* 19, 325-336.

Demarest, S. J., Hopp, J., Chung, J., Hathaway, K., Mertsching, E., Cao, X., George, J., Miatkowski, K., LaBarre, M. J., Shields, M., and Kehry, M. R. (2006). "An intermediate pH unfolding transition abrogates the ability of IgE to interact with its high affinity receptor FceRIa." *J. Biol. Chem.* 281: 30755-30767.

Keynhanfar, M., Booker, G. W., Whittaker, J., Wallace, J. C., and Forbes, B. E. (2007). "Precise mapping of an IGF-1-binding site on IGF-1R." *Biochem. J.* 401: 269-277.

McKern, N. M., Lawrence, M. C., Streltsov, V. A., Lou, M.-Z., Adams, T. E., Lovrecz, G. O., Elleman, T. C., Richards, K. M., Bentley, J. D., Pilling, P., Hoyne, P. A., Cartledge, K. A., Pham, T. M., Lewis, J. L., Sankovich, S. E., Stoichevska, V., Da Silva, E., Robinson, C. P., Frenkel, M. J., Sparrow, L. G., Fernley, R. T., Epa, V. C., and Ward, C. W. (2006). "Structure of the insulin receptor ectodomain reveals a folded-over conformation." *Nature* 443: 218-221.

McKern, N. M., Lou. M., Frenkel, M. J., Verkuylen, A., Bentley, J. D., Lovrecz, G. O., Ivancic, N., Elleman, T. C., Garrett, T. P. J., Cosgrove, L. J., and Ward, C. W. (1997). "Crystallization of the first three domains of the human insulin-like growth factor-1 receptor." *Protein Sci.* 6: 2663-2666.

Soos, M. A., Field, C. E., Lammers, R., Ullrich, A., Zhang, B., Roth, R. A., Andersen, A. S., Kjeldsen, T., Siddle, K. (1992). "A panel of monoclonal antibodies for the type I insulin-like growth factor receptor." *J. Biol. Chem.* 267: 12955-12963.

Soos, M. A., Siddle, K., Baron, M. D., Heward, J. M., Luzio, J. P., Bellatin, J., and Lennox, E. S. (1986). "Monoclonal antibodies reacting with multiple epitopes on the human insulin receptor." *Biochem. J.* 235: 199-208.

Sorensen, H., Whittaker, L., Hinrichsen, J., Groth, A., and Whittaker, J. (2004). "Mapping of the insulin-like growth factor II binding site of the Type I insulin-like growth factor receptor by alanine scanning mutagenesis." *FEBS Lett.* 565: 19-22.

Whittaker, J., Groth, A. V., Mynarcik, D. C., Pluzek, L., Gadsboll, V. L., and Whittaker, L. J. (2001). "Alanine scanning mutagenesis of a type 1 insulin-like growth factor receptor ligand binding site." *J. Biol. Chem.* 276: 43980-43986.

What is claimed is:

1. An isolated antibody or antigen-binding fragment thereof wherein said antibody is M13-C06.G4.P.agly or a fragment thereof which specifically binds to IGF-1R produced by Chinese Hamster Ovary (CHO) cells deposited under American Type Culture Collection (ATCC) Deposit Number PTA-7444.

2. An isolated antibody or antigen-binding fragment thereof, wherein said antibody or fragment thereof comprises an antigen binding domain identical to that of a monoclonal Fab antibody fragment of M13-C06.G4.P.agly produced by Chinese Hamster Ovary (CHO) cells deposited under American Type Culture Collection (ATCC) Deposit Number PTA-7444.

3. An isolated antibody or fragment thereof which specifically binds to IGF-1R, wherein the VH of said antibody or fragment thereof comprises the amino acid sequence of SEQ ID NO: 14.

4. An isolated antibody or fragment thereof which specifically binds to IGF-1R, wherein the VL of said antibody or fragment thereof comprises the amino acid sequence of SEQ ID NO: 78.

5. An isolated antibody or fragment thereof which specifically binds to IGF-1R, wherein the VH and VL of said antibody or fragment thereof comprise, respectively, the amino acid sequences of SEQ ID NO: 14 and SEQ ID NO: 78.

6. An isolated antibody or fragment thereof which specifically binds to IGF-1R, wherein the VH of said antibody or fragment thereof comprises the VH-CDR1, VH-CDR2, and VH-CDR3 amino acid sequences of SEQ ID NOs: 15, 16, and 17.

7. An isolated antibody or fragment thereof which specifically binds to IGF-1R, wherein the VL of said antibody or fragment thereof comprises the VL-CDR1, VL-CDR2, and VL-CDR3 amino acid sequences of SEQ ID NOs: 79, 80, and 81.

8. A method of producing the antibody or fragment thereof of claim 1, comprising culturing a host cell expressing said antibody or fragment thereof, and recovering said antibody or fragment thereof.

9. A method of producing the antibody or fragment thereof of claim 2, comprising culturing a host cell expressing said antibody or fragment thereof, and recovering said antibody or fragment thereof.

10. A method of producing the antibody or fragment thereof of claim 3, comprising culturing a host cell expressing said antibody or fragment thereof, and recovering said antibody or fragment thereof.

11. A method of producing the antibody or fragment thereof of claim 4, comprising culturing a host cell expressing said antibody or fragment thereof, and recovering said antibody or fragment thereof.

12. A method of producing the antibody or fragment thereof of claim 5, comprising culturing a host cell expressing said antibody or fragment thereof, and recovering said antibody or fragment thereof.

13. A method of producing the antibody or fragment thereof of claim 6, comprising culturing a host cell expressing said antibody or fragment thereof, and recovering said antibody or fragment thereof.

14. A method of producing the antibody or fragment thereof of claim 7 comprising culturing a host cell expressing said antibody or fragment thereof, and recovering said antibody or fragment thereof.

15. An isolated antibody comprising the VH-CDR1, VH-CDR2, VH-CDR3, VL-CDR1, VL-CDR2, and VL-CDR3 amino acid sequences of SEQ ID NOs: 15, 16, 17, 79, 80, and 81.

16. A method of producing the antibody of claim 15 comprising culturing a host cell expressing said antibody and recovering said antibody or fragment thereof.

* * * * *

SEQUENCE LISTING

<160> NUMBER OF SEQ ID NOS: 157

<210> SEQ ID NO 1
<211> LENGTH: 4989
<212> TYPE: DNA
<213> ORGANISM: Homo sapiens

<400> SEQUENCE: 1

```
ttttttttt ttttgagaaa gggaatttca tcccaaataa aaggaatgaa gtctggctcc      60
ggaggagggt ccccgacctc gctgtggggg ctcctgtttc tctccgccgc gctctcgctc     120
tggccgacga gtggagaaat ctgcgggcca ggcatcgaca tccgcaacga ctatcagcag      180
ctgaagcgcc tggagaactg cacggtgatc gagggctacc tccacatcct gctcatctcc      240
aaggccgagg actaccgcag ctaccgcttc cccaagctca cggtcattac cgagtacttg      300
ctgctgttcc gagtggctgg cctcgagagc ctcggagacc tcttcccaa cctcacggtc      360 atccgcggct ggaaactctt ctacaactac gccctggtca tcttcgagat gaccaatctc      420
aaggatattg ggctttacaa cctgaggaac attactcggg gggccatcag gattgagaaa      480
aatgctgacc tctgttacct ctccactgtg gactggtcc tgatcctgga tgcggtgtcc      540
aataactaca ttgtggggaa taagccccca aaggaatgtg gggacctgtg tccagggacc      600
```

```
atggaggaga agccgatgtg tgagaagacc accatcaaca atgagtacaa ctaccgctgc     660
tggaccacaa accgctgcca gaaaatgtgc ccaagcacgt gtgggaagcg ggcgtgcacc     720
gagaacaatg agtgctgcca ccccgagtgc ctgggcagct gcagcgcgcc tgacaacgac     780
acggcctgtg tagcttgccg ccactactac tatgccggtg tctgtgtgcc tgcctgcccg     840
cccaacacct acaggtttga gggctggcgc tgtgtggacc gtgacttctg cgccaacatc     900
ctcagcgccg agagcagcga ctccgagggg tttgtgatcc acgacggcga gtgcatgcag     960
gagtgcccct cgggcttcat ccgcaacggc agccagagca tgtactgcat cccttgtgaa    1020
ggtccttgcc cgaaggtctg tgaggaagaa aagaaaacaa agaccattga ttctgttact    1080
tctgctcaga tgctccaagg atgcaccatc ttcaagggca atttgctcat taacatccga    1140
cgggggaata acattgcttc agagctggag aacttcatgg ggctcatcga ggtggtgacg    1200
ggctacgtga agatccgcca ttctcatgcc ttggtctcct tgtccttcct aaaaaacctt    1260
cgcctcatcc taggagagga gcagctgaaa gggaattact ccttctacgt cctcgacaac    1320
cagaacttgc agcaactgtg ggactgggac caccgcaacc tgaccatcaa agcagggaaa    1380
atgtactttg ctttcaatcc caaattatgt gtttccgaaa tttaccgcat ggaggaagtg    1440
acggggacta agggcgccaa agcaaaggg gacataaaca ccaggaacaa cggggagaga    1500
gcctcctgtg aaagtgacgt cctgcatttc acctccacca ccacgtcgaa gaatcgcatc    1560
atcataacct ggcaccggta ccggcccct gactacaggg atctcatcag cttcaccgtt    1620
tactacaagg aagcacccct taagaatgtc acagagtatg atgggcagga tgcctgcggc    1680
tccaacagct ggaacatggt ggacgtggac ctcccgccca caaggacgt ggagcccggc    1740
atcttactac atgggctgaa gccctggact cagtacgccg tttacgtcaa ggctgtgacc    1800
ctcaccatgg tggagaacga ccatatccgt ggggccaaga gtgagatctt gtacattcgc    1860
accaatgctt cagttccttc cattcccttg gacgttcttt cagcatcgaa ctcctcttct    1920
cagttaatcg tgaagtggaa ccctccctct ctgcccaacg gcaacctgag ttactacatt    1980
gtgcgctggc agcggcagcc tcaggacggc taccttacc ggcacaatta ctgctccaaa    2040
gacaaaatcc ccatcaggaa gtatgccgac ggcaccatcg acattgagga ggtcacagag    2100
aaccccaaga ctgaggtgtg tggtggggag aaagggcctt gctgcgcctg ccccaaaact    2160
gaagccgaga agcaggccga gaggaggag gctgaatacc gcaaagtctt tgagaatttc    2220
ctgcacaact ccatcttcgt gcccagacct gaaaggaagc ggagagatgt catgcaagtg    2280
gccaacacca ccatgtccag ccgaagcagg aacaccacgg ccgcagacac ctacaacatc    2340
accgacccgg aagagctgga gacagagtac cctttctttg agagcagagt ggataacaag    2400
gagagaactg tcatttctaa ccttcggcct ttcacattgt accgcatcga tatccacagc    2460
tgcaaccacg aggctgagaa gctgggctgc agcgcctcca acttcgtctt tgcaaggact    2520
atgcccgcag aaggagcaga tgacattcct gggccagtga cctgggagcc aaggcctgaa    2580
aactccatct tttaaagtg gccggaacct gagaatccca atggattgat tctaatgtat    2640
gaaataaaat acgatcaca agttgaggat cagcgagaat gtgtgtccag acaggaatac    2700
aggaagtatg gagggccaa gctaaaccgg ctaaacccgg gaactacac agcccggatt    2760
caggccacat ctctctctgg aatgggtcg tggacagatc ctgtgttctt ctatgtccag    2820
gccaaaacag gatatgaaaa cttcatccat ctgatcatcg ctctgcccgt cgctgtcctg    2880
ttgatcgtgg gagggttggt gattatgctg tacgtcttcc atagaaagag aaataacagc    2940
aggctgggga atggagtgct gtatgcctct gtgaacccgg agtacttcag cgctgctgat    3000
```

-continued

```
gtgtacgttc ctgatgagtg ggaggtggct cgggagaaga tcaccatgag ccgggaactt    3060
gggcaggggt cgtttgggat ggtctatgaa ggagttgcca agggtgtggt gaaagatgaa    3120
cctgaaacca gagtggccat taaaacagtg aacgaggccg caagcatgcg tgagaggatt    3180
gagtttctca acgaagcttc tgtgatgaag gagttcaatt gtcaccatgt ggtgcgattg    3240
ctgggtgtgg tgtcccaagg ccagccaaca ctggtcatca tggaactgat gacacggggc    3300
gatctcaaaa gttatctccg gtctctgagg ccagaaatgg agaataatcc agtcctagca    3360
cctccaagcc tgagcaagat gattcagatg gccggagaga ttgcagacgg catggcatac    3420
ctcaacgcca ataagttcgt ccacagagac cttgctgccc ggaattgcat ggtagccgaa    3480
gatttcacag tcaaaatcgg agattttggt atgacgcgag atatctatga cagagactat    3540
taccggaaag gaggcaaagg gctgctgccc gtgcgctgga tgtctcctga gtccctcaag    3600
gatggagtct tcaccactta ctcggacgtc tggtccttcg gggtcgtcct ctgggagatc    3660
gccacactgg ccgagcagcc ctaccagggc ttgtccaacg agcaagtcct tcgcttcgtc    3720
atggagggcg gccttctgga caagccagac aactgtcctg acatgctgtt tgaactgatg    3780
cgcatgtgct ggcagtataa ccccaagatg aggccttcct tcctggagat catcagcagc    3840
atcaaagagg agatggagcc tggcttccgg gaggtctcct tctactacag cgaggagaac    3900
aagctgcccg agccggagga ctggaccctg agccagagag catggagagg cgtcccctg    3960 gaccctcgg cctcctcgtc tcccgtgcca ctgcccgaca gacactcagg gacacaaggcc    4020 gagaacggcc ccggccctgg ggtgctgtc ctccgcgcca gcttcgacga gagacagcct    4080
tacgcccaca tgaacggggg ccgcaagaac gagcgggcct tgccgctgcc ccagtcttcg    4140
acctgctgat ccttggatcc tgaatctgtg caaacagtaa cgtgtgcgca cgcgcagcgg    4200 ggtgggggg gagagagagt tttaacaatc cattcacaag cctcctgtac ctcagtggat    4260
cttcagttct gcccttgctg cccgcgggag acagcttctc tgcagtaaaa cacatttggg    4320
atgttccttt tttcaatatg caagcagctt tttattccct gcccaaaccc ttaactgaca    4380 tgggcctta agaaccttaa tgacaacact taatagcaac agagcacttg agaaccagtc    4440
tcctcactct gtccctgtcc ttccctgttc tcccttctc tctcctctct gcttcataac    4500
ggaaaaataa ttgccacaag tccagctggg aagcccttt tatcagtttg aggaagtggc    4560
tgtccctgtg gccccatcca accactgtac acacccgcct gacaccgtgg gtcattacaa    4620
aaaaacacgt ggagatggaa attttttacct ttatctttca cctttctagg gacatgaaat    4680
ttacaaaggg ccatcgttca tccaaggctg ttaccatttt aacgctgcct aattttgcca    4740
aaatcctgaa cttttctccct catcggcccg gcgctgattc ctcgtgtccg gaggcatggg    4800
tgagcatggc agctggttgc tccatttgag agacacgctg gcgacacact ccgtccatcc    4860 gactgccct gctgtgctgc tcaaggccac aggcacacag gtctcattgc ttctgactag    4920
attattattt gggggaactg gacacaatag gtctttctct cagtgaaggt ggggagaagc    4980
tgaaccggc                                                             4989
```

<210> SEQ ID NO 2
<211> LENGTH: 1367
<212> TYPE: PRT
<213> ORGANISM: Homo sapiens

<400> SEQUENCE: 2

Met Lys Ser Gly Ser Gly Gly Gly Ser Pro Thr Ser Leu Trp Gly Leu
1               5                   10                  15

-continued

```
Leu Phe Leu Ser Ala Ala Leu Ser Leu Trp Pro Thr Ser Gly Glu Ile
             20                  25                  30
Cys Gly Pro Gly Ile Asp Ile Arg Asn Asp Tyr Gln Gln Leu Lys Arg
         35                  40                  45
Leu Glu Asn Cys Thr Val Ile Glu Gly Tyr Leu His Ile Leu Leu Ile
 50                  55                  60
Ser Lys Ala Glu Asp Tyr Arg Ser Tyr Arg Phe Pro Lys Leu Thr Val
 65                  70                  75                  80
Ile Thr Glu Tyr Leu Leu Leu Phe Arg Val Ala Gly Leu Glu Ser Leu
                 85                  90                  95
Gly Asp Leu Phe Pro Asn Leu Thr Val Ile Arg Gly Trp Lys Leu Phe
            100                 105                 110
Tyr Asn Tyr Ala Leu Val Ile Phe Glu Met Thr Asn Leu Lys Asp Ile
            115                 120                 125
Gly Leu Tyr Asn Leu Arg Asn Ile Thr Arg Gly Ala Ile Arg Ile Glu
            130                 135                 140
Lys Asn Ala Asp Leu Cys Tyr Leu Ser Thr Val Asp Trp Ser Leu Ile
145                 150                 155                 160
Leu Asp Ala Val Ser Asn Asn Tyr Ile Val Gly Asn Lys Pro Pro Lys
                165                 170                 175
Glu Cys Gly Asp Leu Cys Pro Gly Thr Met Glu Glu Lys Pro Met Cys
            180                 185                 190
Glu Lys Thr Thr Ile Asn Asn Glu Tyr Asn Tyr Arg Cys Trp Thr Thr
            195                 200                 205
Asn Arg Cys Gln Lys Met Cys Pro Ser Thr Cys Gly Lys Arg Ala Cys
            210                 215                 220
Thr Glu Asn Asn Glu Cys Cys His Pro Glu Cys Leu Gly Ser Cys Ser
225                 230                 235                 240
Ala Pro Asp Asn Asp Thr Ala Cys Val Ala Cys Arg His Tyr Tyr Tyr
                245                 250                 255
Ala Gly Val Cys Val Pro Ala Cys Pro Pro Asn Thr Tyr Arg Phe Glu
            260                 265                 270
Gly Trp Arg Cys Val Asp Arg Asp Phe Cys Ala Asn Ile Leu Ser Ala
            275                 280                 285
Glu Ser Ser Asp Ser Glu Gly Phe Val Ile His Asp Gly Glu Cys Met
            290                 295                 300
Gln Glu Cys Pro Ser Gly Phe Ile Arg Asn Gly Ser Gln Ser Met Tyr
305                 310                 315                 320
Cys Ile Pro Cys Glu Gly Pro Cys Pro Lys Val Cys Glu Glu Glu Lys
                325                 330                 335
Lys Thr Lys Thr Ile Asp Ser Val Thr Ser Ala Gln Met Leu Gln Gly
            340                 345                 350
Cys Thr Ile Phe Lys Gly Asn Leu Leu Ile Asn Ile Arg Arg Gly Asn
            355                 360                 365
Asn Ile Ala Ser Glu Leu Glu Asn Phe Met Gly Leu Ile Glu Val Val
            370                 375                 380
Thr Gly Tyr Val Lys Ile Arg His Ser His Ala Leu Val Ser Leu Ser
385                 390                 395                 400
Phe Leu Lys Asn Leu Arg Leu Ile Leu Gly Glu Glu Gln Leu Glu Gly
                405                 410                 415
Asn Tyr Ser Phe Tyr Val Leu Asp Asn Gln Asn Leu Gln Gln Leu Trp
            420                 425                 430
```

-continued

Asp Trp Asp His Arg Asn Leu Thr Ile Lys Ala Gly Lys Met Tyr Phe
        435                 440                 445

Ala Phe Asn Pro Lys Leu Cys Val Ser Glu Ile Tyr Arg Met Glu Glu
        450                 455                 460

Val Thr Gly Thr Lys Gly Arg Gln Ser Lys Gly Asp Ile Asn Thr Arg
465                 470                 475                 480

Asn Asn Gly Glu Arg Ala Ser Cys Glu Ser Asp Val Leu His Phe Thr
                485                 490                 495

Ser Thr Thr Thr Ser Lys Asn Arg Ile Ile Ile Thr Trp His Arg Tyr
            500                 505                 510

Arg Pro Pro Asp Tyr Arg Asp Leu Ile Ser Phe Thr Val Tyr Tyr Lys
        515                 520                 525

Glu Ala Pro Phe Lys Asn Val Thr Glu Tyr Asp Gly Gln Asp Ala Cys
        530                 535                 540

Gly Ser Asn Ser Trp Asn Met Val Asp Val Asp Leu Pro Pro Asn Lys
545                 550                 555                 560

Asp Val Glu Pro Gly Ile Leu Leu His Gly Leu Lys Pro Trp Thr Gln
                565                 570                 575

Tyr Ala Val Tyr Val Lys Ala Val Thr Leu Thr Met Val Glu Asn Asp
            580                 585                 590

His Ile Arg Gly Ala Lys Ser Glu Ile Leu Tyr Ile Arg Thr Asn Ala
        595                 600                 605

Ser Val Pro Ser Ile Pro Leu Asp Val Leu Ser Ala Ser Asn Ser Ser
        610                 615                 620

Ser Gln Leu Ile Val Lys Trp Asn Pro Pro Ser Leu Pro Asn Gly Asn
625                 630                 635                 640

Leu Ser Tyr Tyr Ile Val Arg Trp Gln Arg Gln Pro Gln Asp Gly Tyr
                645                 650                 655

Leu Tyr Arg His Asn Tyr Cys Ser Lys Asp Lys Ile Pro Ile Arg Lys
            660                 665                 670

Tyr Ala Asp Gly Thr Ile Asp Ile Glu Glu Val Thr Glu Asn Pro Lys
        675                 680                 685

Thr Glu Val Cys Gly Gly Glu Lys Gly Pro Cys Cys Ala Cys Pro Lys
        690                 695                 700

Thr Glu Ala Glu Lys Gln Ala Glu Lys Glu Glu Ala Glu Tyr Arg Lys
705                 710                 715                 720

Val Phe Glu Asn Phe Leu His Asn Ser Ile Phe Val Pro Arg Pro Glu
                725                 730                 735

Arg Lys Arg Arg Asp Val Met Gln Val Ala Asn Thr Thr Met Ser Ser
            740                 745                 750

Arg Ser Arg Asn Thr Thr Ala Ala Asp Thr Tyr Asn Ile Thr Asp Pro
        755                 760                 765

Glu Glu Leu Glu Thr Glu Tyr Pro Phe Phe Glu Ser Arg Val Asp Asn
        770                 775                 780

Lys Glu Arg Thr Val Ile Ser Asn Leu Arg Pro Phe Thr Leu Tyr Arg
785                 790                 795                 800

Ile Asp Ile His Ser Cys Asn His Glu Ala Glu Lys Leu Gly Cys Ser
                805                 810                 815

Ala Ser Asn Phe Val Phe Ala Arg Thr Met Pro Ala Glu Gly Ala Asp
            820                 825                 830

Asp Ile Pro Gly Pro Val Thr Trp Glu Pro Arg Pro Glu Asn Ser Ile
        835                 840                 845

Phe Leu Lys Trp Pro Glu Pro Glu Asn Pro Asn Gly Leu Ile Leu Met

```
              850                 855                 860
Tyr Glu Ile Lys Tyr Gly Ser Gln Val Glu Asp Gln Arg Glu Cys Val
865                 870                 875                 880

Ser Arg Gln Glu Tyr Arg Lys Tyr Gly Gly Ala Lys Leu Asn Arg Leu
                    885                 890                 895

Asn Pro Gly Asn Tyr Thr Ala Arg Ile Gln Ala Thr Ser Leu Ser Gly
                900                 905                 910

Asn Gly Ser Trp Thr Asp Pro Val Phe Phe Tyr Val Gln Ala Lys Thr
            915                 920                 925

Gly Tyr Glu Asn Phe Ile His Leu Ile Ile Ala Leu Pro Val Ala Val
930                 935                 940

Leu Leu Ile Val Gly Gly Leu Val Ile Met Leu Tyr Val Phe His Arg
945                 950                 955                 960

Lys Arg Asn Asn Ser Arg Leu Gly Asn Gly Val Leu Tyr Ala Ser Val
                965                 970                 975

Asn Pro Glu Tyr Phe Ser Ala Ala Asp Val Tyr Val Pro Asp Glu Trp
            980                 985                 990

Glu Val Ala Arg Glu Lys Ile Thr Met Ser Arg Glu Leu Gly Gln Gly
                995                 1000                1005

Ser Phe Gly Met Val Tyr Glu Gly Val Ala Lys Gly Val Val Lys
     1010                1015                1020

Asp Glu Pro Glu Thr Arg Val Ala Ile Lys Thr Val Asn Glu Ala
     1025                1030                1035

Ala Ser Met Arg Glu Arg Ile Glu Phe Leu Asn Glu Ala Ser Val
     1040                1045                1050

Met Lys Glu Phe Asn Cys His His Val Val Arg Leu Leu Gly Val
     1055                1060                1065

Val Ser Gln Gly Gln Pro Thr Leu Val Ile Met Glu Leu Met Thr
     1070                1075                1080

Arg Gly Asp Leu Lys Ser Tyr Leu Arg Ser Leu Arg Pro Glu Met
     1085                1090                1095

Glu Asn Asn Pro Val Leu Ala Pro Pro Ser Leu Ser Lys Met Ile
     1100                1105                1110

Gln Met Ala Gly Glu Ile Ala Asp Gly Met Ala Tyr Leu Asn Ala
     1115                1120                1125

Asn Lys Phe Val His Arg Asp Leu Ala Ala Arg Asn Cys Met Val
     1130                1135                1140

Ala Glu Asp Phe Thr Val Lys Ile Gly Asp Phe Gly Met Thr Arg
     1145                1150                1155

Asp Ile Tyr Glu Thr Asp Tyr Tyr Arg Lys Gly Gly Lys Gly Leu
     1160                1165                1170

Leu Pro Val Arg Trp Met Ser Pro Glu Ser Leu Lys Asp Gly Val
     1175                1180                1185

Phe Thr Thr Tyr Ser Asp Val Trp Ser Phe Gly Val Val Leu Trp
     1190                1195                1200

Glu Ile Ala Thr Leu Ala Glu Gln Pro Tyr Gln Gly Leu Ser Asn
     1205                1210                1215

Glu Gln Val Leu Arg Phe Val Met Glu Gly Gly Leu Leu Asp Lys
     1220                1225                1230

Pro Asp Asn Cys Pro Asp Met Leu Phe Glu Leu Met Arg Met Cys
     1235                1240                1245

Trp Gln Tyr Asn Pro Lys Met Arg Pro Ser Phe Leu Glu Ile Ile
     1250                1255                1260
```

```
Ser Ser Ile Lys Glu Glu Met Glu Pro Gly Phe Arg Glu Val Ser
    1265                1270                1275

Phe Tyr Tyr Ser Glu Glu Asn Lys Leu Pro Glu Pro Glu Glu Leu
    1280                1285                1290

Asp Leu Glu Pro Glu Asn Met Glu Ser Val Pro Leu Asp Pro Ser
    1295                1300                1305

Ala Ser Ser Ser Ser Leu Pro Leu Pro Asp Arg His Ser Gly His
    1310                1315                1320

Lys Ala Glu Asn Gly Pro Gly Pro Gly Val Leu Val Leu Arg Ala
    1325                1330                1335

Ser Phe Asp Glu Arg Gln Pro Tyr Ala His Met Asn Gly Gly Arg
    1340                1345                1350

Lys Asn Glu Arg Ala Leu Pro Leu Pro Gln Ser Ser Thr Cys
    1355                1360                1365

<210> SEQ ID NO 3
<211> LENGTH: 393
<212> TYPE: DNA
<213> ORGANISM: Artificial Sequence
<220> FEATURE:
<223> OTHER INFORMATION: Antibody variable heavy chain sequence

<400> SEQUENCE: 3
gaagttcaat tgttagagtc tggtggcggt cttgttcagc ctggtggttc tttacgtctt      60
tcttgcgctg cttccggatt cactttctct ccttactcta tgctttgggt tcgccaagct     120
cctggtaaag gtttggagtg gtttcttct atcggttctt ctggtggctc tactcgttat      180
gctgactccg ttaaaggtcg cttcactatc tctagagaca actctaagaa tactctctac     240
ttgcagatga acagcttaag ggctgaggac accgccatgt attactgtgc acgggtacgg     300
gggatccttc attacgatat tttgattggt agaaatctct actactacta catggacgtc     360
tggggcaaag ggaccacggt caccgtctca agc                                  393

<210> SEQ ID NO 4
<211> LENGTH: 131
<212> TYPE: PRT
<213> ORGANISM: Artificial Sequence
<220> FEATURE:
<223> OTHER INFORMATION: Antibody variable heavy chain sequence

<400> SEQUENCE: 4

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Pro Tyr
            20                  25                  30

Ser Met Leu Trp Val Arg Gln Ala Pro Gly Lys Gly Leu Glu Trp Val
        35                  40                  45

Ser Ser Ile Gly Ser Ser Gly Gly Ser Thr Arg Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Met Tyr Tyr Cys
                85                  90                  95

Ala Arg Val Arg Gly Ile Leu His Tyr Asp Ile Leu Ile Gly Arg Asn
            100                 105                 110

Leu Tyr Tyr Tyr Tyr Met Asp Val Trp Gly Lys Gly Thr Thr Val Thr
        115                 120                 125
```

Val Ser Ser
    130

<210> SEQ ID NO 5
<211> LENGTH: 5
<212> TYPE: PRT
<213> ORGANISM: Artificial Sequence
<220> FEATURE:
<223> OTHER INFORMATION: Antibody variable heavy chain sequence

<400> SEQUENCE: 5

Pro Tyr Ser Met Leu
1               5

<210> SEQ ID NO 6
<211> LENGTH: 17
<212> TYPE: PRT
<213> ORGANISM: Artificial Sequence
<220> FEATURE:
<223> OTHER INFORMATION: Antibody variable heavy chain sequence

<400> SEQUENCE: 6

Ser Ile Gly Ser Ser Gly Gly Ser Thr Arg Tyr Ala Asp Ser Val Lys
1               5                   10                  15

Gly

<210> SEQ ID NO 7
<211> LENGTH: 22
<212> TYPE: PRT
<213> ORGANISM: Artificial Sequence
<220> FEATURE:
<223> OTHER INFORMATION: Antibody variable heavy chain sequence

<400> SEQUENCE: 7

Val Arg Gly Ile Leu His Tyr Asp Ile Leu Ile Gly Arg Asn Leu Tyr
1               5                   10                  15

Tyr Tyr Tyr Met Asp Val
            20

<210> SEQ ID NO 8
<211> LENGTH: 390
<212> TYPE: DNA
<213> ORGANISM: Artificial Sequence
<220> FEATURE:
<223> OTHER INFORMATION: Antibody variable heavy chain sequence

<400> SEQUENCE: 8
gaagttcaat tgttagagtc tggtggcggt cttgttcagc ctggtggttc tttacgtctt      60
tcttgcgctg cttccggatt cactttctct aagtacacta tgcattgggt tcgccaagct     120
cctggtaaag gtttggagtg ggtttcttct atcgtttctt ctggtggctg gactgattat     180
gctgactccg ttaaaggtcg cttcactatc tctagagaca actctaagaa tactctctac     240
ttgcagatga acagcttaag ggctgaggac acggccgtgt attactgtgc gagagatcgg     300
agtatagcag cagctggtac cggttggtct gtgagttttg tggactggtt cgaccccctgg     360 ggccagggaa ccctggtcac cgtctcaagc                                      390

<210> SEQ ID NO 9
<211> LENGTH: 130
<212> TYPE: PRT
<213> ORGANISM: Artificial Sequence
<220> FEATURE:
<223> OTHER INFORMATION: Antibody variable heavy chain sequence

<400> SEQUENCE: 9

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Lys Tyr
            20                  25                  30

Thr Met His Trp Val Arg Gln Ala Pro Gly Lys Gly Leu Glu Trp Val
        35                  40                  45

Ser Ser Ile Val Ser Ser Gly Gly Trp Thr Asp Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Ser Ile Ala Ala Ala Gly Thr Gly Trp Ser Val Ser
            100                 105                 110

Phe Val Asp Trp Phe Asp Pro Trp Gly Gln Gly Thr Leu Val Thr Val
        115                 120                 125

Ser Ser
    130

<210> SEQ ID NO 10
<211> LENGTH: 5
<212> TYPE: PRT
<213> ORGANISM: Artificial Sequence
<220> FEATURE:
<223> OTHER INFORMATION: Antibody variable heavy chain sequence

<400> SEQUENCE: 10

Lys Tyr Thr Met His
1               5

<210> SEQ ID NO 11
<211> LENGTH: 17
<212> TYPE: PRT
<213> ORGANISM: Artificial Sequence
<220> FEATURE:
<223> OTHER INFORMATION: Antibody variable heavy chain sequence

<400> SEQUENCE: 11

Ser Ile Val Ser Ser Gly Gly Trp Thr Asp Tyr Ala Asp Ser Val Lys
1               5                   10                  15

Gly

<210> SEQ ID NO 12
<211> LENGTH: 21
<212> TYPE: PRT
<213> ORGANISM: Artificial Sequence
<220> FEATURE:
<223> OTHER INFORMATION: Antibody variable heavy chain sequence

<400> SEQUENCE: 12

Asp Arg Ser Ile Ala Ala Ala Gly Thr Gly Trp Ser Val Ser Phe Val
1               5                   10                  15

Asp Trp Phe Asp Pro
            20

<210> SEQ ID NO 13
<211> LENGTH: 360
<212> TYPE: DNA
<213> ORGANISM: Artificial Sequence
<220> FEATURE:
<223> OTHER INFORMATION: Antibody variable heavy chain sequence

<400> SEQUENCE: 13

```
gaagttcaat tgttagagtc tggtggcggt cttgttcagc ctggtggttc tttacgtctt    60
tcttgcgctg cttccggatt cactttctct atttaccgta tgcagtgggt tcgccaagct   120
cctggtaaag gtttggagtg ggtttctggt atctctcctt ctggtggcac tacttggtat   180
gctgactccg ttaaaggtcg cttcactatc tctagagaca actctaagaa tactctctac   240
ttgcagatga acagcttaag ggctgaggac acggccgtgt attactgtgc gagatggagc   300
gggggttcgg gctatgcttt tgatatctgg ggccaaggga caatggtcac cgtctcaagc   360
```

<210> SEQ ID NO 14
<211> LENGTH: 120
<212> TYPE: PRT
<213> ORGANISM: Artificial Sequence
<220> FEATURE:
<223> OTHER INFORMATION: Antibody variable heavy chain sequence

<400> SEQUENCE: 14

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ile Tyr
            20                  25                  30

Arg Met Gln Trp Val Arg Gln Ala Pro Gly Lys Gly Leu Glu Trp Val
        35                  40                  45

Ser Gly Ile Ser Pro Ser Gly Gly Thr Thr Trp Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Trp Ser Gly Gly Ser Gly Tyr Ala Phe Asp Ile Trp Gly Gln
            100                 105                 110

Gly Thr Met Val Thr Val Ser Ser
        115                 120

<210> SEQ ID NO 15
<211> LENGTH: 5
<212> TYPE: PRT
<213> ORGANISM: Artificial Sequence
<220> FEATURE:
<223> OTHER INFORMATION: Antibody variable heavy chain sequence

<400> SEQUENCE: 15

Ile Tyr Arg Met Gln
1               5

<210> SEQ ID NO 16
<211> LENGTH: 17
<212> TYPE: PRT
<213> ORGANISM: Artificial Sequence
<220> FEATURE:
<223> OTHER INFORMATION: Antibody variable heavy chain sequence

<400> SEQUENCE: 16

Gly Ile Ser Pro Ser Gly Gly Thr Thr Trp Tyr Ala Asp Ser Val Lys
1               5                   10                  15

Gly

<210> SEQ ID NO 17
<211> LENGTH: 11
<212> TYPE: PRT
<213> ORGANISM: Artificial Sequence
<220> FEATURE:
<223> OTHER INFORMATION: Antibody variable heavy chain sequence

<400> SEQUENCE: 17

Trp Ser Gly Gly Ser Gly Tyr Ala Phe Asp Ile
1               5                   10

<210> SEQ ID NO 18
<211> LENGTH: 360
<212> TYPE: DNA
<213> ORGANISM: Artificial Sequence
<220> FEATURE:
<223> OTHER INFORMATION: Antibody variable heavy chain sequence

<400> SEQUENCE: 18
gaggtccagc tgttggagtc cggcggtggc ctggtgcagc tggggggtc cctgagactc      60 tcctgcgcag ctagcggctt caccttcagc atttaccgta tgcagtgggt cgcccaggct     120
cctggaaagg ggctggagtg ggtttccggt atctctccct ctggtggcac gacgtggtat    180
gctgactccg tgaagggccg gttcacaatc tccagagaca attccaagaa cactctgtac    240
ctgcaaatga acagcctgag agctgaggat actgcagtgt actactgcgc cagatggtcc    300
gggggctccg gatacgcctt cgacatctgg ggacagggaa ccatggtcac cgtctcaagc    360

<210> SEQ ID NO 19
<211> LENGTH: 363
<212> TYPE: DNA
<213> ORGANISM: Artificial Sequence
<220> FEATURE:
<223> OTHER INFORMATION: Antibody variable heavy chain sequence

<400> SEQUENCE: 19
gaagttcaat tgttagagtc tggtggcggt cttgttcagc ctggtggttc tttacgtctt     60
tcttgcgctg cttccggatt cacttttctct aattaccata tggcttgggt cgccaagct    120 cctggtaaag gtttggagtg gtttctgtt atctctccta ctggtggccg tactacttat    180
gctgactccg ttaaaggtcg cttcactatc tctagagaca actctaagaa tactctctac    240
ttgcagatga acagcttaag ggctgaggac acagccacat attactgtgc gagagcgggg    300
tacagctatg gttatggcta ctttgactac tggggccagg gaaccctggt caccgtctca    360
agc                                                                  363

<210> SEQ ID NO 20
<211> LENGTH: 121
<212> TYPE: PRT
<213> ORGANISM: Artificial Sequence
<220> FEATURE:
<223> OTHER INFORMATION: Antibody variable heavy chain sequence

<400> SEQUENCE: 20

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

His Met Ala Trp Val Arg Gln Ala Pro Gly Lys Gly Leu Glu Trp Val
        35                  40                  45

Ser Val Ile Ser Pro Thr Gly Gly Arg Thr Thr Tyr Ala Asp Ser Val

```
                50                   55                  60
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Thr Tyr Tyr Cys
                 85                  90                  95

Ala Arg Ala Gly Tyr Ser Tyr Gly Tyr Gly Tyr Phe Asp Tyr Trp Gly
                100                 105                 110

Gln Gly Thr Leu Val Thr Val Ser Ser
        115                 120

<210> SEQ ID NO 21
<211> LENGTH: 5
<212> TYPE: PRT
<213> ORGANISM: Artificial Sequence
<220> FEATURE:
<223> OTHER INFORMATION: Antibody variable heavy chain sequence

<400> SEQUENCE: 21

Asn Tyr His Met Ala
1               5

<210> SEQ ID NO 22
<211> LENGTH: 17
<212> TYPE: PRT
<213> ORGANISM: Artificial Sequence
<220> FEATURE:
<223> OTHER INFORMATION: Antibody variable heavy chain sequence

<400> SEQUENCE: 22

Val Ile Ser Pro Thr Gly Gly Arg Thr Thr Tyr Ala Asp Ser Val Lys
1               5                   10                  15

Gly

<210> SEQ ID NO 23
<211> LENGTH: 12
<212> TYPE: PRT
<213> ORGANISM: Artificial Sequence
<220> FEATURE:
<223> OTHER INFORMATION: Antibody variable heavy chain sequence

<400> SEQUENCE: 23

Ala Gly Tyr Ser Tyr Gly Tyr Gly Tyr Phe Asp Tyr
1               5                   10

<210> SEQ ID NO 24
<211> LENGTH: 363
<212> TYPE: DNA
<213> ORGANISM: Artificial Sequence
<220> FEATURE:
<223> OTHER INFORMATION: Antibody variable heavy chain sequence

<400> SEQUENCE: 24
gaggtccagc tgttggagtc cggcggtggc ctggtgcagc cggggggtc cctgagactc     60 tcctgcgcag ctagcggctt caccttcagc aattaccaca tggcctgggt cgcccaggct    120
cctggaaagg gctggagtg gtttccgtg atctctccta ccggtggcag gaccacttac     180
gctgactccg tgaagggccg gttcacaatc tccagagaca attccaagaa cactctgtac    240
ctgcaaatga acagcctgag agctgaggat actgcaacat actactgcgc cagagccggg    300
tactcctacg gctacggata cttcgactac tggggacagg gaaccctggt caccgtctca    360
agc                                                                  363
```

<210> SEQ ID NO 25
<211> LENGTH: 357
<212> TYPE: DNA
<213> ORGANISM: Artificial Sequence
<220> FEATURE:
<223> OTHER INFORMATION: Antibody variable heavy chain sequence

<400> SEQUENCE: 25

```
gaagttcaat tgttagagtc tggtggcggt cttgttcagc ctggtggttc tttacgtctt    60
tcttgcgctg cttccggatt cactttctct aagtacatga tgtcttgggt tcgccaagct   120
cctggtaaag tttggagtg gtttcttat atctctcctt ctggtggcct tacttggtat     180
gctgactccg ttaaaggtcg cttcactatc tctagagaca actctaagaa tactctctac   240
ttgcagatga acagcttaag ggctgaggac acggccgtgt attactgtgc gagagatgga   300
gctagaggct acggtatgga cgtctggggc caagggacca cggtcaccgt ctcaagc      357
```

<210> SEQ ID NO 26
<211> LENGTH: 119
<212> TYPE: PRT
<213> ORGANISM: Artificial Sequence
<220> FEATURE:
<223> OTHER INFORMATION: Antibody variable heavy chain sequence

<400> SEQUENCE: 26

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Lys Tyr
            20                  25                  30

Met Met Ser Trp Val Arg Gln Ala Pro Gly Lys Gly Leu Glu Trp Val
        35                  40                  45

Ser Tyr Ile Ser Pro Ser Gly Gly Leu Thr Trp Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Gly Ala Arg Gly Tyr Gly Met Asp Val Trp Gly Gln Gly
            100                 105                 110

Thr Thr Val Thr Val Ser Ser
        115
```

<210> SEQ ID NO 27
<211> LENGTH: 5
<212> TYPE: PRT
<213> ORGANISM: Artificial Sequence
<220> FEATURE:
<223> OTHER INFORMATION: Antibody variable heavy chain sequence

<400> SEQUENCE: 27

```
Lys Tyr Met Met Ser
1               5
```

<210> SEQ ID NO 28
<211> LENGTH: 17
<212> TYPE: PRT
<213> ORGANISM: Artificial Sequence
<220> FEATURE:
<223> OTHER INFORMATION: Antibody variable heavy chain sequence

<400> SEQUENCE: 28

```
Tyr Ile Ser Pro Ser Gly Gly Leu Thr Trp Tyr Ala Asp Ser Val Lys
1               5                   10                  15
Gly

<210> SEQ ID NO 29
<211> LENGTH: 10
<212> TYPE: PRT
<213> ORGANISM: Artificial Sequence
<220> FEATURE:
<223> OTHER INFORMATION: Antibody variable heavy chain sequence

<400> SEQUENCE: 29

Asp Gly Ala Arg Gly Tyr Gly Met Asp Val
1               5                   10

<210> SEQ ID NO 30
<211> LENGTH: 357
<212> TYPE: DNA
<213> ORGANISM: Artificial Sequence
<220> FEATURE:
<223> OTHER INFORMATION: Antibody variable heavy chain sequence

<400> SEQUENCE: 30
gaggtccagc tgttggagtc cggcggtggc ctggtgcagc ctgggggtc cctgagactc      60 tcctgcgcag ctagcggctt caccttcagc aagtacatga tgtcttgggt gcgccaggct    120
cctggaaagg gctggagtg gtttcctat atctctccct ctggtggcct gacgtggtat      180
gctgactccg tgaagggccg gttcacaatc tccagagaca attccaagaa cactctgtac    240
ctgcaaatga acagcctgag agctgaggat actgcagtgt actactgcgc cagagatggg    300
gctagaggat acggaatgga cgtctgggga cagggaacca ccgtcaccgt ctcaagc       357

<210> SEQ ID NO 31
<211> LENGTH: 372
<212> TYPE: DNA
<213> ORGANISM: Artificial Sequence
<220> FEATURE:
<223> OTHER INFORMATION: Antibody variable heavy chain sequence

<400> SEQUENCE: 31
gaagttcaat tgttagagtc tggtggcggt cttgttcagc ctggtggttc tttacgtctt     60
tcttgcgctg cttccggatt cacttttctct aattacccta tgtattgggt tcgccaagct   120
cctggtaaag gtttggagtg gtttctcgt atctcttctt ctggtggccg tactgtttat     180
gctgactccg ttaaaggtcg cttcactatc tctagagaca actctaagaa tactctctac    240
ttgcagatga acagcttaag ggctgaggac acggccgtgt attactgtgc gagagatcga    300
tggtccagat ctgcagctga atatggttg ggtggctact ggggccaggg aaccctggtc     360
accgtctcaa gc                                                        372

<210> SEQ ID NO 32
<211> LENGTH: 124
<212> TYPE: PRT
<213> ORGANISM: Artificial Sequence
<220> FEATURE:
<223> OTHER INFORMATION: Antibody variable heavy chain sequence

<400> SEQUENCE: 32

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30
```

```
Pro Met Tyr Trp Val Arg Gln Ala Pro Gly Lys Gly Leu Glu Trp Val
        35                  40                  45

Ser Arg Ile Ser Ser Gly Gly Arg Thr Val Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Asp Arg Trp Ser Arg Ser Ala Ala Glu Tyr Gly Leu Gly Gly
            100                 105                 110

Tyr Trp Gly Gln Gly Thr Leu Val Thr Val Ser Ser
        115                 120

<210> SEQ ID NO 33
<211> LENGTH: 5
<212> TYPE: PRT
<213> ORGANISM: Artificial Sequence
<220> FEATURE:
<223> OTHER INFORMATION: Antibody variable heavy chain sequence

<400> SEQUENCE: 33

Asn Tyr Pro Met Tyr
1               5

<210> SEQ ID NO 34
<211> LENGTH: 17
<212> TYPE: PRT
<213> ORGANISM: Artificial Sequence
<220> FEATURE:
<223> OTHER INFORMATION: Antibody variable heavy chain sequence

<400> SEQUENCE: 34

Arg Ile Ser Ser Gly Gly Arg Thr Val Tyr Ala Asp Ser Val Lys
1               5                   10                  15

Gly

<210> SEQ ID NO 35
<211> LENGTH: 15
<212> TYPE: PRT
<213> ORGANISM: Artificial Sequence
<220> FEATURE:
<223> OTHER INFORMATION: Antibody variable heavy chain sequence

<400> SEQUENCE: 35

Asp Arg Trp Ser Arg Ser Ala Ala Glu Tyr Gly Leu Gly Gly Tyr
1               5                   10                  15

<210> SEQ ID NO 36
<211> LENGTH: 372
<212> TYPE: DNA
<213> ORGANISM: Artificial Sequence
<220> FEATURE:
<223> OTHER INFORMATION: Antibody variable heavy chain sequence

<400> SEQUENCE: 36
gaggtccagc tgttggagtc cggcggtggc ctggtgcagc ctgggggtc cctgagactc      60 tcctgcgcag ctagcggctt caccttcagc aattacccca tgtactgggt gcgccaggct     120
cctggaaagg gctggagtg gttccagg atctctagca gcggtggcag gaccgtgtac        180
gctgactccg tgaagggccg gttcacaatc tccagagaca attccaagaa cactctgtac    240
ctgcaaatga acagcctgag agctgaggat actgcagtgt actactgcgc cagagatagg    300
```

```
tggtccagat ctgcagccga gtacggactg gggggctact ggggacaggg aaccctggtc    360
accgtctcaa gc                                                        372
```

<210> SEQ ID NO 37
<211> LENGTH: 369
<212> TYPE: DNA
<213> ORGANISM: Artificial Sequence
<220> FEATURE:
<223> OTHER INFORMATION: Antibody variable heavy chain sequence

<400> SEQUENCE: 37

```
caggttcagc tgcagcagtc tggacctgag ctagtgaagc ctggggcttc agtgaagatg     60
tcctgcaagg cttctggaaa cacattcact gactatgtta taaactgggt gaagcagaga    120
actggacagg ccttgagtg gattggagag atttatcctg gaaatgaaaa tacttattac    180
aatgagaagt tcaagggcaa ggccacactg actgcagaca atcctccaa cacagcctac    240 atgcagctca gtagcctgac atctgaggac tctgcggtct atttctgtgc aagagggatt    300
tattactacg gtagtaggac gaggactatg gactactggg gtcaaggaac ctcagtcacc    360
gtctcctca                                                           369
```

<210> SEQ ID NO 38
<211> LENGTH: 123
<212> TYPE: PRT
<213> ORGANISM: Artificial Sequence
<220> FEATURE:
<223> OTHER INFORMATION: Antibody variable heavy chain sequence

<400> SEQUENCE: 38

Gln Val Gln Leu Gln Gln Ser Gly Pro Glu Leu Val Lys Pro Gly Ala
1               5                   10                  15

Ser Val Lys Met Ser Cys Lys Ala Ser Gly Asn Thr Phe Thr Asp Tyr
            20                  25                  30

Val Ile Asn Trp Val Lys Gln Arg Thr Gly Gln Gly Leu Glu Trp Ile
        35                  40                  45

Gly Glu Ile Tyr Pro Gly Asn Glu Asn Thr Tyr Tyr Asn Glu Lys Phe
    50                  55                  60

Lys Gly Lys Ala Thr Leu Thr Ala Asp Lys Ser Ser Asn Thr Ala Tyr
65                  70                  75                  80

Met Gln Leu Ser Ser Leu Thr Ser Glu Asp Ser Ala Val Tyr Phe Cys
                85                  90                  95

Ala Arg Gly Ile Tyr Tyr Tyr Gly Ser Arg Thr Arg Thr Met Asp Tyr
            100                 105                 110

Trp Gly Gln Gly Thr Ser Val Thr Val Ser Ser
        115                 120

<210> SEQ ID NO 39
<211> LENGTH: 5
<212> TYPE: PRT
<213> ORGANISM: Artificial Sequence
<220> FEATURE:
<223> OTHER INFORMATION: Antibody variable heavy chain sequence

<400> SEQUENCE: 39

Asp Tyr Val Ile Asn
1               5

<210> SEQ ID NO 40
<211> LENGTH: 16

<212> TYPE: PRT
<213> ORGANISM: Artificial Sequence
<220> FEATURE:
<223> OTHER INFORMATION: Antibody variable heavy chain sequence

<400> SEQUENCE: 40

Ile Tyr Pro Gly Asn Glu Asn Thr Tyr Tyr Asn Glu Lys Phe Lys Gly
1               5                   10                  15

<210> SEQ ID NO 41
<211> LENGTH: 14
<212> TYPE: PRT
<213> ORGANISM: Artificial Sequence
<220> FEATURE:
<223> OTHER INFORMATION: Antibody variable heavy chain sequence

<400> SEQUENCE: 41

Gly Ile Tyr Tyr Tyr Gly Ser Arg Thr Arg Thr Met Asp Tyr
1               5                   10

<210> SEQ ID NO 42
<211> LENGTH: 366
<212> TYPE: DNA
<213> ORGANISM: Artificial Sequence
<220> FEATURE:
<223> OTHER INFORMATION: Antibody variable heavy chain sequence

<400> SEQUENCE: 42
gacgtccaac tgcaggagtc tggacctgac ctggtgaaac cttctcagtc actttcactc      60
acctgcactg tcactggcta ctccatcacc agtggttata ctggcactg gatccggcag     120
tttccaggaa acaaactgga atggatgggc tacatacact acagtggtgg cactaactac     180
aacccatctc tcaaaagtcg aatctctatc actcgagaca catccaagaa ccagttcttc     240
ctccagttga attctgtgac tactgaggac acagccacat attactgtgc aagatcgggg     300
tacggctaca ggagtgcgta ctattttgac tactggggcc aagggaccac ggtcaccgtc     360
tcctca                                                                366

<210> SEQ ID NO 43
<211> LENGTH: 122
<212> TYPE: PRT
<213> ORGANISM: Artificial Sequence
<220> FEATURE:
<223> OTHER INFORMATION: Antibody variable heavy chain sequence

<400> SEQUENCE: 43

Asp Val Gln Leu Gln Glu Ser Gly Pro Asp Leu Val Lys Pro Ser Gln
1               5                   10                  15

Ser Leu Ser Leu Thr Cys Thr Val Thr Gly Tyr Ser Ile Thr Ser Gly
            20                  25                  30

Tyr Ser Trp His Trp Ile Arg Gln Phe Pro Gly Asn Lys Leu Glu Trp
        35                  40                  45

Met Gly Tyr Ile His Tyr Ser Gly Gly Thr Asn Tyr Asn Pro Ser Leu
    50                  55                  60

Lys Ser Arg Ile Ser Ile Thr Arg Asp Thr Lys Asn Gln Phe Phe
65                  70                  75                  80

Leu Gln Leu Asn Ser Val Thr Thr Glu Asp Thr Ala Thr Tyr Tyr Cys
                85                  90                  95

Ala Arg Ser Gly Tyr Gly Tyr Arg Ser Ala Tyr Tyr Phe Asp Tyr Trp
            100                 105                 110

Gly Gln Gly Thr Thr Val Thr Val Ser Ser

<210> SEQ ID NO 44
<211> LENGTH: 6
<212> TYPE: PRT
<213> ORGANISM: Artificial Sequence
<220> FEATURE:
<223> OTHER INFORMATION: Antibody variable heavy chain sequence

<400> SEQUENCE: 44

Ser Gly Tyr Ser Trp His
1               5

<210> SEQ ID NO 45
<211> LENGTH: 16
<212> TYPE: PRT
<213> ORGANISM: Artificial Sequence
<220> FEATURE:
<223> OTHER INFORMATION: Antibody variable heavy chain sequence

<400> SEQUENCE: 45

Tyr Ile His Tyr Ser Gly Gly Thr Asn Tyr Asn Pro Ser Leu Lys Ser
1               5                   10                  15

<210> SEQ ID NO 46
<211> LENGTH: 13
<212> TYPE: PRT
<213> ORGANISM: Artificial Sequence
<220> FEATURE:
<223> OTHER INFORMATION: Antibody variable heavy chain sequence

<400> SEQUENCE: 46

Ser Gly Tyr Gly Tyr Arg Ser Ala Tyr Tyr Phe Asp Tyr
1               5                   10

<210> SEQ ID NO 47
<211> LENGTH: 363
<212> TYPE: DNA
<213> ORGANISM: Artificial Sequence
<220> FEATURE:
<223> OTHER INFORMATION: Antibody variable heavy chain sequence

<400> SEQUENCE: 47
caaatacagt tggttcagag cggacctgag ctgaagaagc tggagagac  agtcaagatc      60 tcctgcaagg cttctgggta taccttcaca aaccatggaa tgaactgggt gaagcaggct    120
ccaggaaagg gtttaaagtg gatgggctgg ataaacacct ccactggaga gccaacatat    180
gctgatgact tcaagggacg ttttgccttc tctttggaaa cctctgccag cactgccttt    240
ttgcagatca caaccctcaa aaatgaggac acggcttcat atttctgtgc aagtccccctc   300 tactatatgt acgggcggta tatcgatgtc tggggcgcag ggaccgcggt caccgtctcc   360
tca                                                                  363

<210> SEQ ID NO 48
<211> LENGTH: 120
<212> TYPE: PRT
<213> ORGANISM: Artificial Sequence
<220> FEATURE:
<223> OTHER INFORMATION: Antibody variable heavy chain sequence

<400> SEQUENCE: 48

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asn His

```
                20                  25                  30
Gly Met Asn Trp Val Lys Gln Ala Pro Gly Lys Gly Leu Lys Trp Met
        35                  40                  45
Gly Trp Asn Thr Ser Thr Gly Glu Pro Thr Tyr Ala Asp Asp Phe Lys
 50                  55                  60
Gly Arg Phe Ala Phe Ser Leu Glu Thr Ser Ala Ser Thr Ala Phe Leu
 65                  70                  75                  80
Gln Ile Asn Asn Leu Lys Asn Glu Asp Thr Ala Ser Tyr Phe Cys Ala
                85                  90                  95
Ser Pro Leu Tyr Tyr Met Tyr Gly Arg Tyr Ile Asp Val Trp Gly Ala
            100                 105                 110
Gly Thr Ala Val Thr Val Ser Ser
        115                 120

<210> SEQ ID NO 49
<211> LENGTH: 5
<212> TYPE: PRT
<213> ORGANISM: Artificial Sequence
<220> FEATURE:
<223> OTHER INFORMATION: Antibody variable heavy chain sequence

<400> SEQUENCE: 49

Asn His Gly Met Asn
1               5

<210> SEQ ID NO 50
<211> LENGTH: 15
<212> TYPE: PRT
<213> ORGANISM: Artificial Sequence
<220> FEATURE:
<223> OTHER INFORMATION: Antibody variable heavy chain sequence

<400> SEQUENCE: 50

Asn Thr Ser Thr Gly Glu Pro Thr Tyr Ala Asp Asp Phe Lys Gly
1               5                   10                  15

<210> SEQ ID NO 51
<211> LENGTH: 12
<212> TYPE: PRT
<213> ORGANISM: Artificial Sequence
<220> FEATURE:
<223> OTHER INFORMATION: Antibody variable heavy chain sequence

<400> SEQUENCE: 51

Pro Leu Tyr Tyr Met Tyr Gly Arg Tyr Ile Asp Val
1               5                   10

<210> SEQ ID NO 52
<211> LENGTH: 315
<212> TYPE: DNA
<213> ORGANISM: Artificial Sequence
<220> FEATURE:
<223> OTHER INFORMATION: Antibody variable heavy chain sequence

<400> SEQUENCE: 52
acgtccaact gcaggagtct ggacctgacc tggtgaaacc ttctcagtca ctttcactca        60
cctgcactgt cactggctac tccatcacca gtggttatag ctggcactgg atccggcagt      120
ttccaggaaa caaactggaa tggatgggct acatacacta cagtggtggc actaactaca      180
acccatctct caaaagtcga atctctatca ctcgagacac atccaagaac cagttcttcc      240
tccagttgaa ttctgtgact actgaggaca cagccacata ttactgtgca agatcggggt      300
```
acggctacag gagtg 315

<210> SEQ ID NO 53
<211> LENGTH: 122
<212> TYPE: PRT
<213> ORGANISM: Artificial Sequence
<220> FEATURE:
<223> OTHER INFORMATION: Antibody variable heavy chain sequence

<400> SEQUENCE: 53

Asp Val Gln Leu Gln Glu Ser Gly Pro Asp Leu Val Lys Pro Ser Gln
1               5                   10                  15

Ser Leu Ser Leu Thr Cys Thr Val Thr Gly Tyr Ser Ile Thr Ser Gly
            20                  25                  30

Tyr Ser Trp His Trp Ile Arg Gln Phe Pro Gly Asn Lys Leu Glu Trp
        35                  40                  45

Met Gly Tyr Ile His Tyr Ser Gly Gly Thr Asn Tyr Asn Pro Ser Leu
    50                  55                  60

Lys Ser Arg Ile Ser Ile Thr Arg Asp Thr Ser Lys Asn Gln Phe Phe
65                  70                  75                  80

Leu Gln Leu Asn Ser Val Thr Thr Glu Asp Thr Ala Thr Tyr Tyr Cys
                85                  90                  95

Ala Arg Ser Gly Tyr Gly Tyr Arg Ser Ala Tyr Tyr Phe Asp Tyr Trp
            100                 105                 110

Gly Gln Gly Thr Thr Leu Thr Val Ser Ser
        115                 120

<210> SEQ ID NO 54
<211> LENGTH: 6
<212> TYPE: PRT
<213> ORGANISM: Artificial Sequence
<220> FEATURE:
<223> OTHER INFORMATION: Antibody variable heavy chain sequence

<400> SEQUENCE: 54

Ser Gly Tyr Ser Trp His
1               5

<210> SEQ ID NO 55
<211> LENGTH: 16
<212> TYPE: PRT
<213> ORGANISM: Artificial Sequence
<220> FEATURE:
<223> OTHER INFORMATION: Antibody variable heavy chain sequence

<400> SEQUENCE: 55

Tyr Ile His Tyr Ser Gly Gly Thr Asn Tyr Asn Pro Ser Leu Lys Ser
1               5                   10                  15

<210> SEQ ID NO 56
<211> LENGTH: 13
<212> TYPE: PRT
<213> ORGANISM: Artificial Sequence
<220> FEATURE:
<223> OTHER INFORMATION: Antibody variable heavy chain sequence

<400> SEQUENCE: 56

Ser Gly Tyr Gly Tyr Arg Ser Ala Tyr Tyr Phe Asp Tyr
1               5                   10

<210> SEQ ID NO 57
<211> LENGTH: 360
<212> TYPE: DNA

```
<213> ORGANISM: Artificial Sequence
<220> FEATURE:
<223> OTHER INFORMATION: Antibody variable heavy chain sequence

<400> SEQUENCE: 57
cagatccagt tggtgcagtc tggacctgac ctgaagaagc tggagagaca agtcaagatc      60
tcctgcaagg cttctgggta taccttcaca aaccatggaa tgaactgggt gaagcaggct     120
ccaggaaagg atttaaagtg gatgggctgg ataaacacca acactggaga gccaacatat     180
gctgatgact tcaagggacg gtttgccttc tctttggaaa cctctgccag cactgcctat     240
ttgcagatca caaccctcaa aaatgaggac acggctacat atttctgtgc aagtcccctc     300
tactatagga acgggcgata cttcgatgtc tggggcgcag ggaccacggt caccgtctcc     360

<210> SEQ ID NO 58
<211> LENGTH: 121
<212> TYPE: PRT
<213> ORGANISM: Artificial Sequence
<220> FEATURE:
<223> OTHER INFORMATION: Antibody variable heavy chain sequence

<400> SEQUENCE: 58

Gln Ile Gln Leu Val Gln Ser Gly Pro Asp Leu Lys Lys Pro Gly Glu
1               5                   10                  15

Thr Val Lys Ile Ser Cys Lys Ala Ser Gly Tyr Thr Phe Thr Asn His
            20                  25                  30

Gly Met Asn Trp Val Lys Gln Ala Pro Gly Lys Asp Leu Lys Trp Met
        35                  40                  45

Gly Trp Ile Asn Thr Asn Thr Gly Glu Pro Thr Tyr Ala Asp Asp Phe
    50                  55                  60

Lys Gly Arg Phe Ala Phe Ser Leu Glu Thr Ser Ala Ser Thr Ala Tyr
65                  70                  75                  80

Leu Gln Ile Asn Asn Leu Lys Asn Glu Asp Thr Ala Thr Tyr Phe Cys
                85                  90                  95

Ala Ser Pro Leu Tyr Tyr Arg Asn Gly Arg Tyr Phe Asp Val Trp Gly
            100                 105                 110

Ala Gly Thr Thr Val Thr Val Ser Ser
        115                 120

<210> SEQ ID NO 59
<211> LENGTH: 5
<212> TYPE: PRT
<213> ORGANISM: Artificial Sequence
<220> FEATURE:
<223> OTHER INFORMATION: Antibody variable heavy chain sequence

<400> SEQUENCE: 59

Asn His Gly Met Asn
1               5

<210> SEQ ID NO 60
<211> LENGTH: 17
<212> TYPE: PRT
<213> ORGANISM: Artificial Sequence
<220> FEATURE:
<223> OTHER INFORMATION: Antibody variable heavy chain sequence

<400> SEQUENCE: 60

Trp Ile Asn Thr Asn Thr Gly Glu Pro Thr Tyr Ala Asp Asp Phe Lys
1               5                   10                  15

Gly
```

<210> SEQ ID NO 61
<211> LENGTH: 12
<212> TYPE: PRT
<213> ORGANISM: Artificial Sequence
<220> FEATURE:
<223> OTHER INFORMATION: Antibody variable heavy chain sequence

<400> SEQUENCE: 61

Pro Leu Tyr Tyr Arg Asn Gly Arg Tyr Phe Asp Val
1               5                   10

<210> SEQ ID NO 62
<211> LENGTH: 354
<212> TYPE: DNA
<213> ORGANISM: Artificial Sequence
<220> FEATURE:
<223> OTHER INFORMATION: Antibody variable heavy chain sequence

<400> SEQUENCE: 62
caggtccaac tgcagcagcc tggggctgaa ctggtgaagc ctggggcttc agtgaagctg      60
tcctgtaagg cttctggcta caccttcacc agctactgga tgcactgggt gaagcagagg     120
cctggacaag gccttgagtg gattggagag attaatccta cctacggtcg tagtaattac     180
aatgagaagt tcaagagtaa ggccacactg actgtagaca atcctccag cacagcctac      240 atgcaactca gcagcctgac atctgaggac tctgcggtct attactgtgc aagattagta     300
cgcctacggt acttcgatgt ctggggcgca gggaccacgg tcaccgtctc ctca           354

<210> SEQ ID NO 63
<211> LENGTH: 118
<212> TYPE: PRT
<213> ORGANISM: Artificial Sequence
<220> FEATURE:
<223> OTHER INFORMATION: Antibody variable heavy chain sequence

<400> SEQUENCE: 63

Gln Val Gln Leu Gln Gln Pro Gly Ala Glu Leu Val Lys Pro Gly Ala
1               5                   10                  15

Ser Val Lys Leu Ser Cys Lys Ala Ser Gly Tyr Thr Phe Thr Ser Tyr
                20                  25                  30

Trp Met His Trp Val Lys Gln Arg Pro Gly Gln Gly Leu Glu Trp Ile
            35                  40                  45

Gly Glu Ile Asn Pro Thr Tyr Gly Arg Ser Asn Tyr Asn Glu Lys Phe
        50                  55                  60

Lys Ser Lys Ala Thr Leu Thr Val Asp Lys Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Leu Val Arg Leu Arg Tyr Phe Asp Val Trp Gly Ala Gly Thr
            100                 105                 110

Thr Val Thr Val Ser Ser
        115

<210> SEQ ID NO 64
<211> LENGTH: 5
<212> TYPE: PRT
<213> ORGANISM: Artificial Sequence
<220> FEATURE:
<223> OTHER INFORMATION: Antibody variable heavy chain sequence

<400> SEQUENCE: 64

```
Ser Tyr Trp Met His
1               5

<210> SEQ ID NO 65
<211> LENGTH: 17
<212> TYPE: PRT
<213> ORGANISM: Artificial Sequence
<220> FEATURE:
<223> OTHER INFORMATION: Antibody variable heavy chain sequence

<400> SEQUENCE: 65

Glu Ile Asn Pro Thr Tyr Gly Arg Ser Asn Tyr Asn Glu Lys Phe Lys
1               5                   10                  15

Ser

<210> SEQ ID NO 66
<211> LENGTH: 9
<212> TYPE: PRT
<213> ORGANISM: Artificial Sequence
<220> FEATURE:
<223> OTHER INFORMATION: Antibody variable heavy chain sequence

<400> SEQUENCE: 66

Leu Val Arg Leu Arg Tyr Phe Asp Val
1               5

<210> SEQ ID NO 67
<211> LENGTH: 330
<212> TYPE: DNA
<213> ORGANISM: Artificial Sequence
<220> FEATURE:
<223> OTHER INFORMATION: Antibody variable light chain sequence

<400> SEQUENCE: 67
cagtacgaat tgactcagcc gccctcggtg tctgaggccc ccggcagag ggtcaccatc      60 tcctgttctg gaagcagctc caacatcgga aataatgcta taaactggta ccagcaactc     120
ccaggaaagc ctcccaaact cctcatctat tatgatgatc tgttgccctc aggggtctct    180
gaccgattct ctggctccaa gtctggcacc tcaggctccc tggccatcag tgggctgcag    240
tctgaggatg aggctgatta ttactgtgca gcatgggatg acaacctgaa tggtgtgatt    300
ttcggcggag ggaccaagct gaccgtccta                                      330

<210> SEQ ID NO 68
<211> LENGTH: 110
<212> TYPE: PRT
<213> ORGANISM: Artificial Sequence
<220> FEATURE:
<223> OTHER INFORMATION: Antibody variable light chain sequence

<400> SEQUENCE: 68

Gln Tyr Glu Leu Thr Gln Pro Pro Ser Val Ser Glu Ala Pro Arg Gln
1               5                   10                  15

Arg Val Thr Ile Ser Cys Ser Gly Ser Ser Ser Asn Ile Gly Asn Asn
            20                  25                  30

Ala Ile Asn Trp Tyr Gln Gln Leu Pro Gly Lys Pro Pro Lys Leu Leu
        35                  40                  45

Ile Tyr Tyr Asp Asp Leu Leu Pro Ser Gly Val Ser Asp Arg Phe Ser
    50                  55                  60

Gly Ser Lys Ser Gly Thr Ser Gly Ser Leu Ala Ile Ser Gly Leu Gln
65                  70                  75                  80
```

Ser Glu Asp Glu Ala Asp Tyr Tyr Cys Ala Ala Trp Asp Asp Asn Leu
            85                  90                  95

Asn Gly Val Ile Phe Gly Gly Thr Lys Leu Thr Val Leu
            100                 105                 110

<210> SEQ ID NO 69
<211> LENGTH: 13
<212> TYPE: PRT
<213> ORGANISM: Artificial Sequence
<220> FEATURE:
<223> OTHER INFORMATION: Antibody variable light chain sequence

<400> SEQUENCE: 69

Ser Gly Ser Ser Ser Asn Ile Gly Asn Asn Ala Ile Asn
1               5                   10

<210> SEQ ID NO 70
<211> LENGTH: 7
<212> TYPE: PRT
<213> ORGANISM: Artificial Sequence
<220> FEATURE:
<223> OTHER INFORMATION: Antibody variable light chain sequence

<400> SEQUENCE: 70

Tyr Asp Asp Leu Leu Pro Ser
1               5

<210> SEQ ID NO 71
<211> LENGTH: 11
<212> TYPE: PRT
<213> ORGANISM: Artificial Sequence
<220> FEATURE:
<223> OTHER INFORMATION: Antibody variable light chain sequence

<400> SEQUENCE: 71

Ala Ala Trp Asp Asp Asn Leu Asn Gly Val Ile
1               5                   10

<210> SEQ ID NO 72
<211> LENGTH: 324
<212> TYPE: DNA
<213> ORGANISM: Artificial Sequence
<220> FEATURE:
<223> OTHER INFORMATION: Antibody variable light chain sequence

<400> SEQUENCE: 72
gacatccaga tgacccagtc tccactctcc ctgtctgcat ctgtaggaga cagagtcacc    60
atcacttgcc gggcaagtca gagcattaac ggctacttaa attggtatca gcagaaacca   120
gggaaagccc ctaacctcct gatctacgct acatccagtt tgcaaagtgg ggtcccatca   180
aggttcagtg gcagtggatc tgggacagat ttcactctca ccatcagcag tctgcaacct   240
gaagattttg caacttacta ctgtcaacag agttacagta ccccccccgta cacttttggc   300 caggggacca agctggagat caaa                                           324

<210> SEQ ID NO 73
<211> LENGTH: 108
<212> TYPE: PRT
<213> ORGANISM: Artificial Sequence
<220> FEATURE:
<223> OTHER INFORMATION: Antibody variable light chain sequence

<400> SEQUENCE: 73

Asp Ile Gln Met Thr Gln Ser Pro Leu Ser Leu Ser Ala Ser Val Gly
1               5                   10                  15

```
Asp Arg Val Thr Ile Thr Cys Arg Ala Ser Gln Ser Ile Asn Gly Tyr
            20                  25                  30

Leu Asn Trp Tyr Gln Gln Lys Pro Gly Lys Ala Pro Asn Leu Leu Ile
            35                  40                  45

Tyr Ala Thr Ser Ser Leu Gln Ser Gly Val Pro Ser Arg Phe Ser Gly
            50                  55                  60

Ser Gly Ser Gly Thr Asp Phe Thr Leu Thr Ile Ser Ser Leu Gln Pro
 65              70                  75                  80

Glu Asp Phe Ala Thr Tyr Tyr Cys Gln Gln Ser Tyr Ser Thr Pro Pro
                85                  90                  95

Tyr Thr Phe Gly Gln Gly Thr Lys Leu Glu Ile Lys
            100                 105
```

<210> SEQ ID NO 74
<211> LENGTH: 11
<212> TYPE: PRT
<213> ORGANISM: Artificial Sequence
<220> FEATURE:
<223> OTHER INFORMATION: Antibody variable light chain sequence

<400> SEQUENCE: 74

```
Arg Ala Ser Gln Ser Ile Asn Gly Tyr Leu Asn
 1               5                   10
```

<210> SEQ ID NO 75
<211> LENGTH: 7
<212> TYPE: PRT
<213> ORGANISM: Artificial Sequence
<220> FEATURE:
<223> OTHER INFORMATION: Antibody variable light chain sequence

<400> SEQUENCE: 75

```
Ala Thr Ser Ser Leu Gln Ser
 1               5
```

<210> SEQ ID NO 76
<211> LENGTH: 10
<212> TYPE: PRT
<213> ORGANISM: Artificial Sequence
<220> FEATURE:
<223> OTHER INFORMATION: Antibody variable light chain sequence

<400> SEQUENCE: 76

```
Gln Gln Ser Tyr Ser Thr Pro Pro Tyr Thr
 1               5                   10
```

<210> SEQ ID NO 77
<211> LENGTH: 321
<212> TYPE: DNA
<213> ORGANISM: Artificial Sequence
<220> FEATURE:
<223> OTHER INFORMATION: Antibody variable light chain sequence

<400> SEQUENCE: 77

```
gacatccaga tgacccagtc tccactctcc ctgtctgcat ctgtaggaga cagagtcacc     60
atcacttgcc aggcgagtcg ggacattaga aactatttaa attggtatca acaaaaacca    120
gggaaagccc cgaagctcct gatctacgat gcatccagtt tgcaaacagg ggtcccatca    180
aggttcggtg gcagtggatc tgggacagac tttagtttca ccatcggcag cctgcagcct    240
gaagatattg caacatatta ctgtcaacag tttgatagtc tccctcacac ttttggccag    300
gggaccaaac tggagatcaa a                                              321
```

<210> SEQ ID NO 78
<211> LENGTH: 107
<212> TYPE: PRT
<213> ORGANISM: Artificial Sequence
<220> FEATURE:
<223> OTHER INFORMATION: Antibody variable light chain sequence

<400> SEQUENCE: 78

Asp Ile Gln Met Thr Gln Ser Pro Leu Ser Leu Ser Ala Ser Val Gly
1               5                   10                  15

Asp Arg Val Thr Ile Thr Cys Gln Ala Ser Arg Asp Ile Arg Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Ser Leu Gln Thr Gly Val Pro Ser Arg Phe Gly Gly
    50                  55                  60

Ser Gly Ser Gly Thr Asp Phe Ser Phe Thr Ile Gly Ser Leu Gln Pro
65                  70                  75                  80

Glu Asp Ile Ala Thr Tyr Tyr Cys Gln Gln Phe Asp Ser Leu Pro His
                85                  90                  95

Thr Phe Gly Gln Gly Thr Lys Leu Glu Ile Lys
            100                 105

<210> SEQ ID NO 79
<211> LENGTH: 11
<212> TYPE: PRT
<213> ORGANISM: Artificial Sequence
<220> FEATURE:
<223> OTHER INFORMATION: Antibody variable light chain sequence

<400> SEQUENCE: 79

Gln Ala Ser Arg Asp Ile Arg Asn Tyr Leu Asn
1               5                   10

<210> SEQ ID NO 80
<211> LENGTH: 7
<212> TYPE: PRT
<213> ORGANISM: Artificial Sequence
<220> FEATURE:
<223> OTHER INFORMATION: Antibody variable light chain sequence

<400> SEQUENCE: 80

Asp Ala Ser Ser Leu Gln Thr
1               5

<210> SEQ ID NO 81
<211> LENGTH: 9
<212> TYPE: PRT
<213> ORGANISM: Artificial Sequence
<220> FEATURE:
<223> OTHER INFORMATION: Antibody variable light chain sequence

<400> SEQUENCE: 81

Gln Gln Phe Asp Ser Leu Pro His Thr
1               5

<210> SEQ ID NO 82
<211> LENGTH: 324
<212> TYPE: DNA
<213> ORGANISM: Artificial Sequence
<220> FEATURE:
<223> OTHER INFORMATION: Antibody variable light chain sequence -continued

```
<400> SEQUENCE: 82
gacatccaga tgacccagtt ccagccacc ctgtctgtgt ctccagggga aagagccacc    60
ctctcctgca gggccagtca gagtgttatg aggaacttag cctggtacca gcagaaacct   120
ggccagcctc ccaggctcct catctatggt gcatccaaaa gggccactgg catcccagcc   180
aggttcagtg gcagtgggtc tgggacagcc ttcactctca ccatcagcaa cctagagcct   240
gaagattttg cagtttatta ctgtcaccaa cgtagcacct ggcctctggg gactttcggc   300
cctgggacca aactggaggc caaa                                          324

<210> SEQ ID NO 83
<211> LENGTH: 108
<212> TYPE: PRT
<213> ORGANISM: Artificial Sequence
<220> FEATURE:
<223> OTHER INFORMATION: Antibody variable light chain sequence

<400> SEQUENCE: 83

Asp Ile Gln Met Thr Gln Phe Pro Ala Thr Leu Ser Val Ser Pro Gly
1               5                   10                  15

Glu Arg Ala Thr Leu Ser Cys Arg Ala Ser Gln Ser Val Met Arg Asn
            20                  25                  30

Leu Ala Trp Tyr Gln Gln Lys Pro Gly Gln Pro Pro Arg Leu Leu Ile
        35                  40                  45

Tyr Gly Ala Ser Lys Arg Ala Thr Gly Ile Pro Ala Arg Phe Ser Gly
    50                  55                  60

Ser Gly Ser Gly Thr Ala Phe Thr Leu Thr Ile Ser Asn Leu Glu Pro
65                  70                  75                  80

Glu Asp Phe Ala Val Tyr Tyr Cys His Gln Arg Ser Thr Trp Pro Leu
                85                  90                  95

Gly Thr Phe Gly Pro Gly Thr Lys Leu Glu Ala Lys
            100                 105

<210> SEQ ID NO 84
<211> LENGTH: 11
<212> TYPE: PRT
<213> ORGANISM: Artificial Sequence
<220> FEATURE:
<223> OTHER INFORMATION: Antibody variable light chain sequence

<400> SEQUENCE: 84

Arg Ala Ser Gln Ser Val Met Arg Asn Leu Ala
1               5                   10

<210> SEQ ID NO 85
<211> LENGTH: 7
<212> TYPE: PRT
<213> ORGANISM: Artificial Sequence
<220> FEATURE:
<223> OTHER INFORMATION: Antibody variable light chain sequence

<400> SEQUENCE: 85

Gly Ala Ser Lys Arg Ala Thr
1               5

<210> SEQ ID NO 86
<211> LENGTH: 10
<212> TYPE: PRT
<213> ORGANISM: Artificial Sequence
<220> FEATURE:
<223> OTHER INFORMATION: Antibody variable light chain sequence
```

<400> SEQUENCE: 86

His Gln Arg Ser Thr Trp Pro Leu Gly Thr
1               5                   10

<210> SEQ ID NO 87
<211> LENGTH: 327
<212> TYPE: DNA
<213> ORGANISM: Artificial Sequence
<220> FEATURE:
<223> OTHER INFORMATION: Antibody variable light chain sequence

<400> SEQUENCE: 87

```
gacatccaga tgacccagtc tccagccacc ctgtctttgt ctccagggga aagagccacc   60
ctctcctgca gggccagtca gagtgttagc agctacttag cctggtacca acagaaacct  120
ggccaggctc ccaggctcct catctatgat gcatccaaca gggccactgg catcccagcc  180
aggttcagtg gcagtgggtc tgggacagac ttcactctca ccatcagcag cctagagcct  240
gaagattttg cagtttatta ctgtcagcag cgtagcaact ggcctccgga ggtcactttc  300
ggccctggga ccaaagtgga tatcaaa                                      327
```

<210> SEQ ID NO 88
<211> LENGTH: 109
<212> TYPE: PRT
<213> ORGANISM: Artificial Sequence
<220> FEATURE:
<223> OTHER INFORMATION: Antibody variable light chain sequence

<400> SEQUENCE: 88

Asp Ile Gln Met Thr Gln Ser Pro Ala Thr Leu Ser Leu Ser Pro Gly
1               5                   10                  15
Glu Arg Ala Thr Leu Ser Cys Arg Ala Ser Gln Ser Val Ser Ser Tyr
            20                  25                  30
Leu Ala Trp Tyr Gln Gln Lys Pro Gly Gln Ala Pro Arg Leu Leu Ile
        35                  40                  45
Tyr Asp Ala Ser Asn Arg Ala Thr Gly Ile Pro Ala Arg Phe Ser Gly
    50                  55                  60
Ser Gly Ser Gly Thr Asp Phe Thr Leu Thr Ile Ser Ser Leu Glu Pro
65                  70                  75                  80
Glu Asp Phe Ala Val Tyr Tyr Cys Gln Gln Arg Ser Asn Trp Pro Pro
                85                  90                  95
Glu Val Thr Phe Gly Pro Gly Thr Lys Val Asp Ile Lys
            100                 105

<210> SEQ ID NO 89
<211> LENGTH: 11
<212> TYPE: PRT
<213> ORGANISM: Artificial Sequence
<220> FEATURE:
<223> OTHER INFORMATION: Antibody variable light chain sequence

<400> SEQUENCE: 89

Arg Ala Ser Gln Ser Val Ser Ser Tyr Leu Ala
1               5                   10

<210> SEQ ID NO 90
<211> LENGTH: 7
<212> TYPE: PRT
<213> ORGANISM: Artificial Sequence
<220> FEATURE:
<223> OTHER INFORMATION: Antibody variable light chain sequence

```
<400> SEQUENCE: 90

Asp Ala Ser Asn Arg Ala Thr
1               5

<210> SEQ ID NO 91
<211> LENGTH: 11
<212> TYPE: PRT
<213> ORGANISM: Artificial Sequence
<220> FEATURE:
<223> OTHER INFORMATION: Antibody variable light chain sequence

<400> SEQUENCE: 91

Gln Gln Arg Ser Asn Trp Pro Pro Glu Val Thr
1               5                   10

<210> SEQ ID NO 92
<211> LENGTH: 336
<212> TYPE: DNA
<213> ORGANISM: Artificial Sequence
<220> FEATURE:
<223> OTHER INFORMATION: Antibody variable light chain

<400> SEQUENCE: 92
gacatccaga tgacccagtc tccagactcc ctggctgtgt ctctgggcga gagggccacc      60
atcaactgca gtccagcca gagtgtttta tacagctcca acaataagaa ctacttagct     120
tggtaccagc agaaaccagg acagcctcct aagctgctca tttacttggc atctacccgg    180
gaatccgggg tccctgaccg attcagtggc agcgggtctg ggacagattt cactctcacc    240
atcagcagcc tgcaggctga agatgtggca gtttattact gtcagcaata ttatagtact    300
tggacgttcg gccaagggac caaggtggaa atcaaa                              336

<210> SEQ ID NO 93
<211> LENGTH: 112
<212> TYPE: PRT
<213> ORGANISM: Artificial Sequence
<220> FEATURE:
<223> OTHER INFORMATION: Antibody variable light chain sequence

<400> SEQUENCE: 93

Asp Ile Gln Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
                20                  25                  30

Ser Asn Asn Lys Asn Tyr Leu Ala Trp Tyr Gln Lys Pro Gly Gln
            35                  40                  45

Pro Pro Lys Leu Leu Ile Tyr Leu Ala Ser Thr Arg Glu Ser Gly Val
        50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Thr Trp Thr Phe Gly Gln Gly Thr Lys Val Glu Ile Lys
            100                 105                 110

<210> SEQ ID NO 94
<211> LENGTH: 17
<212> TYPE: PRT
<213> ORGANISM: Artificial Sequence
<220> FEATURE:
<223> OTHER INFORMATION: Antibody variable light chain sequence
```

```
<400> SEQUENCE: 94

Lys Ser Ser Gln Ser Val Leu Tyr Ser Ser Asn Asn Lys Asn Tyr Leu
1               5                   10                  15
Ala

<210> SEQ ID NO 95
<211> LENGTH: 7
<212> TYPE: PRT
<213> ORGANISM: Artificial Sequence
<220> FEATURE:
<223> OTHER INFORMATION: Antibody variable light chain sequence

<400> SEQUENCE: 95

Leu Ala Ser Thr Arg Glu Ser
1               5

<210> SEQ ID NO 96
<211> LENGTH: 8
<212> TYPE: PRT
<213> ORGANISM: Artificial Sequence
<220> FEATURE:
<223> OTHER INFORMATION: Antibody variable light chain sequence

<400> SEQUENCE: 96

Gln Gln Tyr Tyr Ser Thr Trp Thr
1               5

<210> SEQ ID NO 97
<211> LENGTH: 324
<212> TYPE: DNA
<213> ORGANISM: Artificial Sequence
<220> FEATURE:
<223> OTHER INFORMATION: Antibody variable light chain sequence

<400> SEQUENCE: 97
gaagttgtgc tcacccagtc tccaaccgcc atggctgcat ctcccgggga gaagatcact      60
atcacctgca gtgccagctc aactttaagt tccaattact tgcattggta tcagcagaag     120
ccaggattct cccctaaaact cttgatttat aggacatcca atctggcctc tggagtccca    180
ggtcgcttca gtggcagtgg gtctgggacc tcttactctc tcacaattgg caccatggag    240
gctgaagatg ttgccactta ctactgccag cagggtagta gtataccgct cacgttcggt    300
gctgggacca agctggagct gaag                                            324

<210> SEQ ID NO 98
<211> LENGTH: 108
<212> TYPE: PRT
<213> ORGANISM: Artificial Sequence
<220> FEATURE:
<223> OTHER INFORMATION: Antibody variable light chain sequence

<400> SEQUENCE: 98

Glu Val Val Leu Thr Gln Ser Pro Thr Ala Met Ala Ala Ser Pro Gly
1               5                   10                  15

Glu Lys Ile Thr Ile Thr Cys Ser Ala Ser Ser Thr Leu Ser Ser Asn
                20                  25                  30

Tyr Leu His Trp Tyr Gln Gln Lys Pro Gly Phe Ser Pro Lys Leu Leu
            35                  40                  45

Ile Tyr Arg Thr Ser Asn Leu Ala Ser Gly Val Pro Gly Arg Phe Ser
        50                  55                  60

Gly Ser Gly Ser Gly Thr Ser Tyr Ser Leu Thr Ile Gly Thr Met Glu
65                  70                  75                  80
```

```
Ala Glu Asp Val Ala Thr Tyr Tyr Cys Gln Gln Gly Ser Ser Ile Pro
            85                  90                  95

Leu Thr Phe Gly Ala Gly Thr Lys Leu Glu Leu Lys
            100                 105

<210> SEQ ID NO 99
<211> LENGTH: 12
<212> TYPE: PRT
<213> ORGANISM: Artificial Sequence
<220> FEATURE:
<223> OTHER INFORMATION: Antibody variable light chain sequence

<400> SEQUENCE: 99

Ser Ala Ser Ser Thr Leu Ser Ser Asn Tyr Leu His
1               5                   10

<210> SEQ ID NO 100
<211> LENGTH: 7
<212> TYPE: PRT
<213> ORGANISM: Artificial Sequence
<220> FEATURE:
<223> OTHER INFORMATION: Antibody variable light chain sequence

<400> SEQUENCE: 100

Arg Thr Ser Asn Leu Ala Ser
1               5

<210> SEQ ID NO 101
<211> LENGTH: 9
<212> TYPE: PRT
<213> ORGANISM: Artificial Sequence
<220> FEATURE:
<223> OTHER INFORMATION: Antibody variable light chain sequence

<400> SEQUENCE: 101

Gln Gln Gly Ser Ser Ile Pro Leu Thr
1               5

<210> SEQ ID NO 102
<211> LENGTH: 330
<212> TYPE: DNA
<213> ORGANISM: Artificial Sequence
<220> FEATURE:
<223> OTHER INFORMATION: Antibody variable light chain sequence

<400> SEQUENCE: 102
gacattgtgc tgacacagtc tcctgcttcc ttagctgtat ctctggggca gagggccacc      60
atctcatgca gggccagcaa aagtgtcagt acatctgcct atagttatat gcactggtac     120
caacagaaac caggacagcc acccaaactc ctcatctatc ttgcatccaa cctagaatct     180
ggggtccctg ccaggttcag tggcagtggg tctgggacag acttcaccct caacatccat     240
cctgtggagg aggaggatgc tgcaacctat tactgtcagc acagtaggga gcttccgtat     300
acgttcggag gggggaccaa gctggaaatc                                      330

<210> SEQ ID NO 103
<211> LENGTH: 111
<212> TYPE: PRT
<213> ORGANISM: Artificial Sequence
<220> FEATURE:
<223> OTHER INFORMATION: Antibody variable light chain sequence

<400> SEQUENCE: 103

Asp Ile Val Leu Thr Gln Ser Pro Ala Ser Leu Ala Val Ser Leu Gly
```

```
               1               5                  10                 15
Gln Arg Ala Thr Ile Ser Cys Arg Ala Ser Lys Ser Val Ser Thr Ser
                    20                  25                  30

Ala Tyr Ser Tyr Met His Trp Tyr Gln Gln Lys Pro Gly Gln Pro Pro
            35                  40                  45

Lys Leu Leu Ile Tyr Leu Ala Ser Asn Leu Glu Ser Gly Val Pro Ala
        50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln His Ser Arg
                85                  90                  95

Glu Leu Pro Tyr Thr Phe Gly Gly Gly Thr Lys Leu Glu Ile Lys
            100                 105                 110
```

<210> SEQ ID NO 104
<211> LENGTH: 15
<212> TYPE: PRT
<213> ORGANISM: Artificial Sequence
<220> FEATURE:
<223> OTHER INFORMATION: Antibody variable light chain sequence

<400> SEQUENCE: 104

```
Arg Ala Ser Lys Ser Val Ser Thr Ser Ala Tyr Ser Tyr Met His
1               5                   10                  15
```

<210> SEQ ID NO 105
<211> LENGTH: 7
<212> TYPE: PRT
<213> ORGANISM: Artificial Sequence
<220> FEATURE:
<223> OTHER INFORMATION: Antibody variable light chain sequence

<400> SEQUENCE: 105

```
Leu Ala Ser Asn Leu Glu Ser
1               5
```

<210> SEQ ID NO 106
<211> LENGTH: 9
<212> TYPE: PRT
<213> ORGANISM: Artificial Sequence
<220> FEATURE:
<223> OTHER INFORMATION: Antibody variable light chain sequence

<400> SEQUENCE: 106

```
Gln His Ser Arg Glu Leu Pro Tyr Thr
1               5
```

<210> SEQ ID NO 107
<211> LENGTH: 321
<212> TYPE: DNA
<213> ORGANISM: Artificial Sequence
<220> FEATURE:
<223> OTHER INFORMATION: Antibody variable light chain sequence

<400> SEQUENCE: 107

```
gatatccaga tgacacagac tacatcctcc ctatctgcct ctctgggaga cagagtcacc      60
atcagttgca gggcaagtca ggacattagc aattatttaa actggtatca gcagaaacca     120
gatggaacta ttaaactcct gatctactac acatcaagat tacactcagg agtcccatca     180
aggttcagtg gcagtgggtc tggaacagat tattctctca ccattagcaa cctgaacaa      240 gaagattttg ccacttactt ttgccaacag ggtaaaacgc ttccgtggac gttcggtgga     300
```
ggcaccaagc tggaaatcaa a 321

<210> SEQ ID NO 108
<211> LENGTH: 107
<212> TYPE: PRT
<213> ORGANISM: Artificial Sequence
<220> FEATURE:
<223> OTHER INFORMATION: Antibody variable light chain sequence

<400> SEQUENCE: 108

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Asn Tyr
            20                  25                  30

Leu Asn Trp Tyr Gln Gln Lys Pro Asp Gly Thr Ile Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Phe Ala Thr Tyr Phe Cys Gln Gln Gly Lys Thr Leu Pro Trp
                85                  90                  95

Thr Phe Gly Gly Gly Thr Lys Leu Glu Ile Lys
            100                 105

<210> SEQ ID NO 109
<211> LENGTH: 11
<212> TYPE: PRT
<213> ORGANISM: Artificial Sequence
<220> FEATURE:
<223> OTHER INFORMATION: Antibody variable light chain sequence

<400> SEQUENCE: 109

Arg Ala Ser Gln Asp Ile Ser Asn Tyr Leu Asn
1               5                   10

<210> SEQ ID NO 110
<211> LENGTH: 6
<212> TYPE: PRT
<213> ORGANISM: Artificial Sequence
<220> FEATURE:
<223> OTHER INFORMATION: Antibody variable light chain sequence

<400> SEQUENCE: 110

Thr Ser Arg Leu His Ser
1               5

<210> SEQ ID NO 111
<211> LENGTH: 9
<212> TYPE: PRT
<213> ORGANISM: Artificial Sequence
<220> FEATURE:
<223> OTHER INFORMATION: Antibody variable light chain sequence

<400> SEQUENCE: 111

Gln Gln Gly Lys Thr Leu Pro Trp Thr
1               5

<210> SEQ ID NO 112
<211> LENGTH: 321
<212> TYPE: DNA
<213> ORGANISM: Artificial Sequence
<220> FEATURE:
<223> OTHER INFORMATION: Antibody variable light chain sequence

<400> SEQUENCE: 112

```
gatatccaga tgacacagac tacatcctcc ctgtctgcct ctctgggaga cagagtcacc    60
atcagttgca gggcaagtca ggacattagt aattatttaa attggtatca gcagaaacca   120
gatggatctg ttaaactcct gatctactac acatcaagat tacactcagg agtcccatca   180
aggttcagtg gcagtgggtc tggaacagat tattctctca ccattagcaa cctgaacaa    240
gaagatattg ccacttactt tgccaacag ggaaagacgc ttccgtggac gttcggtgga    300
ggcaccaagc tggaaatcaa a                                              321
```

<210> SEQ ID NO 113
<211> LENGTH: 107
<212> TYPE: PRT
<213> ORGANISM: Artificial Sequence
<220> FEATURE:
<223> OTHER INFORMATION: Antibody variable light chain sequence

<400> SEQUENCE: 113

```
Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Asn Tyr
            20                  25                  30

Leu Asn Trp Tyr Gln Gln Lys Pro Asp Gly Ser Val Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Lys Thr Leu Pro Trp
                85                  90                  95

Thr Phe Gly Gly Gly Thr Lys Leu Glu Ile Lys
            100                 105
```

<210> SEQ ID NO 114
<211> LENGTH: 11
<212> TYPE: PRT
<213> ORGANISM: Artificial Sequence
<220> FEATURE:
<223> OTHER INFORMATION: Antibody variable light chain sequence

<400> SEQUENCE: 114

```
Arg Ala Ser Gln Asp Ile Ser Asn Tyr Leu Asn
1               5                   10
```

<210> SEQ ID NO 115
<211> LENGTH: 5
<212> TYPE: PRT
<213> ORGANISM: Artificial Sequence
<220> FEATURE:
<223> OTHER INFORMATION: Antibody variable light chain sequence

<400> SEQUENCE: 115

```
Thr Ser Arg Leu His
1               5
```

<210> SEQ ID NO 116
<211> LENGTH: 9
<212> TYPE: PRT
<213> ORGANISM: Artificial Sequence
<220> FEATURE:
<223> OTHER INFORMATION: Antibody variable light chain sequence

<400> SEQUENCE: 116

Gln Gln Gly Lys Thr Leu Pro Trp Thr
1               5

<210> SEQ ID NO 117
<211> LENGTH: 336
<212> TYPE: DNA
<213> ORGANISM: Artificial Sequence
<220> FEATURE:
<223> OTHER INFORMATION: Antibody variable light chain sequence

<400> SEQUENCE: 117

```
gatattgtga tgacgcaggc tgcattctcc aatccagtca ctcttggaac atcagcttcc     60
atctcctgca ggtctagtaa gagtctccta catagtaatg gcatcactta tttgtattgg    120
tatctgcaga agccaggcca gtctcctcag ctcctgattt atcagatgtc caaccttgcc    180
tcaggagtcc cagacaggtt cagtagcagt gggtcaggaa ctgatttcac actgagaatc    240
agcagagtgg aggctgagga tgtgggtgtt tattactgtg ctcaaaatct agaacttccg    300
tacacgttcg gaggggggac caagctggaa atcaaa                              336
```

<210> SEQ ID NO 118
<211> LENGTH: 112
<212> TYPE: PRT
<213> ORGANISM: Artificial Sequence
<220> FEATURE:
<223> OTHER INFORMATION: Antibody variable light chain sequence

<400> SEQUENCE: 118

Asp Ile Val Met Thr Gln Ala Ala Phe Ser Asn Pro Val Thr Leu Gly
1               5                   10                  15

Thr Ser Ala Ser Ile Ser Cys Arg Ser Ser Lys Ser Leu Leu His Ser
            20                  25                  30

Asn Gly Ile Thr Tyr Leu Tyr Trp Tyr Leu Gln Lys Pro Gly Gln Ser
        35                  40                  45

Pro Gln Leu Leu Ile Tyr Gln Met Ser Asn Leu Ala Ser Gly Val Pro
    50                  55                  60

Asp Arg Phe Ser Ser Ser Gly Ser Gly Thr Asp Phe Thr Leu Arg Ile
65                  70                  75                  80

Ser Arg Val Glu Ala Glu Asp Val Gly Val Tyr Tyr Cys Ala Gln Asn
                85                  90                  95

Leu Glu Leu Pro Tyr Thr Phe Gly Gly Gly Thr Lys Leu Glu Ile Lys
            100                 105                 110

<210> SEQ ID NO 119
<211> LENGTH: 16
<212> TYPE: PRT
<213> ORGANISM: Artificial Sequence
<220> FEATURE:
<223> OTHER INFORMATION: Antibody variable light chain sequence

<400> SEQUENCE: 119

Arg Ser Ser Lys Ser Leu Leu His Ser Asn Gly Ile Thr Tyr Leu Tyr
1               5                   10                  15

<210> SEQ ID NO 120
<211> LENGTH: 7
<212> TYPE: PRT
<213> ORGANISM: Artificial Sequence
<220> FEATURE:
<223> OTHER INFORMATION: Antibody variable light chain sequence

```
<400> SEQUENCE: 120

Gln Met Ser Asn Leu Ala Ser
1               5

<210> SEQ ID NO 121
<211> LENGTH: 9
<212> TYPE: PRT
<213> ORGANISM: Artificial Sequence
<220> FEATURE:
<223> OTHER INFORMATION: Antibody variable light chain sequence

<400> SEQUENCE: 121

Ala Gln Asn Leu Glu Leu Pro Tyr Thr
1               5

<210> SEQ ID NO 122
<211> LENGTH: 19
<212> TYPE: PRT
<213> ORGANISM: Artificial Sequence
<220> FEATURE:
<223> OTHER INFORMATION: Antibody heavy chain signal sequence

<400> SEQUENCE: 122

Met Gly Trp Ser Leu Ile Leu Leu Phe Leu Val Ala Val Ala Thr Arg
1               5                   10                  15

Val Leu Ser

<210> SEQ ID NO 123
<211> LENGTH: 106
<212> TYPE: DNA
<213> ORGANISM: Artificial Sequence
<220> FEATURE:
<223> OTHER INFORMATION: Oligonucleotide PCR primer

<400> SEQUENCE: 123
cgaacaggcc cagctggcca ccatggacat gagggtcccc gctcagctcc tggggctcct      60
tctgctctgg ctcccaggtg ccagatgtga catccagatg acccag                   106

<210> SEQ ID NO 124
<211> LENGTH: 37
<212> TYPE: DNA
<213> ORGANISM: Artificial Sequence
<220> FEATURE:
<223> OTHER INFORMATION: Oligonucleotide PCR primer

<400> SEQUENCE: 124
tcgcacggcg cgcctcaaca ctctcccctg ttgaagc                              37

<210> SEQ ID NO 125
<211> LENGTH: 83
<212> TYPE: DNA
<213> ORGANISM: Artificial Sequence
<220> FEATURE:
<223> OTHER INFORMATION: Oligonucleotide PCR primer

<400> SEQUENCE: 125
cggccaccat gggttggagc ctcatcttgc tcttccttgt cgctgttgct acgcgtgtcc      60
tgtccgaagt tcaattgtta gag                                             83

<210> SEQ ID NO 126
<211> LENGTH: 47
<212> TYPE: DNA
<213> ORGANISM: Artificial Sequence
```

```
<220> FEATURE:
<223> OTHER INFORMATION: Oligonucleotide PCR primer

<400> SEQUENCE: 126
gggatcggcc agctgggccc cttcgttgag gcgcttgaga cggtgac         47

<210> SEQ ID NO 127
<211> LENGTH: 19
<212> TYPE: PRT
<213> ORGANISM: Artificial Sequence
<220> FEATURE:
<223> OTHER INFORMATION: Antibody heavy chain signal peptide

<400> SEQUENCE: 127

Met Gly Trp Ser Cys Ile Ile Leu Phe Leu Val Ala Thr Ala Thr Gly
1               5                   10                  15

Ala His Ser

<210> SEQ ID NO 128
<211> LENGTH: 22
<212> TYPE: PRT
<213> ORGANISM: Artificial Sequence
<220> FEATURE:
<223> OTHER INFORMATION: Antibody light chain signal peptide

<400> SEQUENCE: 128

Met Asp Met Arg Val Pro Ala Gln Leu Leu Gly Leu Leu Leu Leu Trp
1               5                   10                  15

Leu Arg Gly Ala Arg Cys
            20

<210> SEQ ID NO 129
<211> LENGTH: 20
<212> TYPE: PRT
<213> ORGANISM: Artificial Sequence
<220> FEATURE:
<223> OTHER INFORMATION: Antibody light chain signal peptide

<400> SEQUENCE: 129

Met Glu Thr Asp Thr Leu Leu Leu Trp Val Leu Leu Leu Trp Val Pro
1               5                   10                  15

Gly Ser Thr Gly
            20

<210> SEQ ID NO 130
<211> LENGTH: 39
<212> TYPE: DNA
<213> ORGANISM: Artificial Sequence
<220> FEATURE:
<223> OTHER INFORMATION: Oligonucleotide PCR primer

<400> SEQUENCE: 130
ggggatatcc accatggrat gsagctgkgt matsctctt         39

<210> SEQ ID NO 131
<211> LENGTH: 39
<212> TYPE: DNA
<213> ORGANISM: Artificial Sequence
<220> FEATURE:
<223> OTHER INFORMATION: Oligonucleotide PCR primer

<400> SEQUENCE: 131
aggtctagaa yctccacaca caggrrccag tggatagac         39
```

```
<210> SEQ ID NO 132
<211> LENGTH: 39
<212> TYPE: DNA
<213> ORGANISM: Artificial Sequence
<220> FEATURE:
<223> OTHER INFORMATION: Oligonucleotide PCR primer

<400> SEQUENCE: 132
ggggatatcc accatggatt ttcaggtgca gattttcag                              39

<210> SEQ ID NO 133
<211> LENGTH: 29
<212> TYPE: DNA
<213> ORGANISM: Artificial Sequence
<220> FEATURE:
<223> OTHER INFORMATION: Oligonucleotide PCR primer

<400> SEQUENCE: 133
gcgtctagaa ctggatggtg ggagatgga                                        29

<210> SEQ ID NO 134
<211> LENGTH: 1407
<212> TYPE: DNA
<213> ORGANISM: Artificial Sequence
<220> FEATURE:
<223> OTHER INFORMATION: cDNA encoding antibody chimeric heavy chain

<400> SEQUENCE: 134
atggaatgga gctgtgtcat gctcttcatc ctgtcaggaa ctgcaggtgt ccactcccag       60
gttcagctgc agcagtctgg acctgagcta gtgaagcctg ggcttcagt gaagatgtcc      120 tgcaaggctt ctggaaacac attcactgac tatgttataa actgggtgaa gcagagaact      180
ggacagggcc ttgagtggat tggagagatt tatcctggaa tgaaaatac ttattacaat      240 gagaagttca gggcaaggc cacactgact gcagacaaat cctccaacac agcctacatg      300
cagctcagta gcctgacatc tgaggactct gcggtctatt tctgtgcaag agggattat      360 tactacggta gtaggacgag gactatggac tactggggtc aaggaacctc agtcaccgtc      420
tcctcagcct ccaccaaggg cccatccgtc ttccccctgg cgccctgctc cagatctacc      480
tccgagagca cagccgccct gggctgcctg gtcaaggact acttccccga accggtgacg      540
gtgtcgtgga actcaggcgc cctgaccagc ggcgtgcaca ccttcccggc tgtcctacag      600
tcctcaggac tctactccct cagcagcgtg gtgaccgtgc cctccagcag cttgggcacg      660
aagacctaca cctgcaacgt agatcacaag cccagcaaca ccaaggtgga caagagagtt      720
gagtccaaat atggtccccc atgcccaccg tgcccagcac ctgagttcct ggggggacca      780
tcagtcttcc tgttccccc aaaacccaag gacactctca tgatctcccg acccctgag      840 gtcacgtgcg tggtggtgga cgtgagccag gaagacccg aggtccagtt caactggtac      900
gtggatggcg tggaggtgca taatgccaag acaaagccgc gggaggagca gttcaacagc      960
acgtaccgtg tggtcagcgt cctcaccgtc ctgcaccagg actggctgaa cggcaaggag     1020
tacaagtgca aggtctccaa caaaggcctc ccgtcctcca tcgagaaaac catctccaaa     1080
gccaaagggc agccccgaga gccacaagtg tacaccctgc cccatccca ggaggagatg     1140 accaagaacc aggtcagcct gacctgcctg gtcaaaggct tctacccag cgacatcgcc     1200 gtggagtggg agagcaatgg gcagccggag aacaactaca gaccacgcc tcccgtcctc     1260 gattccgacg gctccttctt cctctacagc aggctaaccg tggacaagag caggtggcag     1320
gaggggaatg tcttctcatg ctccgtgatg catgaggctc tgcacaacca ctacacacag     1380
```
aagagcctct ccctgtctct gggttga    1407

<210> SEQ ID NO 135
<211> LENGTH: 449
<212> TYPE: PRT
<213> ORGANISM: Artificial Sequence
<220> FEATURE:
<223> OTHER INFORMATION: Antibody chimeric heavy chain

<400> SEQUENCE: 135

```
Gln Val Gln Leu Gln Gln Ser Gly Pro Glu Leu Val Lys Pro Gly Ala
1               5                   10                  15

Ser Val Lys Met Ser Cys Lys Ala Ser Gly Asn Thr Phe Thr Asp Tyr
            20                  25                  30

Val Ile Asn Trp Val Lys Gln Arg Thr Gly Gln Gly Leu Glu Trp Ile
        35                  40                  45

Gly Glu Ile Tyr Pro Gly Asn Glu Asn Thr Tyr Tyr Asn Glu Lys Phe
    50                  55                  60

Lys Gly Lys Ala Thr Leu Thr Ala Asp Lys Ser Ser Asn Thr Ala Tyr
65                  70                  75                  80

Met Gln Leu Ser Ser Leu Thr Ser Glu Asp Ser Ala Val Tyr Phe Cys
                85                  90                  95

Ala Arg Gly Ile Tyr Tyr Tyr Gly Ser Arg Thr Arg Thr Met Asp Tyr
            100                 105                 110

Trp Gly Gln Gly Thr Ser Val Thr Val Ser Ser Ala Ser Thr Lys Gly
        115                 120                 125

Pro Ser Val Phe Pro Leu Ala Pro Cys Ser Arg Ser Thr Ser Glu Ser
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Lys Thr Tyr Thr Cys Asn Val
        195                 200                 205

Asp His Lys Pro Ser Asn Thr Lys Val Asp Lys Arg Val Glu Ser Lys
    210                 215                 220

Tyr Gly Pro Pro Cys Pro Pro Cys Pro Ala Pro Glu Phe Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser Gln Glu
            260                 265                 270

Asp Pro Glu Val Gln Phe Asn Trp Tyr Val Asp Gly Val Glu Val His
        275                 280                 285

Asn Ala Lys Thr Lys Pro Arg Glu Glu Gln Phe Asn Ser Ala Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Gly Leu Pro Ser Ser Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Gln Glu Glu Met Thr Lys Asn Gln Val Ser Leu
```

```
            355                 360                 365
Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Arg Leu Thr Val Asp
                405                 410                 415

Lys Ser Arg Trp Gln Glu Gly Asn Val Phe Ser Cys Ser Val Met His
            420                 425                 430

Glu Ala Leu His Asn His Tyr Thr Gln Lys Ser Leu Ser Leu Ser Leu
            435                 440                 445

Gly

<210> SEQ ID NO 136
<211> LENGTH: 32
<212> TYPE: DNA
<213> ORGANISM: Artificial Sequence
<220> FEATURE:
<223> OTHER INFORMATION: Oligonucleotide PCR primer

<400> SEQUENCE: 136
cgccagtgtg cggccgctgg aattcgccct tg                              32

<210> SEQ ID NO 137
<211> LENGTH: 47
<212> TYPE: DNA
<213> ORGANISM: Artificial Sequence
<220> FEATURE:
<223> OTHER INFORMATION: Oligonucleotide PCR primer

<400> SEQUENCE: 137
ggaccaagct ggagctgaag cgtacggatg ctgcaccaac tgtatcc              47

<210> SEQ ID NO 138
<211> LENGTH: 714
<212> TYPE: DNA
<213> ORGANISM: Artificial Sequence
<220> FEATURE:
<223> OTHER INFORMATION: cDNA encoding chimeric antibody light chain

<400> SEQUENCE: 138 atggatttc aggtgcagat tttcagcttg ctgctaatca gtgtcacagt catagtgtct      60 aatgagaag ttgtgctcac ccagtctcca accgccatgg ctgcatctcc ggggagaag     120 atcactatca cctgcagtgc cagctcaact ttaagttcca attacttgca ttggtatcag    180
cagaagccag gattctcccc taaactcttg atttatagga catccaatct ggcctctgga    240
gtcccaggtc gcttcagtgg cagtgggtct ggaacctctt actctctcac aattggcacc    300
atggaggctg aagatgttgc cacttactac tgccagcagg gtagtagtat accgctcacg    360
ttcggtgctg ggaccaagct ggagctgaag cgtacggtgg ctgcaccatc tgtcttcatc    420
ttcccgccat ctgatgagca gttgaaatct ggaactgcct ctgttgtgtg cctgctgaat    480
aacttctatc ccagagaggc caaagtacag tggaaggtgg ataacgccct ccaatcgggt    540
aactcccagg agagtgtcac agagcaggac agcaaggaca gcacctacag cctcagcagc    600
accctgacgc tgagcaaagc agactacgag aaacacaaag tctacgcctg cgaagtcacc    660
catcagggcc tgagctcgcc cgtcacaaag agcttcaaca ggggagagtg ttag          714

<210> SEQ ID NO 139
```

<211> LENGTH: 215
<212> TYPE: PRT
<213> ORGANISM: Artificial Sequence
<220> FEATURE:
<223> OTHER INFORMATION: Chimeric antibody light chain

<400> SEQUENCE: 139

Glu Val Val Leu Thr Gln Ser Pro Thr Ala Met Ala Ala Ser Pro Gly
1               5                   10                  15

Glu Lys Ile Thr Ile Thr Cys Ser Ala Ser Ser Thr Leu Ser Ser Asn
            20                  25                  30

Tyr Leu His Trp Tyr Gln Gln Lys Pro Gly Phe Ser Pro Lys Leu Leu
        35                  40                  45

Ile Tyr Arg Thr Ser Asn Leu Ala Ser Gly Val Pro Gly Arg Phe Ser
    50                  55                  60

Gly Ser Gly Ser Gly Thr Ser Tyr Ser Leu Thr Ile Gly Thr Met Glu
65                  70                  75                  80

Ala Glu Asp Val Ala Thr Tyr Tyr Cys Gln Gln Gly Ser Ser Ile Pro
                85                  90                  95

Leu Thr Phe Gly Ala Gly Thr Lys Leu Glu Leu Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 140
<211> LENGTH: 1404
<212> TYPE: DNA
<213> ORGANISM: Artificial Sequence
<220> FEATURE:
<223> OTHER INFORMATION: cDNA encoding chimeric antibody heavy chain

<400> SEQUENCE: 140
atggactgga cctggagggt cttctgcttg ctggctgtag caccaggtgc ccactccgac      60
gtccaactgc aggagtctgg acctgacctg gtgaaacctt ctcagtcact ttcactcacc     120
tgcactgtca ctggctactc catcaccagt ggttatagcg gcactggat ccggcagttt      180 ccaggaaaca aactggaatg gatgggctac atacactaca gtggtggcac taactacaac     240
ccatctctca aaagtcgaat ctctatcact cgagacacat ccaagaacca gttcttcctc     300
cagttgaatt ctgtgactac tgaggacaca gccacatatt actgtgcaag atcggggtac     360
ggctacagga gtgcgtacta ttttgactac tggggccaag gaccacggt caccgtctcc      420 tcagcttcca ccaagggccc atcgtcttc ccctggcgc cctgctccag atctacctcc       480
gagagcacag ccgccctggg ctgcctggtc aaggactact ccccgaacc ggtgacggtg      540 tcgtggaact caggcgccct gaccagcggc gtgcacacct tcccggctgt cctacagtcc    600

```
tcaggactct actccctcag cagcgtggtg accgtgccct ccagcagctt gggcacgaag    660
acctacacct gcaacgtaga tcacaagccc agcaacacca aggtggacaa gagagttgag    720
tccaaatatg gtccccatg cccaccgtgc ccagcacctg agttcctggg gggaccatca    780
gtcttcctgt tccccccaaa acccaaggac actctcatga tctcccggac ccctgaggtc    840
acgtgcgtgg tggtggacgt gagccaggaa gaccccgagg tccagttcaa ctggtacgtg    900
gatggcgtgg aggtgcataa tgccaagaca aagccgcggg aggagcagtt caacagcgcg    960
taccgtgtgg tcagcgtcct caccgtcctg caccaggact ggctgaacgg caaggagtac   1020
aagtgcaagg tctccaacaa aggcctcccg tcctccatcg agaaaaccat ctccaaagcc   1080
aaagggcagc cccgagagcc acaagtgtac accctgcccc catcccagga ggagatgacc   1140
aagaaccagg tcagcctgac ctgcctggtc aaaggcttct accccagcga catcgccgtg   1200
gagtgggaga gcaatgggca gccggagaac aactacaaga ccacgcctcc cgtcctcgat   1260
tccgacggct ccttcttcct ctacagcagg ctaaccgtgg acaagagcag gtggcaggag   1320
gggaatgtct tctcatgctc cgtgatgcat gaggctctgc acaaccacta cacacagaag   1380
agcctctccc tgtctctggg ttga                                          1404
```

<210> SEQ ID NO 141
<211> LENGTH: 448
<212> TYPE: PRT
<213> ORGANISM: Artificial Sequence
<220> FEATURE:
<223> OTHER INFORMATION: Chimeric antibody heavy chain

<400> SEQUENCE: 141

```
Asp Val Gln Leu Gln Glu Ser Gly Pro Asp Leu Val Lys Pro Ser Gln
1               5                   10                  15

Ser Leu Ser Leu Thr Cys Thr Val Thr Gly Tyr Ser Ile Thr Ser Gly
            20                  25                  30

Tyr Ser Trp His Trp Ile Arg Gln Phe Pro Gly Asn Lys Leu Glu Trp
        35                  40                  45

Met Gly Tyr Ile His Tyr Ser Gly Gly Thr Asn Tyr Asn Pro Ser Leu
    50                  55                  60

Lys Ser Arg Ile Ser Ile Thr Arg Asp Thr Ser Lys Asn Gln Phe Phe
65                  70                  75                  80

Leu Gln Leu Asn Ser Val Thr Thr Glu Asp Thr Ala Thr Tyr Tyr Cys
                85                  90                  95

Ala Arg Ser Gly Tyr Gly Tyr Arg Ser Ala Tyr Tyr Phe Asp Tyr Trp
            100                 105                 110

Gly Gln Gly Thr Thr Val Thr Val Ser Ser Ala Ser Thr Lys Gly Pro
        115                 120                 125

Ser Val Phe Pro Leu Ala Pro Cys Ser Arg Ser Thr Ser Glu Ser Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Lys Thr Tyr Thr Cys Asn Val Asp
        195                 200                 205

His Lys Pro Ser Asn Thr Lys Val Asp Lys Arg Val Glu Ser Lys Tyr
```

```
            210                 215                 220
Gly Pro Pro Cys Pro Pro Cys Pro Ala Pro Glu Phe Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser Gln Glu Asp
                260                 265                 270

Pro Glu Val Gln Phe Asn Trp Tyr Val Asp Gly Val Glu Val His Asn
            275                 280                 285

Ala Lys Thr Lys Pro Arg Glu Glu Gln Phe Asn Ser Ala Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Gly Leu Pro Ser Ser Ile Glu Lys
                325                 330                 335

Thr Ile Ser Lys Ala Lys Gly Gln Pro Arg Glu Pro Gln Val Tyr Thr
                340                 345                 350

Leu Pro Pro Ser Gln Glu Glu Met Thr Lys Asn Gln Val Ser Leu Thr
            355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Arg Leu Thr Val Asp Lys
                405                 410                 415

Ser Arg Trp Gln Glu Gly Asn Val Phe Ser Cys Ser Val Met His Glu
            420                 425                 430

Ala Leu His Asn His Tyr Thr Gln Lys Ser Leu Ser Leu Ser Leu Gly
            435                 440                 445

<210> SEQ ID NO 142
<211> LENGTH: 717
<212> TYPE: DNA
<213> ORGANISM: Artificial Sequence
<220> FEATURE:
<223> OTHER INFORMATION: cDNA encoding chimeric antibody light chain

<400> SEQUENCE: 142
atggagacag acacactcct gttatgggta ctgctgctct gggttccagg ttccactggt      60
gacattgtgc tgacacagtc tcctgcttcc ttagctgtat ctctgggca gagggccacc     120 atctcatgca gggccagcaa agtgtcagt acatctgcct atagttatat gcactggtac     180
caacagaaac aggacagcc acccaaactc ctcatctatc ttgcatccaa cctagaatct     240
ggggtccctg ccaggttcag tggcagtggg tctgggacag acttcaccct caacatccat     300
cctgtggagg aggaggatgc tgcaacctat tactgtcagc acagtaggga gcttccgtat     360
acgttcggag gggggaccaa gctggaaatc aaacgtacgg tggctgcacc atctgtcttc     420
atcttcccgc catctgatga gcagttgaaa tctggaactg cctctgttgt gtgcctgctg     480
aataacttct atcccagaga ggccaaagta cagtggaagg tggataacgc cctccaatcg     540
ggtaactccc aggagagtgt cacagagcag gacagcaagg acagcaccta cagcctcagc     600
agcaccctga cgctgagcaa agcagactac gagaaacaca agtctacgc ctgcgaagtc     660 acccatcagg gcctgagctc gcccgtcaca aagagcttca caggggagag tgttag         717
```

<210> SEQ ID NO 143
<211> LENGTH: 218
<212> TYPE: PRT
<213> ORGANISM: Artificial Sequence
<220> FEATURE:
<223> OTHER INFORMATION: Chimeric antibody light chain

<400> SEQUENCE: 143

```
Asp Ile Val Leu Thr Gln Ser Pro Ala Ser Leu Ala Val Ser Leu Gly
1               5                   10                  15

Gln Arg Ala Thr Ile Ser Cys Arg Ala Ser Lys Ser Val Ser Thr Ser
            20                  25                  30

Ala Tyr Ser Tyr Met His Trp Tyr Gln Gln Lys Pro Gly Gln Pro Pro
        35                  40                  45

Lys Leu Leu Ile Tyr Leu Ala Ser Asn Leu Glu Ser Gly Val Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln His Ser Arg
                85                  90                  95

Glu Leu Pro Tyr Thr Phe Gly Gly Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215
```

<210> SEQ ID NO 144
<211> LENGTH: 1404
<212> TYPE: DNA
<213> ORGANISM: Artificial Sequence
<220> FEATURE:
<223> OTHER INFORMATION: cDNA encoding chimeric antibody heavy chain

<400> SEQUENCE: 144

```
atggactgga cctggagggt cttctgcttg ctggctgtag caccaggtgc ccactccgac      60
gtccaactgc aggagtctgg acctgacctg gtgaaacctt ctcagtcact ttcactcacc     120
tgcactgtca ctggctactc catcaccagt ggttatagct ggcactggat ccggcagttt     180
ccaggaaaca aactggaatg gatgggctac atacactaca gtggtggcac taactacaac     240
ccatctctca aaagtcgaat ctctatcact cgagacacat ccaagaacca gttcttcctc     300
cagttgaatt ctgtgactac tgaggacaca gccacatatt actgtgcaag atcgggtac      360 ggctacagga gtgcgtacta ttttgactac tggggccaag gaccacgtt gacagtctcc      420 tcagcttcca ccaagggccc atccgtcttc cccctggcgc cctgctccag atctacctcc     480
gagagcacag ccgccctggg ctgcctggtc aaggactact ccccgaacc ggtgacggtg      540
```

```
tcgtggaact caggcgccct gaccagcggc gtgcacacct tcccggctgt cctacagtcc    600
tcaggactct actccctcag cagcgtggtg accgtgccct ccagcagctt gggcacgaag    660
acctacacct gcaacgtaga tcacaagccc agcaacacca aggtggacaa gagagttgag    720
tccaaatatg gtcccccatg cccaccgtgc ccagcacctg agttcctggg gggaccatca    780
gtcttcctgt tccccccaaa acccaaggac actctcatga tctcccggac ccctgaggtc    840
acgtgcgtgg tggtggacgt gagccaggaa gaccccgagg tccagttcaa ctggtacgtg    900
gatggcgtgg aggtgcataa tgccaagaca aagccgcggg aggagcagtt caacagcgcg    960
taccgtgtgg tcagcgtcct caccgtcctg caccaggact ggctgaacgg caaggagtac   1020
aagtgcaagg tctccaacaa aggcctcccg tcctccatcg agaaaaccat ctccaaagcc   1080
aaagggcagc cccgagagcc acaagtgtac accctgcccc catcccagga ggagatgacc   1140
aagaaccagg tcagcctgac ctgcctggtc aaaggcttct accccagcga catcgccgtg   1200
gagtgggaga gcaatgggca gccggagaac aactacaaga ccacgcctcc cgtcctcgat   1260
tccgacggct ccttcttcct ctacagcagg ctaaccgtgg acaagagcag gtggcaggag   1320
gggaatgtct tctcatgctc cgtgatgcat gaggctctgc acaaccacta cacacagaag   1380
agcctctccc tgtctctggg ttga                                          1404
```

<210> SEQ ID NO 145
<211> LENGTH: 448
<212> TYPE: PRT
<213> ORGANISM: Artificial Sequence
<220> FEATURE:
<223> OTHER INFORMATION: Chimeric antibody heavy chain

<400> SEQUENCE: 145

```
Asp Val Gln Leu Gln Glu Ser Gly Pro Asp Leu Val Lys Pro Ser Gln
1               5                  10                  15

Ser Leu Ser Leu Thr Cys Thr Val Thr Gly Tyr Ser Ile Thr Ser Gly
            20                  25                  30

Tyr Ser Trp His Trp Ile Arg Gln Phe Pro Gly Asn Lys Leu Glu Trp
        35                  40                  45

Met Gly Tyr Ile His Tyr Ser Gly Gly Thr Asn Tyr Asn Pro Ser Leu
    50                  55                  60

Lys Ser Arg Ile Ser Ile Thr Arg Asp Thr Ser Lys Asn Gln Phe Phe
65                  70                  75                  80

Leu Gln Leu Asn Ser Val Thr Thr Glu Asp Thr Ala Thr Tyr Tyr Cys
                85                  90                  95

Ala Arg Ser Gly Tyr Gly Tyr Arg Ser Ala Tyr Tyr Phe Asp Tyr Trp
            100                 105                 110

Gly Gln Gly Thr Thr Leu Thr Val Ser Ser Ala Ser Thr Lys Gly Pro
        115                 120                 125

Ser Val Phe Pro Leu Ala Pro Cys Ser Arg Ser Thr Ser Glu Ser Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Lys Thr Tyr Thr Cys Asn Val Asp
        195                 200                 205
```

```
His Lys Pro Ser Asn Thr Lys Val Asp Lys Arg Val Glu Ser Lys Tyr
    210                 215                 220
Gly Pro Pro Cys Pro Pro Cys Pro Ala Pro Glu Phe Leu Gly Gly Pro
225                 230                 235                 240
Ser Val Phe Leu Phe Pro Pro Lys Pro Lys Asp Thr Leu Met Ile Ser
                245                 250                 255
Arg Thr Pro Glu Val Thr Cys Val Val Val Asp Val Ser Gln Glu Asp
            260                 265                 270
Pro Glu Val Gln Phe Asn Trp Tyr Val Asp Gly Val Glu Val His Asn
        275                 280                 285
Ala Lys Thr Lys Pro Arg Glu Glu Gln Phe Asn Ser Ala Tyr Arg Val
    290                 295                 300
Val Ser Val Leu Thr Val Leu His Gln Asp Trp Leu Asn Gly Lys Glu
305                 310                 315                 320
Tyr Lys Cys Lys Val Ser Asn Lys Gly Leu Pro Ser Ser Ile Glu Lys
                325                 330                 335
Thr Ile Ser Lys Ala Lys Gly Gln Pro Arg Glu Pro Gln Val Tyr Thr
            340                 345                 350
Leu Pro Pro Ser Gln Glu Glu Met Thr Lys Asn Gln Val Ser Leu Thr
        355                 360                 365
Cys Leu Val Lys Gly Phe Tyr Pro Ser Asp Ile Ala Val Glu Trp Glu
    370                 375                 380
Ser Asn Gly Gln Pro Glu Asn Asn Tyr Lys Thr Thr Pro Pro Val Leu
385                 390                 395                 400
Asp Ser Asp Gly Ser Phe Phe Leu Tyr Ser Arg Leu Thr Val Asp Lys
                405                 410                 415
Ser Arg Trp Gln Glu Gly Asn Val Phe Ser Cys Ser Val Met His Glu
            420                 425                 430
Ala Leu His Asn His Tyr Thr Gln Lys Ser Leu Ser Leu Ser Leu Gly
        435                 440                 445

<210> SEQ ID NO 146
<211> LENGTH: 1401
<212> TYPE: DNA
<213> ORGANISM: Artificial Sequence
<220> FEATURE:
<223> OTHER INFORMATION: cDNA encoding chimeric antibody heavy chain

<400> SEQUENCE: 146
atgggttgga tctgtatctt tctattcttg gtggcagctg cccaaagtgc ccaagcacag      60
atccagttgg tgcagtctgg acctgacctg aagaagcctg agagacagt caagatctcc     120 tgcaaggctt ctgggtatac cttcacaaac catggaatga actgggtgaa gcaggctcca     180
ggaaaggatt taaagtggat gggctggata acaccaaca ctggagagcc aacatatgct     240
gatgacttca agggacggtt tgccttctct ttggaaacct ctgccagcac tgcctatttg     300
cagatcaaca acctcaaaaa tgaggacacg gctacatatt tctgtgcaag tcccctctac     360
tataggaacg gcgatactt cgatgtctgg ggcgcaggga ccacggtcac cgtctcctca     420
gcttccacca agggcccatc cgtcttcccc ctggcgccct gctccagatc tacctccgag     480
agcacagccg ccctgggctg cctggtcaag gactacttcc ccgaaccggt gacggtgtcg     540
tggaactcag gcgccctgac cagcggcgtg cacaccttcc cggctgtcct acagtcctca     600
ggactctact ccctcagcag cgtggtgacc gtgccctcca gcagcttggg cacgaagacc     660
tacacctgca acgtagatca caagcccagc aacaccaagg tggacaagag agttgagtcc     720
```

```
aaatatggtc ccccatgccc accgtgccca gcacctgagt tcctgggggg accatcagtc    780
ttcctgttcc ccccaaaacc caaggacact ctcatgatct cccggacccc tgaggtcacg    840
tgcgtggtgg tggacgtgag ccaggaagac cccgaggtcc agttcaactg gtacgtggat    900
ggcgtggagg tgcataatgc caagacaaag ccgcgggagg agcagttcaa cagcgcgtac    960
cgtgtggtca gcgtcctcac cgtcctgcac caggactggc tgaacggcaa ggagtacaag   1020
tgcaaggtct ccaacaaagg cctcccgtcc tccatcgaga aaaccatctc caaagccaaa   1080
gggcagcccc gagagccaca agtgtacacc ctgcccccat cccaggagga tgaccaag     1140
aaccaggtca gcctgacctg cctggtcaaa ggcttctacc ccagcgacat cgccgtggag   1200
tgggagagca atgggcagcc ggagaacaac tacaagacca cgcctcccgt cctcgattcc   1260
gacggctcct tcttcctcta cagcaggcta accgtggaca agagcaggtg gcaggagggg   1320
aatgtcttct catgctccgt gatgcatgag gctctgcaca accactacac acagaagagc   1380
ctctcccctgt ctctggggttg a                                           1401
```

<210> SEQ ID NO 147
<211> LENGTH: 447
<212> TYPE: PRT
<213> ORGANISM: Artificial Sequence
<220> FEATURE:
<223> OTHER INFORMATION: Chimeric antibody heavy chain

<400> SEQUENCE: 147

```
Gln Ile Gln Leu Val Gln Ser Gly Pro Asp Leu Lys Lys Pro Gly Glu
1               5                   10                  15

Thr Val Lys Ile Ser Cys Lys Ala Ser Gly Tyr Thr Phe Thr Asn His
            20                  25                  30

Gly Met Asn Trp Val Lys Gln Ala Pro Gly Lys Asp Leu Lys Trp Met
        35                  40                  45

Gly Trp Ile Asn Thr Asn Thr Gly Glu Pro Thr Tyr Ala Asp Asp Phe
    50                  55                  60

Lys Gly Arg Phe Ala Phe Ser Leu Glu Thr Ser Ala Ser Thr Ala Tyr
65                  70                  75                  80

Leu Gln Ile Asn Asn Leu Lys Asn Glu Asp Thr Ala Thr Tyr Phe Cys
                85                  90                  95

Ala Ser Pro Leu Tyr Tyr Arg Asn Gly Arg Tyr Phe Asp Val Trp Gly
            100                 105                 110

Ala Gly Thr Thr Val Thr Val Ser Ser Ala Ser Thr Lys Gly Pro Ser
        115                 120                 125

Val Phe Pro Leu Ala Pro Cys Ser Arg Ser Thr Ser Glu Ser Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Lys Thr Tyr Thr Cys Asn Val Asp His
        195                 200                 205

Lys Pro Ser Asn Thr Lys Val Asp Lys Arg Val Glu Ser Lys Tyr Gly
    210                 215                 220

Pro Pro Cys Pro Pro Cys Pro Ala Pro Glu Phe Leu Gly Gly Pro Ser
225                 230                 235                 240
```

Val Phe Leu Phe Pro Pro Lys Pro Lys Asp Thr Leu Met Ile Ser Arg
                245                 250                 255

Thr Pro Glu Val Thr Cys Val Val Val Asp Val Ser Gln Glu Asp Pro
            260                 265                 270

Glu Val Gln Phe Asn Trp Tyr Val Asp Gly Val Glu Val His Asn Ala
        275                 280                 285

Lys Thr Lys Pro Arg Glu Glu Gln Phe Asn Ser Ala Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Gln Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Arg Leu Thr Val Asp Lys Ser
                405                 410                 415

Arg Trp Gln Glu Gly Asn Val Phe Ser Cys Ser Val Met His Glu Ala
            420                 425                 430

Leu His Asn His Tyr Thr Gln Lys Ser Leu Ser Leu Ser Leu Gly
        435                 440                 445

<210> SEQ ID NO 148
<211> LENGTH: 705
<212> TYPE: DNA
<213> ORGANISM: Artificial Sequence
<220> FEATURE:
<223> OTHER INFORMATION: cDNA encoding chimeric antibody light chain

<400> SEQUENCE: 148
atgaggtccc ctgctcagtt tcttggtctc ctgttgctct gttttcaagg tgccagatgt      60
gatatccaga tgacacagac tacatcctcc ctgtctgcct ctctgggaga cagagtcacc     120
atcagttgca gggcaagtca ggacattagt aattatttaa attggtatca gcagaaacca     180
gatggatctg ttaaactcct gatctactac acatcaagat acactcagg agtcccatca      240
aggttcagtg gcagtgggtc tggaacagat tattctctca ccattagcaa cctggaacaa     300
gaagatattg ccacttactt tgccaacag ggaaagacgc ttccgtggac gttcggtgga      360
ggcaccaagc tggaaatcaa acgtacggtg gctgcaccat ctgtcttcat cttcccgcca     420
tctgatgagc agttgaaatc tggaactgcc tctgttgtgt gcctgctgaa taacttctat     480
cccagagagg ccaaagtaca gtggaaggtg gataacgccc tccaatcggg taactcccag     540
gagagtgtca cagagcagga cagcaaggac agcacctaca gcctcagcag cacccctgacg    600
ctgagcaaag cagactacga gaaacacaaa gtctacgcct gcgaagtcac ccatcagggc     660
ctgagctcgc ccgtcacaaa gagcttcaac aggggagagt gttag                     705

<210> SEQ ID NO 149
<211> LENGTH: 214
<212> TYPE: PRT
<213> ORGANISM: Artificial Sequence
<220> FEATURE:

<223> OTHER INFORMATION: Chimeric antibody light chain

<400> SEQUENCE: 149

```
Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Asn Tyr
            20                  25                  30

Leu Asn Trp Tyr Gln Gln Lys Pro Asp Gly Ser Val Lys Leu Leu Ile
        35                  40                  45

Tyr Tyr Thr Ser Arg Leu His Ser Gly Val Pro Ser Arg Phe Ser Gly
50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Lys Thr Leu Pro Trp
                85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 150
<211> LENGTH: 446
<212> TYPE: PRT
<213> ORGANISM: Artificial Sequence
<220> FEATURE:
<223> OTHER INFORMATION: Chimeric antibody heavy chain

<400> SEQUENCE: 150

```
Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asn His
            20                  25                  30

Gly Met Asn Trp Val Lys Gln Ala Pro Gly Lys Gly Leu Lys Trp Met
        35                  40                  45

Gly Trp Asn Thr Ser Thr Gly Glu Pro Thr Tyr Ala Asp Asp Phe Lys
50                  55                  60

Gly Arg Phe Ala Phe Ser Leu Glu Thr Ser Ala Ser Thr Ala Phe Leu
65                  70                  75                  80

Gln Ile Asn Asn Leu Lys Asn Glu Asp Thr Ala Ser Tyr Phe Cys Ala
                85                  90                  95

Ser Pro Leu Tyr Tyr Met Tyr Gly Arg Tyr Ile Asp Val Trp Gly Ala
            100                 105                 110

Gly Thr Ala Val Thr Val Ser Ser Ala Ser Thr Lys Gly Pro Ser Val
        115                 120                 125
```

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Ala Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly
        435                 440                 445

<210> SEQ ID NO 151
<211> LENGTH: 705
<212> TYPE: DNA
<213> ORGANISM: Artificial Sequence
<220> FEATURE:
<223> OTHER INFORMATION: cDNA encoding chimeric antibody light chain

<400> SEQUENCE: 151
atgaggtccc ctgctcagtt tctttggagac ctgttgctct gttttcaagg taccagatgt      60
gatatccaga tgacacagac tacatcctcc ctatctgcct ctctgggaga cagagtcacc     120
atcagttgca gggcaagtca ggacattagc aattatttaa actggtatca gcagaaacca     180
gatggaacta ttaaactcct gatctactac acatcaagat acactcagg agtcccatca     240

```
aggttcagtg gcagtgggtc tggaacagat tattctctca ccattagcaa cctggaacaa      300
gaagattttg ccacttactt ttgccaacag ggtaaaacgc ttccgtggac gttcggtgga      360
ggcaccaagc tggaaatcaa acgtacggtg gctgcaccat ctgtcttcat cttcccgcca      420
tctgatgagc agttgaaatc tggaactgcc tctgttgtgt gcctgctgaa taacttctat      480
cccagagagg ccaaagtaca gtggaaggtg gataacgccc tccaatcggg taactcccag      540
gagagtgtca cagagcagga cagcaaggac agcacctaca gcctcagcag caccctgacg      600
ctgagcaaag cagactacga gaaacacaaa gtctacgcct gcgaagtcac ccatcagggc      660
ctgagctcgc ccgtcacaaa gagcttcaac aggggagagt gttag                     705
```

<210> SEQ ID NO 152
<211> LENGTH: 214
<212> TYPE: PRT
<213> ORGANISM: Artificial Sequence
<220> FEATURE:
<223> OTHER INFORMATION: Chimeric antibody light chain

<400> SEQUENCE: 152

```
Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Asn Tyr
            20                  25                  30

Leu Asn Trp Tyr Gln Gln Lys Pro Asp Gly Thr Ile Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Phe Ala Thr Tyr Phe Cys Gln Gln Gly Lys Thr Leu Pro Trp
                85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 153
<211> LENGTH: 324
<212> TYPE: DNA
<213> ORGANISM: Artificial Sequence
<220> FEATURE:
<223> OTHER INFORMATION: cDNA encoding antibody light chain constant
      domain

<400> SEQUENCE: 153

```
cgaactgtgg ctgcaccatc tgtcttcatc ttcccgccat ctgatgagca gttgaaatct    60
ggaactgcct ctgttgtgtg cctgctgaat aacttctatc ccagagaggc caaagtacag   120
tggaaggtgg ataacgccct ccaatcgggt aactcccagg agagtgtcac agagcaggac   180
agcaaggaca gcacctacag cctcagcagc accctgacgc tgagcaaagc agactacgag   240
aaacacaaag tctacgcctg cgaagtcacc catcagggcc tgagctcgcc cgtcacaaag   300
agcttcaaca ggggagagtg ttga                                          324
```

<210> SEQ ID NO 154
<211> LENGTH: 107
<212> TYPE: PRT
<213> ORGANISM: Artificial Sequence
<220> FEATURE:
<223> OTHER INFORMATION: Antibody light chain constant domain

<400> SEQUENCE: 154

```
Arg Thr Val Ala Ala Pro Ser Val Phe Ile Phe Pro Pro Ser Asp Glu
 1               5                  10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105
```

<210> SEQ ID NO 155
<211> LENGTH: 981
<212> TYPE: DNA
<213> ORGANISM: Artificial Sequence
<220> FEATURE:
<223> OTHER INFORMATION: cDNA encoding antibody aglycosylated heavy
      chain constant domain

<400> SEQUENCE: 155

```
gcctcaacga aggggcccag cgtgttcccc ctggcgccct gctccaggag cacctccgag    60
agcacagccg ccctgggctg cctggtcaag gactacttcc ccgaaccggt gacggtgtcg   120
tggaactcag gcgccctgac cagcggcgtg cacaccttcc cggctgtcct acagtcctca   180
ggactctact ccctcagcag cgtggtgacc gtgccctcca gcagcttggg cacgaagacc   240
tacacctgca acgtagatca caagcccagc aacaccaagg tggacaagag agttgagtcc   300
aaatatggtc cccatgccca ccgtgccca gcacctgagt tcctgggggg accatcagtc   360
ttcctgttcc ccccaaaacc caaggacact ctcatgatct cccggacccc tgaggtcacg   420
tgcgtggtgg tggacgtgag ccaggaagac cccgaggtcc agttcaactg gtacgtggat   480
ggcgtggagg tgcataatgc caagacaaag ccgcgggagg agcagttcaa cagcgcgtac   540
cgtgtggtca gcgtcctcac cgtcctgcac caggactggc tgaacggcaa ggagtacaag   600
tgcaaggtct ccaacaaagg cctcccgtcc tccatcgaga aaaccatctc caaagccaaa   660
gggcagcccc gagagccaca agtgtacacc ctgcccccat cccaggagga gatgaccaag   720
aaccaggtca gcctgacctg cctggtcaaa ggcttctacc ccagcgacat cgccgtggag   780
```

```
tgggagagca atgggcagcc ggagaacaac tacaagacca cgcctcccgt cctcgattcc    840
gacggctcct tcttcctcta cagcaggcta accgtggaca agagcaggtg gcaggagggg    900
aatgtcttct catgctccgt gatgcatgag gctctgcaca accactacac acagaagagc    960 ctctcccctgt ctctgggttg a                                              981
```

<210> SEQ ID NO 156
<211> LENGTH: 326
<212> TYPE: PRT
<213> ORGANISM: Artificial Sequence
<220> FEATURE:
<223> OTHER INFORMATION: Antibody aglycosylated heavy chain constant
      domain

<400> SEQUENCE: 156

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Ala Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320
```

```
Leu Ser Leu Ser Leu Gly
              325

<210> SEQ ID NO 157
<211> LENGTH: 22
<212> TYPE: PRT
<213> ORGANISM: Artificial Sequence
<220> FEATURE:
<223> OTHER INFORMATION: Immunoglobulin light chain signal peptide

<400> SEQUENCE: 157

Met Asp Met Arg Val Pro Ala Gln Leu Leu Gly Leu Leu Leu Leu Trp
1               5                   10                  15

Leu Pro Gly Ala Arg Cys
            20
```